United States Patent
Hopkins et al.

(10) Patent No.: US 10,899,753 B2
(45) Date of Patent: Jan. 26, 2021

(54) INHIBITING AGENTS FOR BRUTON'S TYROSINE KINASE

(71) Applicant: BIOGEN MA INC., Cambridge, MA (US)

(72) Inventors: Brian T. Hopkins, Newton, MA (US); Bin Ma, Arlington, MA (US); Robin Prince, Sharon, MA (US); Isaac Marx, Arlington, MA (US); Jürgen Schulz, Boston, MA (US); Marta Nevalainen, Holliston, MA (US); Michael Dechantsreiter, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 16/410,725

(22) Filed: May 13, 2019

(65) Prior Publication Data

US 2019/0382394 A1    Dec. 19, 2019

Related U.S. Application Data

(60) Provisional application No. 62/671,053, filed on May 14, 2018.

(51) Int. Cl.
| | | |
|---|---|---|
| *C07D 413/14* | (2006.01) | |
| *C07D 403/14* | (2006.01) | |
| *C07D 405/14* | (2006.01) | |

(52) U.S. Cl.
CPC ......... *C07D 413/14* (2013.01); *C07D 403/14* (2013.01); *C07D 405/14* (2013.01)

(58) Field of Classification Search
CPC .................................................. C07D 413/14
See application file for complete search history.

(56) References Cited

FOREIGN PATENT DOCUMENTS

| EP | 2824099 A1 | 1/2015 |
|---|---|---|
| WO | 2015/089337 A1 | 6/2015 |
| WO | 2016/201280 A1 | 12/2016 |

OTHER PUBLICATIONS

International Search Report and Written Opinion for Application No. PCT/US2019/032018, dated Jul. 31, 2019, 13 pages.

*Primary Examiner* — Paul V Ward
(74) *Attorney, Agent, or Firm* — McCarter & English, LLP; Steven G. Davis; Xin Zhang

(57) ABSTRACT

Provided are compounds of Formula (I), or pharmaceutically acceptable salts thereof, and methods for their use and production.

20 Claims, No Drawings

INHIBITING AGENTS FOR BRUTON'S TYROSINE KINASE

RELATED APPLICATIONS

This application claims the benefit of the filing date, under 35 U.S.C. § 119(e), of U.S. Provisional Application No. 62/671,053, filed on May 14, 2018, the entire contents of which are incorporated herein by reference.

TECHNICAL FIELD

Provided are certain agents that inhibit Bruton's tyrosine kinase (Btk), and methods of making and using such agents.

BACKGROUND

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk.

SUMMARY

A first embodiment of the invention is a compound of Formula (I):

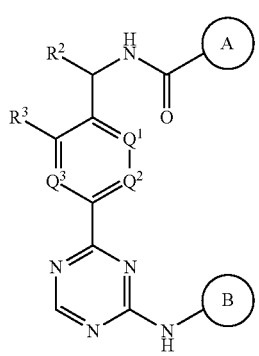

Formula (I)

or a pharmaceutically acceptable salt, wherein:

Ring A is selected from aryl and 5- to 6-membered heteroaryl, wherein said aryl and 5- to 6-membered heteroaryl is optionally substituted with one or more $R^1$;

Ring B is pyrazolyl, wherein said pyrazolyl is optionally substituted with one or more $R^5$;

$Q^1$, $Q^2$, and $Q^3$ are each selected from C—$R^4$ and N, wherein at most one of $Q^1$, $Q^2$, and $Q^3$ is N;

$R^1$ in each occurrence is independently selected from $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)$R^{1a}$, —C(O)$_2R^{1a}$, —C(O)N($R^{1a}$)$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{10}$;

$R^{1a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{10}$;

$R^2$ is selected from H and $C_{1-6}$alkyl;

$R^3$ is selected from $C_{1-6}$alkyl, $C_{2-6}$alkenyl, $C_{2-6}$alkynyl, 3- to 6-membered monocyclic carbocyclyl, and 4- to 6-membered monocyclic heterocyclyl, halo, —CN, —C(O)$R^{3a}$, —C(O)$_2R^{3a}$, —C(O)N($R^{3a}$)$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —N($R^{3a}$)S(O)$_2R^{3a}$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$ wherein said $C_{1-6}$alkyl, $C_{2-6}$alkenyl, $_{2-6}$alkynyl, 3- to 6-membered monocyclic carbocyclyl, and 4- to 6-membered monocyclic heterocyclyl are optionally substituted with one or more $R^{30}$;

$R^{3a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{30}$;

or $R^2$ and $R^3$, together with their intervening atoms, form a seven-membered carbocyclic or heterocyclic ring, wherein said seven-membered carbocyclic or heterocyclic ring is optionally substituted with one or more $R^{20}$;

$R^4$ in each occurrence is independently selected from H, $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)$R^{4a}$, —C(O)$_2R^{4a}$, —C(O)N($R^{4a}$)$_2$, —N($R^{4a}$)$_2$, —N($R^{4a}$)C(O)$R^{4a}$, —N($R^{4a}$)C(O)$_2R^{4a}$, —N($R^{4a}$)C(O)N($R^{4a}$)$_2$, —N($R^{4a}$)S(O)$_2R^{4a}$, —O$R^{4a}$, —OC(O)$R^{4a}$, —OC(O)N($R^{4a}$)$_2$, —S$R^{4a}$, —S(O)$R^{4a}$, —S(O)$_2R^{4a}$, —S(O)N($R^{4a}$)$_2$, and —S(O)$_2$N($R^{4a}$)$_2$, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{40}$;

$R^{4a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{40}$;

$R^5$ in each occurrence is independently selected from $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)R$^{5a}$, —C(O)$_2$R$^{5a}$, —C(O)N(R$^{5a}$)$_2$, —N(R$^{5a}$)$_2$, —N(R$^{5a}$)C(O)R$^{5a}$, —N(R$^{5a}$)C(O)$_2$R$^{5a}$, —N(R$^{5a}$)C(O)N(R$^{5a}$)$_2$, —N(R$^{5a}$)S(O)$_2$R$^{5a}$, —OR$^{5a}$, —OC(O)R$^{5a}$, —OC(O)N(R$^{5a}$)$_2$, —SR$^{5a}$, —S(O)R$^{5a}$, —S(O)$_2$R$^{5a}$, —S(O)N(R$^{5a}$)$_2$, and —S(O)$_2$N(R$^{5a}$)$_2$, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{50}$;

$R^{5a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{50}$;

$R^{10}$ in each occurrence is independently selected from $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)R$^{10a}$, —C(O)$_2$R$^{10a}$, —C(O)N(R$^{10a}$)$_2$, —N(R$^{10a}$)$_2$, —N(R$^{10a}$)C(O)R$^{10a}$, —N(R$^{10a}$)C(O)$_2$R$^{10a}$, —N(R$^{10a}$)C(O)N(R$^{10a}$)$_2$, —N(R$^{10a}$)S(O)$_2$R$^{10a}$, —OR$^{10a}$, —OC(O)R$^{10a}$, —OC(O)N(R$^{10a}$)$_2$, —SR$^{10a}$, —S(O)R$^{10a}$, —S(O)$_2$R$^{10a}$, —S(O)N(R$^{10a}$)$_2$, and —S(O)$_2$N(R$^{10a}$)$_2$, wherein said $C_{1-6}$alkyl, $C_{2-6}$alkenyl, $C_{2-6}$alkynyl, 3- to 6-membered monocyclic carbocyclyl, 4- to 6-membered monocyclic heterocyclyl in each occurrence are optionally and independently substituted with one or more halo;

$R^{10a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl;

$R^{20}$ in each occurrence is independently selected from $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)R$^{20a}$, —C(O)$_2$R$^{20a}$, —C(O)N(R$^{20a}$)$_2$, —N(R$^{20a}$)$_2$, —N(R$^{20a}$)C(O)R$^{20a}$, —N(R$^{20a}$)C(O)$_2$R$^{20a}$, —N(R$^{20a}$)C(O)N(R$^{20a}$)$_2$, —N(R$^{20a}$)S(O)$_2$R$^{20a}$, —OR$^{20a}$, —OC(O)R$^{20a}$, —OC(O)N(R$^{20a}$)$_2$, —SR$^{20a}$, —S(O)R$^{20a}$S(O)$_2$R$^{20a}$, —S(O)N(R$^{20a}$)$_2$, and —S(O)$_2$N(R$^{20a}$)$_2$, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally substituted with one or more $R^{25}$;

$R^{20a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{25}$;

$R^{25}$ in each occurrence is independently selected from halo, $C_{1-6}$alkyl, $C_{2-6}$alkenyl, $C_{2-6}$alkynyl, 3- to 6-membered monocyclic carbocyclyl, 4- to 6-membered monocyclic heterocyclyl, —CN, —C(O)R$^{25a}$, —C(O)$_2$R$^{25a}$, —C(O)N(R$^{25a}$)$_2$, —N(R$^{25a}$)$_2$, —N(R$^{25a}$)C(O)R$^{25a}$, —N(R$^{25a}$)C(O)$_2$R$^{25a}$, —N(R$^{25a}$)C(O)N(R$^{25a}$)$_2$, —N(R$^{25a}$)S(O)$_2$R$^{25a}$, —OR$^{25a}$, —OC(O)R$^{25a}$, —OC(O)N(R$^{25a}$)$_2$, —SR$^{25a}$, —S(O)R$^{25a}$, —S(O)$_2$R$^{25a}$, —S(O)N(R$^{25a}$)$_2$, and —S(O)$_2$N(R$^{25a}$)$_2$;

$R^{25a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl;

$R^{30}$ in each occurrence is independently selected from $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)R$^{30a}$, —C(O)$_2$R$^{30a}$, —C(O)N(R$^{30a}$)$_2$, —N(R$^{30a}$)$_2$, —N(R$^{30a}$)C(O)R$^{30a}$, —N(R$^{30a}$)C(O)$_2$R$^{30a}$, —N(R$^{30a}$)C(O)N(R$^{30a}$)$_2$, —N(R$^{30a}$)S(O)$_2$R$^{30a}$, —OR$^{30a}$, —OC(O)R$^{30a}$, —OC(O)N(R$^{30a}$)$_2$, —SR$^{30a}$, —S(O)R$^{30a}$, —S(O)$_2$R$^{30a}$, —S(O)N(R$^{30a}$)$_2$, and —S(O)$_2$N(R$^{30a}$)$_2$; wherein said $C_{1-6}$alkyl, $C_{2-6}$alkenyl, $C_{2-6}$alkynyl, 3- to 6-membered monocyclic carbocyclyl, 4- to 6-membered monocyclic heterocyclyl in each occurrence are optionally and independently substituted with one or more halo;

$R^{30a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl;

$R^{40}$ in each occurrence is independently selected from $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)R$^{40a}$, —C(O)$_2$R$^{40a}$, —C(O)N(R$^{40a}$)$_2$, —N(R$^{40a}$)$_2$, —N(R$^{40a}$)C(O)R$^{40a}$, —N(R$^{40a}$)C(O)$_2$R$^{40a}$, —N(R$^{40a}$)C(O)N(R$^{40a}$)$_2$, —N(R$^{40a}$)S(O)$_2$R$^{4a}$, —OR$^{40a}$, —OC(O)R$^{40a}$, —OC(O)N(R$^{40a}$)$_2$, —SR$^{40a}$, —S(O)R$^{40a}$S(O)$_2$R$^{40a}$, —S(O)N(R$^{40a}$)$_2$, and —S(O)$_2$N(R$^{40a}$)$_2$;

$R^{40a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl;

$R^{50}$ in each occurrence is independently selected from $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)R$^{50a}$, —C(O)$_2$R$^{50a}$, —C(O)N(R$^{50a}$)$_2$, —N(R$^{50a}$)$_2$, —N(R$^{50a}$)C(O)R$^{50a}$, —N(R$^{50a}$)C(O)$_2$R$^{50a}$ N(R$^{50a}$)C(O)N(R$^{50a}$)$_2$, —N(R$^{50a}$)S(O)$_2$R$^{50a}$, —OR$^{50a}$, —OC(O)R$^{50a}$, —OC(O)N(R$^{50a}$)$_2$, —SR$^{50a}$, —S(O)R$^{50a}$, —S(O)$_2$R$^{50a}$, —S(O)N(R$^{50a}$)$_2$, and —S(O)$_2$N(R$^{50a}$)$_2$; and $R^{50a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl.

A second embodiment of the invention is a compound of Formula (I):

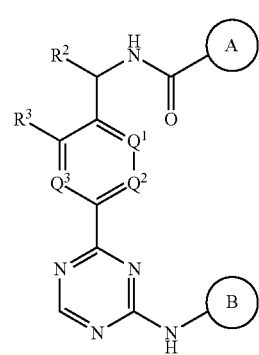

Formula (I)

or a pharmaceutically acceptable salt, wherein:

Ring A is selected from aryl and 5- to 6-membered heteroaryl, wherein said aryl and 5- to 6-membered heteroaryl is optionally substituted with one or more $R^1$;

Ring B is pyrazolyl, wherein said pyrazolyl is optionally substituted with one or more $R^5$;

$Q^1$, $Q^2$, and $Q^3$ are each selected from C—$R^4$ and N, wherein at most one of $Q^1$, $Q^2$, and $Q^3$ is N;

$R^1$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{1a}$, —C(O)$_2R^{1a}$, —C(O)N($R^{1a}$)$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{10}$;

$R^{1a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{10}$;

$R^2$ is selected from H and $C_{1-6}$alkyl;

$R^3$ is selected from $C_{1-6}$alkyl, $C_{2-6}$alkenyl, $C_{2-6}$alkynyl, 4- to 6-membered monocyclic carbocyclyl, and 4- to 6-membered monocyclic heterocyclyl, halo, —CN, —C(O)$R^{3a}$, —C(O)$_2R^{3a}$, —C(O)N($R^{3a}$)$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —N($R^{3a}$)S(O)$_2R^{3a}$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$ wherein said $C_{1-6}$alkyl, $C_{2-6}$alkenyl, $_{2-6}$alkynyl, 4- to 6-membered monocyclic carbocyclyl, and 4- to 6-membered monocyclic heterocyclyl are optionally substituted with one or more $R^{30}$;

$R^{3a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{30}$;

or $R^2$ and $R^3$, together with their intervening atoms, form a seven-membered carbocyclic or heterocyclic ring, wherein said seven-membered carbocyclic or heterocyclic ring is optionally substituted with one or more $R^{20}$;

$R^4$ in each occurrence is independently selected from H, $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{4a}$, —C(O)$_2R^{4a}$, —C(O)N($R^{4a}$)$_2$, —N($R^{4a}$)$_2$, —N($R^{4a}$)C(O)$R^{4a}$, —N($R^{4a}$)C(O)$_2R^{4a}$, —N($R^{4a}$)C(O)N($R^{4a}$)$_2$, —N($R^{4a}$)S(O)$_2R^{4a}$, —O$R^{4a}$, —OC(O)$R^{4a}$, —OC(O)N($R^{4a}$)$_2$, —S$R^{4a}$, —S(O)$R^{4a}$, —S(O)$_2R^{4a}$, —S(O)N($R^{4a}$)$_2$, and —S(O)$_2$N($R^{4a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{40}$;

$R^{4a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{40}$;

$R^5$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{5a}$, —C(O)$_2R^{5a}$, —C(O)N($R^{5a}$)$_2$, —N($R^{5a}$)$_2$, —N($R^{5a}$)C(O)$R^{5a}$, —N($R^{5a}$)C(O)$_2R^{5a}$, —N($R^{5a}$)C(O)N($R^{5a}$)$_2$, —N($R^{5a}$)S(O)$_2R^{5a}$, —O$R^{5a}$, —OC(O)$R^{5a}$, —OC(O)N($R^{5a}$)$_2$, —S$R^{5a}$, —S(O)$R^{5a}$, —S(O)$_2R^{5a}$, —S(O)N($R^{5a}$)$_2$, and —S(O)$_2$N($R^{5a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{50}$;

$R^{5a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{50}$;

$R^{10}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{10a}$, —C(O)$_2R^{10a}$, —C(O)N($R^{10a}$)$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;

$R^{10a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{20}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{20a}$, —C(O)$_2R^{20a}$, —C(O)N($R^{20a}$)$_2$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$S(O)$_2R^{20a}$, —S(O)N($R^{20a}$)$_2$, and —S(O)$_2$N($R^{20a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally substituted with one or more $R^{25}$;

$R^{20a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{25}$;

$R^{25}$ in each occurrence is independently selected from halo, $C_{1-6}$alkyl, $C_{2-6}$alkenyl, $C_{2-6}$alkynyl, 4- to 6-membered monocyclic carbocyclyl, 4- to 6-membered monocyclic heterocyclyl, —CN, —C(O)$R^{25a}$, —C(O)$_2R^{25a}$, —C(O)N($R^{25a}$)$_2$, —N($R^{25a}$)$_2$, —N($R^{25a}$)C(O)$R^{25a}$, —N($R^{25a}$)C(O)$_2R^{25a}$, —N($R^{25a}$)C(O)N($R^{25a}$)$_2$, —N($R^{25a}$)S(O)$_2R^{25a}$, —O$R^{25a}$, —OC(O)$R^{25a}$, —OC(O)N($R^{25a}$)$_2$, —S$R^{25a}$, —S(O)$R^{25a}$, —S(O)$_2R^{25a}$, —S(O)N($R^{25a}$)$_2$, and —S(O)$_2$N($R^{25a}$)$_2$;

$R^{25a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{30}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{30a}$, —C(O)$_2R^{30a}$, —C(O)N($R^{30a}$)$_2$, —N($R^{30a}$)$_2$, —N($R^{30a}$)C(O)$R^{30a}$, —N($R^{30a}$)C(O)$_2R^{30a}$, —N($R^{3a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$S(O)$_2R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{40}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{40a}$, —C(O)$_2R^{40a}$, —C(O)N($R^{40a}$)$_2$, —N($R^{40a}$)$_2$, —N($R^{40a}$)C(O)$R^{40a}$, —N($R^{40a}$)C(O)$_2R^{40a}$, —N($R^{40a}$)C(O)N($R^{40a}$)$_2$, —N($R^{40a}$)S(O)$_2R^{4a}$, —O$R^{40a}$, —OC(O)$R^{40a}$, —OC(O)N($R^{40a}$)$_2$, —S$R^{40a}$, —S(O)$R^{40a}$S(O)$_2R^{40a}$, —S(O)N($R^{40a}$)$_2$, and —S(O)$_2$N($R^{40a}$)$_2$;

$R^{40a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{50}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{50a}$, —C(O)$_2R^{50a}$, —C(O)N($R^{50a}$)$_2$, —N($R^{50a}$)$_2$, —N($R^{50a}$)C(O)$R^{50a}$, —N($R^{50a}$)C(O)$_2R^{50a}$, —N($R^{50a}$)C(O)N($R^{50a}$)$_2$, —N($R^{50a}$)S(O)$_2R^{50a}$, —O$R^{50a}$, —OC(O)$R^{50a}$, —OC(O)N($R^{50a}$)$_2$, —S$R^{50a}$, —S(O)$R^{50a}$S(O)$_2R^{50a}$, —S(O)N($R^{50a}$)$_2$, and —S(O)$_2$N($R^{50a}$)$_2$; and $R^{50a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl.

The present invention also provides a pharmaceutical composition comprising at least one compound described herein, or a pharmaceutically acceptable salt thereof, and at least one pharmaceutically acceptable excipient.

In one embodiment, the invention is a method of treating a disorder responsive to inhibition of Btk in a subject comprising administering to said subject an effective amount of at least one compound described herein, or a pharmaceutically acceptable salt thereof.

The present invention also includes the use of at least one compound described herein, or a pharmaceutically acceptable salt thereof, for the manufacture of a medicament for the treatment of a disorder responsive to inhibition of Btk. Also provided is a compound described herein, or a pharmaceutically acceptable salt thereof for use as a medicament. In one embodiment, the present invention provides a compound described herein, or a pharmaceutically acceptable salt thereof for use in treating a disorder responsive to inhibition of Btk.

Other features or advantages will be apparent from the following detailed description of several embodiments, and also from the appended claims.

DETAILED DESCRIPTION

The compounds or pharmaceutically acceptable salts thereof as described herein, can have activity as Btk modulators. In particular, compounds or pharmaceutically acceptable salts thereof as described herein, can be Btk inhibitors.

In a third embodiment of the present invention, the compound is represented by formula (I), or a pharmaceutically acceptable salt thereof, wherein $Q^1$, $Q^2$, and $Q^3$ are each independently C—$R^4$ and the definitions for the other variables are as defined in the first or second embodiment. In a specific embodiment, $Q^1$ is CH. In another specific embodiment, $Q^1$, $Q^2$, and $Q^3$ are CH.

In a fourth embodiment of the present invention, the compound is represented by Formula (II) or (II'):

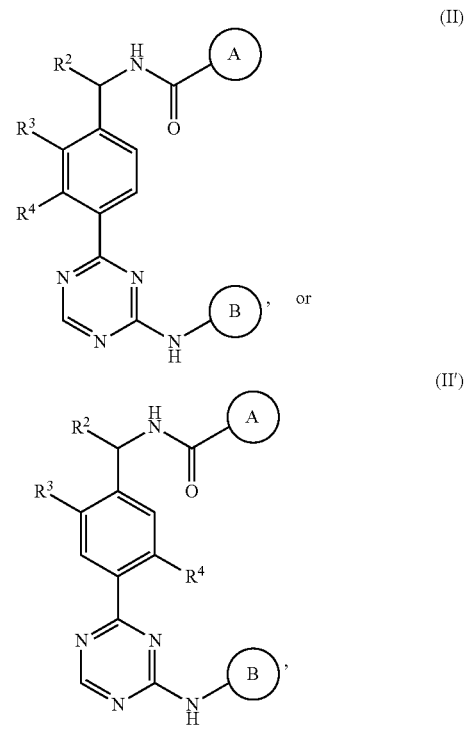

or a pharmaceutically acceptable salt thereof, wherein the definitions for the variables are as defined in the first or second embodiment.

In a fifth embodiment of the present invention, the compound is represented by formula (I), (II), or (II'), or a pharmaceutically acceptable salt thereof, wherein Ring A is a 5-membered N-containing heteroaryl having 1, 2 or 3 additional heteroatoms independently selected from O, N and S, wherein ring A is optionally substituted with 1 or 2 independently selected $R^1$, and the definitions for the other variables are as defined in the first, second, third or fourth embodiment. In a specific embodiment, Ring A is a 5-membered N-containing heteroaryl having 1, 2 or 3 additional heteroatoms independently selected from O, N and S, wherein ring A is optionally substituted with 1 or 2 independently selected $R^1$.

In a sixth embodiment of the present invention, the compound is represented by formula (I), (II), or (II') or a pharmaceutically acceptable salt thereof, wherein Ring A is selected from the group consisting of pyrazole, imidazole, oxazole, isoxazole, thiazole, isothiazole, 1,2,3-oxadiazole, 1,3,4-oxadiazole, 1,2,4-oxadizole, 1,2,3-thiadiazole, 1,3,4-thiadiazole, 1,2,4-thiadiazole, 1,2,3-triazole, 1,2,4-triazole, and tetrazole, each of which is optionally substituted with 1 or 2 independently selected $R^1$; and the definitions for the other variables are as defined in the first, second third, fourth or fifth embodiment. In a specific embodiment, Ring A is 1,2,4-oxadiazole, 1,2,3-triazole, pyrazole, tetrazole, isoxazole or oxazole, each of which is optionally substituted with 1 or 2 independently selected $R^1$.

In a seventh embodiment of the present invention, the compound is represented by formula (I), (II), or (II') or a pharmaceutically acceptable salt thereof, wherein Ring A is selected from the group consisting of pyrazole, imidazole, oxazole, isoxazole, thiazole, isothiazole, 1,2,3-oxadiazole, 1,3,4-oxadiazole, 1,2,4-oxadizole, 1,2,3-thiadiazole, 1,3,4-thiadiazole, 1,2,4-thiadiazole, 1,2,3-triazole, and 1,2,4-triazole, each of which is optionally substituted with 1 or 2 independently selected $R^1$; and the definitions for the other variables are as defined in the first, second third, fourth or fifth embodiment. In a specific embodiment, Ring A is 1,2,4-oxadiazole, 1,2,3-triazole, pyrazole, or oxazole, each of which is optionally substituted with 1 or 2 independently selected $R^1$.

In an eighth embodiment of the present invention, the compound is represented by formula (I), (II), or (II') or a pharmaceutically acceptable salt thereof, $R^1$ in each occurrence is independently halo, $C_{1-6}$alkyl or $C_{3-5}$cycloalkyl; wherein said $C_{1-6}$alkyl and $C_{3-5}$cycloalkyl are optionally substituted with one to three $R^{10}$; $R^{10}$ in each occurrence is independently selected from halo, —CN and $C_{1-6}$alkyl, wherein said $C_{1-6}$alkyl in each occurrence is independently and optionally substituted with one to three halo; and the definitions for the other variables are as defined in the first, second, third, fourth, fifth, sixth or seventh embodiment. In a specific embodiment, $R^1$ is tert-butyl or cyclopropyl, each of which is optionally substituted with one to three $R^{10}$; $R^{10}$ in each occurrence is independently selected from fluoro, methyl, —$CH_2F$, —$CHF_2$ or —$CF_3$.

In a ninth embodiment of the present invention, the compound is represented by formula (I), (II), or (II'), or a pharmaceutically acceptable salt thereof, $R^1$ in each occurrence is independently halo, $C_{1-6}$alkyl or $C_{3-5}$cycloalkyl; wherein said $C_{1-6}$alkyl and $C_{3-5}$cycloalkyl are optionally substituted with one to three $R^{10}$; $R^{10}$ in each occurrence is independently selected from halo, —CN and $C_{1-6}$alkyl; and the definitions for the other variables are as defined in the first, second, third, fourth, fifth, sixth or seventh embodiment.

In a tenth embodiment of the present invention, the compound is represented by formula (I), (II), or (II'), or a pharmaceutically acceptable salt thereof, wherein Ring A is represented by the following formula:

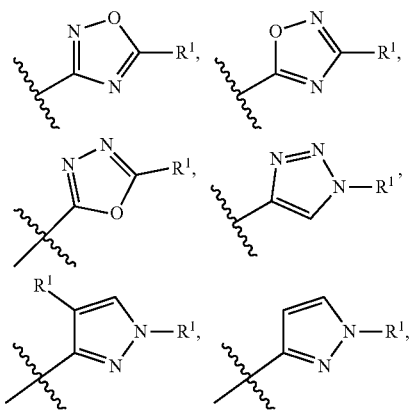

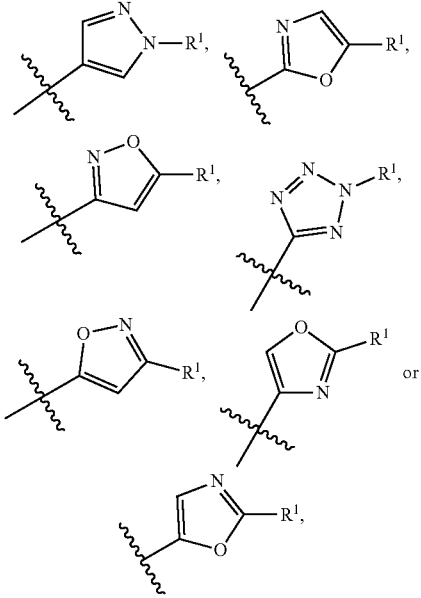

wherein $R^1$ in each occurrence is independently selected from halo, $C_{3-5}$cycloalkyl and $C_{1-6}$alkyl, wherein said $C_{3-5}$cycloalkyl and $C_{1-6}$alkyl are optionally substituted with one to three $R^{10}$; $R^{10}$ in each occurrence is independently selected from halo and $C_{1-6}$alkyl, wherein $C_{1-6}$alkyl is optionally substituted with one to three halo; and the definitions for the other variables are as defined in the first, second, third, fourth, fifth, sixth or seventh embodiment. In a specific embodiment, $R^1$ in each occurrence is independently tert-butyl, cyclopropyl or fluoro, wherein tert-butyl and cyclopropyl are optionally substituted with one to three fluoro, methyl, —$CH_2F$, —$CHF_2$ or —$CF_3$.

In an eleventh embodiment of the present invention, the compound is represented by formula (I), (II), or (II'), or a pharmaceutically acceptable salt thereof, wherein Ring A is represented by the following formula:

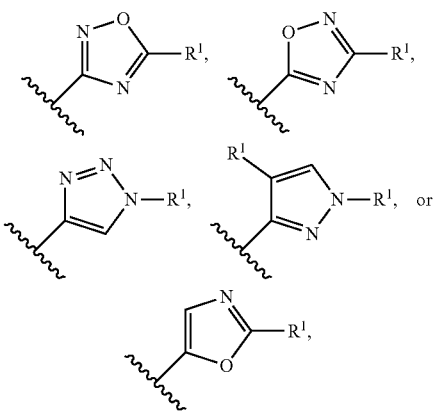

wherein $R^1$ in each occurrence is independently selected from halo and $C_{1-6}$alkyl; and the definitions for the other variables are as defined in the first, second, third, fourth, fifth, sixth or seventh, embodiment. In a specific embodiment, $R^1$ in each occurrence is independently tert-butyl or fluoro.

In a twelfth embodiment of the present invention, the compound is represented by formula (I), (II), or (II'), or a pharmaceutically acceptable salt thereof; wherein Ring B is represented by the following formula:

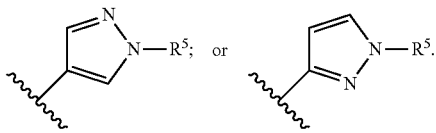

and the definitions for the variables are as defined in the first, second, third, fourth, fifth, sixth, seventh, eighth, ninth, tenth or eleventh embodiment.

In a thirteenth embodiment of the present invention, the compound is represented by formula (I), (II), or (II'), or a pharmaceutically acceptable salt thereof, wherein $R^5$ is $C_{1-4}$alkyl optionally substituted with one to three fluoro; and the definitions for the other variables are as defined in the first, second, third, fourth, fifth, sixth, seventh, eighth, ninth, tenth, eleventh or twelfth embodiment.

In a specific embodiment, $R^5$ is methyl.

In a fourteenth embodiment of the present invention, the compounds is represented by formula (I), (II), or (II'), or a pharmaceutically acceptable salt thereof, wherein $R^4$ is H, halo or $C_{1-3}$alkyl; and the definitions for the other variables are as defined in the first, second, third, fourth, fifth, sixth, seventh, eighth, ninth, tenth, eleventh, twelfth or thirteenth embodiment. In a specific embodiment, $R^4$ is H or F. In a specific embodiment, $R^4$ is H, Cl, F or methyl.

In a fifteenth embodiment of the present invention, the compound is represented by formula (I), (II), or (II'), or a pharmaceutically acceptable salt thereof, wherein $R^2$ is H or $C_{1-3}$alkyl; and the definitions for the other variables are as defined in the first, second, third, fourth, fifth, sixth, seventh, eighth, ninth, tenth, eleventh, twelfth, thirteenth or fourteenth embodiment. In a specific embodiment, $R^2$ is H or methyl.

In aسixteenth embodiment of the present invention, the compound is represented by formula (I), (II), or (II') or a pharmaceutically acceptable salt thereof, wherein $R^2$ is H; and the definitions for the other variables are as defined in the first, second, third, fourth, fifth, sixth, seventh, eighth, ninth, tenth, eleventh, twelfth, thirteenth or fourteenth embodiment.

In a seventeenth embodiment of the present invention, the compound is represented by formula (I), (II), or (II'), or a pharmaceutically acceptable salt thereof, wherein $R^3$ is halo, $C_{3-5}$cycloalkyl or $C_{1-4}$alkyl, wherein said $C_{1-4}$alkyl and $C_{3-5}$alkyl are each optionally substituted with one to three fluoro; and the definitions for the other variables are as defined in the first, second, third, fourth, fifth, sixth, seventh, eighth, ninth, tenth, eleventh, twelfth, thirteenth, fourteenth, fifteenth or sixteenth embodiment. In a specific embodiment, $R^3$ is —$CH_3$, cyclopropyl, —Cl, —$CH_2CHF_2$, —$CHF_2$ or —$CF_3$.

In an eighteenth embodiment of the present invention, the compound is represented by formula (I), (II), or (II'), or a pharmaceutically acceptable salt thereof, wherein $R^3$ is halo or $C_{1-4}$alkyl, wherein said $C_{1-4}$alkyl is optionally substituted with one to three fluoro; and the definitions for the other variables are as defined in the first, second, third, fourth, fifth,سixth, seventh, eighth, ninth, tenth, eleventh, twelfth, thirteenth, fourteenth, fifteenth or sixteenth embodiment. In a specific embodiment, $R^3$ is —$CH_3$, —Cl, or —$CF_3$.

In a nineteenth embodiment of the present invention, the compound is represented by formula (IIIA), (IIIB). (IIIA') or (IIIB'):

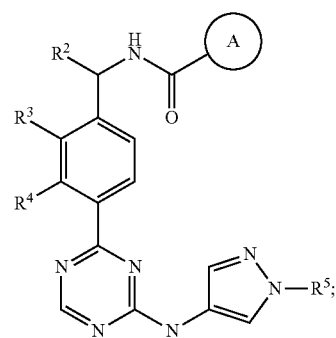

(IIIA)

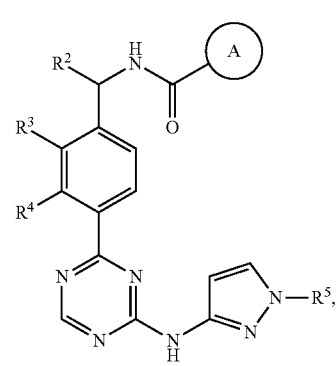

(IIIB)

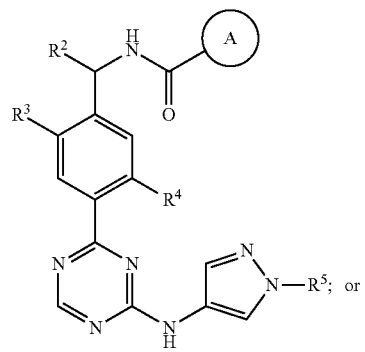

(IIIA')

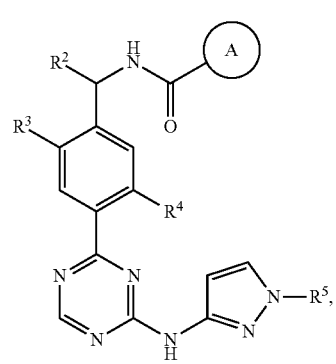

(IIIB')

or a pharmaceutically acceptable salt thereof, wherein:
ring A is represented by the following formula:

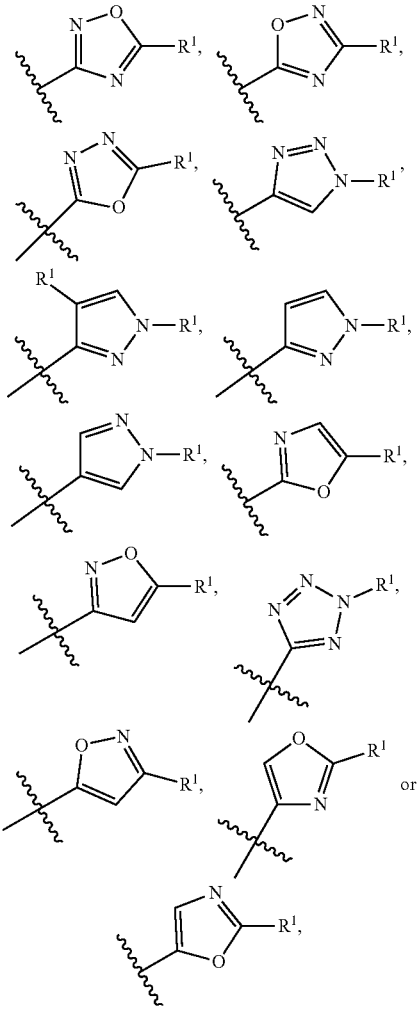

R$^1$ in each occurrence is independently selected from halo, C$_{3-5}$cycloalkyl and C$_{1-6}$alkyl, wherein said C$_{3-5}$cycloalkyl and C$_{1-6}$alkyl are optionally substituted with one to three R$^{10}$; R$^{10}$ in each occurrence is independently selected from halo or C$_{1-6}$alkyl, wherein said C$_{1-6}$alkyl is optionally substituted with one to three halo;

R$^3$ is halo, C$_{3-5}$cycloalkyl or C$_{1-4}$alkyl, wherein said C$_{1-4}$alkyl and C$_{3-5}$cycloalkyl are optionally substituted with one to three fluoro;

R$^4$ is H, C$_{1-4}$alkyl or halo; and

R$^5$ is C$_{1-4}$alkyl; and the definitions for the other variables are as defined in the first embodiment.

In a twentieth embodiment of the present invention, the compound is represented by formula (IIIA), (IIIB), (IIIA') or (IIIB'), or a pharmaceutically acceptable salt thereof, wherein R$^1$ in each occurrence is independently F, 1-methylcyclopropyl, 1-fluoro-2-methylpropan-2-yl, 1-(trifluoromethyl)cyclopropyl, 1-(fluoromethyl)cyclopropyl, 2,3-dimethylcyclopropyl, or tert-butyl; R$^3$ is —CH$_3$, cyclopropyl, —Cl, —CH$_2$CHF$_2$, —CHF$_2$ or —CF$_3$; R$^4$ is H, Cl, F or methyl; and R$^5$ is methyl; and the definitions for the other variables are as defined in the nineteenth embodiment.

In a twenty-first embodiment of the present invention, the compound is represented by formula (IIIA) or (IIIB):

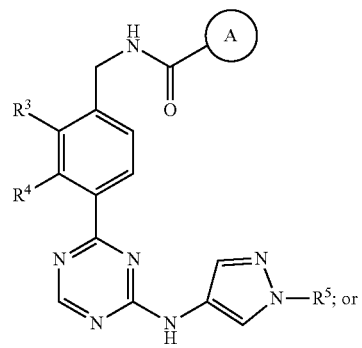
(IIIA)

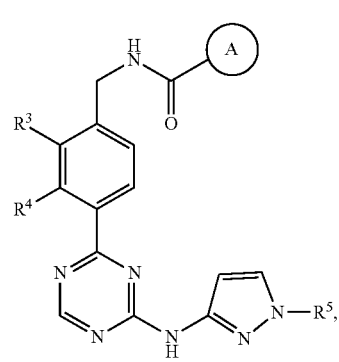
(IIIB)

or a pharmaceutically acceptable salt thereof, wherein:
ring A is represented by the following formula:

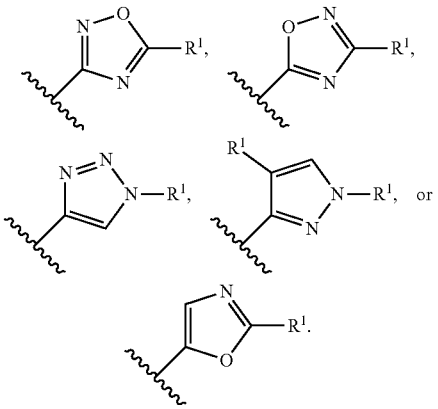

R$^1$ in each occurrence is independently selected from halo and C$_{1-6}$alkyl;

R$^3$ is halo or C$_{1-4}$alkyl, wherein said C$_{1-4}$alkyl is optionally substituted with one to three fluoro;

R$^4$ is H or halo; and

R$^5$ is C$_{1-4}$alkyl; and the definitions for the other variables are as defined in the first embodiment.

In a twenty-second embodiment of the present invention, the compound is represented by formula (IIIA) or (IIIB), or a pharmaceutically acceptable salt thereof, wherein R$^1$ in each occurrence is independently F or tert-butyl; R$^3$ is —CH$_3$, —Cl or —CF$_3$; R$^4$ is H or F; and R$^5$ is methyl; and the definitions for the other variables are as defined in the twenty-first embodiment.

In a twenty-third embodiment of the present invention, the compound is represented by formula (IV), (V), (VI), (VII), (VIII), (IVA), (IVB), (VA), (VB), (VIA), (VIB), (VIIA), (VIIB), (VIIIA), (VIIIB), (IV'), (V'), (VI'), (VII'), (IVA'), (IVB'), (VA'), (VB'), (VIA'), (VIB'), (VIIA'), (VIIB'), (VIIIA') or (VIIIB'):
(IV)
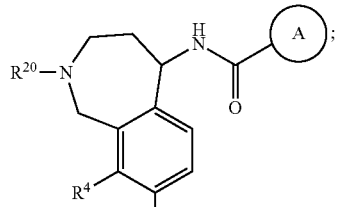
(V)
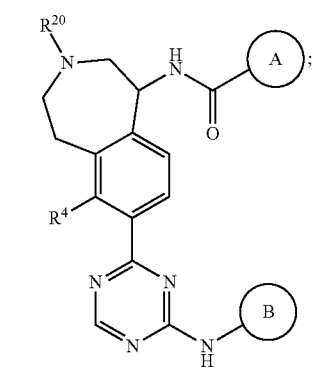
(VI)
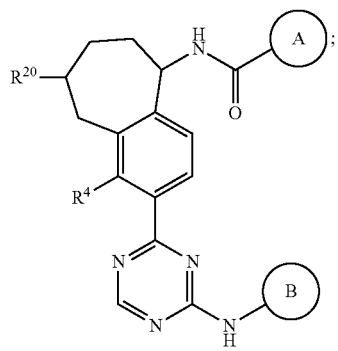
(VII)
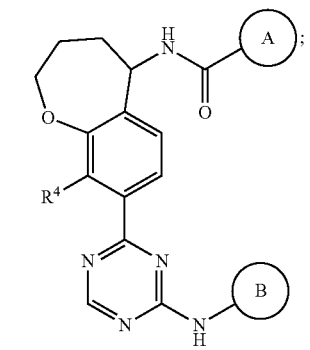
-continued
(VIII)
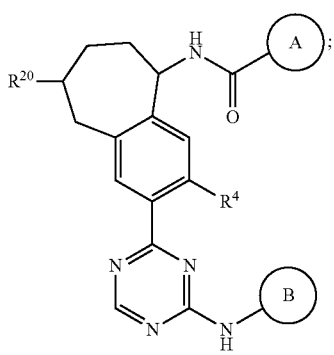
(IVA)
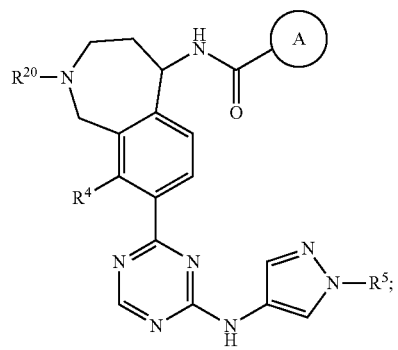
(IVB)
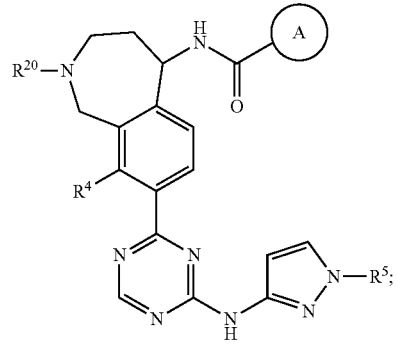
(VA)

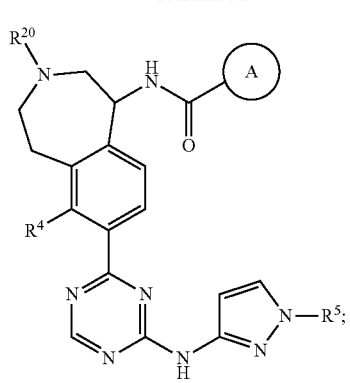 (VB)
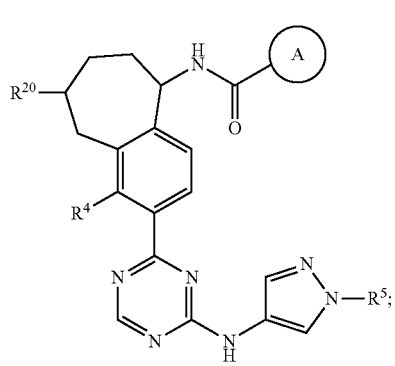 (VIA)
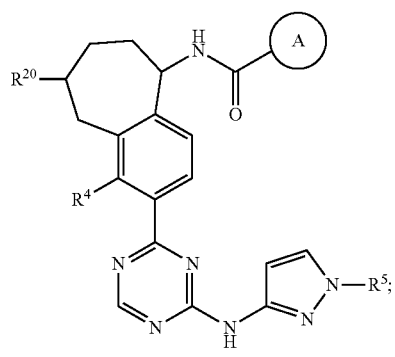 (VIB)
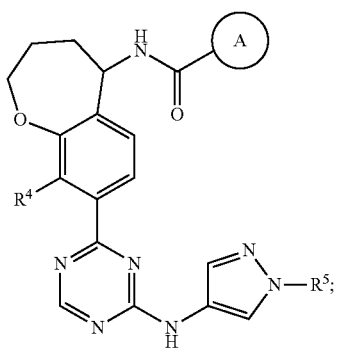 (VIIA)
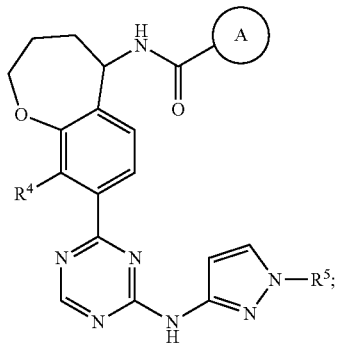 (VIIB)
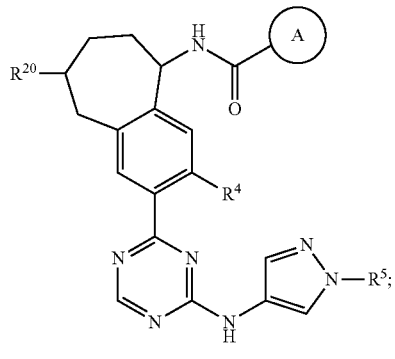 (VIIIA)
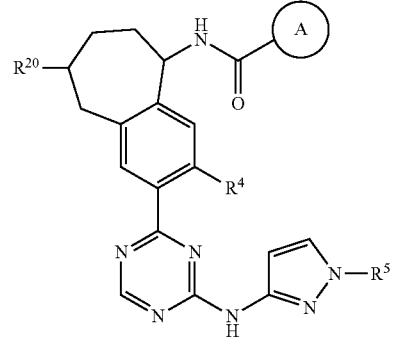 (VIIIB)
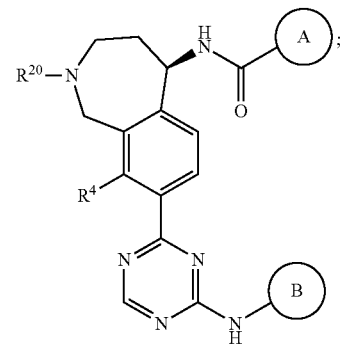 (IV′)

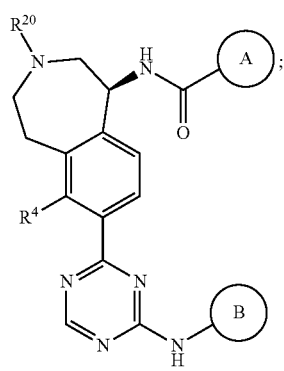
(V′)
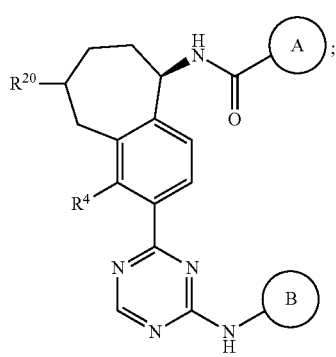
(VI′)
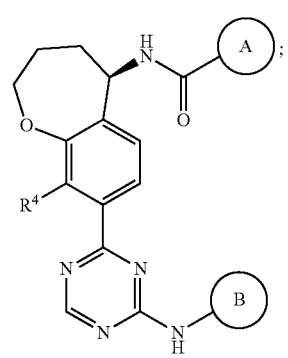
(VII′)
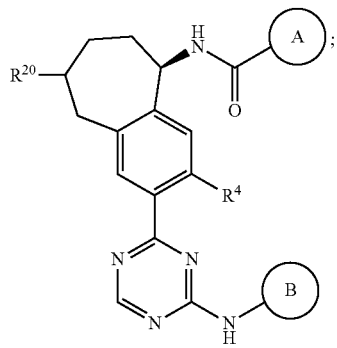
(VIII′)
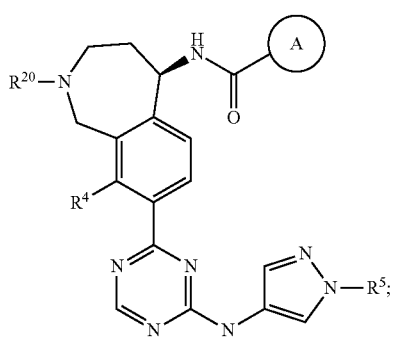
(IVA′)
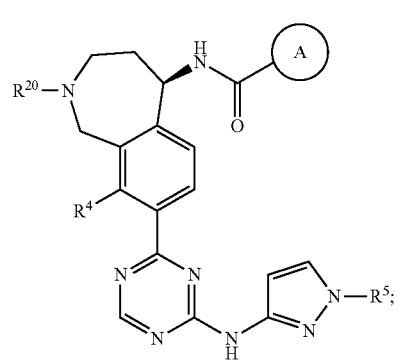
(IVB′)
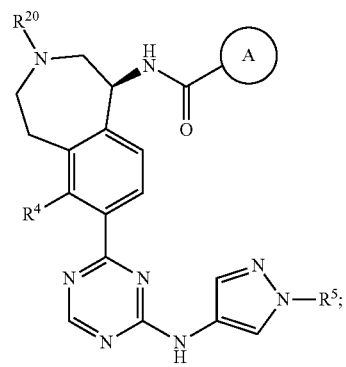
(VA′)
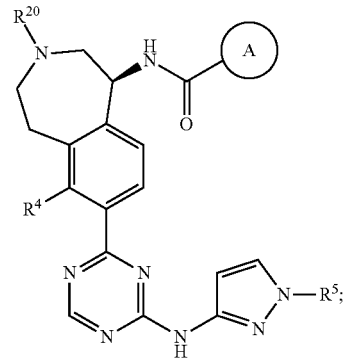
(VB′)

-continued

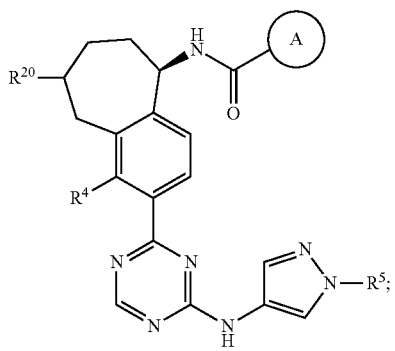
(VIA')

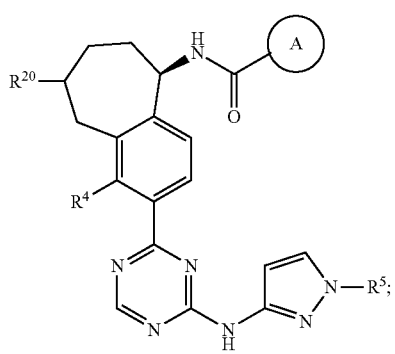
(VIB')

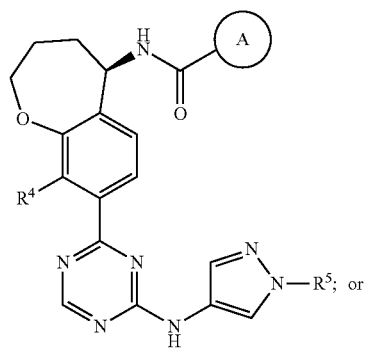
(VIIA')

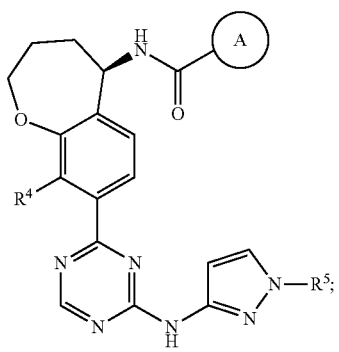
(VIIB')

-continued

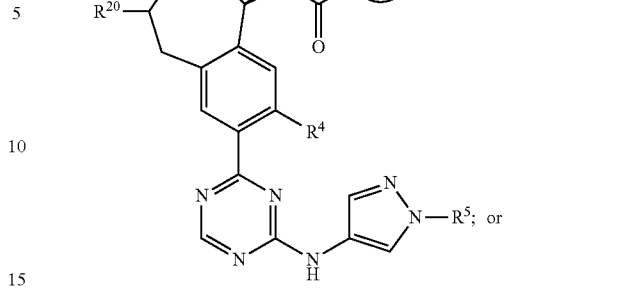
(VIIIA')

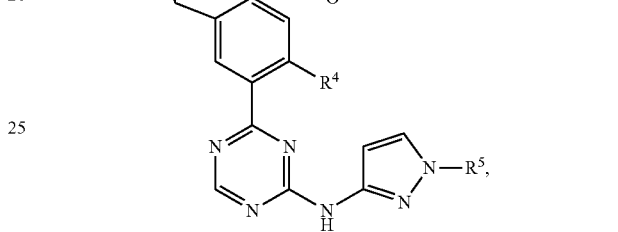
(VIIIB')

or a pharmaceutically acceptable salt thereof, wherein the definitions for the variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first or twenty-second embodiment or any specific embodiments described therein. In a twenty-fourth embodiment, the compound is represented by formula (IV), (V), (IVA), (IVB), (VA), (VB), (IV'), (V'), (IVA'), (IVB'), (VA') or (VB'), or a pharmaceutically acceptable salt thereof, wherein:

$R^{20}$ is selected from H, $C_{1-6}$alkyl, $C_{4-6}$cycloalkyl, saturated 4- to 6-membered monocyclic heterocyclyl, —C(O)$R^{20a}$, —C(O)$_2R^{20a}$, and —S(O)$_2R^{20a}$, wherein said $C_{1-6}$alkyl, $C_{4-6}$cycloalkyl, and saturated 4- to 6-membered monocyclic heterocyclyl are optionally substituted with one to three $R^{25}$;

$R^{20a}$ in each occurrence is independently selected from H, $C_{1-6}$alkyl, $C_{3-6}$cycloalkyl, and saturated 4- to 6-membered monocyclic heterocyclyl, wherein said $C_{1-6}$alkyl, $C_{3-6}$cycloalkyl, and saturated 4- to 6-membered monocyclic heterocyclyl in each occurrence are optionally and independently substituted with one or more $R^{25}$;

$R^{25}$ in each occurrence is independently selected from $C_{1-6}$alkyl, $C_{3-6}$cycloalkyl, saturated 4- to 6-membered monocyclic heterocyclyl, halo, —CN, —N($R^{25a}$)$_2$, and —O$R^{25a}$; and $R^{25a}$ in each occurrence is independently H or $C_{1-6}$alkyl; and the definitions for the other variables are as defined in the first, second, third, fourth, fifth, sixth, seventh, eighth, ninth, tenth, eleventh, tenth, eleventh, twelfth, thirteenth, fourteenth, fifteenth, sixteenth, seventeenth, eighteenth, nineteenth, twentieth, twenty-first or twenty-second embodiment.

In a twenty-fifth embodiment, the compound is represented by formula (IV), (V), (IVA), (IVB), (VA), (VB), (IV'), (V'), (IVA'), (IVB'), (VA') or (VB'), or a pharmaceutically acceptable salt thereof, wherein:

$R^{20}$ is selected from H, $C_{1-6}$alkyl, $C_{4-6}$cycloalkyl, saturated 4- to 6-membered monocyclic heterocyclyl, —C(O)$R^{20a}$, —C(O)$_2R^{20a}$, and —S(O)$_2R^{20a}$, wherein said $C_{1-6}$alkyl, $C_{4-6}$cycloalkyl, and saturated 4- to 6-membered monocyclic heterocyclyl are optionally substituted with one to three $R^{25}$;

$R^{20a}$ in each occurrence is independently selected from H, $C_{1-6}$alkyl, $C_{2-6}$alkenyl, $C_{2-6}$alkynyl, $C_{3-6}$cycloalkyl, and saturated 4- to 6-membered monocyclic heterocyclyl, wherein said $C_{1-6}$alkyl, $C_{3-6}$cycloalkyl, and saturated 4- to 6-membered monocyclic heterocyclyl in each occurrence are optionally and independently substituted with one or more $R^{25}$;

$R^{25}$ in each occurrence is independently selected from $C_{1-6}$alkyl, $C_{3-6}$cycloalkyl, saturated 4- to 6-membered monocyclic heterocyclyl, halo, —CN, —N($R^{25a}$)$_2$, and —O$R^{25a}$; and $R^{25a}$ in each occurrence is independently H or $C_{1-6}$alkyl; and the definitions for the other variables are as defined in the first, second, third, fourth, fifth, sixth, seventh, eighth, ninth, tenth, eleventh, tenth, eleventh, twelfth, thirteenth, fourteenth, fifteenth, sixteenth, seventeenth, eighteenth, nineteenth, twentieth, twenty-first or twenty-second embodiment.

In a twenty-sixth embodiment of the present invention, the compound is represented by formula (IV), (V), (IVA), (IVB), (VA), (VB), (IV'), (V'), (IVA'), (IVB'), (VA') or (VB'), or a pharmaceutically acceptable salt thereof, wherein:

$R^{20}$ is $C_{1-6}$alkyl or saturated 4- to 6-membered monocyclic heterocyclyl, wherein said $C_{1-6}$alkyl and saturated 4- to 6-membered monocyclic heterocyclyl are optionally substituted with one to three $R^{25}$;

$R^{25}$ in each occurrence is independently halo; and the definitions for the other variables are as defined in the twenty-fourth embodiment.

In a twenty-seventh embodiment of the present invention, the compound is represented by formula (IV), (V), (IVA), (IVB), (VA), (VB), (IV'), (V'), (IVA'), (IVB'), (VA') or (VB'), or a pharmaceutically acceptable salt thereof, wherein $R^{20}$ is $C_{1-6}$alkyl or saturated 4- to 6-membered monocyclic heterocyclyl selected from azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, and dioxinyl, wherein aid $C_{1-6}$alkyl is optionally substituted with one to three halo; and the definitions for the other variables are as defined in the twenty-sixth embodiment. In a more specific embodiment, $R^{20}$ is —CH$_3$,

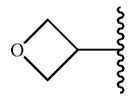

or —CH$_2$CF$_3$. In another specific embodiment, $R^{20}$ is

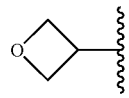

or —CH$_2$CF$_3$.

In a twenty-eighth embodiment of the present invention, the compound is represented by formula (VI), (VIII), (VIA), (VIB), (VIIIA), (VIIIB), (VI'), (VIII'), (VIA'), (VIB'), (VIIIA'), (VIIIB'), or a pharmaceutically acceptable salt thereof, wherein:

$R^{20}$ is selected from H, $C_{1-6}$alkyl, $C_{3-6}$cycloalkyl, saturated 4- to 6-membered monocyclic heterocyclyl, halo, —O$R^{20a}$, —OC(O)$R^{20a}$, —OC(O)N($R^{20a}$)$_2$, and —S$R^{20a}$, wherein said $C_{1-6}$alkyl, $C_{3-6}$cycloalkyl, and saturated 4- to 6-membered monocyclic heterocyclyl are optionally substituted with one to three $R^{25}$;

$R^{20a}$ in each occurrence is independently H or $C_{1-6}$alkyl, wherein said $C_{1-6}$alkyl in each occurrence is optionally and independently substituted with one $R^{25}$;

$R^{25}$ in each occurrence is independently selected from $C_{1-6}$alkyl; and the definitions for the other variables are as defined in the first, second, third, fourth, fifth, sixth, seventh, eighth, ninth, tenth, eleventh, tenth, eleventh, twelfth, thirteenth, fourteenth, fifteenth, sixteenth, seventeenth, eighteenth, nineteenth, twentieth, twenty-first or twenty-second embodiment.

In a twenty-ninth embodiment of the present invention, the compound is represented by formula (VI), (VIII), (VIA), (VIB), (VIIIA), (VIIIB), (VI'), (VIII'), (VIA'), (VIB'), (VIIIA'), (VIIIB'), or a pharmaceutically acceptable salt thereof, wherein $R^{20}$ is H; and the definitions for the other variables are as defined in the twenty-eighth embodiment.

In a thirtieth embodiment of the present invention, the compound is represented by the following formula:

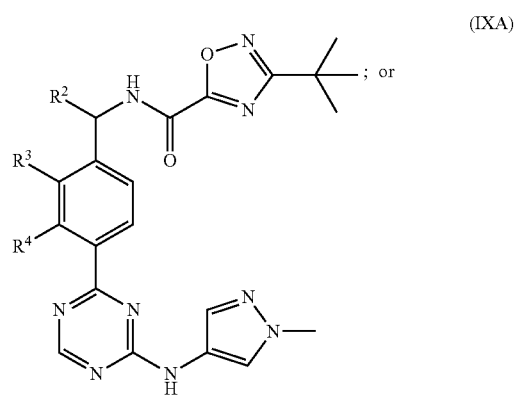

(IXA)

; or

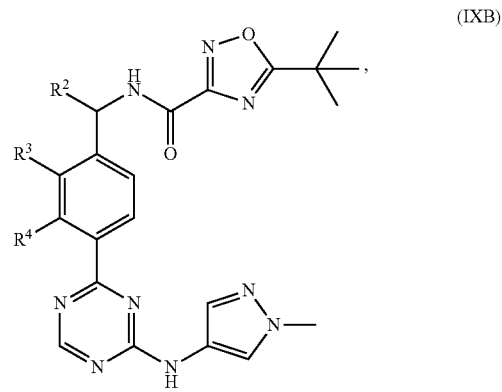

(IXB)

,

-continued

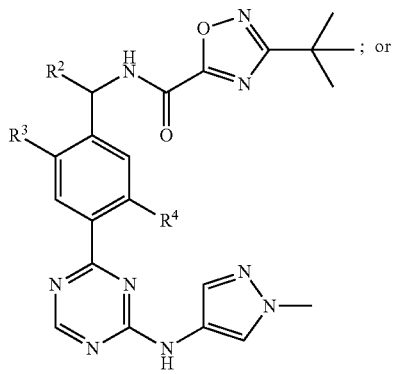
(IXC)

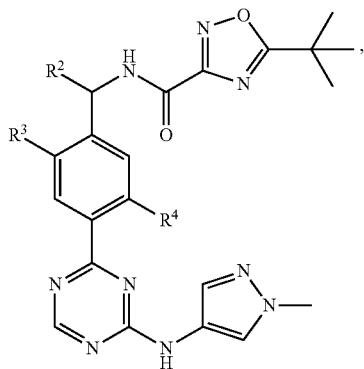
(IXD)

or a pharmaceutically acceptable salt thereof, wherein:

$R^2$ is H or $C_{1-4}$alkyl;

$R^3$ is halo or $C_{1-4}$alkyl, wherein said $C_{1-4}$alkyl is optionally substituted with one to three fluoro;

or $R^2$ and $R^3$, together with their intervening atoms, form a seven-membered carbocyclic or heterocyclic ring, wherein said seven-membered carbocyclic or heterocyclic ring is optionally substituted with one or more $R^{20}$;

$R^{20}$ is H or $C_{1-6}$alkyl optionally substituted with one to three $R^{25}$;

$R^{25}$ is halo; and $R^4$ is H or halo.

In a more specific embodiment, for compounds of formula (IXA), (IXB), (IXC) or (IXD) or a pharmaceutically acceptable salt thereof, $R^2$ is H or methyl; $R^3$ is Cl or methyl; and $R^4$ is H, F or Cl; and the remaining variables are as defined in the thirtieth embodiment.

In a thirty-first embodiment of the present invention, the compound is represented by the following formula:

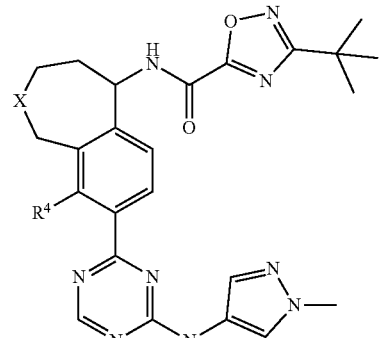
(IXA')

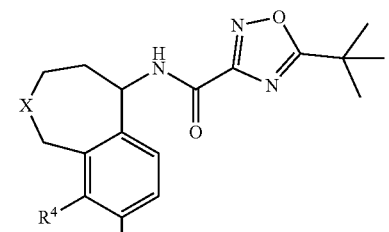
(IXB')

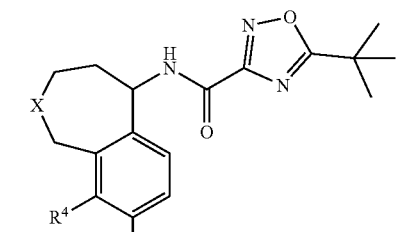
(IXC')

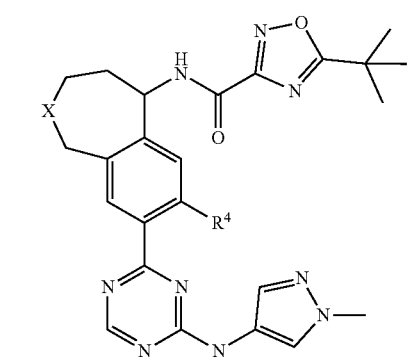
(IXD')

or a pharmaceutically acceptable salt thereof, wherein:

X is CH or $NR^{20}$;

$R^{20}$ is H or $C_{1-3}$alkyl optionally substituted with one to three halo; and $R^4$ is H or halo.

In a specific embodiment, for compounds of formula (IXA'), (IXB'), (IXC') or (IXD') or a pharmaceutically acceptable salt thereof, $R^{20}$ is —$CH_2CF_3$; $R^4$ is H, F or Cl; and the remaining variables are as defined in the thirty-first embodiment.

In a thirty-second embodiment of the present invention, the compound of the present invention is selected from:

5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide;

3-(tert-butyl)-N-(2-methyl-4-(4-((1-methyl-1H-pyrazol-3-yl)amino)-1,3,5-triazin-2-yl)benzyl)-1,2,4-oxadiazole-5-carboxamide;

2-(tert-butyl)-N-(2-methyl-4-(4-((1-methyl-1H-pyrazol-3-yl)amino)-1,3,5-triazin-2-yl)benzyl)oxazole-5-carboxamide;

1-(tert-butyl)-4-fluoro-N-(2-methyl-4-(4-((1-methyl-1H-pyrazol-3-yl)amino)-1,3,5-triazin-2-yl)benzyl)-1H-pyrazole-3-carboxamide;

5-(tert-butyl)-N-(2-chloro-4-(4-((1-methyl-1H-pyrazol-3-yl)amino)-1,3,5-triazin-2-yl)benzyl)-1,2,4-oxadiazole-3-carboxamide;

3-(tert-butyl)-N-(2-chloro-4-(4-((1-methyl-1H-pyrazol-3-yl)amino)-1,3,5-triazin-2-yl)benzyl)-1,2,4-oxadiazole-5-carboxamide;

5-(tert-butyl)-N-(4-(4-((1-methyl-1H-pyrazol-3-yl)amino)-1,3,5-triazin-2-yl)-2-(trifluoromethyl)benzyl)-1,2,4-oxadiazole-3-carboxamide;

3-(tert-butyl)-N-(4-(4-((1-methyl-1H-pyrazol-3-yl)amino)-1,3,5-triazin-2-yl)-2-(trifluoromethyl)benzyl)-1,2,4-oxadiazole-5-carboxamide;

5-(tert-butyl)-N-(3-fluoro-2-methyl-4-(4-((1-methyl-1H-pyrazol-3-yl)amino)-1,3,5-triazin-2-yl)benzyl)-1,2,4-oxadiazole-3-carboxamide;

3-(tert-butyl)-N-(3-fluoro-2-methyl-4-(4-((1-methyl-1H-pyrazol-3-yl)amino)-1,3,5-triazin-2-yl)benzyl)-1,2,4-oxadiazole-5-carboxamide;

5-(tert-butyl)-N-(2-methyl-4-(4-((1-methyl-1H-pyrazol-4-yl)amino)-1,3,5-triazin-2-yl)benzyl)-1,2,4-oxadiazole-3-carboxamide;

3-(tert-butyl)-N-(2-methyl-4-(4-((1-methyl-1H-pyrazol-4-yl)amino)-1,3,5-triazin-2-yl)benzyl)-1,2,4-oxadiazole-5-carboxamide;

5-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-3-carboxamide;

3-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-5-carboxamide;

5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide;

3-(tert-butyl)-N-(2-chloro-4-(4-((1-methyl-1H-pyrazol-4-yl)amino)-1,3,5-triazin-2-yl)benzyl)-1,2,4-oxadiazole-5-carboxamide;

5-(tert-butyl)-N-(4-(4-((1-methyl-1H-pyrazol-4-yl)amino)-1,3,5-triazin-2-yl)-2-(trifluoromethyl)benzyl)-1,2,4-oxadiazole-3-carboxamide;

3-(tert-butyl)-N-(4-(4-((1-methyl-1H-pyrazol-4-yl)amino)-1,3,5-triazin-2-yl)-2-(trifluoromethyl)benzyl)-1,2,4-oxadiazole-5-carboxamide;

5-(tert-butyl)-N-(3-fluoro-4-(4-((1-methyl-1H-pyrazol-3-yl)amino)-1,3,5-triazin-2-yl)-2-(trifluoromethyl)benzyl)-1,2,4-oxadiazole-3-carboxamide;

3-(tert-butyl)-N-(3-fluoro-4-(4-((1-methyl-1H-pyrazol-3-yl)amino)-1,3,5-triazin-2-yl)-2-(trifluoromethyl)benzyl)-1,2,4-oxadiazole-5-carboxamide;

5-(tert-butyl)-N-(2-chloro-3-fluoro-4-(4-((1-methyl-1H-pyrazol-3-yl)amino)-1,3,5-triazin-2-yl)benzyl)-1,2,4-oxadiazole-3-carboxamide;

3-(tert-butyl)-N-(2-chloro-3-fluoro-4-(4-((1-methyl-1H-pyrazol-3-yl)amino)-1,3,5-triazin-2-yl)benzyl)-1,2,4-oxadiazole-5-carboxamide;

5-tert-butyl-N-[2-[4-[(1-methylpyrazol-3-yl)amino]-1,3,5-triazin-2-yl]-6,7,8,9-tetrahydro-5H-benzo[7]annulen-5-yl]-1,2,4-oxadiazole-3-carboxamide;

5-tert-butyl-N-[(5R)-2-[4-[(1-methylpyrazol-3-yl)amino]-1,3,5-triazin-2-yl]-6,7,8,9-tetrahydro-5H-benzo[7]annulen-5-yl]-1,2,4-oxadiazole-3-carboxamide;

5-tert-butyl-N-[(5S)-2-[4-[(1-methylpyrazol-3-yl)amino]-1,3,5-triazin-2-yl]-6,7,8,9-tetrahydro-5H-benzo[7]annulen-5-yl]-1,2,4-oxadiazole-3-carboxamide;

1-tert-butyl-N-[8-[4-[(1-methylpyrazol-4-yl)amino]-1,3,5-triazin-2-yl]-2-(oxetan-3-yl)-1,3,4,5-tetrahydro-2-benzazepin-5-yl]triazole-4-carboxamide;

1-tert-butyl-N-[(5R)-8-[4-[(1-methylpyrazol-4-yl)amino]-1,3,5-triazin-2-yl]-2-(oxetan-3-yl)-1,3,4,5-tetrahydro-2-benzazepin-5-yl]triazole-4-carboxamide;

1-tert-butyl-N-[(5S)-8-[4-[(1-methylpyrazol-4-yl)amino]-1,3,5-triazin-2-yl]-2-(oxetan-3-yl)-1,3,4,5-tetrahydro-2-benzazepin-5-yl]triazole-4-carboxamide;

5-tert-butyl-N-[8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide;

5-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide;

5-tert-butyl-N-[(5S)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide;

3-tert-butyl-N-[8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide;

3-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide;

3-tert-butyl-N-[(5S)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide; and 1-(tert-butyl)-4-fluoro-N-(3-fluoro-2-methyl-4-(4-((1-methyl-1H-pyrazol-4-yl)amino)-1,3,5-triazin-2-yl)benzyl)-1H-pyrazole-3-carboxamide:

5-(tert-butyl)-N-(2-chloro-3-fluoro-4-(4-((1-methyl-1H-pyrazol-4-yl)amino)-1,3,5-triazin-2-yl)benzyl)-1,2,4-oxadiazole-3-carboxamide;

3-(tert-butyl)-N-(2-chloro-3-fluoro-4-(4-((1-methyl-1H-pyrazol-4-yl)amino)-1,3,5-triazin-2-yl)benzyl)-1,2,4-oxadiazole-5-carboxamide;

N-(2-chloro-3-fluoro-4-(4-((1-methyl-1H-pyrazol-4-yl)amino)-1,3,5-triazin-2-yl)benzyl)-5-(1-methylcyclopropyl)-1,2,4-oxadiazole-3-carboxamide;

5-(tert-butyl)-N-(3-fluoro-2-methyl-4-(4-((1-methyl-1H-pyrazol-4-yl)amino)-1,3,5-triazin-2-yl)benzyl)oxazole-2-carboxamide N-(3-fluoro-2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide;

5-tert-butyl-N-[2-[4-[(1-methylpyrazol-4-yl)amino]-1,3,5-triazin-2-yl]-6,7,8,9-tetrahydro-5H-benzo[7]annulen-5-yl]-1,2,4-oxadiazole-3-carboxamide;

5-tert-butyl-N-[(5R)-2-[4-[(1-methylpyrazol-4-yl)amino]-1,
3,5-triazin-2-yl]-6,7,8,9-tetrahydro-5H-benzo[7]annulen-
5-yl]-1,2,4-oxadiazole-3-carboxamide;
5-tert-butyl-N-[(5S)-2-[4-[(1-methylpyrazol-4-yl)amino]-1,
3,5-triazin-2-yl]-6,7,8,9-tetrahydro-5H-benzo[7]annulen-
5-yl]-1,2,4-oxadiazole-3-carboxamide;
3-tert-butyl-N-[2-[4-[(1-methylpyrazol-4-yl)amino]-1,3,5-
triazin-2-yl]-6,7,8,9-tetrahydro-5H-benzo[7]annulen-5-
yl]-1,2,4-oxadiazole-5-carboxamide;
3-tert-butyl-N-[(5R)-2-[4-[(1-methylpyrazol-4-yl)amino]-1,
3,5-triazin-2-yl]-6,7,8,9-tetrahydro-5H-benzo[7]annulen-
5-yl]-1,2,4-oxadiazole-5-carboxamide;
3-tert-butyl-N-[(5S)-2-[4-[(1-methylpyrazol-4-yl)amino]-1,
3,5-triazin-2-yl]-6,7,8,9-tetrahydro-5H-benzo[7]annulen-
5-yl]-1,2,4-oxadiazole-5-carboxamide;
2-tert-butyl-N-[2-[4-[(1-methylpyrazol-4-yl)amino]-1,3,5-
triazin-2-yl]-6,7,8,9-tetrahydro-5H-benzo[7]annulen-5-
yl]-oxazole-5-carboxamide;
2-tert-butyl-N-[(5R)-2-[4-[(1-methylpyrazol-4-yl)amino]-1,
3,5-triazin-2-yl]-6,7,8,9-tetrahydro-5H-benzo[7]annulen-
5-yl]-oxazole-5-carboxamide;
2-tert-butyl-N-[(5S)-2-[4-[(1-methylpyrazol-4-yl)amino]-1,
3,5-triazin-2-yl]-6,7,8,9-tetrahydro-5H-benzo[7]annulen-
5-yl]-oxazole-5-carboxamide;
1-(tert-butyl)-N-(3-fluoro-2-methyl-4-(4-((1-methyl-1H-
pyrazol-4-yl)amino)-1,3,5-triazin-2-yl)benzyl)-1H-pyra-
zole-4-carboxamide;
1-(tert-butyl)-N-(2-methyl-4-(4-((1-methyl-1H-pyrazol-4-
yl)amino)-1,3,5-triazin-2-yl)benzyl)-1H-pyrazole-4-car-
boxamide;
5-tert-butyl-N-((2-methyl-4-(4-((1-methylpyrazol-4-yl)
amino)-1,3,5-triazine-2-yl))phenyl)methyl)isoxazole-3-
carboxamide;
2-(tert-butyl)-N-(2-methyl-4-(4-((1-methyl-1H-pyrazol-4-
yl)amino)-1,3,5-triazin-2-yl)benzyl)-2H-tetrazole-5-car-
boxamide;
N-(2-methyl-4-(4-((1-methyl-1H-pyrazol-4-yl)amino)-1,3,
5-triazin-2-yl)benzyl)-5-(1-methylcyclopropyl)-1,2,4-
oxadiazole-3-carboxamide;
5-(2,3-dimethylcyclopropyl)-N-(2-methyl-4-(4-((1-methyl-
1H-pyrazol-4-yl)amino)-1,3,5-triazin-2-yl)benzyl)-1,2,4-
oxadiazole-3-carboxamide;
5-(2,3-cis-dimethylcyclopropyl)-N-(2-methyl-4-(4-((1-
methyl-1H-pyrazol-4-yl)amino)-1,3,5-triazin-2-yl)ben-
zyl)-1,2,4-oxadiazole-3-carboxamide;
5-(2,3-trans-dimethylcyclopropyl)-N-(2-methyl-4-(4-((1-
methyl-1H-pyrazol-4-yl)amino)-1,3,5-triazin-2-yl)ben-
zyl)-1,2,4-oxadiazole-3-carboxamide;
5-(tert-butyl)-N-(2-methyl-4-(4-((1-methyl-1H-pyrazol-3-
yl)amino)-1,3,5-triazin-2-yl)benzyl)isoxazole-3-carbox-
amide;
3-(tert-butyl)-N-(2-methyl-4-(4-((1-methyl-1H-pyrazol-3-
yl)amino)-1,3,5-triazin-2-yl)benzyl)isoxazole-5-carbox-
amide;
5-(1-fluoro-2-methylpropan-2-yl)-N-(2-methyl-4-(4-((1-
methyl-1H-pyrazol-3-yl)amino)-1,3,5-triazin-2-yl)ben-
zyl)-1,2,4-oxadiazole-3-carboxamide;
N-(3-fluoro-2-methyl-4-(4-((1-methyl-1H-pyrazol-3-yl)
amino)-1,3,5-triazin-2-yl)benzyl)-5-(1-fluoro-2-methyl-
propan-2-yl)-1,2,4-oxadiazole-3-carboxamide;
N-(3-fluoro-2-methyl-4-(4-((1-methyl-1H-pyrazol-3-yl)
amino)-1,3,5-triazin-2-yl)benzyl)-3-(1-(fluoromethyl)cy-
clopropyl)-1,2,4-oxadiazole-5-carboxamide;
N-(3-fluoro-2-methyl-4-(4-((1-methyl-1H-pyrazol-4-yl)
amino)-1,3,5-triazin-2-yl)benzyl)-3-(1-(fluoromethyl)cy-
clopropyl)-1,2,4-oxadiazole-5-carboxamide;
3-(1-(fluoromethyl)cyclopropyl)-N-(2-methyl-4-(4-((1-
methyl-1H-pyrazol-4-yl)amino)-1,3,5-triazin-2-yl)ben-
zyl)-1,2,4-oxadiazole-5-carboxamide;
5-(1-(fluoromethyl)cyclopropyl)-N-(2-methyl-4-(4-((1-
methyl-1H-pyrazol-4-yl)amino)-1,3,5-triazin-2-yl)ben-
zyl)-1,2,4-oxadiazole-3-carboxamide;
N-(3-fluoro-2-methyl-4-(4-((1-methyl-1H-pyrazol-4-yl)
amino)-1,3,5-triazin-2-yl)benzyl)-5-(1-(fluoromethyl)cy-
clopropyl)-1,2,4-oxadiazole-3-carboxamide;
N-(5-fluoro-2-methyl-4-(4-((1-methyl-1H-pyrazol-4-yl)
amino)-1,3,5-triazin-2-yl)benzyl)-5-(1-(fluoromethyl)cy-
clopropyl)-1,2,4-oxadiazole-3-carboxamide;
N-(3-fluoro-2-methyl-4-(4-((1-methyl-1H-pyrazol-3-yl)
amino)-1,3,5-triazin-2-yl)benzyl)-5-(1-(trifluoromethyl)
cyclopropyl)-1,2,4-oxadiazole-3-carboxamide;
5-(1-fluoro-2-methylpropan-2-yl)-N-(2-(4-((1-methyl-1H-
pyrazol-3-yl)amino)-1,3,5-triazin-2-yl)-6,7,8,9-tetra-
hydro-5H-benzo[7]annulen-5-yl)-1,2,4-oxadiazole-3-car-
boxamide;
(R)-5-(1-fluoro-2-methylpropan-2-yl)-N-(2-(4-((1-methyl-
1H-pyrazol-3-yl)amino)-1,3,5-triazin-2-yl)-6,7,8,9-tetra-
hydro-5H-benzo[7]annulen-5-yl)-1,2,4-oxadiazole-3-car-
boxamide;
(S)-5-(1-fluoro-2-methylpropan-2-yl)-N-(2-(4-((1-methyl-
1H-pyrazol-3-yl)amino)-1,3,5-triazin-2-yl)-6,7,8,9-tetra-
hydro-5H-benzo[7]annulen-5-yl)-1,2,4-oxadiazole-3-car-
boxamide;
N-(2-cyclopropyl-4-(4-((1-methyl-1H-pyrazol-3-yl)amino)-
1,3,5-triazin-2-yl)benzyl)-5-(1-fluoro-2-methylpropan-2-
yl)-1,2,4-oxadiazole-3-carboxamide;
3-(tert-butyl)-N-(2-cyclopropyl-3-fluoro-4-(4-((1-methyl-
1H-pyrazol-3-yl)amino)-1,3,5-triazin-2-yl)benzyl)-1,2,4-
oxadiazole-5-carboxamide;
5-(tert-butyl)-N-(5-fluoro-2-methyl-4-(4-((1-methyl-1H-
pyrazol-4-yl)amino)-1,3,5-triazin-2-yl)benzyl)-1,2,4-
oxadiazole-3-carboxamide;
3-(tert-butyl)-N-(5-fluoro-2-methyl-4-(4-((1-methyl-1H-
pyrazol-4-yl)amino)-1,3,5-triazin-2-yl)benzyl)-1,2,4-
oxadiazole-5-carboxamide;
2-(tert-butyl)-N-(5-fluoro-2-methyl-4-(4-((1-methyl-1H-
pyrazol-4-yl)amino)-1,3,5-triazin-2-yl)benzyl)-2H-tetra-
zole-5-carboxamide;
N-(5-fluoro-2-methyl-4-(4-((1-methyl-1H-pyrazol-4-yl)
amino)-1,3,5-triazin-2-yl)benzyl)-5-(1-methylcyclopro-
pyl)-1,2,4-oxadiazole-3-carboxamide;
N-(5-fluoro-2-methyl-4-(4-((1-methyl-1H-pyrazol-4-yl)
amino)-1,3,5-triazin-2-yl)benzyl)-3-(1-(fluoromethyl)cy-
clopropyl)-1,2,4-oxadiazole-5-carboxamide;
1-(tert-butyl)-N-(5-fluoro-2-methyl-4-(4-((1-methyl-1H-
pyrazol-4-yl)amino)-1,3,5-triazin-2-yl)benzyl)-1H-pyra-
zole-4-carboxamide;
1-(tert-butyl)-N-(5-fluoro-2-methyl-4-(4-((1-methyl-1H-
pyrazol-4-yl)amino)-1,3,5-triazin-2-yl)benzyl)-1H-1,2,3-
triazole-4-carboxamide;
3-(tert-butyl)-N-(5-fluoro-2-methyl-4-(4-((1-methyl-1H-
pyrazol-4-yl)amino)-1,3,5-triazin-2-yl)benzyl)isoxazole-
5-carboxamide;
5-(tert-butyl)-N-(5-fluoro-2-methyl-4-(4-((1-methyl-1H-
pyrazol-4-yl)amino)-1,3,5-triazin-2-yl)benzyl)isoxazole-
3-carboxamide;
2-(tert-butyl)-N-(5-fluoro-2-methyl-4-(4-((1-methyl-1H-
pyrazol-4-yl)amino)-1,3,5-triazin-2-yl)benzyl)oxazole-4-
carboxamide;
3-(tert-butyl)-N-(2-(difluoromethyl)-3-fluoro-4-(4-((1-
methyl-1H-pyrazol-3-yl)amino)-1,3,5-triazin-2-yl)ben-
zyl)-1,2,4-oxadiazole-5-carboxamide;

5-(tert-butyl)-N-(2-(2,2-difluoroethyl)-4-(4-((1-methyl-1H-pyrazol-3-yl)amino)-1,3,5-triazin-2-yl)benzyl)-1,2,4-oxadiazole-3-carboxamide;

3-(tert-butyl)-N-(2-(2,2-difluoroethyl)-4-(4-((1-methyl-1H-pyrazol-3-yl)amino)-1,3,5-triazin-2-yl)benzyl)-1,2,4-oxadiazole-5-carboxamide;

5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide;

(R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide;

(S)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide;

3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide;

(R)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide;

(S)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide;

5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide;

(R)-5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide;

(S)-5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide;

3-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-5-carboxamide;

(R)-3-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-5-carboxamide;

(S)-3-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-5-carboxamide;

5-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-3-carboxamide;

(R)-5-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-3-carboxamide;

(S)-5-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-3-carboxamide;

3-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-5-carboxamide;

(R)-3-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-5-carboxamide;

(S)-3-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-5-carboxamide;

5-(tert-butyl)-N-(1-(3-fluoro-2-methyl-4-(4-((1-methyl-1H-pyrazol-4-yl)amino)-1,3,5-triazin-2-yl)phenyl)ethyl)isoxazole-3-carboxamide;

(R)-5-(tert-butyl)-N-(1-(3-fluoro-2-methyl-4-(4-((1-methyl-1H-pyrazol-4-yl)amino)-1,3,5-triazin-2-yl)phenyl)ethyl)isoxazole-3-carboxamide;

(S)-5-(tert-butyl)-N-(1-(3-fluoro-2-methyl-4-(4-((1-methyl-1H-pyrazol-4-yl)amino)-1,3,5-triazin-2-yl)phenyl)ethyl)isoxazole-3-carboxamide;

5-(tert-butyl)-N-(1-(2-chloro-3-methyl-4-(4-((1-methyl-H-pyrazol-4-yl)amino)-1,3,5-triazin-2-yl)phenyl)ethyl)-1,2,4-oxadiazole-3-carboxamide;

(R)-5-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-3-carboxamide;

(S)-5-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-3-carboxamide;

3-(tert-butyl)-N-(1-(2-chloro-3-methyl-4-(4-((1-methyl-H-pyrazol-4-yl)amino)-1,3,5-triazin-2-yl)phenyl)ethyl)-1,2,4-oxadiazole-5-carboxamide;

(R)-3-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-5-carboxamide;

(S)-3-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-5-carboxamide;

5-(tert-butyl)-N-(1-(2-chloro-3-methyl-4-(4-((1-methyl-H-pyrazol-3-yl)amino)-1,3,5-triazin-2-yl)phenyl)ethyl)-1,2,4-oxadiazole-3-carboxamide;

(R)-5-(tert-butyl)-N-(1-(2-chloro-3-methyl-4-(4-((1-methyl-1H-pyrazol-3-yl)amino)-1,3,5-triazin-2-yl)phenyl)ethyl)-1,2,4-oxadiazole-3-carboxamide;

(S)-5-(tert-butyl)-N-(1-(2-chloro-3-methyl-4-(4-((1-methyl-1H-pyrazol-3-yl)amino)-1,3,5-triazin-2-yl)phenyl)ethyl)-1,2,4-oxadiazole-3-carboxamide;

3-(tert-butyl)-N-(1-(3-chloro-2-methyl-4-(4-((1-methyl-H-pyrazol-4-yl)amino)-1,3,5-triazin-2-yl)phenyl)ethyl)-1,2,4-oxadiazole-5-carboxamide;

(R)-3-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-5-carboxamide;

(S)-3-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-5-carboxamide;

5-(tert-butyl)-N-(1-(3-chloro-2-methyl-4-(4-((1-methyl-H-pyrazol-4-yl)amino)-1,3,5-triazin-2-yl)phenyl)ethyl)-1,2,4-oxadiazole-3-carboxamide;

(R)-5-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-3-carboxamide;

(S)-5-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-3-carboxamide;

5-(tert-butyl)-N-(1-(2-(difluoromethyl)-3-fluoro-4-(4-((1-methyl-H-pyrazol-3-yl)amino)-1,3,5-triazin-2-yl)phenyl)ethyl)-1,2,4-oxadiazole-3-carboxamide;

(R)-5-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-3-carboxamide;

(S)-5-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-3-carboxamide;

3-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-5-carboxamide;

(R)-3-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-5-carboxamide;

(S)-3-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-5-carboxamide;

5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

(R)-5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

(S)-5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

3-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;

(R)-3-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;

(S)-3-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;

5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide;

(R)-5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide;

(S)-5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide;

3-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-5-carboxamide;

(R)-3-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-5-carboxamide;

(5)-3-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-5-carboxamide;

5-(tert-butyl)-N-(1-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide;

(R)-5-(tert-butyl)-N-(1-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide;

(S)-5-(tert-butyl)-N-(1-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide;

3-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;

(R)-3-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;

(5)-3-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;

5-(tert-butyl)-N-(8-(4-((1-methyl-1H-pyrazol-4-yl)amino)-1,3,5-triazin-2-yl)-2-(2,2,2-trifluoroethyl)-2,3,4,5-tetrahydro-1H-benzo[c]azepin-5-yl)-1,2,4-oxadiazole-3-carboxamide;

(R)-5-(tert-butyl)-N-(8-(4-((1-methyl-1H-pyrazol-4-yl)amino)-1,3,5-triazin-2-yl)-2-(2,2,2-trifluoroethyl)-2,3,4,5-tetrahydro-1H-benzo[c]azepin-5-yl)-1,2,4-oxadiazole-3-carboxamide;

(s)-5-(tert-butyl)-N-(8-(4-((1-methyl-1H-pyrazol-4-yl)amino)-1,3,5-triazin-2-yl)-2-(2,2,2-trifluoroethyl)-2,3,4,5-tetrahydro-1H-benzo[c]azepin-5-yl)-1,2,4-oxadiazole-3-carboxamide;

3-tert-butyl-N-[8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide;

3-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide;

3-tert-butyl-N-[(5S)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide;

2-tert-butyl-N-[8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-4-carboxamide;

2-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-4-carboxamide;

2-tert-butyl-N-[(5S)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-4-carboxamide;

4-tert-butyl-N-[8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-2-carboxamide;

4-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-2-carboxamide;

4-tert-butyl-N-[(5S)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-2-carboxamide;

2-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)oxazole-4-carboxamide;

(R)-2-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)oxazole-4-carboxamide;

(s)-2-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)oxazole-4-carboxamide;

2-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-4-carboxamide;

(R)-2-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-4-carboxamide;

(S)-2-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-4-carboxamide;

4-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-2-carboxamide;

(R)-4-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-2-carboxamide;

(s)-4-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-2-carboxamide;

2-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)oxazole-4-carboxamide;

(R)-2-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)oxazole-4-carboxamide;

(s)-2-(tert-butyl)-N-(8-(4-((1-methyl-1H-pyrazol-3-yl) amino)-1,3,5-triazin-2-yl)-2-(oxetan-3-yl)-2,3,4,5-tetrahydro-1H-benzo[c]azepin-5-yl)oxazole-4-carboxamide;
3-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)-1,2,4-oxadiazole-5-carboxamide;
(R)-3-(tert-butyl)-N-(8-(4-((1-methyl-1H-pyrazol-3-yl) amino)-1,3,5-triazin-2-yl)-2-(oxetan-3-yl)-2,3,4,5-tetrahydro-1H-benzo[c]azepin-5-yl)-1,2,4-oxadiazole-5-carboxamide;
(s)-3-(tert-butyl)-N-(8-(4-((1-methyl-1H-pyrazol-3-yl) amino)-1,3,5-triazin-2-yl)-2-(oxetan-3-yl)-2,3,4,5-tetrahydro-1H-benzo[c]azepin-5-yl)-1,2,4-oxadiazole-5-carboxamide;
2-(tert-butyl)-N-(2-methyl-4-(4-((1-methyl-1H-pyrazol-4-yl)amino)-1,3,5-triazin-2-yl)benzyl)oxazole-5-carboxamide;
2-(tert-butyl)-N-(3-fluoro-2-methyl-4-(4-((1-methyl-1H-pyrazol-3-yl)amino)-1,3,5-triazin-2-yl)benzyl)oxazole-4-carboxamide;
5-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-3-carboxamide;
(R)-5-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-3-carboxamide;
(S)-5-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-3-carboxamide;
3-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-5-carboxamide;
(R)-3-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-5-carboxamide;
(S)-3-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-5-carboxamide;
2-(tert-butyl)-N-(2-chloro-3-fluoro-4-(4-((1-methyl-1H-pyrazol-4-yl)amino)-1,3,5-triazin-2-yl)benzyl)oxazole-4-carboxamide;
N-(2-chloro-3-fluoro-4-(4-((1-methyl-1H-pyrazol-3-yl) amino)-1,3,5-triazin-2-yl)benzyl)-5-(1-methylcyclopropyl)-1,2,4-oxadiazole-3-carboxamide;
1-(tert-butyl)-N-(3-fluoro-2-methyl-4-(4-((1-methyl-1H-pyrazol-4-yl)amino)-1,3,5-triazin-2-yl)benzyl)-1H-1,2,3-triazole-4-carboxamide;
1-(tert-butyl)-N-(3-fluoro-2-methyl-4-(4-((1-methyl-1H-pyrazol-4-yl)amino)-1,3,5-triazin-2-yl)benzyl)-1H-pyrazole-3-carboxamide;
2-(tert-butyl)-N-(2-methyl-4-(4-((1-methyl-1H-pyrazol-4-yl)amino)-1,3,5-triazin-2-yl)benzyl)oxazole-4-carboxamide;
3-(tert-butyl)-N-(2-methyl-4-(4-((1-methyl-1H-pyrazol-4-yl)amino)-1,3,5-triazin-2-yl)benzyl)isoxazole-5-carboxamide;
1-(tert-butyl)-N-(2-methyl-4-(4-((1-methyl-1H-pyrazol-4-yl)amino)-1,3,5-triazin-2-yl)benzyl)-1H-1,2,3-triazole-4-carboxamide;
5-(tert-butyl)-N-(2-methyl-4-(4-((1-methyl-1H-pyrazol-4-yl)amino)-1,3,5-triazin-2-yl)benzyl)-1,3,4-oxadiazole-2-carboxamide;
5-(tert-butyl)-N-(1-fluoro-2-(4-((1-methyl-1H-pyrazol-3-yl) amino)-1,3,5-triazin-2-yl)-6,7,8,9-tetrahydro-5H-benzo[7]annulen-5-yl)-1,2,4-oxadiazole-3-carboxamide;
(R)-5-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;
(S)-5-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;
2-(tert-butyl)-N-(1-fluoro-2-(4-((1-methyl-1H-pyrazol-3-yl) amino)-1,3,5-triazin-2-yl)-6,7,8,9-tetrahydro-5H-benzo[7]annulen-5-yl)oxazole-4-carboxamide;
(R)-2-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)oxazole-4-carboxamide;
(S)-2-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)oxazole-4-carboxamide; or
N-(3-fluoro-2-methyl-4-(4-((1-methyl-1H-pyrazol-3-yl) amino)-1,3,5-triazin-2-yl)benzyl)-5-(1-methylcyclopropyl)-1,2,4-oxadiazole-3-carboxamide, or a pharmaceutically acceptable salt thereof.

In a thirty-first embodiment of the present invention, the compound of the present invention is selected from:
5-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)-1,2,4-oxadiazole-3-carboxamide;
(R)-5-(tert-butyl)-N-(8-(4-((1-methyl-1H-pyrazol-3-yl) amino)-1,3,5-triazin-2-yl)-2-(2,2,2-trifluoroethyl)-2,3,4,5-tetrahydro-1H-benzo[c]azepin-5-yl)-1,2,4-oxadiazole-3-carboxamide;
(S)-5-(tert-butyl)-N-(8-(4-((1-methyl-1H-pyrazol-3-yl) amino)-1,3,5-triazin-2-yl)-2-(2,2,2-trifluoroethyl)-2,3,4,5-tetrahydro-1H-benzo[c]azepin-5-yl)-1,2,4-oxadiazole-3-carboxamide;
3-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)-1,2,4-oxadiazole-5-carboxamide;
(R)-3-(tert-butyl)-N-(8-(4-((1-methyl-1H-pyrazol-3-yl) amino)-1,3,5-triazin-2-yl)-2-(2,2,2-trifluoroethyl)-2,3,4, 5-tetrahydro-1H-benzo[c]azepin-5-yl)-1,2,4-oxadiazole-5-carboxamide;
(S)-3-(tert-butyl)-N-(8-(4-((1-methyl-1H-pyrazol-3-yl) amino)-1,3,5-triazin-2-yl)-2-(2,2,2-trifluoroethyl)-2,3,4, 5-tetrahydro-1H-benzo[c]azepin-5-yl)-1,2,4-oxadiazole-5-carboxamide;
3-(tert-butyl)-N-(2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;
(R)-3-(tert-butyl)-N-(2-(4-((1-methyl-1H-pyrazol-3-yl) amino)-1,3,5-triazin-2-yl)-6,7,8,9-tetrahydro-5H-benzo[7]annulen-5-yl)-1,2,4-oxadiazole-5-carboxamide;
(S)-3-(tert-butyl)-N-(2-(4-((1-methyl-1H-pyrazol-3-yl) amino)-1,3,5-triazin-2-yl)-6,7,8,9-tetrahydro-5H-benzo[7]annulen-5-yl)-1,2,4-oxadiazole-5-carboxamide;
5-(tert-butyl)-N-(2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;
(R)-5-(tert-butyl)-N-(2-(4-((1-methyl-1H-pyrazol-3-yl) amino)-1,3,5-triazin-2-yl)-6,7,8,9-tetrahydro-5H-benzo[7]annulen-5-yl)-1,2,4-oxadiazole-3-carboxamide;
(S)-5-(tert-butyl)-N-(2-(4-((1-methyl-1H-pyrazol-3-yl) amino)-1,3,5-triazin-2-yl)-6,7,8,9-tetrahydro-5H-benzo[7]annulen-5-yl)-1,2,4-oxadiazole-3-carboxamide;
3-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;

(R)-3-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;

(S)-3-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide;

(R)-5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

(S)-5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

(R)-5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

(S)-5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

5-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

(R)-5-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

(S)-5-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide;

5-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-3-carboxamide;

(R)-5-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-3-carboxamide;

(S)-5-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-3-carboxamide;

5-(tert-butyl)-N-(1-(3-chloro-2-methyl-4-(4-((1-methyl-1H-pyrazol-3-yl)amino)-1,3,5-triazin-2-yl)phenyl)ethyl)-1,2,4-oxadiazole-3-carboxamide;

(R)-5-(tert-butyl)-N-(1-(3-chloro-2-methyl-4-(4-((1-methyl-1H-pyrazol-3-yl)amino)-1,3,5-triazin-2-yl)phenyl)ethyl)-1,2,4-oxadiazole-3-carboxamide;

(S)-5-(tert-butyl)-N-(1-(3-chloro-2-methyl-4-(4-((1-methyl-1H-pyrazol-3-yl)amino)-1,3,5-triazin-2-yl)phenyl)ethyl)-1,2,4-oxadiazole-3-carboxamide;

5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide;

(R)-5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide, or (S)-5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide, or a pharmaceutically acceptable salt thereof.

As used herein, the term "alkyl" refers to a fully saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, iso-propenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Halogen" or "halo" may be fluoro, chloro, bromo or iodo.

As used herein, the term "heterocyclyl" refers to a saturated or unsaturated, monocyclic or bicyclic (e.g., fused, bridged or spiro ring systems) ring system which has from 3- to 11-ring members, or in particular 3- to 8-ring members, 3- to 7-ring members, 3- to 6-ring members, 4- to 6-ring members, 5- to 7-ring members, or 4- to 7-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings.

As used herein, the term "heteroaryl" refers to an aromatic 5- or 6-membered monocyclic ring system, having 1 to 4 heteroatoms independently selected from O, S and N, and wherein N can be oxidized (e.g., N(O)) or quaternized, and S can be optionally oxidized to sulfoxide and sulfone. Examples of heteroaryls include, but are not limited to, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl. In one embodiment, the heteroaryl is an aromatic 5-membered monocyclic ring system. Examples of 5-membered heteroaryl include, but are not limited to, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, and tetrazolyl. As used herein, a "5-membered N-containing heteroaryl" is a 5-membered heteroaryl having at least one nitrogen ring atom.

In one embodiment, a heterocyclyl is a 3- to 7-membered saturated monocyclic or a 3- to 6-membered saturated monocyclic or a 5- to 7-membered saturated monocyclic ring or a 4- to 6-membered saturated monocyclic ring. In one embodiment, a heterocyclyl is a 4- to 6-membered monocyclic ring. In another embodiment, a heterocyclyl is a 11-membered bicyclic ring. In yet another embodiment, a heterocyclyl is a 4- to 7-membered monocyclic non-aromatic ring. In another embodiment, a heterocyclyl is 6- to 8-membered spiro or bridged bicyclic ring. The heterocyclyl group can be attached at a heteroatom or a carbon atom. Examples of heterocyclyls include, but are not limited to, aziridinyl, oxiranyl, thiiranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like.

The term "fused ring system", as used herein, is a ring system that has two rings each of which are independently selected from a carbocyclyl or a heterocyclyl, wherein the two ring structures share two adjacent ring atoms. A fused ring system may have from 9 to 12 ring members.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6 to 8 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 8 ring members.

In one embodiment, a heterocyclyl is a 4- to 6-membered monocyclic heterocyclyl. Examples of 4- to 6-membered monocyclic heterocyclic ring systems include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl.

In another embodiment, a heterocyclyl is a saturated 4- to 6-membered monocyclic heterocyclyl. Examples of saturated 4- to 6-membered monocyclic heterocyclic ring systems include, but are not limited to, azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, and dithiinyl. In another embodiment, a saturated 4- to 6-membered monocyclic heterocyclyl is oxetanyl, tetrahydrofuranyl, or tetrahydropyranyl.

As used herein, the term "carbocyclyl" refers to saturated or unsaturated monocyclic or bicyclic hydrocarbon groups of 3-12, 3-7, 3-5, 3-6, 4-6, or 5-7 carbon atoms. The term "carbocyclyl" encompasses cycloalkyl groups and aromatic groups. The term "cycloalkyl" refers to completely saturated monocyclic or bicyclic or spiro hydrocarbon groups of 3-7 carbon atoms, 3-6 carbon atoms, or 5-7 carbon atoms. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopentenyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1] heptyl, spiro[2.2]pentanyl, and spiro[3.3]heptanyl. In one embodiment, the carbocyclyl is a 4- to 6-membered monocyclic carbocyclyl. In another embodiment, the carbocyclyl is a $C_{3-5}$cycloalkyl, such as cyclopropyl, cyclobutyl, or cyclopentyl. In one embodiment, the carbocyclyl is a $C_{4-6}$ cycloalkyl, such as, cyclobutyl, cyclopentyl or cyclohexyl.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase).

When a particular stereoisomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

When a particular enantiomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired enantiomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 20%, 30%, 40%, 50%, 60%, 70%, 80%, 90%, 95%, 97%, 99%, 99.5% or 99.9%. The stereoisomeric purity the weight percent of the desired stereoisomers encompassed by the name or structure relative to the combined weight of all of the stereoisomers.

When a disclosed compound is named or depicted by structure without indicating the stereochemistry, and the compound has one chiral center, it is to be understood that the name or structure encompasses one enantiomer of compound in pure or substantially pure form, as well as mixtures thereof (such as a racemic mixture of the compound and mixtures enriched in one enantiomer relative to its corresponding optical isomer).

When a disclosed compound is named or depicted by structure without indicating the stereochemistry and, e.g., the compound has at least two chiral centers, it is to be understood that the name or structure encompasses one stereoisomer in pure or substantially pure form, as well as mixtures thereof (such as mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated. In addition, some compounds may exhibit polymorphism.

In one embodiment, the compounds of the invention or a pharmaceutically acceptable salt thereof include deuterium.

Another embodiment is a pharmaceutical composition comprising at least one compound described herein, or a pharmaceutically acceptable salt thereof, and at least one pharmaceutically acceptable carrier.

The compounds, or pharmaceutically acceptable salts thereof described herein may be used to decrease the activity of Btk, or to otherwise affect the properties and/or behavior of Btk, e.g., stability, phosphorylation, kinase activity, interactions with other proteins, etc.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

One embodiment of the invention includes a method of treating a disorder responsive to inhibition of Btk in a subject comprising administering to said subject an effective amount of at least one compound described herein, or a pharmaceutically acceptable salt thereof.

In one embodiment, the present invention provides methods of treating autoimmune disorders, inflammatory disorders, and cancers in a subject in need thereof comprising administering to said subject an effective amount of at least one compound described herein, or a pharmaceutically acceptable salt thereof.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barre syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjogren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis or lupus. In some embodiments, the present invention provides a method of treating multiple sclerosis.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The effective dose of a compound provided herein, or a pharmaceutically acceptable salt thereof, administered to a subject can be 10 µg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of nontoxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXEMPLIFICATIONS

LCMS methods: Samples were analyzed on a Waters Acquity UPLC BEH C18 1.7 µM 2.1×50 mm, part number 186002350 machine, MS mode: MS:ESI+ scan range 100-1000 daltons. PDA detection 210-400 nm. The method utilized was 95% $H_2O$/5% $CH_3CN$ (initial conditions) linear gradient to 5% $H_2O$/95% $CH_3CN$ at 1 min, HOLD 5%

Example 1: 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide (Compound 1)

(Compound 1)

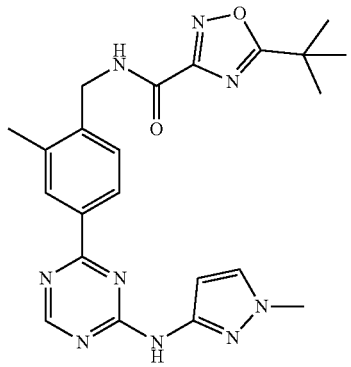

1. Synthesis of 4-chloro-N-(1-methyl-H-pyrazol-3-yl)-1,3,5-triazin-2-amine

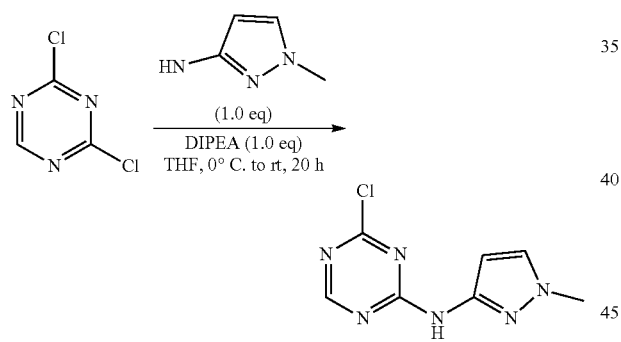

To a mixture of 2,4-dichloro-1,3,5-triazine (3 g, 20 mmol) in THF (40 mL) at 0° C. was added 1-methylpyrazol-3-amine (1.94 g, 20 mmol, 1.73 mL) dropwise. Then DIPEA (2.58 g, 20 mmol, 3.49 mL) was added dropwise. The mixture was stirred at rt for 20 h, diluted with EtOAc (100 mL), and washed with a saturated NaHCO₃ solution (100 mL). The mixture was filtered to give 4-chloro-N-(1-methyl-1H-pyrazol-3-yl)-1,3,5-triazin-2-amine as white solid (2.3 g, yield: 35%).

The filtrate was collected and the organic phase was separated. The basic aqueous phase was extracted with an additional portion of EtOAc (100 mL). The combined organic phase was washed with brine (200 mL), dried (Na₂SO₄), filtered, and concentrated in vacuo to give an additional portion of the title product (0.5 g, yield: 8%; 2.8 g total, combined yield: 43%). ESI-MS (M+H)⁺: 211.0. ¹H NMR (400 MHz, DMSO-d₆) δ: 11.20-10.78 (m, 1H), 8.69-8.42 (m, 1H), 7.75-7.42 (m, 1H), 6.66-6.28 (m, 1H), 3.85-3.64 (m, 3H).

2. Synthesis of (4-bromo-2-methylphenyl)methanamine

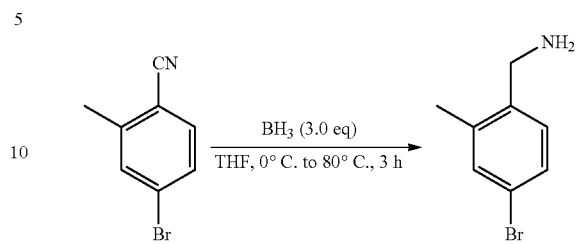

To a solution of 4-bromo-2-methylbenzonitrile (3 g, 15 mmol) in THF (20 mL) was added BH₃.THF (1 M, 45 mL, 45 mmol) at 0° C. The solution was stirred for 1 h and heated to 80° C. for 2 h. The mixture was quenched with H₂O and extracted with EtOAc (50 mL×3). The combined organic extracts were concentrated in vacuo to afford a residue which was suspended in a saturated HCl/EtOAc solution and filtered. The filter cake was washed with diethyl ether (20 mL×3) and dried under vacuum to afford (4-bromo-2-methylphenyl)methanamine hydrochloride as white solid (2.1 g, yield: 69%). ESI-MS (M+H)⁺: 200.1.

3. Synthesis of tert-butyl 4-bromo-2-methylbenzylcarbamate

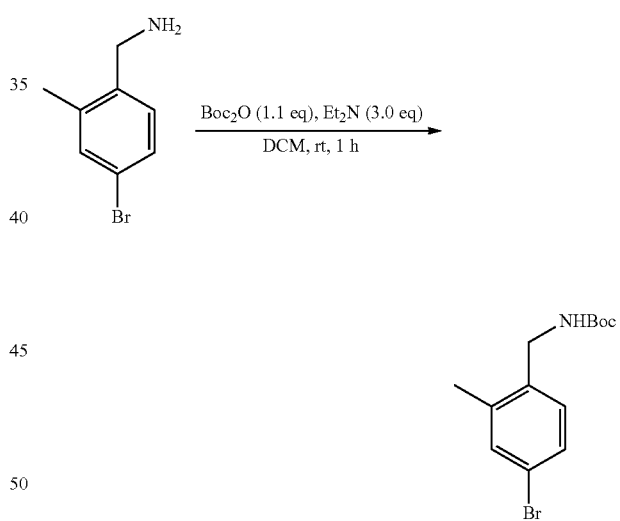

To a solution of (4-bromo-2-methylphenyl)methanamine (1.2 g, 6 mmol) in DCM (30 mL) were added Et₃N (1.82 g, 18 mmol) and Boc₂O (1.43 g, 6.6 mmol). The mixture was stirred at rt for 1 h, diluted with H₂O (50 mL) and extracted with DCM (50 mL×2). The organic phase was washed with brine (50 mL), dried (Na₂SO₄), filtered and concentrated in vacuo to afford tert-butyl (4-bromo-2-methylbenzyl)carbamate as a white solid (1.7 g, yield: 95%), which was used directly in the next step without further purification. ESI-MS (M+H)⁺: 300.1.

4. Synthesis of tert-butyl 2-methyl-4-(4,4,5,5-tetramethyl-1,3,2-dioxaborolan-2-yl)benzylcarbamate

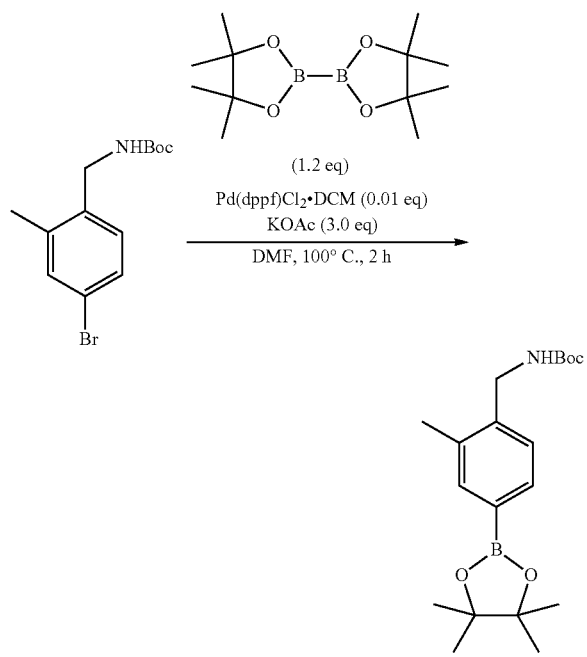

To a solution of tert-butyl (4-bromo-2-methylbenzyl)carbamate (1.5 g, 5.0 mmol) in DMF (6 mL) were added bis(pinacolato)diboron (1.52 g, 6.0 mmol), KOAc (1.75 g, 18 mmol) and Pd(dppf)Cl$_2$.DCM (407 mg, 0.5 mmol) under N$_2$. The mixture was stirred at 100° C. for 2 h, allowed to cool to rt, diluted with H$_2$O (50 mL), and extracted with EtOAc (100 mL×3). The combined organic extracts were washed with brine, dried, concentrated in vacuo, and purified by silica-gel column (petroleum ether/EtOAc, 10:1) to give tert-butyl (2-methyl-4-(4,4,5,5-tetramethyl-1,3,2-dioxaborolan-2-yl)benzyl)carbamate as white solid (1.2 g, yield: 69%). ESI-MS (M+H)$^+$: 348.2. $^1$H NMR (400 MHz, CDCl$_3$) δ: 7.61-7.59 (m, 2H), 7.26 (s, 1H), 4.68 (br s, 1H), 4.33 (d, J=5.6 Hz, 2H), 2.32 (s, 3H), 1.45 (s, 9H), 1.34 (s, 12H).

5. Synthesis of tert-butyl (2-methyl-4-(4-((1-methyl-1H-pyrazol-3-yl)amino)-1,3,5-triazin-2-yl)benzyl)carbamate

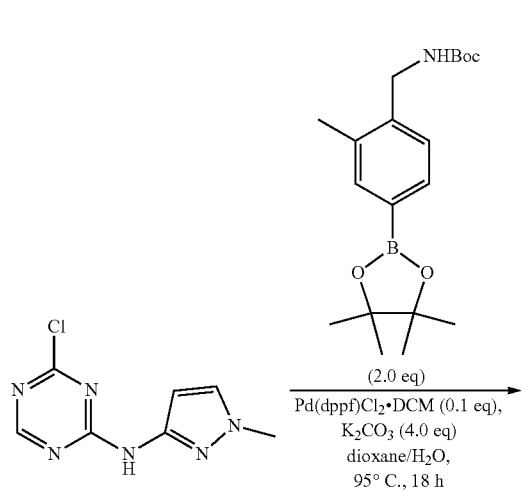

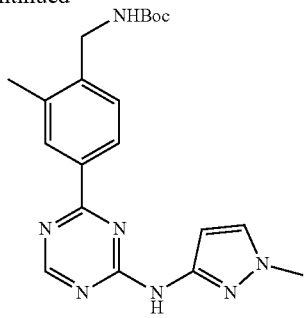

A mixture of 4-chloro-N-(1-methylpyrazol-3-yl)-1,3,5-triazin-2-amine (180 mg, 0.85 mmol), tert-butyl N-[[2-methyl-4-(4,4,5,5-tetramethyl-1,3,2-dioxaborolan-2-yl)phenyl]methyl]carbamate (594 mg, 1.71 mmol), Pd(dppf)Cl$_2$.DCM (70 mg, 0.09 mmol) and K$_2$CO$_3$ (472 mg, 3.42 mmol) in 4 mL of 1,4-dioxane/H$_2$O (3:1) was stirred at 95° C. for 18 h under an N$_2$ atmosphere. After cooling to rt, the reaction mixture was diluted with H$_2$O (10 mL) and extracted with DCM (10 mL). The phases were separated and the aqueous phase was extracted again with DCM (10 mL). The combined organic extracts were dried (MgSO$_4$), filtered, and concentrated in vacuo. The residue was purified by silica-gel column chromatography (petroleum ether/EtOAc) to give tert-butyl (2-methyl-4-(4-((1-methyl-1H-pyrazol-3-yl)amino)-1,3,5-triazin-2-yl)benzyl)carbamate as a pale-yellow solid (220 mg, yield: 65%). ESI-MS (M+H)$^+$: 396.3. $^1$H NMR (400 MHz, CDCl$_3$) δ: 8.90-8.75 (m, 1H), 8.38-8.17 (m, 2H), 7.71-7.57 (m, 1H), 7.47-7.33 (m, 3H), 4.90-4.72 (m, 1H), 4.47-4.35 (m, 2H), 3.96-3.86 (m, 3H), 2.49-2.37 (m, 3H), 1.56-1.49 (m, 9H).

6. Synthesis of 4-(4-(aminomethyl)-3-methyl)-N-(1-methyl-1H-pyrazol-3-yl)-1,3,5-triazin-2-amine

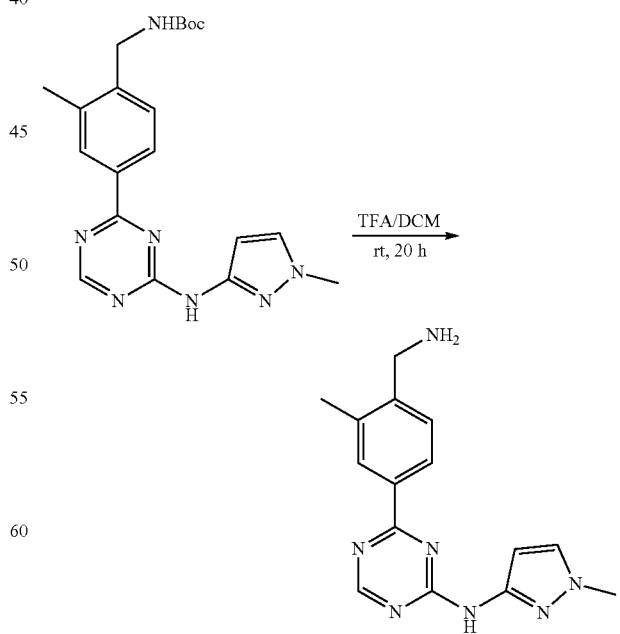

To a solution of tert-butyl (2-methyl-4-(4-((1-methyl-1H-pyrazol-3-yl)amino)-1,3,5-triazin-2-yl)benzyl)carbamate (60 mg, 0.15 mmol) in DCM (3 mL) was added TFA (0.12 mL). The resulting solution was stirred at room temperature for 20 h. After concentration of the reaction mixture, the residue was dissolved in MeOH and loaded onto an silica-based Strong Cation Exchang (SCX) column for purification. The product was recovered by washing with a 2 M ammonia solution in MeOH. The filtrate was concentrated in vacuo to give 4-(4-(aminomethyl)-3-methyl)-N-(1-methyl-1H-pyrazol-3-yl)-1,3,5-triazin-2-amine as a white solid (120 mg, yield: 73%). ESI-MS (M+H)$^+$: 296.2.

7. Synthesis of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide (Compound 1)

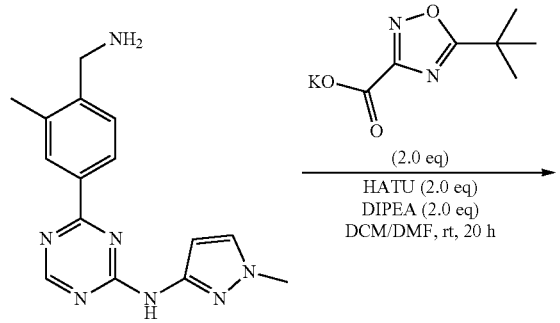

To a solution of 4-(4-(aminomethyl)-3-methylphenyl)-N-(1-methyl-1H-pyrazol-3-yl)-1,3,5-triazin-2-amine (45 mg, 0.15 mmol) and potassium 5-(tert-butyl)-1,2,4-oxadiazole-3-carboxylate (63 mg, 0.30 mmol) in DCM/DMF (1:1, 2 mL) was added DIPEA (39 mg, 0.30 mmol, 53 μL). The white suspension was stirred at rt for 10 minutes before HATU (116 mg, 0.30 mmol) was added. The reaction mixture continued to stir at rt for 20 h. After diluting with H$_2$O (10 mL), the mixture was extracted with EtOAc (20 mL×2). The combined organic extracts were dried (Na$_2$SO$_4$), filtered, and concentrated in vacuo. The crude product was purified by prep-HPLC (CH$_3$CN/H$_2$O with 0.05% TFA/H$_2$O as mobile phase) to give the TFA salt of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide as a yellow solid (23 mg, yield: 25%). ESI-MS (M+H)$^+$: 448.3. $^1$H NMR (400 MHz, DMSO-d$_6$) δ:10.68-10.27 (m, 1H), 9.50-9.27 (m, 1H), 8.80-8.48 (m, 1H), 8.24-8.02 (m, 2H), 7.68-7.47 (m, 1H), 7.40-7.24 (m, 1H), 6.80-6.53 (m, 1H), 4.58-4.39 (m, 2H), 3.78-3.68 (m, 3H), 2.39-2.29 (m, 3H), 1.37 (s, 9H).

Example 2: 3-(tert-butyl)-N-(2-methyl-4-(4-((1-methyl-1H-pyrazol-3-yl)amino)-1,3,5-triazin-2-yl)benzyl)-1,2,4-oxadiazole-5-carboxamide (Compound 2)

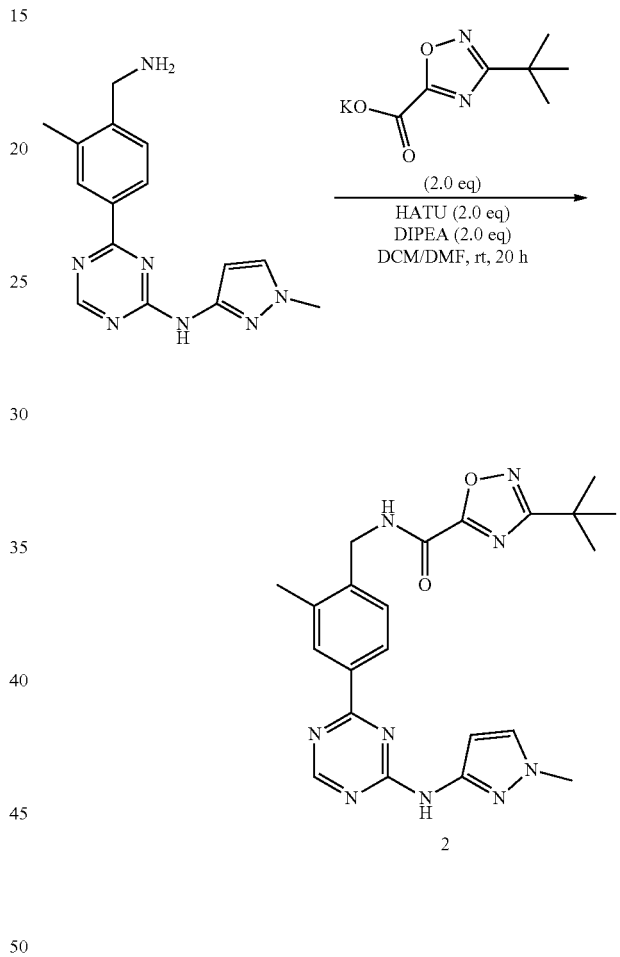

Synthesis of 3-(tert-butyl)-N-(2-methyl-4-(4-((1-methyl-1H-pyrazol-3-yl)amino)-1,3,5-triazin-2-yl)benzyl)-1,2,4-oxadiazole-5-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH$_3$CN/H$_2$O with 0.05% TFA/H$_2$O as mobile phase) to give the TFA salt of 3-(tert-butyl)-N-(2-methyl-4-(4-((1-methyl-1H-pyrazol-3-yl)amino)-1,3,5-triazin-2-yl)benzyl)-1,2,4-oxadiazole-5-carboxamide as a yellow solid (11 mg, yield: 14%). ESI-MS (M+H)$^+$: 448.3. $^1$H NMR (400 MHz, CDCl$_3$) δ: 8.87-8.66 (m, 1H), 8.30-8.14 (m, 2H), 7.44-7.34 (m, 1H), 7.32-7.23 (m, 1H), 6.92-6.68 (m, 1H), 4.73-4.59 (m, 2H), 3.86-3.74 (m, 3H), 2.45-2.31 (m, 3H), 1.31 (s, 9H).

Example 3: 2-(tert-butyl)-N-(2-methyl-4-(4-((1-methyl-1H-pyrazol-3-yl)amino)-1,3,5-triazin-2-yl)benzyl)oxazole-5-carboxamide (Compound 3)

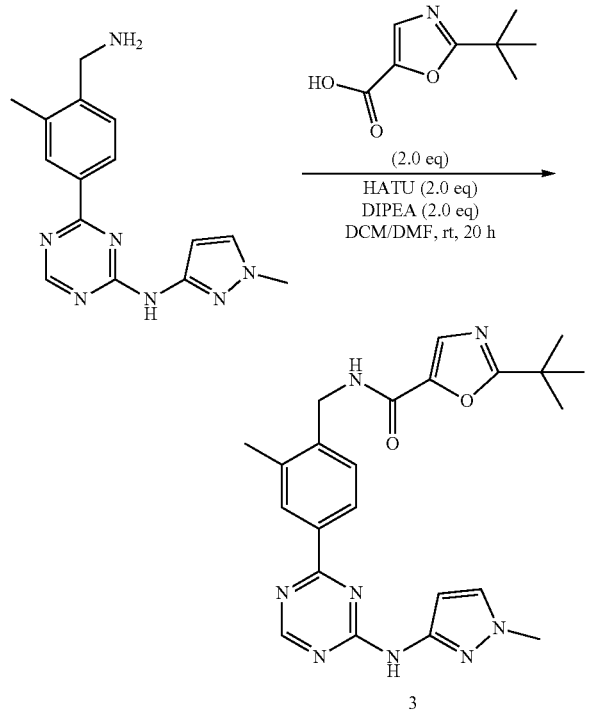

Synthesis of 2-(tert-butyl)-N-(2-methyl-4-(4-((1-methyl-1H-pyrazol-3-yl)amino)-1,3,5-triazin-2-yl)benzyl)oxazole-5-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH$_3$CN/H$_2$O with 0.05% TFA/H$_2$O as mobile phase) to give the TFA salt of 2-(tert-butyl)-N-(2-methyl-4-(4-((1-methyl-1H-pyrazol-3-yl)amino)-1,3,5-triazin-2-yl)benzyl)oxazole-5-carboxamide as a yellow solid (11 mg, yield: 16%). ESI-MS (M+H)$^+$: 447.2. $^1$H NMR (400 MHz, CDCl$_3$) δ: 8.87-8.61 (m, 1H), 8.28-8.14 (m, 2H), 8.10-7.99 (m, 1H), 7.44-7.33 (m, 1H), 7.33-7.24 (m, 1H), 6.99-6.73 (m, 1H), 4.70-4.54 (m, 2H), 3.86-3.72 (m, 3H), 2.53-2.24 (m, 3H), 1.29 (s, 9H).

Example 4: 1-(tert-butyl)-4-fluoro-N-(2-methyl-4-(4-((1-methyl-1H-pyrazol-3-yl)amino)-1,3,5-triazin-2-yl)benzyl)-1H-pyrazole-3-carboxamide (Compound 4)

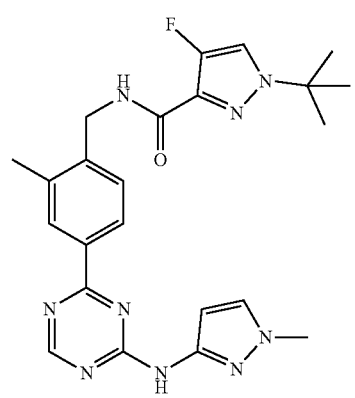

1. Synthesis of 1-(tert-butyl)-1H-pyrazole-3-carboxylic acid

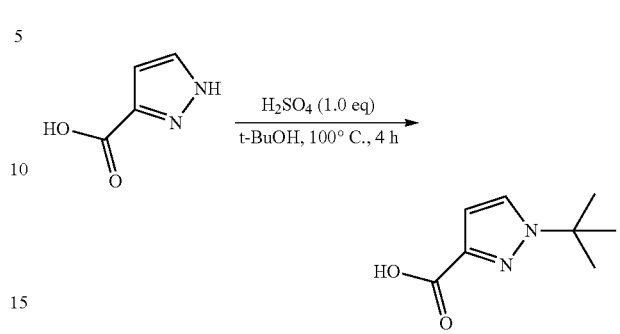

To a mixture of 1H-pyrazole-3-carboxylic acid (2.2 g, 20 mmol) in t-BuOH (9.5 mL) was added concentrated H$_2$SO$_4$ (2.0 g, 20 mmol, 1.1 mL) in a dropwise manner (CAUTION: exothermic reaction). The reaction vessel was sealed and placed behind a blast shield (as a safety precaution) before heating the reaction mixture to 100° C. for 4 h. The reaction mixture was cooled to rt and H$_2$O (10 mL) was added. The reaction mixture was extracted with EtOAc (20 mL×3). The combined organic extracts were dried (MgSO$_4$), filtered, and concentrated in vacuo to give crude 1-(tert-butyl)-1H-pyrazole-3-carboxylic acid (3.5 g, crude) which was carried forward without further purification.

2. Synthesis of ethyl 1-(tert-butyl)-1H-pyrazole-3-carboxylate

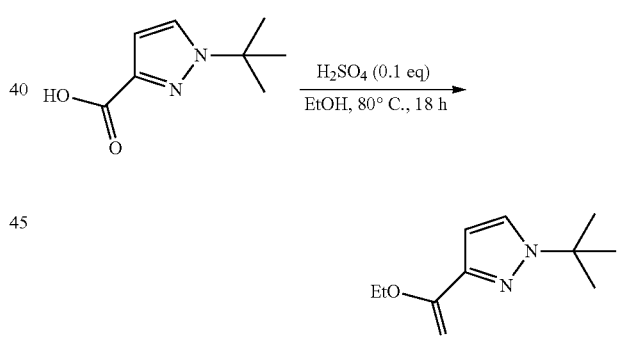

To a solution of crude 1-(tert-butyl)-1H-pyrazole-3-carboxylic acid (3.5 g, 21 mmol) in EtOH (30 mL) was added concentrated H$_2$SO$_4$ (204 mg, 0.21 mmol, 111 μL). The reaction mixture was heated to reflux for 18 h. The reaction mixture was cooled to rt and concentrated in vacuo. The residue was partitioned between DCM (20 mL) and saturated aqueous NaHCO$_3$ (20 mL). The layers were separated and the aqueous phase was extracted with an additional portion of DCM (20 mL). The combined organic extracts were dried (MgSO$_4$), filtered, and concentrated in vacuo. The residue was purified by silica-gel column chromatography (heptanes/EtOAc) to give ethyl 1-(tert-butyl)-1H-pyrazole-3-carboxylate as a colorless oil (3.7 g, yield: 86%). $^1$H NMR (400 MHz, CDCl$_3$) δ: 7.64-7.47 (m, 1H), 6.86-6.71 (m, 1H), 4.48-4.28 (m, 2H), 1.63 (s, 9H), 1.46-1.33 (m, 3H).

3. Synthesis of ethyl 1-(tert-butyl)-4-fluoro-1H-pyrazole-3-carboxylate

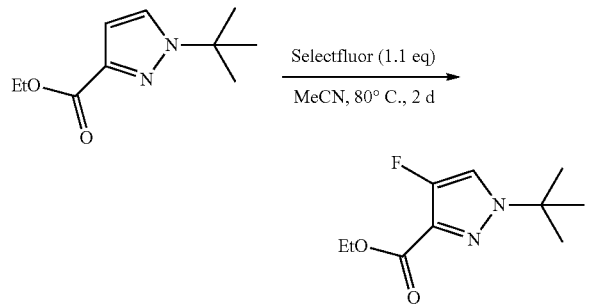

To a solution of ethyl 1-(tert-butyl)-1H-pyrazole-3-carboxylate (400 mg, 2.0 mmol) in MeCN (5 mL) was added 1-(chloromethyl)-4-fluoro-1,4-diazoniabicyclo[2.2.2]octane ditetrafluoroborate (794 mg, 2.2 mmol). The reaction vessel was capped and placed in a heating bath at 80° C. for 48 h. The reaction mixture was cooled to rt and was filtered. The filter residue was washed thoroughly with DCM and the combined filtrates were concentrated in vacuo. The crude material was purified by prep-HPLC (CH$_3$CN/H$_2$O with 0.05% TFA/H$_2$O as mobile phase) to give ethyl 1-(tert-butyl)-4-fluoro-1H-pyrazole-3-carboxylate as a white solid (60 mg, yield: 14%). ESI-MS (M+H)$^+$: 215.2. $^1$H NMR (400 MHz, CDCl$_3$) δ: 7.44 (d, J=4.8 Hz, 1H), 4.49-4.32 (m, 2H), 1.59 (s, 9H), 1.47-1.31 (m, 3H).

4. Synthesis of 1-(tert-butyl)-4-fluoro-1H-pyrazole-3-carboxylic acid

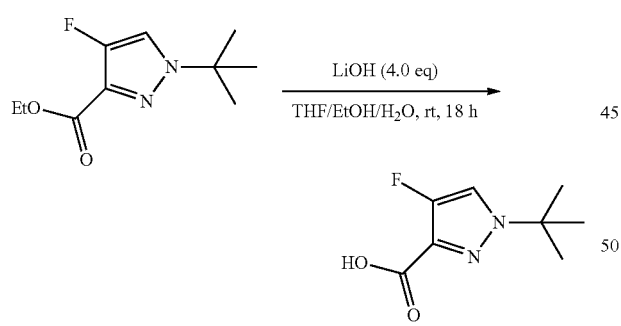

To a solution of ethyl 1-(tert-butyl)-4-fluoro-1H-pyrazole-3-carboxylate (60 mg, 0.28 mmol) in a mixture of THF (2 mL), EtOH (2 mL), and H$_2$O (2 mL) was added LiOH (27 mg, 1.1 mmol). The reaction mixture was stirred at rt for 18 h. The reaction mixture was concentrated in vacuo and 1M HCl solution was added to the remaining aqueous phase until pH=2. The aqueous solution was concentrated in vacuo, yielding a mixture of LiCl and the desired product, 1-(tert-butyl)-4-fluoro-1H-pyrazole-3-carboxylic acid (110 mg, crude), which was carried forward without further purification. ESI-MS (M+H)$^+$: 187.2. $^1$H NMR (400 MHz, CDCl$_3$) δ: 7.46-7.34 (m, 1H), 1.52 (s, 9H).

5. Synthesis of 1-(tert-butyl)-4-fluoro-N-(2-methyl-4-(4-((1-methyl-1H-pyrazol-3-yl)amino)-1,3,5-triazin-2-yl)benzyl)-1H-pyrazole-3-carboxamide (Compound 4)

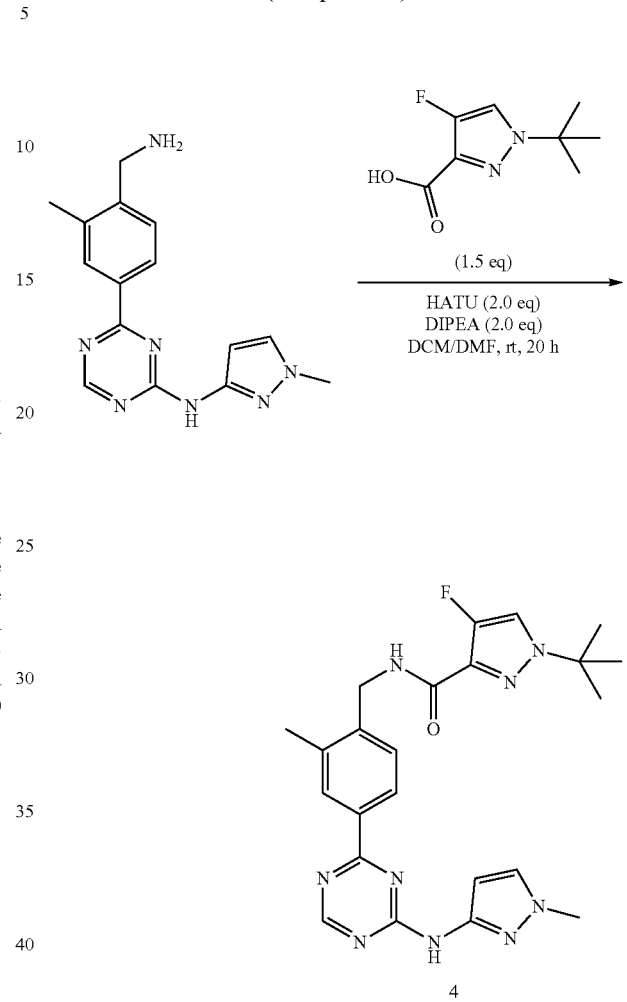

Synthesis of 1-(tert-butyl)-4-fluoro-N-(2-methyl-4-(4-((1-methyl-1H-pyrazol-3-yl)amino)-1,3,5-triazin-2-yl)benzyl)-1H-pyrazole-3-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH$_3$CN/H$_2$O with 0.05% TFA/H$_2$O as mobile phase) to give the TFA salt of 1-(tert-butyl)-4-fluoro-N-(2-methyl-4-(4-((1-methyl-1H-pyrazol-3-yl)amino)-1,3,5-triazin-2-yl)benzyl)-1H-pyrazole-3-carboxamide as a yellow solid (13 mg, yield: 21%). ESI-MS (M+H)$^+$: 464.3. $^1$H NMR (400 MHz, CDCl$_3$) δ: 9.57 (br s, 1H), 8.89-8.62 (m, 1H), 8.26-8.06 (m, 2H), 7.47-7.39 (m, 1H), 7.39-7.34 (m, 1H), 7.32-7.24 (m, 1H), 6.98-6.76 (m, 2H), 4.74-4.55 (m, 2H), 3.82 (s, 3H), 2.40 (s, 3H), 1.47 (s, 9H).

Example 5: 5-(tert-butyl)-N-(2-chloro-4-(4-((1-methyl-1H-pyrazol-3-yl)amino)-1,3,5-triazin-2-yl)benzyl)-1,2,4-oxadiazole-3-carboxamide (Compound 5)

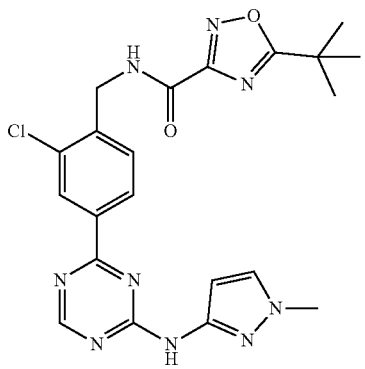

1. Synthesis of (4-bromo-2-chlorophenyl)methanamine

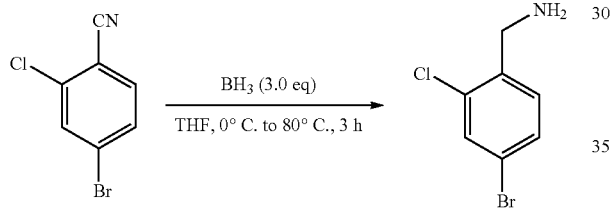

To a solution of 4-bromo-2-chlorobenzonitrile (3.2 g, 15 mmol) in THF (20 mL) at 0° C. was added BH$_3$.THF (1 M, 45 mL, 45 mmol). The solution was stirred at 0° C. for 1 h and then was heated to 80° C. for 2 h. Then the mixture was quenched with H$_2$O and extracted with EtOAc (50 mL×3). The organic layer was collected and concentrated in vacuo. The residue was stirred with a saturated HCl/EtOAc solution and filtered. The filter cake was rinsed with ether (20 mL×3) and dried under vacuum to afford (4-bromo-2-chlorophenyl)methanamine as a white solid (2.3 g, yield: 70%). ESI-MS (M+H)$^+$: 220.1.

2. Synthesis of tert-butyl (4-bromo-2-chlorobenzyl)carbamate

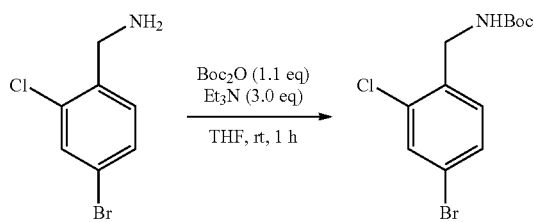 [SMILES: NCc1ccc(Br)cc1Cl ; CC(C)(C)OC(=O)NCc1ccc(Br)cc1Cl]

To a solution of (4-bromo-2-chlorophenyl)methanamine (1.3 g, 6 mmol) in DCM (30 mL) were added Et$_3$N (1.82 g, 18 mmol) and Boc$_2$O (1.43 g, 6.6 mmol). The mixture was stirred at rt for 1 h. After diluting with H$_2$O (50 mL), the mixture was extracted with DCM (50 mL×2). The combined organic extracts were washed with brine (50 mL), dried (Na$_2$SO$_4$), filtered, and concentrated in vacuo to give crude tert-butyl (4-bromo-2-chlorobenzyl)carbamate as a white solid (1.5 g, yield: 80%), which was used directly in the next step without further purification. ESI-MS (M+H)$^+$: 320.1.

3. Synthesis of tert-butyl (2-chloro-4-(4,4,5,5-tetramethyl-1,3,2-dioxaborolan-2-yl)benzyl)carbamate

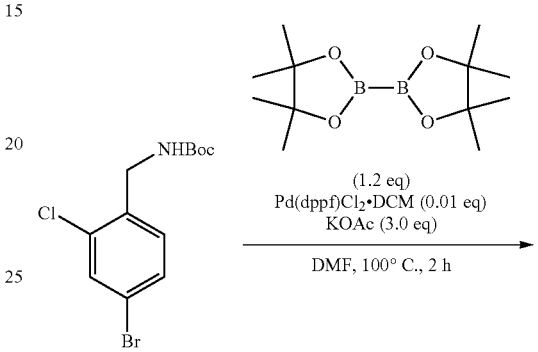

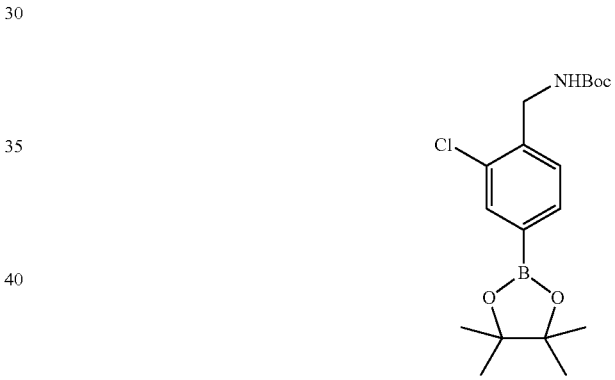

To a solution of tert-butyl (4-bromo-2-chlorobenzyl)carbamate (1.6 g, 5.0 mmol) in DMF (6 mL) were added bis(pinacolato)diboron (1.52 g, 6.0 mmol), KOAc (1.75 g, 18 mmol) and Pd(dppf)Cl$_2$.DCM (407 mg, 0.5 mmol) under N$_2$. The mixture was stirred at 100° C. for 2 h. After cooling to rt, the mixture was diluted with H$_2$O (50 mL) and extracted with EtOAc (100 mL×3). The combined organic layer was washed with brine (200 mL), dried (Na$_2$SO$_4$), concentrated in vacuo, and purified by silica-gel column chromatography (petroleum ether/EtOAc, 10:1) to give tert-butyl (2-chloro-4-(4,4,5,5-tetramethyl-1,3,2-dioxaborolan-2-yl)benzyl)carbamate as a white solid (1.1 g, yield: 60%). ESI-MS (2M+Na)$^+$: 757.2. $^1$H NMR (400 MHz, CDCl$_3$) δ: 7.78 (s, 1H), 7.65 (d, J=7.6 Hz, 1H), 7.37 (d, J=7.6 Hz, 1H), 5.01 (br s, 1H), 4.41 (d, J=6.4 Hz, 2H), 1.44 (s, 9H), 1.35 (s, 12H).

4. Synthesis of tert-butyl (2-chloro-4-(4-((1-methyl-1H-pyrazol-3-yl)amino)-1,2,3-triazin-2-yl)benzyl)carbamate

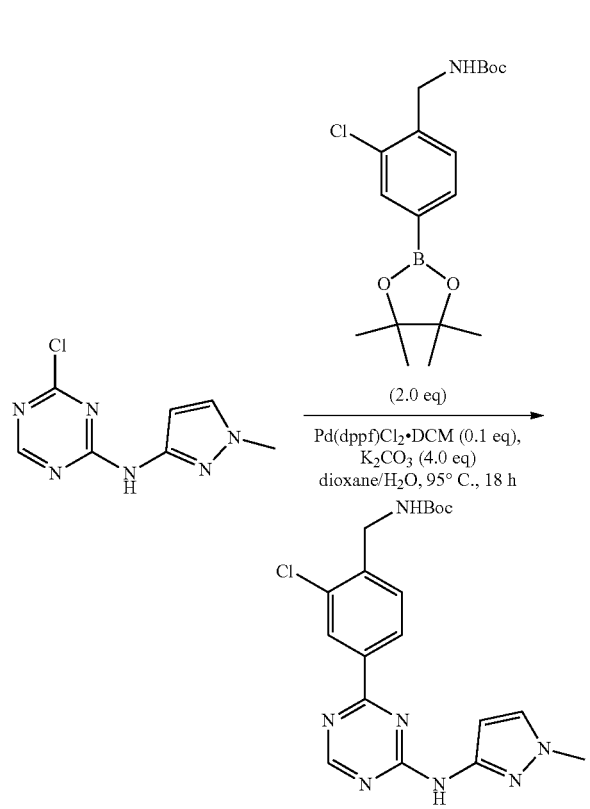

Synthesis of tert-butyl (2-chloro-4-(4-((1-methyl-1H-pyrazol-3-yl)amino)-1,2,3-triazin-2-yl)benzyl)carbamate was similar to that of tert-butyl (2-methyl-4-(4-((1-methyl-1H-pyrazol-3-yl)amino)-1,3,5-triazin-2-yl)benzyl)carbamate in Example 1, Step 5. The residue was purified by silica-gel column chromatography (petroleum ether/EtOAc) to give tert-butyl (2-chloro-4-(4-((1-methyl-1H-pyrazol-3-yl)amino)-1,2,3-triazin-2-yl)benzyl)carbamate as a pale-yellow amorphous solid (420 mg, yield: 95%). ESI-MS (M+H)+: 416.3.

5. Synthesis of 4-(4-(aminomethyl)-3-chlorophenyl)-N-(1-methyl-1H-pyrazol-3-yl)-1,3,5-triazin-2-amine

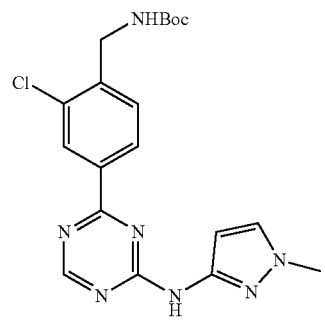

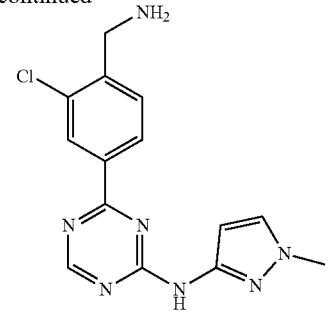

Synthesis of 4-(4-(aminomethyl)-3-chlorophenyl)-N-(1-methyl-1H-pyrazol-3-yl)-1,3,5-triazin-2-amine was similar to that of 4-(4-(aminomethyl)-3-methyl)-N-(1-methyl-1H-pyrazol-3-yl)-1,3,5-triazin-2-amine in Example 1, Step 6. The crude material was dissolved in MeOH and loaded onto an SCX column for purification. The product was recovered by washing with a 2 M ammonia solution in MeOH. The filtrate was concentrated in vacuo to give 4-(4-(aminomethyl)-3-chlorophenyl)-N-(1-methyl-1H-pyrazol-3-yl)-1,3,5-triazin-2-amine as a white solid (180 mg, yield: 47%). ESI-MS (M+H)+: 316.3.

6. Synthesis of 5-(tert-butyl)-N-(2-chloro-4-(4-((1-methyl-1H-pyrazol-3-yl)amino)-1,3,5-triazin-2-yl)benzyl)-1,2,4-oxadiazole-3-carboxamide (Compound 5)

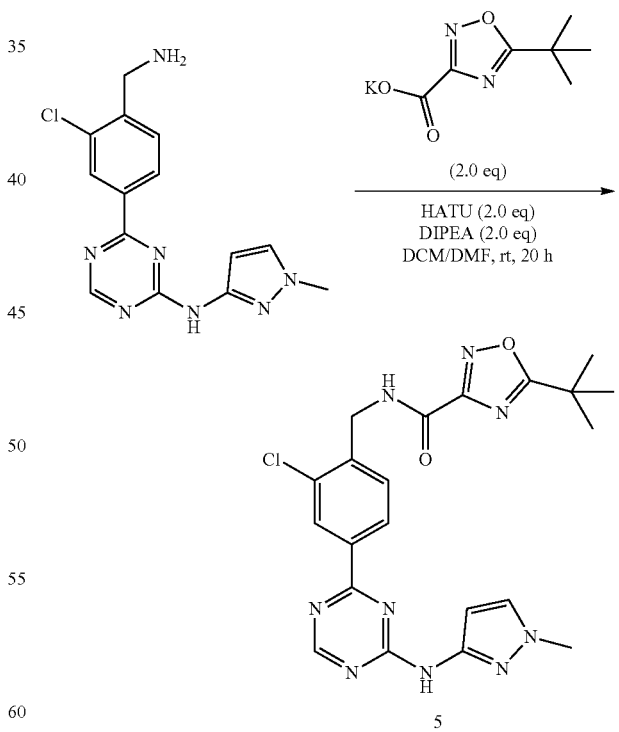

Synthesis of 5-(tert-butyl)-N-(2-chloro-4-(4-((1-methyl-1H-pyrazol-3-yl)amino)-1,3,5-triazin-2-yl)benzyl)-1,2,4-oxadiazole-3-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3- carboxamide in Example 1, Step 7. The crude product was purified by prep-HPLC (CH₃CN/H₂O with 0.05% TFA/H₂O as mobile phase) to give the TFA salt of 5-(tert-butyl)-N-(2-chloro-4-(4-((1-methyl-1H-pyrazol-3-yl)amino)-1,3,5-triazin-2-yl)benzyl)-1,2,4-oxadiazole-3-carboxamide as a pale yellow solid (6 mg, yield: 6%). ESI-MS (M+H)⁺: 468.1. ¹H NMR (400 MHz, CDCl₃) δ: 8.84-8.65 (m, 1H), 8.47-8.33 (m, 1H), 8.31-8.16 (m, 1H), 7.60-7.47 (m, 1H), 7.45-7.35 (m, 1H), 7.35-7.27 (m, 1H), 6.90-6.78 (m, 1H), 4.82-4.55 (m, 2H), 3.87-3.74 (m, 3H), 1.39 (s, 9H).

Example 6: 3-(tert-butyl)-N-(2-chloro-4-(4-((1-methyl-1H-pyrazol-3-yl)amino)-1,3,5-triazin-2-yl)benzyl)-1,2,4-oxadiazole-5-carboxamide (Compound 6)

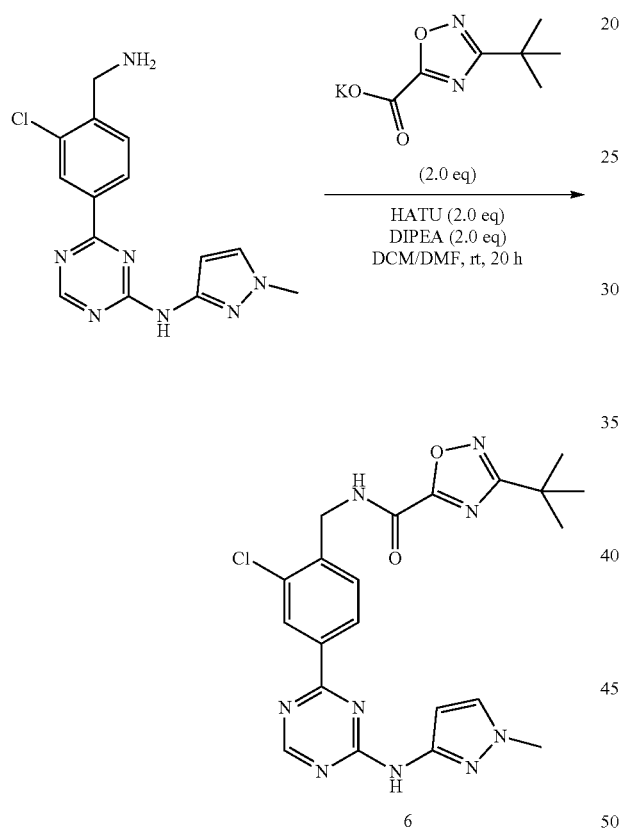

Synthesis of 3-(tert-butyl)-N-(2-chloro-4-(4-((1-methyl-1H-pyrazol-3-yl)amino)-1,3,5-triazin-2-yl)benzyl)-1,2,4-oxadiazole-5-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH₃CN/H₂O with 0.05% TFA/H₂O as mobile phase) to give the TFA salt of 3-(tert-butyl)-N-(2-chloro-4-(4-((1-methyl-1H-pyrazol-3-yl)amino)-1,3,5-triazin-2-yl)benzyl)-1,2,4-oxadiazole-5-carboxamide as a yellow solid (5 mg, yield: 6%). ESI-MS (M+H)⁺: 468.1. ¹H NMR (400 MHz, CDCl₃) δ: 8.90-8.69 (m, 1H), 8.46-8.35 (m, 1H), 8.34-8.18 (m, 1H), 7.61-7.52 (m, 1H), 7.50-7.40 (m, 1H), 7.39-7.28 (m, 1H), 6.94-6.81 (m, 1H), 4.82-4.69 (m, 2H), 3.92-3.78 (m, 3H), 1.33 (s, 9H).

Example 7: 5-(tert-butyl)-N-(4-(4-((1-methyl-1H-pyrazol-3-yl)amino)-1,3,5-triazin-2-yl)-2-(trifluoromethyl)benzyl)-1,2,4-oxadiazole-3-carboxamide (Compound 7)

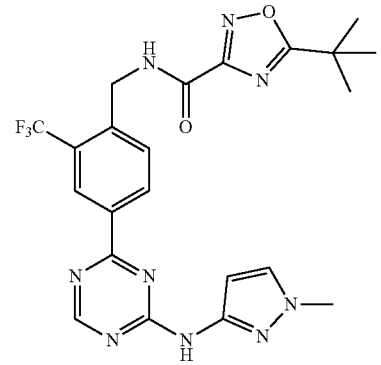

1. Synthesis of tert-butyl (4-(4-((1-methyl-1H-pyrazol-3-yl)amino)-1,3,5-triazin-2-yl)-2-(trifluoromethyl)benzyl)carbamate

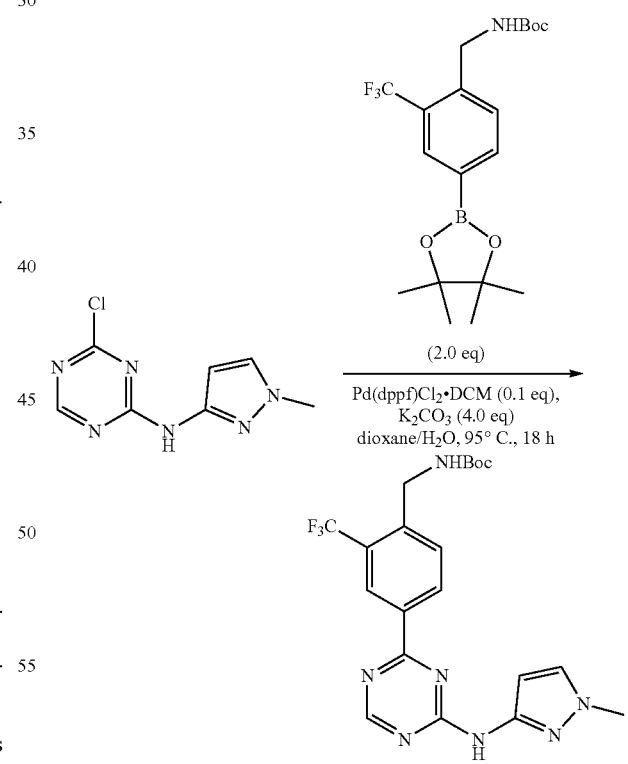

Synthesis of tert-butyl (4-(4-((1-methyl-1H-pyrazol-3-yl)amino)-1,3,5-triazin-2-yl)-2-(trifluoromethyl)benzyl)carbamate was similar to that of tert-butyl (2-methyl-4-(4-((1-methyl-1H-pyrazol-3-yl)amino)-1,3,5-triazin-2-yl)benzyl)carbamate in Example 1, Step 5. tert-Butyl (4-(4,4,5,5-tetramethyl-1,3,2-dioxaborolan-2-yl)-2-(trifluoromethyl)benzyl)carbamate was prepared as described in WO 2015/

089337. The crude material was purified by silica-gel column chromatography (petroleum ether/EtOAc) to give tert-butyl (4-(4-((1-methyl-1H-pyrazol-3-yl)amino)-1,3,5-triazin-2-yl)-2-(trifluoromethyl)benzyl)carbamate as a white solid (150 mg, yield: 16%). ESI-MS (M+H)+: 450.1.

2. Synthesis of 4-(4-(aminomethyl)-3-(trifluoromethyl)phenyl)-N-(1-methyl-1H-pyrazol-3-yl)-1,3,5-triazin-2-amine

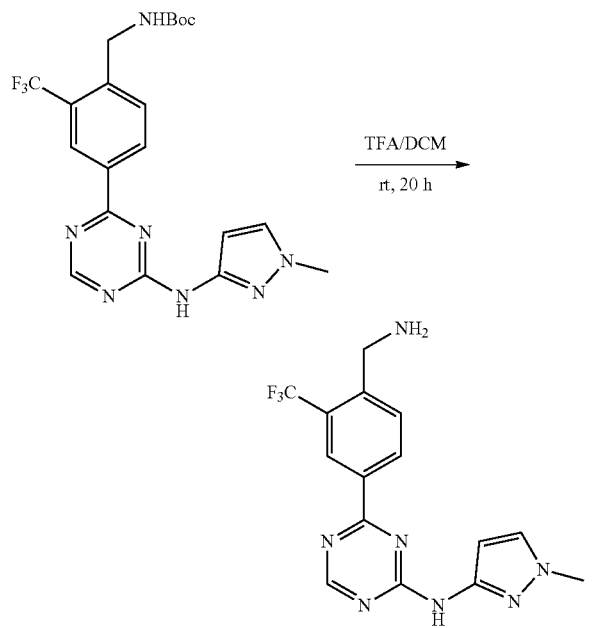

Synthesis of 4-(4-(aminomethyl)-3-(trifluoromethyl)phenyl)-N-(1-methyl-1H-pyrazol-3-yl)-1,3,5-triazin-2-amine was similar to that of 4-(4-(aminomethyl)-3-methyl)-N-(1-methyl-1H-pyrazol-3-yl)-1,3,5-triazin-2-amine in Example 1, Step 6. The crude material was dissolved in MeOH and loaded onto an SCX column for purification. The product was recovered by washing with a 2 M ammonia solution in MeOH. The filtrate was concentrated in vacuo to give 4-(4-(aminomethyl)-3-(trifluoromethyl)phenyl)-N-(1-methyl-1H-pyrazol-3-yl)-1,3,5-triazin-2-amine as a white solid (90 mg, yield: 69%). ESI-MS (M+H)+: 350.3.

3. Synthesis of 5-(tert-butyl)-N-(4-(4-((1-methyl-1H-pyrazol-3-yl)amino)-1,3,5-triazin-2-yl)-2-(trifluoromethyl)benzyl)-1,2,4-oxadiazole-3-carboxamide (Compound 7)

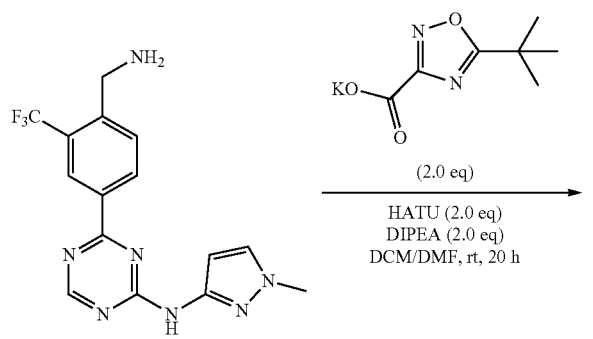

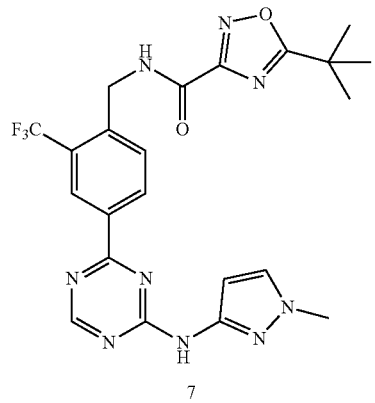

Synthesis of 5-(tert-butyl)-N-(4-(4-((1-methyl-1H-pyrazol-3-yl)amino)-1,3,5-triazin-2-yl)-2-(trifluoromethyl)benzyl)-1,2,4-oxadiazole-3-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH$_3$CN/H$_2$O with 0.05% TFA/H$_2$O as mobile phase) to give the TFA salt of 5-(tert-butyl)-N-(4-(4-((1-methyl-1H-pyrazol-3-yl)amino)-1,3,5-triazin-2-yl)-2-(trifluoromethyl)benzyl)-1,2,4-oxadiazole-3-carboxamide as a pale yellow solid (4 mg, yield: 5%). ESI-MS (M+H)+: 502.3. $^1$H NMR (400 MHz, CDCl$_3$) δ: 9.16-8.91 (m, 1H), 8.85-8.73 (m, 1H), 8.72-8.67 (m, 1H), 8.61-8.47 (m, 1H), 7.84-7.65 (m, 1H), 7.44-7.22 (m, 2H), 6.92-6.72 (m, 1H), 4.93-4.78 (m, 2H), 3.81 (s, 3H), 1.38 (s, 9H).

Example 8: 3-(tert-butyl)-N-(4-(4-((1-methyl-1H-pyrazol-3-yl)amino)-1,3,5-triazin-2-yl)-2-(trifluoromethyl)benzyl)-1,2,4-oxadiazole-5-carboxamide (Compound 8)

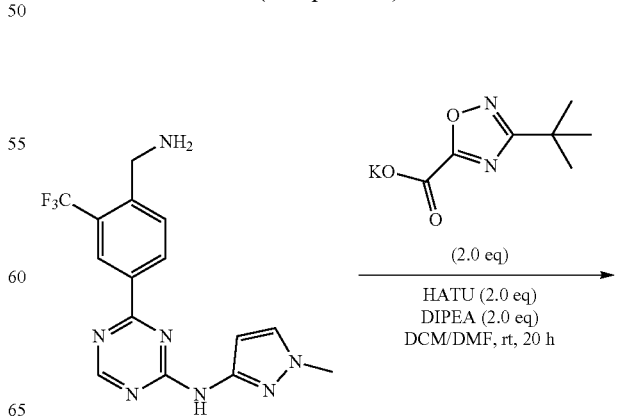

-continued

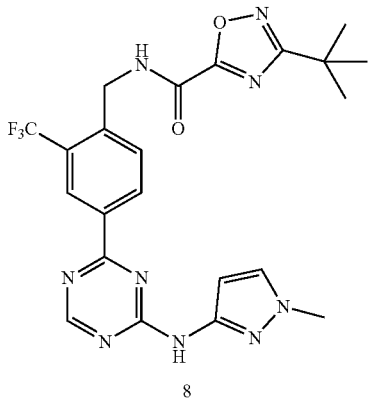

8

Synthesis of 3-(tert-butyl)-N-(4-(4-((1-methyl-1H-pyrazol-3-yl)amino)-1,3,5-triazin-2-yl)-2-(trifluoromethyl)benzyl)-1,2,4-oxadiazole-5-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH$_3$CN/H$_2$O with 0.05% TFA/H$_2$O as mobile phase) to give the TFA salt of 3-(tert-butyl)-N-(4-(4-((1-methyl-1H-pyrazol-3-yl)amino)-1,3,5-triazin-2-yl)-2-(trifluoromethyl)benzyl)-1,2,4-oxadiazole-5-carboxamide as a yellow solid (5 mg, yield: 7%). ESI-MS (M+H)$^+$: 502.3. $^1$H NMR (500 MHz, CDCl$_3$) δ: 8.85-8.65 (m, 2H), 8.63-8.48 (m, 1H), 8.23-8.01 (m, 1H), 7.80-7.62 (m, 1H), 7.46-7.34 (m, 1H), 7.34-7.21 (m, 1H), 6.86-6.63 (m, 1H), 4.93-4.74 (m, 2H), 3.81 (s, 3H), 1.39-1.26 (m, 9H).

Example 9: 5-(tert-butyl)-N-(3-fluoro-2-methyl-4-(4-((1-methyl-1H-pyrazol-3-yl)amino)-1,3,5-triazin-2-yl)benzyl)-1,2,4-oxadiazole-3-carboxamide (Compound 9)

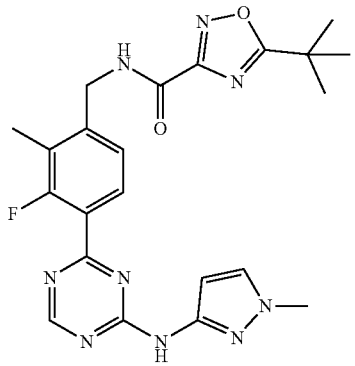

9

1. Synthesis of 4-bromo-2-fluoro-3-methylaniline

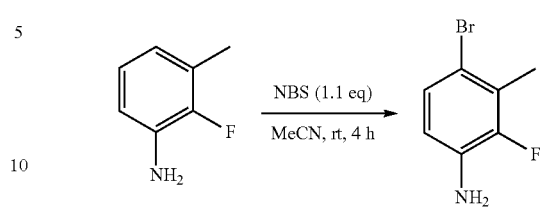

To a solution of 2-fluoro-3-methylaniline (25.0 g, 0.20 mol) in MeCN (200 mL) was added dropwise a solution of NBS (39.1 g, 0.22 mol) in MeCN (100 mL) at 25° C. The reaction mixture was stirred at 25° C. for 4 h. The reaction mixture was concentrated in vacuo and purified by silica-gel column chromatography (petroleum ether/EtOAc, 50:1) to give 4-bromo-2-fluoro-3-methylaniline as a brown oil (30 g, yield: 74%). $^1$H NMR: (400 MHz, DMSO-d$_6$) δ: 7.02 (dd, J=8.8 Hz, 1.6 Hz, 1H), 6.55 (t, J=8.8 Hz, 1H), 5.21 (s, 2H), 2.16 (d, J=2.4 Hz, 3H).

2. Synthesis of N-(4-bromo-2-fluoro-3-methylphenyl)acetamide

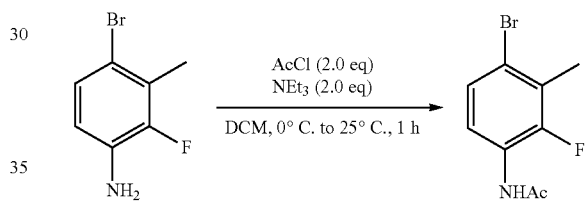

To a solution of 4-bromo-2-fluoro-3-methylaniline (30 g, 147 mmol) and Et$_3$N (29.8 g, 294 mmol) in DCM (300 mL) was added dropwise AcCl (23.1 g, 294 mmol) at 0° C. The mixture was then stirred at 25° C. for 1 h. The reaction mixture was poured into H$_2$O (300 mL) and extracted with DCM (200 mL×2). The combined organic layers were washed with brine (400 mL), dried (Na$_2$SO$_4$), filtered, and concentrated in vacuo to give N-(4-bromo-2-fluoro-3-methylphenyl)acetamide as a brown solid (34.0 g, yield: 94%). $^1$H NMR: (400 MHz, DMSO-d$_6$) δ: 9.74 (s, 1H), 7.71 (t, J=8.4 Hz, 1H), 7.36 (d, J=8.8 Hz, 1H), 2.25 (d, J=2.4 Hz, 3H), 2.06 (s, 3H).

3. Synthesis of N-(4-cyano-2-fluoro-3-methylphenyl)acetamide

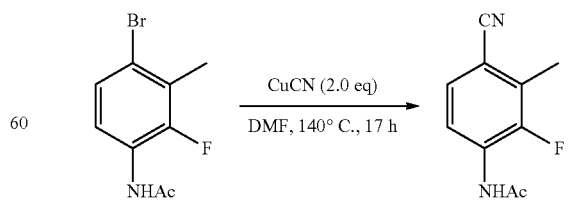

A mixture of N-(4-bromo-2-fluoro-3-methylphenyl)acetamide (32 g, 130 mmol) and Cu(I)CN (23.3 g, 260 mmol) in DMF (300 ml) was prepared under N$_2$ and heated at 140°

C. for 17 h. The reaction mixture was poured into H$_2$O (500 mL) and extracted with EtOAc (300 mL×3). The combined organic extracts were washed with brine (500 mL), dried (Na$_2$SO$_4$), filtered, and concentrated in vacuo to give crude material. The crude material was triturated with a petroleum ether/EtOAc solution (50:1, 300 mL) and dried under vacuum to give N-(4-cyano-2-fluoro-3-methylphenyl)acetamide as a yellow solid (25.0 g, yield: 94%). $^1$H NMR: (400 MHz, DMSO-d$_6$) δ: 10.04 (s, 1H), 8.08 (s, 1H), 7.54 (d, J=8.4 Hz, 1H), 2.36 (s, 3H), 2.11 (s, 3H).

4. Synthesis of 4-amino-3-fluoro-2-methylbenzonitrile

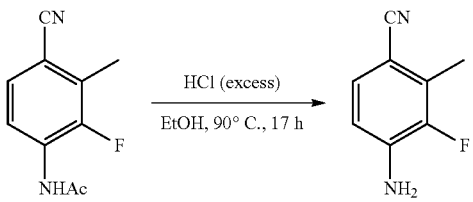

To a solution of N-(4-cyano-2-fluoro-3-methylphenyl)acetamide (25.0 g, 0.13 mol) in EtOH (200 mL) was added concentrated HCl solution (12 N, 100 mL). The mixture was heated at 90° C. for 17 h. The mixture was concentrated in vacuo. The resulting white solid was dissolved in EtOAc (200 mL) and the pH of the solution was adjusted to pH=7 with saturated aqueous Na$_2$CO$_3$ solution (100 mL). The layers were separated and the organic phase was dried (Na$_2$SO$_4$), filtered, and concentrated in vacuo to give 4-amino-3-fluoro-2-methylbenzonitrile as a brown solid (19.0 g, yield: 97%). $^1$H NMR: (400 MHz, DMSO-d$_6$) δ: 7.20 (d, J=8.4 Hz, 1H), 6.61 (t, J=8.4 Hz, 1H), 6.13 (s, 2H), 2.24 (d, J=2.4 Hz, 3H).

5. Synthesis of 4-bromo-3-fluoro-2-methylbenzonitrile

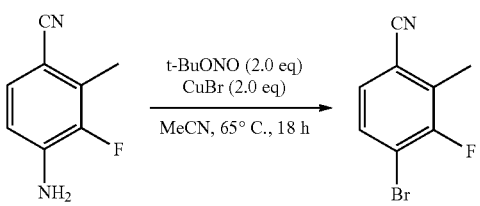

To a suspension of Cu(I)Br (32.5 g, 226 mmol) in MeCN (300 mL) was added tert-butyl nitrite (23.4 g, 226 mmol) at room temperature. Then, a solution of 4-amino-3-fluoro-2-methylbenzonitrile (17 g, 113 mmol) in MeCN (50 mL) was added dropwise at 65° C. over 1 h. The mixture was stirred at 65° C. for 17 h, cooled to rt, and concentrated in vacuo to give crude material. The crude material was purified by silica-gel column chromatography (petroleum ether/EtOAc, 15:1) to give 4-bromo-3-fluoro-2-methylbenzonitrile as a yellow oil (14.5 g, yield: 60%). $^1$H NMR: (400 MHz, DMSO-d$_6$) δ: 7.74 (t, J=7.6 Hz, 1H), 7.59 (dd, J$_1$=8.4 Hz, J$_2$=0.8 Hz, 1H), 2.41 (d, J=2.4 Hz, 3H).

6. Synthesis of (4-bromo-3-fluoro-2-methylphenyl)methanamine

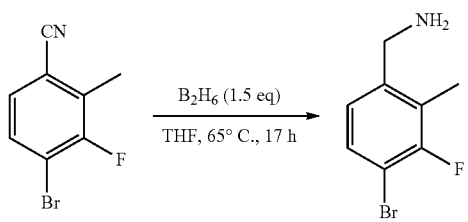

To a solution of 4-bromo-3-fluoro-2-methylbenzonitrile (15.0 g, 70 mmol) in THF (150 mL) was added B$_2$H$_6$ (10.5 mL, 105 mmol, 10 M in Me$_2$S) at 25° C. slowly. The reaction mixture was heated at 65° C. for 17 h. The mixture was quenched with MeOH (10 mL) and concentrated in vacuo to give crude (4-bromo-3-fluoro-2-methylphenyl)methanamine (15 g), which was used for the next step directly without further purification.

7. Synthesis of tert-butyl (4-bromo-3-fluoro-2-methylbenzyl)carbamate

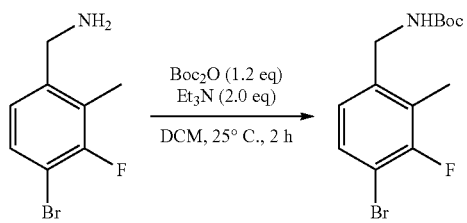 [SMILES: Cc1c(CN)ccc(Br)c1F ; Cc1c(CNC(=O)OC(C)(C)C)ccc(Br)c1F]

To a solution of (4-bromo-3-fluoro-2-methylphenyl)methanamine (14 g, 64 mmol) in DCM (100 mL) was added Et$_3$N (13 g, 128 mmol), Boc$_2$O (16.8 g, 77 mmol) at 25° C. The mixture was heated at 25° C. for 2 h. The mixture was concentrated in vacuo and was purified by silica-gel column chromatography (petroleum ether/EtOAc, 50:1) to give tert-butyl (4-bromo-3-fluoro-2-methylbenzyl)carbamate as a white solid (12.0 g, yield: 59%). $^1$H NMR: (400 MHz, DMSO-d$_6$) δ: 7.47 (t, J=7.6 Hz, 1H), 7.37 (t, J=5.2 Hz, 1H), 6.96 (d, J=8.0 Hz, 1H), 4.07 (d, J=6.0 Hz, 2H), 2.19 (d, J=2.0 Hz, 3H), 1.37 (s, 9H).

8. Synthesis of tert-butyl (3-fluoro-2-methyl-4-(4,4,5,5-tetramethyl-1,3,2-dioxaborolan-2-yl)benzyl)carbamate

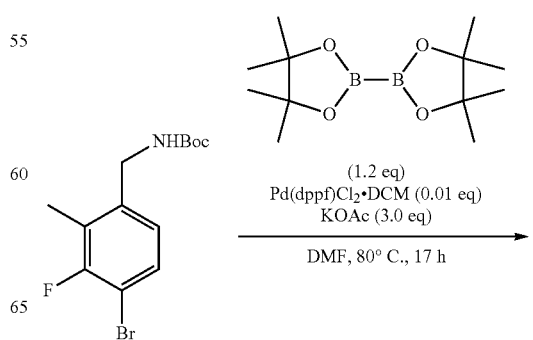

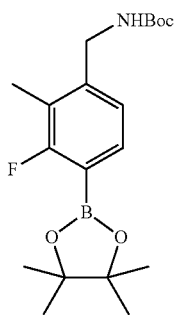

To a solution of tert-butyl (4-bromo-3-fluoro-2-methylbenzyl)carbamate (10 g, 31.4 mmol) in 1,4-dioxane (150 mL) was added bis(pinacolato)diboron (9.6 g, 37.7 mmol) and KOAc (6.2 g, 62.9 mmol). Then Pd(dppf)Cl$_2$.DCM (2.1 g, 2.5 mmol) was added under an N$_2$ atmosphere. The reaction mixture was stirred at 80° C. for 17 h under N$_2$. The reaction mixture was concentrated in vacuo and purified by silica-gel column chromatography (petroleum ether/EtOAc, 20:1) to give tert-butyl (3-fluoro-2-methyl-4-(4,4,5,5-tetramethyl-1,3,2-dioxaborolan-2-yl)benzyl)carbamate as a yellow solid (13.0 g, impure) which was used without additional purification. ESI-MS (M-t-Bu)$^+$: 310.1.

9. Synthesis of tert-butyl (3-fluoro-2-methyl-4-(4-((1-methyl-1H-pyrazol-3-yl)amino)-1,3,5-triazin-2-yl)benzyl)carbamate

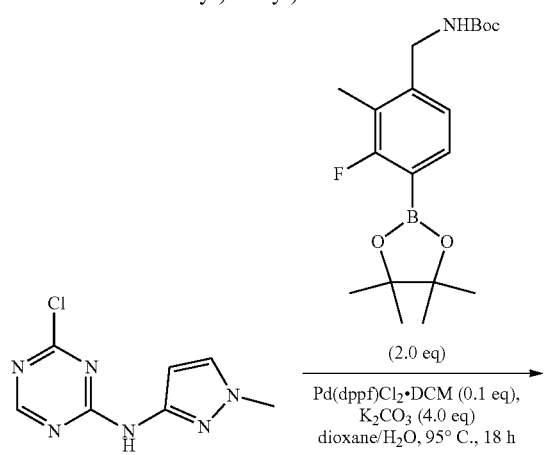

Synthesis of tert-butyl (3-fluoro-2-methyl-4-(4-((1-methyl-1H-pyrazol-3-yl)amino)-1,3,5-triazin-2-yl)benzyl)carbamate was similar to that of tert-butyl (2-methyl-4-(4-((1-methyl-1H-pyrazol-3-yl)amino)-1,3,5-triazin-2-yl)benzyl)carbamate in Example 1, Step 5. The residue was purified by silica-gel column chromatography (petroleum ether/EtOAc) to give tert-butyl (3-fluoro-2-methyl-4-(4-((1-methyl-1H-pyrazol-3-yl)amino)-1,3,5-triazin-2-yl)benzyl)carbamate as a white solid (140 mg, yield: 80%). ESI-MS (M+H)$^+$: 414.3.

10. Synthesis of 4-(4-(aminomethyl)-2-fluoro-3-methylphenyl)-N-(1-methyl-1H-pyrazol-3-yl)-1,3,5-triazin-2-amine

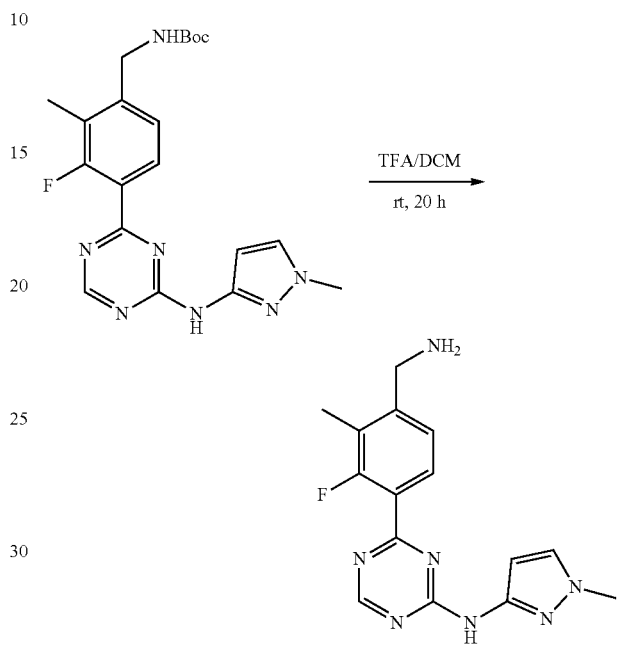

Synthesis of 4-(4-(aminomethyl)-2-fluoro-3-methylphenyl)-N-(1-methyl-1H-pyrazol-3-yl)-1,3,5-triazin-2-amine was similar to that of 4-(4-(aminomethyl)-3-methyl)-N-(1-methyl-1H-pyrazol-3-yl)-1,3,5-triazin-2-amine in Example 1, Step 6. The crude material was dissolved in MeOH and loaded onto an SCX column for purification. The product was recovered by washing with a 2 M ammonia solution in MeOH. The filtrate was concentrated in vacuo to give 4-(4-(aminomethyl)-2-fluoro-3-methylphenyl)-N-(1-methyl-1H-pyrazol-3-yl)-1,3,5-triazin-2-amine as a yellow solid (140 mg, yield: 88%). ESI-MS (M+H)$^+$: 314.2.

11. Synthesis of 5-(tert-butyl)-N-(3-fluoro-2-methyl-4-(4-((1-methyl-1H-pyrazol-3-yl)amino)-1,3,5-triazin-2-yl)benzyl)-1,2,4-oxadiazole-3-carboxamide (Compound 9)

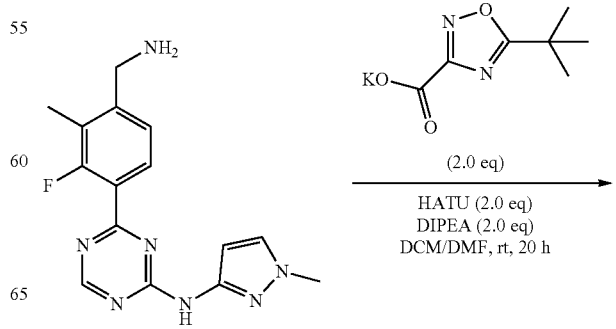

-continued

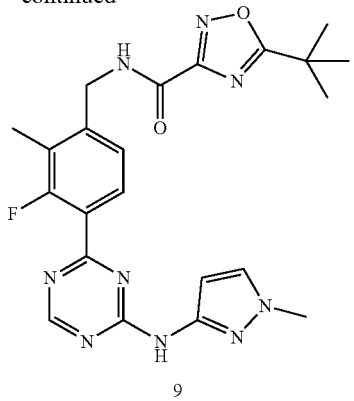

9

Synthesis of 5-(tert-butyl)-N-(3-fluoro-2-methyl-4-(4-((1-methyl-1H-pyrazol-3-yl)amino)-1,3,5-triazin-2-yl)benzyl)-1,2,4-oxadiazole-3-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH$_3$CN/H$_2$O with 0.05% TFA/H$_2$O as mobile phase) to give the TFA salt of 5-(tert-butyl)-N-(3-fluoro-2-methyl-4-(4-((1-methyl-1H-pyrazol-3-yl)amino)-1,3,5-triazin-2-yl)benzyl)-1,2,4-oxadiazole-3-carboxamide as a pale yellow solid (5 mg, yield: 13%). ESI-MS (M+H)$^+$: 466.2. $^1$H NMR (400 MHz, CDCl$_3$) δ: 8.94-8.71 (m, 1H), 8.03-7.77 (m, 1H), 7.30 (d, J=2.5 Hz, 1H), 7.20-7.18 (m, 3H), 7.07-6.89 (m, 1H), 4.67 (d, J=6.0 Hz, 2H), 3.83 (s, 3H), 2.30 (s, 3H), 1.40 (s, 9H).

Example 10: 3-(tert-butyl)-N-(3-fluoro-2-methyl-4-(4-((1-methyl-1H-pyrazol-3-yl)amino)-1,3,5-triazin-2-yl)benzyl)-1,2,4-oxadiazole-5-carboxamide (Compound 10)

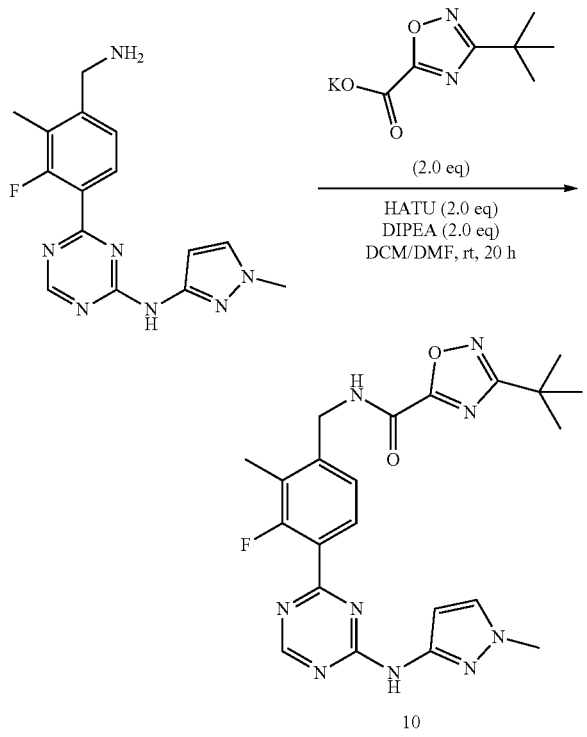

10

Synthesis of 3-(tert-butyl)-N-(3-fluoro-2-methyl-4-((1-methyl-1H-pyrazol-3-yl)amino)-1,3,5-triazin-2-yl)benzyl)-1,2,4-oxadiazole-5-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH$_3$CN/H$_2$O with 0.05% TFA/H$_2$O as mobile phase) to give the TFA salt of 3-(tert-butyl)-N-(3-fluoro-2-methyl-4-(4-((1-methyl-1H-pyrazol-3-yl)amino)-1,3,5-triazin-2-yl)benzyl)-1,2,4-oxadiazole-5-carboxamide as a yellow solid (5 mg, yield: 13%). ESI-MS (M+H)$^+$: 466.2. $^1$H NMR (400 MHz, CDCl$_3$) δ: 9.60-9.30 (br m, 1H), 8.90-8.66 (m, 1H), 8.08-7.71 (m, 1H), 7.32-7.25 (m, 1H), 7.02-6.85 (m, 1H), 4.70-4.56 (m, 2H), 3.88-3.73 (m, 3H), 2.38-2.22 (m, 3H), 1.31 (s, 9H).

Example 11: 5-(tert-butyl)-N-(2-methyl-4-(4-((1-methyl-1H-pyrazol-4-yl)amino)-1,3,5-triazin-2-yl)benzyl)-1,2,4-oxadiazole-3-carboxamide (Compound 11)

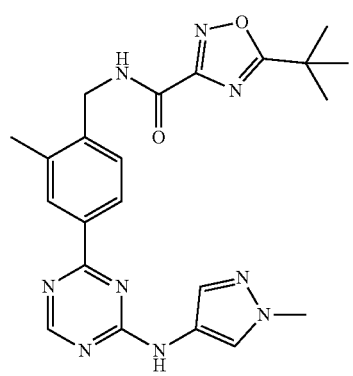

11

1. Synthesis of 4-chloro-N-(1-methyl-1H-pyrazol-4-yl)-1,3,5-triazin-2-amine

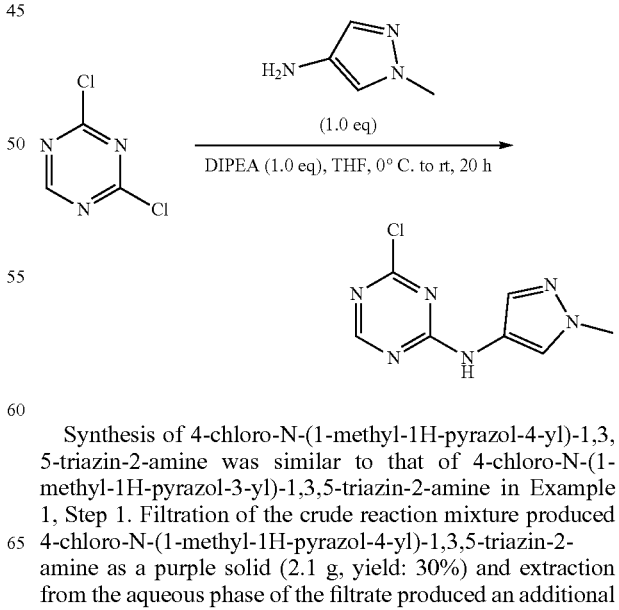

Synthesis of 4-chloro-N-(1-methyl-1H-pyrazol-4-yl)-1,3,5-triazin-2-amine was similar to that of 4-chloro-N-(1-methyl-1H-pyrazol-3-yl)-1,3,5-triazin-2-amine in Example 1, Step 1. Filtration of the crude reaction mixture produced 4-chloro-N-(1-methyl-1H-pyrazol-4-yl)-1,3,5-triazin-2-amine as a purple solid (2.1 g, yield: 30%) and extraction from the aqueous phase of the filtrate produced an additional batch of 4-chloro-N-(1-methyl-1H-pyrazol-4-yl)-1,3,5-triazin-2-amine as a purple solid (2.0 g, yield: 30%; total yield: 60%). ESI-MS (M+H)+: 211.0. 1H NMR (400 MHz, DMSO-d6) δ: 10.81-10.60 (m, 1H), 8.67-8.40 (m, 1H), 8.00-7.79 (m, 1H), 7.58-7.43 (m, 1H), 3.93-3.77 (m, 3H).

2. Synthesis of tert-butyl (2-methyl-4-(4-((1-methyl-1H-pyrazol-4-yl)amino)-1,3,5-triazin-2-yl)benzyl)carbamate

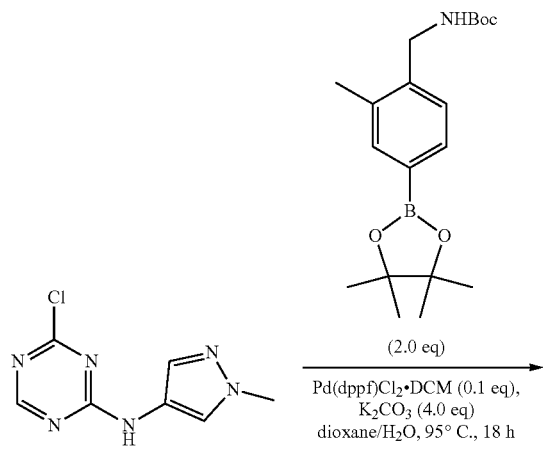

Synthesis of tert-butyl (2-methyl-4-(4-((1-methyl-1H-pyrazol-4-yl)amino)-1,3,5-triazin-2-yl)benzyl)carbamate was similar to that of tert-butyl (2-methyl-4-(4-((1-methyl-1H-pyrazol-3-yl)amino)-1,3,5-triazin-2-yl)benzyl)carbamate in Example 1, Step 5. The residue was purified by silica-gel column chromatography (petroleum ether/EtOAc) to give tert-butyl (2-methyl-4-(4-((1-methyl-1H-pyrazol-4-yl)amino)-1,3,5-triazin-2-yl)benzyl)carbamate as a pale-yellow solid (260 mg, yield: 62%). ESI-MS (M+H)+: 396.3.

3. Synthesis of 4-(4-(aminomethyl)-3-methylphenyl)-N-(1-methyl-1H-pyrazol-4-yl)-1,3,5-triazin-2-amine

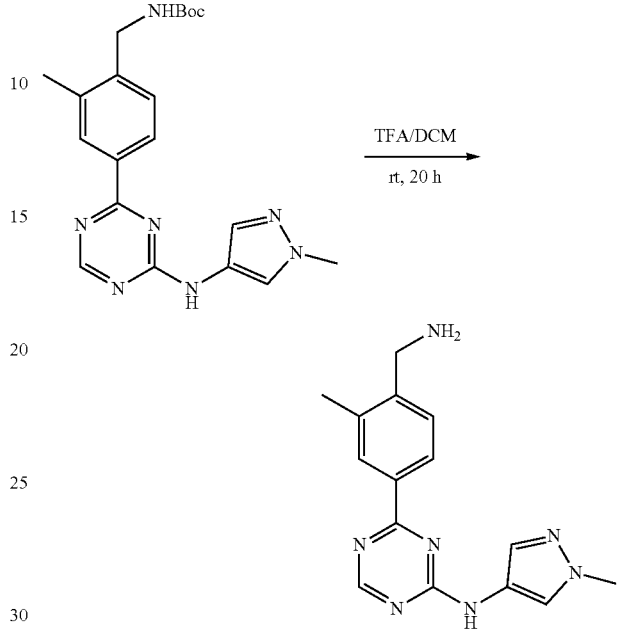

Synthesis of 4-(4-(aminomethyl)-3-methylphenyl)-N-(1-methyl-1H-pyrazol-4-yl)-1,3,5-triazin-2-amine was similar to that of 4-(4-(aminomethyl)-3-methyl)-N-(1-methyl-1H-pyrazol-3-yl)-1,3,5-triazin-2-amine in Example 1, Step 6. The crude material was dissolved in MeOH and loaded onto an SCX column for purification. The product was recovered by washing with a 2 M ammonia solution in MeOH. The filtrate was concentrated in vacuo to give 4-(4-(aminomethyl)-3-methylphenyl)-N-(1-methyl-1H-pyrazol-4-yl)-1,3,5-triazin-2-amine as a white solid (140 mg, yield: 73%). ESI-MS (M+H)+: 296.2.

4. Synthesis of 5-(tert-butyl)-N-(2-methyl-4-(4-((1-methyl-1H-pyrazol-4-yl)amino)-1,3,5-triazin-2-yl)benzyl)-1,2,4-oxadiazole-3-carboxamide (Compound 11)

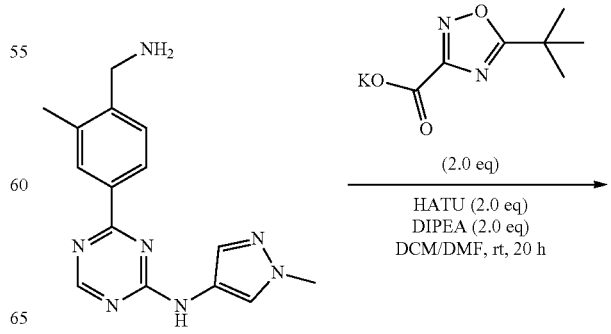

-continued

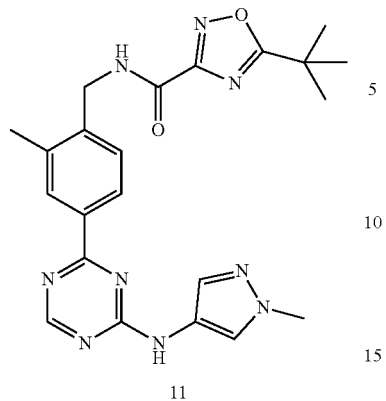

11

-continued

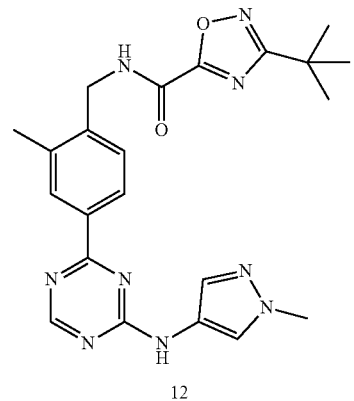

12

Synthesis of 5-(tert-butyl)-N-(2-methyl-4-(4-((1-methyl-1H-pyrazol-4-yl)amino)-1,3,5-triazin-2-yl)benzyl)-1,2,4-oxadiazole-3-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH$_3$CN/H$_2$O with 0.05% TFA/H$_2$O as mobile phase) to give the TFA salt of 5-(tert-butyl)-N-(2-methyl-4-(4-((1-methyl-1H-pyrazol-4-yl)amino)-1,3,5-triazin-2-yl)benzyl)-1,2,4-oxadiazole-3-carboxamide as a yellow solid (8 mg, yield: 12%). ESI-MS (M+H)$^+$: 448.3. $^1$H NMR (400 MHz, DMSO-d$_6$) δ:10.32-10.20 (m, 1H), 9.96-9.78 (m, 1H), 8.87-8.64 (m, 1H), 8.34-8.10 (m, 2H), 8.04-7.90 (m, 1H), 7.71-7.54 (m, 1H), 7.49-7.37 (m, 1H), 4.62-4.47 (m, 2H), 3.99-3.78 (m, 3H), 2.48-2.35 (m, 3H), 1.38 (s, 9H).

Example 12: 3-(tert-butyl)-N-(2-methyl-4-(4-((1-methyl-1H-pyrazol-4-yl)amino)-1,3,5-triazin-2-yl)benzyl)-1,2,4-oxadiazole-5-carboxamide (Compound 12)

Synthesis of 3-(tert-butyl)-N-(2-methyl-4-(4-((1-methyl-1H-pyrazol-4-yl)amino)-1,3,5-triazin-2-yl)benzyl)-1,2,4-oxadiazole-5-carboxamide was similar to that of 5-(tert-butyl)-N-(2-methyl-4-(4-((1-methyl-1H-pyrazol-3-yl)amino)-1,3,5-triazin-2-yl)benzyl)-1,2,4-oxadiazole-3-carboxamide in Example 1, Step 7. The crude product was purified by prep-HPLC (CH$_3$CN/H$_2$O with 0.05% TFA/H$_2$O as mobile phase) to give the TFA salt of 3-(tert-butyl)-N-(2-methyl-4-(4-((1-methyl-1H-pyrazol-4-yl)amino)-1,3,5-triazin-2-yl)benzyl)-1,2,4-oxadiazole-5-carboxamide as a yellow solid (21 mg, yield: 26%). ESI-MS (M+H)$^+$: 448.3. $^1$H NMR (400 MHz, DMSO-d$_6$) δ:10.26 (br s, 1H), 9.51-9.46 (m, 1H), 8.80-8.71 (m, 1H), 8.23-8.15 (m, 2H), 8.00-7.96 (m, 1H), 7.64-7.56 (m, 1H), 7.44-7.39 (m, 1H), 4.55-4.52 (m, 2H), 3.88-3.83 (m, 3H), 2.45-2.42 (m, 3H), 1.44 (s, 9H).

Example 13: 5-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-3-carboxamide (Compound 13)

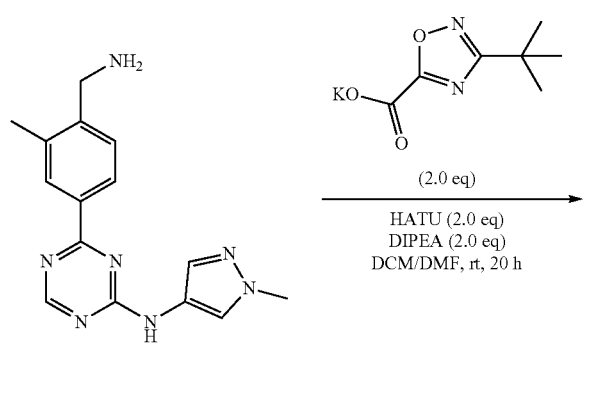

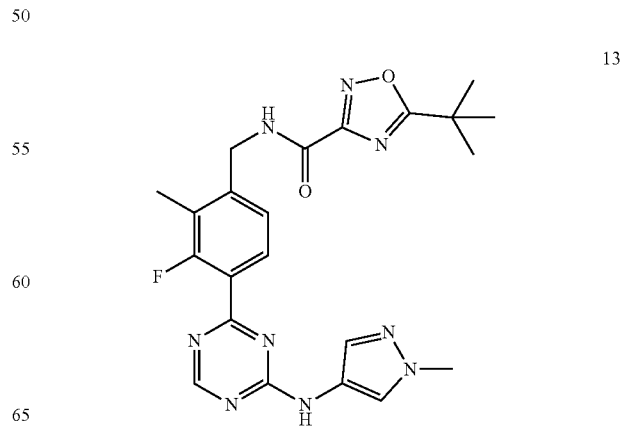

13

1. Synthesis of tert-butyl (3-fluoro-2-methyl-4-(4-((1-methyl-1H-pyrazol-4-yl)amino)-1,3,5-triazin-2-yl)benzyl)carbamate

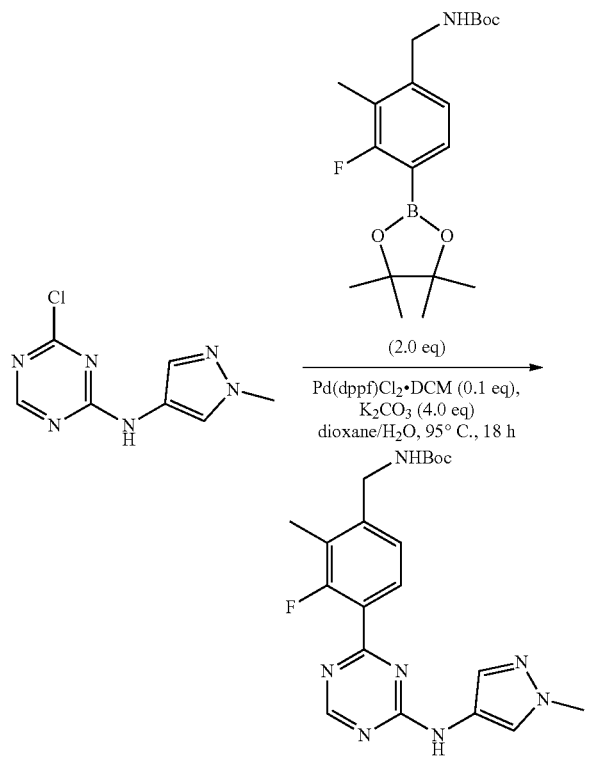

Synthesis of tert-butyl (3-fluoro-2-methyl-4-(4-((1-methyl-1H-pyrazol-4-yl)amino)-1,3,5-triazin-2-yl)benzyl) carbamate was similar to that of tert-butyl (3-fluoro-2-methyl-4-(4-((1-methyl-1H-pyrazol-3-yl)amino)-1,3,5-triazin-2-yl)benzyl)carbamate in Example 9, Step 9. The residue was purified by silica-gel column chromatography (petroleum ether/EtOAc) to give tert-butyl (3-fluoro-2-methyl-4-(4-((1-methyl-1H-pyrazol-4-yl)amino)-1,3,5-triazin-2-yl)benzyl)carbamate as a white solid (220 mg, yield: 42%). ESI-MS (M+H)$^+$: 414.3.

2. Synthesis of 4-(4-(aminomethyl)-2-fluoro-3-methylphenyl)-N-(1-methyl-1H-pyrazol-4-yl)-1,3,5-triazin-2-amine

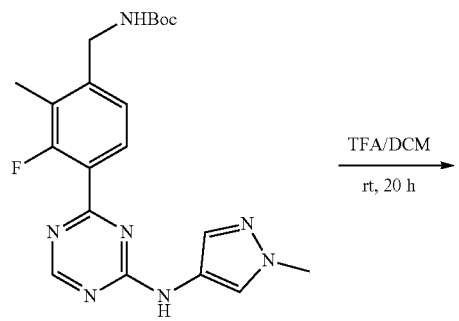

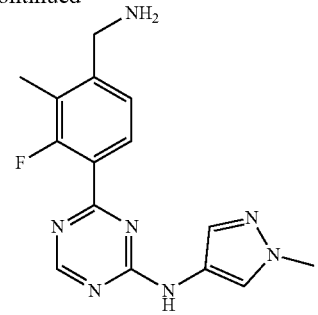

Synthesis of 4-(4-(aminomethyl)-2-fluoro-3-methylphenyl)-N-(1-methyl-1H-pyrazol-4-yl)-1,3,5-triazin-2-amine was similar to that of 4-(4-(aminomethyl)-2-fluoro-3-methylphenyl)-N-(1-methyl-1H-pyrazol-3-yl)-1,3,5-triazin-2-amine in Example 9, Step 10. The crude material was dissolved in MeOH and loaded onto an SCX column for purification. The product was recovered by washing with a 2 M ammonia solution in MeOH. The filtrate was concentrated in vacuo to give 4-(4-(aminomethyl)-2-fluoro-3-methylphenyl)-N-(1-methyl-1H-pyrazol-4-yl)-1,3,5-triazin-2-amine as a yellow solid (200 mg, yield: 99%). ESI-MS (M+H)$^+$: 314.2.

3. Synthesis of 5-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-3-carboxamide (Compound 13)

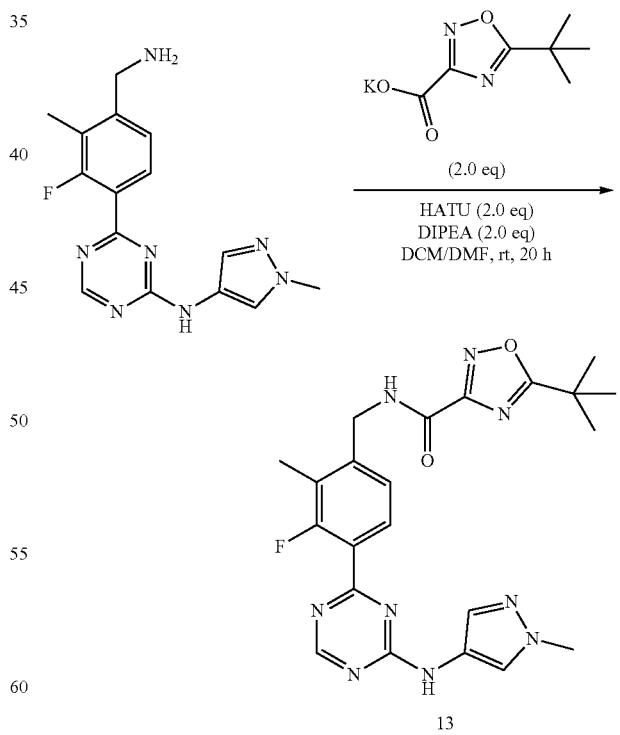

Synthesis of 5-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-3-carboxamide was similar to that of 5-(tert-butyl)-N-(3-fluoro-2-methyl-4-(4-((1-methyl-1H- pyrazol-3-yl)amino)-1,3,5-triazin-2-yl)benzyl)-1,2,4-oxadiazole-3-carboxamide in Example 9, Step 11. The crude product was purified by prep-HPLC (CH₃CN/H₂O with 0.05% TFA/H₂O as mobile phase) to give the TFA salt of 5-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-3-carboxamide as a pale yellow solid (36 mg, yield: 44%). ESI-MS (M+H)⁺: 466.3. ¹H NMR (400 MHz, DMSO-d₆) δ:10.40-10.25 (m, 1H), 9.61-9.46 (m, 1H), 8.88-8.64 (m, 1H), 8.01-7.75 (m, 2H), 7.70-7.51 (m, 1H), 7.33-7.17 (m, 1H), 4.64-4.48 (m, 2H), 3.90-3.76 (m, 3H), 2.40-2.22 (m, 3H), 1.44 (s, 9H).

Example 14: 3-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-5-carboxamide (Compound 14)

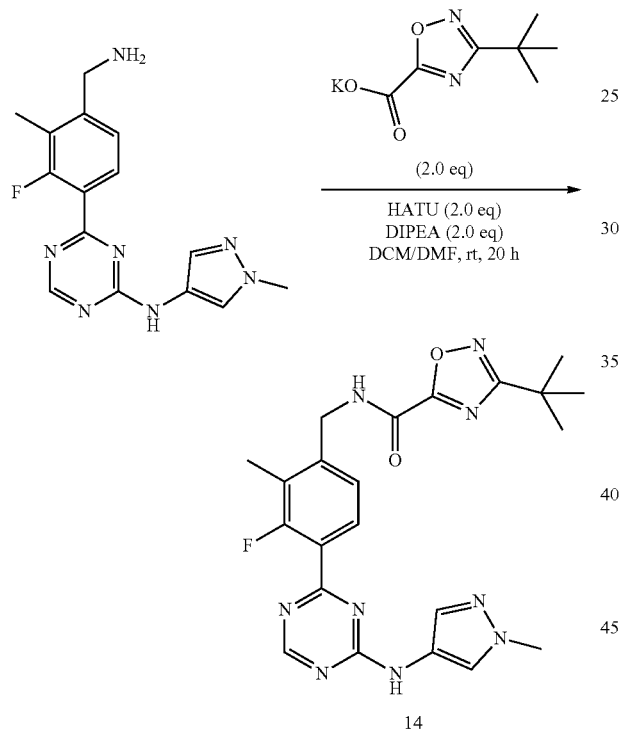

Synthesis of 3-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-5-carboxamide was similar to that of 5-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-3-carboxamide in Example 13. The crude product was purified by prep-HPLC (CH₃CN/H₂O with 0.05% TFA/H₂O as mobile phase) to give the TFA salt of 3-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-5-carboxamide as a yellow solid (16 mg, yield: 19%). ESI-MS (M+H)⁺: 466.3 ¹H NMR (400 MHz, DMSO-d₆) δ: 10.33 (d, J=7.53 Hz, 1H), 9.91-9.87 (m, 1H), 8.81-8.73 (m, 1H), 7.96-7.80 (m, 2H), 7.65-7.55 (m, 1H), 7.31-7.26 (m, 1H), 4.57-4.54 (m, 2H), 3.83 (s, 3H), 2.32 (br d, J=12.8 Hz, 3H), 1.37 (s, 9H).

Example 15: 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide (Compound 15)

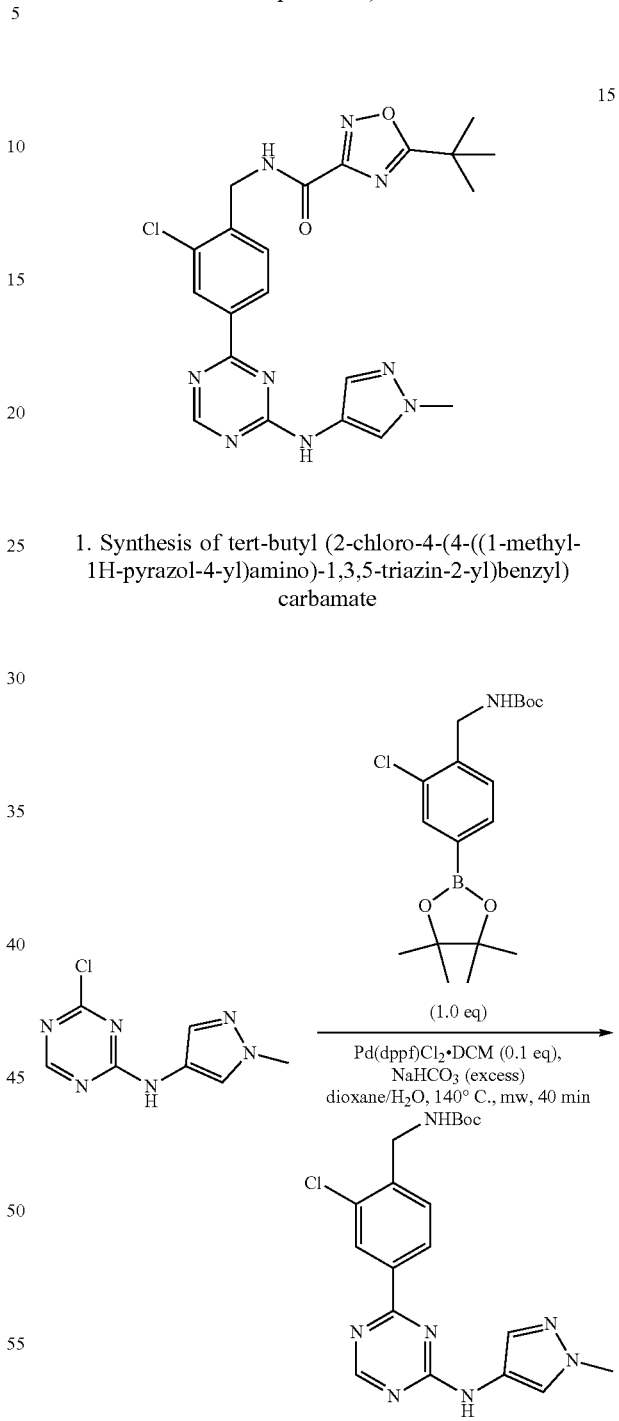

1. Synthesis of tert-butyl (2-chloro-4-(4-((1-methyl-1H-pyrazol-4-yl)amino)-1,3,5-triazin-2-yl)benzyl) carbamate To a suspension of tert-butyl N-[[2-chloro-4-(4,4,5,5-tetramethyl-1,3,2-dioxaborolan-2-yl)phenyl]methyl]carbamate (500 mg, 1.36 mmol) and 4-chloro-N-(1-methylpyrazol-4-yl)-1,3,5-triazin-2-amine (286 mg, 1.36 mmol) in 1,4-dioxane (4 mL) and saturated aqueous NaHCO₃ solution (0.5 mL) was added Pd(dppf)Cl₂.DCM (111 mg, 0.14 mmol). The resulting mixture was heated in the microwave at 140° C. for 40 min. The reaction mixture was diluted with EtOAc (20 mL) and was washed sequentially with H₂O (20 mL) and brine (20 mL). The aqueous layer was extracted with EtOAc (40 mL) and the combined organic extracts were dried (MgSO₄), filtered, and concentrated in vacuo. The crude material was purified by silica-gel column chromatography (EtOAc/heptanes, grading from 20% to 100%) to give tert-butyl (2-chloro-4-(4-((1-methyl-1H-pyrazol-4-yl)amino)-1,3,5-triazin-2-yl)benzyl)carbamate as a yellow foam (130 mg, yield: 23%). ESI-MS (M+H)⁺: 416.1.

2. Synthesis of 4-(4-(aminomethyl)-3-chlorophenyl)-N-(1-methyl-1H-pyrazol-4-yl)-1,3,5-triazin-2-amine

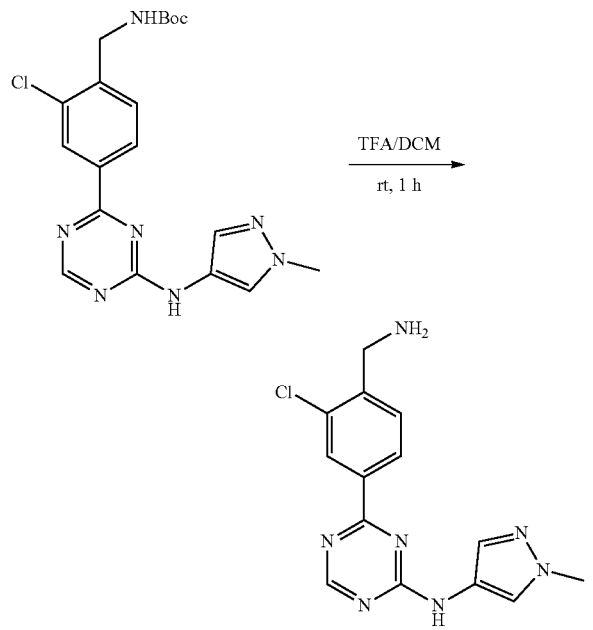

To a suspension of tert-butyl (2-chloro-4-(4-((1-methyl-1H-pyrazol-4-yl)amino)-1,3,5-triazin-2-yl)benzyl)carbamate (130 mg, 0.31 mmol) in DCM (0.5 mL) was added TFA (0.5 mL). The resulting solution was stirred at rt for 1 h and then was concentrated in vacuo. The TFA salt of 4-(4-(aminomethyl)-3-chlorophenyl)-N-(1-methyl-1H-pyrazol-4-yl)-1,3,5-triazin-2-amine was obtained as a yellow solid (134 mg, yield 100%) and was carried forward without further purification. ESI-MS (M+H)⁺: 316.1.

3. Synthesis of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide (Compound 15)

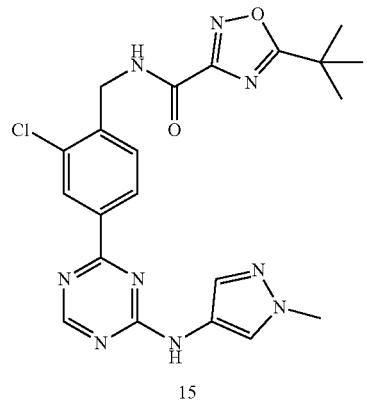

15

To a suspension of the TFA salt of 4-(4-(aminomethyl)-3-chlorophenyl)-N-(1-methyl-1H-pyrazol-4-yl)-1,3,5-triazin-2-amine (45 mg, 105 μmol) and potassium 5-(tert-butyl)-1,2,4-oxadiazole-3-carboxylate (26 mg, 125 μmol) in DMF (1 mL) was added DIPEA (68 mg, 524 μmol, 91 μL), followed by T3P in DMF (80 mg, 125 μmol, 85 μL, 50% purity). The reaction mixture was stirred at rt for 2 h. The reaction mixture was loaded onto a reverse phase column and purified by prep-HPLC (CH₃CN/H₂O with 0.05% TFA/H₂O as mobile phase) to give the TFA salt of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide as a yellow solid (22 mg, yield: 36%). ESI-MS (M+H)⁺: 468.1. ¹H NMR (500 MHz, CD₃OD) δ: 8.74-8.57 (m, 1H), 8.41-8.32 (m, 1H), 8.29-8.23 (m, 1H), 7.99-7.91 (m, 1H), 7.70-7.57 (m, 1H), 7.51 (dd, J=14.7 Hz, J₂=7.9 Hz, 1H), 4.73 (d, J=1.8 Hz, 2H), 3.94-3.85 (m, 3H), 1.51-1.46 (m, 9H).

Example 16: 3-(tert-butyl)-N-(2-chloro-4-(4-((1-methyl-1H-pyrazol-4-yl)amino)-1,3,5-triazin-2-yl)benzyl)-1,2,4-oxadiazole-5-carboxamide (Compound 16)

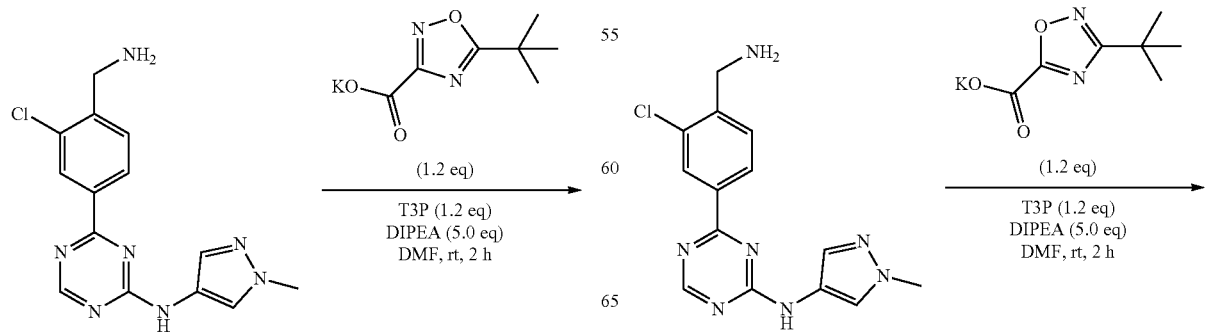

-continued

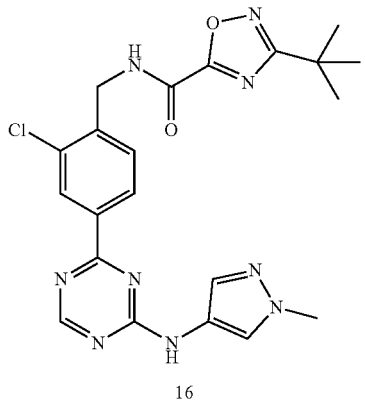

16

Synthesis of 3-(tert-butyl)-N-(2-chloro-4-(4-((1-methyl-1H-pyrazol-4-yl)amino)-1,3,5-triazin-2-yl)benzyl)-1,2,4-oxadiazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 3-(tert-butyl)-N-(2-chloro-4-(4-((1-methyl-1H-pyrazol-4-yl)amino)-1,3,5-triazin-2-yl)benzyl)-1,2,4-oxadiazole-5-carboxamide as a yellow solid (9.3 mg, yield: 9%). ESI-MS (M+H)$^+$: 468.1. $^1$H NMR (500 MHz, CD$_3$OD) δ: 8.80-8.60 (m, 1H), 8.45-8.37 (m, 1H), 8.32 (td, J$_1$=7.9 Hz, J$_2$=2.1 Hz, 1H), 8.04-7.95 (m, 1H), 7.74-7.62 (m, 1H), 7.58 (dd, J$_1$=18.6 Hz, J$_2$=8.2 Hz, 1H), 4.75 (d, J=4.9 Hz, 2H), 3.94-3.86 (m, 3H), 1.42 (s, 9H).

Example 17: 5-(tert-butyl)-N-(4-(4-((1-methyl-1H-pyrazol-4-yl)amino)-1,3,5-triazin-2-yl)-2-(trifluoromethyl)benzyl)-1,2,4-oxadiazole-3-carboxamide (Compound 17)

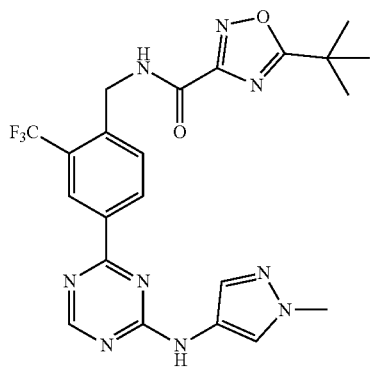

17

1. Synthesis of tert-butyl (4-(4-((1-methyl-1H-pyrazol-4-yl)amino)-1,3,5-triazin-2-yl)-2-(trifluoromethyl)benzyl)carbamate

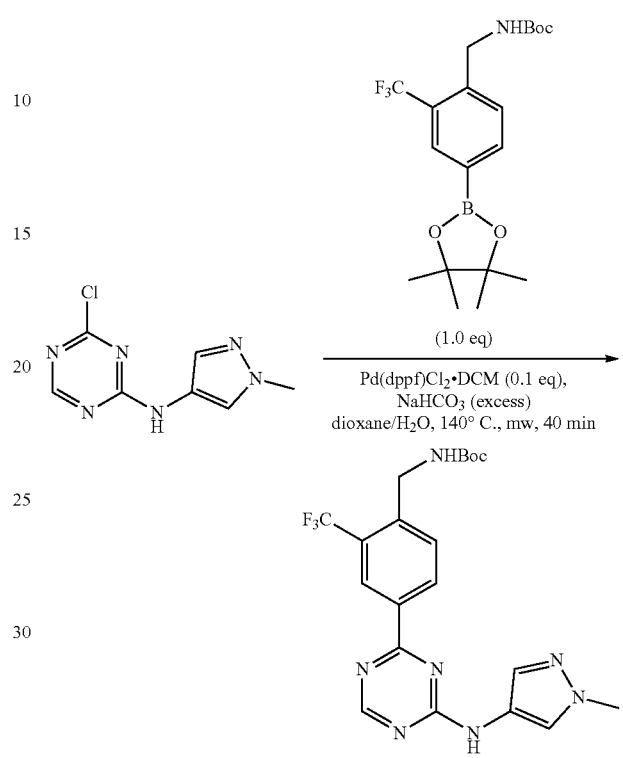

Synthesis of tert-butyl (4-(4-((1-methyl-1H-pyrazol-4-yl)amino)-1,3,5-triazin-2-yl)-2-(trifluoromethyl)benzyl)carbamate was similar to that of tert-butyl (2-chloro-4-(4-((1-methyl-1H-pyrazol-4-yl)amino)-1,3,5-triazin-2-yl)benzyl)carbamate in Example 15, Step 1. The crude material was purified by silica-gel column chromatography (EtOAc/heptanes, grading from 20% to 100%) to give tert-butyl (4-(4-((1-methyl-1H-pyrazol-4-yl)amino)-1,3,5-triazin-2-yl)-2-(trifluoromethyl)benzyl)carbamate as a yellow foam (125 mg, yield: 22%). ESI-MS (M+H)$^+$: 450.0.

2. Synthesis of 4-(4-(aminomethyl)-3-(trifluoromethyl)phenyl)-N-(1-methyl-1H-pyrazol-4-yl)-1,3,5-triazin-2-amine

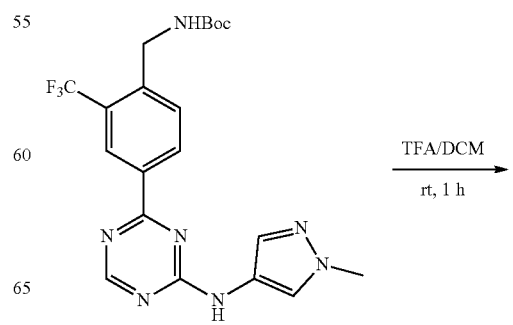

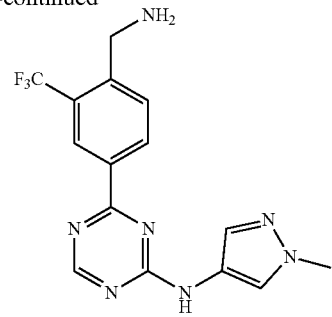

Synthesis of 4-(4-(aminomethyl)-3-(trifluoromethyl)phenyl)-N-(1-methyl-1H-pyrazol-4-yl)-1,3,5-triazin-2-amine was similar to that of 4-(4-(aminomethyl)-3-chlorophenyl)-N-(1-methyl-1H-pyrazol-4-yl)-1,3,5-triazin-2-amine in Example 15, Step 2. The TFA salt of 4-(4-(aminomethyl)-3-(trifluoromethyl)phenyl)-N-(1-methyl-1H-pyrazol-4-yl)-1,3,5-triazin-2-amine was obtained as a yellow solid (134 mg, yield: 100%) and was carried forward without further purification. ESI-MS (M+H)$^+$: 350.0.

3. Synthesis of 5-(tert-butyl)-N-(4-(4-((1-methyl-1H-pyrazol-4-yl)amino)-1,3,5-triazin-2-yl)-2-(trifluoromethyl)benzyl)-1,2,4-oxadiazole-3-carboxamide (Compound 17)

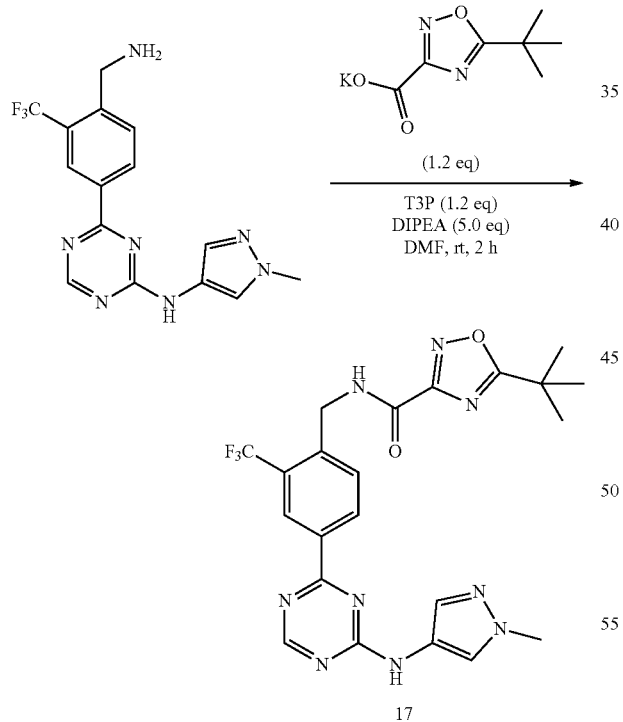

Synthesis of 5-(tert-butyl)-N-(4-(4-((1-methyl-1H-pyrazol-4-yl)amino)-1,3,5-triazin-2-yl)-2-(trifluoromethyl)benzyl)-1,2,4-oxadiazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 5-(tert-butyl)-N-(4-(4-((1-methyl-1H-pyrazol-4-yl)amino)-1,3,5-triazin-2-yl)-2-(trifluoromethyl)benzyl)-1,2,4-oxadiazole-3-carboxamide as a yellow solid (22 mg, yield: 36%). ESI-MS (M+H)$^+$: 502.2. $^1$H NMR (500 MHz, CD$_3$OD) δ: 8.79-8.63 (m, 2H), 8.59 (br d, J=7.9 Hz, 1H), 7.99 (d, J=11.0 Hz, 1H), 7.75-7.69 (m, 1H), 7.68 (s, 1H), 4.90-4.87 (m, 2H), 3.90 (d, J=12.8 Hz, 3H), 1.52-1.47 (m, 9H).

Example 18: 3-(tert-butyl)-N-(4-(4-((1-methyl-1H-pyrazol-4-yl)amino)-1,3,5-triazin-2-yl)-2-(trifluoromethyl)benzyl)-1,2,4-oxadiazole-5-carboxamide (Compound 18)

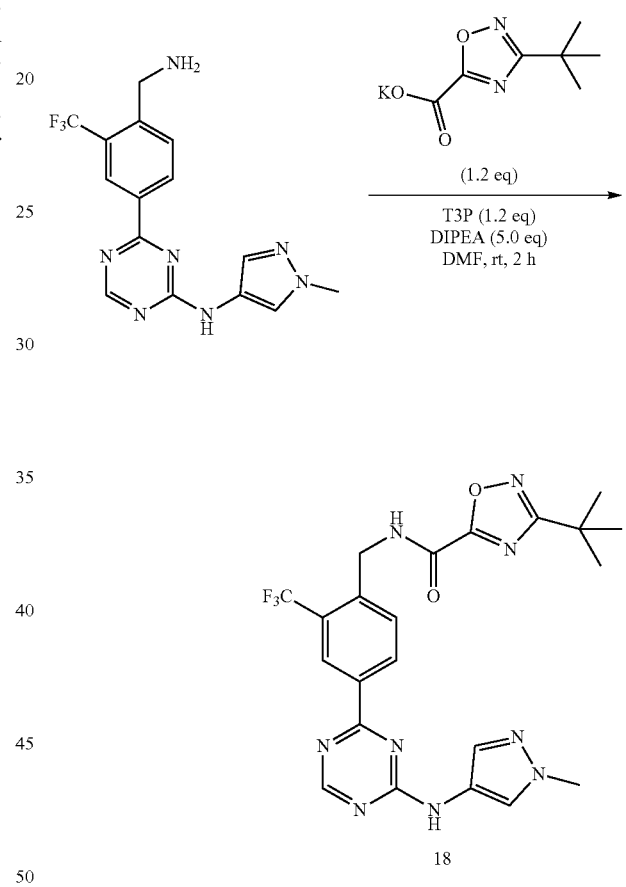

Synthesis of 3-(tert-butyl)-N-(4-(4-((1-methyl-1H-pyrazol-4-yl)amino)-1,3,5-triazin-2-yl)-2-(trifluoromethyl)benzyl)-1,2,4-oxadiazole-5-carboxamide was similar to that of 3-(tert-butyl)-N-(2-chloro-4-(4-((1-methyl-1H-pyrazol-4-yl)amino)-1,3,5-triazin-2-yl)benzyl)-1,2,4-oxadiazole-5-carboxamide in Example 16. The crude product was purified by prep-HPLC (CH$_3$CN/H$_2$O with 0.05% TFA/H$_2$O as mobile phase) to give the TFA salt of 3-(tert-butyl)-N-(4-(4-((1-methyl-1H-pyrazol-4-yl)amino)-1,3,5-triazin-2-yl)-2-(trifluoromethyl)benzyl)-1,2,4-oxadiazole-5-carboxamide as a yellow solid (9.3 mg, yield: 9%). ESI-MS (M+H)$^+$: 502.0. $^1$H NMR (500 MHz, CD$_3$OD) δ: 9.83 (br dd, J$_1$=11.0 Hz, J$_2$=5.5 Hz, 1H), 8.82-8.63 (m, 3H), 8.02 (d, J=4.3 Hz, 1H), 7.80-7.72 (m, 1H), 7.71-7.60 (m, 1H), 4.90-4.86 (m, 2H), 3.91 (d, J=16.5 Hz, 3H), 1.43 (s, 9H).

Example 19: 5-(tert-butyl)-N-(3-fluoro-4-(4-((1-methyl-1H-pyrazol-3-yl)amino)-1,3,5-triazin-2-yl)-2-(trifluoromethyl)benzyl)-1,2,4-oxadiazole-3-carboxamide (Compound 19)

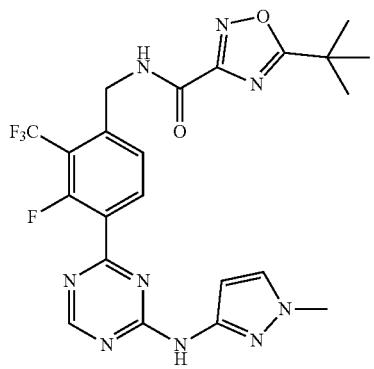

1. Synthesis of 4-bromo-2-fluoro-3-(trifluoromethyl)aniline

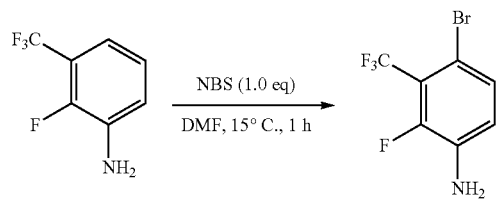 [SMILES: Nc1cccc(C(F)(F)F)c1F ; Nc1ccc(Br)c(C(F)(F)F)c1F]

To a mixture of 2-fluoro-3-(trifluoromethyl)aniline (21.0 g, 117 mmol) in DMF (150 mL) was added NBS (20.9 g, 117 mmol) in portions. The mixture was stirred at 15° C. for 1 h. The reaction mixture was diluted with EtOAc (500 mL) and was washed sequentially with H₂O (500 mL) and brine (500 mL). The organic layer was dried (Na₂SO₄), filtered, and concentrated in vacuo to give the crude product. The crude material was purified by silica-gel column chromatography (petroleum ether/EtOAc, grading from 10:1 to 4:1) to give 4-bromo-2-fluoro-3-(trifluoromethyl)aniline as a yellow oil (29.0 g, yield: 97%). $^1$H NMR: (400 MHz, DMSO-$d_6$) δ: 7.32 (d, J=8.8 Hz, 1H), 6.93 (t, J=8.8 Hz, 1H), 5.81 (br s, 2H).

2. Synthesis of methyl 4-amino-3-fluoro-2-(trifluoromethyl)benzoate

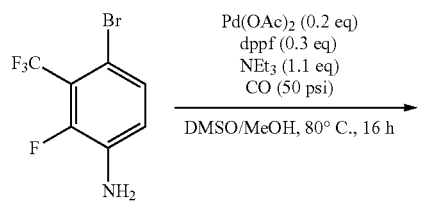

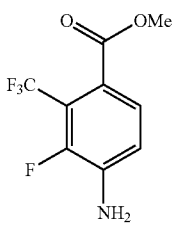

To a solution of 4-bromo-2-fluoro-3-(trifluoromethyl)aniline (29.0 g, 112 mmol) in DMSO (0.4 L) and MeOH (0.4 L) were added Pd(OAc)₂ (5.03 g, 22.4 mmol), dppf (18.6 g, 33.6 mmol) and Et₃N (12.4 g, 123 mmol). The mixture was stirred at 80° C. under a CO (50 Psi) atmosphere for 16 h. The reaction mixture was cooled to 15° C. and MeOH was removed under reduced pressure. The residue was diluted with EtOAc (1 L) and washed sequentially with H₂O (1 L) and brine (1 L). The organic layer was dried (Na₂SO₄), filtered, and concentrated in vacuo to give crude product. The crude material was purified by silica-gel column chromatography (petroleum ether/EtOAc, grading from 10:1 to 3:1) to give methyl 4-amino-3-fluoro-2-(trifluoromethyl)benzoate (20.2 g, yield: 76%) as colorless oil. $^1$H NMR: (400 MHz, DMSO-$d_6$) δ: 7.29 (d, J=8.4 Hz, 1H), 7.00 (t, J=8.4 Hz, 1H), 6.23 (br s, 2H), 3.77 (s, 3H).

3. Synthesis of methyl 4-bromo-3-fluoro-2-(trifluoromethyl)benzoate

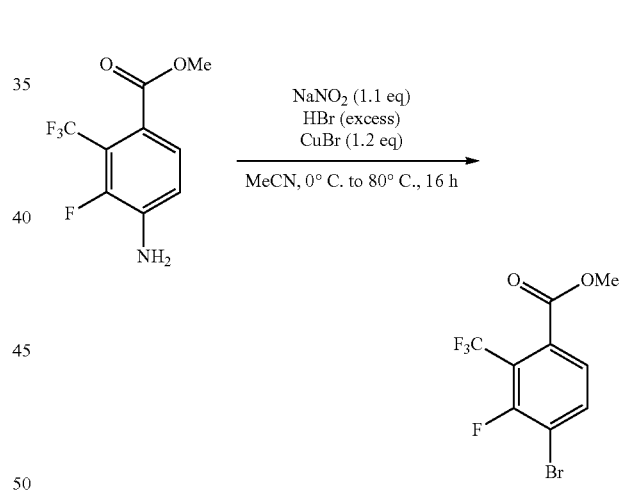

To a solution of methyl 4-amino-3-fluoro-2-(trifluoromethyl)benzoate (20.2 g, 85.2 mmol) in MeCN (100 mL) cooled to 0° C. in an ice-water cooling bath was added HBr (120 mL, 47% w/w) in a drop-wise manner. A solution of NaNO₂ (6.46 g, 93.7 mmol) dissolved in H₂O (20 mL) was then added in a drop-wise manner. After stirring at 0° C. for 20 min, Cu(I)Br (14.7 g, 102 mmol) was added to the reaction mixture in portions. The resulting reaction mixture was heated to 70° C. and stirred at that temperature for 16 h. The reaction mixture was cooled to 15° C., diluted with H₂O (300 mL), and extracted with EtOAc (400 mL×3). The combined organic extracts were washed with brine (800 mL), dried (Na₂SO₄), filtered, and concentrated in vacuo. The crude material was purified by silica-gel column chromatography (petroleum ether/EtOAc, grading from 10:1 to 5:1) to give methyl 4-bromo-3-fluoro-2-(trifluoromethyl)

benzoate as a yellow oil (16.5 g, yield: 64%). ¹H NMR: (400 MHz, CDCl₃) δ: 7.82 (dd, J=8.0, 6.8 Hz, 1H), 7.26 (d, J=8.0 Hz, 1H), 3.93 (s, 3H).

4. Synthesis of (4-bromo-3-fluoro-2-(trifluoromethyl)phenyl)methanol

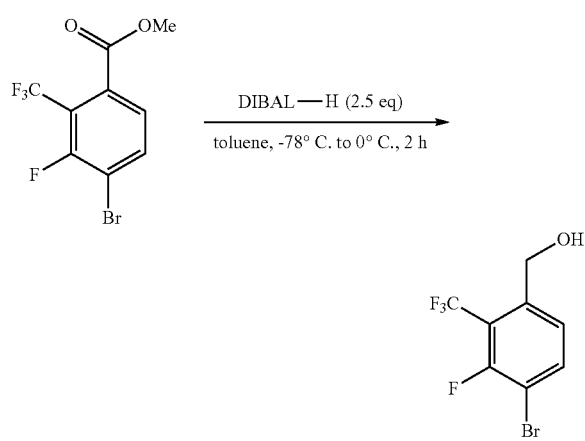

To a solution of methyl 4-bromo-3-fluoro-2-(trifluoromethyl)benzoate (6.00 g, 19.9 mmol) in toluene (50 mL) cooled to −78° C. in a dry ice/acetone cooling bath was added DIBAL-H (49.8 mL, 49.8 mmol, 1 M in toluene). The reaction mixture was then placed in an ice-water cooling bath and was stirred at 0° C. for 2 h. The reaction mixture was re-cooled to −78° C. and MeOH (50 mL) was added to quench the reaction mixture. The quenched reaction mixture was warmed to rt, was diluted with EtOAc (800 mL), and was washed with brine (500 mL×3). The organic layer was dried (Na₂SO₄), filtered, and concentrated in vacuo. The crude material was purified by silica-gel column chromatography (petroleum ether/EtOAc, grading from 10:1 to 4:1) to give (4-bromo-3-fluoro-2-(trifluoromethyl)phenyl)methanol as an off-white solid (5.00 g, yield: 93%). ¹H NMR: (400 MHz, CDCl₃) δ: 7.76 (t, J=8.0 Hz, 1H), 7.45 (d, J=8.4 Hz, 1H), 4.86 (s, 2H), 2.10 (br s, 1H).

5. Synthesis of 4-bromo-3-fluoro-2-(trifluoromethyl)benzyl methanesulfonate

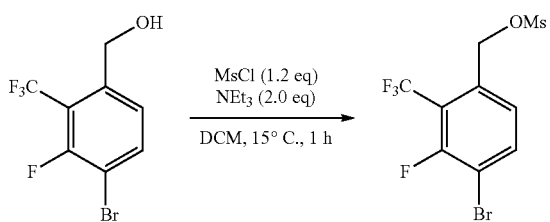 [SMILES: OCc1ccc(Br)c(F)c1C(F)(F)F ; CS(=O)(=O)OCc1ccc(Br)c(F)c1C(F)(F)F]

To a solution of (4-bromo-3-fluoro-2-(trifluoromethyl)phenyl)methanol (5.00 g, 18.3 mmol) in DCM (20 mL) at 0° C. was added Et₃N (3.71 g, 36.6 mmol) and MsCl (2.52 g, 22.0 mmol). The mixture was stirred at 15° C. for 1 h. H₂O (50 mL) was added and the quenched reaction mixture was washed with DCM (100 mL×2). The combined organic extracts were dried (Na₂SO₄), filtered, and concentrated in vacuo to give 4-bromo-3-fluoro-2-(trifluoromethyl)benzyl methanesulfonate as a yellow oil (6.50 g, crude), which was carried forward without further purification.

6. Synthesis of (4-bromo-3-fluoro-2-(trifluoromethyl)phenyl)methanamine

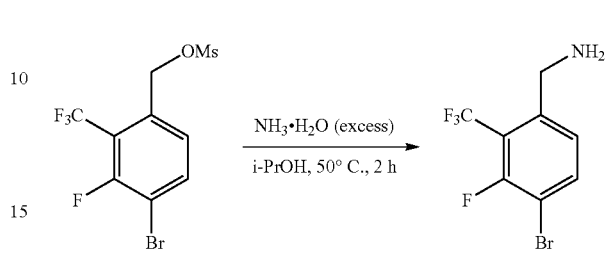

A mixture of 4-bromo-3-fluoro-2-(trifluoromethyl)benzyl methanesulfonate (6.50 g, crude) in NH₃·H₂O (50 mL) and i-PrOH (50 mL) was stirred at 50° C. for 2 h. The reaction mixture was cooled to 15° C. and concentrated in vacuo. H₂O (100 mL) was added to the residue and the mixture was extracted with EtOAc (100 mL×2). The combined organic extracts were washed with brine (200 mL), dried (Na₂SO₄), filtered, and concentrated in vacuo. The crude material was purified by silica-gel column chromatography (petroleum ether/EtOAc, grading from 3:1 to 1:1) to give (4-bromo-3-fluoro-2-(trifluoromethyl)phenyl)methanamine as a yellow oil (3.50 g, 2-step yield: 70%). ¹H NMR: (400 MHz, CDCl₃) δ: 7.72 (t, J=8.0 Hz, 1H), 7.31 (d, J=8.4 Hz, 1H), 4.01 (s, 2H), 1.52 (br s, 2H).

7. Synthesis of tert-butyl (4-bromo-3-fluoro-2-(trifluoromethyl)benzyl)carbamate

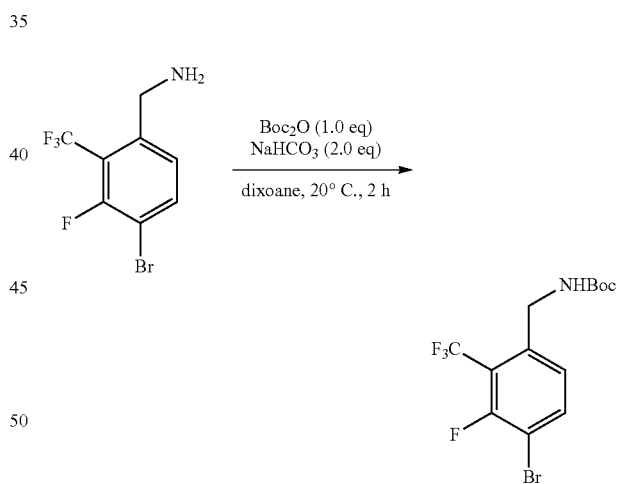

To a solution of (4-bromo-3-fluoro-2-(trifluoromethyl)phenyl)methanamine (3.50 g, 12.9 mmol) in 1,4-dioxane (20 mL) and H₂O (5 mL) was added Boc₂O (2.81 g, 12.9 mmol) and NaHCO₃ (2.16 g, 25.7 mmol). The mixture was stirred at 20° C. for 2 h. The reaction mixture was diluted with H₂O (100 mL) and was extracted with EtOAc (150 mL×2). The combined organic extracts were washed with brine (200 mL), dried (Na₂SO₄), filtered, and concentrated in vacuo. The crude material was purified by silica-gel column chromatography (petroleum ether/EtOAc, grading from 50:1 to 10:1) to give tert-butyl (4-bromo-3-fluoro-2-(trifluoromethyl)benzyl)-carbamate as a colorless oil (3.80 g, yield: 79%). ¹H NMR: (400 MHz, CDCl₃) δ: 7.71 (t, J=7.6 Hz, 1H), 7.28 (d, J=6.0 Hz, 1H), 4.98 (br s, 1H), 4.45 (d, J=5.2 Hz, 2H), 1.45 (s, 9H).

8. Synthesis of tert-butyl (3-fluoro-4-(4,4,5,5-tetramethyl-1,3,2-dioxaborolan-2-yl)-2-(trifluoromethyl)benzyl)carbamate

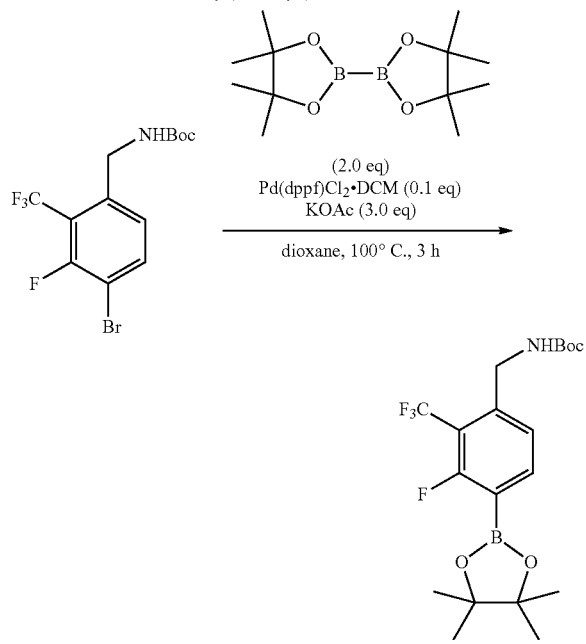

To a solution of tert-butyl (4-bromo-3-fluoro-2-(trifluoromethyl)benzyl)carbamate (3.80 g, 10.2 mmol) and bis(pinacolato)diboron (5.19 g, 20.4 mmol) in 1,4-dioxane (50 mL) were added Pd(dppf)Cl$_2$·DCM (833 mg, 1.02 mmol) and KOAc (3.01 g, 30.6 mmol). The mixture was heated to 100° C. under N$_2$ and stirred at that temperature for 3 h. The reaction mixture was cooled to 15° C. and was diluted with EtOAc (200 mL). The organic phase was washed sequentially with H$_2$O (200 mL) and brine (200 mL). The organic layer was dried (Na$_2$SO$_4$), filtered, and concentrated in vacuo. The crude material was purified by silica-gel column chromatography (petroleum ether/EtOAc, 3:1) to give tert-butyl (3-fluoro-4-(4,4,5,5-tetramethyl-1,3,2-dioxaborolan-2-yl)-2-(trifluoromethyl)benzyl)carbamate as a yellow solid (5.20 g, impure), which was carried forward without further purification.

9. Synthesis of tert-butyl (3-fluoro-4-(4-((1-methyl-1H-pyrazol-3-yl)amino)-1,3,5-triazin-2-yl)-2-(trifluoromethyl)benzyl)carbamate

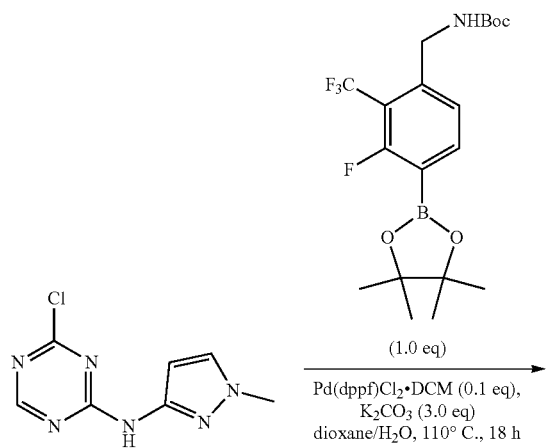

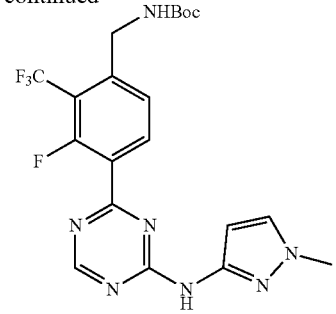

A mixture of 4-chloro-N-(1-methylpyrazol-3-yl)-1,3,5-triazin-2-amine (200 mg, 0.95 mmol), tert-butyl (3-fluoro-4-(4,4,5,5-tetramethyl-1,3,2-dioxaborolan-2-yl)-2-(trifluoromethyl)benzyl)carbamate (398 mg, 0.95 mmol), Pd(dppf)Cl$_2$.DCM (70 mg, 0.09 mmol) and K$_2$CO$_3$ (394 mg, 2.85 mmol) in 2.2 mL of 1,4-dioxane/H$_2$O (10:1) was stirred at 110° C. for 18 h under an N$_2$ atmosphere. After cooling to rt, the reaction mixture was filtered through Celite® and extracted with DCM (10 mL). The phases were separated and the aqueous phase was extracted again with DCM (10 mL). The combined organic extracts were dried (Na$_2$SO$_4$), filtered, and concentrated in vacuo. The residue was purified by silica-gel column chromatography (heptanes/EtOAc) to give tert-butyl (3-fluoro-4-(4-((1-methyl-1H-pyrazol-3-yl)amino)-1,3,5-triazin-2-yl)-2-(trifluoromethyl)benzyl)carbamate as a pale-yellow solid (102 mg, yield: 23%). ESI-MS (M+H)$^+$: 468.2.

10. Synthesis of 4-[4-(aminomethyl)-2-fluoro-3-(trifluoromethyl)phenyl]-3-fluoro-N-(1-methylpyrazol-3-yl)pyridin-2-amine

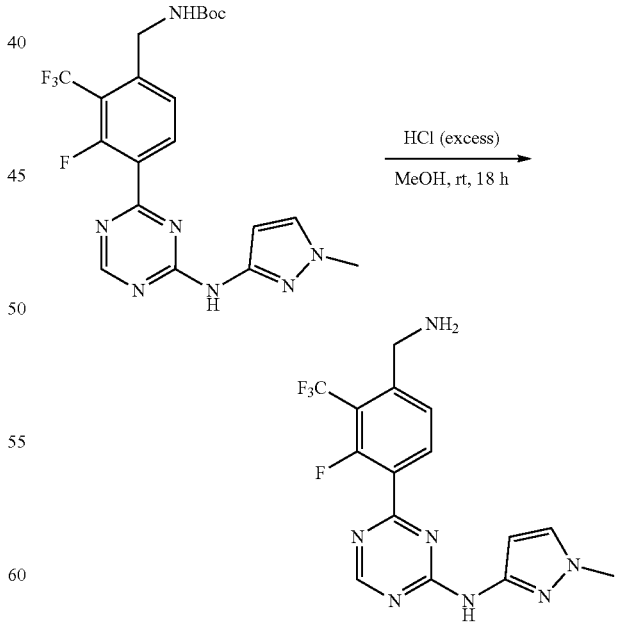

To a solution of tert-butyl (3-fluoro-4-(4-((1-methyl-1H-pyrazol-3-yl)amino)-1,3,5-triazin-2-yl)-2-(trifluoromethyl)benzyl)carbamate (52 mg, 0.11 mmol) in MeOH (2 mL) was added HCl (4 M solution in 1,4-dioxane, 0.11 mL) and the reaction mixture continued to stir at rt for 18 h. The reaction mixture was concentrated in vacuo to give the HCl salt of 4-[4-(aminomethyl)-2-fluoro-3-(trifluoromethyl)phenyl]-3-fluoro-N-(1-methylpyrazol-3-yl)pyridin-2-amine (55 mg, 0.13 mmol) and the crude material was carried forward without further purification. ESI-MS (M+H)+: 384.1.

11. Synthesis of 5-(tert-butyl)-N-(3-fluoro-4-(4-((1-methyl-1H-pyrazol-3-yl)amino)-1,3,5-triazin-2-yl)-2-(trifluoromethyl)benzyl)-1,2,4-oxadiazole-3-carboxamide (Compound 19)

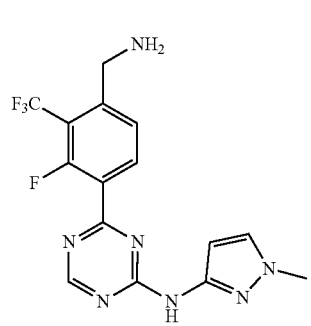

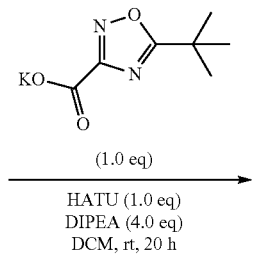

(1.0 eq)
→
HATU (1.0 eq)
DIPEA (4.0 eq)
DCM, rt, 20 h

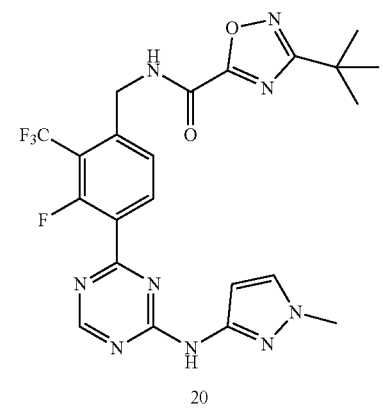

19

To a solution of 4-(4-(aminomethyl)-2-fluoro-3-(trifluoromethyl)phenyl)-N-(1-methyl-1H-pyrazol-3-yl)-1,3,5-triazin-2-amine (20 mg, 0.54 µmol) and potassium 5-(tert-butyl)-1,2,4-oxadiazole-3-carboxylate (11 mg, 0.54 µmol) in DCM (2 mL) was added DIPEA (28 mg, 0.22 mmol, 38 µL). The white suspension was stirred at rt for 10 minutes before HATU (21 mg, 0.54 µmol) was added. The reaction mixture continued to stir at rt for 20 h. The reaction mixture was concentrated in vacuo and the crude material was purified by prep-HPLC (CH3CN/H2O with 0.05% TFA/H2O as mobile phase) to give the TFA salt of 5-(tert-butyl)-N-(3-fluoro-4-(4-((1-methyl-1H-pyrazol-3-yl)amino)-1,3,5-triazin-2-yl)-2-(trifluoromethyl)benzyl)-1,2,4-oxadiazole-3-carboxamide as a yellow solid (5.3 mg, yield: 18%). ESI-MS (M+H)+: 520.1 1H NMR (400 MHz, CDCl3) δ: 11.15 (br s, 1H), 8.84 (br s, 1H), 8.58-7.98 (m, 2H), 7.42 (br s 2H), 7.12-6.26 (m, 1H), 4.99-4.80 (m, 2H), 3.87 (s, 3H), 1.48 (s, 9H).

Example 20: 3-(tert-butyl)-N-(3-fluoro-4-(4-((1-methyl-1H-pyrazol-3-yl)amino)-1,3,5-triazin-2-yl)-2-(trifluoromethyl)benzyl)-1,2,4-oxadiazole-5-carboxamide (Compound 20)

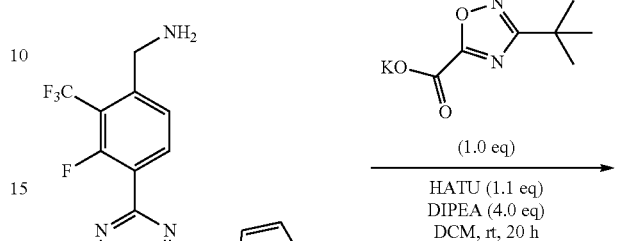

20

Synthesis of 3-(tert-butyl)-N-(3-fluoro-4-(4-((1-methyl-1H-pyrazol-3-yl)amino)-1,3,5-triazin-2-yl)-2-(trifluoromethyl)benzyl)-1,2,4-oxadiazole-5-carboxamide was similar to that of 5-(tert-butyl)-N-(3-fluoro-4-(4-((1-methyl-1H-pyrazol-3-yl)amino)-1,3,5-triazin-2-yl)-2-(trifluoromethyl)benzyl)-1,2,4-oxadiazole-3-carboxamide in Example 19. The crude product was purified by prep-HPLC (CH3CN/H2O with 0.05% TFA/H2O as mobile phase) to give the TFA salt of 3-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-5-carboxamide as a yellow solid (9.3 mg, yield: 5%). ESI-MS (M+H)+: 520.1 1H NMR (400 MHz, CD3OD) δ: 9.99-9.71 (m, 1H), 8.77 (br t, J=8.3 Hz, 1H), 8.55-8.27 (m, 1H), 7.58-7.48 (m, 2H), 6.91-6.62 (m, 1H), 6.29-6.02 (m, 1H), 4.85-4.73 (m, 2H), 4.04-3.78 (m, 3H), 1.44 (s, 9H).

Example 21: 5-(tert-butyl)-N-(2-chloro-3-fluoro-4-(4-((1-methyl-1H-pyrazol-3-yl)amino)-1,3,5-triazin-2-yl)benzyl)-1,2,4-oxadiazole-3-carboxamide (Compound 21)

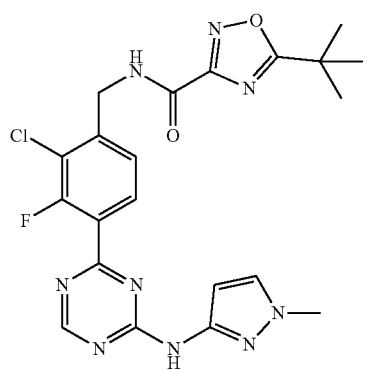

1. Synthesis of 4-bromo-3-chloro-2-fluoroaniline

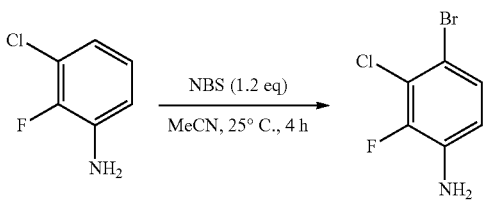 [SMILES: Nc1cccc(Cl)c1F ; Nc1ccc(Br)c(Cl)c1F]

To a mixture of 3-chloro-2-fluoroaniline (18.0 g, 124 mmol) in MeCN (100 mL) was added a solution of NBS (26.4 g, 148 mmol) in MeCN (100 mL) in a dropwise manner at 25° C. The mixture was stirred at 25° C. for 4 h. The reaction mixture was concentrated in vacuo to give the crude product. The crude material was purified by silica-gel column chromatography (petroleum ether/EtOAc, 50:1) to give 4-bromo-3-chloro-2-fluoroaniline as a brown oil (18.0 g, yield: 65%). $^1$H NMR: (400 MHz, CD$_3$OD) δ: 7.13 (dd, J$_1$=8.8 Hz, J$_2$=2.0 Hz, 1H), 6.66 (t, J=8.4 Hz, 1H).

2. Synthesis of N-(4-bromo-3-chloro-2-fluorophenyl)acetamide

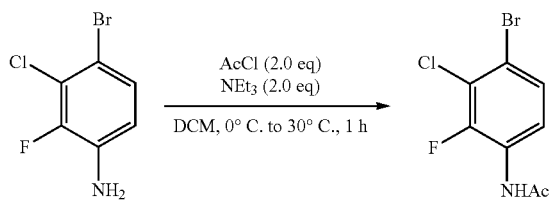

To a solution of 4-bromo-3-chloro-2-fluoroaniline (18.0 g, 80 mmol) in DCM (150 mL) in an ice-water cooling bath at 0° C. was added AcCl (12.6 g, 160 mmol) in a dropwise manner, followed by Et$_3$N (16.2 g, 160 mmol). The mixture was then stirred at 30° C. for 1 h. The reaction mixture was poured in H$_2$O (200 mL) and extracted with DCM (100 mL×2). The combined organic extracts were washed with brine (400 mL), dried (Na$_2$SO$_4$), filtered, and concentrated in vacuo to give crude N-(4-bromo-3-chloro-2-fluorophenyl)acetamide (20.0 g, crude). The crude material was carried forward without further purification. $^1$H NMR: (400 MHz, CD$_3$OD) δ: 7.85 (t, J=8.8 Hz, 1H), 7.44 (d, J=10.0 Hz, 1H), 2.17 (s, 3H).

3. Synthesis of N-(3-chloro-4-cyano-2-fluorophenyl)acetamide

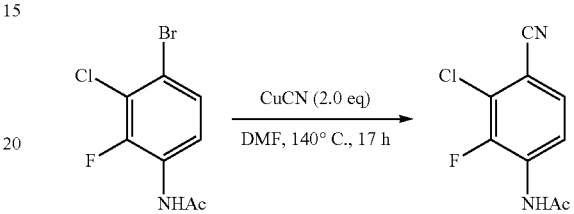

A solution of N-(4-bromo-3-chloro-2-fluorophenyl)acetamide (20.0 g, 75 mmol) and Cu(I)CN (13.4 g, 150 mmol) in DMF (200 mL) was heated to 140° C. and stirred at that temperature under N$_2$ for 17 h. The reaction mixture was poured in H$_2$O (500 mL) and extracted with EtOAc (200 mL×3). The combined organic extracts were washed with brine (500 mL), dried (Na$_2$SO$_4$), filtered, and concentrated in vacuo to give crude N-(3-chloro-4-cyano-2-fluorophenyl)acetamide as a brown solid (14.0 g, yield: 88%). The crude material was carried forward without further purification. $^1$H NMR: (400 MHz, CD$_3$OD) δ: 8.30 (t, J=7.2 Hz, 1H), 7.57 (d, J=8.0 Hz, 1H), 2.19 (s, 3H).

4. Synthesis of 4-amino-2-chloro-3-fluorobenzonitrile

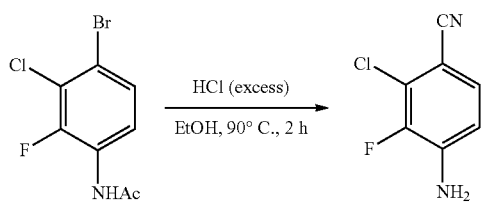

To a solution of N-(3-chloro-4-cyano-2-fluorophenyl)acetamide (8.0 g, 38 mmol) in EtOH (100 mL) was added concentrated HCl solution (12N, 50 mL). The mixture was heated at 90° C. for 2 h. The reaction mixture was concentrated in vacuo and the resulting white solid was dissolved in EtOAc (100 mL). The pH of the solution was adjusted to pH=7 with saturated aqueous Na$_2$CO$_3$ solution (100 mL) and the layers were separated. The organic phase was dried (Na$_2$SO$_4$), filtered, and concentrated in vacuo. The crude material was purified by silica-gel column chromatography (petroleum ether/EtOAc, 2:1) to give 4-amino-2-chloro-3-fluorobenzonitrile as a yellow solid (5.0 g, yield: 78%). $^1$H NMR: (400 MHz, CDCl$_3$) δ: 7.23 (dd, J$_1$=8.8 Hz, J$_2$=1.6 Hz, 1H), 6.66 (t, J=8.4 Hz, 1H), 4.36 (s, 2H).

5. Synthesis of 2-chloro-3-fluoro-4-iodobenzonitrile

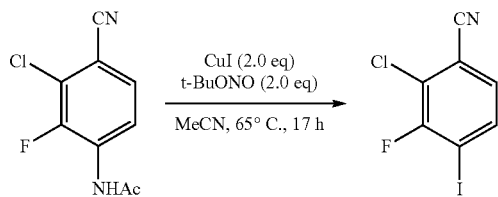

To a suspension of Cu(I)I (11.2 g, 59 mmol) in MeCN (50 mL) was added tert-butyl nitrite (6.0 g, 59 mmol) at room temperature. The reaction mixture was heated to 65° C. and a solution of 4-amino-2-chloro-3-fluorobenzonitrile (5.0 g, 29 mmol) in MeCN (50 mL) was added dropwise at 65° C. over 1 h. The mixture was stirred at 65° C. for 17 h and then was concentrated in vacuo. The crude material was purified by silica-gel column chromatography (petroleum ether/EtOAc, 2:1) to give 2-chloro-3-fluoro-4-iodobenzonitrile as a yellow solid (6.0 g, yield: 73%). $^1$H NMR: (400 MHz, CDCl$_3$) δ: 7.78 (s, 1H), 7.20 (d, J=7.2 Hz, 1H).

6. Synthesis of (2-chloro-3-fluoro-4-iodophenyl)methanamine

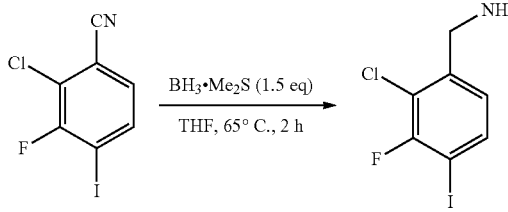

To a solution of 2-chloro-3-fluoro-4-iodobenzonitrile (6.0 g, 21 mmol) in THF (50 mL) was added BH$_3$.Me$_2$S (3.2 mL, 32 mmol, 10 M) at 30° C. The mixture was heated to 65° C. and stirred at that temperature for 2 h. MeOH (5 mL) was added and the reaction mixture was concentrated in vacuo. The crude material was purified by silica-gel column chromatography (petroleum ether/EtOAc, grading from 5:1 to 2:1) to give (2-chloro-3-fluoro-4-iodophenyl)methanamine as a yellow solid (3.5 g, yield: 58%). $^1$H NMR: (400 MHz, DMSO-d$_6$) δ: 7.79 (dd, J$_1$=8.4 Hz, J$_2$=6.4 Hz, 1H), 7.24 (d, J=8.0 Hz, 1H), 3.77 (s, 2H).

7. Synthesis of tert-butyl (2-chloro-3-fluoro-4-iodobenzyl)carbamate

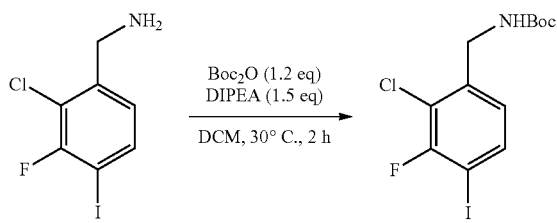

To a solution of (2-chloro-3-fluoro-4-iodophenyl)methanamine (3.5 g, 12 mmol) in DCM (50 mL) was added DIPEA (2.4 g, 18 mmol) and Boc$_2$O (3.2 g, 15 mmol). The mixture was heated at 30° C. for 2 h. The mixture was concentrated in vacuo and the crude material was purified by silica-gel column chromatography (petroleum ether/EtOAc, 10:1) to give tert-butyl (2-chloro-3-fluoro-4-iodobenzyl)carbamate as a yellow oil (4.5 g, yield: 95%). $^1$H NMR: (400 MHz, DMSO-d$_6$) δ: 7.77 (dd, J$_1$=8.0 Hz, J$_2$=6.4 Hz, 1H), 7.48 (t, J=4.8 Hz, 1H), 6.92 (d, J=8.4 Hz, 1H), 4.14 (d, J=6.0 Hz, 2H), 1.36 (s, 9H).

8. Synthesis of tert-butyl (2-chloro-3-fluoro-4-(4,4,5,5-tetramethyl-1,3,2-dioxaborolan-2-yl)benzyl)carbamate

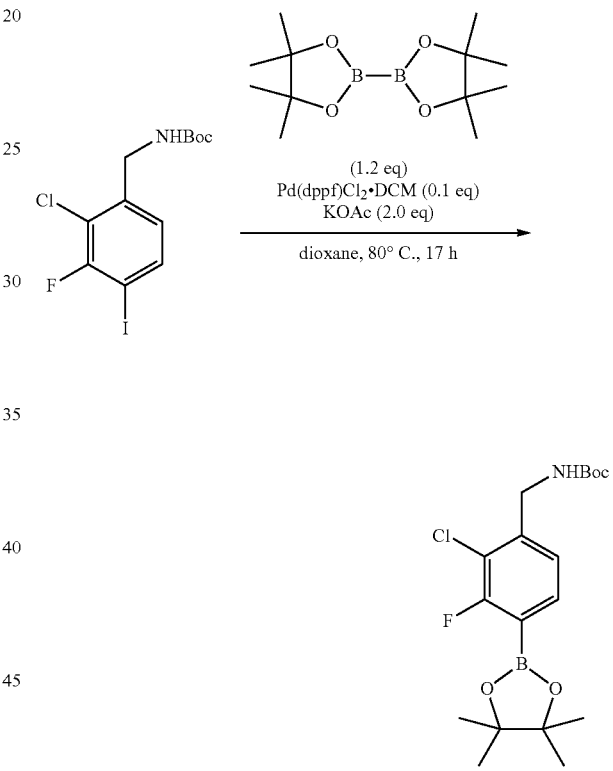

To a solution of tert-butyl (2-chloro-3-fluoro-4-iodobenzyl)carbamate (3.5 g, 9.1 mmol) in 1,4-dioxane (50 mL) under an N$_2$ atmosphere was added bis(pinacolato)diboron (2.8 g, 10.9 mmol), KOAc (1.8 g, 18.2 mmol), and Pd(dppf)Cl$_2$.DCM (734 mg, 0.9 mmol) sequentially. The mixture was heated to 80° C. with stirring for 17 h under N$_2$. The mixture was poured into H$_2$O (100 mL) and extracted with DCM (50 mL×3). The combined organic extracts were washed with brine (100 mL), dried (Na$_2$SO$_4$), filtered, and concentrated in vacuo. The crude material, tert-butyl (2-chloro-3-fluoro-4-(4,4,5,5-tetramethyl-1,3,2-dioxaborolan-2-yl)benzyl)carbamate, was used for the next step without further purification. ESI-MS (M-t-Bu)$^+$: 329.9.

9. Synthesis of tert-butyl (2-chloro-3-fluoro-4-((1-methyl-1H-pyrazol-3-yl)amino)-1,3,5-triazin-2-yl)benzyl)carbamate

10. Synthesis of 4-(4-(aminomethyl)-3-chloro-2-fluorophenyl)-N-(1-methyl-1H-pyrazol-3-yl)-1,3,5-triazin-2-amine

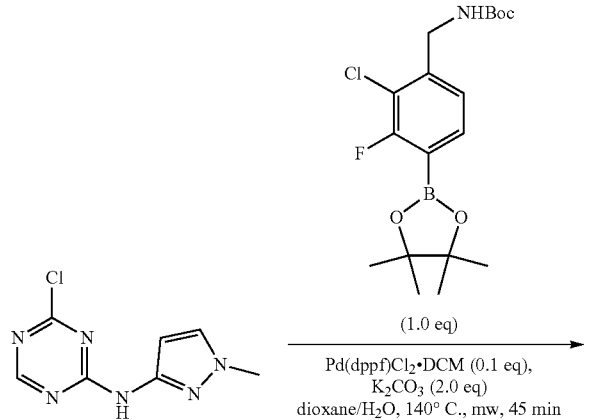

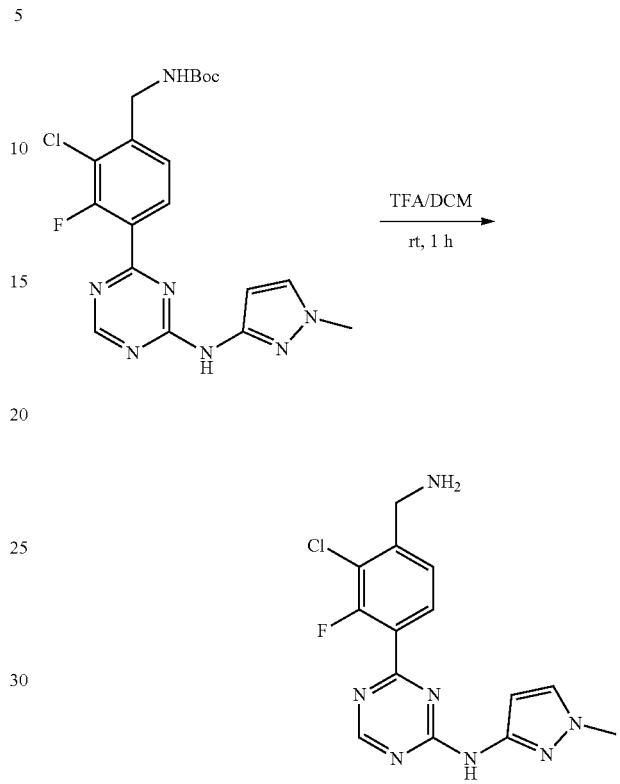

A suspension of tert-butyl (2-chloro-3-fluoro-4-(4,4,5,5-tetramethyl-1,3,2-dioxaborolan-2-yl)benzyl)carbamate (500 mg, 1.3 mmol), 4-chloro-N-(1-methyl-1H-pyrazol-3-yl)-1,3,5-triazin-2-amine (273 mg, 1.3 mmol), and K$_2$CO$_3$ (358 mg, 2.6 mmol) in 1,4-dioxane (4 mL) and H$_2$O (0.4 mL) was degassed with N$_2$ for 5 min. Then Pd(dppf)Cl$_2$.DCM (106 mg, 0.13 mmol) was added. The resulting mixture was heated in the microwave at 140° C. for 45 min. The reaction mixture was diluted with EtOAc (20 mL) and was washed sequentially with H$_2$O (20 mL) and brine (20 mL). The aqueous layer was extracted with EtOAc (40 mL) and the combined organic extracts were dried (MgSO$_4$), filtered, and concentrated in vacuo. The crude material was purified by silica-gel column chromatography (EtOAc/heptanes, grading from 20% to 100%) to give tert-butyl (2-chloro-3-fluoro-4-(4-((1-methyl-1H-pyrazol-3-yl)amino)-1,3,5-triazin-2-yl)benzyl)carbamate as a pale yellow solid (244 mg, yield: 43%). ESI-MS (M+H)$^+$: 434.1.

Synthesis of 4-(4-(aminomethyl)-3-chloro-2-fluorophenyl)-N-(1-methyl-1H-pyrazol-3-yl)-1,3,5-triazin-2-amine was similar to that of 4-(4-(aminomethyl)-3-chlorophenyl)-N-(1-methyl-1H-pyrazol-4-yl)-1,3,5-triazin-2-amine in Example 15, Step 2. The TFA salt of 4-(4-(aminomethyl)-3-chloro-2-fluorophenyl)-N-(1-methyl-1H-pyrazol-3-yl)-1,3,5-triazin-2-amine was obtained as a yellow solid (248 mg, yield: 100%) and was carried forward without further purification. ESI-MS (M+H)$^+$: 334.0.

11. Synthesis of 5-(tert-butyl)-N-(2-chloro-3-fluoro-4-(4-((1-methyl-1H-pyrazol-3-yl)amino)-1,3,5-triazin-2-yl)benzyl)-1,2,4-oxadiazole-3-carboxamide (Compound 21)

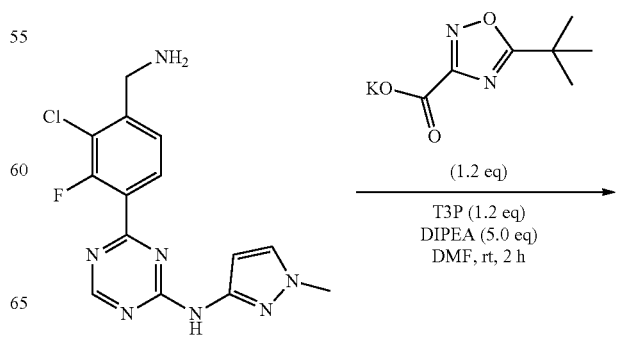

-continued

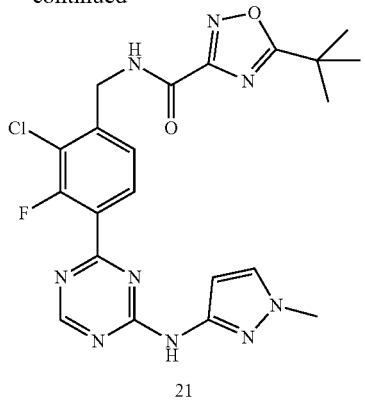

21

Synthesis of 5-(tert-butyl)-N-(2-chloro-3-fluoro-4-(4-((1-methyl-1H-pyrazol-3-yl)amino)-1,3,5-triazin-2-yl)benzyl)-1,2,4-oxadiazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 5-(tert-butyl)-N-(2-chloro-3-fluoro-4-(4-((1-methyl-1H-pyrazol-3-yl)amino)-1,3,5-triazin-2-yl)benzyl)-1,2,4-oxadiazole-3-carboxamide as a yellow solid (18 mg, yield: 22%). ESI-MS (M+H)$^+$: 486.1. $^1$H NMR (500 MHz, CD$_3$OD) δ: 8.73 (br s, 1H), 8.17-7.86 (m, 1H), 7.69-7.49 (m, 1H), 7.46-7.31 (m, 1H), 6.92-6.61 (m, 1H), 6.28-6.05 (m, 1H), 4.76 (s, 2H), 3.99-3.74 (m, 3H), 1.49 (s, 9H).

Example 22: 3-(tert-butyl)-N-(2-chloro-3-fluoro-4-(4-((1-methyl-1H-pyrazol-3-yl)amino)-1,3,5-triazin-2-yl)benzyl)-1,2,4-oxadiazole-5-carboxamide (Compound 22)

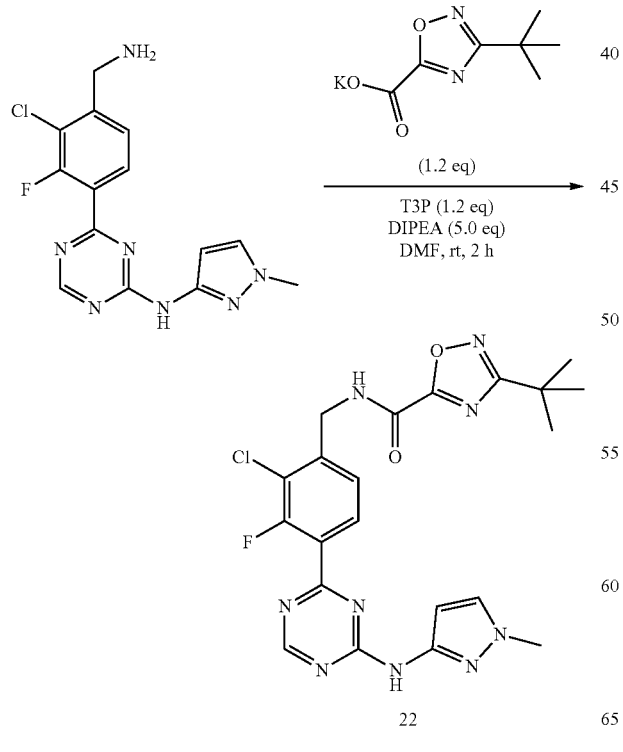

22

Synthesis of 3-(tert-butyl)-N-(2-chloro-3-fluoro-4-(4-((1-methyl-1H-pyrazol-3-yl)amino)-1,3,5-triazin-2-yl)benzyl)-1,2,4-oxadiazole-5-carboxamide was similar to that of 3-(tert-butyl)-N-(2-chloro-4-(4-((1-methyl-1H-pyrazol-4-yl)amino)-1,3,5-triazin-2-yl)benzyl)-1,2,4-oxadiazole-5-carboxamide in Example 16. The crude product was purified by prep-HPLC (CH$_3$CN/H$_2$O with 0.05% TFA/H$_2$O as mobile phase) to give the TFA salt of 3-(tert-butyl)-N-(2-chloro-3-fluoro-4-(4-((1-methyl-1H-pyrazol-3-yl)amino)-1,3,5-triazin-2-yl)benzyl)-1,2,4-oxadiazole-5-carboxamide as a yellow solid (7.7 mg, yield: 4%). ESI-MS (M+H)$^+$: 486.1. $^1$H NMR (500 MHz, DMSO-d$_6$) δ: 10.84-10.55 (m, 1H), 9.95 (br t, J=6.1 Hz, 1H), 8.86-8.72 (m, 1H), 8.14-7.94 (m, 1H), 7.66-7.60 (m, 1H), 7.43 (d, J=8.5 Hz, 1H), 6.77-6.52 (m, 1H), 4.63 (d, J=4.3 Hz, 2H), 3.77 (s, 3H), 1.38 (s, 9H).

Example 23: 5-tert-butyl-N-[(5R)-2-[4-[(1-methylpyrazol-3-yl)amino]-1,3,5-triazin-2-yl]-6,7,8,9-tetrahydro-5H-benzo[7]annulen-5-yl]-1,2,4-oxadiazole-3-carboxamide (Compound 23)

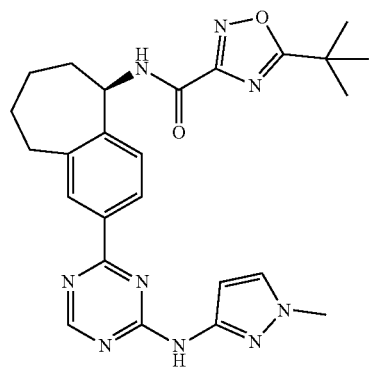

23

1. Synthesis of tert-butyl N-[(5R)-2-(4,4,5,5-tetramethyl-1,3,2-dioxaborolan-2-yl)-6,7,8,9-tetrahydro-5H-benzo[7]annulen-5-yl]carbamate

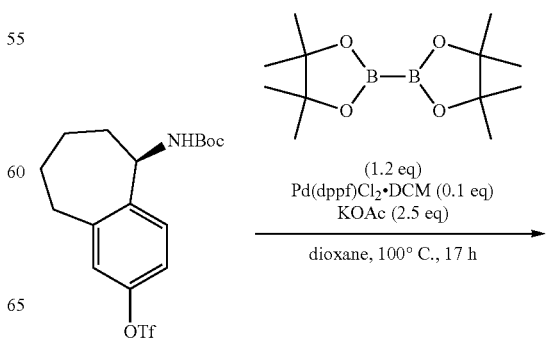

-continued

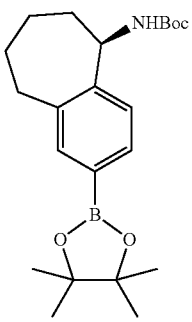

A vial was charged with bis(pinacolato)diboron (744 mg, 2.93 mmol), [(5R)-5-(tert-butoxycarbonylamino)-6,7,8,9-tetrahydro-5H-benzo[7]annulen-2-yl]trifluoromethanesulfonate (prepared as described in WO 2015/089327, 1.0 g, 2.44 mmol), Pd(dppf)Cl$_2$·DCM (199 mg, 0.24 mmol) and KOAc (718 mg, 7.32 mmol). 1,4-Dioxane (16 mL) was added and the reaction mixture was stirred overnight at 100° C. The reaction was filtered through a pad of Celite®, rinsing with EtOAc (100 mL). The filtrate was concentrated in vacuo and the crude material was purified by silica-gel column chromatography (EtOAc/heptanes, grading from 0% to 100%) to give tert-butyl N-[(5R)-2-(4,4,5,5-tetramethyl-1,3,2-dioxaborolan-2-yl)-6,7,8,9-tetrahydro-5H-benzo[7]annulen-5-yl]carbamate as a light yellow solid (844 mg, yield: 89%). ESI-MS (M+Na)$^+$: 410.2.

2. Synthesis of tert-butyl N-[(5R)-2-[4-[(1-methylpyrazol-3-yl)amino]-1,3,5-triazin-2-yl]-6,7,8,9-tetrahydro-5H-benzo[7]annulen-5-yl]carbamate

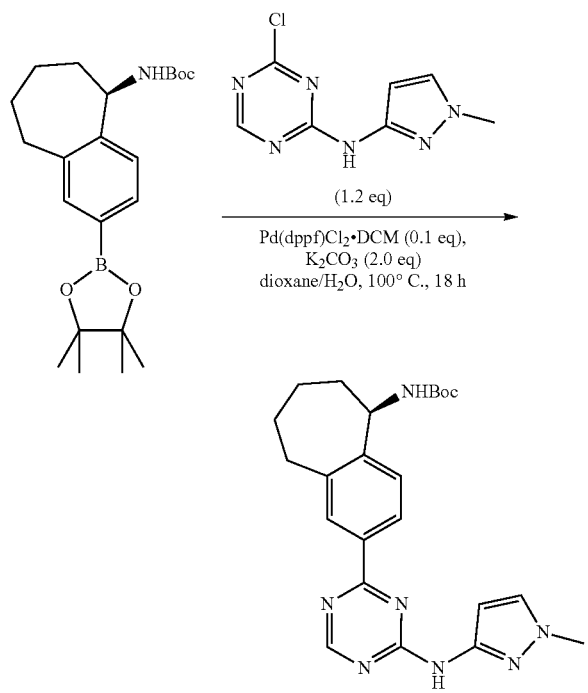

A solution of tert-butyl (R)-(2-(4,4,5,5-tetramethyl-1,3,2-dioxaborolan-2-yl)-6,7,8,9-tetrahydro-5H-benzo[7]annulen-5-yl)carbamate (200 mg, 0.52 mmol), 4-chloro-N-(1-methylpyrazol-3-yl)-1,3,5-triazin-2-amine (131 mg, 0.62 mmol), Pd(dppf)Cl$_2$·DCM (42 mg, 0.05 mmol), and K$_2$CO$_3$ (143 mg, 1.03 mmol) in 1,4-dioxane (4.13 mL) and H$_2$O (1.03 mL) was degassed with N$_2$ for 5 minutes. The reaction mixture was then heated to 100° C. under an atmosphere of nitrogen and stirred at that temperature for 18 h. The reaction mixture was diluted with EtOAc (20 mL), and filtered through a plug of Celite®, rinsing with an additional portion of EtOAc (50 mL). The filtrate was concentrated in vacuo and purified by silica-gel column chromatography ([3:1 EtOAc:EtOH]/heptanes, grading from 0% to 75%) to give tert-butyl N-[(5R)-2-[4-[(1-methylpyrazol-3-yl)amino]-1,3,5-triazin-2-yl]-6,7,8,9-tetrahydro-5H-benzo[7]annulen-5-yl]carbamate as a dark orange solid (185 mg, yield: 82%). ESI-MS (M+H)$^+$: 436.2.

3. Synthesis of (R)-4-(5-amino-6,7,8,9-tetrahydro-5H-benzo[7]annulen-2-yl)-N-(1-methyl-1H-pyrazol-3-yl)-1,3,5-triazin-2-amine hydrochloride

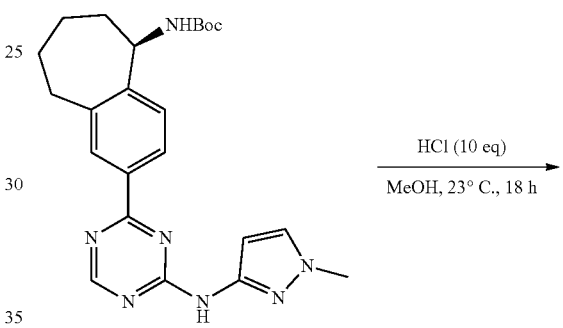

To a solution of tert-butyl N-[(5R)-2-[4-[(1-methylpyrazol-3-yl)amino]-1,3,5-triazin-2-yl]-6,7,8,9-tetrahydro-5H-benzo[7]annulen-5-yl]carbamate (185 mg, 0.43 mmol) in MeOH (2.1 mL) was added a solution of HCl (1.25 M in MeOH, 3.40 mL) in a dropwise manner over 2 min. The reaction was stirred for 18 h at rt and then was concentrated in vacuo to afford crude 4-[(5R)-5-amino-6,7,8,9-tetrahydro-5H-benzo[7]annulen-2-yl]-N-(1-methylpyrazol-3-yl)-1,3,5-triazin-2-amine hydrochloride as an off-white solid (189 mg, crude), which was carried forward without further purification. ESI-MS (M+H)$^+$: 336.1.

4. Synthesis of 5-tert-butyl-N-[(5R)-2-[4-[(1-methylpyrazol-3-yl)amino]-1,3,5-triazin-2-yl]-6,7,8,9-tetrahydro-5H-benzo[7]annulen-5-yl]-1,2,4-oxadiazole-3-carboxamide (Compound 23)

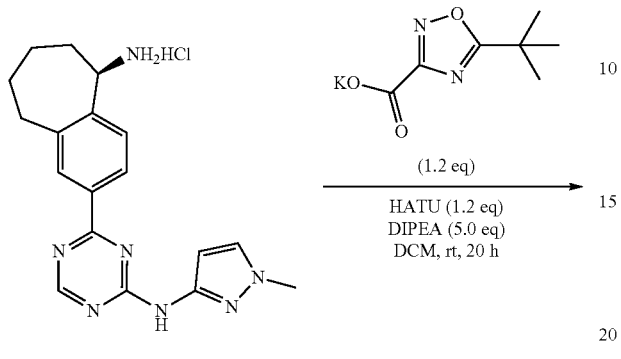

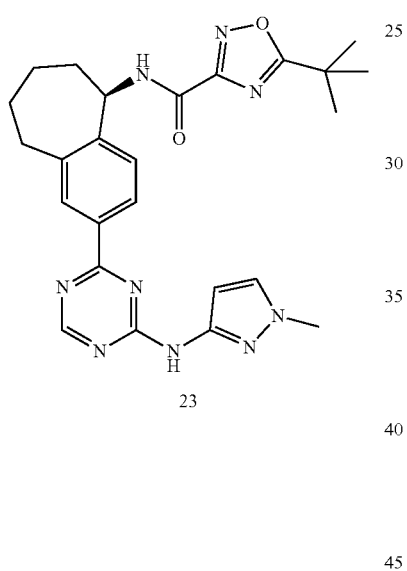

23

To a solution of 4-[(5R)-5-amino-6,7,8,9-tetrahydro-5H-benzo[7]annulen-2-yl]-N-(1-methylpyrazol-3-yl)-1,3,5-triazin-2-amine hydrochloride (75 mg, 0.20 mmol), and potassium 5-tert-butyl-1,2,4-oxadiazole-3-carboxylate (51 mg, 0.24 mmol) in DCM (2 mL) was added DIPEA (130 mg, 1.01 mmol, 176 µL). The reaction mixture was cooled to 0° C., then HATU (93 mg, 0.24 mmol) was added in a single portion and the reaction was stirred for 20 h at rt. The reaction mixture was concentrated in vacuo and purified by silica-gel column chromatography ([3:1 EtOAc:EtOH]/heptanes, grading from 0% to 100%) to give 5-tert-butyl-N-[(5R)-2-[4-[(1-methylpyrazol-3-yl)amino]-1,3,5-triazin-2-yl]-6,7,8,9-tetrahydro-5H-benzo[7]annulen-5-yl]-1,2,4-oxadiazole-3-carboxamide as an off-white solid (39 mg, yield: 40%). ESI-MS (M+H)+: 488.2. $^1$H NMR (500 MHz, DMSO-$d_6$) δ:10.64-10.37 (m, 1H), 9.58 (d, J=7.9 Hz, 1H), 8.75 (br s, 1H), 8.16 (d, J=6.7 Hz, 2H), 7.69-7.59 (m, 1H), 7.36 (d, J=7.9 Hz, 1H), 6.80-6.49 (m, 1H), 5.28 (br t, J=8.9 Hz, 1H), 3.78 (s, 3H) 3.03-2.88 (m, 2H), 1.93 (br d, J=15.3 Hz, 3H), 1.88-1.70 (m, 2H), 1.45 (s, 9H), 1.37-1.22 (m, 1H).

Example 24: 1-tert-butyl-N-[(5R)-8-[4-[(1-methylpyrazol-4-yl)amino]-1,3,5-triazin-2-yl]-2-(oxetan-3-yl)-1,3,4,5-tetrahydro-2-benzazepin-5-yl]triazole-4-carboxamide (Compound 24)

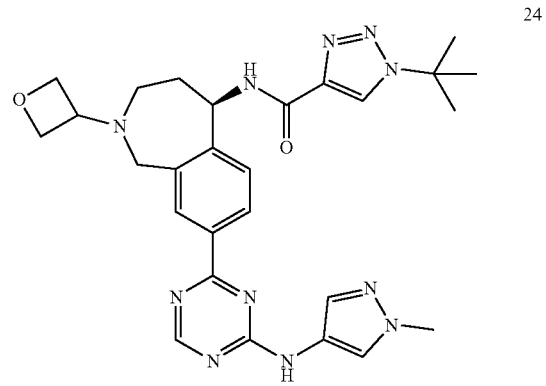 [SMILES: Cn1cc(Nc2ncnc(-c3ccc4c(c3)CN(C3COC3)CC[C@H]4NC(=O)c3cn(C(C)(C)C)nn3)n2)cn1]

24

1. Synthesis of tert-butyl (5R)-5-[(1-tert-butyltriazole-4-carbonyl)amino]-8-[4-[(1-methylpyrazol-4-yl)amino]-1,3,5-triazin-2-yl]-1,3,4,5-tetrahydro-2-benzazepine-2-carboxylate

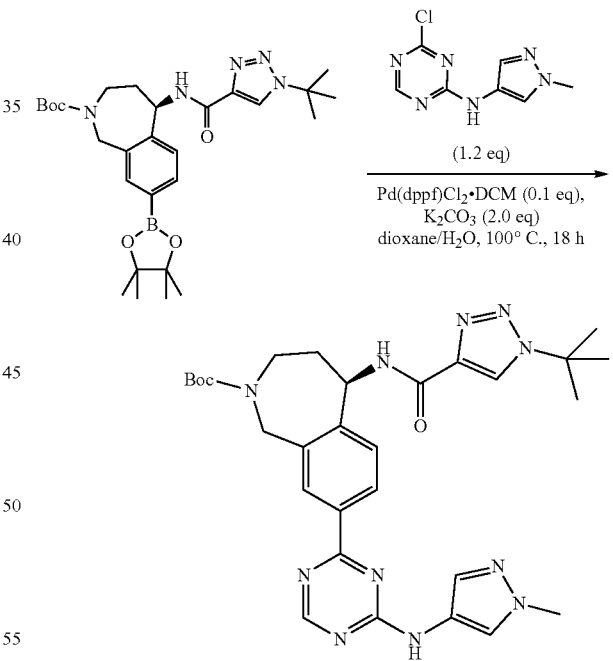

A solution of tert-butyl (5R)-5-[(1-tert-butyltriazole-4-carbonyl)amino]-8-(4,4,5,5-tetramethyl-1,3,2-dioxaborolan-2-yl)-1,3,4,5-tetrahydro-2-benzazepine-2-carboxylate (prepared as described in WO 2015/089337, 300 mg, 0.56 mmol), 4-chloro-N-(1-methylpyrazol-4-yl)-1,3,5-triazin-2-amine (129 mg, 0.61 mmol), Pd(dppf)Cl$_2$.DCM (45 mg, 0.06 mmol), and K$_2$CO$_3$ (154 mg, 1.11 mmol) in 1,4-dioxane (4.45 mL) and H$_2$O (1.11 mL) was degassed with N$_2$ for 5 min. The reaction mixture was heated to 100° C. under an atmosphere of nitrogen and stirred at that tempera- 2. Synthesis of 1-tert-butyl-N-[(5R)-8-[4-[(1-methylpyrazol-4-yl)amino]-1,3,5-triazin-2-yl]-2,3,4,5-tetrahydro-1H-2-benzazepin-5-yl]triazole-4-carboxamide hydrochloride

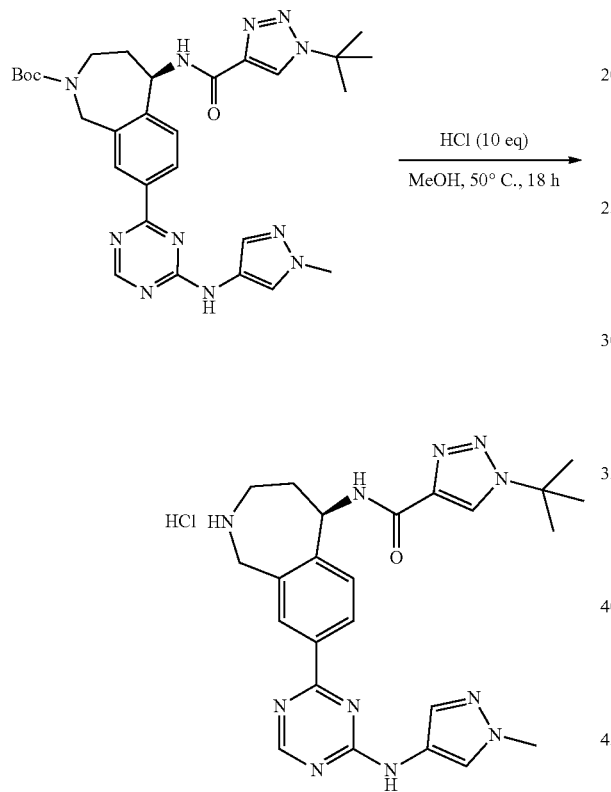

To a solution of tert-butyl (5R)-5-[(1-tert-butyltriazole-4-carbonyl)amino]-8-[4-[(1-methylpyrazol-4-yl)amino]-1,3,5-triazin-2-yl]-1,3,4,5-tetrahydro-2-benzazepine-2-carboxylate (175 mg, 0.30 mmol) in MeOH (2.98 mL) was added an HCl solution (1.25 M in MeOH, 2.38 mL). The reaction mixture was heated to 50° C. and stirred at that temperature for 18 h. The reaction mixture was cooled to rt and concentrated in vacuo to afford 1-tert-butyl-N-[(5R)-8-[4-[(1-methylpyrazol-4-yl)amino]-1,3,5-triazin-2-yl]-2,3,4,5-tetrahydro-1H-2-benzazepin-5-yl]triazole-4-carboxamide hydrochloride as a yellow solid (173 mg, crude), which was carried forward without further purification. ESI-MS (M+H)+: 488.2.

3. Synthesis of 1-tert-butyl-N-[(5R)-8-[4-[(1-methylpyrazol-4-yl)amino]-1,3,5-triazin-2-yl]-2-(oxetan-3-yl)-1,3,4,5-tetrahydro-2-benzazepin-5-yl]triazole-4-carboxamide (Compound 24)

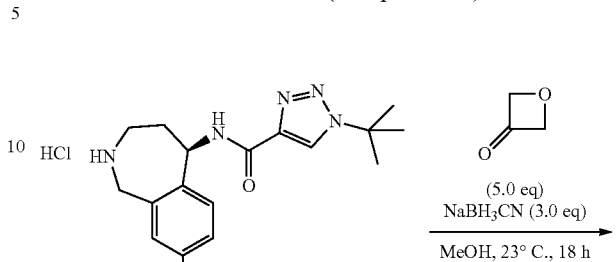

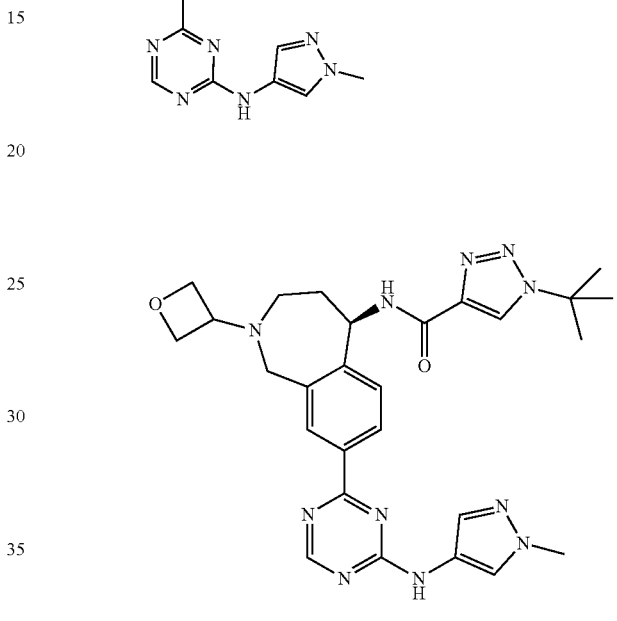

To a solution of 1-tert-butyl-N-[(5R)-8-[4-[(1-methylpyrazol-4-yl)amino]-1,3,5-triazin-2-yl]-2,3,4,5-tetrahydro-1H-2-benzazepin-5-yl]triazole-4-carboxamide hydrochloride (84 mg, 0.16 mmol) in MeOH (8 mL) was added oxetan-3-one (58 mg, 0.80 mmol, 47 µL), followed by NaBH$_3$CN (30 mg, 0.48 mmol). The reaction mixture was stirred at rt for 18 h. The reaction mixture was concentrated in vacuo and the residue was diluted with H$_2$O (20 mL). The aqueous phase was extracted EtOAc (50 mL×2). The combined organic extracts were washed with brine (50 mL), dried (Na$_2$SO$_4$), filtered, and concentrated in vacuo. The crude product was purified by silica-gel column chromatography ([3:1 EtOAc:EtOH]/heptanes, grading from 50% to 100%) to give 1-tert-butyl-N-[(5R)-8-[4-[(1-methylpyrazol-4-yl)amino]-1,3,5-triazin-2-yl]-2-(oxetan-3-yl)-1,3,4,5-tetrahydro-2-benzazepin-5-yl]triazole-4-carboxamide as a pale yellow solid (22 mg, yield: 25%). ESI-MS (M+H)+: 544.2. $^1$H NMR (500 MHz, DMSO-d$_6$) δ: 10.26 (d, J=8.6 Hz, 1H), 9.03 (br dd, J$_1$=15.6 Hz, J$_2$=8.2 Hz, 1H), 8.82-8.68 (m, 2H), 8.27-8.17 (m, 1H), 8.14-8.09 (m, 1H), 8.05-7.92 (m, 1H), 7.63-7.53 (m, 1H), 7.41 (dd, J$_1$=10.7 Hz, J$_2$=8.2 Hz, 1H), 5.46 (br t, J=9.8 Hz, 1H), 4.60 (br t, J=6.4 Hz, 1H), 4.50 (br d, J=6.1 Hz, 2H), 4.48-4.41 (m, 1H), 3.92-3.71 (m, 5H), 3.70-3.61 (m, 1H), 2.97-2.87 (m, 1H), 2.86-2.73 (m, 1H), 2.11 (q, J=10.8 Hz, 1H), 1.86 (br d, J=12.2 Hz, 1H), 1.65 (d, J=1.8 Hz, 9H).

Example 25: 5-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide (Compound 25)

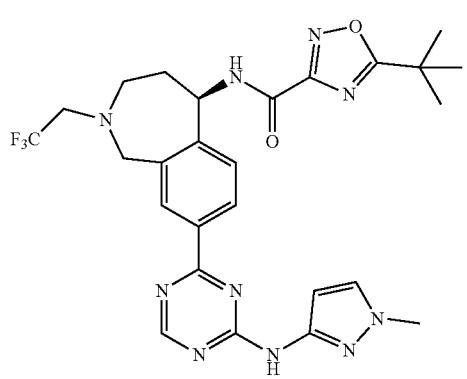

1. Synthesis of tert-butyl (5R)-8-bromo-5-[(5-tert-butyl-1,2,4-oxadiazole-3-carbonyl)amino]-1,3,4,5-tetrahydro-2-benzazepine-2-carboxylate

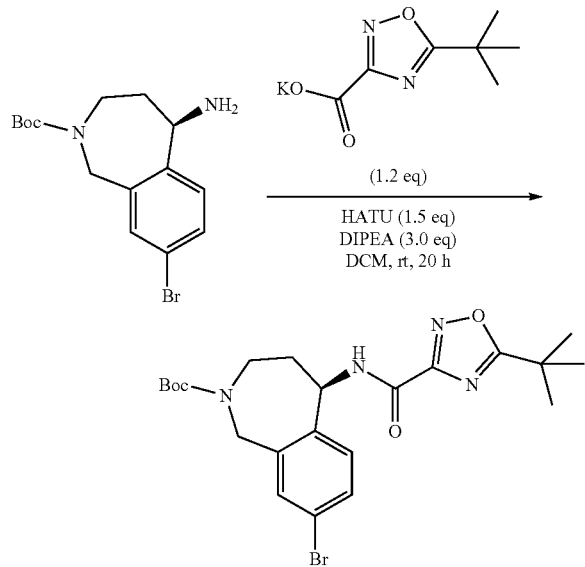

A solution of tert-butyl (5R)-5-amino-8-bromo-1,3,4,5-tetrahydro-2-benzazepine-2-carboxylate (prepared as described in WO 2015/089337, 600 mg, 1.76 mmol), and potassium 5-tert-butyl-1,2,4-oxadiazole-3-carboxylate (442 mg, 2.11 mmol) in DCM (18 mL) was cooled to 0° C. in an ice-water cooling bath. DIPEA (682 mg, 5.28 mmol, 921 µL) was added, followed by HATU (1.01 g, 2.64 mmol). The reaction mixture was warmed to rt and stirred for 20 h. The reaction mixture was concentrated in vacuo and purified by silica-gel column chromatography (EtOAc/heptanes, grading from 0% to 100%) to give tert-butyl (5R)-8-bromo-5-[(5-tert-butyl-1,2,4-oxadiazole-3-carbonyl)amino]-1,3,4,5-tetrahydro-2-benzazepine-2-carboxylate as an off-white solid (727 mg, yield: 84%) ESI-MS (M+Na)$^+$: 517.0.

2. Synthesis of N-[(5R)-8-bromo-2,3,4,5-tetrahydro-1H-2-benzazepin-5-yl]-5-tert-butyl-1,2,4-oxadiazole-3-carboxamide hydrochloride

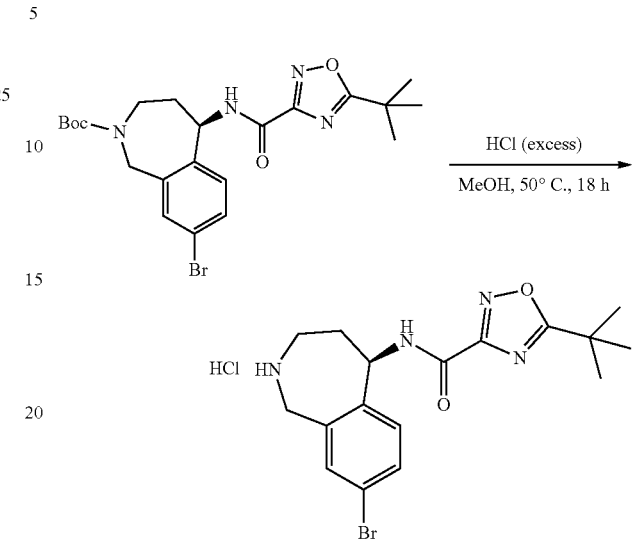

To a solution of tert-butyl (5R)-8-bromo-5-[(5-tert-butyl-1,2,4-oxadiazole-3-carbonyl)amino]-1,3,4,5-tetrahydro-2-benzazepine-2-carboxylate (726 mg, 1.47 mmol) in MeOH (5.88 mL) was added HCl (1.25 M in MeOH, 5.88 mL). The reaction mixture was heated to 50° C. and stirred at that temperature for 18 h. The reaction mixture was concentrated in vacuo to afford crude N-[(5R)-8-bromo-2,3,4,5-tetrahydro-1H-2-benzazepin-5-yl]-5-tert-butyl-1,2,4-oxadiazole-3-carboxamide hydrochloride as a white solid (6380 mg, crude) which was carried forward without further purification. ESI-MS (M+H)$^+$: 395.1.

3. Synthesis of N-[(5R)-8-bromo-2-(2,2,2-trifluoroethyl)-1,3,4,5-tetrahydro-2-benzazepin-5-yl]-5-tert-butyl-1,2,4-oxadiazole-3-carboxamide

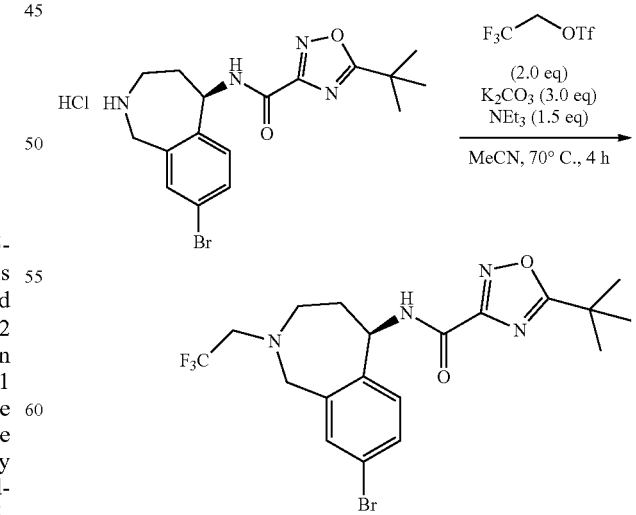

To a mixture of N-[(5R)-8-bromo-2,3,4,5-tetrahydro-1H-2-benzazepin-5-yl]-5-tert-butyl-1,2,4-oxadiazole-3-carboxamide hydrochloride (632 mg, 1.47 mmol) in MeCN (7.4 mL) was added $K_2CO_3$ (610 mg, 4.41 mmol), followed by 2,2,2-trifluoroethyl trifluoromethanesulfonate (683 mg, 2.94 mmol, 424 µL) and $Et_3N$ (223 mg, 2.21 mmol, 306 µL). The reaction mixture was heated at 70° C. and stirred at that temperature for 4 h. The reaction mixture was diluted with DCM (20 mL) and filtered. The filter cake was washed with DCM (50 mL) and the combined filtrates were concentrated in vacuo. The crude material was purified by silica-gel column chromatography (EtOAc/heptanes, grading from 0% to 100%) to give N-[(5R)-8-bromo-2-(2,2,2-trifluoroethyl)-1,3,4,5-tetrahydro-2-benzazepin-5-yl]-5-tert-butyl-1,2,4-oxadiazole-3-carboxamide as an off-white solid (484 mg, yield: 69%). ESI-MS $(M+H)^+$: 475.0.

4. Synthesis of 5-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-3-carboxamide A solution of N-[(5R)-8-bromo-2-(2,2,2-trifluoroethyl)-1,3,4,5-tetrahydro-2-benzazepin-5-yl]-5-tert-butyl-1,2,4-oxadiazole-3-carboxamide (485 mg, 1.02 mmol), bis(pinacolato)diboron (288 mg, 1.12 mmol), KOAc (300 mg, 3.06 mmol), and $Pd(dppf)Cl_2 \cdot DCM$ (83 mg, 0.10 mmol) in 1,4-dioxane (10 mL) was degassed with $N_2$ for 5 min. The reaction mixture was heated to 100° C. and stirred at that temperature for 4 h. The reaction mixture was cooled to rt, diluted with EtOAc (50 mL), and filtered through a pad of Celite®. The solids were washed with EtOAc (50 mL), and the combined filtrates were concentrated in vacuo. The crude material was purified by silica-gel column chromatography (EtOAc/heptanes, grading from 0% to 100%) to give 5-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-3-carboxamide as an off-white solid (315 mg, yield: 59%). ESI-MS $(M+H)^+$: 523.2.

5. Synthesis of tert-butyl (5R)-5-[(1-tert-butyltriazole-4-carbonyl)amino]-8-[4-[(1-methylpyrazol-4-yl)amino]-1,3,5-triazin-2-yl]-1,3,4,5-tetrahydro-2-benzazepine-2-carboxylate (Compound 25)

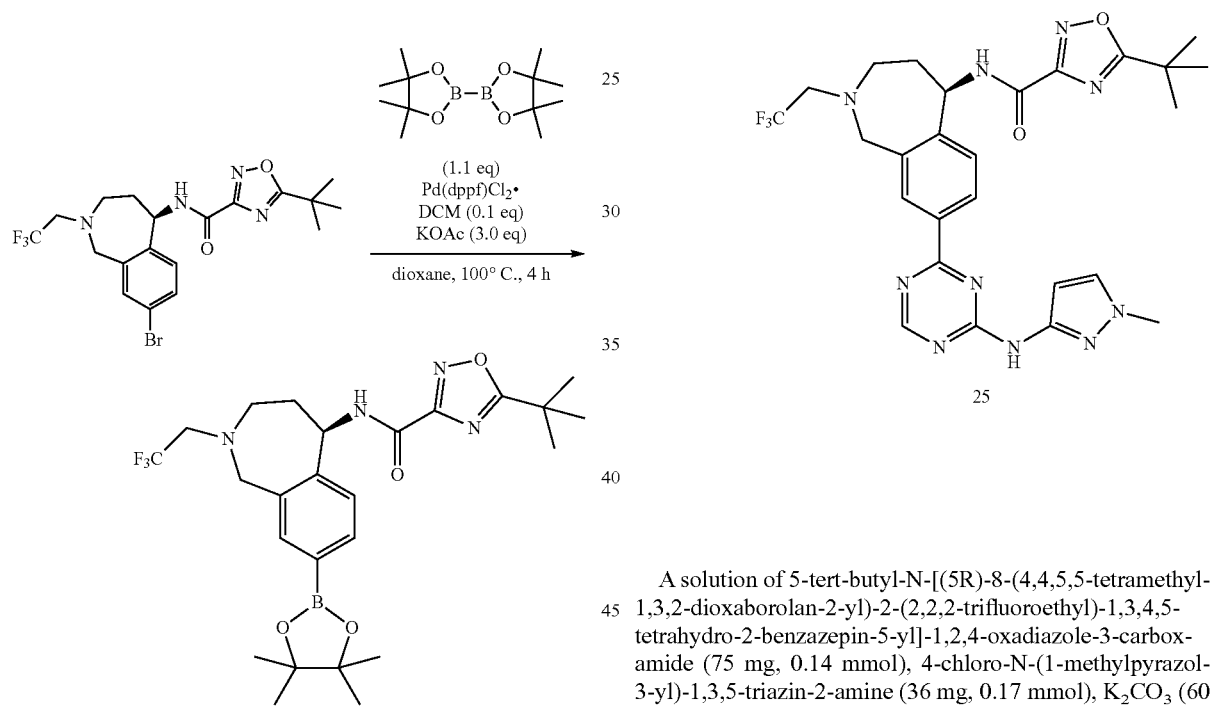

A solution of 5-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-3-carboxamide (75 mg, 0.14 mmol), 4-chloro-N-(1-methylpyrazol-3-yl)-1,3,5-triazin-2-amine (36 mg, 0.17 mmol), $K_2CO_3$ (60 mg, 0.43 mmol) and $Pd(dppf)Cl_2 \cdot DCM$ (12 mg, 0.01 mmol) in 1,4-dioxane (1.15 mL) and $H_2O$ (288 µL) was degassed with $N_2$ for 5 min. The reaction mixture was heated to 100° C. and stirred at that temperature for 18 h. The reaction mixture was concentrated in vacuo and purified by silica-gel column chromatography ([3:1 EtOAc:EtOH]/heptanes, grading from 0% to 50%) to give 5-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide as a light yellow solid (18 mg, yield: 20%). ESI-MS $(M+H)^+$: 571.2. $^1H$ NMR (500 MHz, DMSO-$d_6$) δ: 10.69-10.42 (m, 1H), 9.56 (br d, J=7.3 Hz, 1H), 8.77 (br s, 1H), 8.25 (d, J=7.9 Hz, 1H), 8.17 (s, 1H), 7.63 (br s, 1H), 7.41 (d, J=7.9 Hz, 1H), 6.79-6.53 (m, 1H), 5.46 (br t, J=9.5 Hz, 1H), 4.30 (br d, J=15.3 Hz, 1H), 3.98 (br d, J=15.3 Hz, 1H), 3.78 (s, 3H), 3.38-3.32 (m, 1H), 3.25-3.16 (m, 2H), 3.11-2.98 (m, 1H), 2.15-2.00 (m, 1H), 1.81 (br d, J=14.0 Hz, 1H), 1.45 (s, 9H).

Example 26: 3-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide (Compound 26)

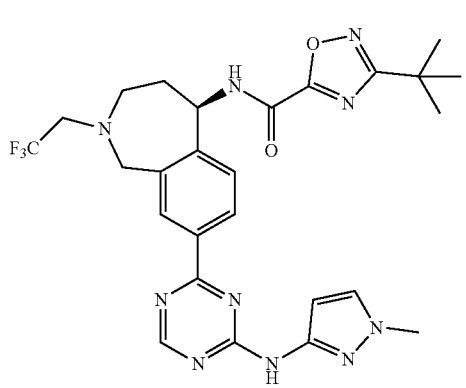

1. Synthesis of tert-butyl (5R)-8-bromo-5-[(3-tert-butyl-1,2,4-oxadiazole-5-carbonyl)amino]-1,3,4,5-tetrahydro-2-benzazepine-2-carboxylate

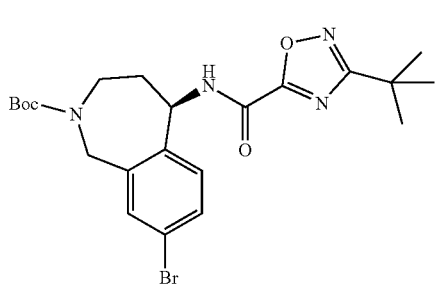

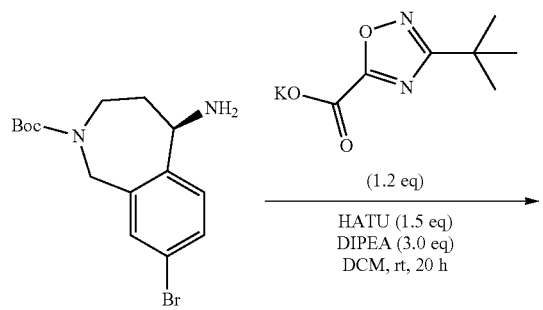

Synthesis of tert-butyl (5R)-8-bromo-5-[(3-tert-butyl-1,2,4-oxadiazole-5-carbonyl)amino]-1,3,4,5-tetrahydro-2-benzazepine-2-carboxylate was similar to that of tert-butyl (5R)-8-bromo-5-[(5-tert-butyl-1,2,4-oxadiazole-3-carbonyl)amino]-1,3,4,5-tetrahydro-2-benzazepine-2-carboxylate in Example 25, Step 1. The crude material was purified by silica-gel column chromatography (EtOAc/heptanes, grading from 0% to 100%) to give tert-butyl (5R)-8-bromo-5-[(3-tert-butyl-1,2,4-oxadiazole-5-carbonyl)amino]-1,3,4,5-tetrahydro-2-benzazepine-2-carboxylate as an off-white solid (700 mg, yield: 81%). ESI-MS (M+Na)$^+$: 517.0.

2. Synthesis of N-[(5R)-8-bromo-2,3,4,5-tetrahydro-1H-2-benzazepin-5-yl]-3-tert-butyl-1,2,4-oxadiazole-5-carboxamide hydrochloride

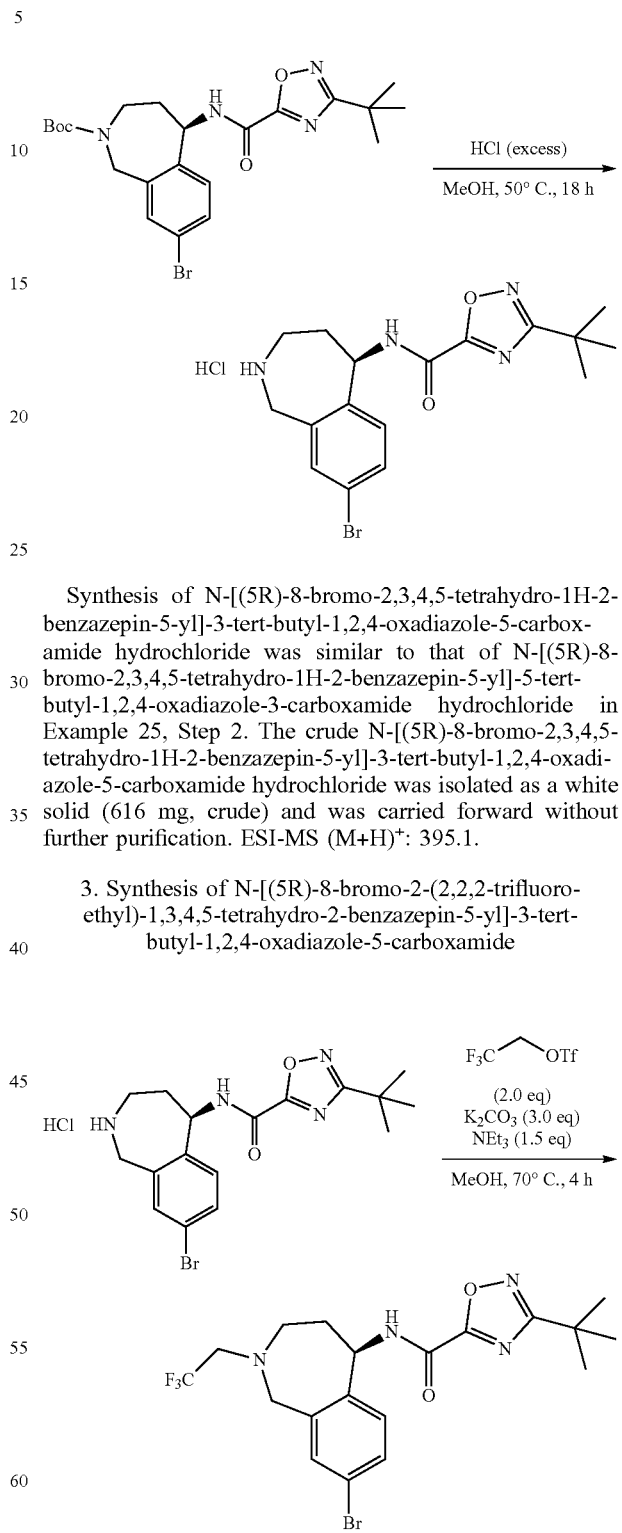

Synthesis of N-[(5R)-8-bromo-2,3,4,5-tetrahydro-1H-2-benzazepin-5-yl]-3-tert-butyl-1,2,4-oxadiazole-5-carboxamide hydrochloride was similar to that of N-[(5R)-8-bromo-2,3,4,5-tetrahydro-1H-2-benzazepin-5-yl]-5-tert-butyl-1,2,4-oxadiazole-3-carboxamide hydrochloride in Example 25, Step 2. The crude N-[(5R)-8-bromo-2,3,4,5-tetrahydro-1H-2-benzazepin-5-yl]-3-tert-butyl-1,2,4-oxadiazole-5-carboxamide hydrochloride was isolated as a white solid (616 mg, crude) and was carried forward without further purification. ESI-MS (M+H)$^+$: 395.1.

3. Synthesis of N-[(5R)-8-bromo-2-(2,2,2-trifluoroethyl)-1,3,4,5-tetrahydro-2-benzazepin-5-yl]-3-tert-butyl-1,2,4-oxadiazole-5-carboxamide Synthesis of N-[(5R)-8-bromo-2-(2,2,2-trifluoroethyl)-1,3,4,5-tetrahydro-2-benzazepin-5-yl]-3-tert-butyl-1,2,4-oxadiazole-5-carboxamide was similar to that of N-[(5R)-8-bromo-2-(2,2,2-trifluoroethyl)-1,3,4,5-tetrahydro-2- benzazepin-5-yl]-5-tert-butyl-1,2,4-oxadiazole-3-carboxamide in Example 25, Step 3. The crude material was purified by silica-gel column chromatography (EtOAc/heptanes, grading from 0% to 100%) to give N-[(5R)-8-bromo-2-(2,2,2-trifluoroethyl)-1,3,4,5-tetrahydro-2-benzazepin-5-yl]-3-tert-butyl-1,2,4-oxadiazole-5-carboxamide as an off-white solid (491 mg, yield: 73%). ESI-MS (M+H)+: 477.0.

4. Synthesis of 3-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-5-carboxamide

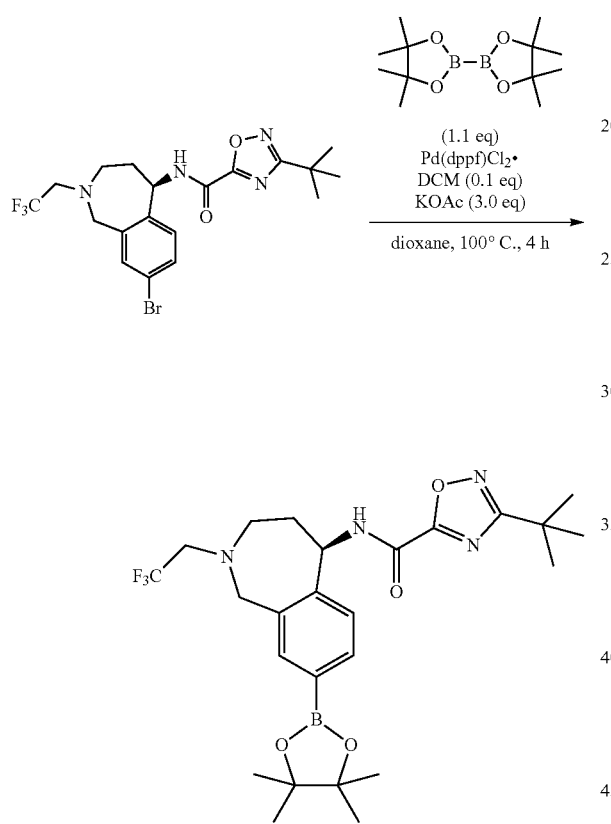

Synthesis of 3-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-5-carboxamide was similar to that of 5-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-3-carboxamide in Example 25, Step 4. The crude material was purified by silica-gel column chromatography (EtOAc/heptanes, grading from 0% to 100%) to give 3-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-5-carboxamide as an off-white solid (394 mg, yield: 73%). ESI-MS (M+H)+: 523.2.

5. Synthesis of 3-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide (Compound 26)

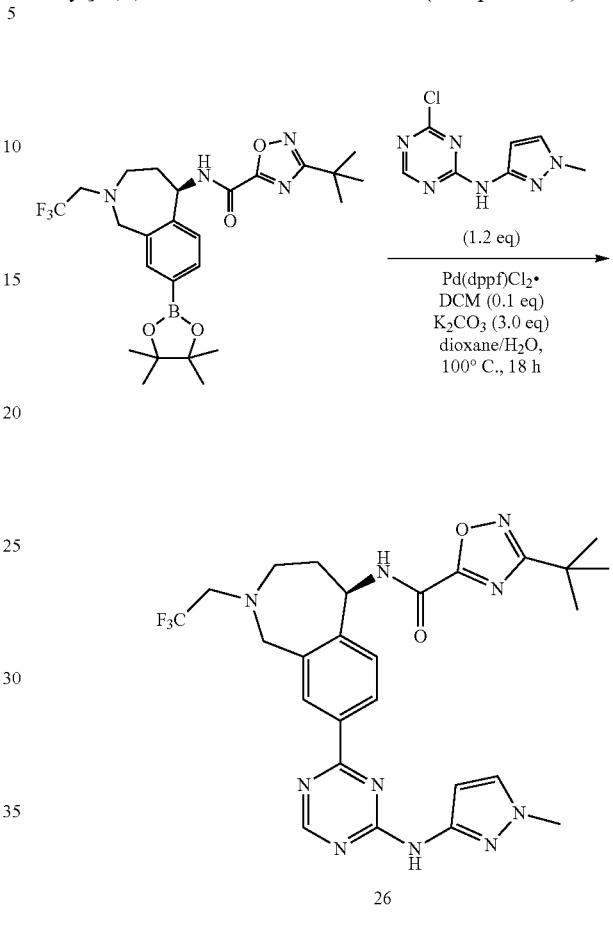

Synthesis of 3-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide was similar to that of 5-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide in Example 25, Step 5. The crude material was purified by silica-gel column chromatography ([3:1 EtOAc:EtOH]/heptanes, grading from 0% to 50%) to give 3-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide as a light yellow solid (25 mg, yield: 30%). ESI-MS (M+H)+: 571.2. $^1$H NMR (500 MHz, DMSO-$d_6$) δ: 10.71-10.45 (m, 1H), 9.95 (br d, J=7.9 Hz, 1H), 8.77 (br s, 1H), 8.28-8.22 (m, 1H), 8.17 (s, 1H), 7.63 (s, 1H), 7.45 (d, J=7.9 Hz, 1H), 6.79-6.53 (m, 1H), 5.44 (br t, J=9.5 Hz, 1H), 4.31 (br d, J=15.9 Hz, 1H), 3.98 (br d, J=15.3 Hz, 1H), 3.78 (s, 3H), 3.41-3.33 (m, 1H), 3.25-3.14 (m, 2H), 3.11-2.94 (m, 1H), 2.16-2.03 (m, 1H), 1.83 (br d, J=13.4 Hz, 1H), 1.41-1.38 (m, 9H).

Example 27. 1-(tert-butyl)-4-fluoro-N-(3-fluoro-2-methyl-4-(4-((1-methyl-1H-pyrazol-4-yl)amino)-1,3,5-triazin-2-yl)benzyl)-1H-pyrazole-3-carboxamide (Compound 27)

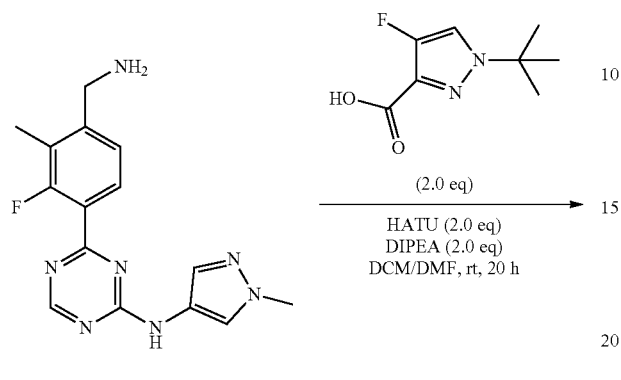

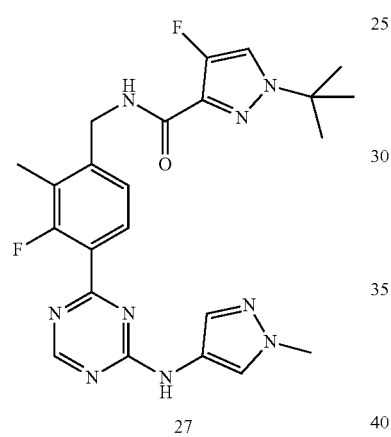

Synthesis of 1-(tert-butyl)-4-fluoro-N-(3-fluoro-2-methyl-4-(4-((1-methyl-1H-pyrazol-4-yl)amino)-1,3,5-triazin-2-yl)benzyl)-1H-pyrazole-3-carboxamide was similar to that of 5-(tert-butyl)-N-(3-fluoro-2-methyl-4-(4-((1-methyl-1H-pyrazol-4-yl)amino)-1,3,5-triazin-2-yl)benzyl)-1,2,4-oxadiazole-3-carboxamide in Example 13. The crude product was purified by prep-HPLC (CH$_3$CN/H$_2$O with 0.05% TFA/H$_2$O as mobile phase) to give the TFA salt of 1-(tert-butyl)-4-fluoro-N-(3-fluoro-2-methyl-4-(4-((1-methyl-1H-pyrazol-4-yl)amino)-1,3,5-triazin-2-yl)benzyl)-1H-pyrazole-3-carboxamide as a yellow solid (14.5 mg, yield: 24%). ESI-MS (M+H)$^+$: 482.2 $^1$H NMR (DMSO-$d_6$, 400 MHz) δ: 10.33 (d, J=6.0 Hz, 1H), 8.86-8.68 (m, 1H), 8.56 (br d, J=5.5 Hz, 1H), 8.15 (d, J=4.5 Hz, 1H), 8.00-7.74 (m, 2H), 7.69-7.47 (m, 1H), 7.32-7.16 (m, 1H), 4.60-4.42 (m, 2H), 3.83 (s, 3H), 2.32 (dd, J$_1$=12.8 Hz, J$_2$=2.0 Hz, 3H), 1.54 (s, 9H).

Example 28: 5-(tert-butyl)-N-(2-chloro-3-fluoro-4-(4-((1-methyl-1H-pyrazol-4-yl)amino)-1,3,5-triazin-2-yl)benzyl)-1,2,4-oxadiazole-3-carboxamide (Compound 28)

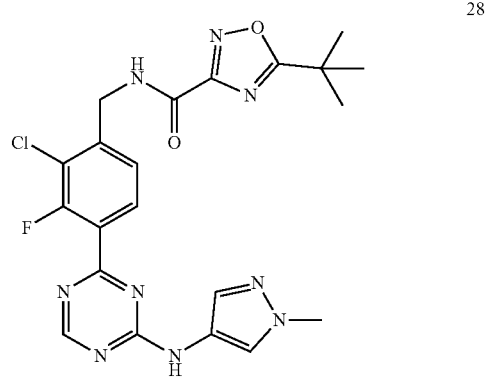 [SMILES: Cn1cc(Nc2ncnc(-c3ccc(CNC(=O)c4noc(C(C)(C)C)n4)c(Cl)c3F)n2)cn1]

1. Synthesis of tert-butyl N-((2-chloro-3-fluoro-4-(4-((1-methylpyrazol-4-yl)amino)-1,3,5-triazin-2-yl)benzyl)carbamate

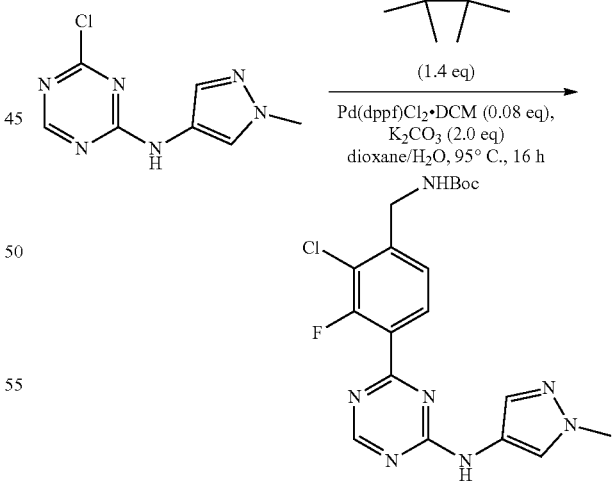

A suspension of tert-butyl N-[[2-chloro-3-fluoro-4-(4,4,5,5-tetramethyl-1,3,2-dioxaborolan-2-yl)phenyl]methyl]carbamate (1.08 g, 2.80 mmol), 4-chloro-N-(1-methylpyrazol-4-yl)-1,3,5-triazin-2-amine (421 mg, 2.0 mmol), and K$_2$CO$_3$ (830 mg, 6 mmol) in 1,4-dioxane (7.5 mL) and H$_2$O (2.5 mL) was degassed with N$_2$ for 5 min. Then Pd(dppf)Cl$_2$.DCM (131 mg, 0.16 mmol) was added. The resulting mixture was heated at 95° C. for 16 h. The reaction mixture was cooled to ambient temperature, diluted with EtOAc (20 mL), and filtered. The solids were washed with EtOAc (20 mL), and the combined organic filtrates were dried (MgSO$_4$), filtered, and concentrated in vacuo. The crude material was purified by silica-gel column chromatography (EtOAc/heptanes, grading from 10% to 100%) to give tert-butyl N-((2-chloro-3-fluoro-4-(4-((1-methylpyrazol-4-yl)amino)-1,3,5-triazin-2-yl)benzyl)carbamate as a yellow solid (840 mg, yield: 87%). ESI-MS (M+H)$^+$: 434.5.

2. Synthesis of 4-(4-(aminomethyl)-3-chloro-2-fluorophenyl)-N-(1-methyl-1H-pyrazol-4-yl)-1,3,5-triazin-2-amine

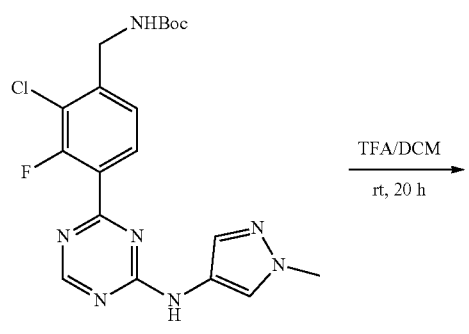

Synthesis of 4-(4-(aminomethyl)-3-chloro-2-fluorophenyl)-N-(1-methyl-1H-pyrazol-4-yl)-1,3,5-triazin-2-amine was similar to that of 4-(4-(aminomethyl)-3-chlorophenyl)-N-(1-methyl-1H-pyrazol-4-yl)-1,3,5-triazin-2-amine in Example 15, Step 2. The reaction mixture was diluted with MeOH (10 mL) and purified on an SCX column. The crude material was eluted with 2M NH$_3$-MeOH and concentrated in vacuo to give 4-(4-(aminomethyl)-3-chloro-2-fluorophenyl)-N-(1-methyl-1H-pyrazol-4-yl)-1,3,5-triazin-2-amine as a yellow solid (589 mg, yield: 72%), and it was carried forward without further purification. ESI-MS (M+H)$^+$: 334.4.

3. Synthesis of 5-(tert-butyl)-N-(2-chloro-3-fluoro-4-(4-((1-methyl-1H-pyrazol-4-yl)amino)-1,3,5-triazin-2-yl)benzyl)-1,2,4-oxadiazole-3-carboxamide (Compound 28)

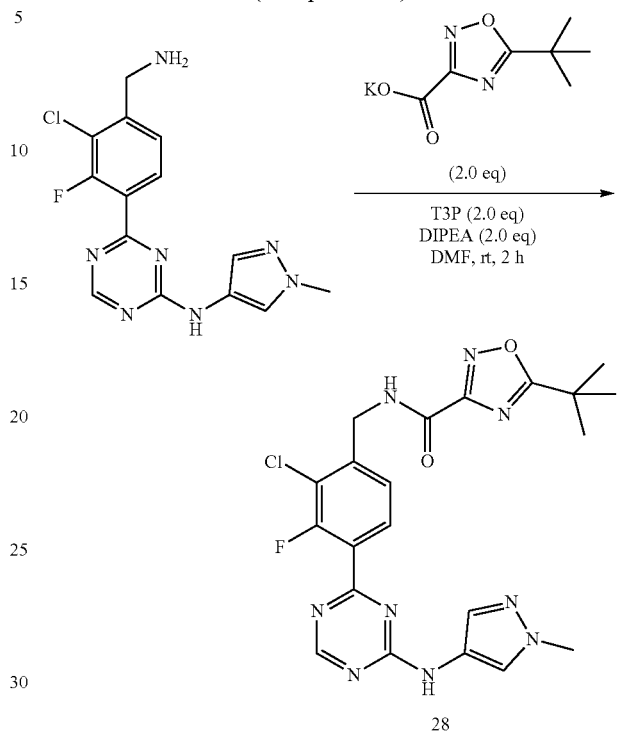

Synthesis of 5-(tert-butyl)-N-(2-chloro-3-fluoro-4-(4-((1-methyl-1H-pyrazol-4-yl)amino)-1,3,5-triazin-2-yl)benzyl)-1,2,4-oxadiazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 5-(tert-butyl)-N-(2-chloro-3-fluoro-4-(4-((1-methyl-1H-pyrazol-4-yl)amino)-1,3,5-triazin-2-yl)benzyl)-1,2,4-oxadiazole-3-carboxamide as a yellow solid (29 mg, yield: 47%). ESI-MS (M+H)$^+$: 486.3. $^1$H NMR (500 MHz, DMSO-d$_6$) δ: 10.43-10.39 (m, 1H), 9.65-9.52 (m, 1H), 8.84-8.75 (m, 1H), 8.13-7.97 (m, 1H), 7.96-7.91 (m, 1H), 7.65-7.56 (m, 1H), 7.38-7.34 (m, 1H), 4.64-4.61 (m, 2H), 3.83 (m, 3H), 1.44 (s, 9H).

Example 29: 3-(tert-butyl)-N-(2-chloro-3-fluoro-4-(4-((1-methyl-1H-pyrazol-4-yl)amino)-1,3,5-triazin-2-yl)benzyl)-1,2,4-oxadiazole-5-carboxamide (Compound 29)

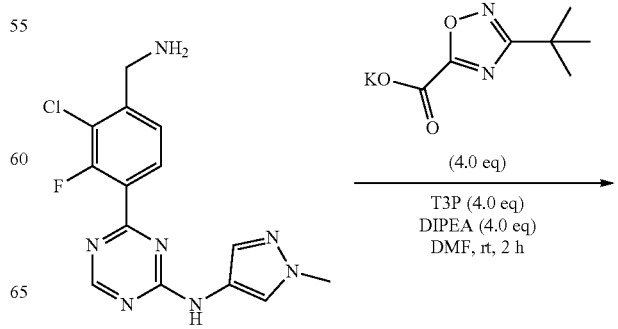

-continued

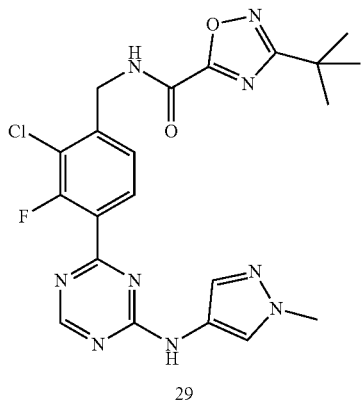

29

Synthesis of 3-(tert-butyl)-N-(2-chloro-3-fluoro-4-(4-((1-methyl-1H-pyrazol-4-yl)amino)-1,3,5-triazin-2-yl)benzyl)-1,2,4-oxadiazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 3-(tert-butyl)-N-(2-chloro-3-fluoro-4-(4-((1-methyl-1H-pyrazol-4-yl)amino)-1,3,5-triazin-2-yl)benzyl)-1,2,4-oxadiazole-5-carboxamide as a yellow solid (21 mg, yield: 25%). ESI-MS (M+H)$^+$: 486.3. $^1$H NMR (500 MHz, DMSO-d$_6$) δ: 10.43-10.39 (m, 1H), 10.02-9.90 (m, 1H), 8.84-8.76 (m, 1H), 8.13-7.97 (m, 1H), 7.96-7.91 (m, 1H), 7.66-7.56 (m, 1H), 7.45-7.42 (m, 1H), 4.64-4.62 (m, 2H), 3.83 (m, 3H), 1.38 (s, 9H).

Example 30: N-(2-chloro-3-fluoro-4-(4-((1-methyl-1H-pyrazol-4-yl)amino)-1,3,5-triazin-2-yl)benzyl)-5-(1-methylcyclopropyl)-1,2,4-oxadiazole-3-carboxamide (Compound 30)

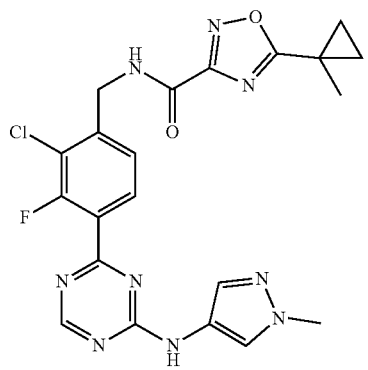

30

1. Synthesis of (2-chloro-3-fluoro-4-(4,4,5,5-tetramethyl-1,3,2-dioxaborolan-2-yl)phenyl)methanamine

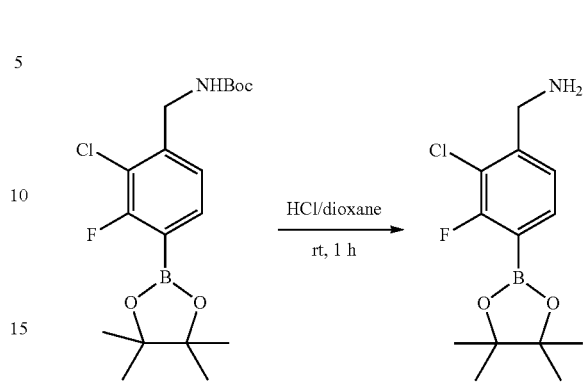

To solid tert-butyl (2-chloro-3-fluoro-4-(4,4,5,5-tetramethyl-1,3,2-dioxaborolan-2-yl)benzyl)carbamate (1.66 g, 4.30 mmol) in a round bottom flask was added an HCl solution (3.23 mL, 4 M in 1,4-dioxane) and the reaction mixture was stirred at ambient temperature for 1 h. The reaction mixture was concentrated in vacuo to give crude (2-chloro-3-fluoro-4-(4,4,5,5-tetramethyl-1,3,2-dioxaborolan-2-yl)phenyl)methanamine (1.23 g, crude), which was carried forward without further purification. ESI-MS (M+H)$^+$: 286.3.

2. Synthesis of N-(2-chloro-3-fluoro-4-(4,4,5,5-tetramethyl-1,3,2-dioxaborolan-2-yl)benzyl)-5-(1-methylcyclopropyl)-1,2,4-oxadiazole-3-carboxamide

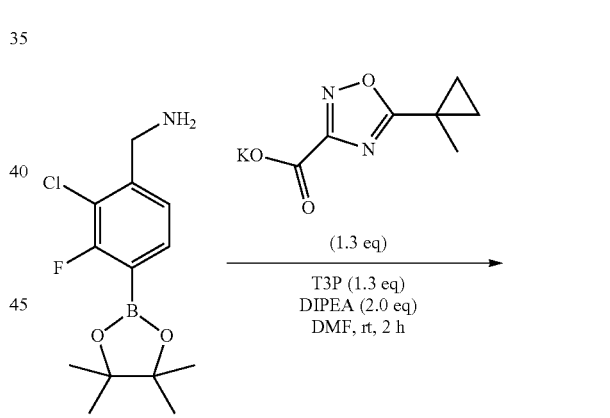

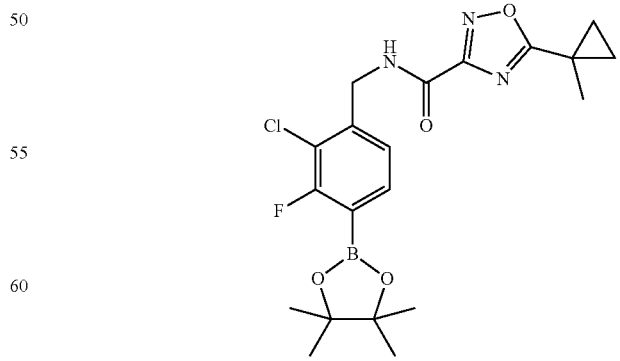

Synthesis of N-(2-chloro-3-fluoro-4-(4,4,5,5-tetramethyl-1,3,2-dioxaborolan-2-yl)benzyl)-5-(1-methylcyclopropyl)-1,2,4-oxadiazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. (Synthetic protocols for potassium 5-(1-methylcyclopropyl)-1,2,4-oxadiazole-3-carboxylate can be found in the BIIB091 patent.) The crude material was purified by silica-gel column chromatography (heptanes/EtOAc, grading from 0% to 100%) to give N-(2-chloro-3-fluoro-4-(4,4,5,5-tetramethyl-1,3,2-dioxaborolan-2-yl)benzyl)-5-(1-methylcyclopropyl)-1,2,4-oxadiazole-3-carboxamide (524 mg, yield: 28% over 2 steps). ESI-MS (M+H)+: 436.5.

3. Synthesis of N-(2-chloro-3-fluoro-4-(4-((1-methyl-1H-pyrazol-4-yl)amino)-1,3,5-triazin-2-yl)benzyl)-5-(1-methylcyclopropyl)-1,2,4-oxadiazole-3-carboxamide (Compound 30)

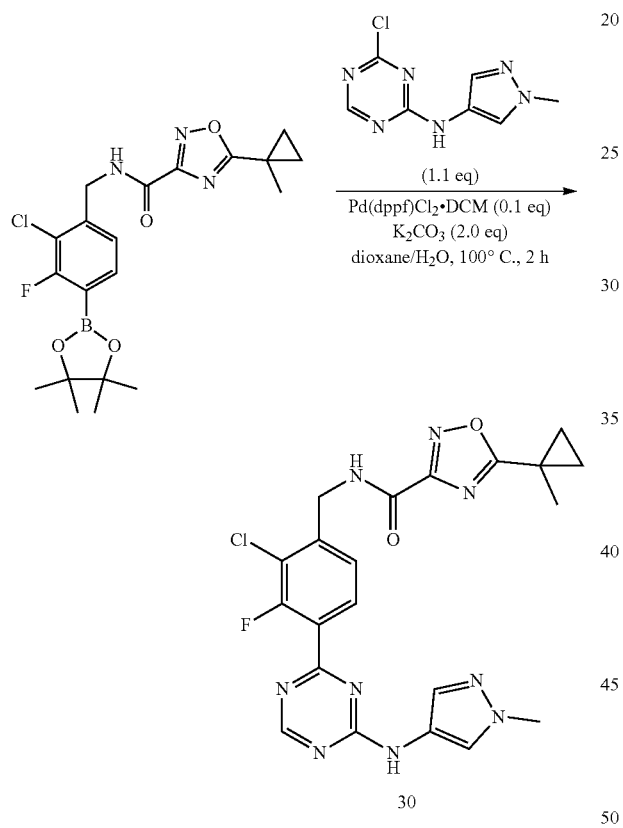

A suspension of N-(2-chloro-3-fluoro-4-(4,4,5,5-tetramethyl-1,3,2-dioxaborolan-2-yl)benzyl)-5-(1-methylcyclopropyl)-1,2,4-oxadiazole-3-carboxamide (75 mg, 0.17 mmol), 4-chloro-N-(1-methyl-1H-pyrazol-4-yl)-1,3,5-triazin-2-amine (40 mg, 0.19 mmol), and $K_2CO_3$ (48 mg, 0.34 mmol) in 1,4-dioxane (1.5 mL) and $H_2O$ (0.3 mL) was degassed with $N_2$ for 5 min. Then Pd(dppf)Cl$_2$·DCM (14 mg, 0.02 mmol) was added. The resulting mixture was heated at 100° C. under $N_2$ for 2 h. The reaction mixture was cooled to ambient temperature, diluted with EtOAc (20 mL), and filtered. The solids were washed with EtOAc (20 mL), and the combined organic filtrates were dried ($Na_2SO_4$), filtered, and concentrated in vacuo. The crude material was purified by prep-HPLC ($CH_3CN/H_2O$ with 0.05% $NH_4OH$ as mobile phase) to give as a yellow solid (18 mg, yield: 21%). ESI-MS (M+H)+: 484.5. $^1$H NMR (500 MHz, CDCl$_3$) δ: 8.86-8.71 (m, 1H), 8.15-8.02 (m, 1H), 8.01-7.87 (m, 1H), 7.61-7.52 (m, 1H), 7.45-7.34 (m, 2H), 7.20-7.10 (m, 1H), 4.89-4.79 (m, 2H), 4.05-3.85 (m, 3H), 1.63-1.58 (m, 3H), 1.53-1.48 (m, 2H), 1.13-1.08 (m, 2H).

Example 31: 5-(tert-butyl)-N-(3-fluoro-2-methyl-4-(4-((1-methyl-1H-pyrazol-4-yl)amino)-1,3,5-triazin-2-yl)benzyl)oxazole-2-carboxamide (Compound 31)

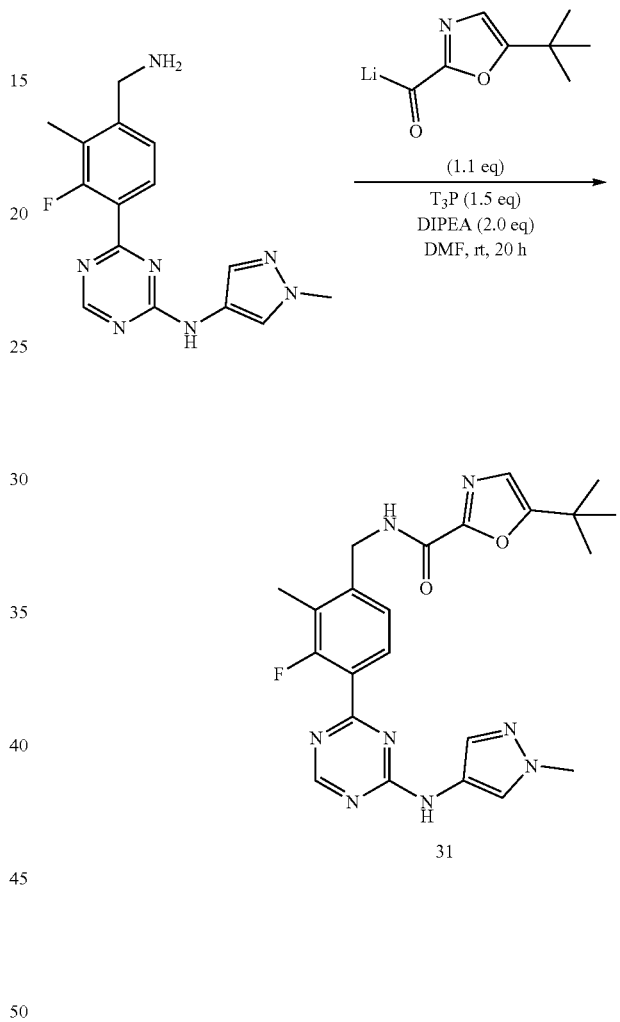

Synthesis of 5-(tert-butyl)-N-(3-fluoro-2-methyl-4-(4-((1-methyl-1H-pyrazol-4-yl)amino)-1,3,5-triazin-2-yl)benzyl)oxazole-2-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude material was purified by prep-HPLC ($CH_3CN/H_2O$ with 0.05% TFA/$H_2O$ as mobile phase) to give 5-(tert-butyl)-N-(3-fluoro-2-methyl-4-(4-((1-methyl-1H-pyrazol-4-yl)amino)-1,3,5-triazin-2-yl)benzyl)oxazole-2-carboxamide as a yellow solid (6.1 mg, yield: 15%). ESI-MS (M+H)+: 465.0. $^1$H NMR (500 MHz, DMSO-d$_6$) δ:10.34-10.33 (m, 1H), 9.44-9.38 (m, 1H), 8.80-8.72 (m, 1H), 7.95-7.91 (m, 1H), 7.80 (br t, J=7.9 Hz, 1H), 7.64-7.55 (m, 1H), 7.22 (br dd, J=14.0 Hz, 7.9 Hz, 1H), 7.12 (s, 1H), 4.51-4.49 (m, 2H), 3.82 (s, 3H), 2.33-2.23 (m, 3H), 1.30 (s, 9H).

Example 32: N-(3-fluoro-2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide (Compound 32)

Example 33: 5-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-1,2,4-oxadiazole-3-carboxamide (Compound 33)

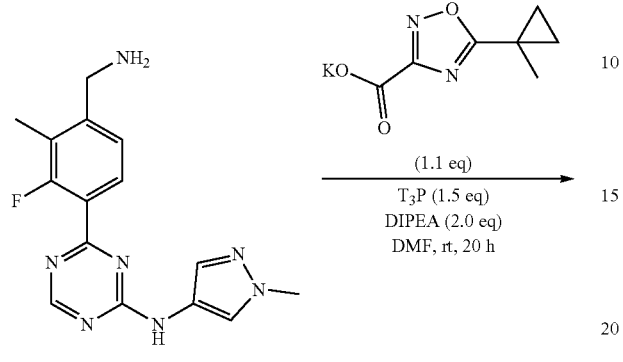

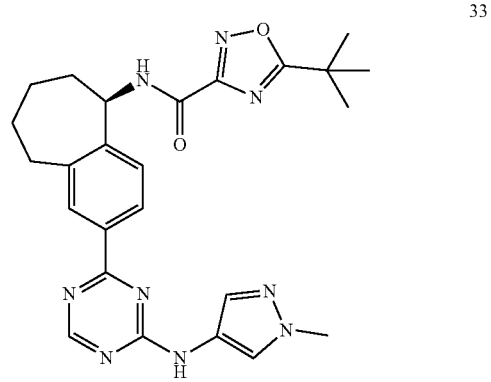 [SMILES: Cn1cc(Nc2ncnc(-c3ccc4c(c3)CCCC[C@H]4NC(=O)c3noc(C(C)(C)C)n3)n2)cn1]

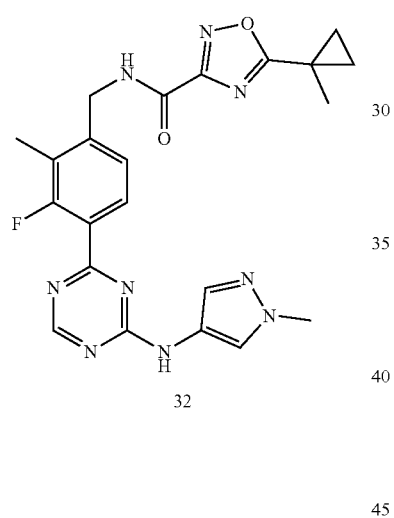

1. Synthesis of tert-butyl N-[(5R)-2-[4-[(1-methylpyrazol-4-yl)amino]-1,3,5-triazin-2-yl]-6,7,8,9-tetrahydro-5H-benzo[7]annulen-5-yl]carbamate Synthesis of N-(3-fluoro-2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give N-(3-fluoro-2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide as a yellow solid (14.1 mg, yield: 35%). ESI-MS (M+H)$^+$: 464.0. $^1$H NMR (500 MHz, DMSO-d$_6$) δ: 10.35-10.33 (m, 1H), 9.48-9.44 (m, 1H), 8.81-8.72 (m, 1H), 7.96-7.91 (m, 1H), 7.83-7.77 (m, 1H), 7.64-7.55 (m, 1H), 7.24-7.18 (m, 1H), 4.52 (br t, J=5.5 Hz, 2H), 3.83 (s, 3H), 2.33-2.28 (m, 3H), 1.54 (s, 3H), 1.40-1.37 (m, 2H), 1.19-1.15 (m, 2H).

A solution of tert-butyl (R)-(2-(4,4,5,5-tetramethyl-1,3,2-dioxaborolan-2-yl)-6,7,8,9-tetrahydro-5H-benzo[7]annulen-5-yl)carbamate (540 mg, 1.42 mmol), 4-chloro-N-(1-methylpyrazol-3-yl)-1,3,5-triazin-2-amine (300 mg, 1.42 mmol), Pd(dppf)Cl$_2$.DCM (116 mg, 0.14 mmol), and K$_2$CO$_3$ (392 mg, 2.84 mmol) in 1,4-dioxane (6 mL) and H$_2$O (2 mL) was degassed with N$_2$ for 5 minutes. The reaction mixture was then heated to 95° C. under an atmosphere of nitrogen and stirred at that temperature for 18 h. The reaction mixture was cooled to ambient temperature, diluted with H₂O (20 mL), and extracted with DCM (20 mL). The phases were separated and the aqueous phase was extracted with DCM (10 mL). The combined organic extracts were dried (MgSO₄), filtered, and concentrated in vacuo. The residue was purified by silica-gel column chromatography (petroleum ether/EtOAc, grading from 0% to 100%) to give tert-butyl N-[(5R)-2-[4-[(1-methylpyrazol-4-yl)amino]-1,3,5-triazin-2-yl]-6,7,8,9-tetrahydro-5H-benzo[7]annulen-5-yl]carbamate as a pale-yellow solid (250 mg, yield: 40%). ESI-MS (M+H)⁺: 436.4.

2. Synthesis of 4-[(5R)-5-amino-6,7,8,9-tetrahydro-5H-benzo[7]annulen-2-yl]-N-(1-methylpyrazol-4-yl)-1,3,5-triazin-2-amine

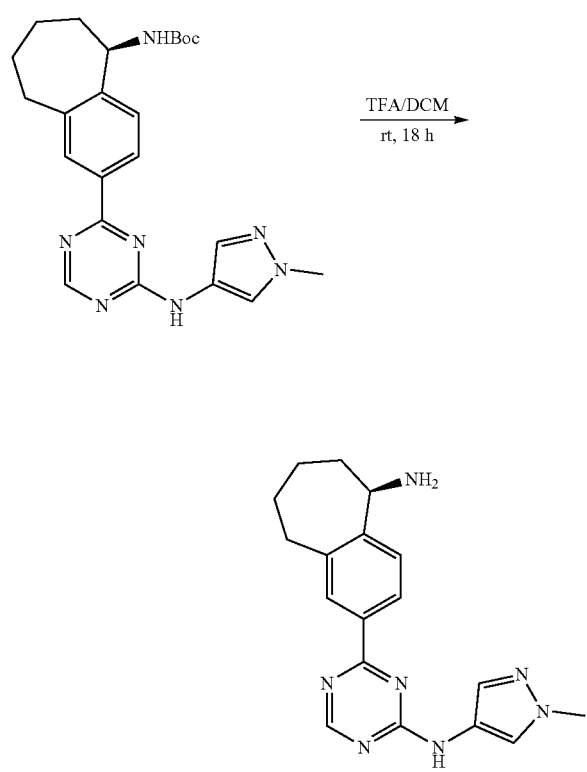

To a solution of tert-butyl N-[(5R)-2-[4-[(1-methylpyrazol-4-yl)amino]-1,3,5-triazin-2-yl]-6,7,8,9-tetrahydro-5H-benzo[7]annulen-5-yl]carbamate (185 mg, 0.43 mmol) in DCM (5.0 mL) was added TFA (1.31 g, 11.5 mmol, 0.88 mL). The reaction was stirred for at ambient temperature for 18 h and then was diluted with MeOH (10 mL). The mixture was purified on an SCX column and the crude product was eluted with 2M NH₃-MeOH to give 4-[(5R)-5-amino-6,7,8,9-tetrahydro-5H-benzo[7]annulen-2-yl]-N-(1-methylpyrazol-4-yl)-1,3,5-triazin-2-amine as a pale-yellow solid (175 mg, yield: 91%), which was carried forward without further purification. ESI-MS (M+H)⁺: 336.3.

3. Synthesis of 5-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-1,2,4-oxadiazole-3-carboxamide (Compound 33)

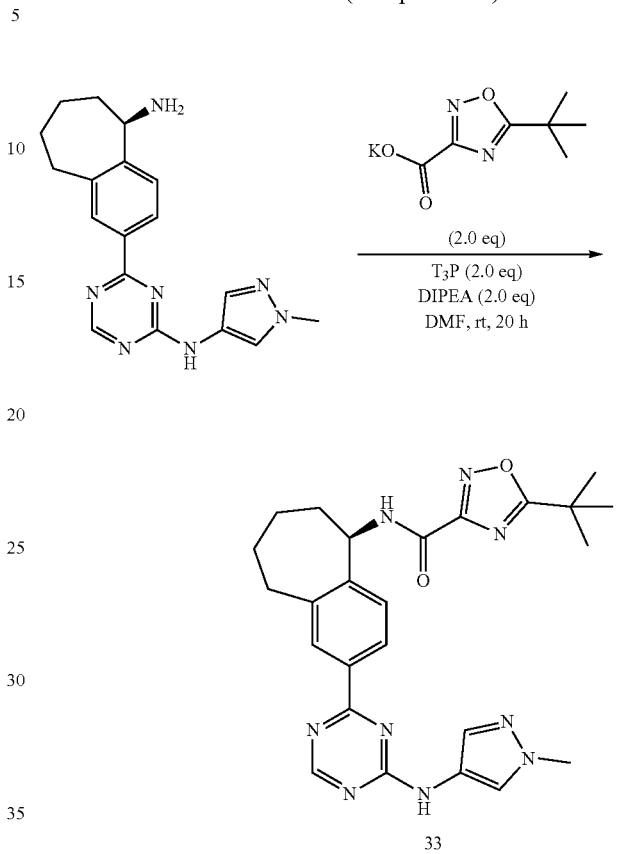

33

To a mixture of 4-[(5R)-5-amino-6,7,8,9-tetrahydro-5H-benzo[7]annulen-2-yl]-N-(1-methylpyrazol-4-yl)-1,3,5-triazin-2-amine (34 mg, 0.135 mmol), and potassium 5-tert-butyl-1,2,4-oxadiazole-3-carboxylate (51 mg, 0.27 mmol) in DMF (1 mL) was added DIPEA (35 mg, 0.27 mmol, 47 µL). The reaction mixture was cooled to 0° C., then T3P (171 mg, 0.27 mmol, 50% solution in DMF) was added dropwise and the reaction was stirred for 30 min at 0° C., followed by 20 h at rt. The mixture was diluted with EtOAc (5 mL) and H₂O (5 mL). The phases were separated and the aqueous phase was extracted with EtOAc (10 mL). The combined organic extracts were washed with brine (10 mL), dried (MgSO₄), filtered, and concentrated in vacuo. The crude product was purified by prep-HPLC (CH₃CN/H₂O with 0.05% TFA/H₂O as mobile phase) to give the TFA salt of 5-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-1,2,4-oxadiazole-3-carboxamide as a yellow solid (14 mg, yield: 16%). ESI-MS (M+H)⁺: 488.4. ¹H NMR (400 MHz, DMSO-d₆) δ:10.25 (s, 1H), 9.61-9.57 (m, 1H), 8.79-8.70 (m, 1H), 8.21-8.13 (m, 2H), 7.99-7.95 (m, 1H), 7.64-7.55 (m, 1H), 7.40-7.35 (m, 1H), 5.29 (br t, J=8.8 Hz, 1H), 3.87-3.83 (m, 3H), 2.98-2.95 (m, 2H), 2.06-1.71 (m, 6H), 1.46 (s, 9H).

Example 34: 3-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-1,2,4-oxadiazole-5-carboxamide (Compound 34)

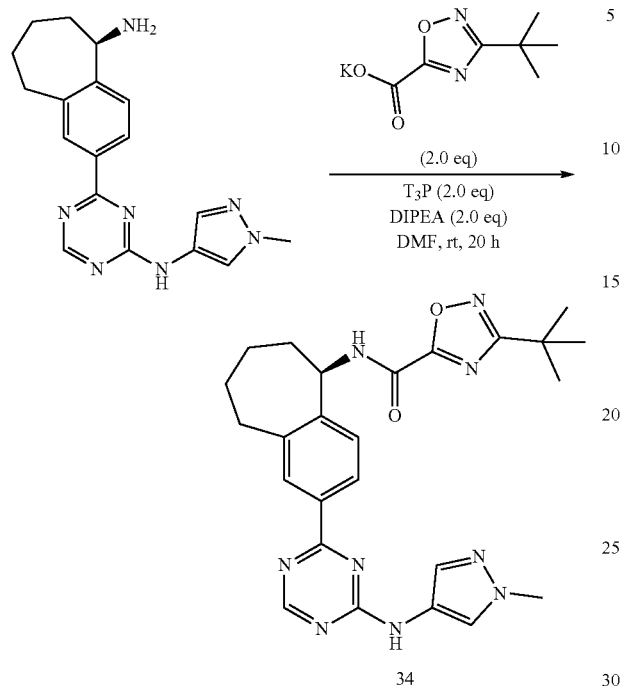

Synthesis of 3-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-1,2,4-oxadiazole-5-carboxamide was similar to that of 5-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-1,2,4-oxadiazole-3-carboxamide in Example 33, Step 3. The crude product was purified by prep-HPLC (CH$_3$CN/H$_2$O with 0.05% TFA/H$_2$O as mobile phase) to give the TFA salt of 3-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-1,2,4-oxadiazole-5-carboxamide as a yellow solid (21 mg, yield: 25%). ESI-MS (M+H)$^+$: 488.4. $^1$H NMR (400 MHz, DMSO-d$_6$) δ:10.28 (m, 1H), 10.06-9.93 (m, 1H), 8.78-8.70 (m, 1H), 8.24-8.10 (m, 2H), 8.99-7.95 (m, 1H), 7.65-7.56 (m, 1H), 7.45-7.34 (m, 1H), 5.34-5.21 (m, 1H), 3.86-3.83 (m, 3H), 3.04-2.89 (m, 2H), 2.11-1.70 (m, 6H), 1.40 (s, 9H).

Example 35: 2-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-oxazole-5-carboxamide (Compound 35)

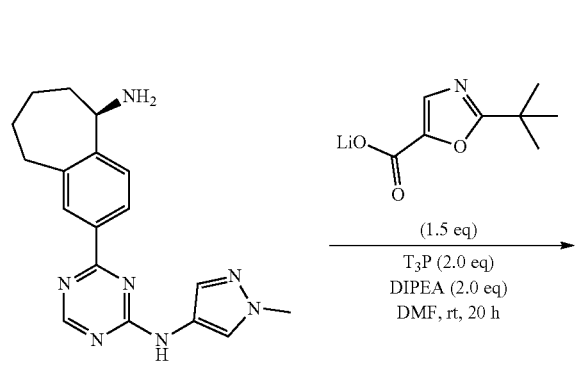

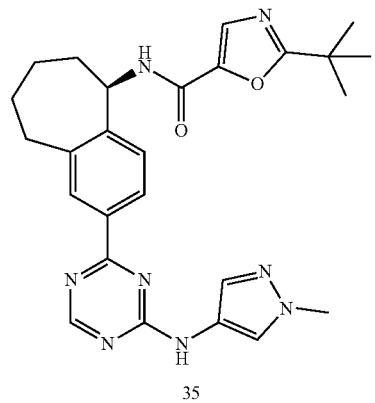

Synthesis of 2-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-oxazole-5-carboxamide was similar to that of 5-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-1,2,4-oxadiazole-3-carboxamide in Example 33, Step 3. The crude product was purified by prep-HPLC (CH$_3$CN/H$_2$O with 0.05% TFA/H$_2$O as mobile phase) to give the TFA salt of 2-tert-butyl-N-[(5R)-2-[4-[(1-methylpyrazol-4-yl)amino]-1,3,5-triazin-2-yl]-6,7,8,9-tetrahydro-5H-benzo[7]annulen-5-yl]-oxazole-5-carboxamide as a white solid (18 mg, yield: 16%). ESI-MS (M+H)$^+$: 487.4. $^1$H NMR (400 MHz, DMSO-d$_6$) δ: 10.23 (s, 1H), 8.78-8.69 (m, 1H), 8.59-8.56 (m, 2H), 8.25-8.07 (m, 2H), 7.99-7.95 (m, 1H), 7.64-7.55 (m, 1H), 7.38-7.32 (m, 1H), 5.26 (br t, J=8.4 Hz, 1H), 3.86-3.83 (m, 3H), 2.97 (br s, 2H), 2.05-1.73 (m, 6H), 1.39 (s, 9H).

Example 36: 1-(tert-butyl)-N-(3-fluoro-2-methyl-4-(4-((1-methyl-1H-pyrazol-4-yl)amino)-1,3,5-triazin-2-yl)benzyl)-1H-pyrazole-4-carboxamide (Compound 36)

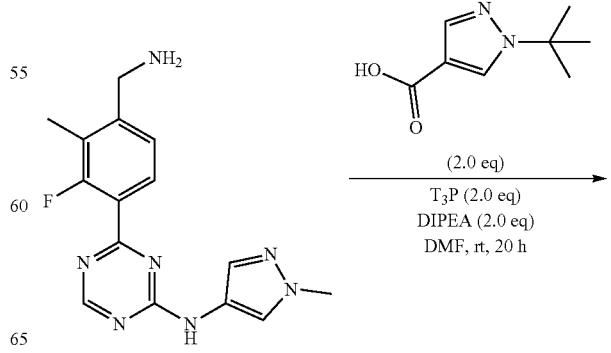

-continued

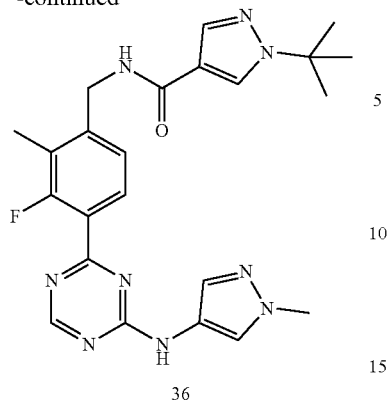

36

-continued

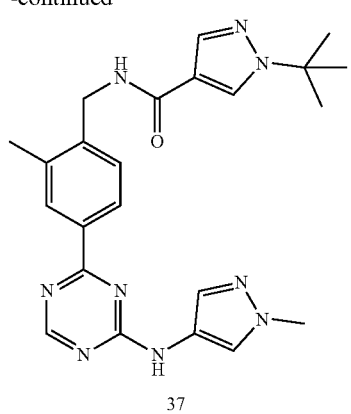

37

Synthesis of 1-(tert-butyl)-N-(3-fluoro-2-methyl-4-(4-((1-methyl-1H-pyrazol-4-yl)amino)-1,3,5-triazin-2-yl)benzyl)-1H-pyrazole-4-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 1-(tert-butyl)-N-(3-fluoro-2-methyl-4-(4-((1-methyl-1H-pyrazol-4-yl)amino)-1,3,5-triazin-2-yl)benzyl)-1H-pyrazole-4-carboxamide as a yellow solid (5.5 mg, yield: 8%). ESI-MS (M+H)$^+$: 464.6. $^1$H NMR (500 MHz, CDCl$_3$) δ:10.20 (br s, 1H), 8.85-8.73 (m, 1H), 8.14 (s, 1H), 8.02-7.93 (m, 2H), 7.90-7.85 (m, 1H), 7.73-7.68 (m, 1H), 7.25-7.17 (m, 1H), 6.56-6.39 (m, 1H), 4.68-4.63 (m, 2H), 3.96 (s, 3H), 2.35-2.24 (m, 3H), 1.62 (m, 9H).

Example 37: 1-(tert-butyl)-N-(2-methyl-4-(4-((1-methyl-1H-pyrazol-4-yl)amino)-1,3,5-triazin-2-yl)benzyl)-1H-pyrazole-4-carboxamide (Compound 37)

Synthesis of 1-(tert-butyl)-N-(2-methyl-4-(4-((1-methyl-1H-pyrazol-4-yl)amino)-1,3,5-triazin-2-yl)benzyl)-1H-pyrazole-4-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 1-(tert-butyl)-N-(2-methyl-4-(4-((1-methyl-1H-pyrazol-4-yl)amino)-1,3,5-triazin-2-yl)benzyl)-1H-pyrazole-4-carboxamide as a yellow solid (24.9 mg, yield: 47%). ESI-MS (M+H)$^+$: 446.0. $^1$H NMR (500 MHz, DMSO-d$_6$) δ: 10.26-10.25 (m, 1H), 8.79-8.70 (m, 1H), 8.53-8.49 (m, 1H), 8.33 (d, J=3.1 Hz, 1H), 8.22-8.14 (m, 1H), 7.99-7.95 (m, 1H), 7.93 (m, 1H), 7.64-7.55 (m, 2H), 7.41 (br dd, J=15.0 Hz, 8.2 Hz, 1H), 4.48 (br t, J=4.6 Hz, 2H), 3.87-3.83 (m, 3H), 2.43-2.41 (m 3H), 1.53 (s, 9H).

Example 38: 5-tert-butyl-N-((2-methyl-4-(4-((1-methylpyrazol-4-yl)amino)-1,3,5-triazine-2-yl))phenyl)methyl)isoxazole-3-carboxamide (Compound 38)

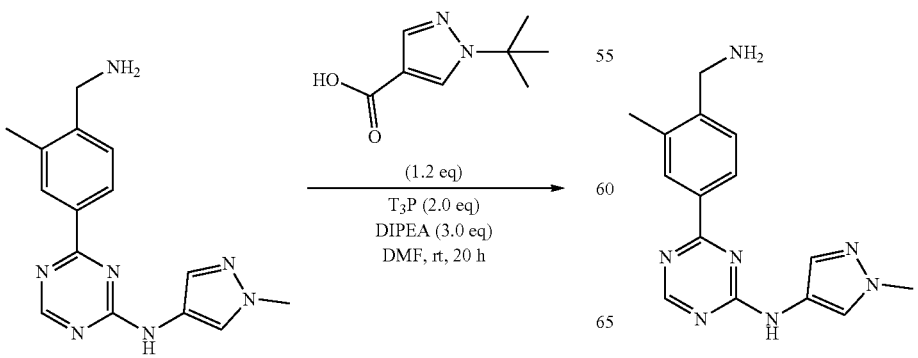

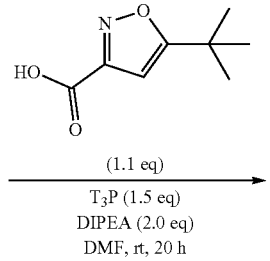

| 131 | 132 |
|---|---|
| -continued | -continued |
| 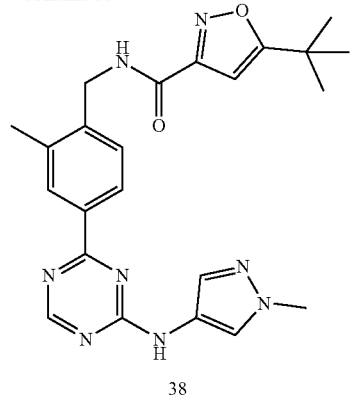 | 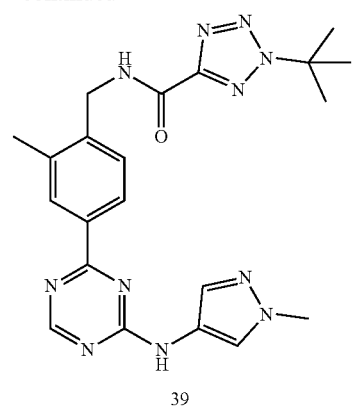 |
| 38 | 39 |

Synthesis of 5-tert-butyl-N-((2-methyl-4-(4-((1-methylpyrazol-4-yl)amino)-1,3,5-triazine-2-yl))phenyl)methyl)isoxazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 5-tert-butyl-N-((2-methyl-4-(4-((1-methylpyrazol-4-yl)amino)-1,3,5-triazine-2-yl))phenyl)methyl)isoxazole-3-carboxamide as a yellow solid (14.3 mg, yield: 24%). ESI-MS (M+H)$^+$: 447.3. $^1$H NMR (500 MHz, DMSO-d$_6$) δ: 10.27-10.25 (m, 1H), 9.28-9.24 (m, 1H), 8.79-8.70 (m, 1H), 8.22-8.14 (m, 2H), 8.00-7.95 (m, 1H), 7.63-7.55 (m, 1H), 7.42-7.37 (m, 1H), 6.61 (s, 1H), 4.51-4.50 (m, 2H), 3.88-3.83 (m, 3H), 2.43-2.41 (m, 3H), 1.33 (s, 9H).

Example 39: 2-(tert-butyl)-N-(2-methyl-4-(4-((1-methyl-1H-pyrazol-4-yl)amino)-1,3,5-triazin-2-yl)benzyl)-2H-tetrazole-5-carboxamide (Compound 39)

Synthesis of 2-(tert-butyl)-N-(2-methyl-4-(4-((1-methyl-1H-pyrazol-4-yl)amino)-1,3,5-triazin-2-yl)benzyl)-2H-tetrazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 2-(tert-butyl)-N-(2-methyl-4-(4-((1-methyl-1H-pyrazol-4-yl)amino)-1,3,5-triazin-2-yl)benzyl)-2H-tetrazole-5-carboxamide as a yellow solid (11.4 mg, yield: 19%). ESI-MS (M+H)$^+$: 448.3. $^1$H NMR (500 MHz, DMSO-d$_6$) δ: 10.26-10.24 (m, 1H), 9.59-9.52 (m, 1H), 8.79-8.70 (m, 1H), 8.22-8.14 (m, 2H), 8.00-7.95 (m, 1H), 7.63-7.55 (m, 1H), 7.44-7.40 (m, 1H), 4.59-4.53 (m, 2H), 3.87-3.83 (m, 3H), 2.45-2.43 (m, 3H), 1.74 (s, 9H).

Example 40: N-(2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide (Compound 40)

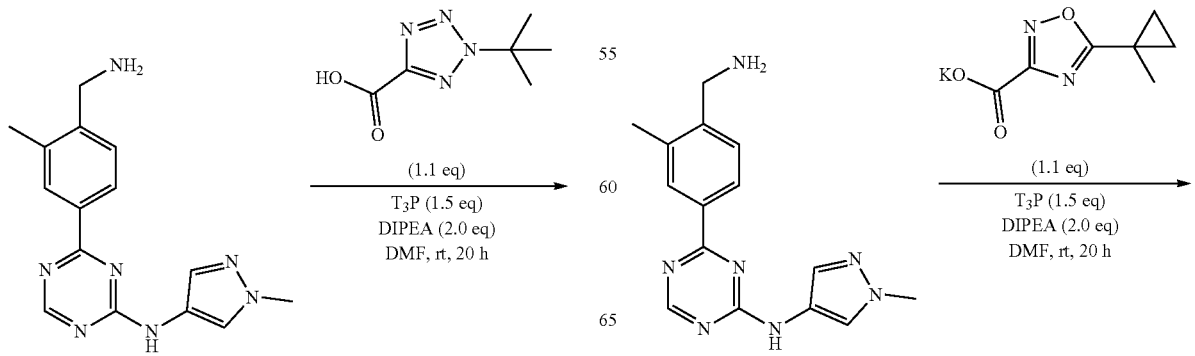

-continued

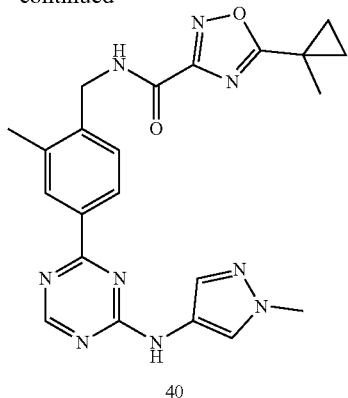

40

Synthesis of N-(2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of N-(2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide as a yellow solid (8.3 mg, yield: 16%). ESI-MS (M+H)$^+$: 446.0. $^1$H NMR (500 MHz, DMSO-d$_6$) δ: 10.27-10.23 (m, 1H), 9.46-9.40 (m, 1H), 8.79-8.70 (m, 1H), 8.23-8.18 (m, 1H), 8.17-8.13 (m, 1H), 8.00-7.95 (m, 1H), 7.63-7.55 (m, 1H), 7.41-7.37 (m, 1H), 4.51 (br t, J=4.9 Hz, 2H), 3.88-3.83 (m, 3H), 2.43-2.41 (m, 3H), 1.55 (s, 3H), 1.41-1.37 (m, 2H), 1.22-1.15 (m, 2H).

Example 41: 5-(2,3-cis-dimethylcyclopropyl)-N-(2-methyl-4-(4-((1-methyl-1H-pyrazol-4-yl)amino)-1,3,5-triazin-2-yl)benzyl)-1,2,4-oxadiazole-3-carboxamide

41

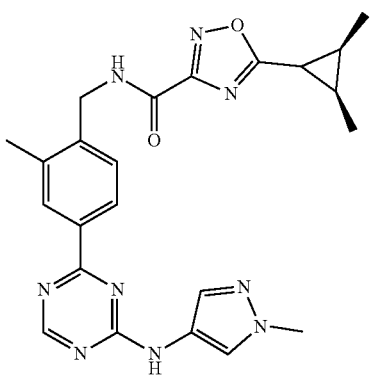

Mixture of Cis Isomers

1. Synthesis of ethyl 2,3-cis-dimethylcyclopropane-1-carboxylate

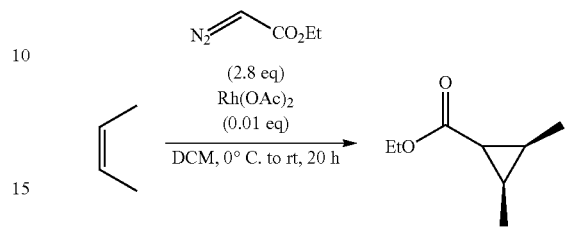

To a solution of (Z)-but-2-ene (22.5 g, 401 mmol) and Rh(OAc)$_2$ dimer (2.35 g, 5.3 mmol) in DCM (1.5 L) at 0° C. was added ethyl 2-diazoacetate (130 g, 1140 mmol) over 4 h. The mixture was stirred at 20° C. for 16 h. The reaction mixture was filtered through a pad of silica gel and concentrated in vacuo to give ethyl 2,3-cis-dimethylcyclopropane-1-carboxylate as a yellow oil (60 g, crude), which was carried forward without further purification.

2. Synthesis of 2,3-cis-dimethylcyclopropane-1-carboxylic acid

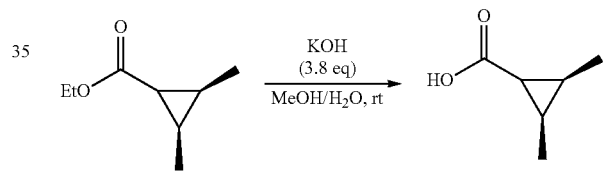

A solution of ethyl 2,3-cis-dimethylcyclopropane-1-carboxylate (60 g, 422 mmol) in MeOH (400 mL) was added to KOH (90 g, 1.6 mol) in H$_2$O (200 mL) at rt. After the reaction was completed, the solvent was removed by distillation in vacuo and DCM (700 mL) was added. The aqueous layer was separated and acidified with 4 M aqueous HCl solution until pH=1. The acidic aqueous phase was extracted with EtOAc (3×20 mL). The combined organic extracts were washed with brine (50 mL), dried (Na$_2$SO$_4$), filtered, and concentrated in vacuo to give 2,3-cis-dimethylcyclopropane-1-carboxylic acid (36.1 g, yield: 75% over 2 steps), which was carried forward without further purification.

3. Synthesis of ethyl 5-(2,3-cis-dimethylcyclopropyl)-1,2,4-oxadiazole-3-carboxylate

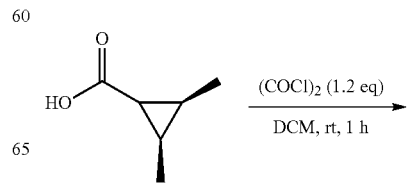

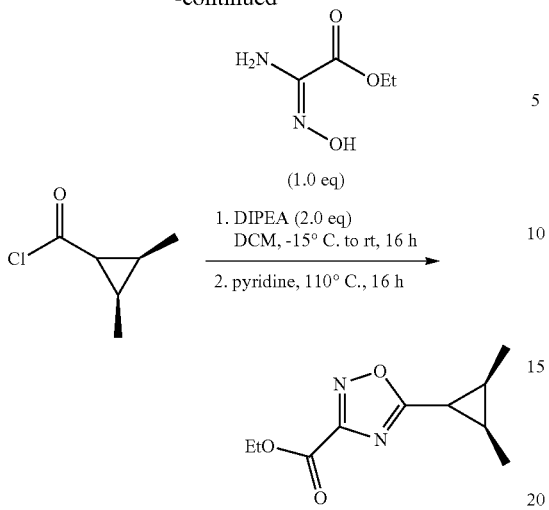

To a solution of oxalyl chloride (28.2 mL, 328 mmol) in DCM (500 mL) was added 2,3-cis-dimethylcyclopropane-1-carboxylic acid (30 g, 263 mmol), and the reaction mixture was stirred at ambient temperature for 1 h. Excess oxalyl chloride was removed by distillation to give crude 2,3-cis-dimethylcyclopropane-1-carbonyl chloride. To a solution of ethyl (E)-2-amino-2-(hydroxyimino)acetate (34.7 g, 263 mmol) and DIPEA (67.8 g, 526 mmol) in DCM (500 mL) at −15° C. was added dropwise crude 2,3-cis-dimethylcyclopropane-1-carbonyl chloride. The resulting solution was stirred as it warmed to ambient temperature and continued to stir at that temperature for 16 h. Water (800 mL) was added and the layers were separated. The aqueous phase was extracted with DCM (300 mL×3) and the combined organic phases were dried (Na₂SO₄), filtered, and concentrated in vacuo. To the residue was added pyridine (400 mL) and the mixture was heated to 110° C. and stirred at that temperature for 16 h. The reaction mixture was then cooled to ambient temperature and concentrated in vacuo. The crude product was purified by silica-gel column chromatography (EtOAc/hexanes, grading from 1% to 10%) to give ethyl 5-(2,3-cis-dimethylcyclopropyl)-1,2,4-oxadiazole-3-carboxylate as a yellow oil (9 g, yield: 16%), which was carried forward without further purification.

4. Synthesis of potassium 5-(2,3-cis-dimethylcyclopropyl)-1,2,4-oxadiazole-3-carboxylate

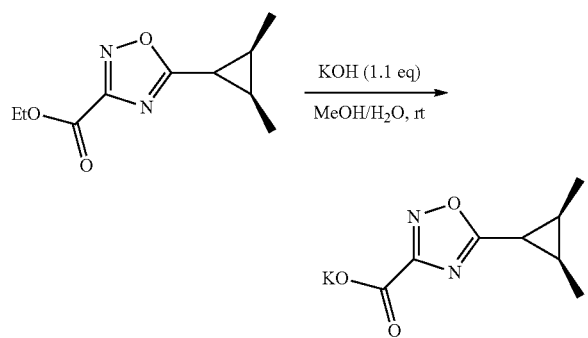

A solution of ethyl 5-(2,3-cis-dimethylcyclopropyl)-1,2,4-oxadiazole-3-carboxylate (6 g, 28.5 mmol) in MeOH (40 mL) was added to a solution of KOH (1.75 g, 31.2 mmol) dissolved in H₂O (20 mL). When the reaction was complete, the solvent was removed by distillation in vacuo and DCM (70 mL) was added. The aqueous layer was separated and concentrated in vacuo to give potassium 5-(2,3-cis-dimethylcyclopropyl)-1,2,4-oxadiazole-3-carboxylate as a white solid (5.21 g, 82% yield). ESI-MS (M+H)⁺: 183.0. Major isomer: ¹H NMR (500 MHz, DMSO-d₆) δ: 1.11-1.08 (m, 1H), 1.04 (td, J=4.3 Hz, 1.8 Hz, 1H), 0.97-0.95 (m, 6H), 0.76-0.72 (m, 1H). Minor isomer: ¹H NMR (500 MHz, DMSO-d₆) δ: 1.08-1.05 (m, 1H), 1.02-0.99 (m, 1H), 0.99-0.97 (m, 6H), 0.72-0.69 (m, 1H).

5. Synthesis of 5-(2,3-cis-dimethylcyclopropyl)-N-(2-methyl-4-(4-((1-methyl-1H-pyrazol-4-yl)amino)-1,3,5-triazin-2-yl)benzyl)-1,2,4-oxadiazole-3-carboxamide (Compound 41)

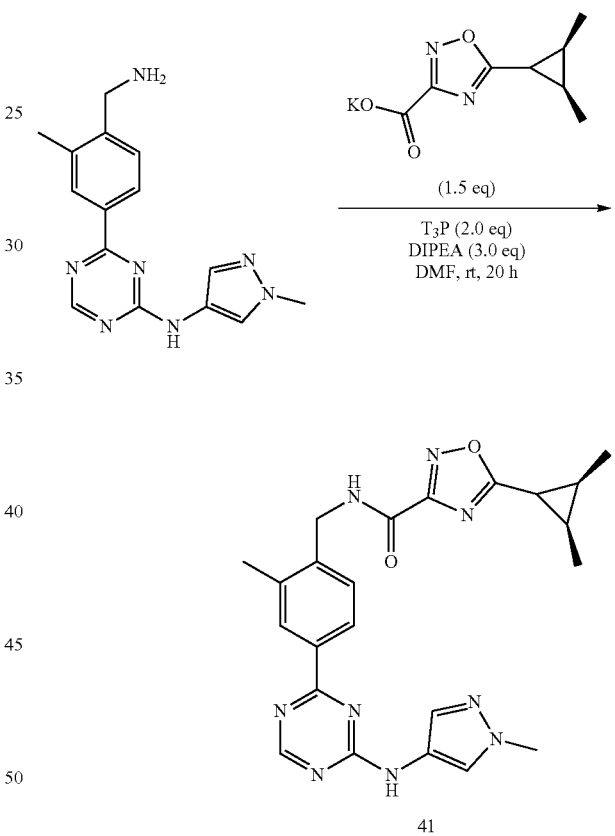

Synthesis of 5-(2,3-cis-dimethylcyclopropyl)-N-(2-methyl-4-(4-((1-methyl-1H-pyrazol-4-yl)amino)-1,3,5-triazin-2-yl)benzyl)-1,2,4-oxadiazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH₃CN/H₂O with 0.05% TFA/H₂O as mobile phase) to give the TFA salt of 5-(2,3-cis-dimethylcyclopropyl)-N-(2-methyl-4-(4-((1-methyl-1H-pyrazol-4-yl)amino)-1,3,5-triazin-2-yl)benzyl)-1,2,4-oxadiazole-3-carboxamide as a yellow solid (2.3 mg, yield: 3%). ESI-MS (M+H)⁺: 446.2. No NMR data available.

Example 42: 5-(tert-butyl)-N-(2-methyl-4-(4-((1-methyl-1H-pyrazol-3-yl)amino)-1,3,5-triazin-2-yl)benzyl)isoxazole-3-carboxamide (Compound 42)

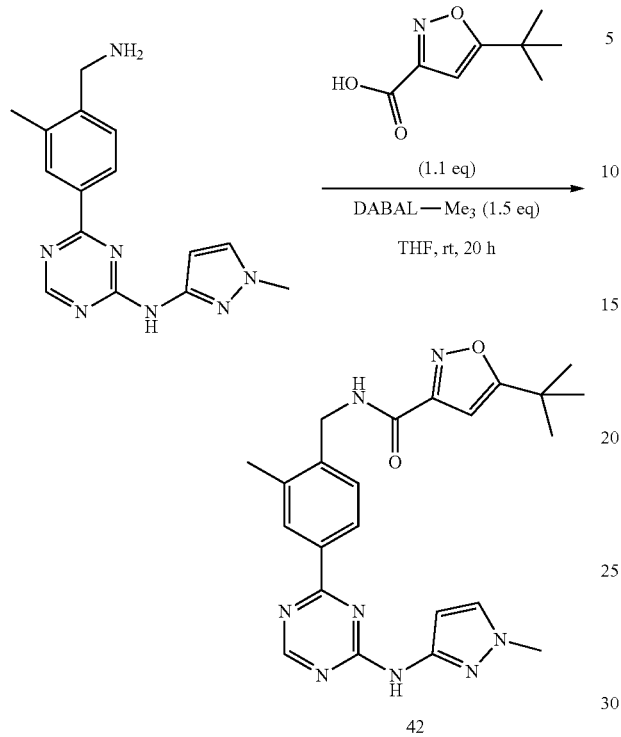

Synthesis of 5-(tert-butyl)-N-(2-methyl-1H-pyrazol-3-yl)amino)-1,3,5-triazin-2-yl)benzyl)isoxazole-3-carboxamide was similar to that of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide in Example 49, Step 4. The crude material was purified by prep-HPLC (CH$_3$CN/H$_2$O with 0.05% NH$_3$/H$_2$O as mobile phase) to give 5-(tert-butyl)-N-(2-methyl-4-(4-((1-methyl-1H-pyrazol-3-yl)amino)-1,3,5-triazin-2-yl)benzyl)isoxazole-3-carboxamide as a white solid (11.4 mg, yield: 13%). ESI-MS (M+H)$^+$: 447.0. $^1$H NMR (500 MHz, DMSO-d$_6$) δ:10.60-10.49 (br m, 2H), 9.25 (br t, J=5.8 Hz, 1H), 8.75 (br s, 1H), 8.19-8.16 (m, 1H), 7.65 (br s, 1H), 7.38 (br d, J=7.9 Hz, 1H), 6.75 (br s, 1H), 6.60 (s, 1H), 4.50 (br d, J=6.1 Hz, 2H), 3.78 (s, 3H), 2.41 (s, 3H), 1.33 (s, 9H).

Example 43: 3-(tert-butyl)-N-(2-methyl-4-(4-((1-methyl-1H-pyrazol-3-yl)amino)-1,3,5-triazin-2-yl)benzyl)isoxazole-5-carboxamide (Compound 43)

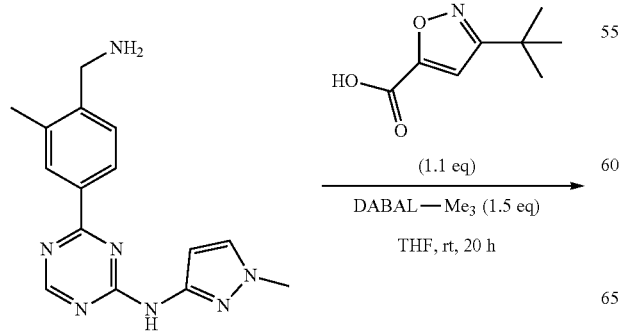

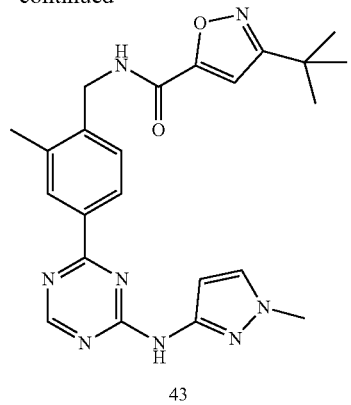

Synthesis of 3-(tert-butyl)-N-(2-methyl-4-(4-((1-methyl-1H-pyrazol-3-yl)amino)-1,3,5-triazin-2-yl)benzyl)isoxazole-5-carboxamide was similar to that of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide in Example 49, Step 4. The crude material was purified by prep-HPLC (CH$_3$CN/H$_2$O with 0.05% NH$_3$/H$_2$O as mobile phase) to give 3-(tert-butyl)-N-(2-methyl-4-(4-((1-methyl-1H-pyrazol-3-yl)amino)-1,3,5-triazin-2-yl)benzyl)isoxazole-5-carboxamide as a white solid (7.2 mg, yield: 8%). ESI-MS (M+H)$^+$: 447.0. $^1$H NMR (500 MHz, DMSO-d$_6$) δ:10.63-10.46 (m, 1H), 9.40 (br t, J=5.8 Hz, 1H), 8.75 (br s, 1H), 8.19-8.17 (m, 1H), 7.65 (br s, 1H), 7.39 (d, J=7.9 Hz, 1H), 7.18 (s, 1H), 6.79-6.50 (m, 2H), 4.51 (d, J=6.1 Hz, 2H), 3.78 (s, 3H), 2.41 (s, 3H), 1.31 (s, 9H).

Example 44: 5-(1-fluoro-2-methylpropan-2-yl)-N-(2-methyl-4-(4-((1-methyl-1H-pyrazol-3-yl)amino)-1,3,5-triazin-2-yl)benzyl)-1,2,4-oxadiazole-3-carboxamide

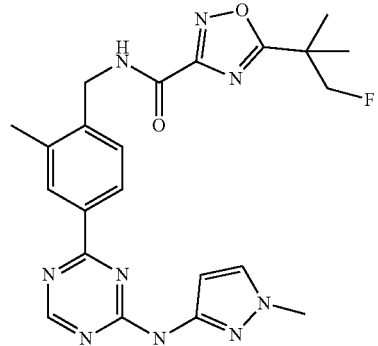

1. Synthesis of ethyl (E)-2-amino-2-(hydroxyimino)acetate

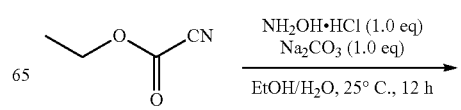

-continued

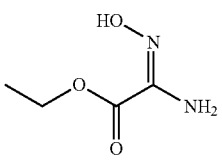

To a solution of ethyl carbonocyanidate (10 g, 101 mmol) in EtOH (75 mL) and H₂O (25 mL) was added Na₂CO₃ (10.7 g, 101 mmol) and hydroxylamine hydrochloride (7.0 g, 101 mmol, 1.0 eq.) at 25° C. The reaction mixture was stirred at 25° C. for 12 h. The reaction mixture was poured into EtOAc (100 mL), filtered, and the filtrate was concentrated in vacuo. The residue was re-dissolved in EtOAc (100 mL), filtered, and the filtrate was concentrated in vacuo to give ethyl (E)-2-amino-2-(hydroxyimino)acetate as a yellow solid (10 g, crude), which was carried forward without further purification. ESI-MS (M+H)⁺: does not ionize. ¹H NMR (400 MHz, CDCl₃) δ: 4.37-4.32 (m, 2H), 1.38-1.30 (m, 3H).

2. Synthesis of ethyl (E)-2-(3-hydroxy-2,2-dimethylpropanamido)-2-(hydroxyimino)acetate

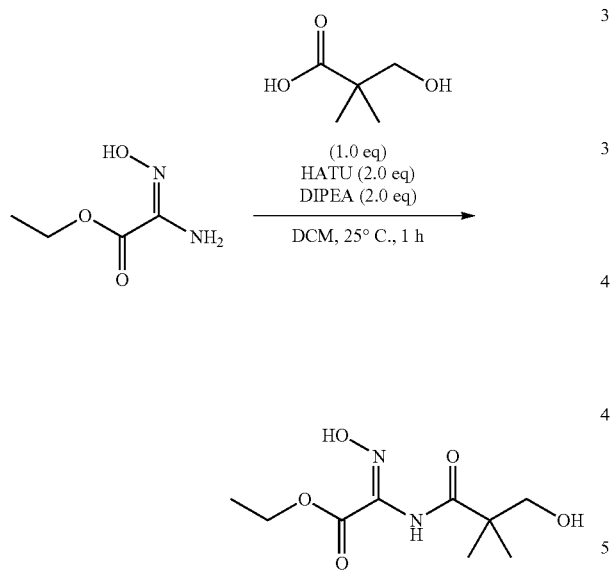

A mixture of ethyl (E)-2-amino-2-(hydroxyimino)acetate (500 mg, 3.8 mmol), 3-hydroxy-2,2-dimethylpropanoic acid (447 mg, 3.8 mmol), HATU (2.9 g, 7.6 mmol), and DIPEA (977 mg, 7.6 mmol) in DCM (10 mL) was stirred at 25° C. for 1 h. An additional portion of DCM (30 mL) was added and the organic phase was washed with H₂O (10 mL×3). The organic phase was dried (Na₂SO₄), filtered, and concentrated in vacuo. The crude product was purified by silica-gel column chromatography (petroleum ether/EtOAc, grading from 5:1 to 0:1) to give ethyl (E)-2-(3-hydroxy-2,2-dimethylpropanamido)-2-(hydroxyimino)acetate as a white solid (500 mg, yield: 57%). ESI-MS (M+H)⁺: 233.1. ¹H NMR (500 MHz, CD₃OD) δ: 4.37 (q, J=7.5 Hz, 2H), 3.66 (s, 2H), 1.38 (t, J=7.0 Hz, 3H), 1.28 (s, 6H).

3. Synthesis of ethyl 5-(1-hydroxy-2-methylpropan-2-yl)-1,2,4-oxadiazole-3-carboxylate

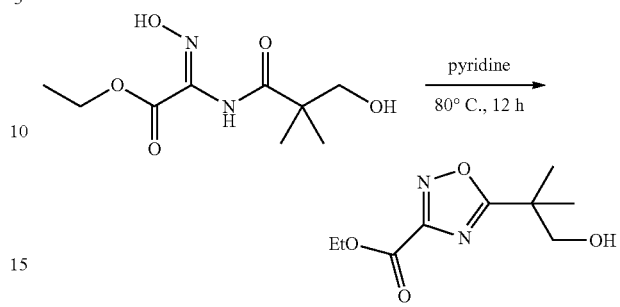

A solution of ethyl (E)-2-(3-hydroxy-2,2-dimethylpropanamido)-2-(hydroxyimino)acetate (500 mg, 2.2 mmol) in pyridine (10 mL) was heated to 80° C. and was stirred at that temperature for 12 h. The reaction mixture was concentrated in vacuo and the residue was purified by silica-gel column chromatography (petroleum ether/EtOAc, grading from 10:1 to 1:1) to give ethyl 5-(1-hydroxy-2-methylpropan-2-yl)-1,2,4-oxadiazole-3-carboxylate as a colorless oil (250 mg, yield: 54%). ESI-MS (M+H)⁺: 215.1. ¹H NMR (500 MHz, CDCl₃) δ: 4.50 (q, J=7.0 Hz, 2H), 3.81 (s, 2H), 1.46 (s, 6H), 1.28-1.14 (m, 3H).

4. Synthesis of ethyl 5-(2-methyl-1-(((trifluoromethyl)sulfonyl)oxy)propan-2-yl)-1,2,4-oxadiazole-3-carboxylate

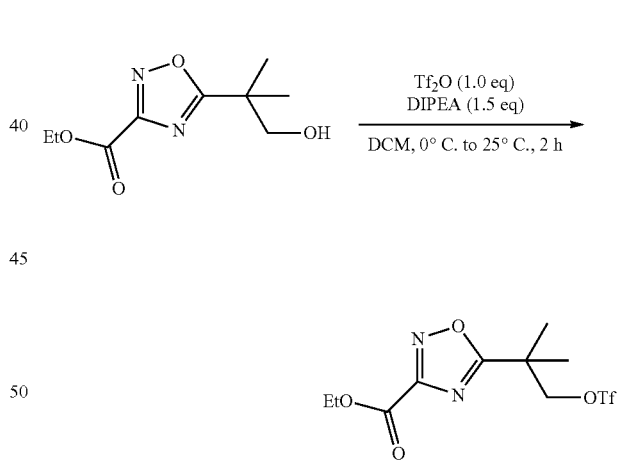

To a solution of ethyl 5-(1-hydroxy-2-methylpropan-2-yl)-1,2,4-oxadiazole-3-carboxylate (430 mg, 2.0 mmol) and DIPEA (390 mg, 3.0 mmol) in DCM (10 mL) at 0° C. was added Tf₂O (566 mg, 2.0 eq). The reaction mixture was stirred at 25° C. for 2 h. An additional portion of DCM (40 mL) was added and the organic phase was washed with H₂O (20 mL×3). The organic phase was dried (Na₂SO₄), filtered, and concentrated in vacuo. The crude product was purified by silica-gel column chromatography (petroleum ether/EtOAc, grading from 10:1 to 1:1) to give ethyl 5-(2-methyl-1-(((trifluoromethyl)sulfonyl)oxy)propan-2-yl)-1,2,4-oxadiazole-3-carboxylate as a colorless oil (600 mg, yield: 86%). ESI-MS (M+H)⁺: 347.1.

5. Synthesis of ethyl 5-(1-fluoro-2-methylpropan-2-yl)-1,2,4-oxadiazole-3-carboxylate

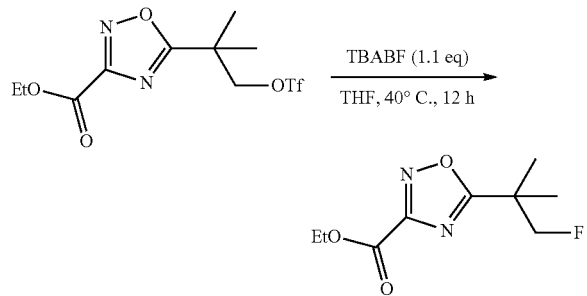

A solution of ethyl 5-(2-methyl-1-(((trifluoromethyl)sulfonyl)oxy)propan-2-yl)-1,2,4-oxadiazole-3-carboxylate (600 mg, 1.7 mmol) and tetrabutylammonium bifluoride (536 mg, 1.9 mmol) in THF (30 mL) was heated to 40° C. and stirred at that temperature for 12 h. The reaction mixture was cooled to ambient temperature and was concentrated in vacuo. The crude product was purified by silica-gel column chromatography (petroleum ether/EtOAc, grading from 10:1 to 3:1) to give ethyl 5-(1-fluoro-2-methylpropan-2-yl)-1,2,4-oxadiazole-3-carboxylate as a colorless oil (330 mg, yield: 88%). ESI-MS (M+H)+: 217.1. $^1$H NMR (500 MHz, CDCl$_3$) δ: 4.63 (s, 1H), 4.53-4.51 (m, 3H), 1.52 (s, 6H), 1.44 (t, J=7.5 Hz, 3H).

6. Synthesis of 5-(1-fluoro-2-methylpropan-2-yl)-1,2,4-oxadiazole-3-carboxylic acid

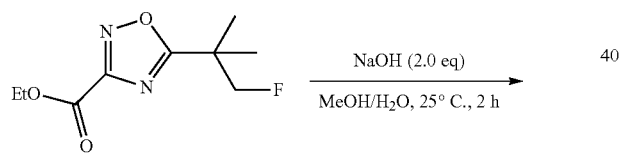

To a solution of ethyl 5-(1-fluoro-2-methylpropan-2-yl)-1,2,4-oxadiazole-3-carboxylate (300 mg, 1.4 mmol) in MeOH (20 mL) was added a solution of NaOH (111 mg, 2.8 mmol) in H$_2$O (10 mL) at 25° C. The reaction mixture was stirred at that temperature for 2 h. The pH of the reaction mixture was adjusted to pH=6 with the addition of an aqueous HCl solution (1 M). The reaction mixture was concentrated in vacuo to remove MeOH and the aqueous phase was lyophilized to give 5-(1-fluoro-2-methylpropan-2-yl)-1,2,4-oxadiazole-3-carboxylic acid as a white solid (300 mg, crude), which was carried forward without further purification. ESI-MS (M+H)+: does not ionize.

7. Synthesis of 5-(1-fluoro-2-methylpropan-2-yl)-N-(2-methyl-4-(4-((1-methyl-1H-pyrazol-3-yl)amino)-1,3,5-triazin-2-yl)benzyl)-1,2,4-oxadiazole-3-carboxamide (Compound 44)

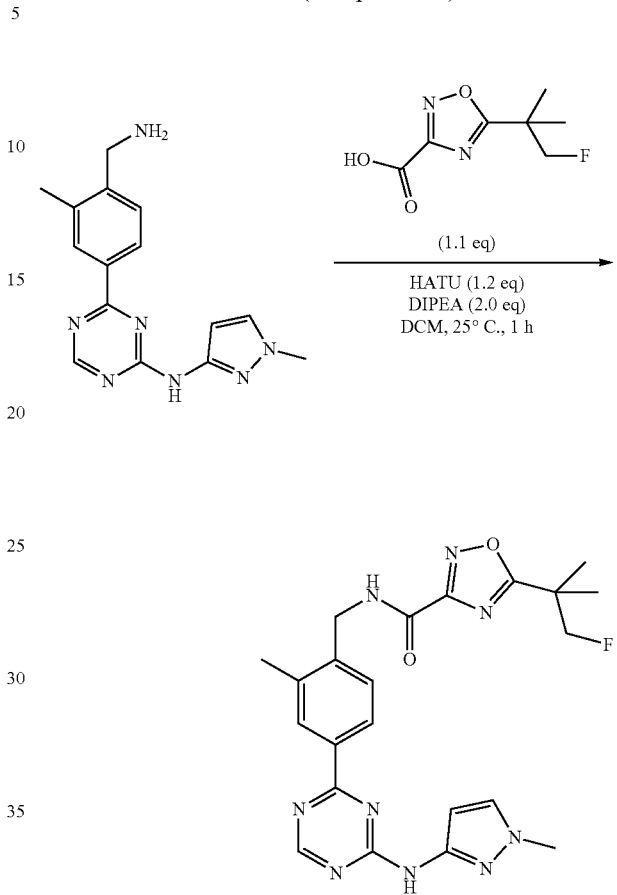

A mixture of 4-(4-(aminomethyl)-3-methylphenyl)-N-(1-methyl-1H-pyrazol-3-yl)-1,3,5-triazin-2-amine (100 mg, 0.34 mmol), 5-(1-fluoro-2-methylpropan-2-yl)-1,2,4-oxadiazole-3-carboxylic acid (64 mg, 0.34 mmol), HATU (155 mg, 0.41 mmol), and DIPEA (88 mg, 0.68 mmol) in DCM (60 mL) was stirred at 25° C. for 1 h. An additional portion of DCM (30 mL) was added and the organic phase was washed with H$_2$O (10 mL×3). The organic phase was dried (Na$_2$SO$_4$), filtered, and concentrated in vacuo. The crude product was purified by prep-HPLC (CH$_3$CN/H$_2$O with 0.05% HCl/H$_2$O as mobile phase) to give the HCl salt of 5-(1-fluoro-2-methylpropan-2-yl)-N-(2-methyl-4-(4-((1-methyl-1H-pyrazol-3-yl)amino)-1,3,5-triazin-2-yl)benzyl)-1,2,4-oxadiazole-3-carboxamide as a white solid (39 mg, yield: 22%). ESI-MS (M+H)+: 466.1. $^1$H NMR (500 MHz, DMSO-d$_6$) δ: 10.05 (s, 1H), 9.12 (s, 1H), 8.72 (s, 1H), 8.19-8.15 (m, 2H), 7.58 (s, 1H), 7.44-7.42 (m, 1H), 6.63 (s, 1H), 4.65-4.55 (m, 4H), 3.78 (s, 3H), 2.43 (s, 3H), 1.46 (s, 6H).

143

Example 45. N-(3-fluoro-2-methyl-4-(4-((1-methyl-1H-pyrazol-3-yl)amino)-1,3,5-triazin-2-yl)benzyl)-5-(1-fluoro-2-methylpropan-2-yl)-1,2,4-oxadiazole-3-carboxamide (Compound 45)

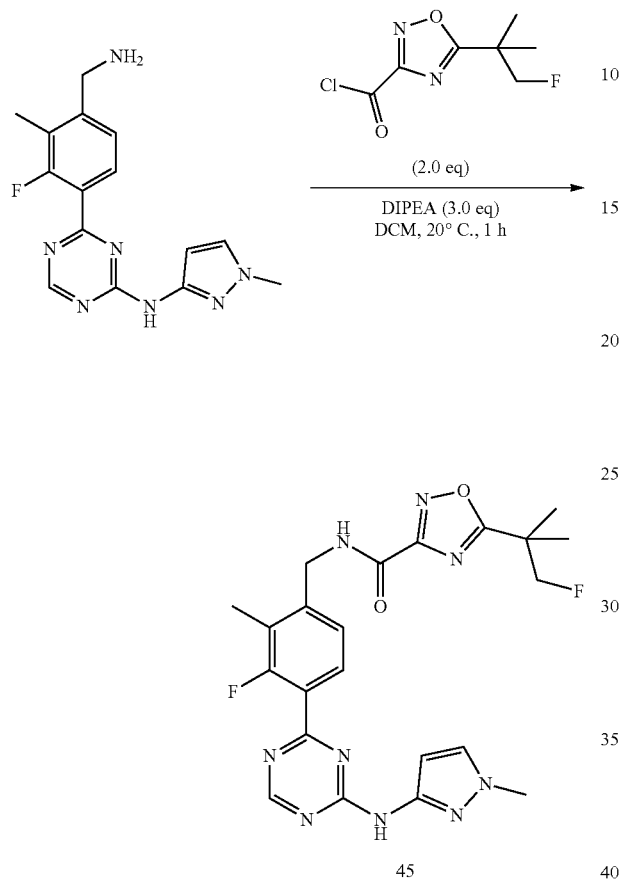

To a solution of the HCl salt of 4-(4-(aminomethyl)-2-fluoro-3-methylphenyl)-N-(1-methyl-1H-pyrazol-3-yl)-1,3,5-triazin-2-amine (120 mg, 0.38 mmol) in DCM (20 mL) at 20° C. was added DIPEA (148 mg, 1.2 mmol), followed by 5-(1-fluoro-2-methylpropan-2-yl)-1,2,4-oxadiazole-3-carbonyl chloride (158 mg, 0.76 mmol). The reaction mixture continued to stir at that temperature for 1 h. The reaction mixture was concentrated in vacuo and the crude material was purified by prep-HPLC (CH$_3$CN/H$_2$O with 0.05% HCl/H$_2$O as mobile phase) to give the HCl salt of N-(3-fluoro-2-methyl-4-(4-((1-methyl-1H-pyrazol-3-yl)amino)-1,3,5-triazin-2-yl)benzyl)-5-(1-fluoro-2-methylpropan-2-yl)-1,2,4-oxadiazole-3-carboxamide as a white solid (44 mg, yield: 23%). ESI-MS (M+H)$^+$: 484.1. $^1$H NMR (500 MHz, DMSO-d$_6$, t=80° C.) δ: 10.14 (s, 1H), 9.18 (s, 1H), 8.76 (s, 1H), 7.88 (t, J=8.0 Hz, 1H), 7.58 (d, J=2.0 Hz, 1H), 7.29 (d, J=8.0 Hz, 1H), 6.67 (d, J=2.0 Hz, 1H), 4.63 (d, J=47 Hz, 2H), 4.60-4.58 (m, 2H), 3.80 (s, 3H), 2.35 (s, 3H), 1.49 (d, J=2.0 Hz, 6H).

144

Example 46: N-(3-fluoro-2-methyl-4-(4-((1-methyl-1H-pyrazol-3-yl)amino)-1,3,5-triazin-2-yl)benzyl)-3-(1-(fluoromethyl)cyclopropyl)-1,2,4-oxadiazole-5-carboxamide

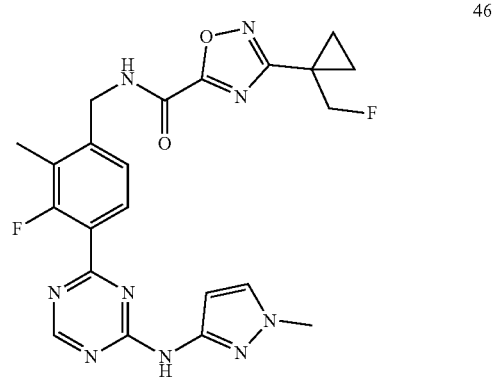 [SMILES: Cc1c(CNC(=O)c2nc(C3(CF)CC3)no2)ccc(-c2ncnc(Nc3ccn(C)n3)n2)c1F]

46

1. Synthesis of (E)-1-(fluoromethyl)-N'-hydroxycyclopropane-1-carboximidamide

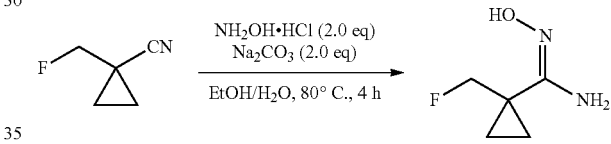

To a solution of 1-(fluoromethyl)cyclopropane-1-carbonitrile (850 mg, 8.5 mmol) in EtOH (15 mL) and H$_2$O (1 mL) were added Na$_2$CO$_3$ (1.8 g, 17 mmol) and hydroxylamine hydrochloride (1.2 g, 17 mmol). The reaction mixture was heated to 80° C. and was stirred at that temperature for 4 h. The reaction mixture was cooled to ambient temperature, poured into H$_2$O (50 mL), and extracted with EtOAc (150 mL). The organic phase was dried (Na$_2$SO$_4$), filtered, and concentrated in vacuo. The crude product was purified by silica-gel column chromatography to give (E)-1-(fluoromethyl)-N'-hydroxycyclopropane-1-carboximidamide as a white solid (1 g, yield: 90%), which was carried forward without further purification.

2. Synthesis of ethyl 3-(1-(fluoromethyl)cyclopropyl)-1,2,4-oxadiazole-5-carboxylate

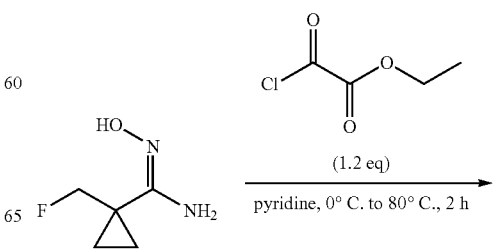

-continued

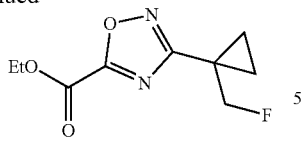

A solution of (E)-1-(fluoromethyl)-N'-hydroxycyclopropane-1-carboximidamide (5.2 g, 39 mmol) in pyridine (20 mL) was cooled to 0° C. Then ethyl chlorooxoacetate (5.3 mL, 47 mmol) was added dropwise. After the addition was complete, the reaction mixture was heated to 80° C. and was stirred at that temperature for 2 h. The reaction mixture was poured into ice-water (100 mL) and the aqueous phase was extracted with DCM (30 mL×3). The organic phase was washed with an HCl solution (30 mL, 1 M), followed by brine (30 mL). The organic phase was dried (Na2SO4), filtered and concentrated in vacuo to give ethyl 3-(1-(fluoromethyl)cyclopropyl)-1,2,4-oxadiazole-5-carboxylate (6.1 g, yield: 85%), which was carried forward without further purification.

3. Synthesis of potassium 3-(1-(fluoromethyl)cyclopropyl)-1,2,4-oxadiazole-5-carboxylate

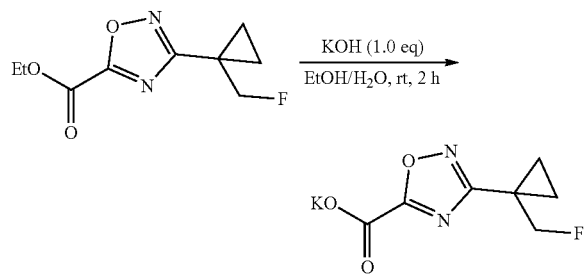

Synthesis of potassium 3-(1-(fluoromethyl)cyclopropyl)-1,2,4-oxadiazole-5-carboxylate was similar to that of potassium 5-(2,3-cis-dimethylcyclopropyl)-1,2,4-oxadiazole-3-carboxylate in Example 41, Step 4. The crude material was concentrated in vacuo to give potassium 3-(1-(fluoromethyl)cyclopropyl)-1,2,4-oxadiazole-5-carboxylate as a white solid (4 g, yield: 78%). ESI-MS (M+H)$^+$: 187.0. $^1$H NMR (500 MHz, DMSO-$d_6$) δ: 4.72 (s, 1H), 4.62 (s, 1H), 1.20-1.26 (m, 2H), 1.13-1.19 (m, 2H). $^{13}$C NMR (126 MHz, DMSO-$d_6$) δ: 174.7, 170.6, 155.7, 86.8, 85.5, 19.0 (d, J=24 Hz), 12.9 (d, J=5 Hz).

4. Synthesis of N-(3-fluoro-2-methyl-4-(4-((1-methyl-1H-pyrazol-3-yl)amino)-1,3,5-triazin-2-yl)benzyl)-3-(1-(fluoromethyl)cyclopropyl)-1,2,4-oxadiazole-5-carboxamide (Compound 46)

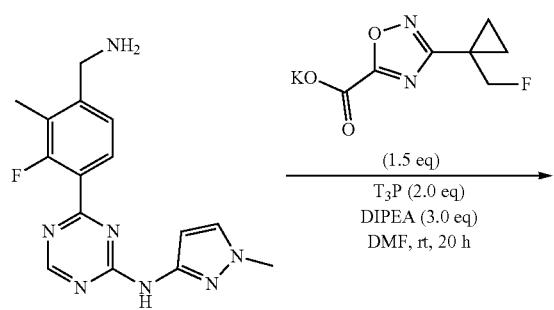

-continued

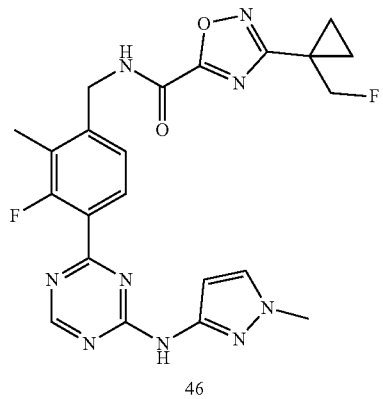

Synthesis of N-(3-fluoro-2-methyl-4-(4-((1-methyl-1H-pyrazol-3-yl)amino)-1,3,5-triazin-2-yl)benzyl)-3-(1-(fluoromethyl)cyclopropyl)-1,2,4-oxadiazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of N-(3-fluoro-2-methyl-4-(4-((1-methyl-1H-pyrazol-3-yl)amino)-1,3,5-triazin-2-yl)benzyl)-3-(1-(fluoromethyl)cyclopropyl)-1,2,4-oxadiazole-5-carboxamide as a yellow solid (12.8 mg, yield: 12%). ESI-MS (M+H)$^+$: 482.2. $^1$H NMR (500 MHz, CDCl$_3$) δ: 9.70 (br s, 1H), 8.88 (br s, 1H), 8.13-7.82 (br s, 1H), 7.39-7.37 (m, 1H), 7.28-7.24 (br s, 2H), 7.14-6.98 (br s, 1H), 4.77 (s, 1H), 4.73 (d, J=6.1 Hz, 2H), 4.67 (s, 1H), 3.90 (s, 3H), 2.38 (br s, 3H), 1.47-1.41 (m, 2H), 1.27-1.22 (m, 2H).

Example 47. N-(3-fluoro-2-methyl-4-(4-((1-methyl-1H-pyrazol-4-yl)amino)-1,3,5-triazin-2-yl)benzyl)-3-(1-(fluoromethyl)cyclopropyl)-1,2,4-oxadiazole-5-carboxamide (Compound 47)

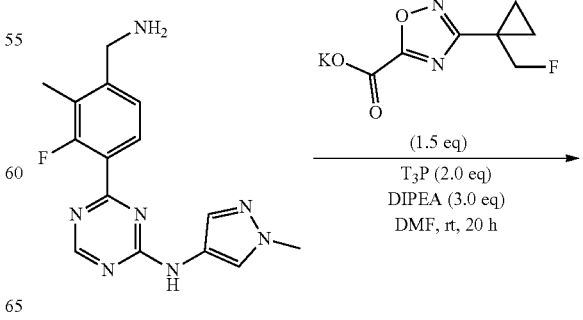

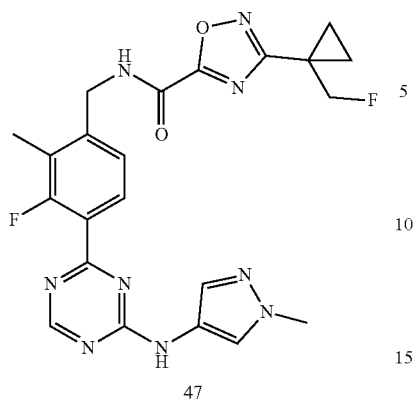

47

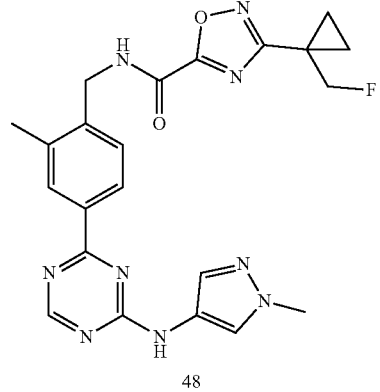

48

Synthesis of N-(3-fluoro-2-methyl-4-(4-((1-methyl-1H-pyrazol-4-yl)amino)-1,3,5-triazin-2-yl)benzyl)-3-(1-(fluoromethyl)cyclopropyl)-1,2,4-oxadiazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of N-(3-fluoro-2-methyl-4-(4-((1-methyl-1H-pyrazol-4-yl)amino)-1,3,5-triazin-2-yl)benzyl)-3-(1-(fluoromethyl)cyclopropyl)-1,2,4-oxadiazole-5-carboxamide as a yellow solid (14.9 mg, yield: 36%). ESI-MS (M+H)$^+$: 482.0. $^1$H NMR (500 MHz, DMSO-d$_6$) δ:10.35-10.33 (m, 1H), 9.90-9.84 (m, 1H), 8.81-8.72 (m, 1H), 7.95-7.90 (m, 1H), 7.83-7.78 (m, 1H), 7.65-7.55 (m, 1H), 7.29-7.25 (m, 1H), 4.78-4.68 (m, 2H), 4.55-4.52 (m, 2H), 3.83-3.82 (m, 3H), 2.33-2.28 (m, 3H), 1.36-1.31 (m, 2H), 1.31-1.28 (m, 2H).

Example 48. 3-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-5-carboxamide (Compound 48)

Synthesis of 3-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give 3-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-5-carboxamide as a yellow solid (24.9 mg, yield: 20%). ESI-MS (M+H)$^+$: 464.0. $^1$H NMR (500 MHz, DMSO-d$_6$) δ: 10.27-10.26 (m, 1H), 9.87-9.83 (m, 1H), 8.79-8.70 (m, 1H), 8.24-8.13 (m, 2H), 7.99-7.95 (m, 1H), 7.64-7.55 (m, 1H), 7.44 (br dd, J=13.1 Hz, 8.2 Hz, 1H), 4.78-4.68 (m, 2H), 4.52 (br t, J=4.9 Hz, 2H), 3.87-3.83 (m, 3H), 2.43-2.41 (m, 3H), 1.36-1.32 (m, 2H), 1.32-1.28 (m, 2H).

Example 49: 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide

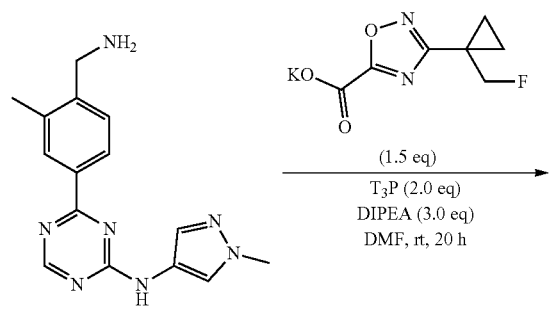

(1.5 eq)
T$_3$P (2.0 eq)
DIPEA (3.0 eq)
DMF, rt, 20 h

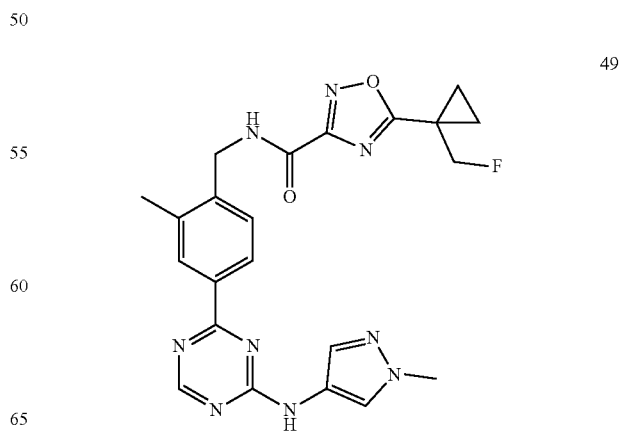

49

1. Synthesis of ethyl 1-(fluoromethyl)cyclopropane-1-carboxylate

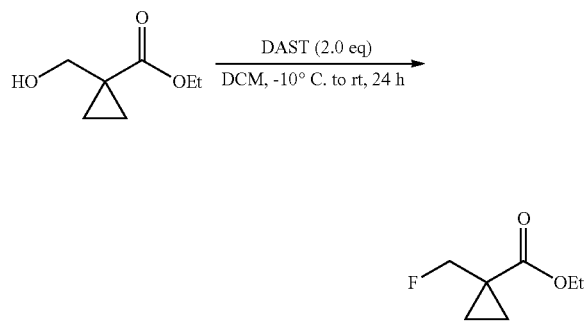

To a solution of ethyl 1-(hydroxymethyl)cyclopropane-1-carboxylate (3.0 g, 21 mmol) in DCM (50 mL) at −10° C. was added DAST (6.0 g, 40 mmol) under Ar. The reaction mixture was stirred as it warmed to ambient temperature over 1 h and continued to stir at that temperature for 23 h. An aqueous solution of HCl (10%, 5 drops) and H$_2$O (50 mL) were added, and the layers were separated. The aqueous layer was extracted with DCM (50 mL) and the combined organic phases were washed sequentially with H$_2$O (50 mL) and brine (50 mL), dried (MgSO$_4$), and filtered. The filtrate was concentrated in vacuo to give ethyl 1-(fluoromethyl)cyclopropane-1-carboxylate (3.0 g, yield: 99%), which was carried forward without further purification.

2. Synthesis of 1-(fluoromethyl)cyclopropane-1-carboxylic acid

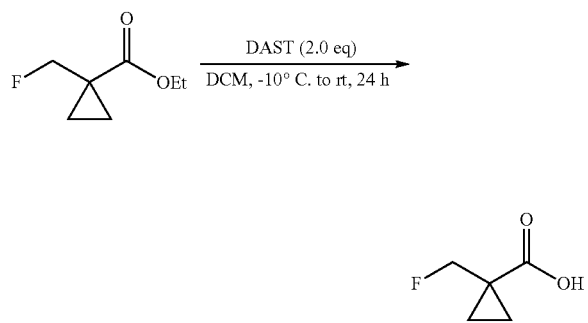

To a solution of ethyl 1-(fluoromethyl)cyclopropane-1-carboxylate (5.0 g, 34 mmol) in a mixture of THF and MeOH (1:1, 50 mL) was added an aqueous solution of LiOH (2.1 g in 50 mL). The homogeneous mixture was stirred at ambient temperature for 18 h and an HCl solution (10%) was added until pH=2. The acidic aqueous phase was extracted with Et$_2$O (100 mL×3) and the ethereal extracts were concentrated in vacuo to give 1-(fluoromethyl)cyclopropane-1-carboxylic acid as a light brown oil (3.4 g, yield: 85%), which was carried forward without further purification.

3. Synthesis of ethyl 5-(1-(fluoromethyl)cyclopropyl)-1,2,4-oxadiazole-3-carboxylate

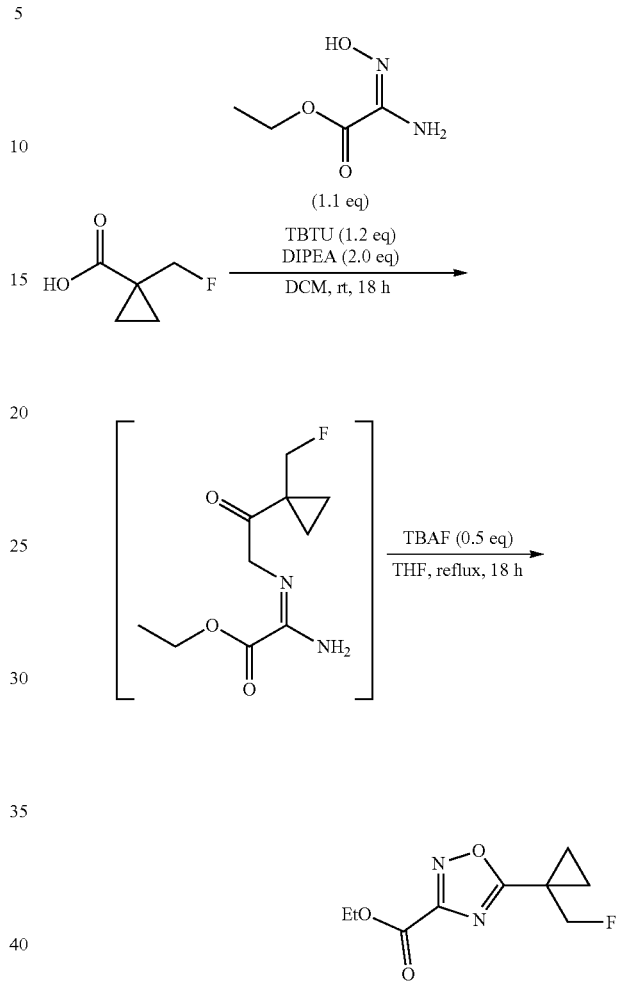

To a solution of 1-(fluoromethyl)cyclopropane-1-carboxylic acid (1.0 g, 8.5 mmol), TBTU (3.3 g, 10.2 mmol), and DIPEA (2.2 g, 16.9 mmol) in DCM (20 mL) at ambient temperature was added ethyl (E)-2-amino-2-(hydroxyimino)acetate (1.2 g, 9.3 mmol). The reaction mixture was stirred at ambient temperature for 18 h and EtOAc (100 mL) was added. The layers were separated and the organic phase was washed with a saturated aqueous NaHCO$_3$ solution (100 mL). The organic phase was then dried (Na$_2$SO$_4$), filtered, and concentrated in vacuo. The crude material (white solid) was dissolved in THF (20 mL) and TBAF (1.1 g, 4.2 mmol) was added. The reaction mixture was heated to reflux and was stirred at that temperature for 18 h. The reaction mixture was cooled to ambient temperature and diluted with EtOAc (100 mL). The organic phase was washed with a saturated aqueous NaHCO$_3$ solution (100 mL), dried (Na$_2$SO$_4$), filtered, and concentrated in vacuo. The crude material was purified by silica-gel column chromatography (petroleum ether/EtOAc, 1:1) to give ethyl 5-(1-(fluoromethyl)cyclopropyl)-1,2,4-oxadiazole-3-carboxylate as a brown oil (1.1 g, yield: 60%). $^1$H NMR (500 MHz, CDCl$_3$) δ: 4.81 (s, 1H), 4.71 (s, 1H), 4.50 (q, J=7.1 Hz, 2H), 1.71-1.66 (m, 2H), 1.46-1.42 (m, 3H), 1.42-1.38 (m, 2H).

4. Synthesis of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide (Compound 49)

Example 50: N-(3-fluoro-2-methyl-4-(4-((1-methyl-1H-pyrazol-4-yl)amino)-1,3,5-triazin-2-yl)benzyl)-5-(1-(fluoromethyl)cyclopropyl)-1,2,4-oxadiazole-3-carboxamide (Compound 50)

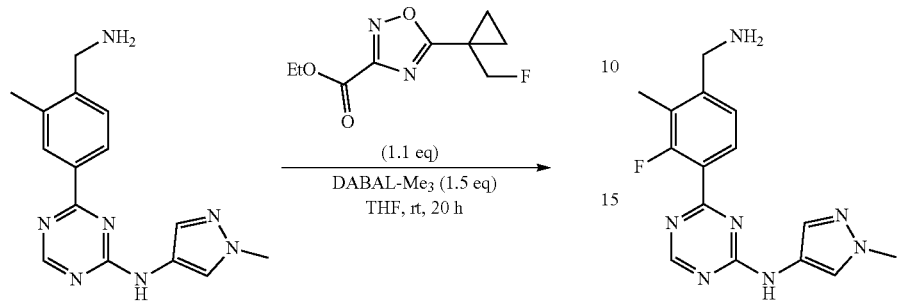

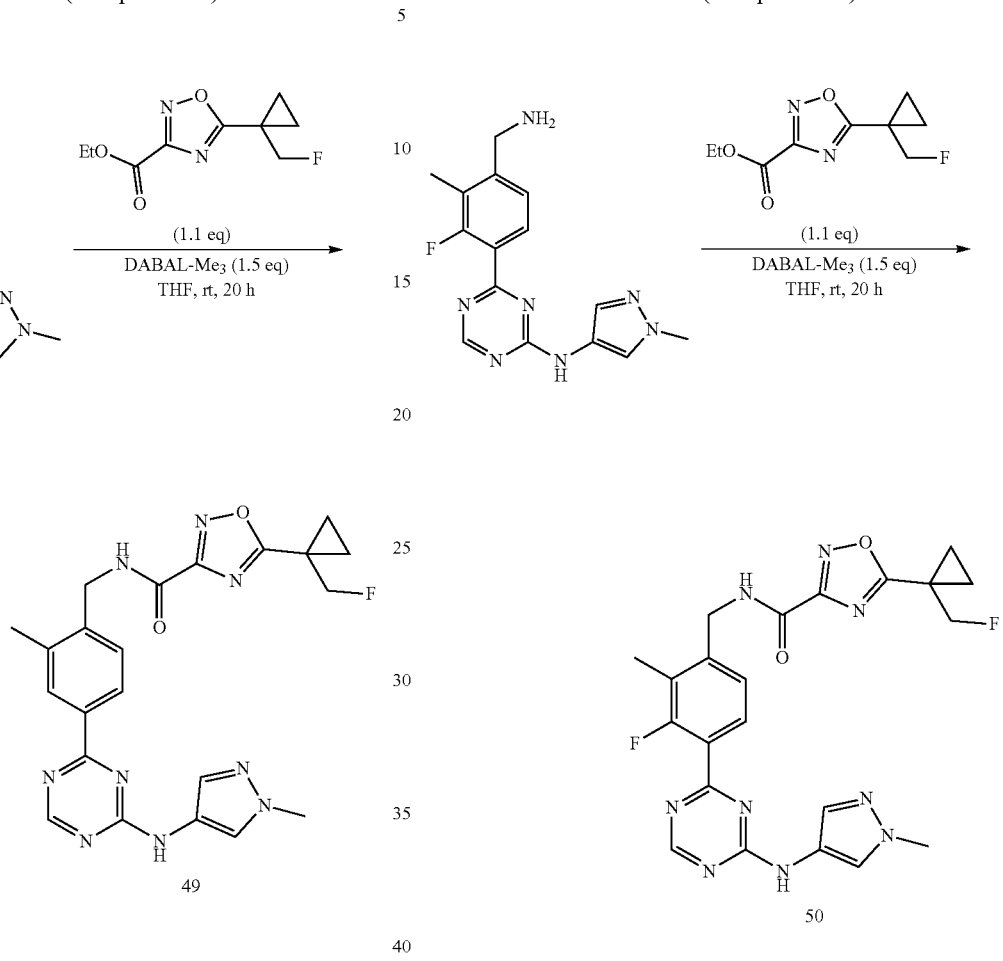

To a solution of 4-(4-(aminomethyl)-3-methylphenyl)-N-(1-methyl-1H-pyrazol-4-yl)-1,3,5-triazin-2-amine (28 mg, 93 μmol) and ethyl 5-(1-(fluoromethyl)cyclopropyl)-1,2,4-oxadiazole-3-carboxylate (22 mg, 102 μmol) in THF (500 μL) was added DABAL-Me$_3$ (36 mg, 140 μmol). The reaction mixture was stirred at ambient temperature for 20 h. The reaction mixture was diluted with MeOH (5 mL) and was stirred at ambient temperature for 15 min. The reaction mixture was filtered, and the residue was washed with MeOH (5 mL). The combined organic phases were concentrated in vacuo and purified by prep-HPLC (CH$_3$CN/H$_2$O with 0.05% TFA/H$_2$O as mobile phase) to give the TFA salt of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide as a yellow solid (22.2 mg, yield: 49%). ESI-MS (M+H)$^+$: 464.2. $^1$H NMR (500 MHz, DMSO-d$_6$) δ:10.27-10.24 (m, 1H), 9.53-9.45 (m, 1H), 8.79-8.70 (m, 1H), 8.23-8.13 (m, 1H), 8.00-7.95 (m, 2H), 7.63-7.55 (m, 1H), 7.44-7.36 (m, 1H), 4.83-4.73 (m, 2H), 4.53 (br t, J=4.9 Hz, 2H), 3.87-3.83 (m, 3H), 2.43-2.41 (s, 3H), 1.58-1.50 (m, 2H), 1.49-1.45 (m, 2H).

Synthesis of N-(3-fluoro-2-methyl-4-(4-((1-methyl-1H-pyrazol-4-yl)amino)-1,3,5-triazin-2-yl)benzyl)-5-(1-(fluoromethyl)cyclopropyl)-1,2,4-oxadiazole-3-carboxamide was similar to that of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide in Example 49, Step 4. The crude material was purified by prep-HPLC (CH$_3$CN/H$_2$O with 0.05% TFA/H$_2$O as mobile phase) to give the TFA salt of N-(3-fluoro-2-methyl-4-(4-((1-methyl-1H-pyrazol-4-yl)amino)-1,3,5-triazin-2-yl)benzyl)-5-(1-(fluoromethyl)cyclopropyl)-1,2,4-oxadiazole-3-carboxamide (22.2 mg, yield: 49%). ESI-MS (M+H)$^+$: 482.1. $^1$H NMR (500 MHz, DMSO-d$_6$) δ: 10.35-10.31 (m, 1H), 9.55-9.49 (m, 1H), 8.81-8.72 (m, 1H), 7.96-7.92 (m, 1H), 7.83-7.78 (m, 1H), 7.64-7.55 (m, 1H), 7.26-7.19 (m, 1H), 4.82 (d, J=7.3 Hz, 1H), 4.73 (d, J=7.3 Hz, 1H), 4.55-4.51 (m, 2H), 3.92-3.82 (m, 3H), 2.33-2.28 (m, 3H), 1.57-1.51 (m, 2H), 1.50-1.45 (m, 2H).

Example 51: N-(5-fluoro-2-methyl-4-(4-((1-methyl-1H-pyrazol-4-yl)amino)-1,3,5-triazin-2-yl)benzyl)-5-(1-(fluoromethyl)cyclopropyl)-1,2,4-oxadiazole-3-carboxamide (Compound 51)

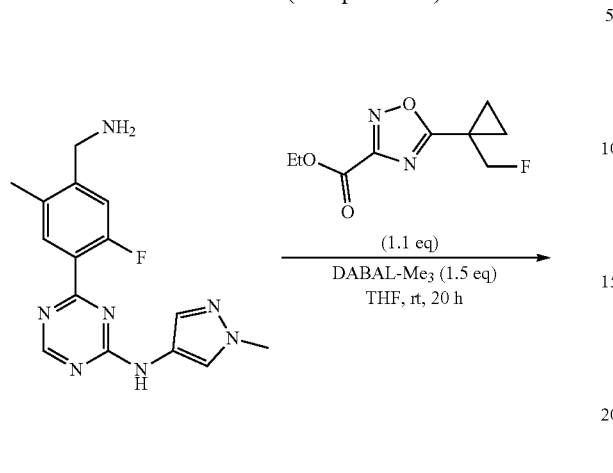

Synthesis of N-(5-fluoro-2-methyl-4-(4-((1-methyl-1H-pyrazol-4-yl)amino)-1,3,5-triazin-2-yl)benzyl)-5-(1-(fluoromethyl)cyclopropyl)-1,2,4-oxadiazole-3-carboxamide was similar to that of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide in Example 49, Step 4. The crude material was purified by prep-HPLC (CH$_3$CN/H$_2$O with 0.05% NH$_3$/H$_2$O as mobile phase) to give N-(5-fluoro-2-methyl-4-(4-((1-methyl-1H-pyrazol-4-yl)amino)-1,3,5-triazin-2-yl)benzyl)-5-(1-(fluoromethyl)cyclopropyl)-1,2,4-oxadiazole-3-carboxamide as a yellow solid (8.8 mg, yield: 19%). ESI-MS (M+H)$^+$: 482.1. $^1$H NMR (500 MHz, DMSO-d$_6$) δ:10.36-10.32 (m, 1H), 9.55-9.50 (m, 1H), 8.00-7.89 (m, 2H), 7.63-7.55 (m, 1H), 7.19-6.98 (m, 2H), 4.83-4.72 (m, 2H), 4.49 (br t, J=5.5 Hz, 2H), 3.83-3.82 (m, 3H), 2.37-2.35 (m, 3H), 1.58-1.52 (m, 2H), 1.50-1.43 (m, 2H).

Example 52: N-(3-fluoro-2-methyl-4-(4-((1-methyl-1H-pyrazol-3-yl)amino)-1,3,5-triazin-2-yl)benzyl)-5-(1-(trifluoromethyl)cyclopropyl)-1,2,4-oxadiazole-3-carboxamide

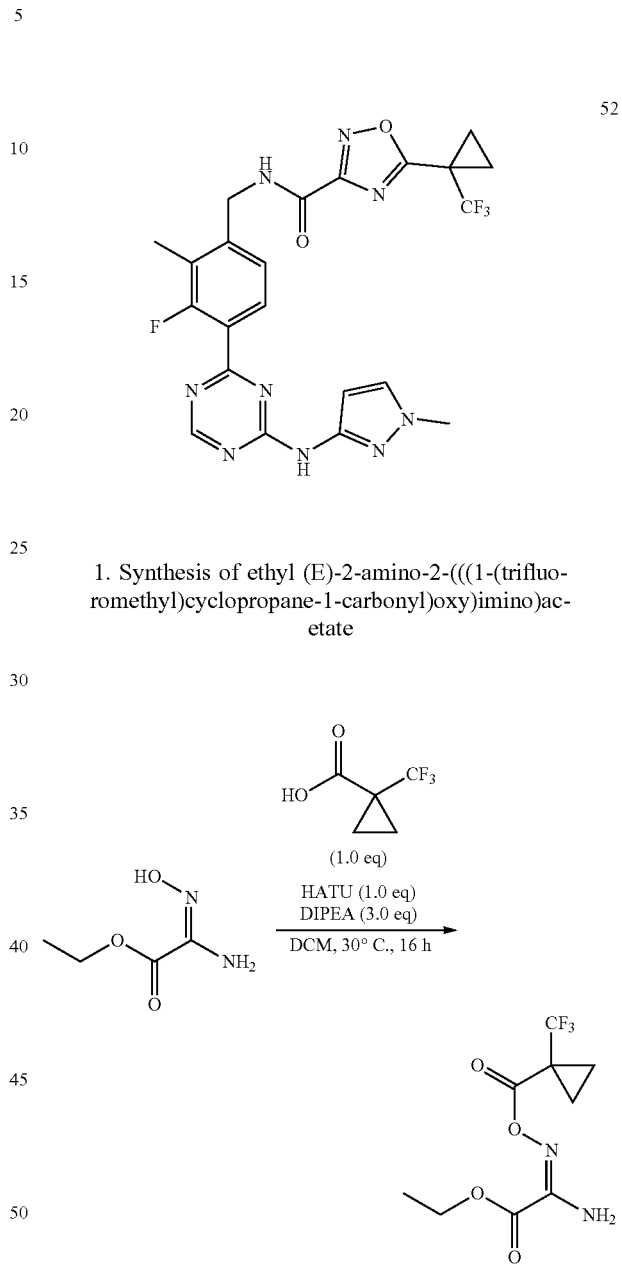

1. Synthesis of ethyl (E)-2-amino-2-(((1-(trifluoromethyl)cyclopropane-1-carbonyl)oxy)imino)acetate To a solution of ethyl (E)-2-amino-2-(hydroxyimino)acetate (924 mg, 6 mmol) and 1-(trifluoromethyl)cyclopropane-1-carboxylic acid (792 mg, 6 mmol) in DCM (75 mL) was added HATU (2.28 g, 6 mmol) and DIPEA (2.32 g, 18 mmol) at 30° C. The reaction mixture was stirred at that temperature for 16 h. The reaction mixture was concentrated in vacuo and the crude material was purified by silica-gel column chromatography (petroleum ether/EtOAc, grading from 10:1 to 3:1) to give ethyl (E)-2-amino-2-(((1-(trifluoromethyl)cyclopropane-1-carbonyl)oxy)imino)acetate as a light gray solid (723 mg, yield: 45%). $^1$H NMR (400 MHz, CDCl$_3$) δ: 5.48 (br s, 2H), 4.38 (q, J=7.2 Hz, 2H), 1.57-1.56 (m, 2H), 1.45-1.43 (m, 2H), 1.38 (t, J=7.2 Hz, 3H).

2. Synthesis of ethyl 5-(1-(trifluoromethyl)cyclopropyl)-1,2,4-oxadiazole-3-carboxylate

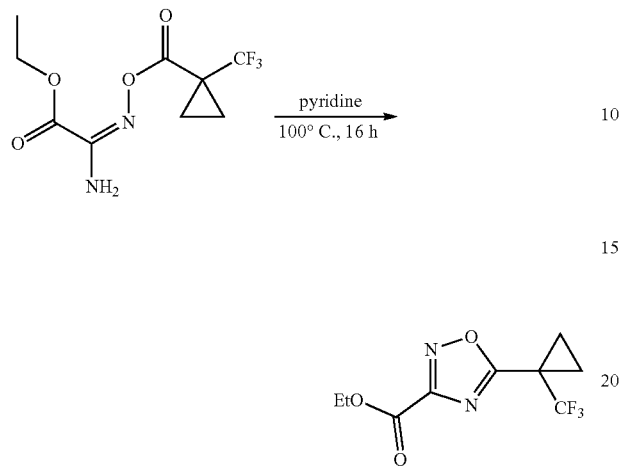

Synthesis of ethyl 5-(1-(trifluoromethyl)cyclopropyl)-1,2,4-oxadiazole-3-carboxylate was similar to that of ethyl 5-(1-hydroxy-2-methylpropan-2-yl)-1,2,4-oxadiazole-3-carboxylate in Example 44, Step 3. The crude material was purified by prep-TLC (petroleum ether/EtOAc, 5:1) to give ethyl 5-(1-(trifluoromethyl)cyclopropyl)-1,2,4-oxadiazole-3-carboxylate as a colorless oil (202 mg, yield: 30%). $^1$H NMR (400 MHz, CDCl$_3$) δ: 4.54-4.47 (m, 2H), 1.74-1.73 (m, 4H), 1.44-1.41 (m, 3H).

3. Synthesis of 5-(1-(trifluoromethyl)cyclopropyl)-1,2,4-oxadiazole-3-carboxylic acid

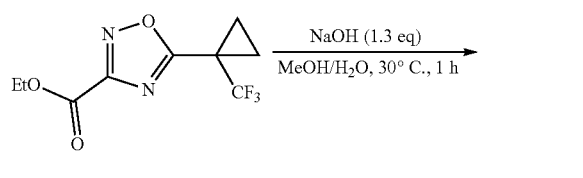

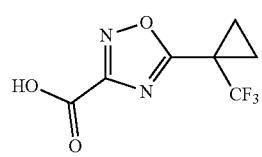

Synthesis of 5-(1-(trifluoromethyl)cyclopropyl)-1,2,4-oxadiazole-3-carboxylic acid was similar to that of 5-(1-fluoro-2-methylpropan-2-yl)-1,2,4-oxadiazole-3-carboxylic acid in Example 44, Step 6. The crude reaction mixture was concentrated in vacuo to give 5-(1-(trifluoromethyl)cyclopropyl)-1,2,4-oxadiazole-3-carboxylic acid as a light gray solid (180 mg, crude), which was carried forward without further purification. ESI-MS (M+H)$^+$: 223.1.

4. Synthesis of N-(3-fluoro-2-methyl-4-(4-((1-methyl-1H-pyrazol-3-yl)amino)-1,3,5-triazin-2-yl)benzyl)-5-(1-(trifluoromethyl)cyclopropyl)-1,2,4-oxadiazole-3-carboxamide (Compound 52)

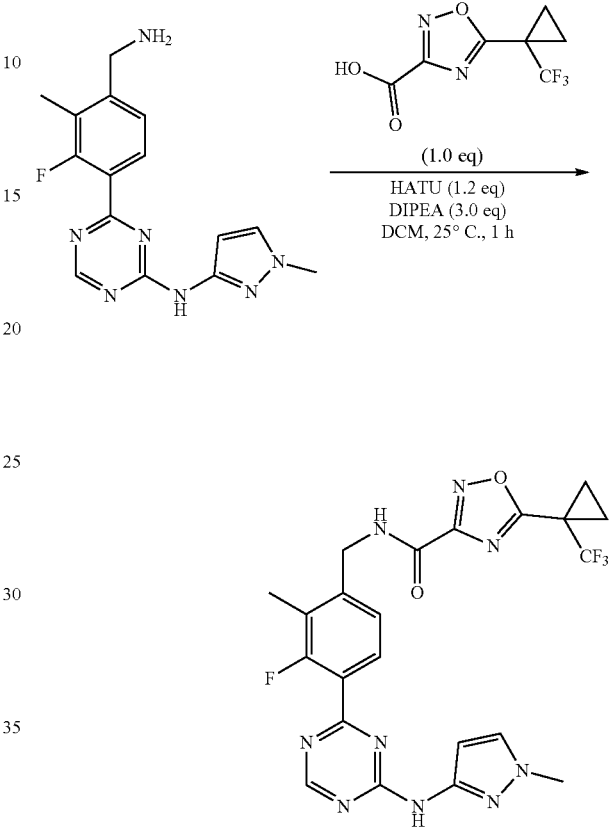

Synthesis of N-(3-fluoro-2-methyl-4-(4-((1-methyl-1H-pyrazol-3-yl)amino)-1,3,5-triazin-2-yl)benzyl)-5-(1-(trifluoromethyl)cyclopropyl)-1,2,4-oxadiazole-3-carboxamide was similar to that of 5-(1-fluoro-2-methylpropan-2-yl)-N-(2-methyl-4-(4-((1-methyl-1H-pyrazol-3-yl)amino)-1,3,5-triazin-2-yl)benzyl)-1,2,4-oxadiazole-3-carboxamide in Example 44, Step 7. The crude product was purified by prep-HPLC (CH$_3$CN/H$_2$O with 0.05% HCl/H$_2$O as mobile phase) to give the HCl salt of N-(3-fluoro-2-methyl-4-(4-((1-methyl-1H-pyrazol-3-yl)amino)-1,3,5-triazin-2-yl)benzyl)-5-(1-(trifluoromethyl)cyclopropyl)-1,2,4-oxadiazole-3-carboxamide as a yellow solid (40 mg, yield: 23%). ESI-MS (M+H)$^+$: 518.1. $^1$H NMR (500 MHz, DMSO-d$_6$) δ: 10.17 (s, 1H), 9.24 (s, 1H), 8.75 (s, 1H), 7.86 (t, J=7.5 Hz, 1H), 7.56 (s, 1H), 7.26 (d, J=8.0 Hz, 1H), 6.65 (s, 1H), 4.57 (d, J=6.0 Hz, 2H), 3.78 (s, 3H), 2.32 (d, J=2.0 Hz, 3H), 1.80 (s, 4H).

Example 53: (R)-5-(1-fluoro-2-methylpropan-2-yl)-N-(2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide (Compound 53)

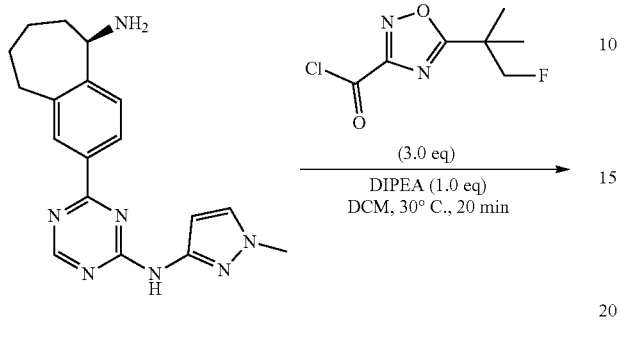

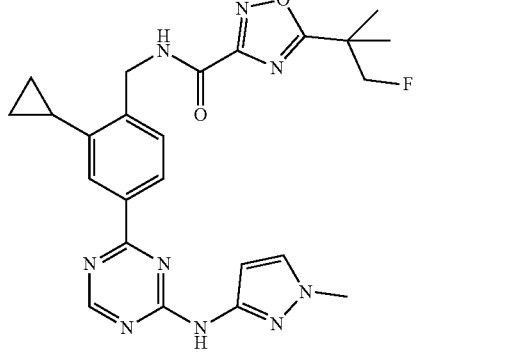

To a solution of the HCl salt of (R)-4-(5-amino-6,7,8,9-tetrahydro-5H-benzo[7]annulen-2-yl)-N-(1-methyl-1H-pyrazol-3-yl)-1,3,5-triazin-2-amine (130 mg, 0.32 mmol) in DCM (70 mL) was added DIPEA (41 mg, 0.32 mmol), followed by a dropwise addition of a solution of 5-(1-fluoro-2-methylpropan-2-yl)-1,2,4-oxadiazole-3-carbonyl chloride (197 mg, 0.96 mmol) in DCM (10 mL). The reaction mixture was heated to 30° C. and stirred at that temperature for 20 min. The reaction mixture was poured into H$_2$O (100 mL) and the layers were separated. The aqueous phase was extracted with DCM (50 mL×3), and the combined organic extracts were concentrated in vacuo. The crude material was purified by prep-HPLC (CH$_3$CN/H$_2$O with 0.05% HCl/H$_2$O as mobile phase) to give the HCl salt of (R)-5-(1-fluoro-2-methylpropan-2-yl)-N-(2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide as a yellow solid (62 mg, yield: 35%). ESI-MS (M+H)$^+$: 506.2. $^1$H NMR (500 MHz, DMSO-d$_6$) δ: 10.03 (s, 1H), 9.11 (s, 1H), 8.72 (s, 1H), 8.17-8.14 (m, 2H), 7.58 (s, 1H), 7.40 (d, J=7.5 Hz, 1H), 6.63 (s, 1H), 5.31 (m, 1H), 4.63 (d, J=47 Hz, 2H), 3.78 (s, 3H), 2.97 (s, 2H), 2.52-1.84 (m, 5H), 1.49-1.43 (m, 7H).

Example 54: N-(2-cyclopropyl-4-(4-((1-methyl-1H-pyrazol-3-yl)amino)-1,3,5-triazin-2-yl)benzyl)-5-(1-fluoro-2-methylpropan-2-yl)-1,2,4-oxadiazole-3-carboxamide

54

1. Synthesis of 4-chloro-2-cyclopropylbenzonitrile

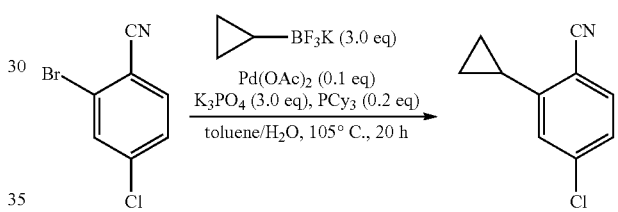

To a solution of 2-bromo-4-chlorobenzonitrile (2.2 g, 10 mmol) and potassium cyclopropyltrifluoroborate (4.4 g, 30 mmol) in a mixture of toluene (60 mL) and H$_2$O (6 mL) was added Pd(OAc)$_2$ (224 mg, 1 mmol), K$_3$PO$_4$ (6.4 g, 30 mmol), and PCy$_3$ (560 mg, 2 mmol). The reaction mixture was heated to 105° C. under N$_2$ and was stirred at that temperature for 20 h. The reaction mixture was cooled to ambient temperature and poured in H$_2$O (200 mL). The aqueous phase was extracted with EtOAc (150 mL). The organic layer was dried (Na2SO4), filtered, and concentrated in vacuo. The crude material was purified by silica-gel column chromatography (petroleum ether/EtOAc, grading from 60:1 to 30:1) to give 4-chloro-2-cyclopropylbenzonitrile as a light yellow solid (900 mg, yield: 51%). $^1$H NMR (400 MHz, CDCl$_3$) δ: 7.51 (d, J=8.4 Hz, 1H), 7.21 (dd, J=8.4 Hz, 1.6 Hz, 1H), 6.91 (d, J=2.0 Hz, 1H), 2.30-2.23 (m, 1H), 1.21-1.16 (m, 2H), 0.83-0.80 (m, 2H).

2. Synthesis of tert-butyl (4-chloro-2-cyclopropylbenzyl)carbamate

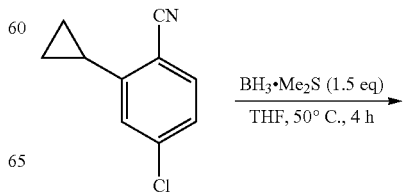

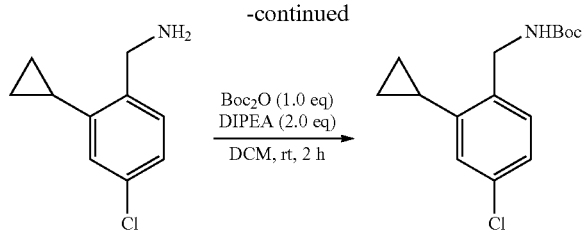

To a solution of 4-chloro-2-cyclopropylbenzonitrile (900 mg, 5.1 mmol) in THF (30 mL) was added BH₃·Me₂S (0.8 mL, 8 mmol). The reaction mixture was heated to 50° C. under N₂ and was stirred at that temperature for 4 h. MeOH (5 mL) was added and the reaction mixture was concentrated in vacuo to give crude (4-chloro-2-cyclopropylphenyl)methanamine as a black solid (1 g, crude), which was carried forward without further purification.

To a solution of (4-chloro-2-cyclopropylphenyl)methanamine (1 g, crude) and DIPEA (826 mg, 6.4 mmol) in DCM (35 mL) was added Boc₂O (700 mg, 3.2 mmol) at ambient temperature. The reaction mixture was stirred at that temperature for 2 h and then was concentrated in vacuo. The crude material was purified by silica-gel column chromatography (petroleum ether/EtOAc, grading from 30:1 to 10:1) to give tert-butyl (4-chloro-2-cyclopropylbenzyl)carbamate as a white solid (600 mg, yield: 42% over 2 steps). ESI-MS (M+H−56)⁺: 226.0.

3. Synthesis of tert-butyl (2-cyclopropyl-4-(4,4,5,5-tetramethyl-1,3,2-dioxaborolan-2-yl)benzyl)carbamate

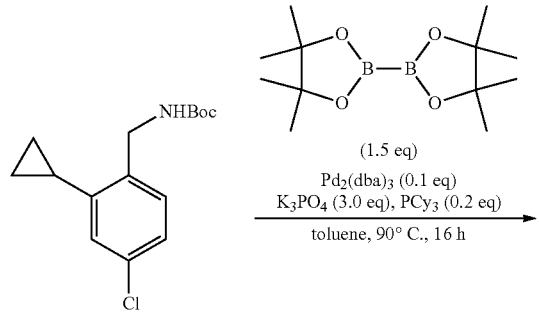

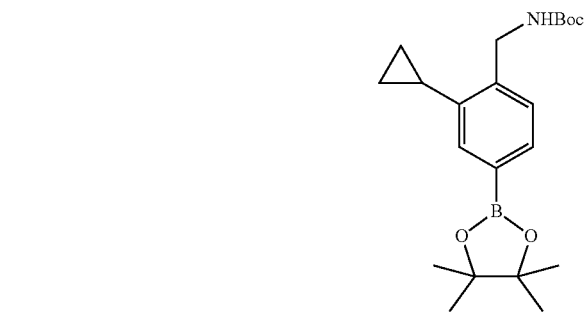

To a solution of tert-butyl (4-chloro-2-cyclopropylbenzyl)carbamate (600 mg, 2.1 mmol) and (bispinacolato)diboron (811 mg, 3.2 mmol) in toluene (30 mL) was added Pd₂(dba)₃ (183 mg, 0.2 mmol), K₃PO₄ (1.35 g, 6.4 mmol), and PCy₃ (121 mg, 0.43 mmol). The reaction mixture was heated to 90° C. and was stirred at that temperature for 16 h. The reaction mixture was cooled to ambient temperature and concentrated in vacuo. The crude material was purified by silica-gel column chromatography (petroleum ether/EtOAc, grading from 20:1 to 6:1) to give tert-butyl (2-cyclopropyl-4-(4,4,5,5-tetramethyl-1,3,2-dioxaborolan-2-yl)benzyl)carbamate as a light brown solid (450 mg, yield: 57%), which was carried forward without further purification. ESI-MS (M+H−56)⁺: 318.1.

4. Synthesis of tert-butyl (2-cyclopropyl-4-(4-((1-methyl-1H-pyrazol-3-yl)amino)-1,3,5-triazin-2-yl)benzyl)carbamate

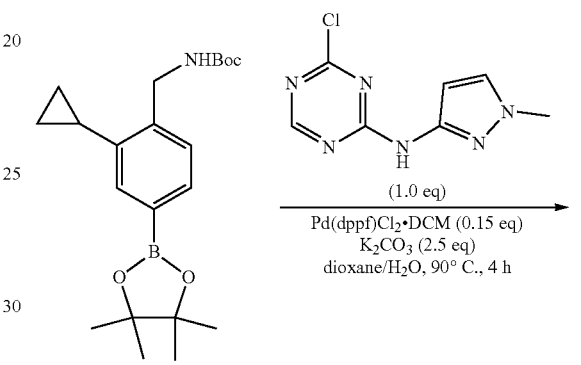

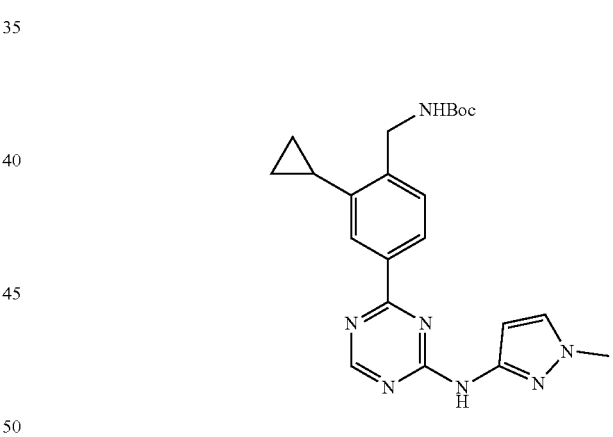

Synthesis of tert-butyl (2-cyclopropyl-4-(4-((1-methyl-1H-pyrazol-3-yl)amino)-1,3,5-triazin-2-yl)benzyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (petroleum ether/EtOAc, grading from 10:1 to 1:2) to give tert-butyl (2-cyclopropyl-4-(4-((1-methyl-1H-pyrazol-3-yl)amino)-1,3,5-triazin-2-yl)benzyl)carbamate as a white solid (100 mg, yield: 44%). ESI-MS (M+H)⁺: 422.2.

5. Synthesis of 4-(4-(aminomethyl)-3-cyclopropylphenyl)-N-(1-methyl-1H-pyrazol-3-yl)-1,3,5-triazin-2-amine hydrochloride

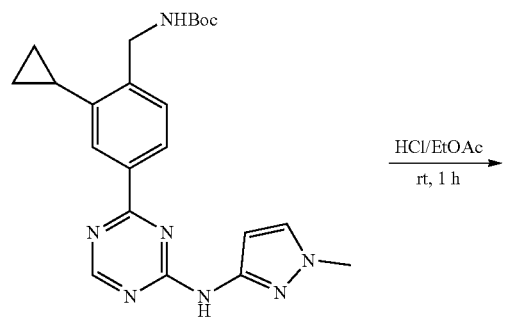

Synthesis of 4-(4-(aminomethyl)-3-cyclopropylphenyl)-N-(1-methyl-1H-pyrazol-3-yl)-1,3,5-triazin-2-amine hydrochloride was similar to that of (R)-4-(4-(1-aminoethyl)-3-chloro-2-fluorophenyl)-N-(1-methyl-1H-pyrazol-4-yl)-1,3,5-triazin-2-amine hydrochloride in Example 69, Step 10. The crude material was concentrated in vacuo to give 4-(4-(aminomethyl)-3-cyclopropylphenyl)-N-(1-methyl-1H-pyrazol-3-yl)-1,3,5-triazin-2-amine hydrochloride as a gray solid (80 mg, crude), which was carried forward without further purification. ESI-MS (M+H+41)+: 363.0.

6. Synthesis of N-(2-cyclopropyl-4-(4-((1-methyl-1H-pyrazol-3-yl)amino)-1,3,5-triazin-2-yl)benzyl)-5-(1-fluoro-2-methylpropan-2-yl)-1,2,4-oxadiazole-3-carboxamide (Compound 54)

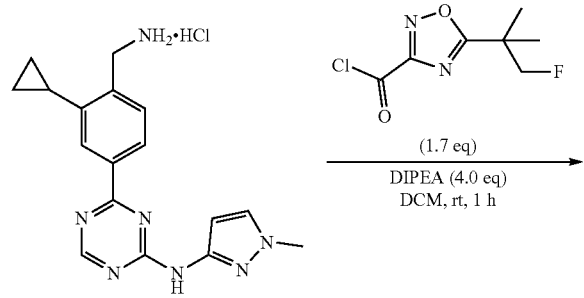

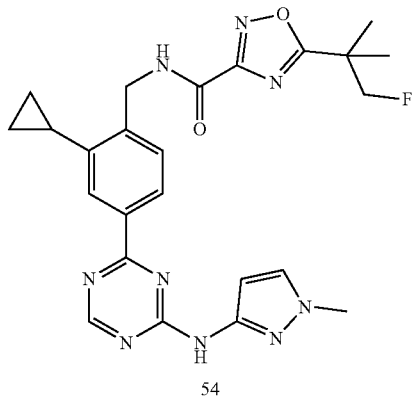

Synthesis of N-(2-cyclopropyl-4-(4-((1-methyl-1H-pyrazol-3-yl)amino)-1,3,5-triazin-2-yl)benzyl)-5-(1-fluoro-2-methylpropan-2-yl)-1,2,4-oxadiazole-3-carboxamide was similar to that of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide in Example 69, Step 11. The crude material was purified by prep-HPLC (CH$_3$CN/H$_2$O with 0.23% formic acid/H$_2$O as mobile phase) to give N-(2-cyclopropyl-4-(4-((1-methyl-1H-pyrazol-3-yl)amino)-1,3,5-triazin-2-yl)benzyl)-5-(1-fluoro-2-methylpropan-2-yl)-1,2,4-oxadiazole-3-carboxamide as a white solid (30 mg, yield: 25%). ESI-MS (M+H)+: 492.2. $^1$H NMR (500 MHz, DMSO-d$_6$) δ: 10.08 (s, 1H), 9.13 (s, 1H), 8.74 (s, 1H), 8.18 (d, J=8.0 Hz, 1H), 8.10 (s, 1H), 7.62 (s, 1H), 7.46 (d, J=8.0 Hz, 1H), 6.65 (s, 1H), 4.79 (d, J=6.0 Hz, 2H), 4.63 (d, J=42 Hz, 2H), 3.81 (s, 3H), 2.20-2.16 (m, 1H), 1.49 (s, 6H), 1.07-1.05 (m, 2H), 0.76-0.74 (m, 2H).

Example 55: 3-(tert-butyl)-N-(2-cyclopropyl-3-fluoro-4-(4-((1-methyl-1H-pyrazol-3-yl)amino)-1,3,5-triazin-2-yl)benzyl)-1,2,4-oxadiazole-5-carboxamide

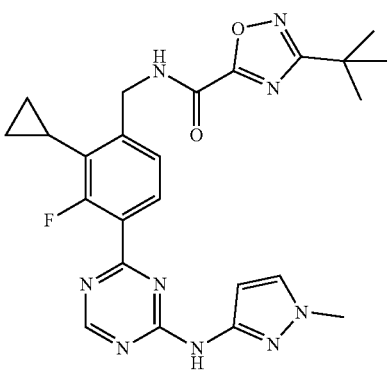

1. Synthesis of 2-bromo-4-chloro-3-fluorobenzoic acid

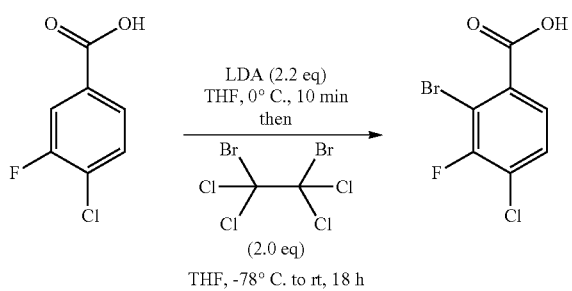 [SMILES: O=C(O)c1ccc(Cl)c(F)c1 ; ClC(Cl)(Br)C(Cl)(Cl)Br ; O=C(O)c1ccc(Cl)c(F)c1Br]

A solution of diisopropylamine (185 mL, 1.32 mol) in THF (200 mL) was placed under an N₂ atmosphere and cooled in an ice-water bath. Then n-BuLi (2.5 M in hexanes, 504 mL, 1.26 mol) was added dropwise with stirring. After stirring at 0° C. for an additional 5 min, the mixture was cooled to −78° C. and stirred for 30 min. Then, a solution of 4-chloro-3-fluorobenzoic acid (100 g, 573 mmol) in THF (400 mL) was added dropwise to the freshly prepared LDA-solution. After 2 h at −78° C., a solution of 1,2-dibromotetrachloroethane (375 g, 1.15 mol) in THF (400 mL) was added and the reaction mixture was allowed to stir at room temperature overnight. The mixture was diluted with H₂O (500 mL) and extracted with EtOAc (500 mL×3). The aqueous layer was acidified with 4 N HCl to pH=2 and extracted with EtOAc (500 mL×3). The combined organic layers were washed with brine, dried (Na₂SO₄), filtered and concentrated in vacuo to give 2-bromo-4-chloro-3-fluorobenzoic acid as an off-white solid (134 g, yield: 92%). $^1$H NMR (300 MHz, CDCl₃) δ: 7.79 (dd J=8.2 Hz, 1.8 Hz, 1H), 7.55-7.42 (m, 1H).

2. Synthesis of 2-bromo-4-chloro-3-fluoro-N-methoxy-N-methylbenzamide

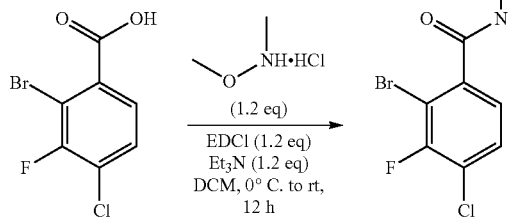

To a solution of 2-bromo-4-chloro-3-fluorobenzoic acid (134 g, 529 mmol) in DCM (1 L) at 0° C. were added N,O-dimethylhydroxylamine hydrochloride (62 g, 634 mmol), Et₃N (88.4 mL, 634 mmol) and EDCI (122 g, 634 mmol, 1.2 eq.) slowly, keeping the temperature <5° C. After the addition of all the reagents, the reaction was allowed to warm up to ambient temperature and was stirred at that temperature for 12 h. Then, H₂O (1 L) was added and the layers were separated. The organic layer was washed sequentially with 2 M aqueous HCl solution (500 mL), H₂O (500 mL), and brine (500 mL). The organic phase was dried (Na₂SO₄), filtered, and concentrated in vacuo to give 2-bromo-4-chloro-3-fluoro-N-methoxy-N-methylbenzamide as a brown solid (143 g, yield: 91%). $^1$H NMR (300 MHz, CDCl₃) δ:7.46-7.37 (m, 1H), 7.08 (dd, J=8.5 Hz, 1.5 Hz, 1H), 3.49 (br s, 2H), 3.38 (br s, 3H).

3. Synthesis of 2-bromo-4-chloro-3-fluorobenzaldehyde

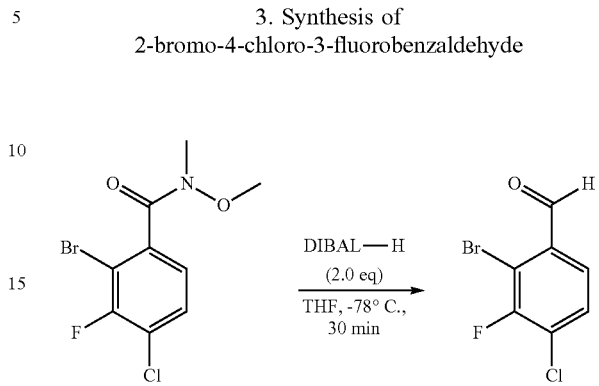

To a solution of 2-bromo-4-chloro-3-fluoro-N-methoxy-N-methylbenzamide (158 g, 0.53 mol) in THF (500 mL) was added DIBAL-H (520 mL of 1 M in hexanes and 460 mL of 1.2 M in toluene, 1.07 mol) at −78° C. The solution was stirred at −78° C. for 30 min under an N₂-atmosphere. An aqueous solution of potassium sodium tartrate (500 mL) was added. The resulting solid was filtered off and the filtrate was extracted with EtOAc (500 mL×2). The organic layers were dried (Na₂SO₄), filtered, and concentrated in vacuo to give 2-bromo-4-chloro-3-fluorobenzaldehyde as a brown solid (131 g, crude), which was carried forward without further purification.

4. Synthesis of (E)-N-(2-bromo-4-chloro-3-fluorobenzylidene)-2-methylpropane-2-sulfinamide

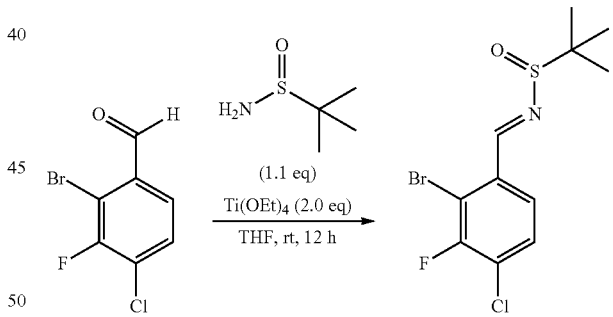

To a solution of 2-bromo-4-chloro-3-fluorobenzaldehyde (131 g, 0.55 mol) in THF (1 L) was added tert-butylsulfinamide (73 g, 0.60 mol) and Ti(OEt)₄ (232 mL, 1.10 mol). The solution was stirred at ambient temperature for 12 h and then H₂O (500 mL) was added. The resulting solid was filtered off and washed with EtOAc (250 mL×2). The aqueous phase was extracted with EtOAc (250 mL×2). The combined organic layers were washed sequentially with 2 M aqueous HCl solution (500 mL), H₂O (500 mL) and brine (500 mL). The organic phase was dried (Na₂SO₄), filtered, and concentrated in vacuo to give (E)-N-(2-bromo-4-chloro-3-fluorobenzylidene)-2-methylpropane-2-sulfinamide as a beige solid (144 g, yield: 77% over 2 steps). $^1$H NMR (300 MHz, CDCl₃) δ: 8.91 (s, 1H), 7.81 (dd, J=8.2 Hz, 1.8 Hz, 1H), 7.44 (dd, J=8.2 Hz, 7.0 Hz, 1H), 1.28 (s, 9H).

5. Synthesis of (2-bromo-4-chloro-3-fluorophenyl)methanamine hydrochloride

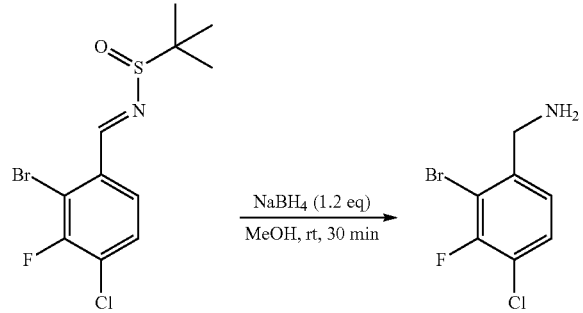 [SMILES: CC(C)(C)S(=O)/N=C/c1ccc(Cl)c(F)c1Br ; NCc1ccc(Cl)c(F)c1Br]

To a solution of (E)-N-(2-bromo-4-chloro-3-fluorobenzylidene)-2-methylpropane-2-sulfinamide (144 g, 0.42 mol) in MeOH (1.5 L) was added NaBH$_4$ (19.2 g, 0.51 mol). The solution was stirred at ambient temperature for 1 h. The reaction mixture was concentrated until 150 mL of solvent were left. The residue was diluted with H$_2$O (500 mL) and the solution was extracted with EtOAc (500 mL×3). The organic layers were dried (Na$_2$SO$_4$), filtered, and concentrated. The residue was dissolved in 2 M HCl in Et$_2$O and stirred at ambient temperature for 10 min. The resulting solid was filtered off, washed with heptane (500 mL), and dried in vacuo to give (2-bromo-4-chloro-3-fluorophenyl)methanamine hydrochloride as a white solid (92.0 g, yield: 80%). $^1$H NMR (300 MHz, DMSO-d$_6$) δ: 8.78 (br s, 3H), 7.76 (t, J=8.2 Hz, 1H), 7.56-7.52 (m, 1H), 4.14 (br s, 2H).

6. Synthesis of tert-butyl (2-bromo-4-chloro-3-fluorobenzyl)carbamate

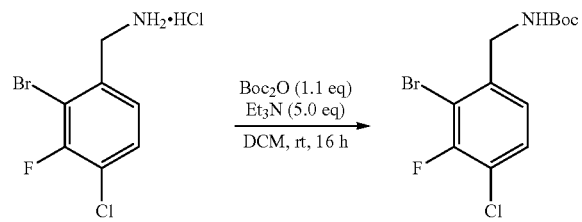

To a solution of (2-bromo-4-chloro-3-fluorophenyl)methanamine hydrochloride (92 g, 0.33 mol) in DCM (1.5 L) were added Et$_3$N (233 mL, 1.67 mol) and Boc$_2$O (80 g, 0.37 mol). The solution was stirred at ambient temperature for 16 h. After dilution with H$_2$O (1 L), the layers were separated, and the aqueous phase was extracted with DCM (500 mL×2). The combined organic layers were washed sequentially with H$_2$O (500 mL), 1 M aqueous HCl (500 mL) and brine (500 mL). The organic phase was dried (Na$_2$SO$_4$), filtered, and concentrated in vacuo to give tert-butyl (2-bromo-4-chloro-3-fluorobenzyl)carbamate as a white solid (95.2 g, yield: 84%). $^1$H NMR (300 MHz, CDCl$_3$) δ: 7.34 (dd, J=8.2 Hz, 7.0 Hz, 1H), 7.15 (br d, J=8.2 Hz, 1H), 5.04 (br s, 1H), 4.38 (br d, J=5.9 Hz, 2H), 1.45 (s, 9H).

7. Synthesis of tert-butyl (4-chloro-2-cyclopropyl-3-fluorobenzyl)carbamate

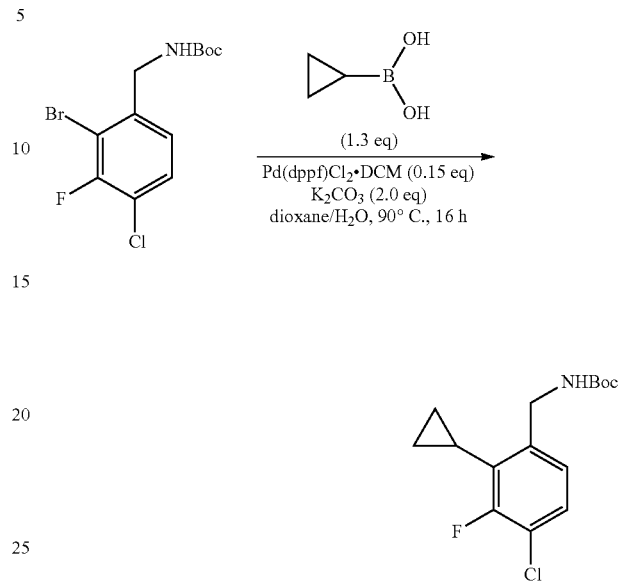

To a solution of tert-butyl (2-bromo-4-chloro-3-fluorobenzyl)carbamate (72 g, 0.21 mol) in 1,4-dioxane (1 L) were added cyclopropylboronic acid (23 g, 0.27 mol), K$_2$CO$_3$ (58 g, 0.42 mol), Pd(dppf)Cl$_2$·DCM (25.7 g, 32 mmol) and H$_2$O (200 mL). The mixture was stirred at 90° C. for 16 h under an N$_2$ atmosphere. The reaction mixture was cooled to ambient temperature, concentrated in vacuo, diluted with EtOAc (500 mL) and filtered over Celite®. The filtrate was washed with H$_2$O (500 mL), 1 M aqueous HCl solution (500 mL) and brine (500 mL). The organic layer was dried (Na$_2$SO$_4$), filtered, and concentrated in vacuo. The crude material was purified by silica-gel column chromatography (EtOAc/heptane, grading from 0% to 5%) to give tert-butyl (4-chloro-2-cyclopropyl-3-fluorobenzyl)carbamate as a white solid (48.4 g, yield: 76%). $^1$H NMR (300 MHz, CDCl$_3$) δ: 7.23 (t, J=7.6 Hz, 1H), 7.01 (d, J=8.2 Hz, 1H), 4.82 (br s, 1H), 4.49 (br d, J=5.9 Hz, 2H), 1.75-1.61 (m, 1H), 1.47 (s, 9H), 1.10-1.01 (m, 2H), 0.78 (q, J=5.1 Hz, 2H).

8. Synthesis of tert-butyl (2-cyclopropyl-3-fluoro-4-(4,4,5,5-tetramethyl-1,3,2-dioxaborolan-2-yl)benzyl)carbamate

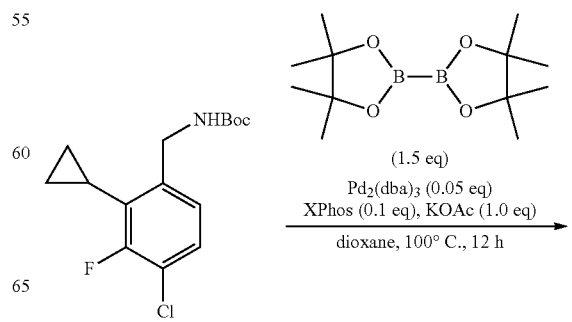

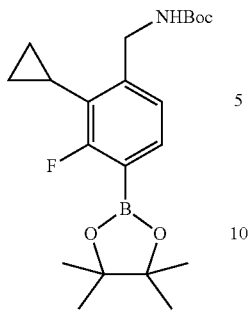

A solution of Pd$_2$(dba)$_3$ (2.4 g, 4.2 mmol, 0.05 eq.) and XPhos (4.0 g, 8.3 mmol) in 1,4-dioxane (500 mL) was stirred for 30 min at ambient temperature. Then, KOAc (16.4 g, 0.17 mol), tert-butyl (4-chloro-2-cyclopropyl-3-fluorobenzyl)carbamate (25 g, 83 mmol) and bis(pinacolato)diboron (31.8 g, 125 mmol) were added and the reaction mixture was heated to 100° C. and stirred at that temperature for 12 h. The reaction mixture was cooled to ambient temperature, filtered over Celite®, and concentrated in vacuo. The residue was diluted with EtOAc (500 mL) and washed sequentially with H$_2$O (500 mL) and brine (500 mL). The organic layer was dried (Na$_2$SO$_4$), filtered, and concentrated in vacuo. The crude material was purified by silica-gel column chromatography (EtOAc/heptane, grading from 0% to 10%) to give crude tert-butyl (2-cyclopropyl-3-fluoro-4-(4,4,5,5-tetramethyl-1,3,2-dioxaborolan-2-yl)benzyl)carbamate as a brown oil (26.9 g, yield: 82%).

This batch was mixed with other batches and dissolved in EtOAc (1 L). The solution was treated with activated charcoal for 30 min and filtered. The organic phase was concentrated in vacuo and the resulting yellow oil was purified by silica-gel column chromatography (3 CV flush with pentane, then EtOAc/heptane, grading from 0% to 10%) to give tert-butyl (2-cyclopropyl-3-fluoro-4-(4,4,5,5-tetramethyl-1,3,2-dioxaborolan-2-yl)benzyl)carbamate as a yellow oil which solidified to a white solid upon standing. $^1$H NMR (300 MHz, CDCl$_3$) δ: 7.56 (dd, J=7.6 Hz, 5.9 Hz, 1H), 7.06 (d, J=7.6 Hz, 1H), 4.84 (br s, 1H), 4.53 (br d, J=5.9 Hz, 2H), 1.70-1.55 (m, 1H), 1.46 (s, 9H), 1.35 (s, 12H), 1.05-0.95 (m, 2H), 0.82-0.74 (m, 2H).

9. Synthesis of tert-butyl (2-cyclopropyl-3-fluoro-4-(4-((1-methyl-1H-pyrazol-3-yl)amino)-1,3,5-triazin-2-yl)benzyl)carbamate

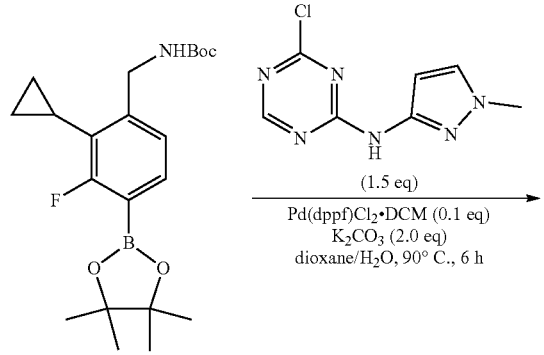

Synthesis of tert-butyl (2-cyclopropyl-3-fluoro-4-(4-((1-methyl-1H-pyrazol-3-yl)amino)-1,3,5-triazin-2-yl)benzyl)carbamate was similar to that of tert-butyl (R)-(1-(2-chloro-3-fluoro-4-(4-(((1-methyl-1H-pyrazol-4-yl)amino)-1,3,5-triazin-2-yl)phenyl)ethyl)carbamate in Example 69, Step 9. The residue was purified by silica-gel column chromatography (EtOAc/heptane, grading from 0% to 100%) to give tert-butyl (2-cyclopropyl-3-fluoro-4-(4-((1-methyl-1H-pyrazol-3-yl)amino)-1,3,5-triazin-2-yl)benzyl)carbamate as an off-white solid. (520 mg, yield: 75%). ESI-MS (M+H)$^+$: 340.6.

10. Synthesis of 4-(4-(aminomethyl)-3-cyclopropyl-2-fluorophenyl)-N-(1-methyl-1H-pyrazol-3-yl)-1,3,5-triazin-2-amine

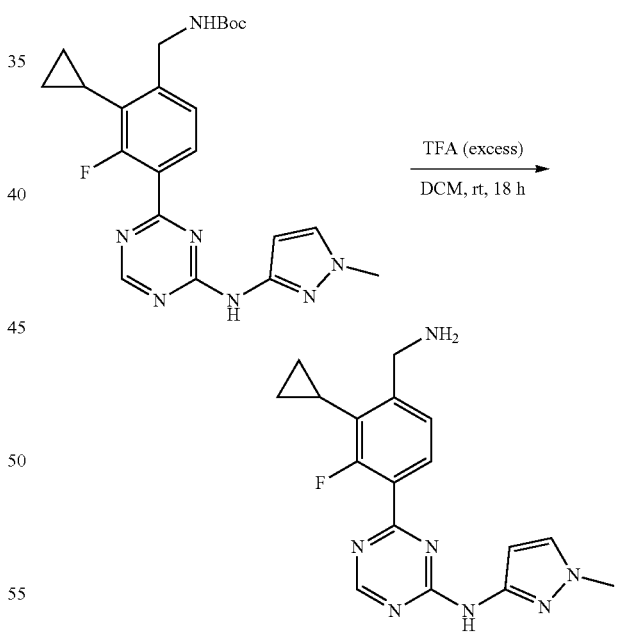

Synthesis of 4-(4-(aminomethyl)-3-cyclopropyl-2-fluorophenyl)-N-(1-methyl-1H-pyrazol-3-yl)-1,3,5-triazin-2-amine was similar to that of 4-(4-(aminomethyl)-3-chlorophenyl)-N-(1-methyl-1H-pyrazol-4-yl)-1,3,5-triazin-2-amine in Example 15, Step 2. The reaction mixture was diluted with MeOH (10 mL) and purified on an SCX column. The product was eluted with 2M NH$_3$-MeOH and concentrated in vacuo to give 4-(4-(aminomethyl)-3-cyclopropyl-2-fluorophenyl)-N-(1-methyl-1H-pyrazol-3-yl)-1,3, 5-triazin-2-amine as a pale-yellow solid (180 mg, yield: 40%). ESI-MS (M+H)+: 340.5.

11. Synthesis of 3-(tert-butyl)-N-(2-cyclopropyl-3-fluoro-4-(4-((1-methyl-1H-pyrazol-3-yl)amino)-1,3,5-triazin-2-yl)benzyl)-1,2,4-oxadiazole-5-carboxamide (Compound 55)

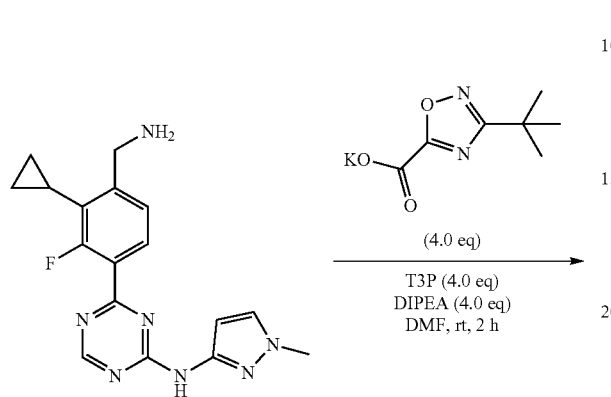

Synthesis of 3-(tert-butyl)-N-(2-cyclopropyl-3-fluoro-4-(4-((1-methyl-1H-pyrazol-3-yl)amino)-1,3,5-triazin-2-yl)benzyl)-1,2,4-oxadiazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 3-(tert-butyl)-N-(2-cyclopropyl-3-fluoro-4-(4-((1-methyl-1H-pyrazol-3-yl)amino)-1,3,5-triazin-2-yl)benzyl)-1,2,4-oxadiazole-5-carboxamide as a pale yellow solid (12 mg, yield: 13%). ESI-MS (M+H)+: 492.6. $^1$H NMR (400 MHz, CDCl$_3$) δ: 8.87 (br s, 1H), 8.00 (br s, 1H), 7.47-7.34 (m, 2H), 7.29-7.23 (m, 2H), 7.01 (s, 1H), 4.96 (d, J=6.0 Hz, 2H), 3.89 (s, 3H), 1.80-1.73 (m, 1H), 1.41 (s, 9H), 1.18-1.13 (m 2H), 0.89-0.85 (m, 2H).

Example 56: 5-(tert-butyl)-N-(5-fluoro-2-methyl-4-(4-((1-methyl-1H-pyrazol-4-yl)amino)-1,3,5-triazin-2-yl)benzyl)-1,2,4-oxadiazole-3-carboxamide (Compound 56)

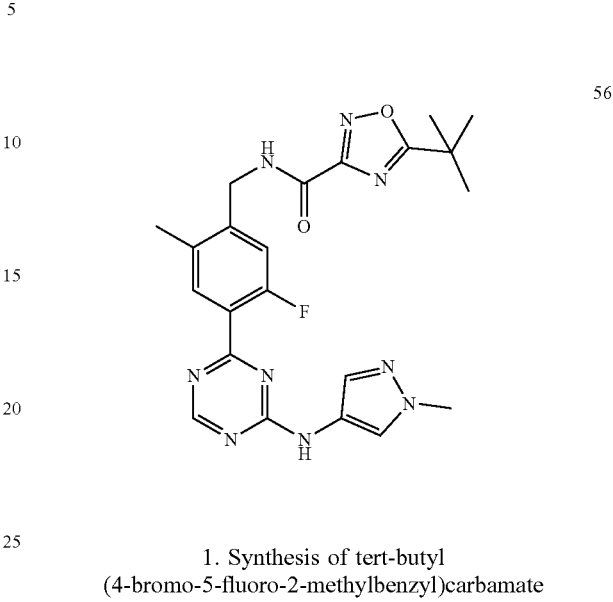

1. Synthesis of tert-butyl (4-bromo-5-fluoro-2-methylbenzyl)carbamate

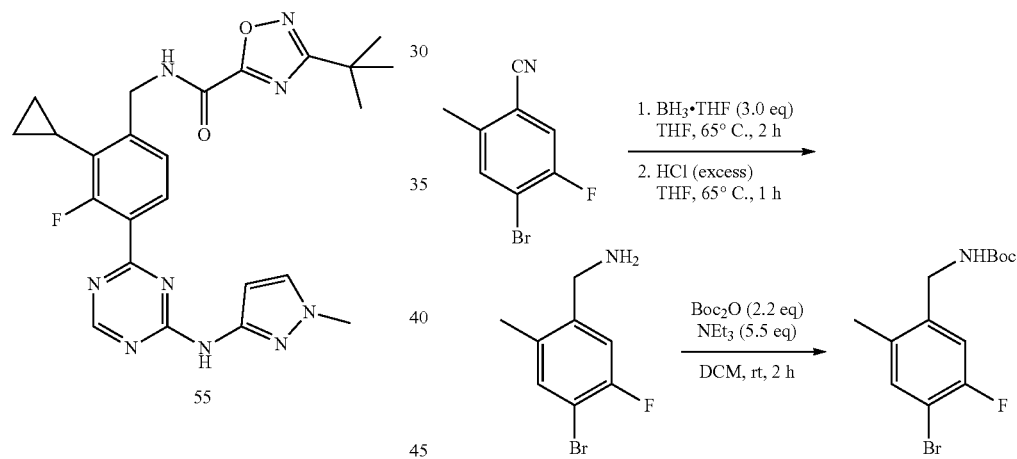

To a solution of 4-bromo-5-fluoro-2-methylbenzonitrile (15.4 g, 72.0 mmol) in THF (185 mL), was added BH$_3$·THF (1.0 M in THF, 223 mL, 223 mmol) and the mixture was heated under reflux for 2 h. The reaction was cooled down to rt and an HCl solution (1 M, 45 mL) was added dropwise to the solution (CAUTION: REACTION VERY EXOTHERMIC!) and the mixture was again heated to refluxed for 1 h. Then, it was cooled down to ambient temperature and the solvent was removed in vacuo. The residue was dissolved in DCM (690 mL) and Et$_3$N (57 mL, 409 mmol) and Boc$_2$O (35 mL, 152 mmol) were added. The mixture was left to stir at ambient temperature for 2 h. Then, H$_2$O (500 mL) was added and the layers were separated. The aqueous layer was extracted with DCM (500 mL×2) and the combined organic layers were dried (Na$_2$SO$_4$), filtered, and concentrated in vacuo. The crude material was purified by silica-gel column chromatography (EtOAc/heptanes, grading from 0% to 20%) to give tert-butyl (4-bromo-5-fluoro-2-methylbenzyl)carbamate as a white solid (17.2 g, yield: 75%). ESI-MS (M+H−56)+: 262.0.

2. Synthesis of tert-butyl (5-fluoro-2-methyl-4-(4,4,5,5-tetramethyl-1,3,2-dioxaborolan-2-yl)benzyl)carbamate

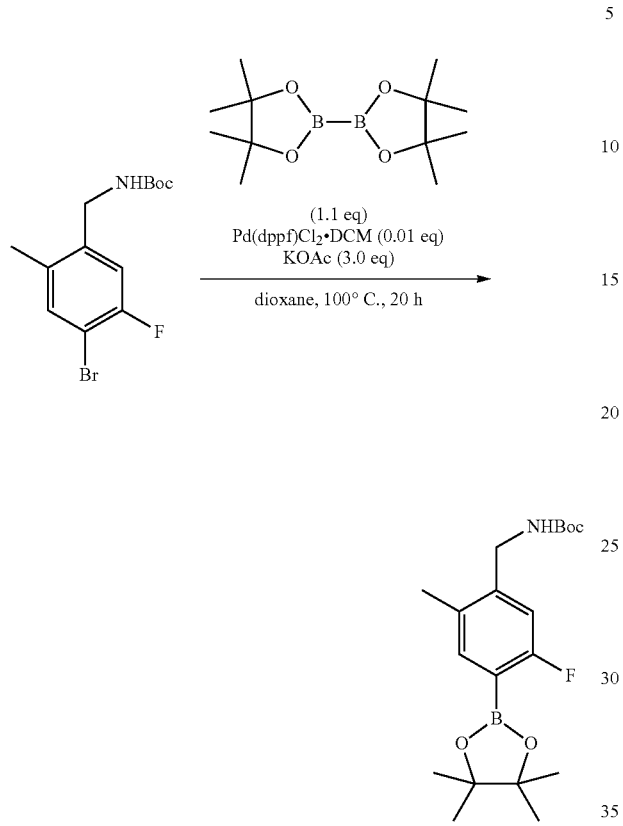

A solution of tert-butyl (4-bromo-5-fluoro-2-methylbenzyl)carbamate (2.45 g, 6.73 mmol) and bis(pinacolato)diboron (1.88 g, 7.40) in dry 1,4-dioxane (58 mL) was degassed with $N_2$ for 10 min. Then, KOAc (1.98 g, 20.2 mmol) and Pd(dppf)Cl$_2$.DCM (0.49 g, 0.67 mmol) were added and the solution was degassed with $N_2$ for 10 min. The reaction mixture was heated to 100° C. and stirred at that temperature for 20 h. The reaction mixture was cooled to ambient temperature and filtered through a pad of Celite®. The solvent was removed under reduced pressure and the residue was diluted with EtOAc (100 mL). Water (100 mL) was added and the layers were separated. The aqueous layer was extracted with EtOAc (100 mL×2). The combined organic extracts were dried (Na$_2$SO$_4$), filtered, and concentrated in vacuo. The crude material was purified by silica-gel column chromatography (EtOAc/heptanes, grading from 0% to 10%) to give impure product as a light-yellow oil. This impure oil was triturated with pentane to give tert-butyl (5-fluoro-2-methyl-4-(4,4,5,5-tetramethyl-1,3,2-dioxaborolan-2-yl)benzyl)carbamate as a white solid (1.89 g, yield: 77%). ESI-MS (M+H−56)$^+$: 310.2.

3. Synthesis of tert-butyl (5-fluoro-2-methyl-4-(4-((1-methyl-1H-pyrazol-4-yl)amino)-1,3,5-triazin-2-yl)benzyl)carbamate

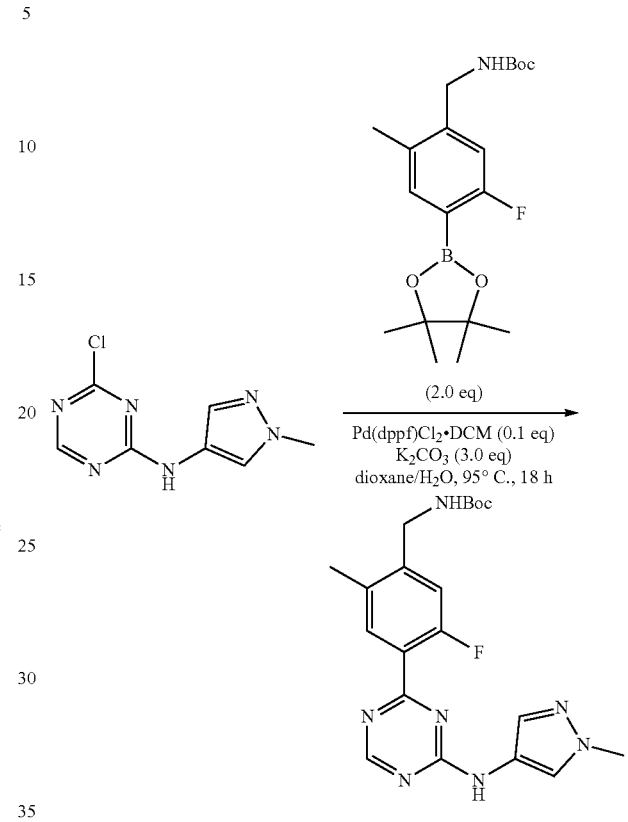

Synthesis of tert-butyl (5-fluoro-2-methyl-4-(4-((1-methyl-1H-pyrazol-4-yl)amino)-1,3,5-triazin-2-yl)benzyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (EtOAc/heptane, grading from 0% to 100%) to give tert-butyl (5-fluoro-2-methyl-4-(4-((1-methyl-1H-pyrazol-4-yl)amino)-1,3,5-triazin-2-yl)benzyl)carbamate as a beige solid (1.20 g, yield: 79%). ESI-MS (M+H)$^+$: 414.3.

4. Synthesis of 4-(4-(aminomethyl)-2-fluoro-5-methylphenyl)-N-(1-methyl-1H-pyrazol-4-yl)-1,3,5-triazin-2-amine

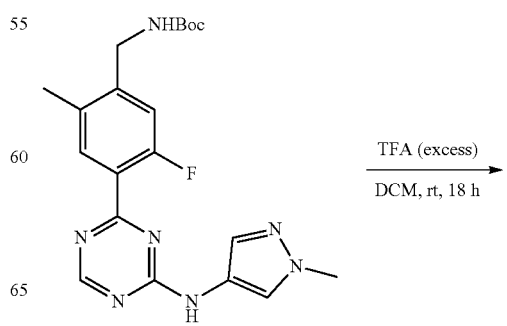

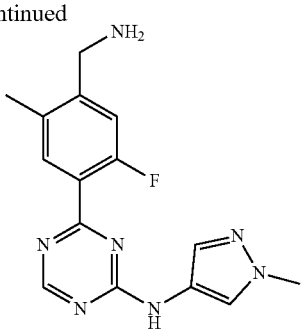

Synthesis of 4-(4-(aminomethyl)-2-fluoro-5-methylphenyl)-N-(1-methyl-1H-pyrazol-4-yl)-1,3,5-triazin-2-amine was similar to that of 4-(4-(aminomethyl)-3-chlorophenyl)-N-(1-methyl-1H-pyrazol-4-yl)-1,3,5-triazin-2-amine in Example 15, Step 2. The reaction mixture was diluted with MeOH (10 mL) and purified on an SCX column. The product was eluted with 2M $NH_3$-MeOH and concentrated in vacuo to give 4-(4-(aminomethyl)-2-fluoro-5-methylphenyl)-N-(1-methyl-1H-pyrazol-4-yl)-1,3,5-triazin-2-amine as a beige solid (769 mg, yield: 75%). ESI-MS $(M+H)^+$: 314.1.

5. Synthesis of 5-(tert-butyl)-N-(5-fluoro-2-methyl-4-(4-((1-methyl-1H-pyrazol-4-yl)amino)-1,3,5-triazin-2-yl)benzyl)-1,2,4-oxadiazole-3-carboxamide (Compound 56)

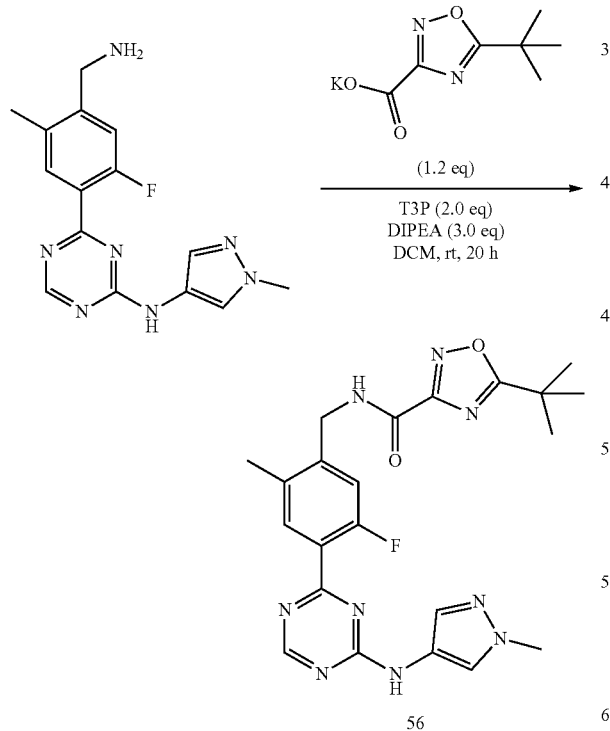

Synthesis of 5-(tert-butyl)-N-(5-fluoro-2-methyl-4-(4-((1-methyl-1H-pyrazol-4-yl)amino)-1,3,5-triazin-2-yl)benzyl)-1,2,4-oxadiazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC ($CH_3CN/H_2O$ with 0.05% $TFA/H_2O$ as mobile phase) to give the TFA salt of 5-(tert-butyl)-N-(5-fluoro-2-methyl-4-(4-((1-methyl-1H-pyrazol-4-yl)amino)-1,3,5-triazin-2-yl)benzyl)-1,2,4-oxadiazole-3-carboxamide as a yellow solid (27.5 mg, yield: 23%). ESI-MS $(M+H)^+$: 466.2. $^1$H NMR (500 MHz, DMSO-$d_6$) δ: 10.35-10.32 (m, 1H), 9.55-9.50 (m, 1H), 8.80-8.72 (m, 1H), 8.00-7.89 (m, 2H), 7.63-7.55 (m, 1H), 7.20-7.13 (m, 1H), 4.50 (br t, J=5.5 Hz, 2H), 3.82 (m, 3H), 2.38-236 (m, 3H), 1.44 (s, 9H).

Example 57: 3-(tert-butyl)-N-(5-fluoro-2-methyl-4-(4-((1-methyl-1H-pyrazol-4-yl)amino)-1,3,5-triazin-2-yl)benzyl)-1,2,4-oxadiazole-5-carboxamide (Compound 57)

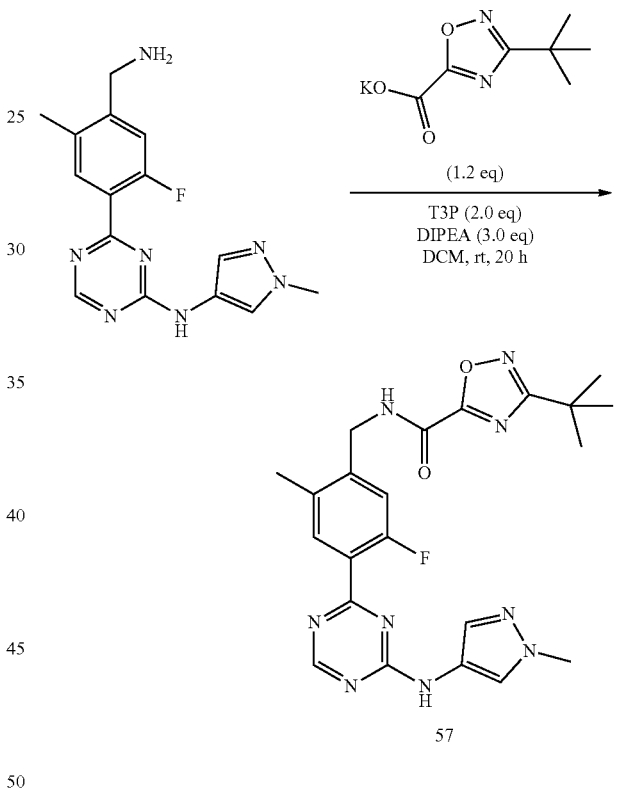

Synthesis of 3-(tert-butyl)-N-(5-fluoro-2-methyl-4-(4-((1-methyl-1H-pyrazol-4-yl)amino)-1,3,5-triazin-2-yl)benzyl)-1,2,4-oxadiazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC ($CH_3CN/H_2O$ with 0.05% $TFA/H_2O$ as mobile phase) to give the TFA salt of 3-(tert-butyl)-N-(5-fluoro-2-methyl-4-(4-((1-methyl-1H-pyrazol-4-yl)amino)-1,3,5-triazin-2-yl)benzyl)-1,2,4-oxadiazole-5-carboxamide as an off-white solid (40.4 mg, yield: 30%). ESI-MS $(M+H)^+$: 466.2. $^1$H NMR (500 MHz, DMSO-$d_6$) δ: 10.35-10.32 (m, 1H), 9.85 (m, 1H), 8.81-8.72 (m, 1H), 8.00-7.89 (m, 2H), 7.64-7.55 (m, 1H), 7.32-7.20 (m, 1H), 4.50 (br t, J=5.2 Hz, 2H), 3.82 (m, 3H), 2.38-2.35 (m, 3H), 1.38 (s, 9H).

Example 58: 2-(tert-butyl)-N-(5-fluoro-2-methyl-4-(4-((1-methyl-1H-pyrazol-4-yl)amino)-1,3,5-triazin-2-yl)benzyl)-2H-tetrazole-5-carboxamide (Compound 58)

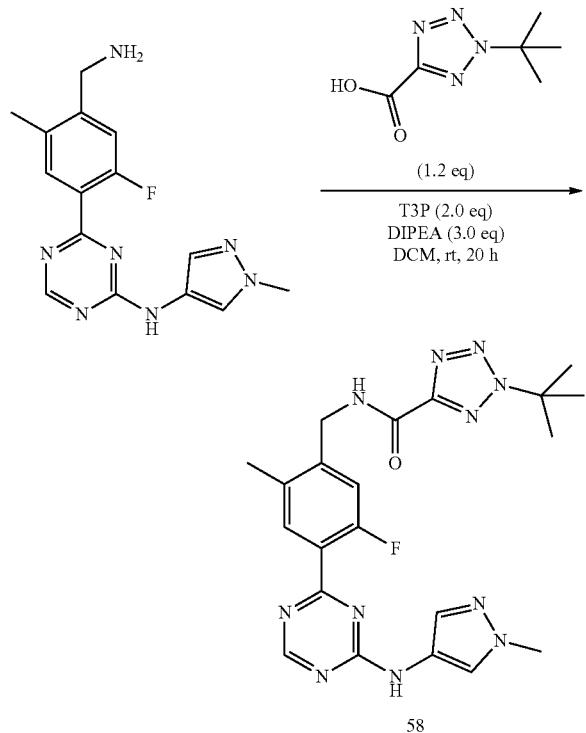

Synthesis of 2-(tert-butyl)-N-(5-fluoro-2-methyl-4-(4-((1-methyl-1H-pyrazol-4-yl)amino)-1,3,5-triazin-2-yl)benzyl)-2H-tetrazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 2-(tert-butyl)-N-(5-fluoro-2-methyl-4-(4-((1-methyl-1H-pyrazol-4-yl)amino)-1,3,5-triazin-2-yl)benzyl)-2H-tetrazole-5-carboxamide as a yellow solid (44.8 mg, yield: 75%). ESI-MS (M+H)$^+$: 466.0. $^1$H NMR (500 MHz, DMSO-d$_6$) δ: 10.35-10.32 (m, 1H), 9.63-9.57 (m, 1H), 8.80-8.72 (m, 1H), 8.00-7.89 (m, 2H), 7.63-7.55 (m, 1H), 7.21-7.13 (m, 1H), 4.53 (br t, J=5.5 Hz, 2H), 3.83-3.81 (m, 3H), 2.39-2.37 (m, 3H), 1.75 (s, 9H).

Example 59: N-(5-fluoro-2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide (Compound 59)

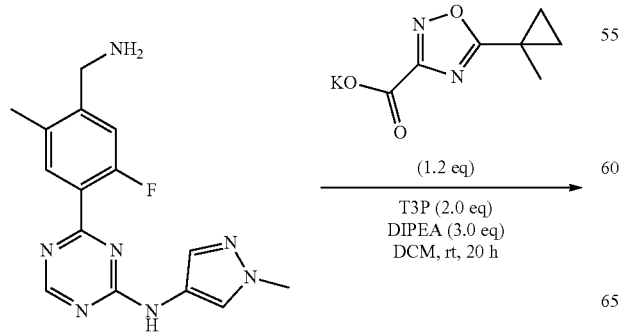

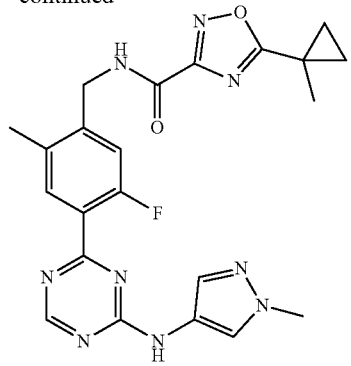

Synthesis of N-(5-fluoro-2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of N-(5-fluoro-2-methyl-4-(4-((1-methyl-1H-pyrazol-4-yl)amino)-1,3,5-triazin-2-yl)benzyl)-5-(1-methylcyclopropyl)-1,2,4-oxadiazole-3-carboxamide as a yellow solid (21.1 mg, yield: 36%). ESI-MS (M+H)$^+$: 463.9. $^1$H NMR (500 MHz, DMSO-d$_6$) δ: 10.35-10.32 (m, 1H), 9.49-9.44 (m, 1H), 8.80-8.72 (m, 1H), 8.00-7.88 (m, 2H), 7.63-7.55 (m, 1H), 7.18-7.11 (m, 1H), 4.48 (br t, J=5.5 Hz, 2H), 3.83-382 (m, 3H), 2.37-2.35 (m, 3H), 1.55 (s, 3H), 1.42-1.37 (m, 2H), 1.19-1.16 (m, 2H).

Example 60: N-(5-fluoro-2-methyl-4-(4-((1-methyl-1H-pyrazol-4-yl)amino)-1,3,5-triazin-2-yl)benzyl)-3-(1-(fluoromethyl)cyclopropyl)-1,2,4-oxadiazole-5-carboxamide (Compound 60)

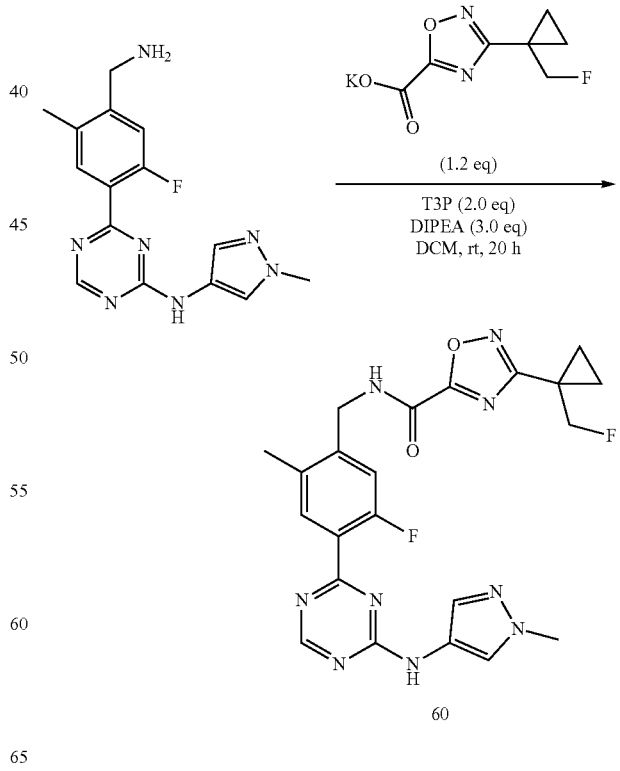

Synthesis of N-(5-fluoro-2-methyl-4-(4-((1-methyl-1H-pyrazol-4-yl)amino)-1,3,5-triazin-2-yl)benzyl)-3-(1-(fluoromethyl)cyclopropyl)-1,2,4-oxadiazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC ($CH_3CN/H_2O$ with 0.05% $TFA/H_2O$ as mobile phase) to give the TFA salt of N-(5-fluoro-2-methyl-4-(4-((1-methyl-1H-pyrazol-4-yl)amino)-1,3,5-triazin-2-yl)benzyl)-3-(1-(fluoromethyl)cyclopropyl)-1,2,4-oxadiazole-5-carboxamide as a yellow solid (23.1 mg, yield: 38%). ESI-MS (M+H)$^+$: 482.2. $^1$H NMR (500 MHz, DMSO-d$_6$) δ:10.35-10.32 (m, 1H), 9.86-9.81 (m, 1H), 8.81-8.72 (m, 1H), 7.99-7.88 (m, 2H), 7.64-7.55 (m, 1H), 7.30-7.22 (m, 1H), 4.74 (d, J=48.2 Hz, 2H), 4.49 (br t, J=5.5 Hz, 2H), 3.83-3.81 (m, 3H), 2.37-2.34 (m, 3H), 1.38-1.27 (m, 4H).

Example 61: 1-(tert-butyl)-N-(5-fluoro-2-methyl-4-(4-((1-methyl-1H-pyrazol-4-yl)amino)-1,3,5-triazin-2-yl)benzyl)-1H-pyrazole-4-carboxamide (Compound 61)

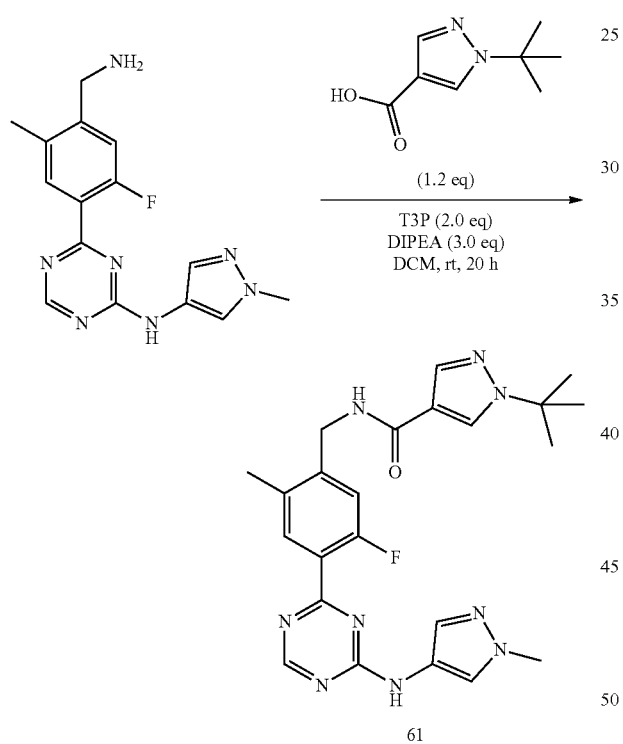

Synthesis of 1-(tert-butyl)-N-(5-fluoro-2-methyl-4-(4-((1-methyl-1H-pyrazol-4-yl)amino)-1,3,5-triazin-2-yl)benzyl)-1H-pyrazole-4-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC ($CH_3CN/H_2O$ with 0.05% $TFA/H_2O$ as mobile phase) to give the TFA salt of 1-(tert-butyl)-N-(5-fluoro-2-methyl-4-(4-((1-methyl-1H-pyrazol-4-yl)amino)-1,3,5-triazin-2-yl)benzyl)-1H-pyrazole-4-carboxamide as a yellow solid (15.4 mg, yield: 25%). ESI-MS (M+H)$^+$: 464.2. $^1$H NMR (500 MHz, DMSO-d$_6$) δ: 10.34-10.31 (m, 1H), 8.88-8.68 (m, 1H), 8.61-8.52 (m, 2H), 8.34-8.33 (m, 1H), 8.02-7.88 (m, 2H), 7.65-7.50 (m, 1H), 7.18-7.07 (m, 1H), 4.45 (br t, J=4.9 Hz, 2H), 3.83-3.81 (m, 3H), 2.37-2.35 (m, 3H), 1.54 (s, 9H).

Example 62: 1-(tert-butyl)-N-(5-fluoro-2-methyl-4-(4-((1-methyl-1H-pyrazol-4-yl)amino)-1,3,5-triazin-2-yl)benzyl)-1H-1,2,3-triazole-4-carboxamide (Compound 62)

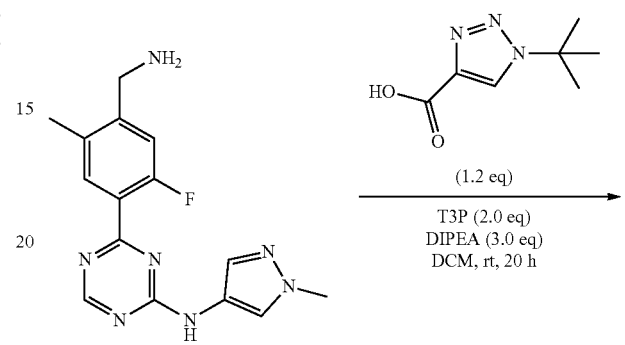

Synthesis of 1-(tert-butyl)-N-(5-fluoro-2-methyl-4-(4-((1-methyl-1H-pyrazol-4-yl)amino)-1,3,5-triazin-2-yl)benzyl)-1H-1,2,3-triazole-4-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC ($CH_3CN/H_2O$ with 0.05% $TFA/H_2O$ as mobile phase) to give the TFA salt of 1-(tert-butyl)-N-(5-fluoro-2-methyl-4-(4-((1-methyl-1H-pyrazol-4-yl)amino)-1,3,5-triazin-2-yl)benzyl)-1H-1,2,3-triazole-4-carboxamide as a yellow solid (41.0 mg, yield: 66%). ESI-MS (M+H)$^+$: 465.2. $^1$H NMR (500 MHz, DMSO-d$_6$) δ: 10.34-10.31 (m, 1H), 9.17-9.10 (m, 1H), 8.73-8.71 (m, 2H), 7.99-7.89 (m, 2H), 7.62-7.55 (m, 1H), 7.18-7.07 (m, 1H), 4.49 (br t, J=5.5 Hz, 2H), 3.83-3.80 (m, 3H), 2.38-2.36 (m, 3H), 1.65 (s, 9H).

Example 63: 3-(tert-butyl)-N-(5-fluoro-2-methyl-4-(4-((1-methyl-1H-pyrazol-4-yl)amino)-1,3,5-triazin-2-yl)benzyl)isoxazole-5-carboxamide (Compound 63)

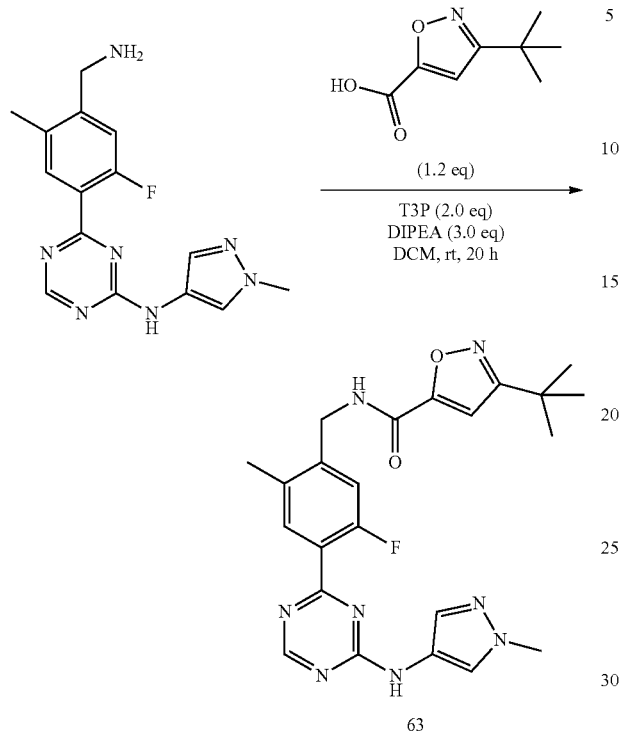

Synthesis of 3-(tert-butyl)-N-(5-fluoro-2-methyl-4-(4-((1-methyl-1H-pyrazol-4-yl)amino)-1,3,5-triazin-2-yl)benzyl)isoxazole-5-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 3-(tert-butyl)-N-(5-fluoro-2-methyl-4-(4-((1-methyl-1H-pyrazol-4-yl)amino)-1,3,5-triazin-2-yl)benzyl)isoxazole-5-carboxamide as a yellow solid (40.1 mg, yield: 64%). ESI-MS (M+H)$^+$: 465.2. $^1$H NMR (500 MHz, DMSO-d$_6$) δ:10.35-10.32 (m, 1H), 9.50-9.37 (m, 1H), 8.80-8.72 (m, 1H), 8.00-7.89 (m, 2H), 7.21-7.16 (m, 2H), 7.15-7.12 (m, 1H), 4.52-4.47 (m, 2H), 3.84-3.81 (m, 3H), 2.38-2.34 (m, 3H), 1.31 (m, 9H).

Example 64: 5-(tert-butyl)-N-(5-fluoro-2-methyl-4-(4-((1-methyl-1H-pyrazol-4-yl)amino)-1,3,5-triazin-2-yl)benzyl)isoxazole-3-carboxamide (Compound 64)

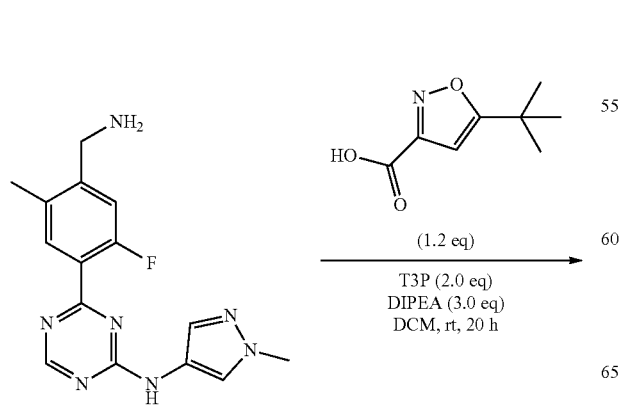

-continued

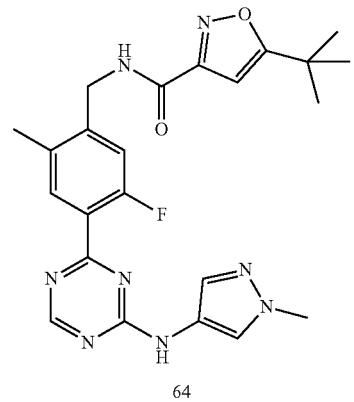

Synthesis of 5-(tert-butyl)-N-(5-fluoro-2-methyl-4-(4-((1-methyl-1H-pyrazol-4-yl)amino)-1,3,5-triazin-2-yl)benzyl)isoxazole-3-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 5-(tert-butyl)-N-(5-fluoro-2-methyl-4-(4-((1-methyl-1H-pyrazol-4-yl)amino)-1,3,5-triazin-2-yl)benzyl)isoxazole-3-carboxamide as a yellow solid (45.9 mg, yield: 74%). ESI-MS (M+H)$^+$: 465.2. $^1$H NMR (500 MHz, DMSO-d$_6$) δ: 10.35-10.32 (m, 1H), 9.35-9.27 (m, 1H), 8.80-8.72 (m, 1H), 8.00-7.89 (m, 2H), 7.63-7.55 (m, 1H), 7.18-7.07 (m, 1H), 6.62-6.61 (m, 1H), 4.48 (br t, J=5.2 Hz, 2H), 3.83-3.82 (m, 3H), 2.37-2.35 (m, 3H), 1.34 (s, 9H).

Example 65: 2-(tert-butyl)-N-(5-fluoro-2-methyl-4-(4-((1-methyl-1H-pyrazol-4-yl)amino)-1,3,5-triazin-2-yl)benzyl)oxazole-4-carboxamide (Compound 65)

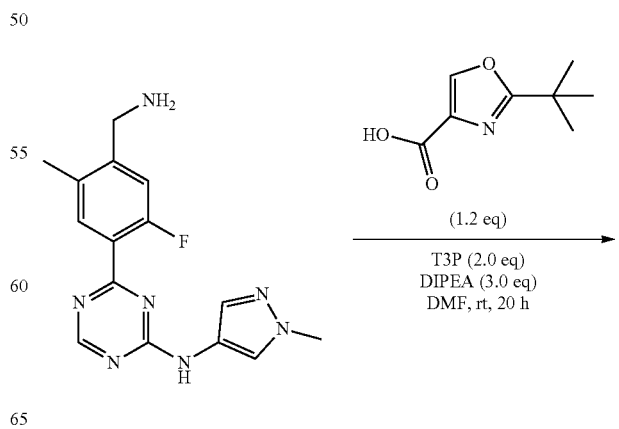

-continued

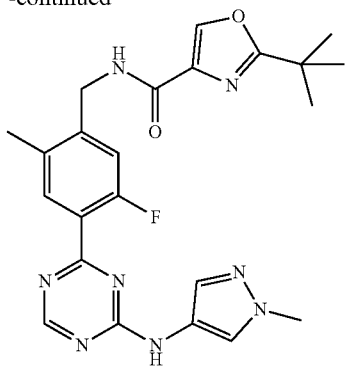

65

Synthesis of 2-(tert-butyl)-N-(5-fluoro-2-methyl-4-(4-((1-methyl-1H-pyrazol-4-yl)amino)-1,3,5-triazin-2-yl)benzyl)oxazole-4-carboxamide was similar to that of 5-(tert-butyl)-N-(2-chloro-4-(4-((1-methyl-1H-pyrazol-4-yl)amino)-1,3,5-triazin-2-yl)benzyl)-1,2,4-oxadiazole-3-carboxamide in Example 15, Step 3. The crude product was purified by prep-HPLC (CH$_3$CN/H$_2$O with 0.05% TFA/H$_2$O as mobile phase) to give the TFA salt of 2-(tert-butyl)-N-(5-fluoro-2-methyl-4-(4-((1-methyl-1H-pyrazol-4-yl)amino)-1,3,5-triazin-2-yl)benzyl)oxazole-4-carboxamide as a yellow solid (29.2 mg, yield: 38%). ESI-MS (M+H)$^+$: 465.3. $^1$H NMR (500 MHz, DMSO-d$_6$) δ: 10.34-10.31 (m, 1H), 8.84-8.67 (m, 2H), 8.56 (s, 1H), 8.05-7.86 (m, 2H), 7.65-7.53 (m, 1H), 7.16-7.06 (m, 1H), 4.45 (br t, J=5.8 Hz, 2H), 3.85-3.79 (m, 3H), 2.37-2.35 (m, 3H), 1.37 (s, 9H).

Example 66: 3-(tert-butyl)-N-(2-(difluoromethyl)-3-fluoro-4-(4-((1-methyl-1H-pyrazol-3-yl)amino)-1,3,5-triazin-2-yl)benzyl)-1,2,4-oxadiazole-5-carboxamide (Compound 66)

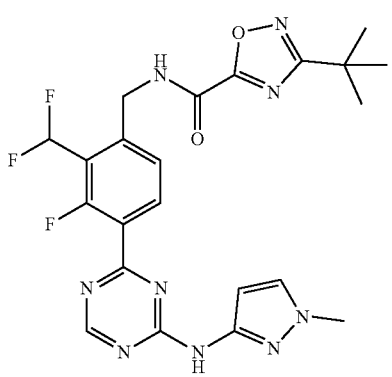

66

1. Synthesis of 2-fluoro-3-nitrobenzaldehyde

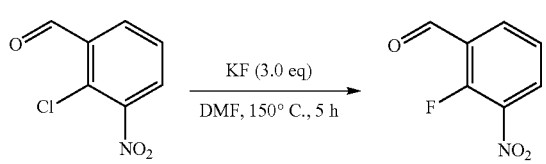 [SMILES: O=Cc1cccc([N+](=O)[O-])c1Cl ; O=Cc1cccc([N+](=O)[O-])c1F]

To a solution of 2-chloro-3-nitrobenzaldehyde (9.5 g, 51.2 mmol) in DMF (100 mL) was added KF (8.9 g, 154 mmol). The reaction mixture was heated to 150° C. and stirred at that temperature for 5 h. The reaction mixture was cooled to ambient temperature and concentrated in vacuo. The crude material was poured into H$_2$O (400 mL) and extracted with DCM (100 mL×4). The combined organic extracts were concentrated in vacuo and the crude material was purified by silica-gel column chromatography (petroleum ether/EtOAc, 20:1) to give 2-fluoro-3-nitrobenzaldehyde as a yellow oil (6.7 g, yield: 77%). $^1$H NMR (400 MHz, CDCl$_3$) δ: 10.44 (s, 1H), 8.36-8.30 (m, 1H), 8.22-8.16 (m, 1H), 7.47 (t, J=8.0 Hz, 1H).

2. Synthesis of 1-(difluoromethyl)-2-fluoro-3-nitrobenzene

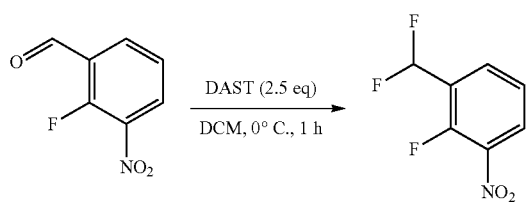

To a solution of 2-fluoro-3-nitrobenzaldehyde (6.7 g, 40 mmol) in DCM (100 mL) at 0° C. was added a slurry of DAST (16.0 g, 99 mmol) in DCM (50 mL) slowly. The reaction mixture was stirred in an ice-water bath for 1 h and H$_2$O (300 mL) was added. The aqueous phase was extracted with DCM (!50 mL×3) and the combined organic extracts were dried (Na$_2$SO$_4$), filtered, and concentrated in vacuo. The crude material was purified by silica-gel column chromatography (petroleum ether/EtOAc, 20:1) to give 1-(difluoromethyl)-2-fluoro-3-nitrobenzene as an orange oil (6.6 g, yield: 87%). $^1$H NMR (400 MHz, CDCl$_3$) δ: 8.20 (t, J=8.0 Hz, 1H), 7.92 (t, J=6.8 Hz, 1H), 7.44 (t, J=8.0 Hz, 1H), 6.97 (t, J=54.4 Hz, 1H).

3. Synthesis of 3-(difluoromethyl)-2-fluoroaniline

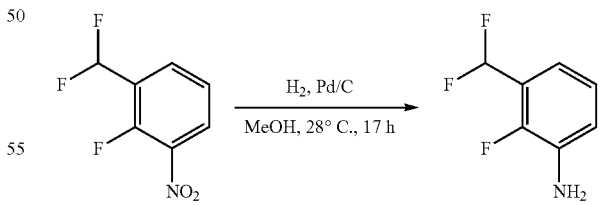

To a solution of 1-(difluoromethyl)-2-fluoro-3-nitrobenzene (6.6 g, 35 mmol) in MeOH (100 mL) was added Pd/C (1.4 g). The mixture was stirred at 28° C. under an H$_2$ balloon (15 psi) for 17 h. The mixture was filtered and the filtrate was concentrated in vacuo to give 3-(difluoromethyl)-2-fluoroaniline as a yellow oil (4.7 g, yield: 83%), which was carried forward without further purification. ESI-MS (M+H)$^+$: 162.0.

4. Synthesis of 4-bromo-3-(difluoromethyl)-2-fluoroaniline

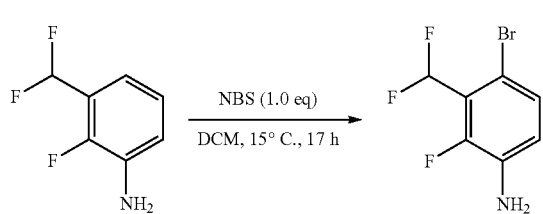 [SMILES: Nc1cccc(C(F)F)c1F ; Nc1ccc(Br)c(C(F)F)c1F]

To a solution of 3-(difluoromethyl)-2-fluoroaniline (4.7 g, 29 mmol) in DCM (100 mL) was added NBS (5.1 g, 29 mmol) slowly. The reaction mixture was stirred at 15° C. for 17 h. The reaction mixture was concentrated in vacuo and the crude material was purified by silica-gel column chromatography (petroleum ether/EtOAc, grading from 50:1 to 10:1) to give 4-bromo-3-(difluoromethyl)-2-fluoroaniline as a brown solid (3.3 g, yield: 48% over 2 steps). $^1$H NMR (400 MHz, CDCl$_3$) δ: 7.16 (dd, J=8.8 Hz, 1.6 Hz, 1H), 6.99 (td, J=52.8 Hz, 1.2 Hz, 1H), 6.79-6.73 (m, 1H), 3.87 (s, 2H).

5. Synthesis of methyl 4-amino-2-(difluoromethyl)-3-fluorobenzoate

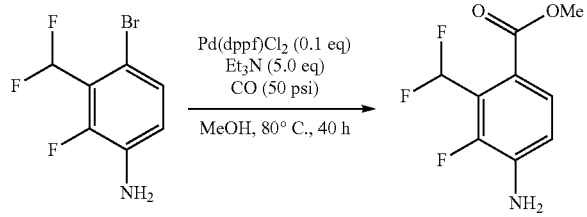 [SMILES: Nc1ccc(Br)c(C(F)F)c1F ; COC(=O)c1ccc(N)c(F)c1C(F)F]

A solution of 4-bromo-3-(difluoromethyl)-2-fluoroaniline (3.1 g, 13 mmol), Pd(dppf)Cl$_2$ (945 mg, 1.3 mmol), and Et$_3$N (6.5 g, 65 mmol) in MeOH (100 mL) was stirred for 40 h at 80° C. under an atmosphere of CO (50 psi). The reaction mixture was cooled to ambient temperature, filtered, and concentrated in vacuo. The crude material was purified by silica-gel column chromatography (petroleum ether/EtOAc, 20:1) to give methyl 4-amino-2-(difluoromethyl)-3-fluorobenzoate as an orange solid (2.2 g, yield: 75%). ESI-MS (M+H)$^+$: 220.0.

6. Synthesis of methyl 4-bromo-2-(difluoromethyl)-3-fluorobenzoate

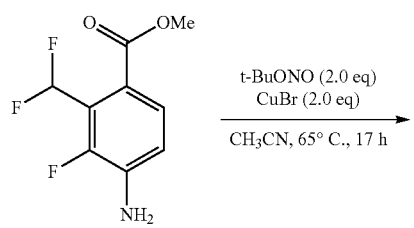

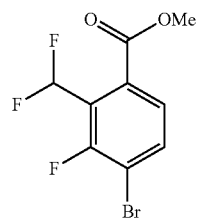

Synthesis of methyl 4-bromo-2-(difluoromethyl)-3-fluorobenzoate was similar to that of 4-bromo-3-chloro-2-methylbenzonitrile in Example 80, Step 5. The crude material was purified by silica-gel column chromatography (petroleum ether/EtOAc, 20:1) to give methyl 4-bromo-2-(difluoromethyl)-3-fluorobenzoate as a pale, yellow solid (1.7 g, yield: 68%). $^1$H NMR (400 MHz, CDCl$_3$) δ: 7.77-7.73 (m, 1H), 7.64-7.61 (m, 1H), 7.62-7.42 (m, 1H), 3.95 (s, 3H).

7. Synthesis of (4-bromo-2-(difluoromethyl)-3-fluorophenyl)methanol

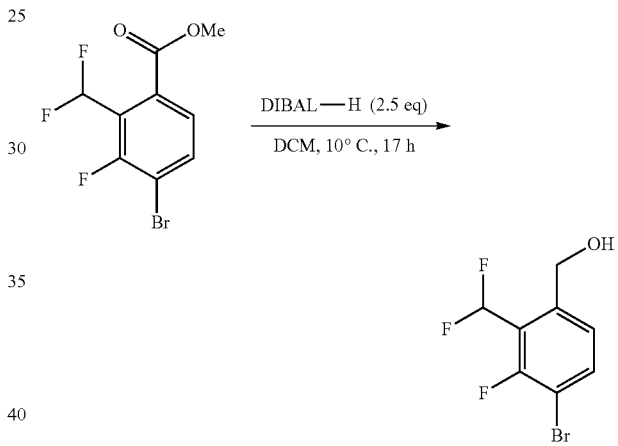

To a solution of methyl 4-bromo-2-(difluoromethyl)-3-fluorobenzoate (1.2 g, 4.2 mmol) in DCM (60 mL) in an ethanol-dry ice bath was added DIBAL-H (1.0 M, 10.6 mL) slowly. The reaction mixture was stirred at 10° C. for 17 h. Water (1 mL) was added, followed by a 10% NaOH solution (1 mL), more water (1 mL) and Na$_2$SO$_4$. The reaction mixture was filtered and the filtrate was concentrated in vacuo to give (4-bromo-2-(difluoromethyl)-3-fluorophenyl)methanol (1.1 g, crude), which was carried forward without further purification.

8. Synthesis of 1-bromo-4-(chloromethyl)-3-(difluoromethyl)-2-fluorobenzene

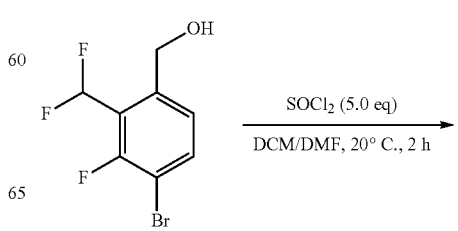

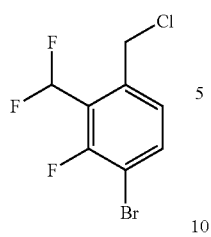

To a solution of (4-bromo-2-(difluoromethyl)-3-fluorophenyl)methanol (1.1 g, 4.3 mmol) in DCM (50 mL) was added DMF (1 mL), followed by thionyl chloride (2.5 g, 22 mmol) dropwise. The reaction mixture was stirred at 20° C. for 2 h. The reaction mixture was then poured into H₂O (100 mL) and extracted with DCM (50 mL×3). The combined organic extracts were dried (Na₂SO₄), filtered, and concentrated in vacuo to give 1-bromo-4-(chloromethyl)-3-(difluoromethyl)-2-fluorobenzene (1.1 g, crude), which was carried forward without further purification.

9. Synthesis of (4-bromo-2-(difluoromethyl)-3-fluorophenyl)methanamine

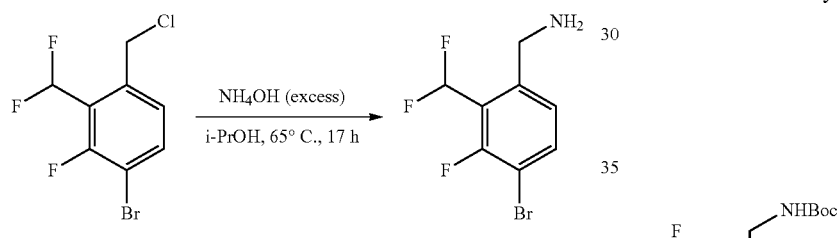

To a solution of 1-bromo-4-(chloromethyl)-3-(difluoromethyl)-2-fluorobenzene (1.1 g, 4.0 mmol) in i-PrOH (60 mL) was added NH₄OH (100 mL). The reaction mixture was heated to 65° C. and stirred at that temperature for 17 h. The reaction mixture was concentrated in vacuo and the residue was dissolved in DCM (100 mL). The organic phase was washed with H₂O (100 mL), dried (Na₂SO₄), filtered, and concentrated in vacuo to give (4-bromo-2-(difluoromethyl)-3-fluorophenyl)methanamine (1.0 g, crude), which was carried forward without further purification. ESI-MS (M+H−NH₂)⁺: 236.9.

10. Synthesis of tert-butyl (4-bromo-2-(difluoromethyl)-3-fluorobenzyl)carbamate

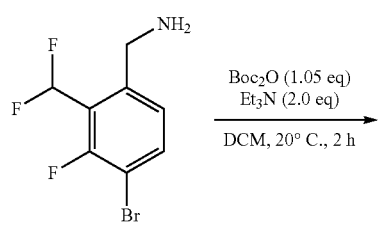

To a solution of (4-bromo-2-(difluoromethyl)-3-fluorophenyl)methanamine (1.0 g, 3.9 mmol) in DCM (30 mL) was added Et₃N (797 mg, 7.9 mmol), followed by Boc₂O (902 mg, 4.1 mmol). The reaction mixture was stirred at ambient temperature for 2 h and then poured into H₂O (100 mL). The layers were separated, and the aqueous phase was extracted with DCM (50 mL×3). The combined organic extracts were concentrated in vacuo and the crude material was purified by silica-gel column chromatography (petroleum ether/EtOAc, grading from 20:1 to 10:1) to give tert-butyl (4-bromo-2-(difluoromethyl)-3-fluorobenzyl)carbamate as a yellow oil (900 mg, yield: 85% over 4 steps). ESI-MS (M+H−t-Bu)⁺: 297.9.

11. Synthesis of tert-butyl (2-(difluoromethyl)-3-fluoro-4-(4,4,5,5-tetramethyl-1,3,2-dioxaborolan-2-yl)benzyl)carbamate

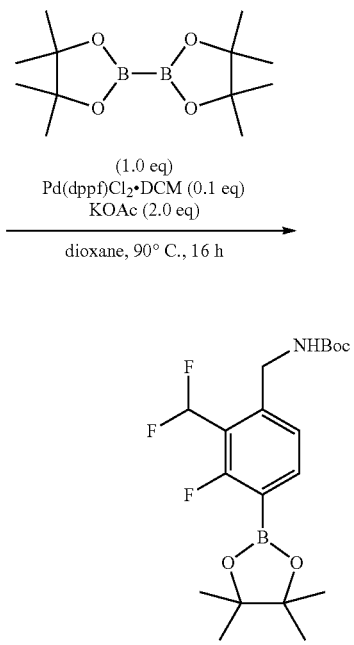

Synthesis of tert-butyl (2-(difluoromethyl)-3-fluoro-4-(4,4,5,5-tetramethyl-1,3,2-dioxaborolan-2-yl)benzyl)carbamate was similar to that of tert-butyl (R)-(1-(2-chloro-3-fluoro-4-(4,4,5,5-tetramethyl-1,3,2-dioxaborolan-2-yl)phenyl)ethyl)carbamate in Example 69, Step 8. The crude material was purified by silica-gel column chromatography (petroleum ether/EtOAc, grading from 20:1 to 6:1) to give tert-butyl (2-(difluoromethyl)-3-fluoro-4-(4,4,5,5-tetramethyl-1,3,2-dioxaborolan-2-yl)benzyl)carbamate as a white solid (700 mg, yield: 80%). ¹H NMR (500 MHz, CDCl₃) δ:

7.81 (t, J=7.0 Hz, 1H), 7.32 (d, J=7.5 Hz, 1H), 7.09 (t, J=54.0 Hz, 1H), 4.96 (t, J=6.0 Hz, 1H), 4.56 (d, J=6.5 Hz, 2H), 1.44 (s, 9H), 1.35 (s, 12H).

12. Synthesis of tert-butyl (2-(difluoromethyl)-3-fluoro-4-(4-((1-methyl-1H-pyrazol-3-yl)amino)-1,3,5-triazin-2-yl)benzyl)carbamate

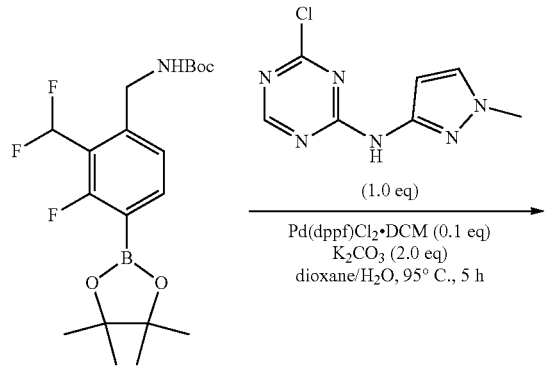

Synthesis of tert-butyl (2-(difluoromethyl)-3-fluoro-4-(4-((1-methyl-1H-pyrazol-3-yl)amino)-1,3,5-triazin-2-yl)benzyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (petroleum ether/EtOAc, grading from 8:1 to 1:3) to give tert-butyl (2-(difluoromethyl)-3-fluoro-4-(4-((1-methyl-1H-pyrazol-3-yl)amino)-1,3,5-triazin-2-yl)benzyl)carbamate as an off-white solid (180 mg, yield: 70%). $^1$H NMR (500 MHz, CDCl$_3$) δ: 9.19-9.08 (m, 2H), 8.41-8.19 (m, 1H), 7.47-7.41 (m, 1H), 7.33-7.21 (m, 1H), 7.17-6.77 (m, 2H), 5.04 (br s, 1H), 4.63 (d, J=5.0 Hz, 2H), 3.88 (s, 3H), 1.46 (s, 9H).

13. Synthesis of 4-(4-(aminomethyl)-3-(difluoromethyl)-2-fluorophenyl)-N-(1-methyl-1H-pyrazol-3-yl)-1,3,5-triazin-2-amine hydrochloride

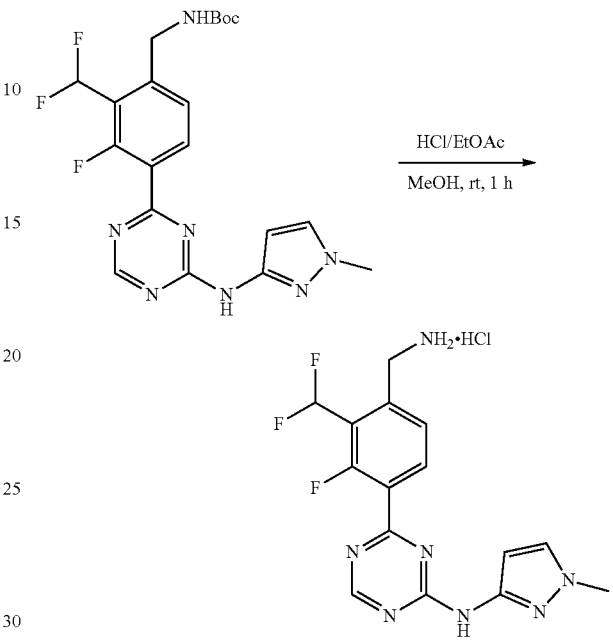

Synthesis of 4-(4-(aminomethyl)-3-(difluoromethyl)-2-fluorophenyl)-N-(1-methyl-1H-pyrazol-3-yl)-1,3,5-triazin-2-amine hydrochloride was similar to that of (R)-4-(4-(1-aminoethyl)-2-fluoro-3-methylphenyl)-N-(1-methyl-1H-pyrazol-3-yl)-1,3,5-triazin-2-amine hydrochloride in Example WX-D, Step 10. The reaction mixture was concentrated in vacuo to give 4-(4-(aminomethyl)-3-(difluoromethyl)-2-fluorophenyl)-N-(1-methyl-1H-pyrazol-3-yl)-1,3,5-triazin-2-amine hydrochloride as a gray solid (153 mg, crude), which was carried forward without further purification. ESI-MS (M+H)$^+$: 350.1.

14. Synthesis of 3-(tert-butyl)-N-(2-(difluoromethyl)-3-fluoro-4-(4-((1-methyl-1H-pyrazol-3-yl)amino)-1,3,5-triazin-2-yl)benzyl)-1,2,4-oxadiazole-5-carboxamide (Compound 66)

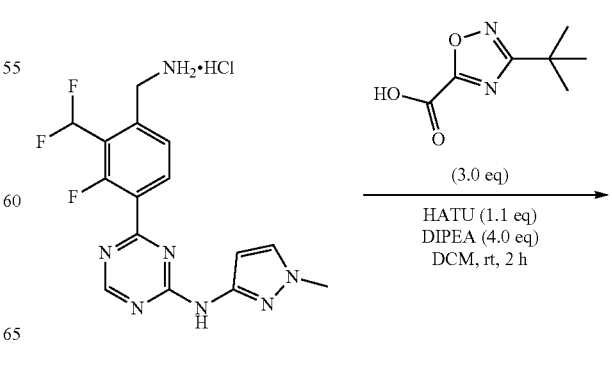

189
-continued

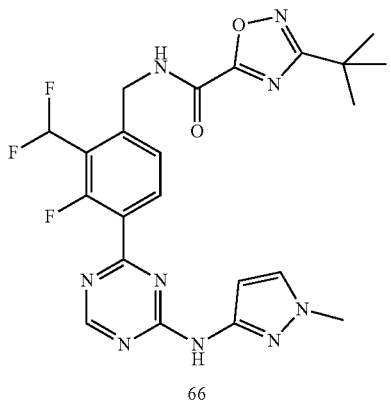

66

Synthesis of 3-(tert-butyl)-N-(2-(difluoromethyl)-3-fluoro-4-(4-((1-methyl-1H-pyrazol-3-yl)amino)-1,3,5-triazin-2-yl)benzyl)-1,2,4-oxadiazole-5-carboxamide was similar to that of (R)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide in Example 70. The crude material was purified by prep-HPLC (CH₃CN/H₂O with 0.05% HCl/H₂O as mobile phase) to give the HCl salt of 3-(tert-butyl)-N-(2-(difluoromethyl)-3-fluoro-4-(4-((1-methyl-1H-pyrazol-3-yl)amino)-1,3,5-triazin-2-yl)benzyl)-1,2,4-oxadiazole-5-carboxamide as a white solid (50 mg, yield: 72%). ESI-MS (M+H)⁺: 502.1. ¹H NMR (500 MHz, DMSO-d₆) δ: 10.19 (s, 1H), 9.60 (s, 1H), 8.79 (s, 1H), 8.21 (t, J=8.0 Hz, 1H), 7.58 (d, J=2.0 Hz, 1H), 7.51-7.39 (m, 2H), 6.64 (d, J=2.0 Hz, 1H), 4.80 (d, J=6.0 Hz, 2H), 3.80 (s, 3H), 1.41 (s, 9H).

Example 67: 5-(tert-butyl)-N-(2-(2,2-difluoroethyl)-4-(4-((1-methyl-1H-pyrazol-3-yl)amino)-1,3,5-triazin-2-yl)benzyl)-1,2,4-oxadiazole-3-carboxamide (Compound 67)

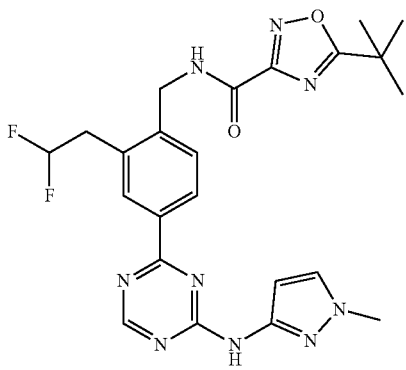

67

190

1. Synthesis of (E)-4-bromo-2-(2-(dimethylamino)vinyl)benzonitrile

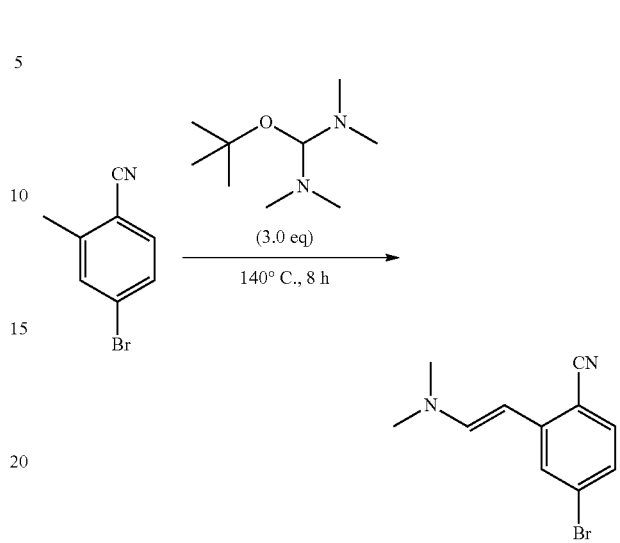

A solution of 4-bromo-2-methylbenzonitrile (20 g, 102 mmol) in neat 1-tert-butoxy-N,N,N',N'-tetramethylmethanediamine (53 g, 306 mmol) was heated to 140° C. and was stirred at that temperature for 8 h. The reaction mixture was cooled to ambient temperature and filtered. The filter cake was washed with petroleum ether (100 mL) and dried in vacuo to give (E)-4-bromo-2-(2-(dimethylamino)vinyl)benzonitrile as a yellow solid (15 g, crude), which was carried forward without further purification. ¹H NMR (500 MHz, CDCl₃) δ: 7.73 (d, J=1.5 Hz, 1H), 7.56-7.49 (m, 1H), 7.28-7.21 (m, 2H), 5.53 (d, J=13.5 Hz, 1H), 3.18 (s, 6H).

2. Synthesis of 4-bromo-2-(2-oxoethyl)benzonitrile

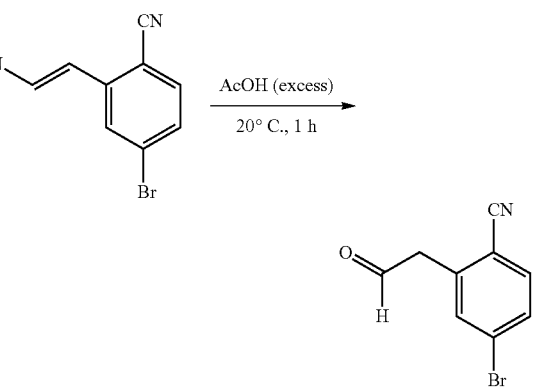

A solution of (E)-4-bromo-2-(2-(dimethylamino)vinyl)benzonitrile (15 g, 54 mmol) in an aqueous acetic acid solution (250 mL, 4 M) was stirred at ambient temperature for 1 h. The reaction mixture was filtered, and the filter cake was washed with H₂O (100 mL). The crude material was dried in vacuo to give 4-bromo-2-(2-oxoethyl)benzonitrile as a yellow solid (10 g, crude), which was carried forward without further purification. ¹H NMR (400 MHz, CDCl₃) δ: 9.84 (s, 1H), 7.58-7.56 (m, 2H), 7.52 (s, 1H), 4.01 (s, 2H).

3. Synthesis of 4-bromo-2-(2,2-difluoroethyl)benzonitrile

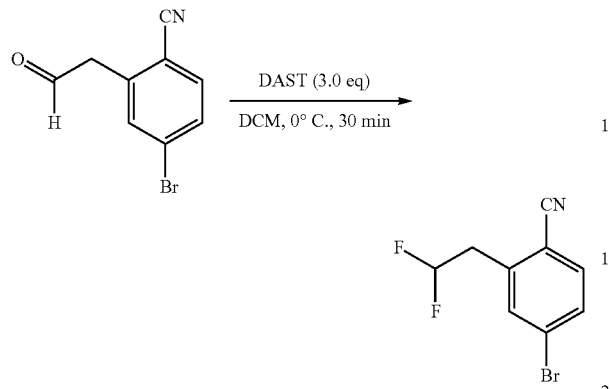

To a solution of 4-bromo-2-(2-oxoethyl)benzonitrile (10 g, 40 mmol) in DCM (100 mL) at 0° C. was added DAST (19.4 g, 121 mmol) slowly. The reaction mixture was stirred as it warmed to 15° C. over 30 min. MeOH (50 mL) was added and the reaction mixture was concentrated in vacuo. The residue was poured into H$_2$O (200 mL) and extracted with EtOAc (200 mL×3). The combined organic layers were washed with brine (200 mL), dried (Na$_2$SO$_4$), filtered, and concentrated in vacuo. The crude material was purified by silica-gel column chromatography (petroleum ether/EtOAc, 5:1) to give 4-bromo-2-(2,2-difluoroethyl)benzonitrile as a yellow solid (9.5 g, yield: 91% over 3 steps). $^1$H NMR (400 MHz, CDCl$_3$) δ: 7.66-7.51 (m, 3H), 6.28-5.79 (m, 1H), 3.41-3.31 (m, 2H).

4. Synthesis of (4-bromo-2-(2,2-difluoroethyl)phenyl)methanamine

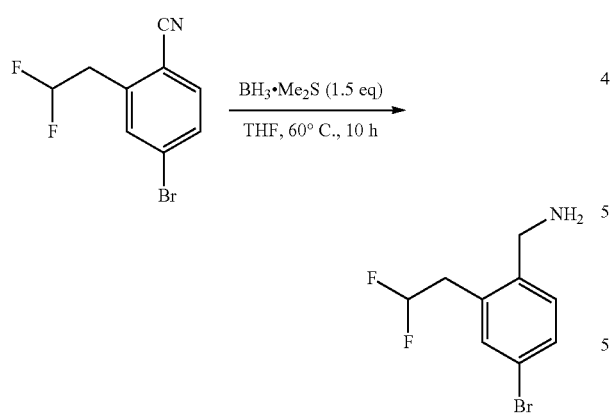

To a solution of 4-bromo-2-(2,2-difluoroethyl)benzonitrile (3.5 g, 14.2 mmol) in THF at 15° C. (100 mL) was added BH$_3$.Me$_2$S (1 M, 21.3 mL, 21.3 mmol) under N$_2$. The reaction mixture was heated to 60° C. and was stirred at that temperature for 10 h under N$_2$. The reaction mixture was cooled to ambient temperature and MeOH (50 mL) was added. The mixture was filtered and the filtrate was concentrated in vacuo to give (4-bromo-2-(2,2-difluoroethyl)phenyl)methanamine as a colorless oil (3.0 g, crude), which was carried forward without further purification. ESI-MS (M+H)$^+$: 252.0.

5. Synthesis of tert-butyl (4-bromo-2-(2,2-difluoroethyl)benzyl)carbamate

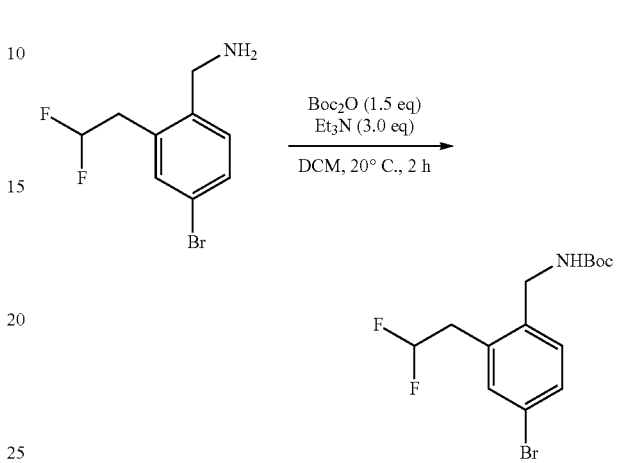

Synthesis of tert-butyl (4-bromo-2-(2,2-difluoroethyl)benzyl)carbamate was similar to that of tert-butyl (4-bromo-2-(difluoromethyl)-3-fluorobenzyl)carbamate in Example 66, Step 10. The crude material was purified by silica-gel column chromatography (petroleum ether/EtOAc, 10:1) to give tert-butyl (4-bromo-2-(2,2-difluoroethyl)benzyl)carbamate as a colorless oil (3.8 g, yield: 90% over 2 steps). ESI-MS (M+H−56)$^+$: 295.9.

6. Synthesis of tert-butyl (2-(2,2-difluoroethyl)-4-(4,4,5,5-tetramethyl-1,3,2-dioxaborolan-2-yl)benzyl)carbamate

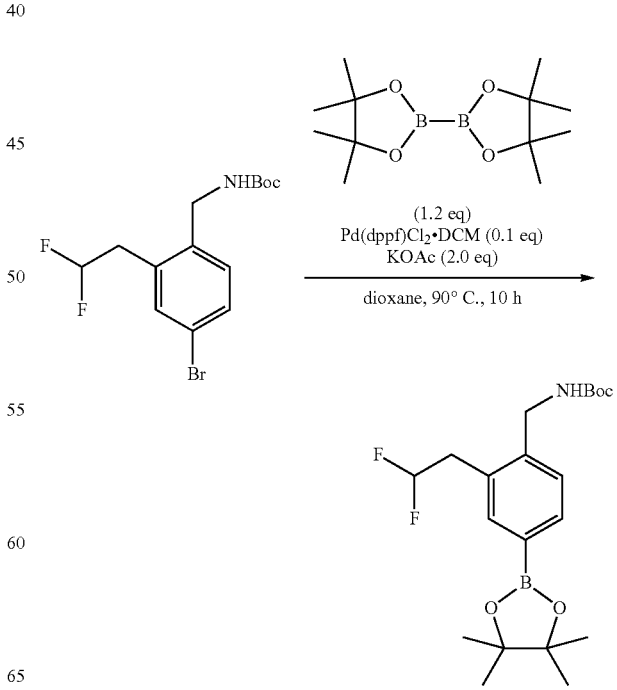

Synthesis of tert-butyl (2-(2,2-difluoroethyl)-4-(4,4,5,5-tetramethyl-1,3,2-dioxaborolan-2-yl)benzyl)carbamate was similar to that of tert-butyl (R)-(1-(2-chloro-3-fluoro-4-(4,4,5,5-tetramethyl-1,3,2-dioxaborolan-2-yl)phenyl)ethyl)carbamate in Example 69, Step 8. The crude material was purified by silica-gel column chromatography (petroleum ether/EtOAc, 10:1) to give tert-butyl (2-(2,2-difluoroethyl)-4-(4,4,5,5-tetramethyl-1,3,2-dioxaborolan-2-yl)benzyl)carbamate as a yellow solid (4.0 g, yield: 86%). ESI-MS (M+H−56)$^+$: 342.1.

7. Synthesis of tert-butyl (2-(2,2-difluoroethyl)-4-(4-((1-methyl-1H-pyrazol-3-yl)amino)-1,3,5-triazin-2-yl)benzyl)carbamate

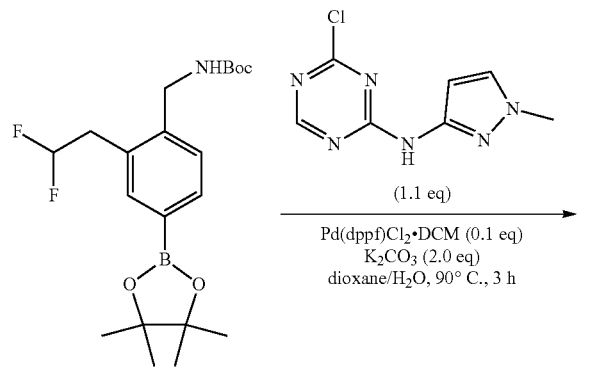

8. Synthesis of 4-(4-(aminomethyl)-3-(2,2-difluoroethyl)phenyl)-N-(1-methyl-1H-pyrazol-3-yl)-1,3,5-triazin-2-amine hydrochloride

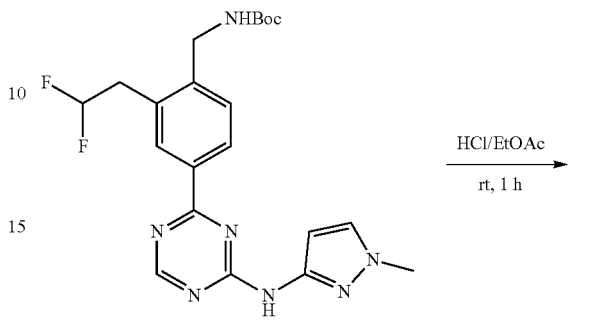

Synthesis of 4-(4-(aminomethyl)-3-(2,2-difluoroethyl)phenyl)-N-(1-methyl-1H-pyrazol-3-yl)-1,3,5-triazin-2-amine hydrochloride was similar to that of (R)-4-(4-(1-aminoethyl)-2-fluoro-3-methylphenyl)-N-(1-methyl-1H-pyrazol-3-yl)-1,3,5-triazin-2-amine hydrochloride in Example 71, Step 10. The reaction mixture was concentrated in vacuo to give 4-(4-(aminomethyl)-3-(2,2-difluoroethyl)phenyl)-N-(1-methyl-1H-pyrazol-3-yl)-1,3,5-triazin-2-amine hydrochloride as a white solid (200 mg, crude), which was carried forward without further purification. ESI-MS (M+H)$^+$: 345.9.

9. Synthesis of 5-(tert-butyl)-N-(2-(2,2-difluoroethyl)-4-(4-((1-methyl-1H-pyrazol-3-yl)amino)-1,3,5-triazin-2-yl)benzyl)-1,2,4-oxadiazole-3-carboxamide (Compound 67)

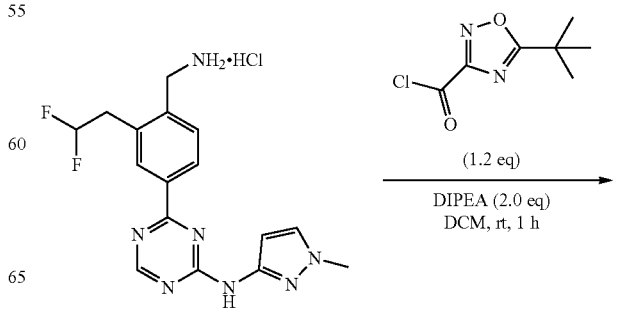

Synthesis of tert-butyl (2-(2,2-difluoroethyl)-4-(4-((1-methyl-1H-pyrazol-3-yl)amino)-1,3,5-triazin-2-yl)benzyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (EtOAc, 100%) to give tert-butyl (2-(2,2-difluoroethyl)-4-(4-((1-methyl-1H-pyrazol-3-yl)amino)-1,3,5-triazin-2-yl)benzyl)carbamate as a yellow solid (300 mg, yield: 74%). ESI-MS (M+H)$^+$: 446.2.

-continued

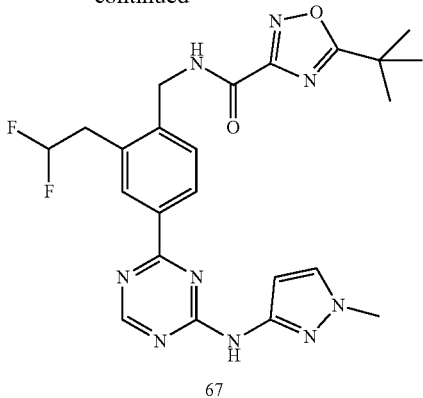

67

Synthesis of 5-(tert-butyl)-N-(2-(2,2-difluoroethyl)-4-(4-((1-methyl-1H-pyrazol-3-yl)amino)-1,3,5-triazin-2-yl)benzyl)-1,2,4-oxadiazole-3-carboxamide was similar to that of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide in Example 69, Step 11. The crude material was purified by prep-HPLC (CH$_3$CN/H$_2$O with 0.05% HCl/H$_2$O as mobile phase) to give 5-(tert-butyl)-N-(2-(2,2-difluoroethyl)-4-(4-((1-methyl-1H-pyrazol-3-yl)amino)-1,3,5-triazin-2-yl)benzyl)-1,2,4-oxadiazole-3-carboxamide as a yellow solid (38 mg, yield: 37%). ESI-MS (M+H)$^+$: 498.2. $^1$H NMR (500 MHz, DMSO-d$_6$) δ: 10.04 (s, 1H), 9.11 (s, 1H), 8.76 (s, 1H), 8.34 (s, 1H), 8.28 (d, J=8.5 Hz, 1H), 7.61-7.56 (m, 2H), 6.66 (s, 1H), 6.35-6.32 (m, 1H), 4.63 (d, J=6.0 Hz, 2H), 3.81 (s, 3H), 3.53-3.44 (m, 2H), 1.46 (s, 9H).

Example 68: 3-(tert-butyl)-N-(2-(2,2-difluoroethyl)-4-(4-((1-methyl-1H-pyrazol-3-yl)amino)-1,3,5-triazin-2-yl)benzyl)-1,2,4-oxadiazole-5-carboxamide (Compound 68)

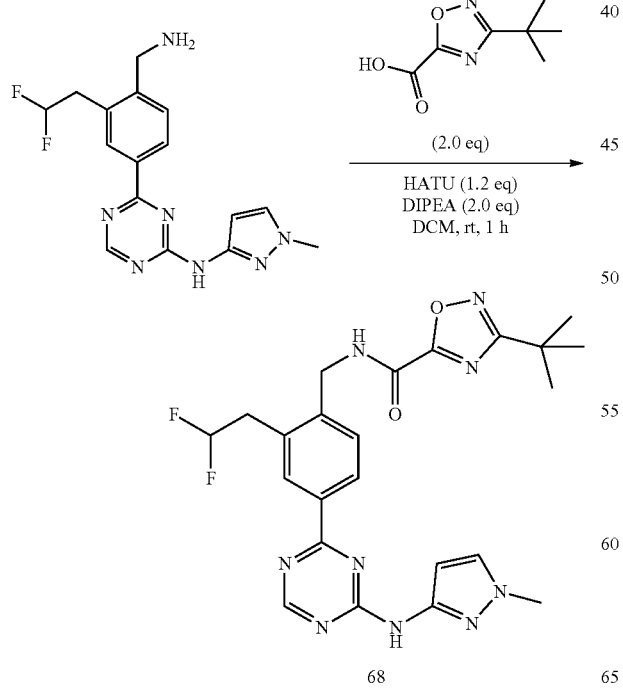

68

Synthesis of 3-(tert-butyl)-N-(2-(2,2-difluoroethyl)-4-(4-((1-methyl-1H-pyrazol-3-yl)amino)-1,3,5-triazin-2-yl)benzyl)-1,2,4-oxadiazole-5-carboxamide was similar to that of (R)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide in Example 70. The crude product was purified by prep-HPLC (CH$_3$CN/H$_2$O with 0.05% HCl/H$_2$O as mobile phase) to give the HCl salt of 3-(tert-butyl)-N-(2-(2,2-difluoroethyl)-4-(4-((1-methyl-1H-pyrazol-3-yl)amino)-1,3,5-triazin-2-yl)benzyl)-1,2,4-oxadiazole-5-carboxamide as a white solid (58.4 mg, yield: 56%). ESI-MS (M+Na)$^+$: 520.0. $^1$H NMR (500 MHz, DMSO-d$_6$) δ: 10.05 (s, 1H), 9.52 (s, 1H), 8.76 (s, 1H), 8.35 (s, 1H), 8.29 (d, J=9.5 Hz, 1H), 7.61-7.58 (m, 2H), 6.65 (s, 1H), 6.45-6.22 (m, 1H), 4.64 (d, J=5.5 Hz, 2H), 3.81 (s, 3H), 3.52-3.43 (m, 2H), 1.40 (s, 9H).

Example 69: (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide (Compound 69)

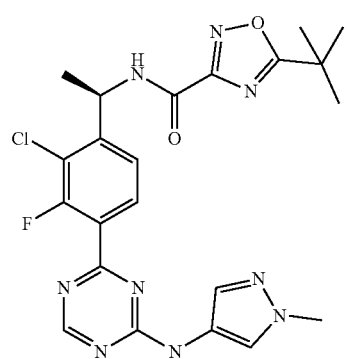

69

1. Synthesis of 4-bromo-2-chloro-3-fluorobenzoic acid

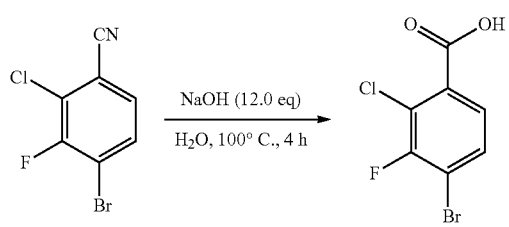 [SMILES: N#Cc1ccc(Br)c(F)c1Cl ; O=C(O)c1ccc(Br)c(F)c1Cl]

To a suspension of 4-bromo-2-chloro-3-fluorobenzonitrile (6.0 g, 25.6 mmol) in H$_2$O (80 mL) was added NaOH (12.6 g, 315 mmol) at 25° C. The reaction mixture was stirred at 100° C. for 4 h. The reaction was neutralized until pH=7 with aq. HCl (4 M). The resulting suspension was filtered, and the filter cake was dried to give 4-bromo-2-chloro-3-fluorobenzoic acid as a light gray solid (4.5 g, yield: 69%). $^1$H NMR (400 MHz, DMSO-d$_6$) δ: 7.81-7.77 (m, 1H), 7.60-7.58 (m, 1H).

2. Synthesis of 4-bromo-2-chloro-3-fluoro-N-methoxy-N-methylbenzamide

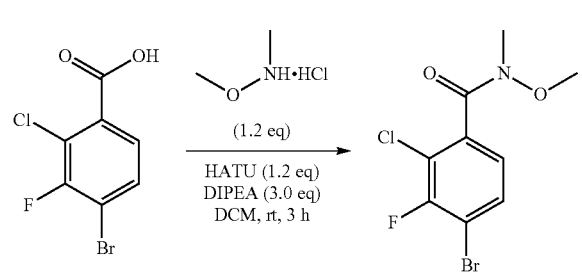

To a solution of 4-bromo-2-chloro-3-fluorobenzoic acid (4.5 g, 17.8 mmol) and N-methoxymethanamine hydrochloride (2.1 g, 21.3 mmol) in DCM (110 mL) was added DIPEA (6.87 g, 53.3 mmol) and HATU (8.12 g, 21.3 mmol) at 25° C. The reaction mixture was stirred at 25° C. for 3 h. The reaction mixture was concentrated in vacuo and the crude material was purified by silica-gel column chromatography (petroleum ether/EtOAc, grading from 10:1 to 5:1) to give 4-bromo-2-chloro-3-fluoro-N-methoxy-N-methylbenzamide as a light gray solid (4.0 g, yield: 76%). ESI-MS (M+H)$^+$: 298.0.

3. Synthesis of 4-bromo-2-chloro-3-fluorobenzaldehyde

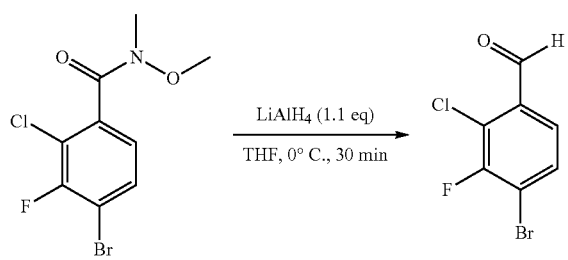

To a solution of 4-bromo-2-chloro-3-fluoro-N-methoxy-N-methylbenzamide (5.5 g, 18.6 mmol) in THF (100 mL) at 0° C. was added LiAlH$_4$ (774 mg, 20.4 mmol) over 20 min. The reaction mixture was stirred at 0° C. for 30 minutes. The reaction mixture was quenched with H$_2$O (2 mL). The suspension was filtered, and the filtrate was concentrated in vacuo to give crude 4-bromo-2-chloro-3-fluorobenzaldehyde as a light brown oil (4.2 g, crude), which was carried forward without further purification. $^1$H NMR (400 MHz, CDCl$_3$) δ:10.39 (s, 1H), 7.61-7.60 (m, 2H).

4. Synthesis of (S,E)-N-(4-bromo-2-chloro-3-fluorobenzylidene)-2-methylpropane-2-sulfinamide

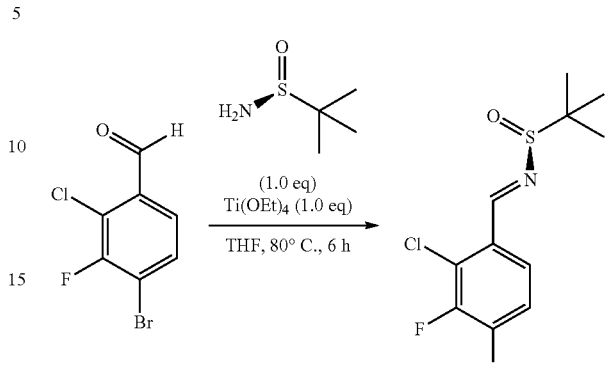

To a solution of (S)-2-methylpropane-2-sulfinamide (5.6 g, 46.2 mmol) and 4-bromo-2-chloro-3-fluorobenzaldehyde (4.2 g, 17.7 mmol) in THF (100 mL) was added Ti(OEt)$_4$ (10.5 g, 46.2 mmol, 9.67 mL) at 25° C. The reaction mixture was heated to 80° C. and stirred at that temperature for 6 h. The mixture was cooled to ambient temperature and concentrated in vacuo. The residue was poured into a saturated aqueous NH$_4$Cl solution (300 mL) and the aqueous phase was extracted with EtOAc (100 mL×4). The combined organic extracts were dried (Na$_2$SO$_4$), filtered, and concentrated in vacuo to give crude product. The crude material was purified by silica-gel column chromatography (petroleum ether/EtOAc, grading from 20:1 to 8:1) to give (S,E)-N-(4-bromo-2-chloro-3-fluorobenzylidene)-2-methylpropane-2-sulfinamide as a white solid (4.0 g, yield: 63% over 2 steps). $^1$H NMR (400 MHz, CDCl$_3$) δ: 8.94 (s, 1H), 7.76-7.74 (m, 1H), 7.56-7.52 (m, 1H), 1.27 (s, 9H).

5. Synthesis of (S)—N—((R)-1-(4-bromo-2-chloro-3-fluorophenyl)ethyl)-2-methylpropane-2-sulfinamide

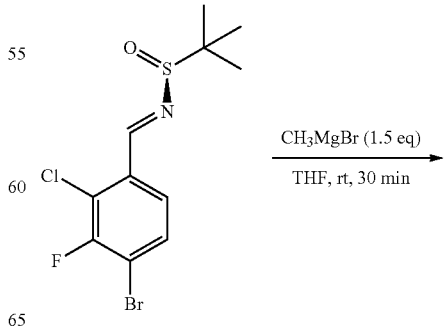

-continued

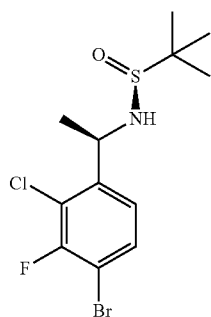

To a solution of (S,E)-N-(4-bromo-2-chloro-3-fluorobenzylidene)-2-methylpropane-2-sulfinamide (4.0 g, 11.7 mmol) in THF (100 mL) was added dropwise CH₃MgBr (6.0 mL, 18 mmol) at 20° C. The reaction mixture was stirred at 20° C. for 30 minutes. The reaction mixture was concentrated in vacuo and the residue was poured into a saturated aqueous NH₄Cl solution (150 mL). The aqueous phase was extracted with EtOAc (100 mL×4). The combined organic extracts were concentrated in vacuo to give crude product. The crude material was purified by silica-gel column chromatography (petroleum ether/EtOAc, grading from 5:1 to 1:2) to give (S)—N—((R)-1-(4-bromo-2-chloro-3-fluorophenyl)ethyl)-2-methylpropane-2-sulfinamide as a white solid (2.5 g, yield: 60%). ¹H NMR (400 MHz, CDCl₃) δ: 7.47-7.43 (m, 1H), 7.16-7.13 (m, 1H), 5.04-4.98 (m, 1H), 3.34 (d, J=3.6 Hz, 1H), 1.53 (d, J=6.8 Hz, 3H), 1.21 (s, 9H).

6. Synthesis of (R)-1-(4-bromo-2-chloro-3-fluorophenyl)ethan-1-amine hydrochloride

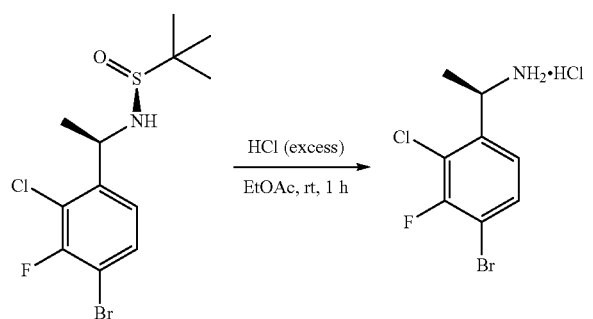

(S)—N—((R)-1-(4-Bromo-2-chloro-3-fluorophenyl)ethyl)-2-methylpropane-2-sulfinamide (2.5 g, 7.0 mmol) was added to a solution of HCl (45 mL, 4 M in EtOAc) at 20° C. The reaction mixture was stirred at 20° C. for 1 h. The suspension was filtered, and the filter cake was dried in vacuo to give (R)-1-(4-bromo-2-chloro-3-fluorophenyl)ethan-1-amine hydrochloride as a light gray solid (1.9 g, yield: 94%). ESI-MS (M+H)⁺: 294.9.

7. Synthesis of tert-butyl (R)-(1-(4-bromo-2-chloro-3-fluorophenyl)ethyl)carbamate

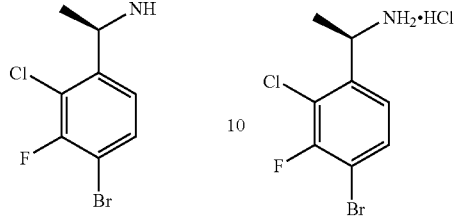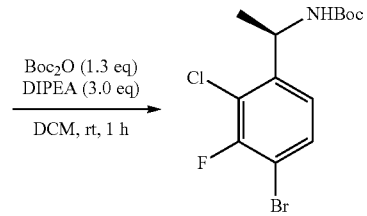

To a solution of (R)-1-(4-bromo-2-chloro-3-fluorophenyl)ethan-1-amine hydrochloride (1.9 g, 6.6 mmol) and DIPEA (2.6 g, 19.7 mmol, 3.45 mL) in DCM (65 mL) was added (Boc)₂O (1.9 g, 8.6 mmol, 1.97 mL) at 20° C. The reaction mixture was stirred at 20° C. for 1 h and then the reaction mixture was concentrated in vacuo to give crude product. The crude material was purified by silica-gel column chromatography (petroleum ether/EtOAc, grading from 10:1 to 3:1) to give tert-butyl (R)-(1-(4-bromo-2-chloro-3-fluorophenyl)ethyl)carbamate as a white solid (1.8 g, yield: 78%). ¹H NMR (400 MHz, CDCl₃) δ: 7.45-7.41 (m, 1H), 7.05-7.03 (m, 1H), 5.05-4.96 (m, 2H), 1.41-1.40 (m, 12H).

8. Synthesis of tert-butyl (R)-(1-(2-chloro-3-fluoro-4-(4,4,5,5-tetramethyl-1,3,2-dioxaborolan-2-yl)phenyl)ethyl)carbamate

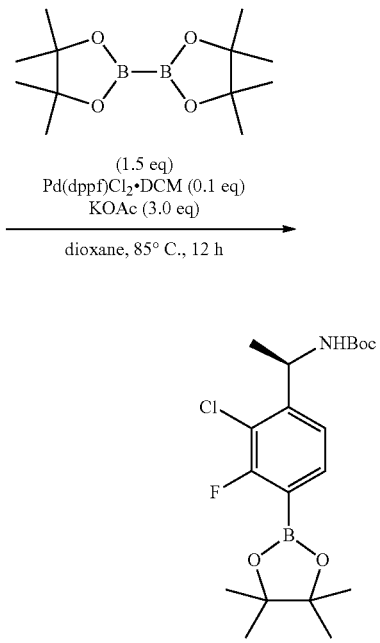

To a solution of tert-butyl (R)-(1-(4-bromo-2-chloro-3-fluorophenyl)ethyl)carbamate (800 mg, 2.3 mmol) and bis(pinacolato)diboron (865 mg, 3.4 mmol) in 1,4-dioxane (45 mL) was added KOAc (668 mg, 6.8 mmol) and Pd(dppf)Cl₂.DCM (166 mg, 0.23 mmol) at 20° C. The reaction mixture was heated to 85° C. under N₂ and stirred at that temperature for 12 h. The reaction mixture was cooled to ambient temperature and concentrated in vacuo to give tert-butyl (R)-(1-(2-chloro-3-fluoro-4-(4,4,5,5-tetramethyl-1,3,2-dioxaborolan-2-yl)phenyl)ethyl)carbamate as a black solid, which was carried forward without further purification (1.30 g, crude). ESI-MS (M+H−56)⁺: 344.1.

9. Synthesis of tert-butyl (R)-(1-(2-chloro-3-fluoro-4-(4-((1-methyl-1H-pyrazol-4-yl)amino)-1,3,5-triazin-2-yl)phenyl)ethyl)carbamate

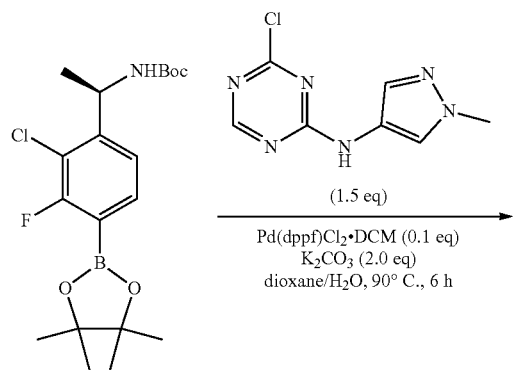

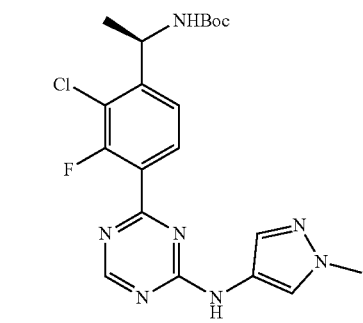

A solution of tert-butyl (R)-(1-(2-chloro-3-fluoro-4-(4,4,5,5-tetramethyl-1,3,2-dioxaborolan-2-yl)phenyl)ethyl)carbamate (200 mg, 0.50 mmol), 4-chloro-N-(1-methyl-1H-pyrazol-4-yl)-1,3,5-triazin-2-amine (158 mg, 0.75 mmol), Pd(dppf)Cl₂·DCM (37 mg, 0.05 mmol) and K₂CO₃ (138 mg, 1.0 mmol) in 1,4-dioxane (15 mL) and H₂O (1.5 mL) was heated to 90° C. and stirred at that temperature for 6 h under N₂. The mixture was cooled to ambient temperature and concentrated in vacuo to give crude product. The crude material was purified by silica-gel column chromatography (petroleum ether/EtOAc, grading from 1:0 to 1:9) to give tert-butyl (R)-(1-(2-chloro-3-fluoro-4-(4-((1-methyl-1H-pyrazol-4-yl)amino)-1,3,5-triazin-2-yl)phenyl)ethyl)carbamate as a yellow solid (132 mg, yield: 59%). ESI-MS (M+H)⁺: 448.2.

10. Synthesis of (R)-4-(4-(1-aminoethyl)-3-chloro-2-fluorophenyl)-N-(1-methyl-1H-pyrazol-4-yl)-1,3,5-triazin-2-amine hydrochloride

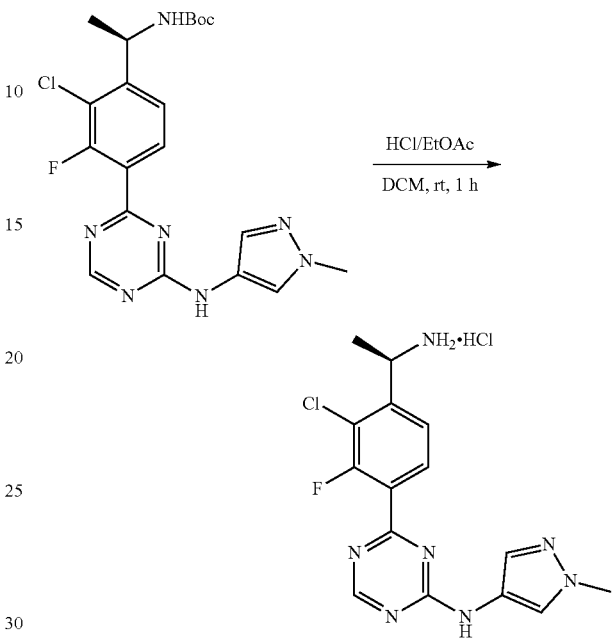

To a solution of tert-butyl (R)-(1-(2-chloro-3-fluoro-4-(4-((1-methyl-1H-pyrazol-4-yl)amino)-1,3,5-triazin-2-yl)phenyl)ethyl)carbamate (132 mg, 0.29 mmol) in DCM (10 mL) was added HCl (10 mL, 4 M in EtOAc). The reaction mixture was stirred at ambient temperature for 1 h. The reaction mixture was concentrated in vacuo to give (R)-4-(4-(1-aminoethyl)-3-chloro-2-fluorophenyl)-N-(1-methyl-1H-pyrazol-4-yl)-1,3,5-triazin-2-amine hydrochloride as a yellow solid, which was carried forward without further purification (110 mg, crude). ESI-MS (M+H)⁺: 348.1.

11. Synthesis of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide (Compound 69)

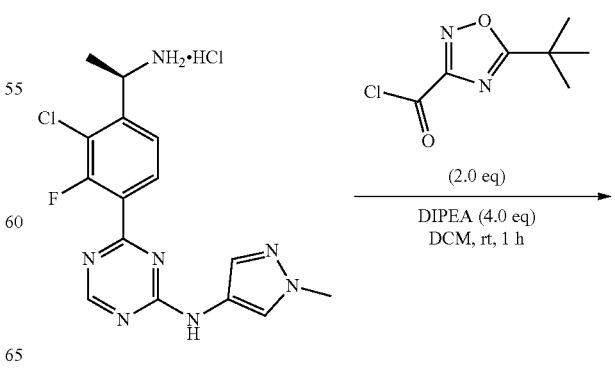

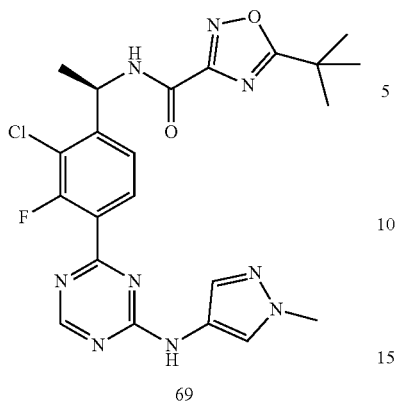

69

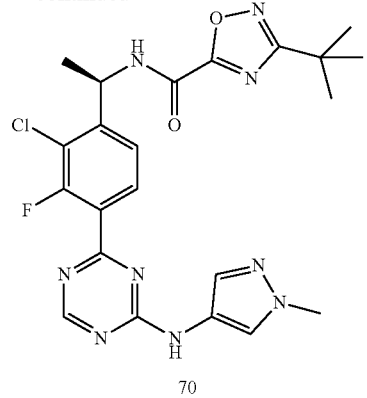

70

To a solution of (R)-4-(4-(1-aminoethyl)-3-chloro-2-fluorophenyl)-N-(1-methyl-1H-pyrazol-4-yl)-1,3,5-triazin-2-amine hydrochloride (45 mg, 0.13 mmol) in DCM (40 mL) was added DIPEA (67 mg, 0.52 mmol), followed by a slow addition of 5-(tert-butyl)-1,2,4-oxadiazole-3-carbonyl chloride (49 mg, 0.26 mmol). The reaction mixture was stirred at 20° C. for 1 hour. The mixture was concentrated in vacuo and the crude material was purified by prep-HPLC (CH$_3$CN/H$_2$O with 0.05% HCl/H$_2$O as mobile phase) to give the HCl salt of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide as a yellow solid (27.6 mg, yield: 43%). ESI-MS (M+H)$^+$: 500.3. $^1$H NMR (DMSO-d$_6$, 400 MHz, t=80° C.) δ: 10.17 (s, 1H), 9.35 (s, 1H), 8.77 (s, 1H), 8.08 (s, 1H), 7.92 (s, 1H), 7.64-7.54 (m, 2H), 5.51 (t, J=7.2 Hz, 1H), 3.84 (s, 3H), 1.56 (d, J=7.2 Hz, 3H), 1.46 (s, 9H).

Example 70: (R)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide (Compound 70)

To a solution of (R)-4-(4-(1-aminoethyl)-3-chloro-2-fluorophenyl)-N-(1-methyl-1H-pyrazol-4-yl)-1,3,5-triazin-2-amine hydrochloride (55 mg, 0.16 mmol) in DCM (50 mL) was added DIPEA (82 mg, 0.63 mmol) and 3-(tert-butyl)-1,2,4-oxadiazole-5-carboxylic acid (108 mg, 0.63 mmol), followed by a slow addition of HATU (121 mg, 0.32 mmol). The reaction mixture was stirred at 20° C. for 1 hour. The mixture was concentrated in vacuo and the crude material was purified by prep-HPLC (CH$_3$CN/H$_2$O with 0.05% HCl/H$_2$O as mobile phase) to give the HCl salt of (R)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide as a yellow solid (35.6 mg, yield: 45%). ESI-MS (M+H)$^+$: 500.3. $^1$H NMR (DMSO-d$_6$, 400 MHz, t=80° C.) δ: 10.13 (s, 1H), 9.75-9.72 (m, 1H), 8.77 (s, 1H), 8.09 (s, 1H), 7.91 (s, 1H), 7.64-7.57 (m, 2H), 5.53-5.47 (m, 1H), 3.84 (s, 3H), 1.59 (d, J=6.8 Hz, 3H), 1.40-1.38 (m, 9H).

Example 71: (R)-5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide (Compound 71)

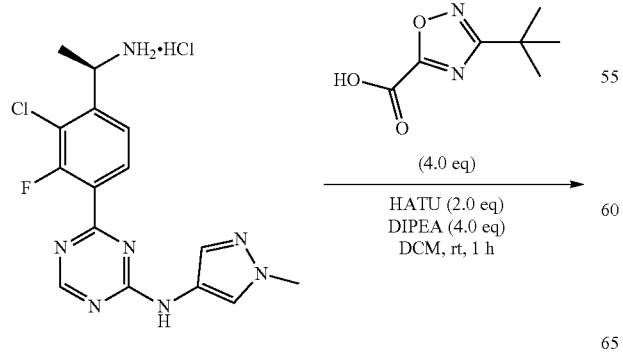

HATU (2.0 eq)
DIPEA (4.0 eq)
DCM, rt, 1 h

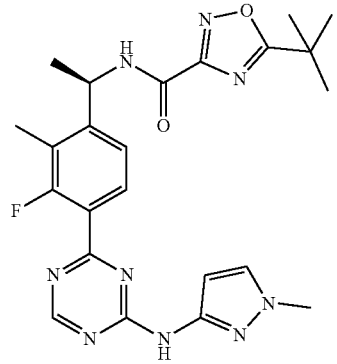

71

1. Synthesis of 4-bromo-3-fluoro-2-methylbenzoic acid

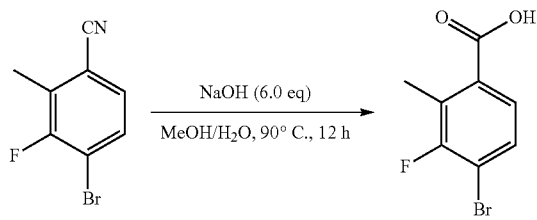

To a suspension of 4-bromo-3-fluoro-2-methylbenzonitrile (3.0 g, 14 mmol) in MeOH (30 mL) and H$_2$O (40 mL) was added NaOH (3.4 g, 84 mmol) at 25° C. The reaction mixture was heated to 90° C. and stirred at that temperature for 12 h. The reaction was neutralized until pH=2 with aq. HCl (10 M). The resulting suspension was filtered, and the filter cake was dried to give 4-bromo-3-fluoro-2-methylbenzoic acid as an off-white solid (2.0 g, yield: 61%). $^1$H NMR (400 MHz, DMSO-d$_6$) δ: 13.32 (s, 1H), 7.65-7.54 (m, 2H), 2.44 (s, 3H).

2. Synthesis of 4-bromo-3-fluoro-N-methoxy-N,2-dimethylbenzamide

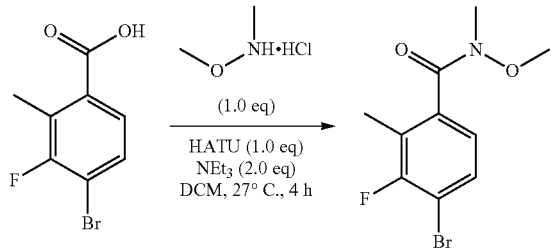

Synthesis of 4-bromo-3-fluoro-N-methoxy-N,2-dimethylbenzamide was similar to that of 4-bromo-2-chloro-3-fluoro-N-methoxy-N-methylbenzamide in Example 69, Step 2. The crude material was purified by silica-gel column chromatography (petroleum ether/EtOAc, 6:1) to give 4-bromo-3-fluoro-N-methoxy-N,2-dimethylbenzamide as a brown oil (4.8 g, yield: 70%). ESI-MS (M+H)$^+$: 277.8. $^1$H NMR (400 MHz, CD$_3$OD) δ: 7.52 (t, J=8.4 Hz 1H), 7.05 (d, J=8.0 Hz, 1H), 3.47 (s, 3H), 3.35 (s, 3H), 2.25 (s, 3H).

3. Synthesis of 4-bromo-3-fluoro-2-methylbenzaldehyde

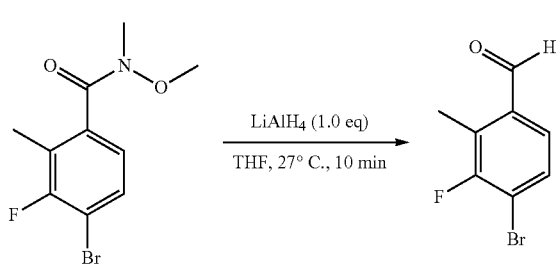

Synthesis of 4-bromo-3-fluoro-2-methylbenzaldehyde was similar to that of 4-bromo-2-chloro-3-fluorobenzaldehyde in Example 69, Step 3. The crude material was purified by silica-gel column chromatography (petroleum ether/EtOAc, 10:1) to give 4-bromo-3-fluoro-2-methylbenzaldehyde as a yellow oil (3.4 g, yield: 90%). $^1$H NMR (400 MHz, CD$_3$OD) δ: 10.19 (s, 1H), 7.67 (t, J=4.4 Hz 1H), 7.57 (d, J=8.3 Hz, 1H), 2.60 (s, 3H).

4. Synthesis of (S,E)-N-(4-bromo-3-fluoro-2-methylbenzylidene)-2-methylpropane-2-sulfinamide

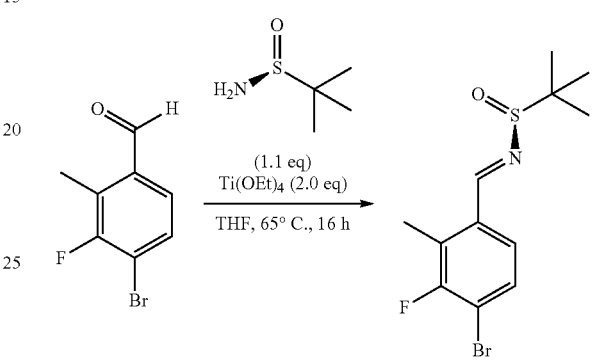

Synthesis of (S,E)-N-(4-bromo-3-fluoro-2-methylbenzylidene)-2-methylpropane-2-sulfinamide was similar to that of (S,E)-N-(4-bromo-2-chloro-3-fluorobenzylidene)-2-methylpropane-2-sulfinamide in Example 69, Step 4. The crude material was purified by silica-gel column chromatography (petroleum ether/EtOAc, 3:1) to give (S,E)-N-(4-bromo-3-fluoro-2-methylbenzylidene)-2-methylpropane-2-sulfinamide as a yellow solid (3.3 g, yield: 61%). $^1$H NMR (400 MHz, CD$_3$OD) δ: 8.78 (s, 1H), 7.69-7.50 (m, 2H), 2.54 (s, 3H), 1.27 (s, 9H).

5. Synthesis of (S)—N—((R)-1-(4-bromo-3-fluoro-2-methylphenyl)ethyl)-2-methylpropane-2-sulfinamide

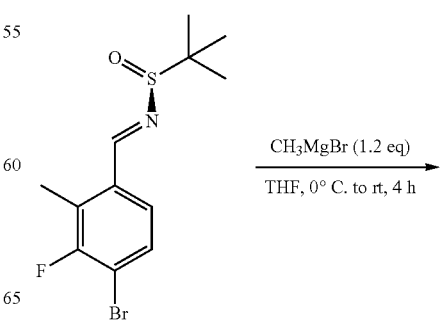

7. Synthesis of tert-butyl (R)-(1-(4-bromo-3-fluoro-2-methylphenyl)ethyl)carbamate

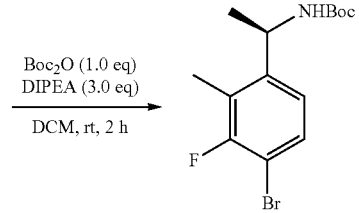

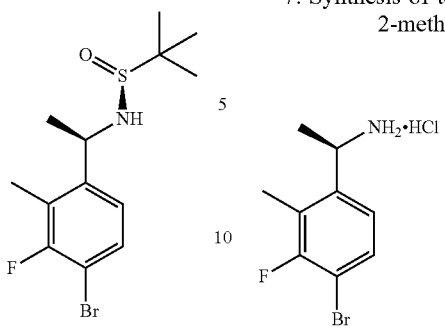

Synthesis of (S)—N—((R)-1-(4-bromo-3-fluoro-2-methylphenyl)ethyl)-2-methylpropane-2-sulfinamide was similar to that of (S)—N—((R)-1-(4-bromo-2-chloro-3-fluorophenyl)ethyl)-2-methylpropane-2-sulfinamide in Example 69, Step 5. The crude material was purified by silica-gel column chromatography (petroleum ether/EtOAc, grading from 3:1 to 1:1) to give (S)—N—((R)-1-(4-bromo-3-fluoro-2-methylphenyl)ethyl)-2-methylpropane-2-sulfinamide as an off-white solid (2.0 g, yield: 56%). $^1$H NMR (400 MHz, CD$_3$OD) δ: 7.42 (t, J=7.6 Hz, 1H), 7.16 (d, J=7.6 Hz, 1H), 4.76-4.60 (m, 1H), 2.32 (d, J=2.4 Hz, 3H), 1.51 (d, J=6.8 Hz, 3H), 1.19 (s, 9H).

Synthesis of tert-butyl (R)-(1-(4-bromo-3-fluoro-2-methylphenyl)ethyl)carbamate was similar to that of tert-butyl (R)-(1-(4-bromo-2-chloro-3-fluorophenyl)ethyl)carbamate in Example 69, Step 7. The crude material was purified by silica-gel column chromatography (petroleum ether/EtOAc, 5:1) to give tert-butyl (R)-(1-(4-bromo-3-fluoro-2-methylphenyl)ethyl)carbamate as a white solid (2.0 g, yield: 74% over 2 steps). $^1$H NMR (400 MHz, CDCl$_3$) δ: 7.38-7.34 (m, 1H), 7.00-6.95 (m, 1H), 4.92-4.78 (m, 2H), 2.32 (s, 3H), 1.47-1.36 (m, 12H).

6. Synthesis of (R)-1-(4-bromo-3-fluoro-2-methylphenyl)ethan-1-amine

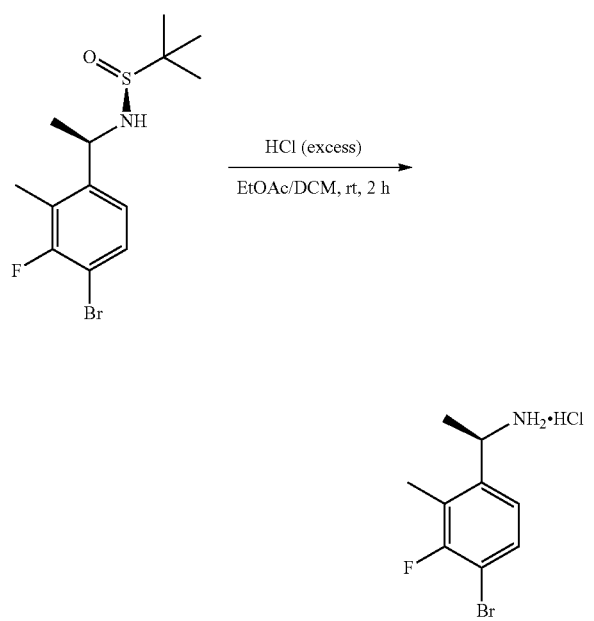

8. Synthesis of tert-butyl (R)-(1-(3-fluoro-2-methyl-4-(4,4,5,5-tetramethyl-1,3,2-dioxaborolan-2-yl)phenyl)ethyl)carbamate

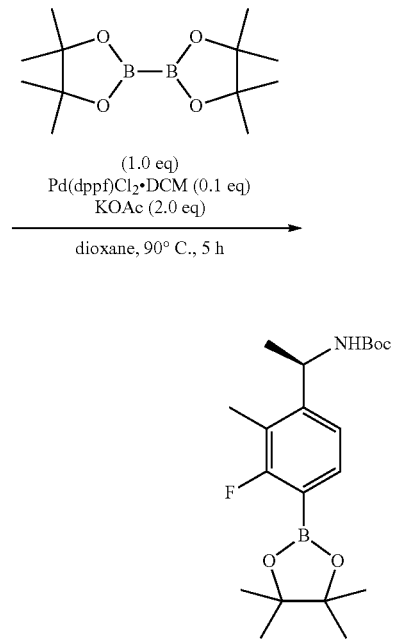

To a solution of (S)—N—((R)-1-(4-bromo-3-fluoro-2-methylphenyl)ethyl)-2-methylpropane-2-sulfinamide (2.0 g, 5.9 mmol) in DCM (40 mL) at ambient temperature was added an HCl solution (20 mL, 4 M in EtOAc). The reaction mixture continued to stir at that temperature for 2 h. The reaction mixture was concentrated in vacuo to give the HCl salt of (R)-1-(4-bromo-3-fluoro-2-methylphenyl)ethan-1-amine as a brown solid (1.9 g, crude), which was carried forward without further purification.

Synthesis of tert-butyl (R)-(1-(3-fluoro-2-methyl-4-(4,4,5,5-tetramethyl-1,3,2-dioxaborolan-2-yl)phenyl)ethyl)carbamate was similar to that of tert-butyl (R)-(1-(2-chloro-3-fluoro-4-(4,4,5,5-tetramethyl-1,3,2-dioxaborolan-2-yl)phenyl)ethyl)carbamate in Example 69, Step 8. The crude material was purified by silica-gel column chromatography (petroleum ether/EtOAc, grading from 2:1 to 1:1) to give tert-butyl (R)-(1-(3-fluoro-2-methyl-4-(4,4,5,5-tetramethyl-1,3,2-dioxaborolan-2-yl)phenyl)ethyl)carbamate as an off-white gum (1.3 g, yield: 56%). ESI-MS (M+H−56)$^+$: 324.2.

9. Synthesis of tert-butyl (R)-(1-(3-fluoro-2-methyl-4-(4-((1-methyl-1H-pyrazol-3-yl)amino)-1,3,5-triazin-2-yl)phenyl)ethyl)carbamate

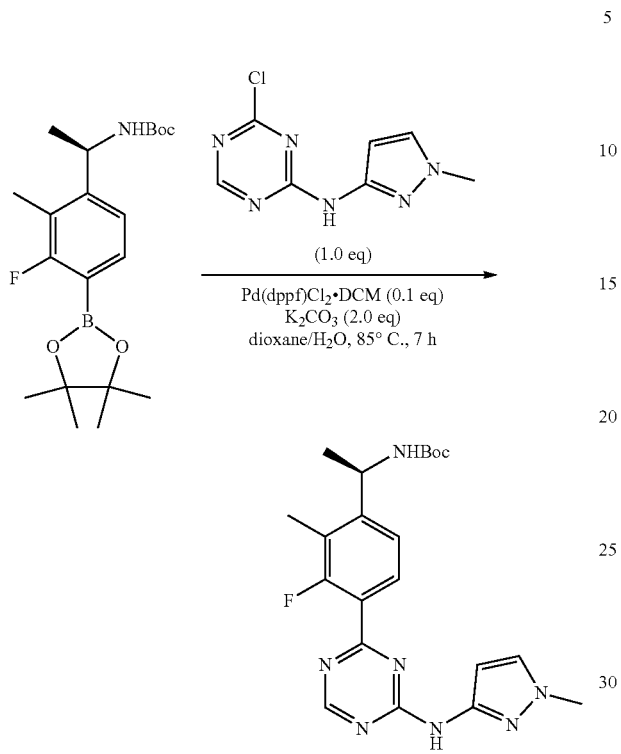

Synthesis of tert-butyl (R)-(1-(3-fluoro-2-methyl-4-(4-((1-methyl-1H-pyrazol-3-yl)amino)-1,3,5-triazin-2-yl)phenyl)ethyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (petroleum ether/EtOAc, 1:1) to give tert-butyl (R)-(1-(3-fluoro-2-methyl-4-(4-((1-methyl-1H-pyrazol-3-yl)amino)-1,3,5-triazin-2-yl)phenyl)ethyl)carbamate as a yellow solid (285 mg, yield: 78%). ESI-MS (M+H)$^+$: 428.1.

10. Synthesis of (R)-4-(4-(1-aminoethyl)-2-fluoro-3-methylphenyl)-N-(1-methyl-1H-pyrazol-3-yl)-1,3,5-triazin-2-amine hydrochloride

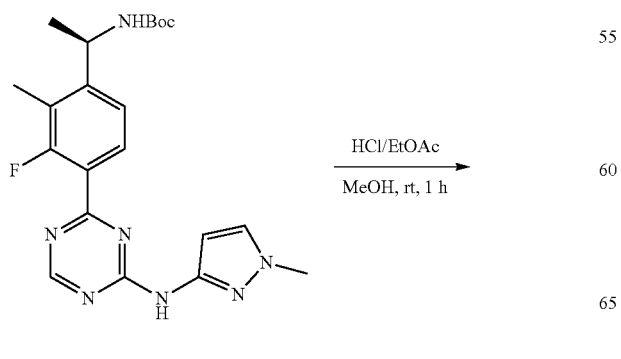

To a solution of tert-butyl (R)-(1-(3-fluoro-2-methyl-4-(4-((1-methyl-1H-pyrazol-3-yl)amino)-1,3,5-triazin-2-yl)phenyl)ethyl)carbamate (284 mg, 0.66 mmol) in MeOH (3 mL) was added an HCl solution (10 mL, 4 M in EtOAc). The reaction mixture was stirred at ambient temperature for 1 h. The reaction mixture was concentrated in vacuo to give (R)-4-(4-(1-aminoethyl)-2-fluoro-3-methylphenyl)-N-(1-methyl-1H-pyrazol-3-yl)-1,3,5-triazin-2-amine hydrochloride as a brown solid (280 mg, crude), which was carried forward without further purification. ESI-MS (M+H)$^+$: 328.2.

11. Synthesis of 5-(tert-butyl)-1,2,4-oxadiazole-3-carbonyl chloride

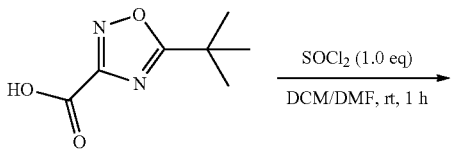

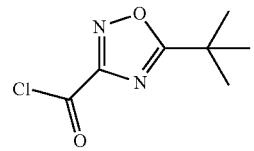

To a solution of 5-(tert-butyl)-1,2,4-oxadiazole-3-carboxylic acid (200 mg, 1.2 mmol) in DCM (10 mL) was added thionyl chloride (140 mg, 1.2 mmol, 86 μL) and DMF (200 μL). The reaction mixture was stirred at ambient temperature for 1 h. The reaction mixture was concentrated in vacuo to give 5-(tert-butyl)-1,2,4-oxadiazole-3-carbonyl chloride (230 mg, crude), which was used directly without further purification.

12. Synthesis of (R)-5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide (Compound 71)

Example 72: (R)-3-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-5-carboxamide (Compound 72)

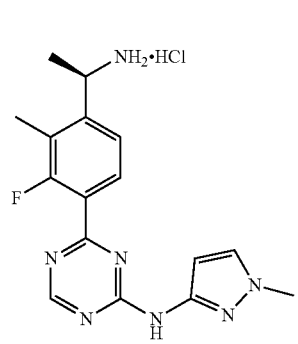 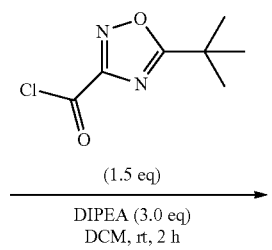 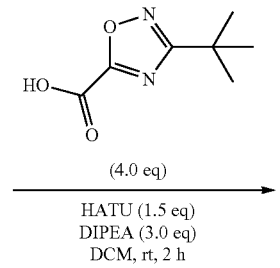

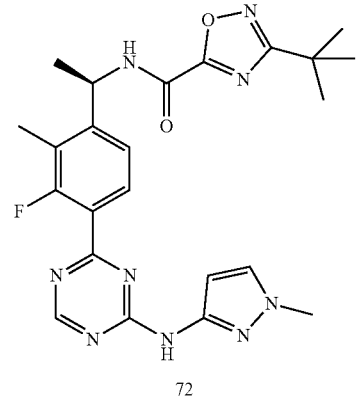

Synthesis of (R)-5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide was similar to that of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide in Example 69, Step 11. The crude material was purified by prep-HPLC (CH$_3$CN/H$_2$O with 0.05% HCl/H$_2$O as mobile phase) to give the HCl salt of (R)-5-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-3-carboxamide as a white solid (136 mg, yield: 37%). ESI-MS (M+H)$^+$: 480.2. $^1$H NMR (500 MHz, DMSO-d$_6$, t=80° C.) δ: 10.12 (s, 1H), 9.08 (d, J=7.0 Hz, 1H), 8.75 (s, 1H), 7.88 (t, J=8.0 Hz, 1H), 7.56 (d, J=2.0 Hz, 1H), 7.43 (d, J=8.5 Hz, 1H), 6.66 (s, 1H), 5.40-5.34 (m, 1H), 3.78 (s, 3H), 2.37-2.36 (m, 3H), 1.53 (d, J=7.0 Hz, 3H), 1.44 (s, 9H).

Synthesis of (R)-3-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-5-carboxamide was similar to that of (R)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide in Example 70. The crude material was purified by prep-HPLC (CH$_3$CN/H$_2$O with 0.05% HCl/H$_2$O as mobile phase) to give the HCl salt of (R)-3-(tert-butyl)-N-(1-(3-fluoro-2-methyl-4-(4-((1-methyl-1H-pyrazol-3-yl)amino)-1,3,5-triazin-2-yl)phenyl)ethyl)-1,2,4-oxadiazole-5-carboxamide as a white solid (40 mg, yield: 35%). ESI-MS (M+H)$^+$: 480.2. $^1$H NMR (500 MHz, DMSO-d$_6$) δ: 10.11 (s, 1H), 9.50 (d, J=7.0 Hz, 1H), 8.76 (s, 1H), 7.90 (t, J=8.0 Hz, 1H), 7.58 (d, J=2.0 Hz, 1H), 7.46 (d, J=8.5 Hz, 1H), 6.66 (s, 1H), 5.42-5.35 (m, 1H), 3.80 (s, 3H), 2.38 (d, J=2.0 Hz, 3H), 1.57 (d, J=7.0 Hz, 3H), 1.40 (s, 9H).

213

Example 73: (R)-5-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-3-carboxamide (Compound 73)

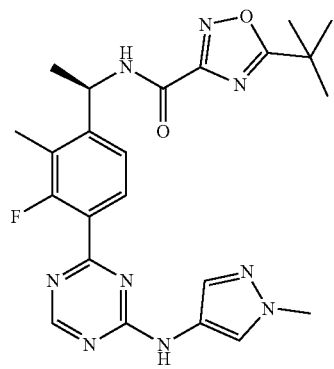

1. Synthesis of tert-butyl (R)-(1-(3-fluoro-2-methyl-4-(4-((1-methyl-1H-pyrazol-4-yl)amino)-1,3,5-triazin-2-yl)phenyl)ethyl)carbamate

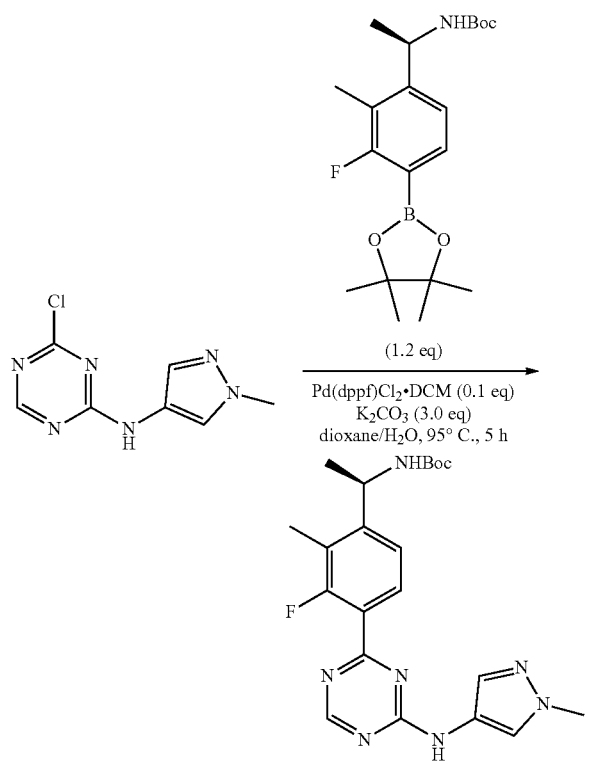

Synthesis of tert-butyl (R)-(1-(3-fluoro-2-methyl-4-(4-((1-methyl-1H-pyrazol-4-yl)amino)-1,3,5-triazin-2-yl)phenyl)ethyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (petroleum ether/EtOAc, 1:1) to give tert-butyl (R)-(1-(3-fluoro-2-methyl-4-(4-((1-methyl-1H-pyrazol-4-yl)amino)-1,3,5-triazin-2-yl)phenyl)ethyl)carbamate as an off-white solid (700 mg, yield: 82%). ESI-MS (M+H)⁺: 428.1.

2. Synthesis of (R)-4-(4-(1-aminoethyl)-2-fluoro-3-methylphenyl)-N-(1-methyl-1H-pyrazol-4-yl)-1,3,5-triazin-2-amine

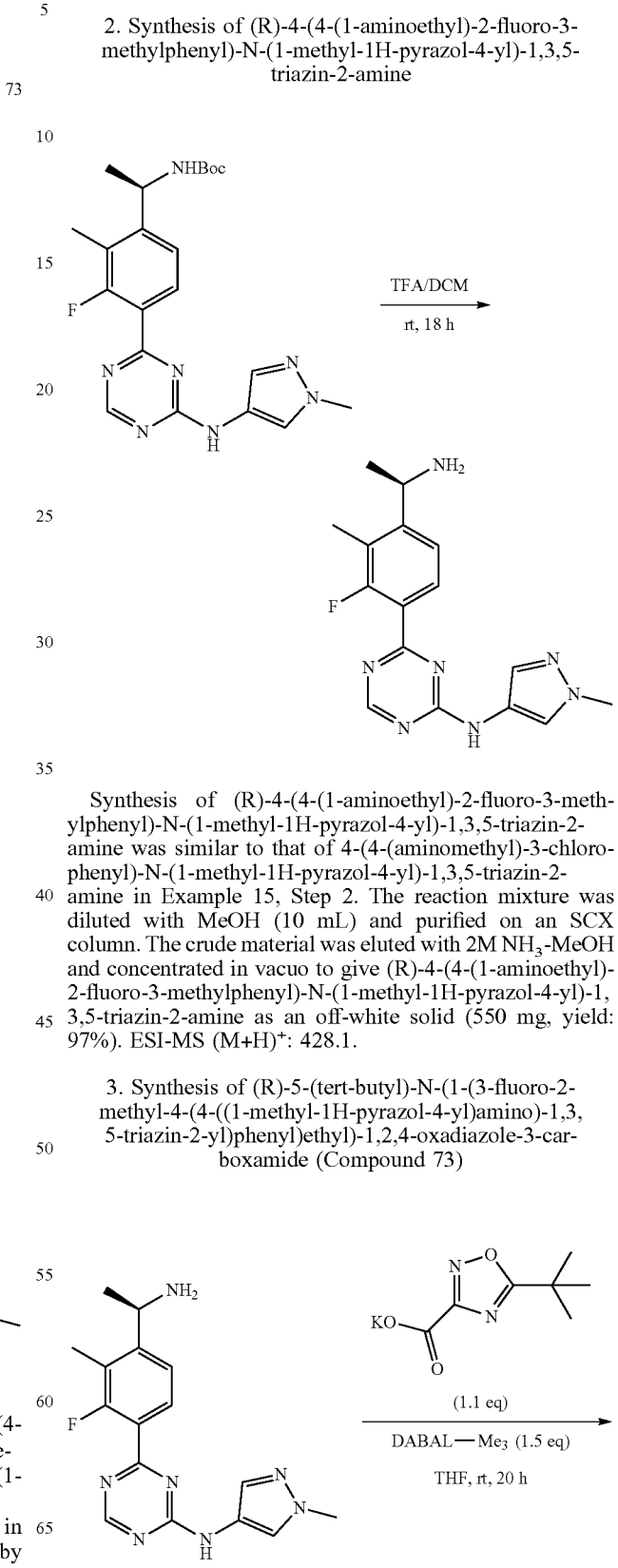

Synthesis of (R)-4-(4-(1-aminoethyl)-2-fluoro-3-methylphenyl)-N-(1-methyl-1H-pyrazol-4-yl)-1,3,5-triazin-2-amine was similar to that of 4-(4-(aminomethyl)-3-chlorophenyl)-N-(1-methyl-1H-pyrazol-4-yl)-1,3,5-triazin-2-amine in Example 15, Step 2. The reaction mixture was diluted with MeOH (10 mL) and purified on an SCX column. The crude material was eluted with 2M NH₃-MeOH and concentrated in vacuo to give (R)-4-(4-(1-aminoethyl)-2-fluoro-3-methylphenyl)-N-(1-methyl-1H-pyrazol-4-yl)-1,3,5-triazin-2-amine as an off-white solid (550 mg, yield: 97%). ESI-MS (M+H)⁺: 428.1.

3. Synthesis of (R)-5-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-3-carboxamide (Compound 73)

-continued

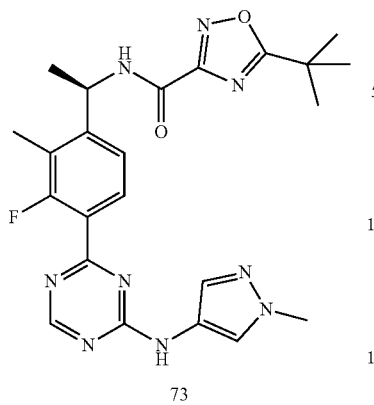

73

-continued

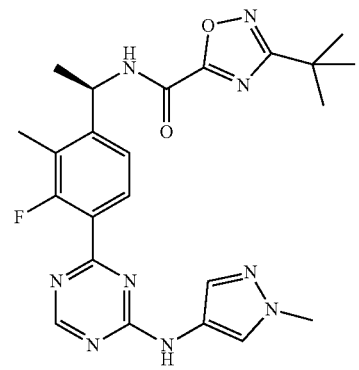

74

Synthesis of (R)-5-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-3-carboxamide was similar to that of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide in Example 49, Step 4. The crude material was purified by prep-HPLC (CH$_3$CN/H$_2$O with 0.05% TFA/H$_2$O as mobile phase) to give the TFA salt of (R)-5-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-3-carboxamide as a yellow solid (21.5 mg, yield: 31%). ESI-MS (M+H)$^+$: 480.0. $^1$H NMR (500 MHz, DMSO-d$_6$) δ: 10.34-10.30 (m, 1H), 9.58-9.53 (m, 1H), 8.81-8.72 (m, 1H), 7.98-7.94 (m, 1H), 7.85-7.81 (m, 1H), 7.64-7.55 (m, 1H), 7.44-7.40 (m, 1H), 5.38-5.31 (m, 1H), 3.83 (s, 3H), 2.37-2.34 (m, 3H), 1.50-1.48 (m, 3H), 1.42 (s, 9H).

Example 74: Synthesis of (R)-3-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-5-carboxamide (Compound 74)

Synthesis of (R)-3-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-5-carboxamide was similar to that of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide in Example 49, Step 4. The crude material was purified by prep-HPLC (CH$_3$CN/H$_2$O with 0.05% NH$_3$/H$_2$O as mobile phase) to give (R)-3-(tert-butyl)-N-(1-(3-fluoro-2-methyl-4-(4-((1-methyl-1H-pyrazol-4-yl)amino)-1,3,5-triazin-2-yl)phenyl)ethyl)-1,2,4-oxadiazole-5-carboxamide as a yellow solid (28.7 mg, yield: 60%). ESI-MS (M+H)$^+$: 480.0. $^1$H NMR (500 MHz, DMSO-d$_6$) δ: 10.35-10.30 (m, 1H), 9.97-9.93 (m, 1H), 8.81-8.72 (m, 1H), 7.98-7.83 (m, 2H), 7.64-7.55 (m, 1H), 7.44 (br dd, J=11.3 Hz, 8.2 Hz, 1H), 5.38-5.31 (m, 1H), 3.83 (s, 3H), 2.37-2.34 (m, 3H), 1.53-1.50 (m 3H), 1.36 (s, 9H).

Example 75: Synthesis of (R)-3-(tert-butyl)-N-(1-(3-fluoro-2-methyl-4-(4-((1-methyl-1H-pyrazol-4-yl)amino)-1,3,5-triazin-2-yl)phenyl)ethyl)isoxazole-5-carboxamide (Compound 75)

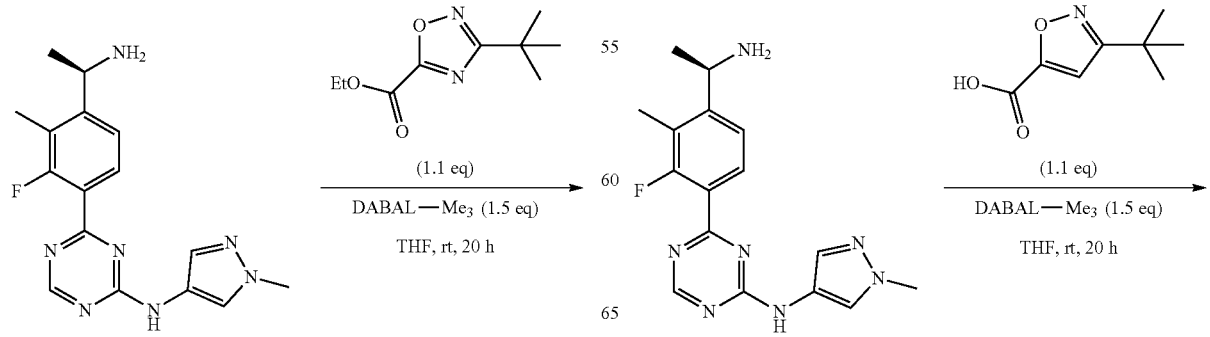

-continued

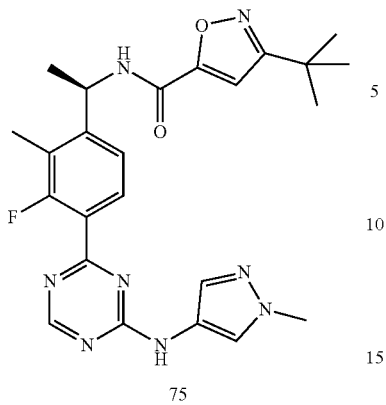

75

-continued

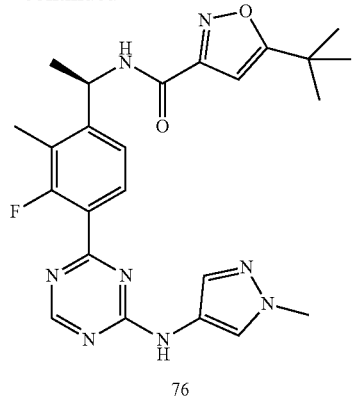

76

Synthesis of (R)-3-(tert-butyl)-N-(1-(3-fluoro-2-methyl-4-(4-((1-methyl-1H-pyrazol-4-yl)amino)-1,3,5-triazin-2-yl)phenyl)ethyl)isoxazole-5-carboxamide was similar to that of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide in Example 49, Step 4. The crude material was purified by prep-HPLC (CH$_3$CN/H$_2$O with 0.05% NH$_3$/H$_2$O as mobile phase) to give (R)-3-(tert-butyl)-N-(1-(3-fluoro-2-methyl-4-(4-((1-methyl-1H-pyrazol-4-yl)amino)-1,3,5-triazin-2-yl)phenyl)ethyl)isoxazole-5-carboxamide as a white solid (8.5 mg, yield: 12%). ESI-MS (M+H)$^+$: 479.0. $^1$H NMR (500 MHz, DMSO-d$_6$) δ: 10.33-10.29 (m, 1H), 9.43-9.39 (m, 1H), 8.80-8.72 (m, 1H), 7.97-7.82 (m, 2H), 7.64-7.55 (m, 1H), 7.40 (br dd, J=11.3 Hz, 8.2 Hz, 1H), 7.16-7.14 (m, 1H), 5.35-5.27 (m, 1H), 3.83 (s, 3H), 2.36-2.33 (m, 3H), 1.49-1.47 (m, 3H), 1.30 (s, 9H).

Example 76: Synthesis of (R)-5-(tert-butyl)-N-(1-(3-fluoro-2-methyl-4-(4-((1-methyl-1H-pyrazol-4-yl)amino)-1,3,5-triazin-2-yl)phenyl)ethyl)isoxazole-3-carboxamide (Compound 76)

Synthesis of (R)-5-(tert-butyl)-N-(1-(3-fluoro-2-methyl-4-(4-((1-methyl-1H-pyrazol-4-yl)amino)-1,3,5-triazin-2-yl)phenyl)ethyl)isoxazole-3-carboxamide was similar to that of 5-(1-(fluoromethyl)cyclopropyl)-N-(2-methyl-4-(4-((1-methyl-1H-pyrazol-4-yl)amino)-1,3,5-triazin-2-yl)benzyl)-1,2,4-oxadiazole-3-carboxamide in Example 49, Step 4. The crude material was purified by prep-HPLC (CH$_3$CN/H$_2$O with 0.05% NH$_3$/H$_2$O as mobile phase) to give (R)-5-(tert-butyl)-N-(1-(3-fluoro-2-methyl-4-(4-((1-methyl-1H-pyrazol-4-yl)amino)-1,3,5-triazin-2-yl)phenyl)ethyl)isoxazole-3-carboxamide as a yellow solid (14.3 mg, yield: 21%). ESI-MS (M+H)$^+$: 479.0. $^1$H NMR (500 MHz, DMSO-d$_6$) δ: 10.33-10.29 (m, 1H), 9.32-9.29 (m, 1H), 8.80-8.72 (m, 1H), 7.95-7.81 (m, 2H), 7.64-7.55 (m, 1H), 7.42-7.38 (m, 1H), 6.55 (s, 1H), 5.36-5.30 (m, 1H), 3.83 (s, 3H), 2.34-2.33 (m, 3H), 1.48-1.45 (m, 3H), 1.32 (s, 9H).

Example 77: (R)-5-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-3-carboxamide (Compound 77)

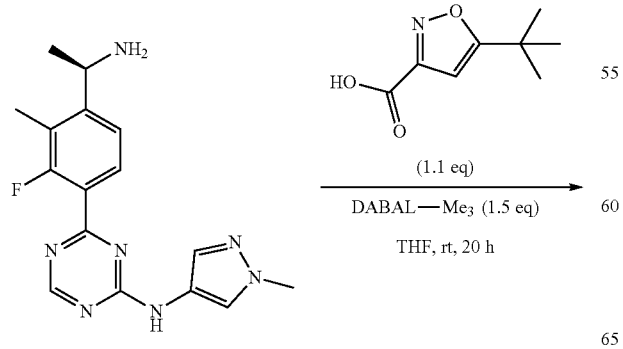

77

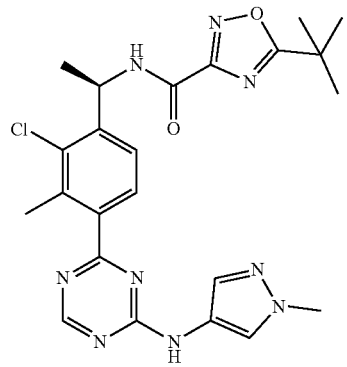

1. Synthesis of 4-bromo-2-chloro-3-methylbenzoic acid

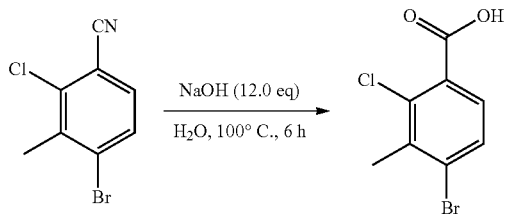

Synthesis of 4-bromo-2-chloro-3-methylbenzoic acid was similar to that of 4-bromo-2-chloro-3-fluorobenzoic acid in Example 69, Step 1. The crude material was dried in vacuo to give 4-bromo-2-chloro-3-methylbenzoic acid as a white solid (3.3 g, yield: 87%), which was carried forward without further purification.

2. Synthesis of 4-bromo-2-chloro-N-methoxy-N,3-dimethylbenzamide

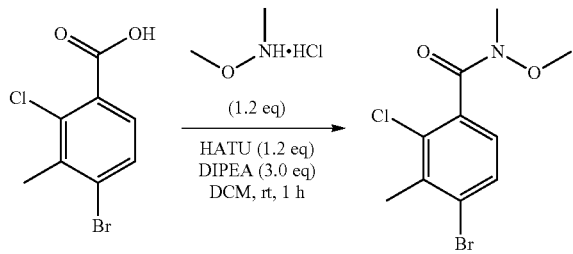

Synthesis of 4-bromo-2-chloro-N-methoxy-N,3-dimethylbenzamide was similar to that of 4-bromo-2-chloro-3-fluoro-N-methoxy-N-methylbenzamide in Example 69, Step 2. The crude material was purified by silica-gel column chromatography (petroleum ether/EtOAc, grading from 1:0 to 3:1) to give 4-bromo-2-chloro-N-methoxy-N,3-dimethylbenzamide as a white solid (3.5 g, yield: 93% over 2 steps). ESI-MS (M+H)$^+$: 293.8.

3. Synthesis of 4-bromo-2-chloro-3-methylbenzaldehyde

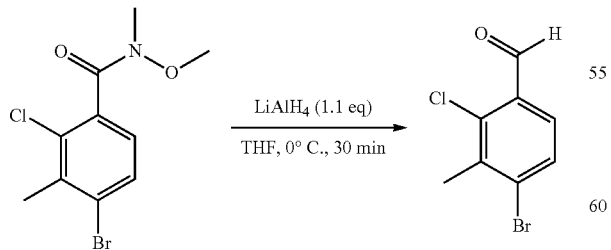

Synthesis of 4-bromo-2-chloro-3-methylbenzaldehyde was similar to that of 4-bromo-2-chloro-3-fluorobenzaldehyde in Example 69, Step 3. The crude material was concentrated in vacuo to give 4-bromo-2-chloro-3-methylbenzaldehyde as a light brown oil (2.0 g, crude), which was carried forward without further purification.

4. Synthesis of (S,E)-N-(4-bromo-2-chloro-3-methylbenzylidene)-2-methylpropane-2-sulfinamide

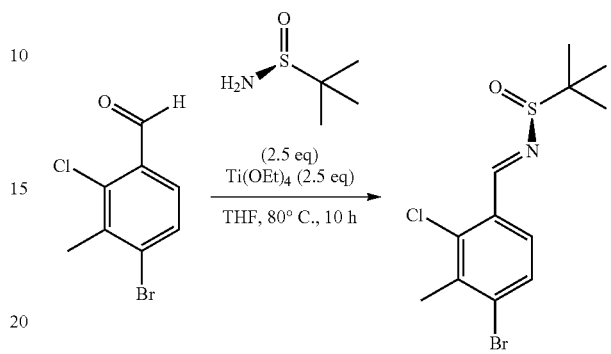

Synthesis of (S,E)-N-(4-bromo-2-chloro-3-methylbenzylidene)-2-methylpropane-2-sulfinamide was similar to that of (S,E)-N-(4-bromo-2-chloro-3-fluorobenzylidene)-2-methylpropane-2-sulfinamide in Example 69, Step 4. The crude material was purified by silica-gel column chromatography (petroleum ether/EtOAc, grading from 1:0 to 8:1) to give (S,E)-N-(4-bromo-2-chloro-3-methylbenzylidene)-2-methylpropane-2-sulfinamide as a white solid (2.5 g, yield: 87% over 2 steps). ESI-MS (M+H)$^+$: 338.0.

5. Synthesis of (S)—N—((R)-1-(4-bromo-2-chloro-3-methylphenyl)ethyl)-2-methylpropane-2-sulfinamide

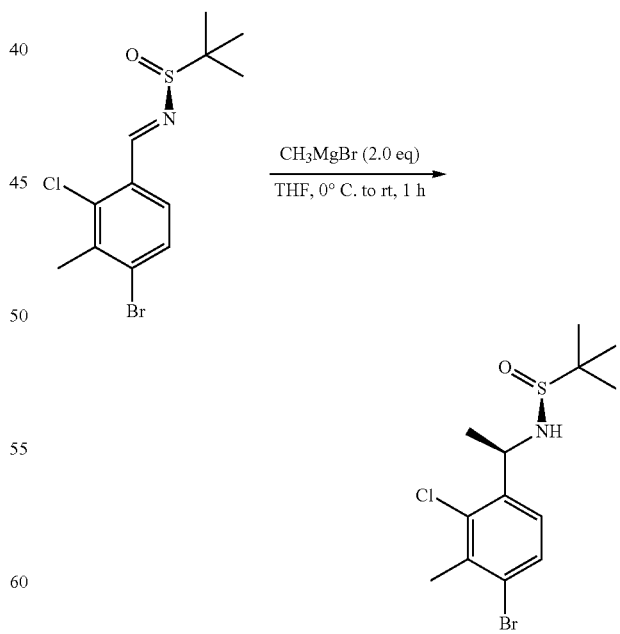

Synthesis of (S)—N—((R)-1-(4-bromo-2-chloro-3-methylphenyl)ethyl)-2-methylpropane-2-sulfinamide was similar to that of (S)—N—((R)-1-(4-bromo-2-chloro-3-fluorophenyl)ethyl)-2-methylpropane-2-sulfinamide in Example 69, Step 5. The crude material was purified by silica-gel column chromatography (petroleum ether/EtOAc, grading from 5:1 to 1:1) to give (S)—N—((R)-1-(4-bromo-2-chloro-3-methylphenyl)ethyl)-2-methylpropane-2-sulfinamide as a white solid (1.7 g, yield: 65%). ESI-MS (M+H)$^+$: 353.9.

6. Synthesis of (R)-1-(4-bromo-2-chloro-3-methylphenyl)ethan-1-amine

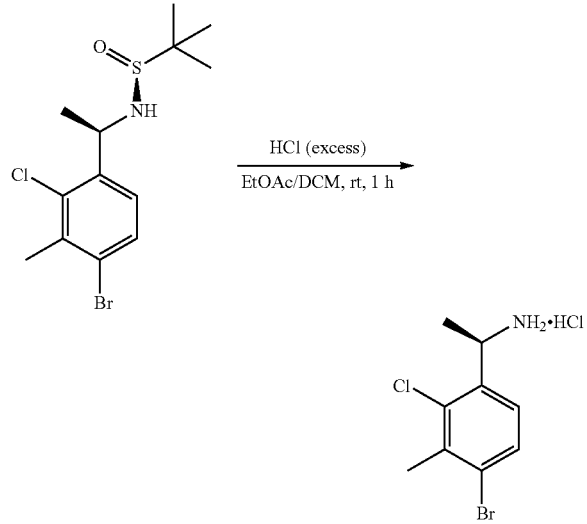

Synthesis of (R)-1-(4-bromo-2-chloro-3-methylphenyl)ethan-1-amine was similar to that of (R)-1-(4-bromo-3-fluoro-2-methylphenyl)ethan-1-amine in Example 71, Step 6. The reaction mixture was concentrated in vacuo to give the HCl salt of (R)-1-(4-bromo-2-chloro-3-methylphenyl)ethan-1-amine as a white solid (1.5 g, crude), which was carried forward without further purification. ESI-MS (M+H−18)$^+$: 232.8.

7. Synthesis of tert-butyl (R)-(1-(4-bromo-2-chloro-3-methylphenyl)ethyl)carbamate

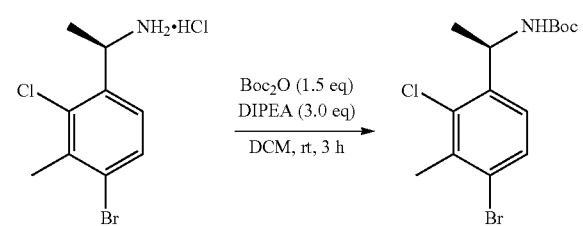

Synthesis of tert-butyl (R)-(1-(4-bromo-2-chloro-3-methylphenyl)ethyl)carbamate was similar to that of tert-butyl (R)-(1-(4-bromo-2-chloro-3-fluorophenyl)ethyl)carbamate in Example 69, Step 7. The crude material was purified by silica-gel column chromatography (petroleum ether/EtOAc, grading from 1:0 to 10:1) to give tert-butyl (R)-(1-(4-bromo-2-chloro-3-methylphenyl)ethyl)carbamate as a white solid (300 mg, yield: 82% over 2 steps). ESI-MS (M+H−56+41)$^+$: 334.9.

8. Synthesis of tert-butyl (R)-(1-(2-chloro-3-methyl-4-(4,4,5,5-tetramethyl-1,3,2-dioxaborolan-2-yl)phenyl)ethyl)carbamate

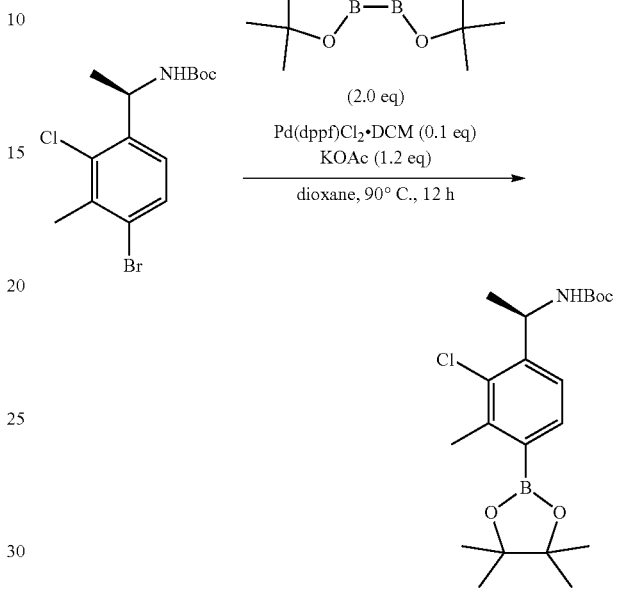

Synthesis of tert-butyl (R)-(1-(2-chloro-3-methyl-4-(4,4,5,5-tetramethyl-1,3,2-dioxaborolan-2-yl)phenyl)ethyl)carbamate was similar to that of tert-butyl (R)-(1-(2-chloro-3-fluoro-4-(4,4,5,5-tetramethyl-1,3,2-dioxaborolan-2-yl)phenyl)ethyl)carbamate in Example 69, Step 8. The crude material was concentrated in vacuo to give tert-butyl (R)-(1-(2-chloro-3-methyl-4-(4,4,5,5-tetramethyl-1,3,2-dioxaborolan-2-yl)phenyl)ethyl)carbamate as a black solid (220 mg, crude), which was carried forward without further purification. ESI-MS (M+Na−56−84)$^+$: 279.0.

9. Synthesis of tert-butyl (R)-(1-(2-chloro-3-methyl-4-(4-((1-methyl-1H-pyrazol-4-yl)amino)-1,3,5-triazin-2-yl)phenyl)ethyl)carbamate

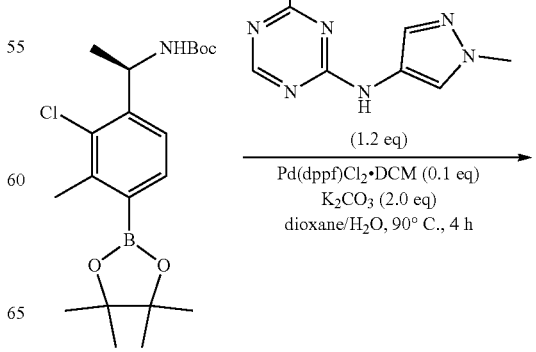

-continued

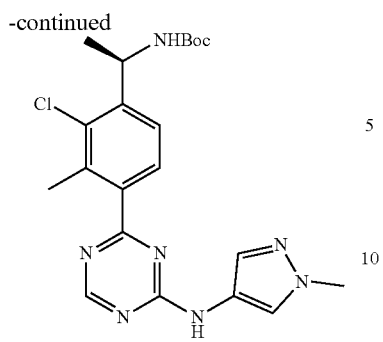

Synthesis of tert-butyl (R)-(1-(2-chloro-3-methyl-4-(4-((1-methyl-1H-pyrazol-4-yl)amino)-1,3,5-triazin-2-yl)phenyl)ethyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (petroleum ether/EtOAc, grading from 1:0 to 0:1) to give tert-butyl (R)-(1-(2-chloro-3-methyl-4-(4-((1-methyl-1H-pyrazol-4-yl)amino)-1,3,5-triazin-2-yl)phenyl)ethyl)carbamate as a yellow oil (180 mg, yield: 40%). ESI-MS (M+H)+: 444.3.

10. Synthesis of (R)-4-(4-(1-aminoethyl)-3-chloro-2-methylphenyl)-N-(1-methyl-1H-pyrazol-4-yl)-1,3,5-triazin-2-amine hydrochloride

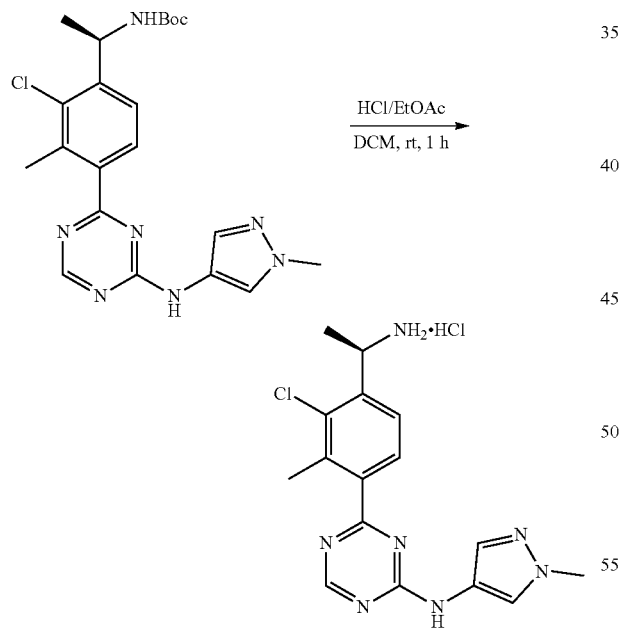

Synthesis of (R)-4-(4-(1-aminoethyl)-3-chloro-2-methylphenyl)-N-(1-methyl-1H-pyrazol-4-yl)-1,3,5-triazin-2-amine hydrochloride was similar to that of (R)-4-(4-(1-aminoethyl)-2-fluoro-3-methylphenyl)-N-(1-methyl-1H-pyrazol-3-yl)-1,3,5-triazin-2-amine hydrochloride in Example 71, Step 10. The reaction mixture was concentrated in vacuo to give (R)-4-(4-(1-aminoethyl)-3-chloro-2-methylphenyl)-N-(1-methyl-1H-pyrazol-4-yl)-1,3,5-triazin-2-amine hydrochloride (150 mg, crude), which was carried forward without further purification. ESI-MS (M+H)+: 344.0.

11. Synthesis of (R)-5-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-3-carboxamide (Compound 77)

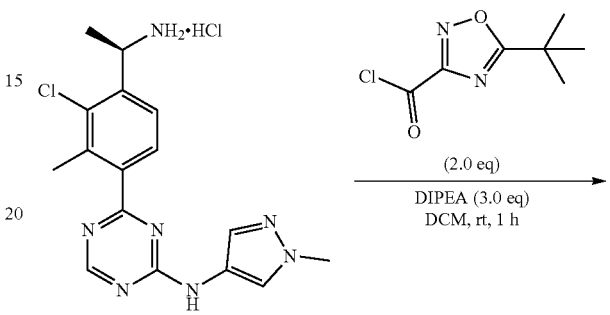

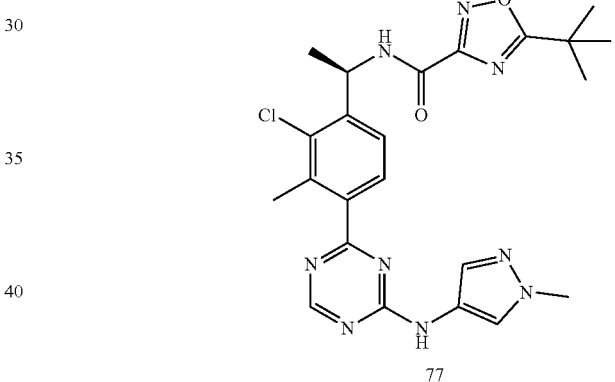

77

Synthesis of (R)-5-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-3-carboxamide was similar to that of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide in Example 69, Step 11. The crude material was purified by prep-HPLC (CH$_3$CN/H$_2$O with 0.05% HCl/H$_2$O as mobile phase) to give the HCl salt of (R)-5-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-3-carboxamide as a white solid (21 mg, yield: 24%). ESI-MS (M+H)+: 496.2. $^1$H NMR (500 MHz, DMSO-d$_6$, t=80° C.) δ: 9.97 (s, 1H), 9.08 (d, J=7.5 Hz, 1H), 8.76 (s, 1H), 7.87 (s, 1H), 7.71 (d, J=8.0 Hz, 1H), 7.60-7.54 (m, 2H), 5.62-5.55 (m, 1H), 3.83 (s, 3H), 2.59 (s, 3H), 1.56 (d, J=7.0 Hz, 3H), 1.47 (s, 9H).

225

Example 78: (R)-3-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-5-carboxamide (Compound 78)

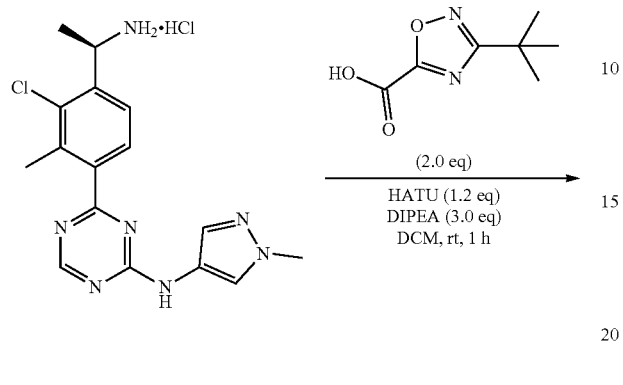

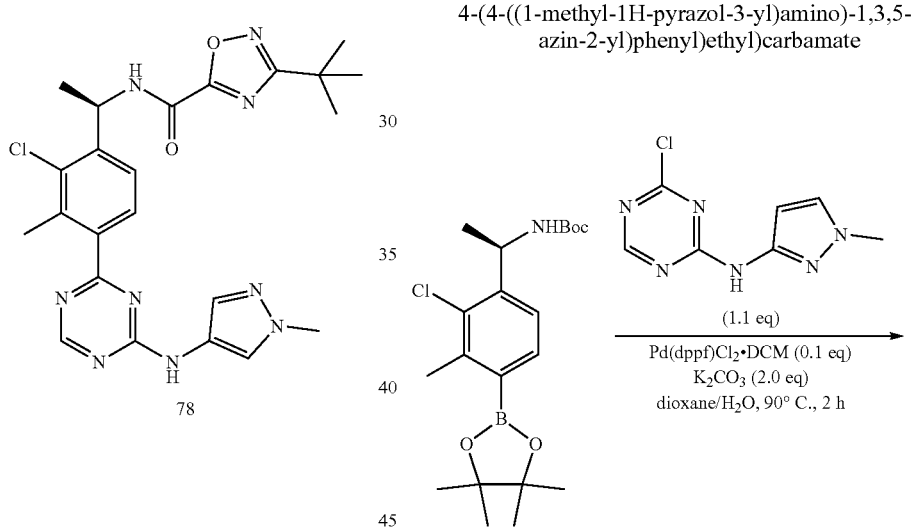

Synthesis of (R)-3-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-5-carboxamide was similar to that of (R)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide in Example 70. The crude material was purified by prep-HPLC (CH$_3$CN/H$_2$O with 0.05% HCl/H$_2$O as mobile phase) to give the HCl salt of (R)-3-(tert-butyl)-N-(1-(2-chloro-3-methyl-4-(4-((1-methyl-1H-pyrazol-4-yl)amino)-1,3,5-triazin-2-yl)phenyl)ethyl)-1,2,4-oxadiazole-5-carboxamide as a white solid (32 mg, yield: 36%). ESI-MS (M+H)$^+$: 496.2. $^1$H NMR (500 MHz, DMSO-d$_6$, t=80° C.) δ: 10.08 (s, 1H), 9.64 (d, J=7.2 Hz, 1H), 8.76 (s, 1H), 7.87 (s, 1H), 7.71 (d, J=8.0 Hz, 1H), 7.58-7.55 (m, 2H), 5.60-5.52 (m, 1H), 3.83 (s, 3H), 2.58 (s, 3H), 1.57 (d, J=6.8 Hz, 3H), 1.40 (s, 9H).

226

Example 79: (R)-5-(tert-butyl)-N-(1-(2-chloro-3-methyl-4-(4-((1-methyl-1H-pyrazol-3-yl)amino)-1,3,5-triazin-2-yl)phenyl)ethyl)-1,2,4-oxadiazole-3-carboxamide (Compound 79)

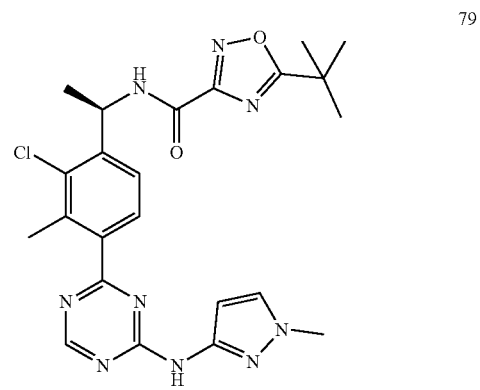 [SMILES: Cc1c(-c2ncnc(Nc3ccn(C)n3)n2)ccc([C@@H](C)NC(=O)c2noc(C(C)(C)C)n2)c1Cl]

1. Synthesis of tert-butyl (R)-(1-(2-chloro-3-methyl-4-(4-((1-methyl-1H-pyrazol-3-yl)amino)-1,3,5-triazin-2-yl)phenyl)ethyl)carbamate Synthesis of tert-butyl (R)-(1-(2-chloro-3-methyl-4-(4-((1-methyl-1H-pyrazol-3-yl)amino)-1,3,5-triazin-2-yl)phenyl)ethyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (petroleum ether/EtOAc, grading from 1:0 to 0:1) to give tert-butyl (R)-(1-(2-chloro-3-methyl-4-(4-((1-methyl-1H-pyrazol-3-yl)amino)-1,3,5- triazin-2-yl)phenyl)ethyl)carbamate as a white solid (50 mg, yield: 22%). ESI-MS (M+H−56)+: 388.0.

2. Synthesis of (R)-4-(4-(1-aminoethyl)-3-chloro-2-methylphenyl)-N-(1-methyl-1H-pyrazol-3-yl)-1,3,5-triazin-2-amine hydrochloride

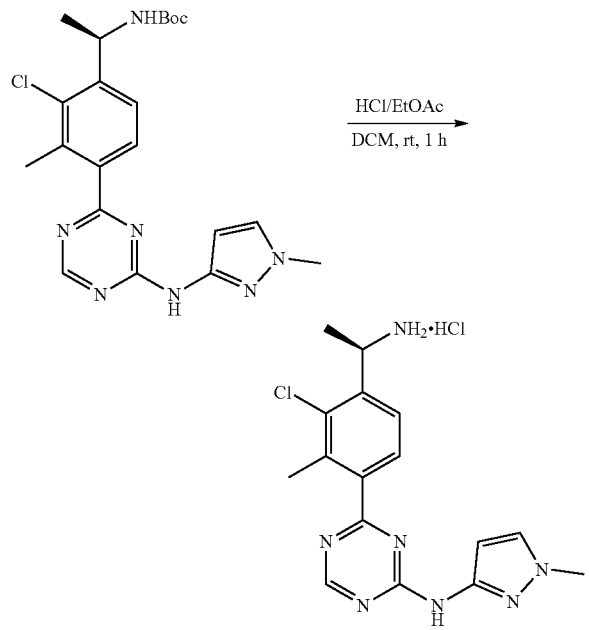

Synthesis of (R)-4-(4-(1-aminoethyl)-3-chloro-2-methylphenyl)-N-(1-methyl-1H-pyrazol-3-yl)-1,3,5-triazin-2-amine hydrochloride was similar to that of (R)-4-(4-(1-aminoethyl)-2-fluoro-3-methylphenyl)-N-(1-methyl-1H-pyrazol-3-yl)-1,3,5-triazin-2-amine hydrochloride in Example 71, Step 10. The reaction mixture was concentrated in vacuo to give (R)-4-(4-(1-aminoethyl)-3-chloro-2-methylphenyl)-N-(1-methyl-1H-pyrazol-3-yl)-1,3,5-triazin-2-amine hydrochloride (50 mg, crude), which was carried forward without further purification. ESI-MS (M+H)+: 344.2.

3. Synthesis of (R)-5-(tert-butyl)-N-(1-(2-chloro-3-methyl-4-(4-((1-methyl-1H-pyrazol-3-yl)amino)-1,3,5-triazin-2-yl)phenyl)ethyl)-1,2,4-oxadiazole-3-carboxamide (Compound 79)

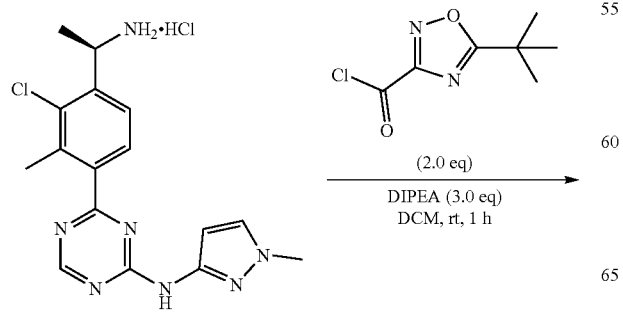

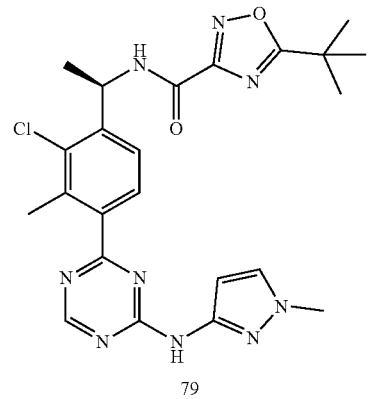

79

Synthesis of (R)-5-(tert-butyl)-N-(1-(2-chloro-3-methyl-4-(4-((1-methyl-1H-pyrazol-3-yl)amino)-1,3,5-triazin-2-yl)phenyl)ethyl)-1,2,4-oxadiazole-3-carboxamide was similar to that of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide in Example 69, Step 11. The crude material was purified by prep-HPLC ($CH_3CN/H_2O$ with 0.05% $HCl/H_2O$ as mobile phase) to give the HCl salt of (R)-5-(tert-butyl)-N-(1-(2-chloro-3-methyl-4-(4-((1-methyl-1H-pyrazol-3-yl)amino)-1,3,5-triazin-2-yl)phenyl)ethyl)-1,2,4-oxadiazole-3-carboxamide as a white solid (17 mg, yield: 25%). ESI-MS (M+Na)+: 518.2. $^1$H NMR (500 MHz, DMSO-$d_6$, t=80° C.) δ:10.17 (s, 1H), 9.10 (d, J=7.5 Hz, 1H), 8.79-8.77 (m, 1H), 7.71 (d, J=8.5 Hz, 1H), 7.57-7.54 (m, 2H), 6.54 (d, J=2.0 Hz, 1H), 5.61-5.55 (m, 1H), 3.79 (s, 3H), 2.58 (s, 3H), 1.56 (d, J=7.0 Hz, 3H), 1.47 (s, 9H).

Example 80: (R)-3-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-5-carboxamide (Compound 80)

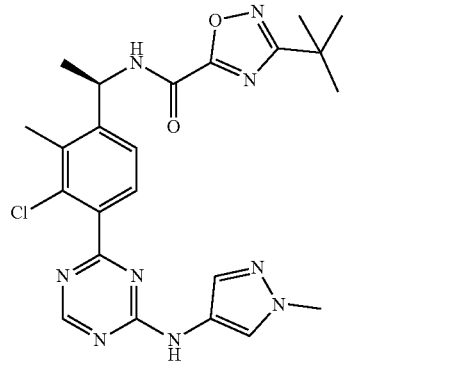

80

1. Synthesis of 2-chloro-1-methyl-3-nitrobenzene

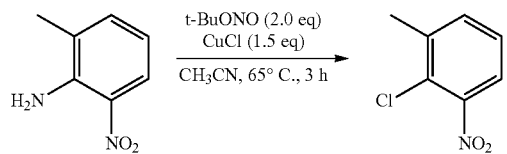

A solution of 2-methyl-6-nitroaniline (25 g, 0.16 mol) in acetonitrile (300 mL) was added to a solution of tert-butyl nitrite (34 g, 0.33 mol, 39 mL) and Cu(I)Cl (24 g, 0.25 mol) in acetonitrile (300 mL). The reaction mixture was then heated to 65° C. under an atmosphere of $N_2$ and was stirred at that temperature for 3 h. The reaction mixture was cooled to ambient temperature, filtered, and the filtrate was concentrated in vacuo. The crude material was purified by silica-gel column chromatography (petroleum ether/EtOAc, 100:1) to give 2-chloro-1-methyl-3-nitrobenzene as a yellow oil (23 g, yield: 82%) $^1$H NMR (400 MHz, DMSO-$d_6$) δ: 7.84 (d, J=8.0 Hz, 1H), 7.68 (d, J=8.0 Hz, 1H), 7.50-7.46 (m, 1H), 2.44 (s, 3H).

2. Synthesis of 2-chloro-3-methylaniline

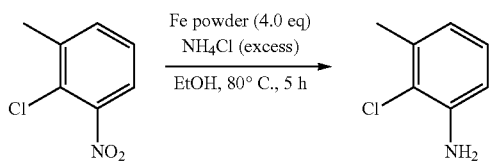

To a solution of 2-chloro-1-methyl-3-nitrobenzene (23 g, 0.14 mol) in EtOH (200 mL) was added iron powder (31 g, 0.56 mol) and a solution of $NH_4Cl$ (200 mL, 7 M). The reaction mixture was heated to 80° C. and was stirred at that temperature for 5 h. The reaction mixture was cooled to ambient temperature and filtered. The filtrate was poured into $H_2O$ (200 mL) and was extracted with EtOAc (200 mL×3). The combined organic extracts were dried ($Na_2SO_4$), filtered, and concentrated in vacuo. The crude material was purified by silica-gel column chromatography (petroleum ether/EtOAc, 99:1) to give 2-chloro-3-methylaniline as a yellow oil (16 g, yield: 84%). ESI-MS (M+H)$^+$: 142.0. $^1$H NMR (400 MHz, DMSO-$d_6$) δ: 6.90-9.87 (m, 1H), 6.64 (d, J=4.0 Hz, 1H), 6.50-6.48 (m, 1H), 5.24 (s, 2H), 2.23 (s, 3H).

3. Synthesis of 4-bromo-2-chloro-3-methylaniline

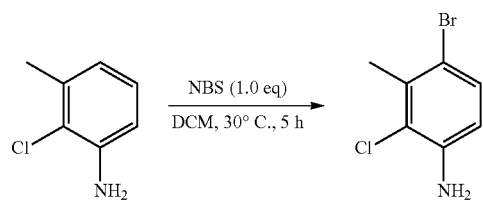

To a solution of 2-chloro-3-methylaniline (16 g, 106 mmol) in DCM (150 mL) at 0° C. was added slowly a solution of NBS (18.9 g, 106 mmol) in DCM (150 mL). The reaction mixture was warmed to 30° C. and was stirred at that temperature for 5 h. To the reaction mixture was added a saturated aqueous $Na_2CO_3$ solution (100 mL), followed by EtOAc (100 mL). The layers were separated and the aqueous phase was extracted with EtOAc (100 mL×4). The combined organic extracts were dried ($Na_2SO_4$), filtered, and concentrated in vacuo. The crude material was purified by silica-gel column chromatography (petroleum ether/EtOAc, 100:1) to give 4-bromo-2-chloro-3-methylaniline as a yellow oil (18 g, yield: 72%). ESI-MS (M+H)$^+$: 221.9. $^1$H NMR (400 MHz, DMSO-$d_6$) δ: 7.20 (d, J=8.0 Hz, 1H), 6.61 (d, J=12.0 Hz, 1H), 5.48 (s, 2H), 2.36 (s, 3H).

4. Synthesis of 4-amino-3-chloro-2-methylbenzonitrile

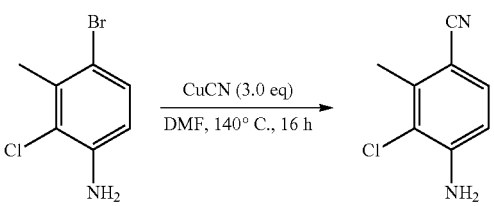

To a solution of 4-bromo-2-chloro-3-methylaniline (25 g, 113 mmol) in DMF (300 mL) was added Cu(I)CN (30 g, 340 mmol) under $N_2$. The reaction mixture was heated to 140° C. and was stirred at that temperature for 16 h. The reaction mixture was cooled to ambient temperature and a solution of $NH_4OH$ (100 mL) was added. The reaction mixture was filtered and $H_2O$ (200 mL) was added to the filtrate. The aqueous phase was extracted with EtOAc (200 mL×4). The combined organic extracts were dried ($Na_2SO_4$), filtered, and concentrated in vacuo. The crude material was purified by silica-gel column chromatography (petroleum ether/EtOAc, 7:3) to give 4-amino-3-chloro-2-methylbenzonitrile as a brown oil (16 g, yield: 85%). ESI-MS (M+H)$^+$: 167.0.

5. Synthesis of 4-bromo-3-chloro-2-methylbenzonitrile

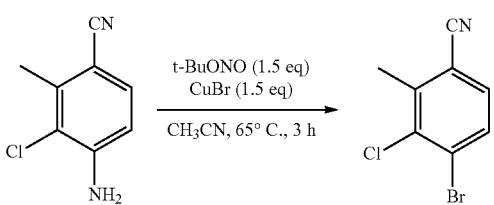

A solution of 4-amino-3-chloro-2-methylbenzonitrile (16 g, 96 mmol) in acetonitrile (200 mL) was added to a solution of tert-butyl nitrite (15 g, 72 mmol, 8.5 mL) and Cu(I)Br (21 g, 144 mmol) in acetonitrile (200 mL). The reaction mixture was then heated to 65° C. under an atmosphere of $N_2$ and was stirred at that temperature for 3 h. The reaction mixture was cooled to ambient temperature, filtered, and the filtrate was concentrated in vacuo. The crude material was purified by silica-gel column chromatography (petroleum ether/EtOAc, 9:1) to give 4-bromo-3-chloro-2-methylbenzonitrile as a yellow solid (12.5 g, yield: 56%). $^1$H NMR (400 MHz, DMSO-$d_6$) δ: 7.84 (d, J=8.0 Hz, 1H), 7.72 (d, J=8.0 Hz, 1H), 2.59 (s, 3H).

6. Synthesis of 4-bromo-2-chloro-3-methylbenzoic acid

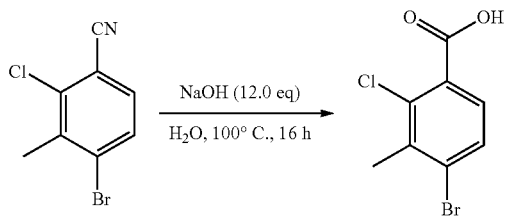

Synthesis of 4-bromo-2-chloro-3-methylbenzoic acid was similar to that of 4-bromo-2-chloro-3-fluorobenzoic acid In Example 69, Step 1. The crude material was dried in vacuo to give 4-bromo-2-chloro-3-methylbenzoic acid as a white solid (8 g, crude), which was carried forward without further purification. ESI-MS (M+H+41)$^+$: 249.9.

7. Synthesis of 4-bromo-3-chloro-N-methoxy-N,2-dimethylbenzamide

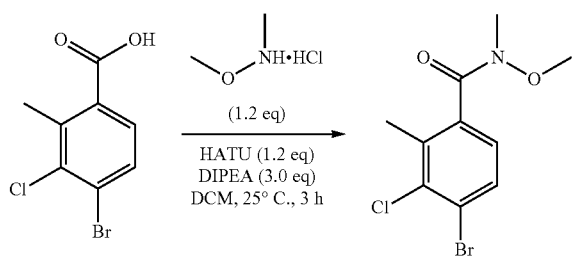

Synthesis of 4-bromo-3-chloro-N-methoxy-N,2-dimethylbenzamide was similar to that of 4-bromo-2-chloro-3-fluoro-N-methoxy-N-methylbenzamide in Example 69, Step 2. The crude material was purified by silica-gel column chromatography (petroleum ether/EtOAc, 7:3) to give 4-bromo-3-chloro-N-methoxy-N,2-dimethylbenzamide as a colorless oil (7.8 g, yield: 83%). ESI-MS (M+H)$^+$: 294.0.

8. Synthesis of 4-bromo-3-chloro-2-methylbenzaldehyde

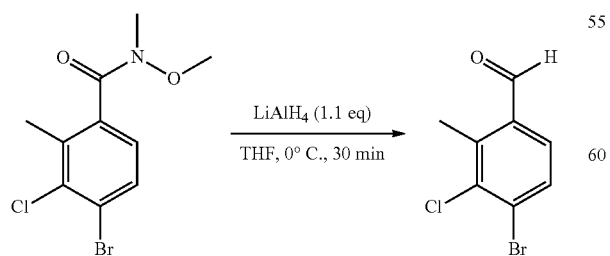

Synthesis of 4-bromo-3-chloro-2-methylbenzaldehyde was similar to that of 4-bromo-2-chloro-3-fluorobenzalde-hyde in Example 69, Step 3. The crude material was concentrated in vacuo to give 4-bromo-3-chloro-2-methylbenzaldehyde as a colorless oil (5.2 g, yield: 84%), which was carried forward without further purification. $^1$H NMR (400 MHz, CDCl$_3$) δ: 10.25 (s, 1H), 7.66 (s, 1H), 7.26 (s, 1H), 2.79 (s, 3H).

8. Synthesis of (S,E)-N-(4-bromo-3-chloro-2-methylbenzylidene)-2-methylpropane-2-sulfinamide

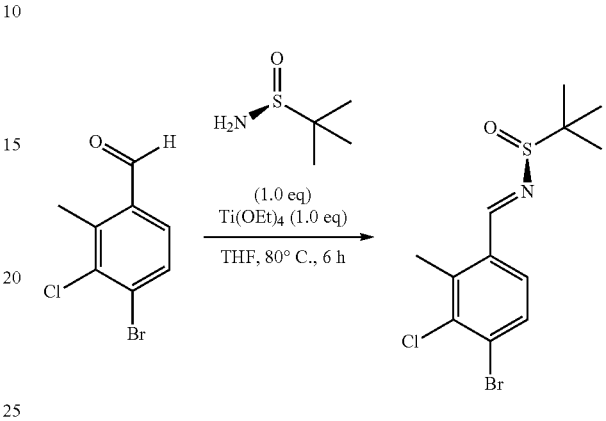

Synthesis of (S,E)-N-(4-bromo-3-chloro-2-methylbenzylidene)-2-methylpropane-2-sulfinamide was similar to that of (S,E)-N-(4-bromo-2-chloro-3-fluorobenzylidene)-2-methylpropane-2-sulfinamide in Example 69, Step 4. The crude material was purified by silica-gel column chromatography (petroleum ether/EtOAc, 20:1) to give (S,E)-N-(4-bromo-3-chloro-2-methylbenzylidene)-2-methylpropane-2-sulfinamide as a white solid (4.6 g, yield: 61%). $^1$H NMR (400 MHz, CDCl$_3$) δ: 8.83 (s, 1H), 7.72 (d, J=8.0 Hz, 1H), 7.58 (d, J=8.0 Hz, 1H), 2.70 (s, 3H), 1.26 (s, 9H).

9. Synthesis of (S)—N—((R)-1-(4-bromo-3-chloro-2-methylphenyl)ethyl)-2-methylpropane-2-sulfinamide

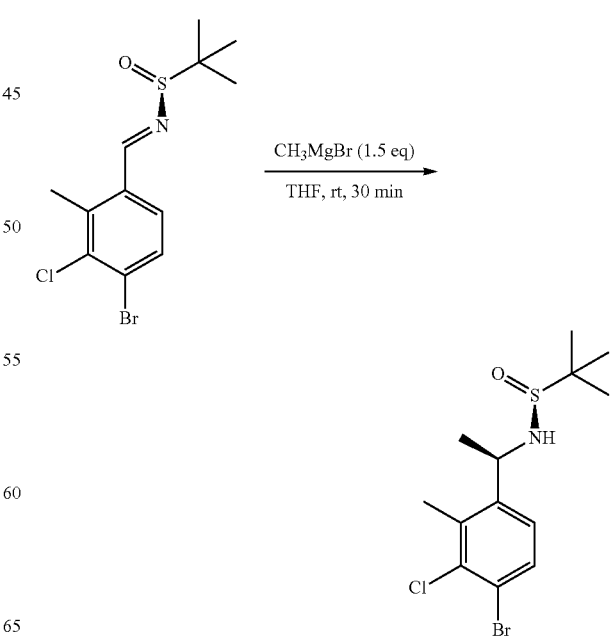

Synthesis of (S)—N—((R)-1-(4-bromo-3-chloro-2-methylphenyl)ethyl)-2-methylpropane-2-sulfinamide was similar to that of (S)—N—((R)-1-(4-bromo-2-chloro-3-fluorophenyl)ethyl)-2-methylpropane-2-sulfinamide in Example 69, Step 5. The crude material was purified by silica-gel column chromatography (petroleum ether/EtOAc, 1:1) to give (S)—N—((R)-1-(4-bromo-3-chloro-2-methylphenyl)ethyl)-2-methylpropane-2-sulfinamide as a white solid (2 g, yield: 48%). ESI-MS (M+H)$^+$: 353.9.

10. Synthesis of (R)-1-(4-bromo-3-chloro-2-methylphenyl)ethan-1-amine

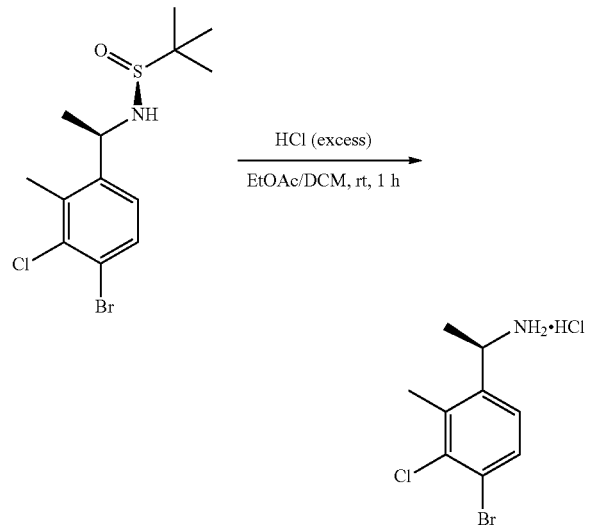

Synthesis of (R)-1-(4-bromo-3-chloro-2-methylphenyl)ethan-1-amine was similar to that of (R)-1-(4-bromo-3-fluoro-2-methylphenyl)ethan-1-amine in Example 71, Step 6. The reaction mixture was concentrated in vacuo to give the HCl salt of (R)-1-(4-bromo-3-chloro-2-methylphenyl)ethan-1-amine as a yellow solid (1.75 g, crude), which was carried forward without further purification. ESI-MS (M+H)$^+$: 249.9.

11. Synthesis of tert-butyl (R)-(1-(4-bromo-3-chloro-2-methylphenyl)ethyl)carbamate

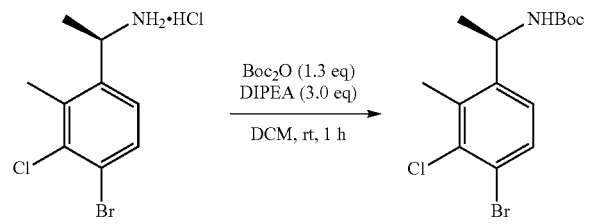

Synthesis of tert-butyl (R)-(1-(4-bromo-3-chloro-2-methylphenyl)ethyl)carbamate was similar to that of tert-butyl (R)-(1-(4-bromo-2-chloro-3-fluorophenyl)ethyl)carbamate in Example 69, Step 7. The crude material was purified by silica-gel column chromatography (petroleum ether/EtOAc, grading from 10:1 to 3:1) to give tert-butyl (R)-(1-(4-bromo-3-chloro-2-methylphenyl)ethyl)carbamate as a white solid (1.5 g, yield: 79% over 2 steps). ESI-MS (M+H−56)$^+$: 293.9.

12. Synthesis of tert-butyl (R)-(1-(3-chloro-2-methyl-4-(4,4,5,5-tetramethyl-1,3,2-dioxaborolan-2-yl)phenyl)ethyl)carbamate

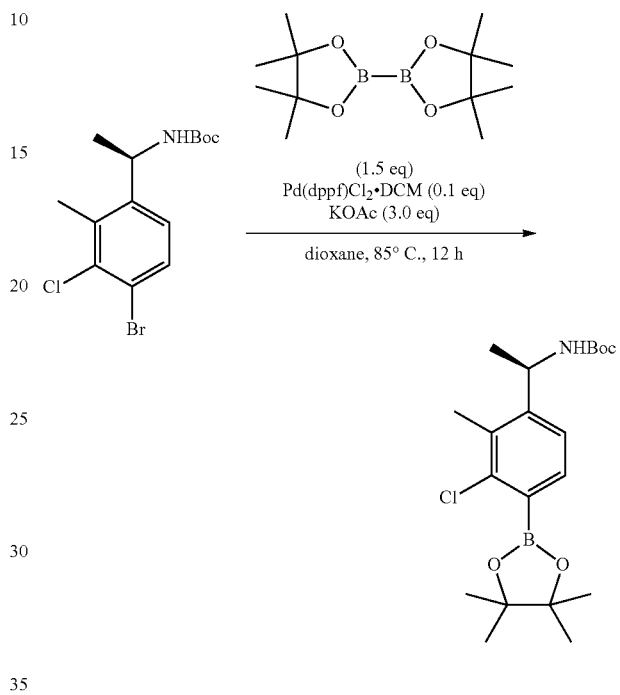

Synthesis of tert-butyl (R)-(1-(3-chloro-2-methyl-4-(4,4,5,5-tetramethyl-1,3,2-dioxaborolan-2-yl)phenyl)ethyl)carbamate was similar to that of tert-butyl (R)-(1-(2-chloro-3-fluoro-4-(4,4,5,5-tetramethyl-1,3,2-dioxaborolan-2-yl)phenyl)ethyl)carbamate. The crude material was purified by silica-gel column chromatography (petroleum ether/EtOAc, 9:1) to give tert-butyl (R)-(1-(3-chloro-2-methyl-4-(4,4,5,5-tetramethyl-1,3,2-dioxaborolan-2-yl)phenyl)ethyl)carbamate as a colorless oil (510 mg, yield: 72%). ESI-MS (M+H−56)$^+$: 340.1.

13. Synthesis of tert-butyl (R)-(1-(3-chloro-2-methyl-4-(4-((1-methyl-1H-pyrazol-4-yl)amino)-1,3,5-triazin-2-yl)phenyl)ethyl)carbamate

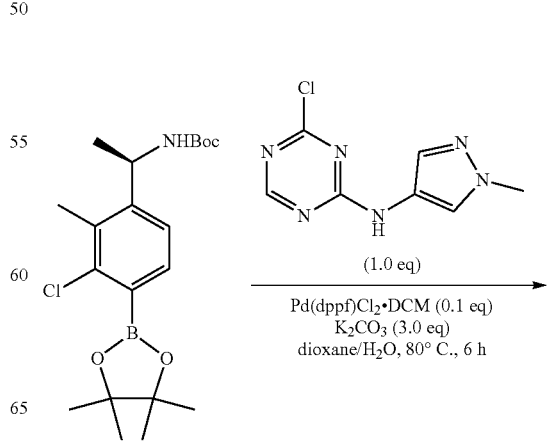

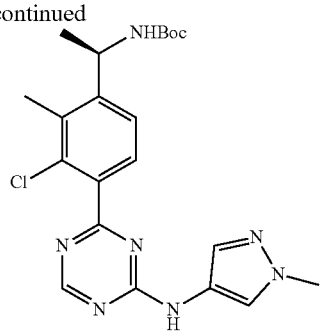

Synthesis of tert-butyl (R)-(1-(3-chloro-2-methyl-4-(4-((1-methyl-1H-pyrazol-4-yl)amino)-1,3,5-triazin-2-yl)phenyl)ethyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (petroleum ether/EtOAc, 1:99) to give tert-butyl (R)-(1-(3-chloro-2-methyl-4-(4-((1-methyl-1H-pyrazol-4-yl)amino)-1,3,5-triazin-2-yl)phenyl)ethyl)carbamate as a white solid (120 mg, yield: 60%). ESI-MS (M+H)$^+$: 444.3.

14. Synthesis of (R)-4-(4-(1-aminoethyl)-2-chloro-3-methylphenyl)-N-(1-methyl-1H-pyrazol-4-yl)-1,3,5-triazin-2-amine hydrochloride

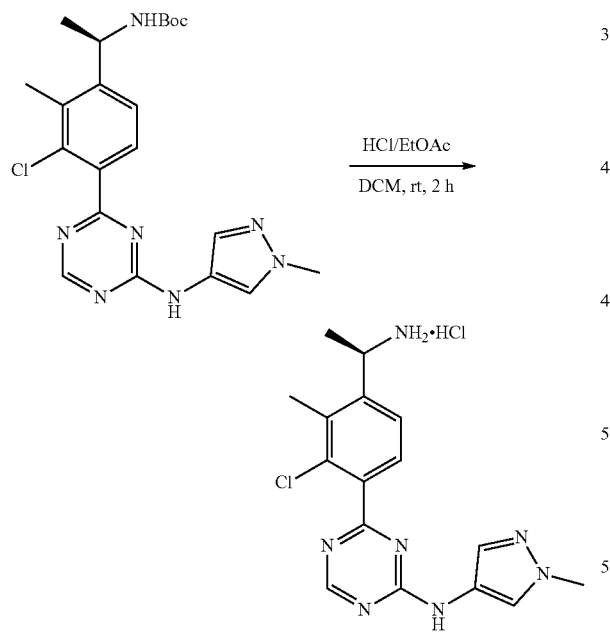

Synthesis of (R)-4-(4-(1-aminoethyl)-2-chloro-3-methylphenyl)-N-(1-methyl-1H-pyrazol-4-yl)-1,3,5-triazin-2-amine hydrochloride was similar to that of (R)-4-(4-(1-aminoethyl)-2-fluoro-3-methylphenyl)-N-(1-methyl-1H-pyrazol-3-yl)-1,3,5-triazin-2-amine hydrochloride in Example 71, Step 10. The reaction mixture was concentrated in vacuo to give (R)-4-(4-(1-aminoethyl)-2-chloro-3-methylphenyl)-N-(1-methyl-1H-pyrazol-4-yl)-1,3,5-triazin-2-amine hydrochloride as a yellow solid (100 mg, crude), which was carried forward without further purification. ESI-MS (M+H)$^+$: 344.2.

15. Synthesis of (R)-3-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-5-carboxamide (Compound 80)

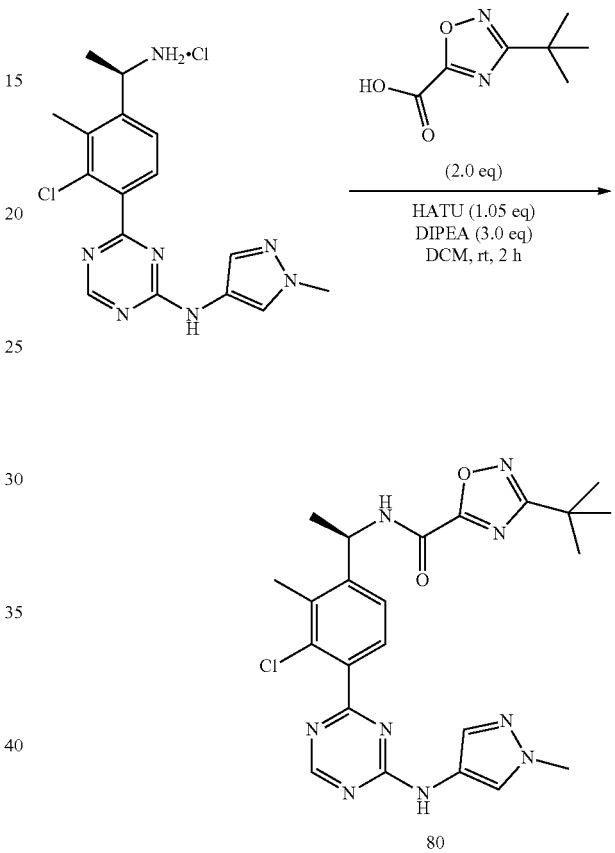

Synthesis of (R)-3-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-5-carboxamide was similar to that of (R)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide in Example 70. The crude material was purified by prep-HPLC (CH$_3$CN/H$_2$O with 0.05% HCl/H$_2$O as mobile phase) to give (R)-3-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-5-carboxamide as a gray solid (20 mg, yield: 31%). ESI-MS (M+H)$^+$: 496.1. $^1$H NMR (500 MHz, DMSO-d$_6$) δ: 9.93 (s, 1H), 9.48 (d, J=5.0 Hz, 1H), 7.35 (s, 1H), 7.85 (s, 1H), 7.60-7.50 (m, 3H), 5.42 (q, J=15.0 Hz, 1H), 3.81 (s, 3H), 2.52 (s, 3H), 1.56 (d, J=5.0 Hz, 3H), 1.39 (s, 9H).

237

Example 81: (R)-5-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-3-carboxamide (Compound 81)

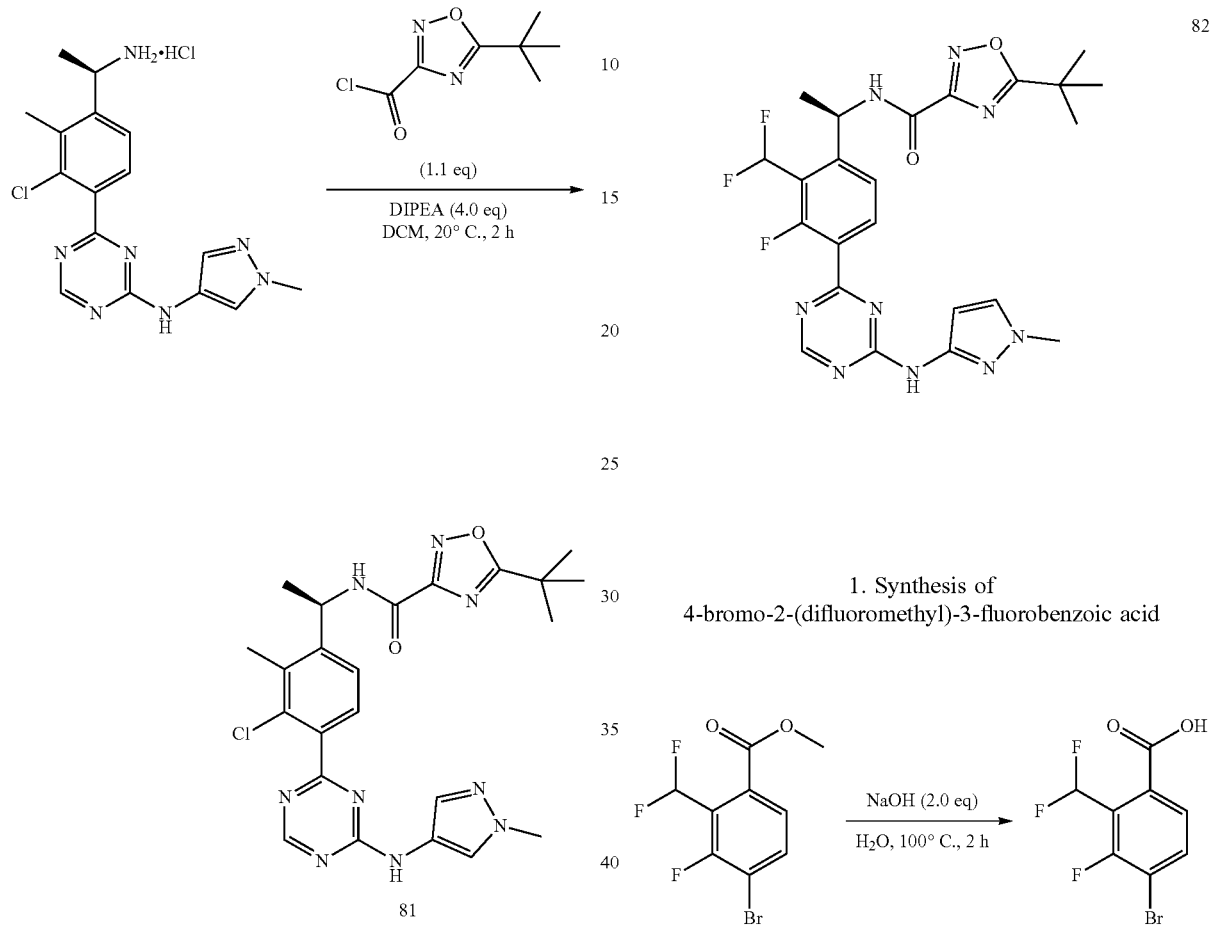

Synthesis of (R)-5-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-3-carboxamide was similar to that of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide in Example 69, Step 11. The crude material was purified by prep-HPLC (CH$_3$CN/H$_2$O with 0.225% formic acid/H$_2$O as mobile phase) to give (R)-5-(tert-butyl)-N-(1-(3-chloro-2-methyl-4-(4-((1-methyl-1H-pyrazol-4-yl)amino)-1,3,5-triazin-2-yl)phenyl)ethyl)-1,2,4-oxadiazole-3-carboxamide as a gray solid (8.5 mg, yield: 19%). ESI-MS (M+H)$^+$: 496.1. $^1$H NMR (400 MHz, DMSO-d$_6$) δ: 9.92 (s, 1H), 9.04 (d, J=10.0 Hz, 1H), 8.73 (s, 1H), 7.86 (s, 1H), 7.64-7.52 (m, 3H), 5.44-5.41 (m, 1H), 3.81 (s, 3H), 2.46 (s, 3H), 1.54 (d, J=10.0 Hz, 3H), 1.44 (s, 9H).

238

Example 82: (R)-5-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-3-carboxamide (Compound 82)

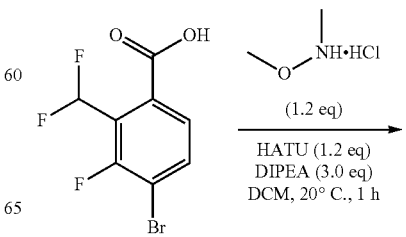

82

1. Synthesis of 4-bromo-2-(difluoromethyl)-3-fluorobenzoic acid

Synthesis of 4-bromo-2-(difluoromethyl)-3-fluorobenzoic acid was similar to that of 4-bromo-3-fluoro-2-methylbenzoic acid in Example 71, Step 1. The filter cake was dried in vacuo to give 4-bromo-2-(difluoromethyl)-3-fluorobenzoic acid as a white solid (3.0 g, crude), which was carried forward without further purification.

2. Synthesis of 4-bromo-2-(difluoromethyl)-3-fluoro-N-methoxy-N-methylbenzamide

3. Synthesis of 4-bromo-2-(difluoromethyl)-3-fluorobenzaldehyde

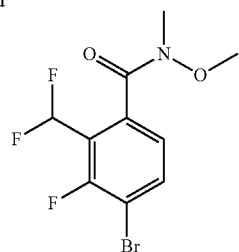

Synthesis of 4-bromo-2-(difluoromethyl)-3-fluoro-N-methoxy-N-methylbenzamide was similar to that of 4-bromo-2-chloro-3-fluoro-N-methoxy-N-methylbenzamide in Example 69, Step 2. The crude material was purified by silica-gel column chromatography (petroleum ether/EtOAc, grading from 1:0 to 3:1) to give 4-bromo-2-(difluoromethyl)-3-fluoro-N-methoxy-N-methylbenzamide as a colorless oil (3.3 g, yield: 95% over 2 steps). ESI-MS (M+H)$^+$: 313.9. $^1$H NMR (400 MHz, DMSO-d$_6$) δ: 7.99-7.95 (m, 1H), 7.30-7.24 (m, 1H), 7.20-6.94 (m, 1H), 3.27 (s, 3H), 2.67-2.61 (m, 3H).

3. Synthesis of 4-bromo-2-(difluoromethyl)-3-fluorobenzaldehyde

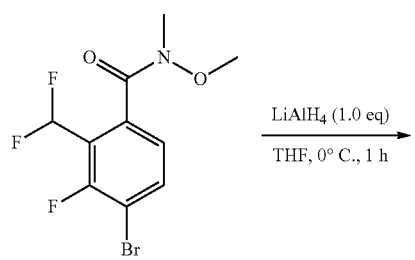

Synthesis of 4-bromo-2-(difluoromethyl)-3-fluorobenzaldehyde was similar to that of 4-bromo-2-chloro-3-fluorobenzaldehyde in Example 69, Step 3. The crude material was concentrated in vacuo to give 4-bromo-2-(difluoromethyl)-3-fluorobenzaldehyde as a light brown oil (360 mg, crude), which was carried forward without further purification. $^1$H NMR (400 MHz, CDCl$_3$) δ: 10.32 (s, 1H), 7.82-7.78 (m, 1H), 7.69-7.66 (m, 1H), 7.28-7.19 (m, 1H).

4. Synthesis of (S,E)-N-(4-bromo-2-(difluoromethyl)-3-fluorobenzylidene)-2-methylpropane-2-sulfinamide

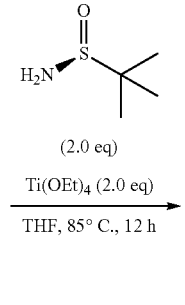

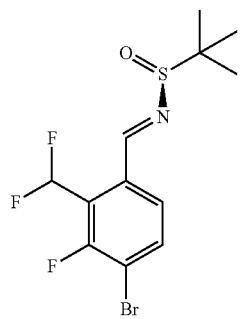

Synthesis of (S,E)-N-(4-bromo-2-(difluoromethyl)-3-fluorobenzylidene)-2-methylpropane-2-sulfinamide was similar to that of (S,E)-N-(4-bromo-2-chloro-3-fluorobenzylidene)-2-methylpropane-2-sulfinamide in Example 69, Step 4. The crude material was purified by silica-gel column chromatography (petroleum ether/EtOAc, grading from 15:1 to 5:1) to give (S,E)-N-(4-bromo-2-(difluoromethyl)-3-fluorobenzylidene)-2-methylpropane-2-sulfinamide as a colorless oil (1.8 g, yield: 57% over 2 steps). $^1$H NMR (400 MHz, CDCl$_3$) δ: 8.95 (s, 1H), 7.78-7.76 (m, 1H), 7.41-7.14 (m, 2H).

5. Synthesis of (S)—N—((R)-1-(4-bromo-2-(difluoromethyl)-3-fluorophenyl)ethyl)-2-methylpropane-2-sulfinamide

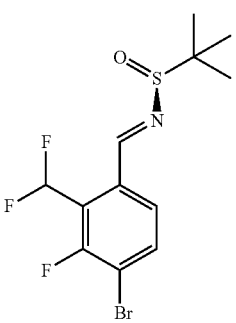

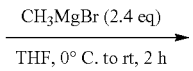

7. Synthesis of tert-butyl (R)-(1-(4-bromo-2-(difluoromethyl)-3-fluorophenyl)ethyl) carbamate

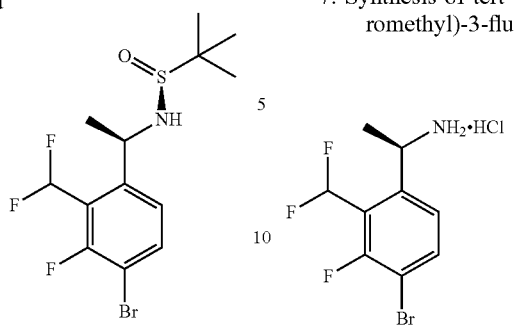

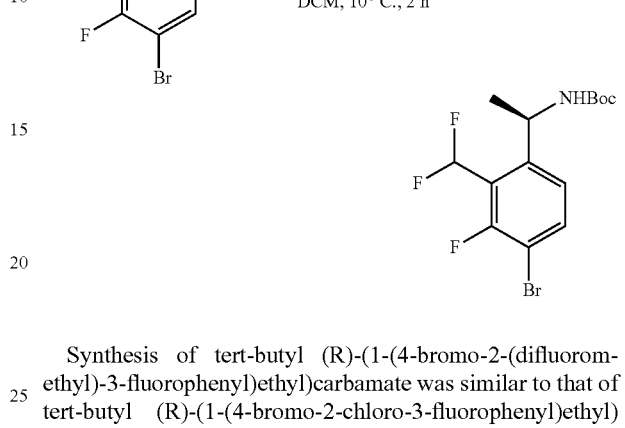

Synthesis of tert-butyl (R)-(1-(4-bromo-2-(difluoromethyl)-3-fluorophenyl)ethyl)carbamate was similar to that of tert-butyl (R)-(1-(4-bromo-2-chloro-3-fluorophenyl)ethyl) carbamate in Example 69, Step 7. The crude material was purified by silica-gel column chromatography (petroleum ether/EtOAc, grading from 15:1 to 3:1) to give tert-butyl (R)-(1-(4-bromo-2-(difluoromethyl)-3-fluorophenyl)ethyl) carbamate as a white solid (750 mg, yield: 74% over 2 steps). ESI-MS (M+H−56)$^+$: 311.9.

8. Synthesis of tert-butyl (R)-(1-(2-(difluoromethyl)-3-fluoro-4-(4,4,5,5-tetramethyl-1,3,2-dioxaborolan-2-yl)phenyl)ethyl)carbamate

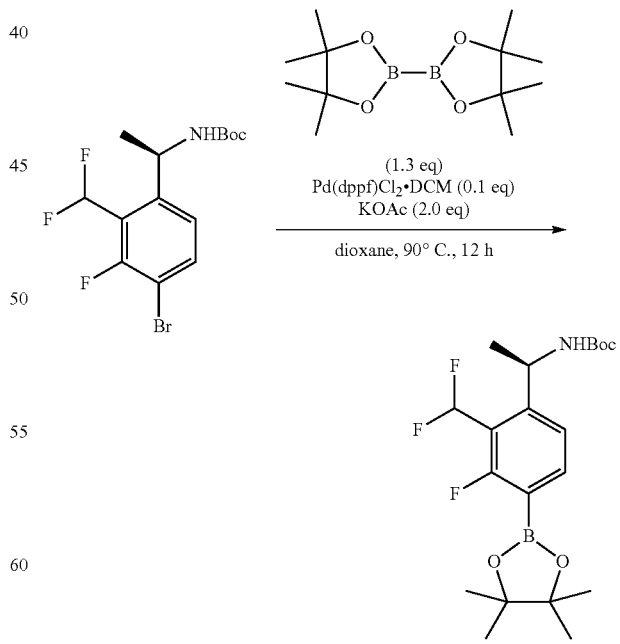

Synthesis of tert-butyl (R)-(1-(2-(difluoromethyl)-3-fluoro-4-(4,4,5,5-tetramethyl-1,3,2-dioxaborolan-2-yl)phenyl)ethyl)carbamate was similar to that of tert-butyl (R)-(1-

Synthesis of (S)—N—((R)-1-(4-bromo-2-(difluoromethyl)-3-fluorophenyl)ethyl)-2-methylpropane-2-sulfinamide was similar to that of (S)—N—((R)-1-(4-bromo-2-chloro-3-fluorophenyl)ethyl)-2-methylpropane-2-sulfinamide in Example 69, Step 5. The crude material was purified by silica-gel column chromatography (petroleum ether/EtOAc, grading from 10:1 to 1:2) to give (S)—N—((R)-1-(4-bromo-2-(difluoromethyl)-3-fluorophenyl)ethyl)-2-methylpropane-2-sulfinamide as a white solid (900 mg, yield: 48%). ESI-MS (M+H+2)$^+$: 373.8.

6. Synthesis of (R)-1-(4-bromo-2-(difluoromethyl)-3-fluorophenyl)ethan-1-amine

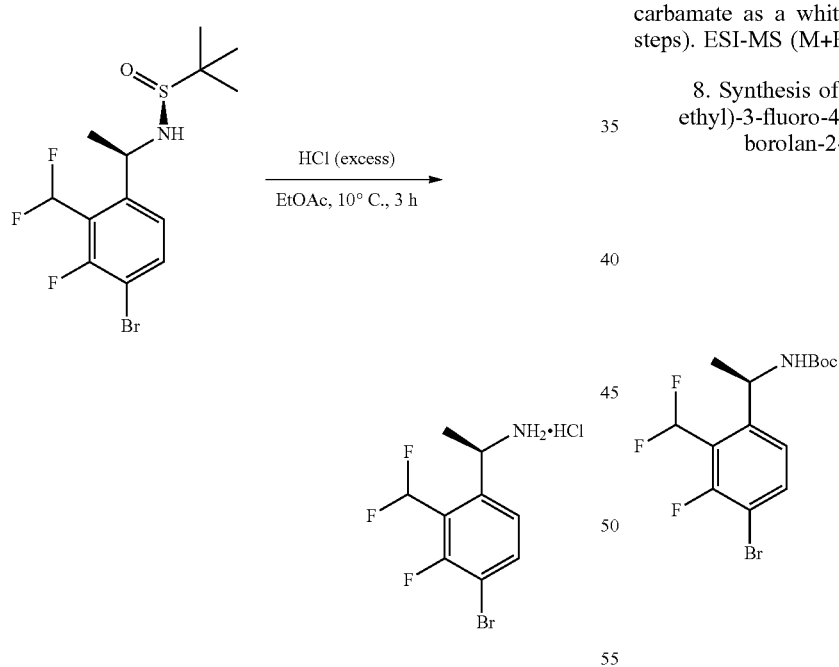

Synthesis of (R)-1-(4-bromo-2-(difluoromethyl)-3-fluorophenyl)ethan-1-amine was similar to that of (R)-1-(4-bromo-3-fluoro-2-methylphenyl)ethan-1-amine in Example 71, Step 6. The crude material was concentrated in vacuo to give the HCl salt of (R)-1-(4-bromo-2-(difluoromethyl)-3-fluorophenyl)ethan-1-amine as a gray solid (700 mg, crude), which was carried forward without further purification. ESI-MS (M+H+2)$^+$: 270.0.

(2-chloro-3-fluoro-4-(4,4,5,5-tetramethyl-1,3,2-dioxaborolan-2-yl)phenyl)ethyl)carbamate in Example 69, Step 8. The crude material was concentrated in vacuo to give tert-butyl (R)-(1-(2-(difluoromethyl)-3-fluoro-4-(4,4,5,5-tetramethyl-1,3,2-dioxaborolan-2-yl)phenyl)ethyl)carbamate as black oil (400 mg, crude), which was carried forward without further purification. ESI-MS (M+H−56)⁺: 350.0.

9. Synthesis of tert-butyl (R)-(1-(2-(difluoromethyl)-3-fluoro-4-(4-((1-methyl-1H-pyrazol-3-yl)amino)-1,3,5-triazin-2-yl)phenyl)ethyl)carbamate

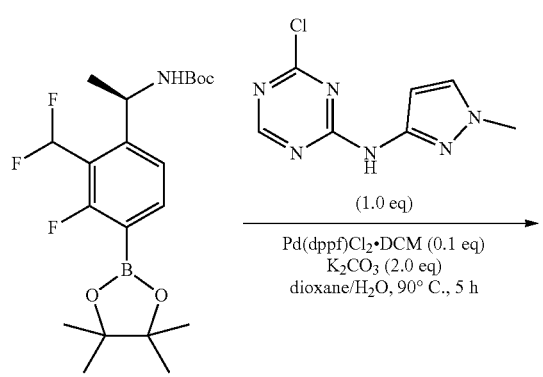

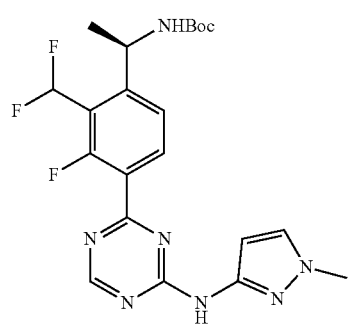

Synthesis of tert-butyl (R)-(1-(2-(difluoromethyl)-3-fluoro-4-(4-((1-methyl-1H-pyrazol-3-yl)amino)-1,3,5-triazin-2-yl)phenyl)ethyl)carbamate was similar to that of tert-butyl (R)-(1-(2-chloro-3-fluoro-4-(4-((1-methyl-1H-pyrazol-4-yl)amino)-1,3,5-triazin-2-yl)phenyl)ethyl)carbamate in Example 69, Step 9. The crude material was purified by silica-gel column chromatography (petroleum ether/EtOAc, grading from 8:1 to 0:1) to give tert-butyl (R)-(1-(2-(difluoromethyl)-3-fluoro-4-(4-((1-methyl-1H-pyrazol-3-yl)amino)-1,3,5-triazin-2-yl)phenyl)ethyl)carbamate as a gray solid (150 mg, yield: 27% over 2 steps). ESI-MS (M+H)⁺: 464.2.

10. Synthesis of (R)-4-(4-(1-aminoethyl)-3-(difluoromethyl)-2-fluorophenyl)-N-(1-methyl-1H-pyrazol-3-yl)-1,3,5-triazin-2-amine hydrochloride

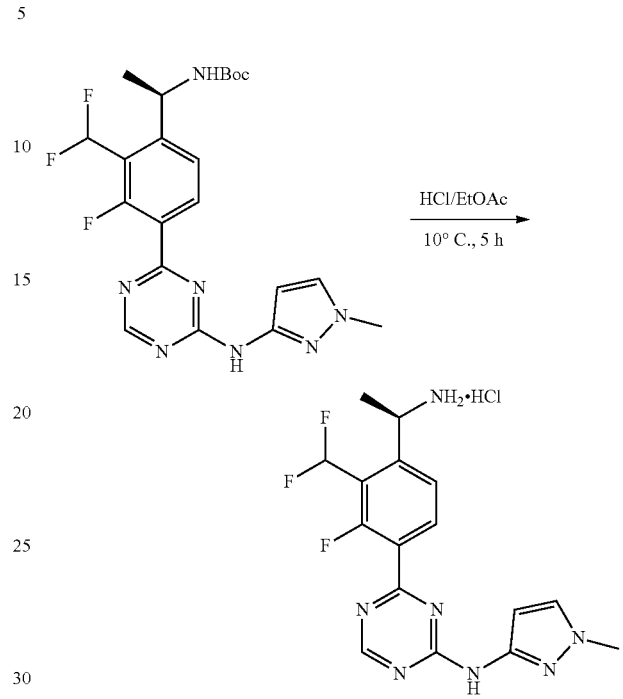

Synthesis of (R)-4-(4-(1-aminoethyl)-3-(difluoromethyl)-2-fluorophenyl)-N-(1-methyl-1H-pyrazol-3-yl)-1,3,5-triazin-2-amine hydrochloride was similar to that of (R)-4-(4-(1-aminoethyl)-2-fluoro-3-methylphenyl)-N-(1-methyl-1H-pyrazol-3-yl)-1,3,5-triazin-2-amine hydrochloride in Example 71, Step 10. The crude material was concentrated in vacuo to give (R)-4-(4-(1-aminoethyl)-3-(difluoromethyl)-2-fluorophenyl)-N-(1-methyl-1H-pyrazol-3-yl)-1,3,5-triazin-2-amine hydrochloride as a gray solid (120 mg, crude), which was carried forward without further purification. ESI-MS (M+H)⁺: 364.1.

11. Synthesis of (R)-5-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-3-carboxamide (Compound 82)

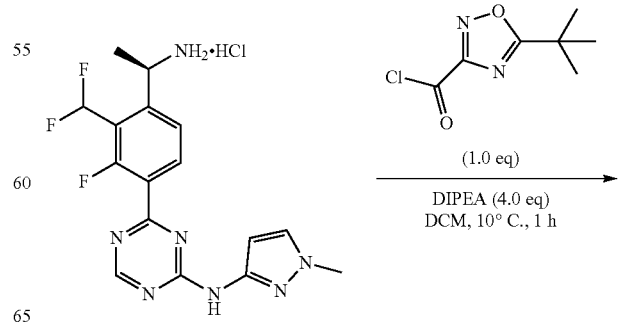

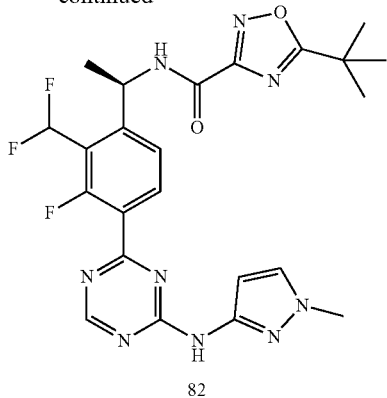

82

Synthesis of (R)-5-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-3-carboxamide was similar to that of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide in Example 69, Step 11. The crude material was purified by prep-HPLC (CH$_3$CN/H$_2$O with 0.05% HCl/H$_2$O as mobile phase) to give the HCl salt of (R)-5-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-3-carboxamide as an off-white solid (40 mg, yield: 48% over 2 steps). ESI-MS (M+H)$^+$: 516.2. $^1$H NMR (500 MHz, DMSO-d$_6$) δ:10.17 (s, 1H), 9.18 (d, J=7.5 Hz, 1H), 8.79 (s, 1H), 8.21 (t, J=8.0 Hz, 1H), 7.67 (d, J=8.5 Hz, 1H), 7.58-7.48 (m, 2H), 6.64 (d, J=2.5 Hz, 1H), 5.64-5.60 (m, 1H), 3.80 (s, 3H), 1.59 (d, J=7.0 Hz, 3H), 1.46 (s, 9H).

Example 83: (R)-3-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-5-carboxamide (Compound 83)

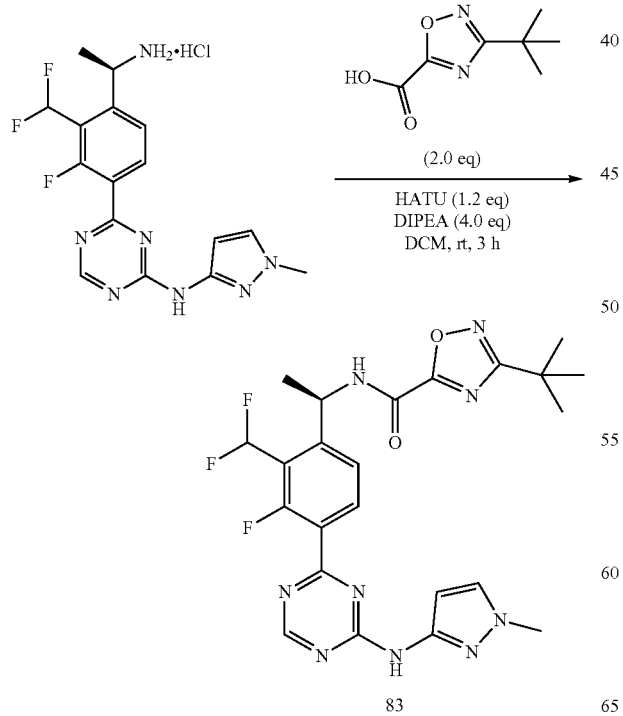

83

Synthesis of (R)-3-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-5-carboxamide was similar to that of (R)-3-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-5-carboxamide in Example 70. The crude material was purified by prep-HPLC (CH$_3$CN/H$_2$O with 0.05% HCl/H$_2$O as mobile phase) to give the HCl salt of (R)-3-(tert-butyl)-N-(1-(2-(difluoromethyl)-3-fluoro-4-(4-((1-methyl-1H-pyrazol-3-yl)amino)-1,3,5-triazin-2-yl)phenyl)ethyl)-1,2,4-oxadiazole-5-carboxamide as a white solid (45 mg, yield: 54%). ESI-MS (M+H)$^+$: 516.2. $^1$H NMR (500 MHz, DMSO-d$_6$, t=80° C.) δ: 10.18 (s, 1H), 9.60 (s, 1H), 8.79-8.78 (m, 1H), 8.22 (t, J=8.0 Hz, 1H), 7.68 (d, J=8.0 Hz, 1H), 7.58-7.48 (m, 2H), 6.63 (d, J=1.5 Hz, 1H), 5.65-5.59 (m, 1H), 3.80 (s, 3H), 1.61 (d, J=6.5 Hz, 3H), 1.40 (s, 9H).

Example 84: (R)-5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide (Compound 84)

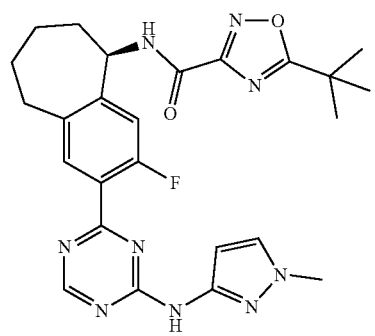

84

1. Synthesis of (E)-5-(4-fluoro-3-methoxyphenyl)pent-4-enal

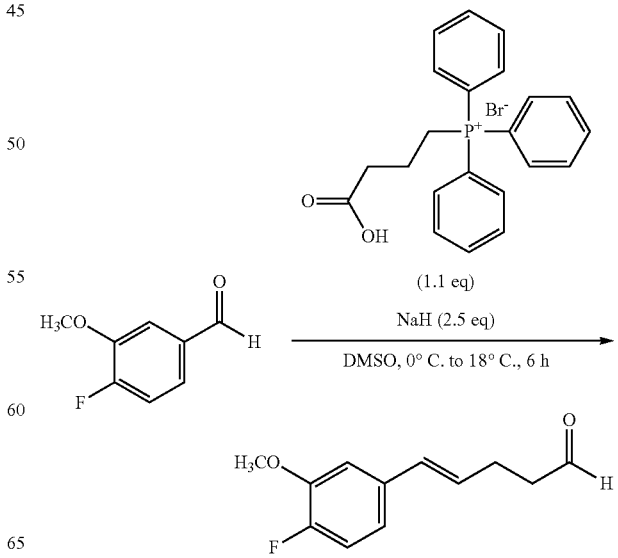

To a solution of (3-carboxypropyl)triphenylphosphonium bromide (79 g, 186 mmol) in dry DMSO (900 mL) in an ice-water cooling bath at 0° C. was added NaH (16.9 g, 422 mmol, 60% in oil) in portions. The cooling bath was removed and the reaction mixture was stirred at 18° C. for 1 h.

A solution of 4-fluoro-3-methoxybenzaldehyde (26 g, 169 mmol) in DMSO (100 mL) was added dropwise into the reaction mixture and the reaction mixture continued to stir at 18° C. for 5 h. The reaction mixture was poured into H₂O (2 L). The aqueous phase was extracted with EtOAc (400 mL). The organic layer was separated, and the aqueous solution was treated with a concentrated HCl solution (36 wt %) until pH=5. The aqueous phase was extracted with EtOAc (700 mL×2). The combined organic layers were concentrated in vacuo to give crude material. The crude product was purified by silica-gel column chromatography (petroleum ether/EtOAc, grading from 6:1 to 1:1) to give (E)-5-(4-fluoro-3-methoxyphenyl)pent-4-enal as a pale white solid (21.2 g, yield: 56%). $^1$H NMR (DMSO-d$_6$, 400 MHz) δ: 12.18 (br, 1H), 7.35-7.08 (m, 2H), 6.88-6.81 (m, 1H), 6.38-5.57 (m, 2H), 3.81 (s, 3H), 2.48-2.46 (m, 2H), 2.36-2.34 (m, 2H).

2. Synthesis of 5-(4-fluoro-3-methoxyphenyl)pentanal

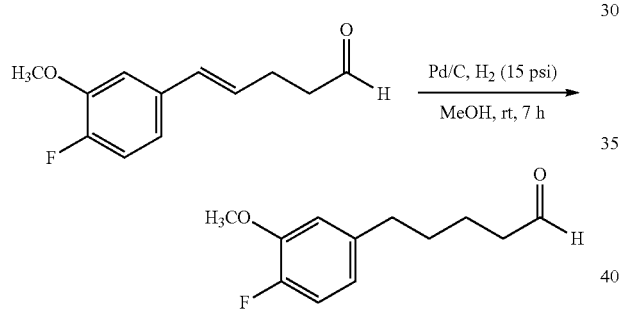

To a solution of (E)-5-(4-fluoro-3-methoxyphenyl)pent-4-enal (21.2 g, 95 mmol) in MeOH (350 mL) was added Pd/C (3 g, 10 wt %) at ambient temperature. The reaction mixture was stirred under an atmosphere of H₂ (15 psi) for 7 h. The suspension was filtered, and the filtrate was concentrated in vacuo to give 5-(4-fluoro-3-methoxyphenyl)pentanal as a white solid (20 g, yield: 94%), which was carried forward without further purification. $^1$H NMR (400 MHz, DMSO-d$_6$) δ: 7.06-7.01 (m, 1H), 6.96-6.94 (m, 1H), 6.69-6.67 (m, 1H), 3.78 (s, 3H), 2.54-2.50 (m, 2H), 2.20-2.18 (m, 2H), 1.56-1.47 (m, 4H).

3. Synthesis of 3-fluoro-2-methoxy-6,7,8,9-tetrahydro-5H-benzo[7]annulen-5-one

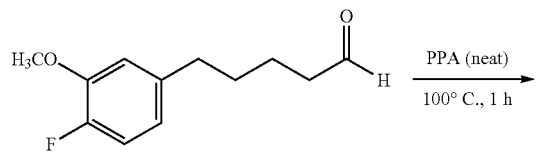

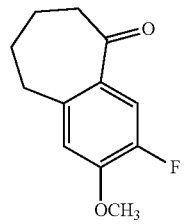

5-(4-Fluoro-3-methoxyphenyl)pentanal (20 g, 88.5 mmol) was added into polyphosphoric acid (80 mL) at ambient temperature. The reaction mixture was heated to 100° C. and stirred at that temperature for 1 h. The reaction mixture was cooled to ambient temperature and poured into H₂O (600 mL). The acidic aqueous phase was neutralized with Na₂CO₃ until pH=7. The aqueous phase was extracted with EtOAc (300 mL×3). The combined organic extracts were concentrated in vacuo to give crude material. The crude product was purified by silica-gel column chromatography (petroleum ether/EtOAc, grading from 8:1 to 3:1) to give 3-fluoro-2-methoxy-6,7,8,9-tetrahydro-5H-benzo[7]annulen-5-one as a light brown solid (15 g, yield: 82%). $^1$H NMR (400 MHz, CDCl$_3$) δ: 7.59 (d, J=12.0 Hz, 1H), 6.79 (d, J=7.6 Hz, 1H), 3.98 (s, 3H), 2.97-2.94 (m, 2H), 2.78-2.75 (m, 2H), 1.94-1.83 (m, 4H).

4. Synthesis of 3-fluoro-2-hydroxy-6,7,8,9-tetrahydro-5H-benzo[7]annulen-5-one

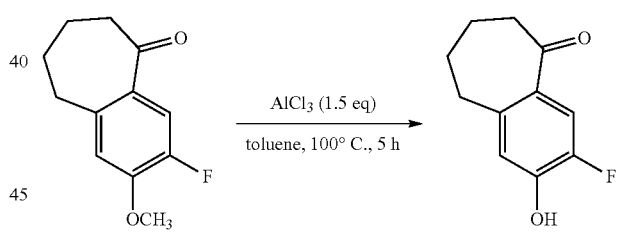

To a solution of 3-fluoro-2-methoxy-6,7,8,9-tetrahydro-5H-benzo[7]annulen-5-one (11.9 g, 57 mmol) in toluene (450 mL) was added AlCl₃ (11.4 g, 86 mmol) at ambient temperature. The reaction mixture was heated to 100° C. under N₂ for 5 h. The reaction mixture was cooled to ambient temperature and poured into an aqueous HCl solution (500 mL, 3 M). The aqueous phase was extracted with EtOAc (200 mL×3). The combined organic extracted were dried (Na₂SO₄), filtered, and concentrated in vacuo to give crude material. The crude product was purified by silica-gel column chromatography (petroleum ether/EtOAc, grading from 7:1 to 2:1) to give 3-fluoro-2-hydroxy-6,7,8,9-tetrahydro-5H-benzo[7]annulen-5-one as a gray solid (8.9 g, yield: 80%). $^1$H NMR (400 MHz, CDCl$_3$) δ: 7.57 (d, J=11.2 Hz, 1H), 6.84 (d, J=8.4 Hz, 1H), 6.15 (br, 1H), 2.88-2.85 (m, 2H), 2.74-2.71 (m, 2H), 1.87-1.78 (m, 4H).

5. Synthesis of (S,E)-N-(3-fluoro-2-hydroxy-6,7,8,9-tetrahydro-5H-benzo[7]annulen-5-ylidene)-2-methylpropane-2-sulfinamide

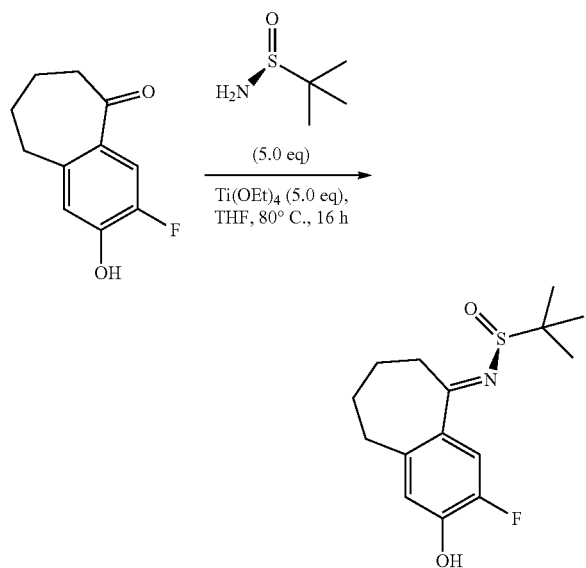

To a solution of 3-fluoro-2-hydroxy-6,7,8,9-tetrahydro-5H-benzo[7]annulen-5-one (8.9 g, 46 mmol) and (S)-2-methylpropane-2-sulfinamide (27.7 g, 229 mmol) in THF (450 mL) was added Ti(OEt)$_4$ (52.2 g, 229 mmol) at ambient temperature. The reaction mixture was heated to 80° C. and stirred at that temperature for 16 h. The reaction mixture was cooled to ambient temperature and concentrated in vacuo. The reaction residue was poured into H$_2$O (500 mL) and the aqueous phase was extracted with EtOAc (200 mL×4). The combined organic extracts were dried (Na$_2$SO$_4$), filtered, and concentrated in vacuo to give crude material. The crude product was purified by silica-gel column chromatography (petroleum ether/EtOAc, grading from 7:1 to 2:1) to give (S,E)-N-(3-fluoro-2-hydroxy-6,7,8,9-tetrahydro-5H-benzo[7]annulen-5-ylidene)-2-methylpropane-2-sulfinamide as a gray solid (10.6 g, yield: 78%). $^1$H NMR (400 MHz, DMSO-d$_6$) δ: 10.38 (br, 1H), 7.27 (d, J=12.0 Hz, 1H), 6.79 (d, J=8.4 Hz, 1H), 3.15-3.09 (m, 1H), 2.91-2.87 (m, 1H), 2.73-2.71 (m, 2H), 1.73-1.57 (m, 4H), 1.17 (s, 9H).

6. Synthesis of (S)—N—((R)-3-fluoro-2-hydroxy-6,7,8,9-tetrahydro-5H-benzo[7]annulen-5-yl)-2-methylpropane-2-sulfinamide

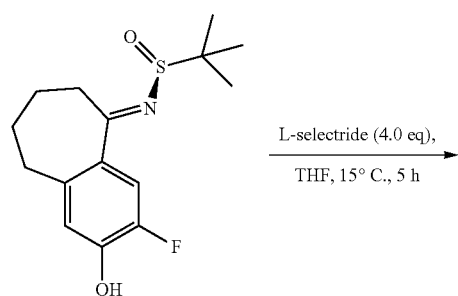

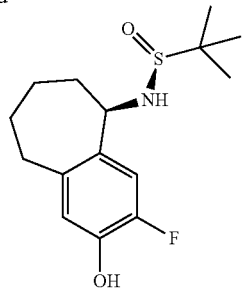

To a solution of (S,E)-N-(3-fluoro-2-hydroxy-6,7,8,9-tetrahydro-5H-benzo[7]annulen-5-ylidene)-2-methylpropane-2-sulfinamide 4 (2.98 g, 10 mmol) in THF (50 mL) at 15° C. was added dropwise L-selectride (40 mL, 40 mmol). The reaction mixture continued to stir at 15° C. for 5 h. The reaction mixture was concentrated in vacuo and the residue was poured into H$_2$O (450 mL). The aqueous phase was extracted with EtOAc (150 mL×3). The combined organic extracts were dried (Na$_2$SO$_4$), filtered, and concentrated in vacuo to give crude material. The crude product was purified by silica-gel column chromatography (petroleum ether/EtOAc, grading from 5:2 to 1:3) to give (S)—N—((R)-3-fluoro-2-hydroxy-6,7,8,9-tetrahydro-5H-benzo[7]annulen-5-yl)-2-methylpropane-2-sulfinamide as a white solid (700 mg, yield: 23%). $^1$H NMR (400 MHz, DMSO-d$_6$) δ: 9.58 (br, 1H), 7.13 (d, J=12.8 Hz, 1H), 6.65 (d, J=9.2 Hz, 1H), 5.25 (d, J=5.2 Hz, 1H), 4.31-4.27 (m, 1H), 2.74-2.69 (m, 1H), 2.59-2.53 (m, 1H), 1.91-1.88 (m, 2H), 1.76-1.42 (m, 3H), 1.38-1.36 (m, 1H), 1.15 (s, 9H).

7. Synthesis of (R)-5-amino-3-fluoro-6,7,8,9-tetrahydro-5H-benzo[7]annulen-2-ol

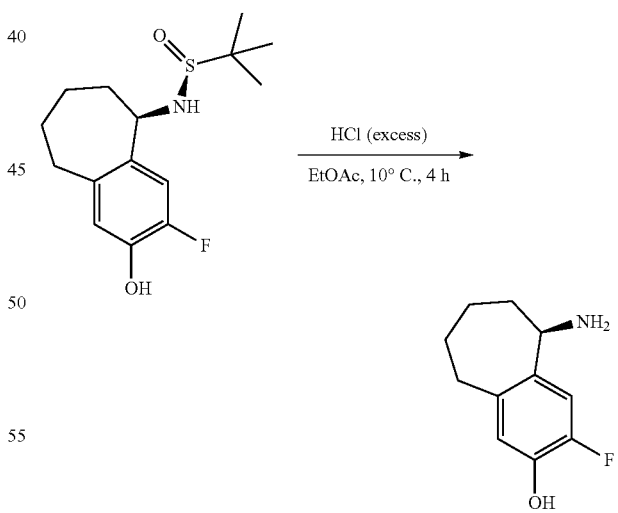

(S)—N—((R)-3-Fluoro-2-hydroxy-6,7,8,9-tetrahydro-5H-benzo[7]annulen-5-yl)-2-methylpropane-2-sulfinamide (700 mg, 2.34 mmol) was added into an HCl solution (25 mL, 2 M in EtOAc) at 10° C. The reaction mixture was stirred at that temperature for 4 h. The suspension was filtered and the filter cake was dried in vacuo to give the HCl salt of (R)-5-amino-3-fluoro-6,7,8,9-tetrahydro-5H-benzo[7]annulen-2-ol as a gray solid (520 mg, yield: 96%). $^1$H NMR (400 MHz, DMSO-$d_6$) δ: 9.93 (br, 1H), 8.53 (br, 2H), 6.96 (d, J=12.8 Hz, 1H), 6.78 (d, J=8.8 Hz, 1H), 4.36-4.34 (m, 1H), 2.72-2.63 (m, 2H), 1.98-1.84 (m, 2H), 1.73-1.68 (m, 2H), 1.55-1.52 (m, 1H), 1.24-1.22 (m, 1H).

8. Synthesis of tert-butyl (R)-(3-fluoro-2-hydroxy-6,7,8,9-tetrahydro-5H-benzo[7]annulen-5-yl)carbamate

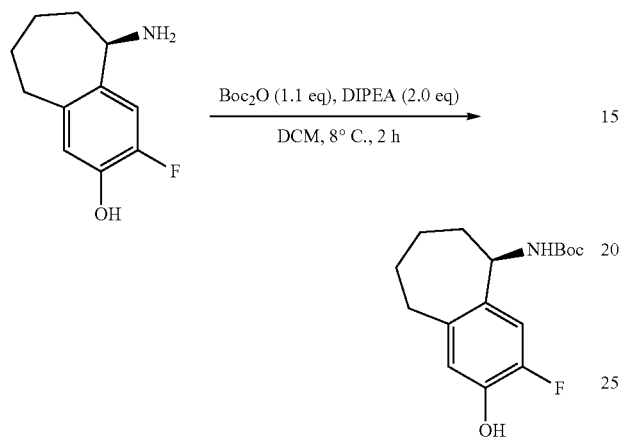

To a solution of the HCl salt of (R)-5-amino-3-fluoro-6,7,8,9-tetrahydro-5H-benzo[7]annulen-2-ol (520 mg, 2.25 mmol) and DIPEA (581 mg, 4.5 mmol) in DCM (15 mL) at 8° C. was added (Boc)$_2$O (539 mg, 2.5 mmol). The reaction mixture was stirred at 8° C. for 2 h. The reaction mixture was concentrated in vacuo to give crude material. The crude product was purified by silica-gel column chromatography (petroleum ether/EtOAc, grading from 15:1 to 3:1) to give tert-butyl (R)-(3-fluoro-2-hydroxy-6,7,8,9-tetrahydro-5H-benzo[7]annulen-5-yl)carbamate as a white solid (530 mg, yield: 80%). $^1$H NMR (400 MHz, DMSO-$d_6$) δ: 9.49 (br, 1H), 7.42 (d, J=8.0 Hz, 1H), 6.81 (d, J=13.2 Hz, 1H), 6.66 (d, J=8.8 Hz, 1H), 4.55-4.51 (m, 1H), 2.63-2.61 (m, 2H), 1.77-1.45 (m, 5H), 1.38 (s, 9H), 1.21-1.15 (m, 1H).

9. Synthesis of (R)-5-((tert-butoxycarbonyl)amino)-3-fluoro-6,7,8,9-tetrahydro-5H-benzo[7]annulen-2-yl trifluoromethanesulfonate

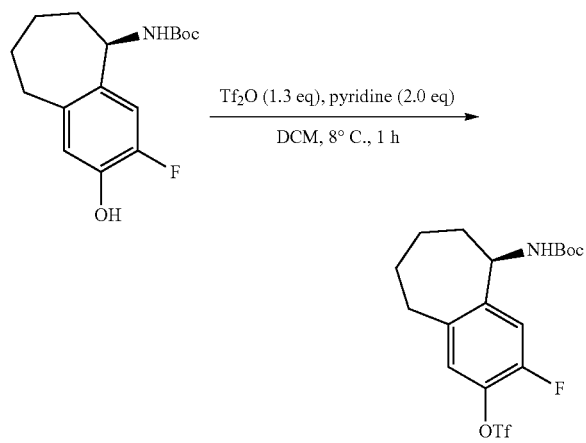

To a solution of tert-butyl (R)-(3-fluoro-2-hydroxy-6,7,8,9-tetrahydro-5H-benzo[7]annulen-5-yl)carbamate (530 mg, 1.79 mmol) and pyridine (283 mg, 3.58 mmol) in DCM (25 mL) at 8° C. was added Tf$_2$O (656 mg, 2.33 mmol). The reaction mixture was stirred at 8° C. for 1 h. The reaction mixture was concentrated in vacuo to give crude material. The crude product was purified by silica-gel column chromatography (petroleum ether/EtOAc, grading from 15:1 to 5:1) to give (R)-5-((tert-butoxycarbonyl)amino)-3-fluoro-6,7,8,9-tetrahydro-5H-benzo[7]annulen-2-yl trifluoromethanesulfonate as a white solid (540 mg, yield: 71%). ESI-MS (M+H−56+41)$^+$: 413.1.

10. Synthesis of tert-butyl (R)-(3-fluoro-2-(4,4,5,5-tetramethyl-1,3,2-dioxaborolan-2-yl)-6,7,8,9-tetrahydro-5H-benzo[7]annulen-5-yl)carbamate

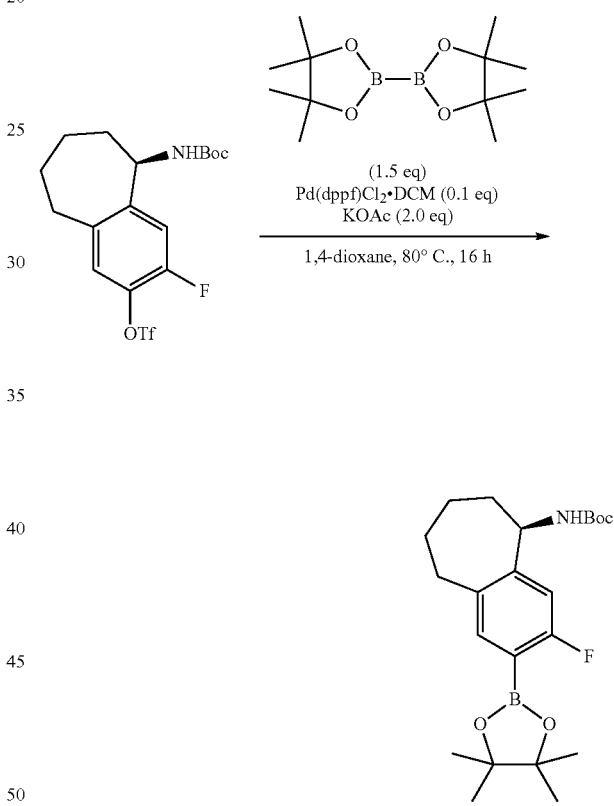

To a solution of (R)-5-((tert-butoxycarbonyl)amino)-3-fluoro-6,7,8,9-tetrahydro-5H-benzo[7]annulen-2-yl trifluoromethanesulfonate (540 mg, 1.3 mmol) and bis(pinacolato)diboron (480 mg, 1.9 mmol) in 1,4-dioxane (15 mL) at 8° C. was added Pd(dppf)Cl$_2$.DCM (82 mg, 0.1 mmol) and KOAc (247 mg, 2.5 mmol). The reaction mixture was heated to 80° C. and stirred at that temperature under an atmosphere of nitrogen for 16 h. The reaction mixture was cooled to ambient temperature and concentrated in vacuo to give crude material. The crude product was purified by silica-gel column chromatography (petroleum ether/EtOAc, grading from 15:1 to 5:1) to give tert-butyl (R)-(3-fluoro-2-(4,4,5,5-tetramethyl-1,3,2-dioxaborolan-2-yl)-6,7,8,9-tetrahydro-5H-benzo[7]annulen-5-yl)carbamate as a white solid (408 mg, yield: 80%). ESI-MS (M+H−56)$^+$: 350.1.

11. Synthesis of tert-butyl (R)-(3-fluoro-2-(4-((1-methyl-1H-pyrazol-3-yl)amino)-1,3,5-triazin-2-yl)-6,7,8,9-tetrahydro-5H-benzo[7]annulen-5-yl)carbamate

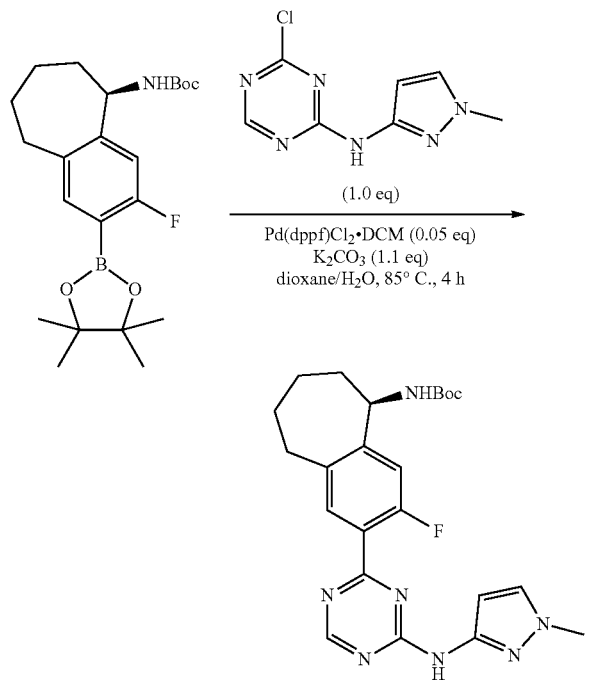

A mixture of tert-butyl (R)-(3-fluoro-2-(4,4,5,5-tetramethyl-1,3,2-dioxaborolan-2-yl)-6,7,8,9-tetrahydro-5H-benzo[7]annulen-5-yl)carbamate (240 mg, 0.59 mmol), 4-chloro-N-(1-methyl-1H-pyrazol-3-yl)-1,3,5-triazin-2-amine (125 mg, 0.59 mmol), Pd(dppf)Cl$_2$.DCM (21 mg, 0.03 mmol), K$_2$CO$_3$ (90 mg, 0.65 mmol) in 1,4-dioxane (10 mL) and H$_2$O (2 mL) was heated to 85° C. under an atmosphere of nitrogen and stirred at that temperature for 4 h. The reaction mixture was cooled to ambient temperature, concentrated in vacuo, and the residue was purified by silica-gel column chromatography (petroleum ether/EtOAc, 1:1) to give tert-butyl (R)-(3-fluoro-2-(4-((1-methyl-1H-pyrazol-3-yl)amino)-1,3,5-triazin-2-yl)-6,7,8,9-tetrahydro-5H-benzo[7]annulen-5-yl)carbamate as a brown solid (166 mg, yield: 62%). ESI-MS (M+H)$^+$: 454.2.

12. Synthesis of (R)-4-(5-amino-3-fluoro-6,7,8,9-tetrahydro-5H-benzo[7]annulen-2-yl)-N-(1-methyl-1H-pyrazol-3-yl)-1,3,5-triazin-2-amine

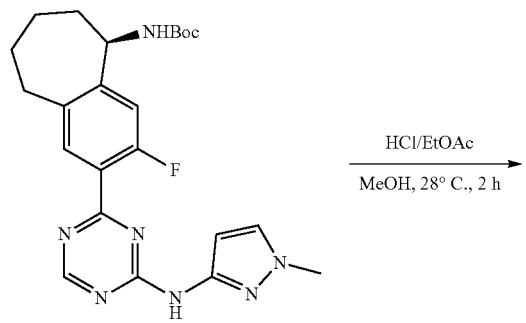

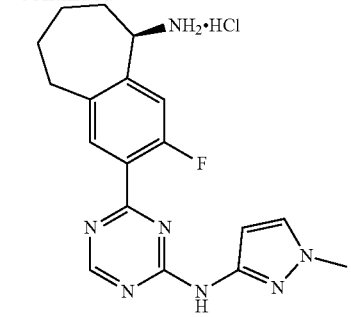

To a solution of tert-butyl (R)-(3-fluoro-2-(4-((1-methyl-1H-pyrazol-3-yl)amino)-1,3,5-triazin-2-yl)-6,7,8,9-tetrahydro-5H-benzo[7]annulen-5-yl)carbamate (166 mg, 0.36 mmol) in MeOH (5 mL) was added an HCl solution (5 mL, 4 M in EtOAc). The reaction mixture was heated to 28° C. and was stirred at that temperature for 2 h. The reaction mixture was concentrated in vacuo and the residue was triturated with a mixture of petroleum ether and EtOAc (50 mL, 10:1). The remaining solid was dried in vacuo to provide the HCl salt of (R)-4-(5-amino-3-fluoro-6,7,8,9-tetrahydro-5H-benzo[7]annulen-2-yl)-N-(1-methyl-1H-pyrazol-3-yl)-1,3,5-triazin-2-amine as a brown solid (135 mg, yield: 95%), which was carried forward without further purification. ESI-MS (M+H)$^+$: 354.1.

13. Synthesis of (R)-5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide (Compound 84)

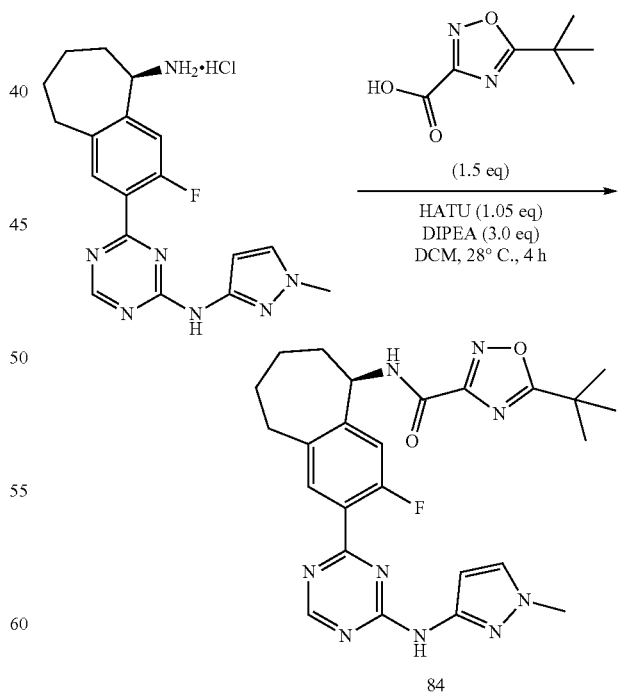

A mixture of (R)-4-(5-amino-3-fluoro-6,7,8,9-tetrahydro-5H-benzo[7]annulen-2-yl)-N-(1-methyl-1H-pyrazol-3-yl)-1,3,5-triazin-2-amine hydrochloride (60 mg, 0.15 mmol)

and DIPEA (60 mg, 0.46 mmol, 81 μL) in DCM (30 mL) was stirred at 28° C. until the solution turned clear. Then, 5-(tert-butyl)-1,2,4-oxadiazole-3-carboxylic acid (39 mg, 0.23 mmol) was added, followed by portion-wise addition of HATU (62 mg, 0.16 mmol). The reaction mixture continued to stir at 28° C. for 4 h. Water (20 mL) was added and the layers were separated. The organic phase was dried (Na₂SO₄), filtered, and concentrated in vacuo. The residue was purified by preparative TLC (petroleum ether/EtOAc, 1:2) to provide a crude material. The crude material was purified by prep-HPLC (CH₃CN/H₂O with 0.05% HCl/H₂O as mobile phase) to give the HCl salt of (R)-5-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide as an off-white solid (11.5 mg, yield: 15%). ESI-MS (M+Na)⁺: 528.2. ¹H NMR (500 MHz, DMSO-d₆, t=80° C.) δ:10.15 (s, 1H), 9.17 (d, J=8.0 Hz, 1H), 8.76 (s, 1H), 7.91 (d, J=8.0 Hz, 1H), 7.57 (s, 1H), 7.15 (d, J=12.5 Hz, 1H), 6.68 (s, 1H), 5.32-5.27 (m, 1H), 3.79 (s, 3H), 2.97-2.92 (m, 2H), 2.06-1.79 (m, 5H), 1.44-1.38 (m, 10H).

Example 85: (R)-3-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide (Compound 85)

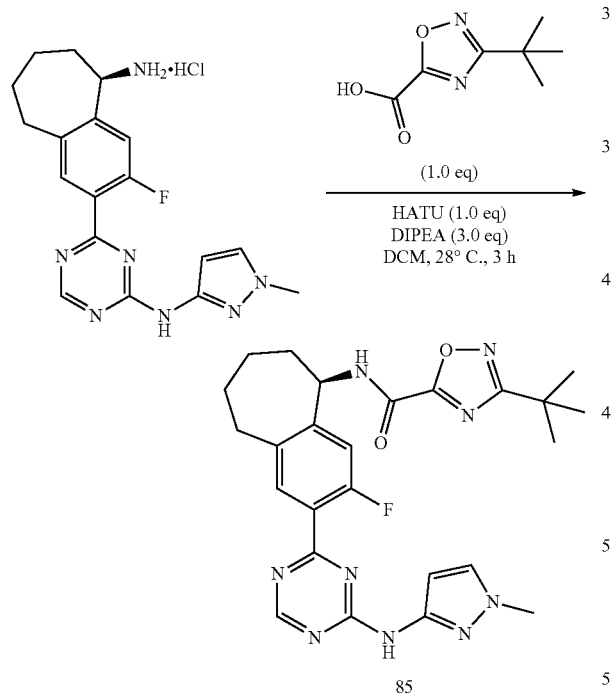

Synthesis of (R)-3-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide was similar to that of (R)-5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide in Example 84, Step 13. The crude material was purified by prep-HPLC (CH₃CN/H₂O with 0.05% HCl/H₂O as mobile phase) to give the HCl salt of (R)-3-(tert-butyl)-N-(3-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide as an off-white solid (12 mg, yield: 11%). ESI-MS (M+Na)⁺: 528.2. ¹H NMR (500 MHz, DMSO-d₆, t=80° C.) δ: 10.16 (s, 1H), 9.58 (s, 1H), 8.76 (s, 1H), 7.91 (s, d, J=7.5 Hz, 1H), 7.57 (s, 1H), 7.15 (d, J=12.5 Hz, 1H), 6.68 (s, 1H), 5.30-5.26 (m, 1H), 3.79 (s, 3H), 2.97-2.92 (m, 2H), 2.06-1.79 (m, 5H), 1.44-1.39 (m, 10H).

Example 86: (R)-5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide (Compound 86)

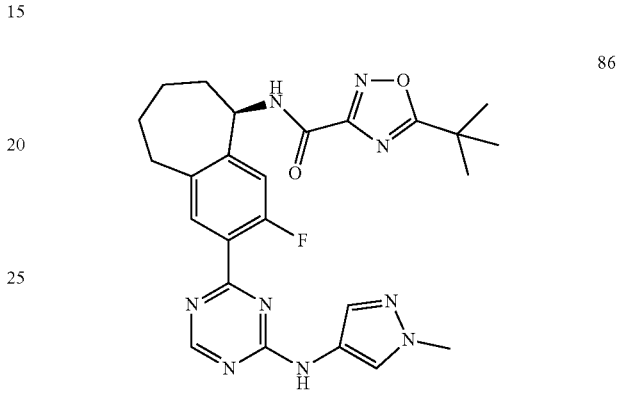

1. Synthesis of tert-butyl (R)-(3-fluoro-2-(4-((1-methyl-1H-pyrazol-4-yl)amino)-1,3,5-triazin-2-yl)-6,7,8,9-tetrahydro-5H-benzo[7]annulen-5-yl)carbamate

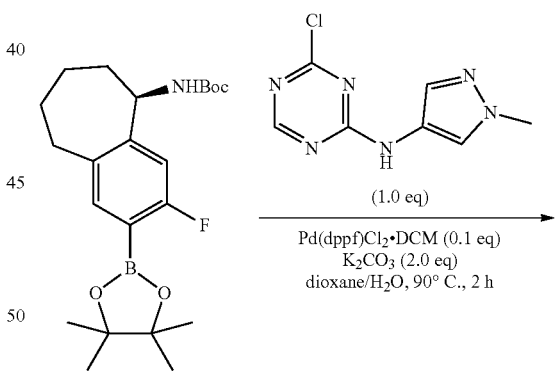

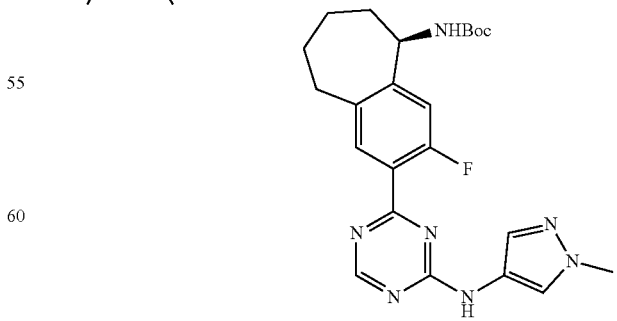

Synthesis of tert-butyl (R)-(3-fluoro-2-(4-((1-methyl-1H-pyrazol-4-yl)amino)-1,3,5-triazin-2-yl)-6,7,8,9-tetrahydro- 5H-benzo[7]annulen-5-yl)carbamate was similar to that of tert-butyl (R)-(3-fluoro-2-(4-((1-methyl-1H-pyrazol-3-yl)amino)-1,3,5-triazin-2-yl)-6,7,8,9-tetrahydro-5H-benzo[7]annulen-5-yl)carbamate in Example 84, Step 11. The crude material was purified by silica-gel column chromatography (petroleum ether/EtOAc, grading from 1:0 to 1:1) to give tert-butyl (R)-(3-fluoro-2-(4-((1-methyl-1H-pyrazol-4-yl)amino)-1,3,5-triazin-2-yl)-6,7,8,9-tetrahydro-5H-benzo[7]annulen-5-yl)carbamate as a white solid (110 mg, yield: 66%). ESI-MS (M+H)$^+$: 454.2.

2. Synthesis of (R)-4-(5-amino-3-fluoro-6,7,8,9-tetrahydro-5H-benzo[7]annulen-2-yl)-N-(1-methyl-1H-pyrazol-4-yl)-1,3,5-triazin-2-amine

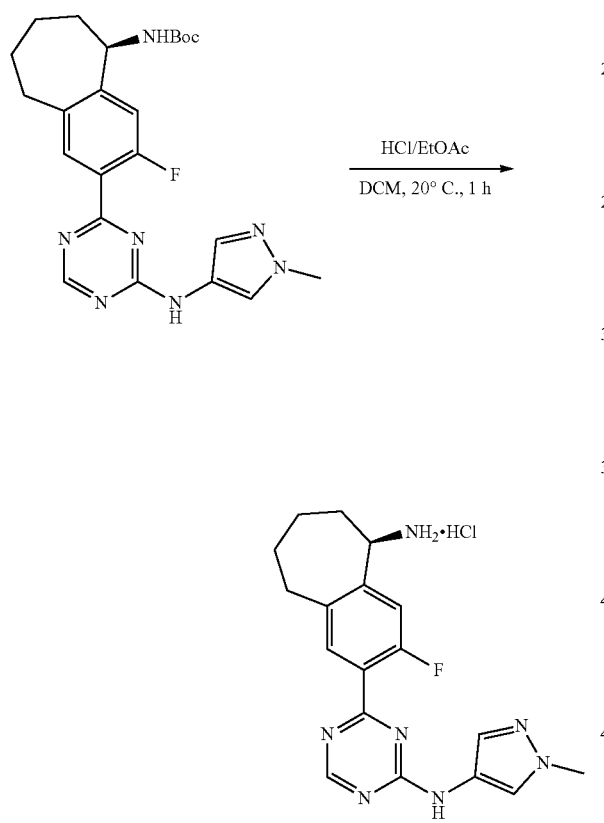

To a solution of tert-butyl (R)-(3-fluoro-2-(4-((1-methyl-1H-pyrazol-4-yl)amino)-1,3,5-triazin-2-yl)-6,7,8,9-tetrahydro-5H-benzo[7]annulen-5-yl)carbamate (110 mg, 0.24 mmol) in DCM (8 mL) was added an HCl solution (5 mL, 4 M in EtOAc) and the mixture was stirred at 20° C. for 1 h. The reaction mixture was concentrated in vacuo to give the HCl salt of (R)-4-(5-amino-3-fluoro-6,7,8,9-tetrahydro-5H-benzo[7]annulen-2-yl)-N-(1-methyl-1H-pyrazol-4-yl)-1,3,5-triazin-2-amine (100 mg, crude), which was carried forward without further purification. ESI-MS (M+H)$^+$: 354.1.

3. Synthesis of (R)-5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide (Compound 86)

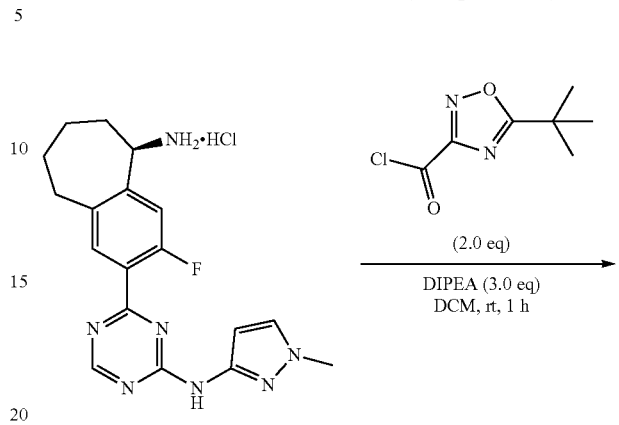

Synthesis of (R)-5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide was similar to that of (R)-5-(tert-butyl)-N-(1-(2-chloro-3-fluoro-4-(4-((1-methyl-1H-pyrazol-4-yl)amino)-1,3,5-triazin-2-yl)phenyl)ethyl)-1,2,4-oxadiazole-3-carboxamide in Example 69, Step 11. The crude material was purified by prep-HPLC (CH$_3$CN/H$_2$O with 0.05% HCl/H$_2$O as mobile phase) to give the HCl salt of (R)-5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide as a white solid (51 mg, yield: 40%). ESI-MS (M+Na)$^+$: 528.2. $^1$H NMR (500 MHz, DMSO-d$_6$, t=80° C.) δ: 10.02 (s, 1H), 9.18 (s, 1H), 8.74 (s, 1H), 7.94 (s, 2H), 7.64 (s, 1H), 7.17 (d, J=12.5 Hz, 1H), 5.32-5.29 (m, 1H), 3.84 (s, 3H), 2.97-2.95 (m, 2H), 2.03-1.80 (m, 5H), 1.50 (s, 9H), 1.43-1.37 (m, 1H).

259

Example 87: (R)-3-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-5-carboxamide (Compound 87)

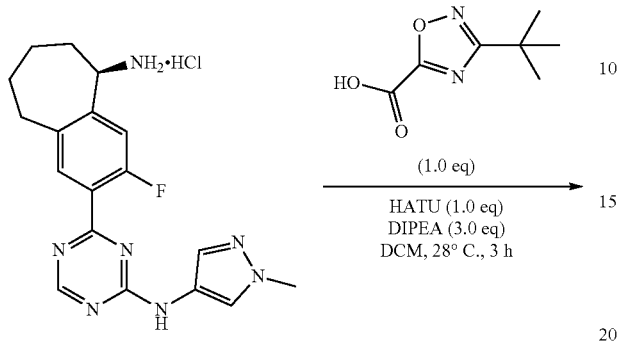

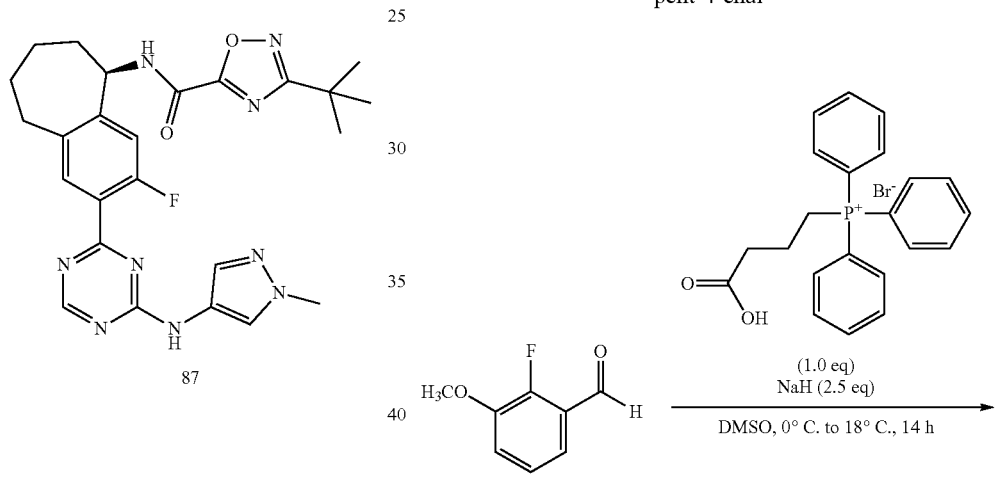

Synthesis of (R)-3-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-5-carboxamide was similar to that of (R)-5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide in Example 84, Step 13. The crude material was purified by prep-HPLC (CH$_3$CN/H$_2$O with 0.05% HCl/H$_2$O as mobile phase) to give the HCl salt of (R)-3-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-5-carboxamide as a yellow solid (21 mg, yield: 16%). ESI-MS (M+Na)$^+$: 528.2. $^1$H NMR (500 MHz, DMSO-d$_6$, t=80° C.) δ: 9.99 (s, 1H), 9.57 (d, J=8.0 Hz, 1H), 8.74 (s, 1H), 7.93 (s, 2H), 7.63 (s, 1H), 7.19 (d, J=12.5 Hz, 1H), 5.31-5.27 (m, 1H), 3.84 (s, 3H), 2.97-2.92 (m, 2H), 2.06-1.79 (m, 5H), 1.44-1.39 (m, 10H).

260

Example 88: (R)-5-(tert-butyl)-N-(1-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide (Compound 88)

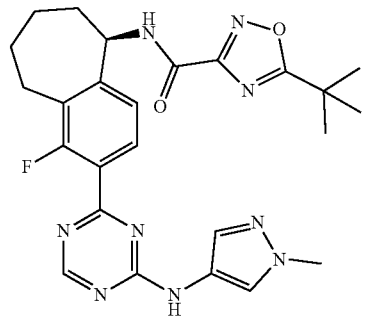

88

1. Synthesis of (E)-5-(2-fluoro-3-methoxyphenyl)pent-4-enal

Synthesis of (E)-5-(2-fluoro-3-methoxyphenyl)pent-4-enal was similar to that of (E)-5-(4-fluoro-3-methoxyphenyl)pent-4-enal in Example 84, Step 1. The crude product was purified by silica-gel column chromatography (petroleum ether/EtOAc, grading from 5:1 to 1:1) to give (E)-5-(2-fluoro-3-methoxyphenyl)pent-4-enal as a yellow oil (22.0 g, yield: 76%). $^1$H NMR (400 MHz, CDCl$_3$) δ: 11.27 (br s, 1H), 7.10-7.00 (m, 1.5H), 6.90-6.80 (m, 1.5H), 6.70-6.60 (m, 0.5H), 6.50-6.40 (m, 0.5H), 6.40-6.30 (m, 0.5H), 5.80-5.70 (m, 0.5H), 3.90-3.85 (m, 3H), 2.60-2.40 (m, 4H). Note: it was cis-trans isomerism.

2. Synthesis of 5-(2-fluoro-3-methoxyphenyl)pentanal

4. Synthesis of 1-fluoro-2-hydroxy-6,7,8,9-tetrahydro-5H-benzo[7]annulen-5-one

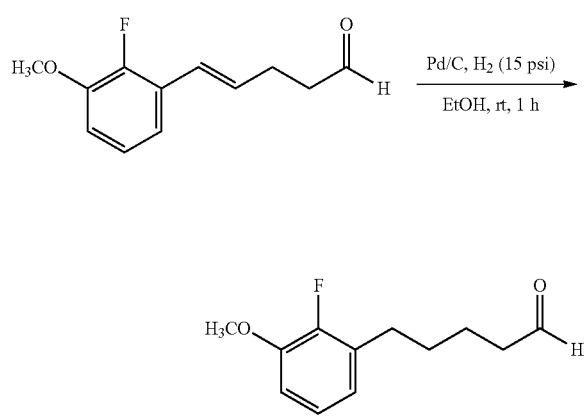

Synthesis of 5-(2-fluoro-3-methoxyphenyl)pentanal was similar to that of 5-(4-fluoro-3-methoxyphenyl)pentanal in Example 84, Step 2. The reaction mixture was filtered and the filtrate was concentrated in vacuo to give 5-(2-fluoro-3-methoxyphenyl)pentanal as an off-white solid (22.0 g, crude), which was carried forward without further purification. $^1$H NMR (400 MHz, DMSO-$d_6$) δ: 12.04 (br s, 1H), 7.10-6.90 (m, 2H), 6.80-6.70 (m, 1H), 3.80 (s, 3H), 2.58 (t, J=6.0 Hz, 2H), 2.22 (t, J=6.8 Hz, 2H), 1.10-0.90 (m, 4H).

3. Synthesis of 1-fluoro-2-methoxy-6,7,8,9-tetrahydro-5H-benzo[7]annulen-5-one

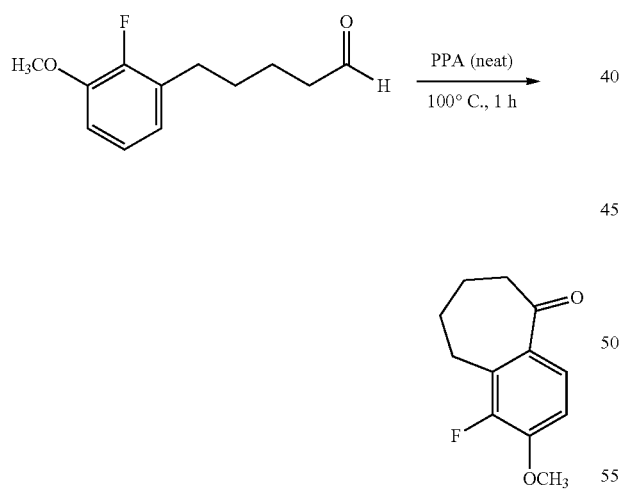

Synthesis of 1-fluoro-2-methoxy-6,7,8,9-tetrahydro-5H-benzo[7]annulen-5-one was similar to that of 3-fluoro-2-methoxy-6,7,8,9-tetrahydro-5H-benzo[7]annulen-5-one in Example 84, Step 3. The crude product was purified by silica-gel column chromatography (petroleum ether/EtOAc, 3:1) to give 1-fluoro-2-methoxy-6,7,8,9-tetrahydro-5H-benzo[7]annulen-5-one as a yellow oil (15 g, yield: 74%). $^1$H NMR (400 MHz, CDCl$_3$) δ: 7.58 (dd, J=8.8 Hz, 1.2 Hz, 1H), 6.89 (t, J=8.0 Hz, 1H), 3.94 (s, 3H), 3.01 (t, J=5.6 Hz, 2H), 2.73 (t, J=6.4 Hz, 2H), 1.90-1.60 (m, 4H).

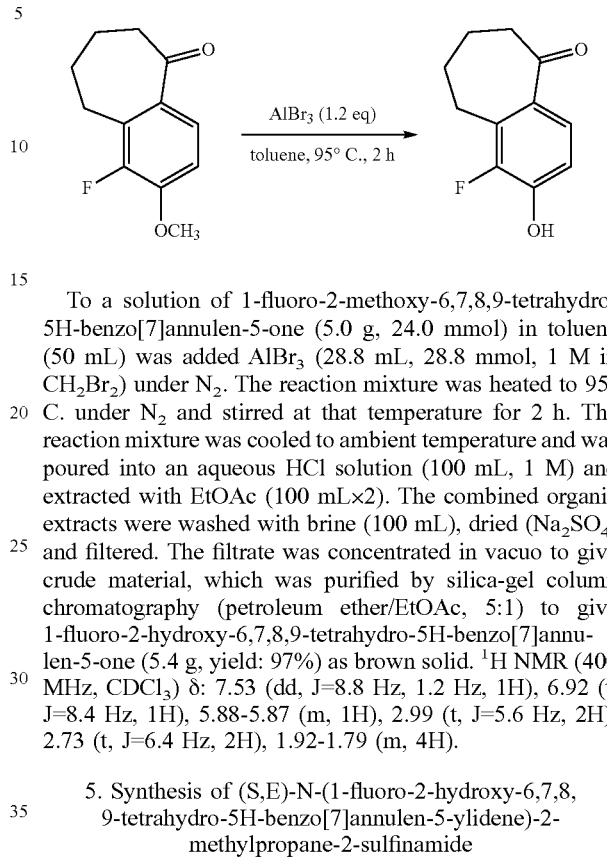

To a solution of 1-fluoro-2-methoxy-6,7,8,9-tetrahydro-5H-benzo[7]annulen-5-one (5.0 g, 24.0 mmol) in toluene (50 mL) was added AlBr$_3$ (28.8 mL, 28.8 mmol, 1 M in CH$_2$Br$_2$) under N$_2$. The reaction mixture was heated to 95° C. under N$_2$ and stirred at that temperature for 2 h. The reaction mixture was cooled to ambient temperature and was poured into an aqueous HCl solution (100 mL, 1 M) and extracted with EtOAc (100 mL×2). The combined organic extracts were washed with brine (100 mL), dried (Na$_2$SO$_4$) and filtered. The filtrate was concentrated in vacuo to give crude material, which was purified by silica-gel column chromatography (petroleum ether/EtOAc, 5:1) to give 1-fluoro-2-hydroxy-6,7,8,9-tetrahydro-5H-benzo[7]annulen-5-one (5.4 g, yield: 97%) as brown solid. $^1$H NMR (400 MHz, CDCl$_3$) δ: 7.53 (dd, J=8.8 Hz, 1.2 Hz, 1H), 6.92 (t, J=8.4 Hz, 1H), 5.88-5.87 (m, 1H), 2.99 (t, J=5.6 Hz, 2H), 2.73 (t, J=6.4 Hz, 2H), 1.92-1.79 (m, 4H).

5. Synthesis of (S,E)-N-(1-fluoro-2-hydroxy-6,7,8,9-tetrahydro-5H-benzo[7]annulen-5-ylidene)-2-methylpropane-2-sulfinamide Synthesis of (S,E)-N-(1-fluoro-2-hydroxy-6,7,8,9-tetrahydro-5H-benzo[7]annulen-5-ylidene)-2-methylpropane-2-sulfinamide was similar to that of (S,E)-N-(3-fluoro-2-hydroxy-6,7,8,9-tetrahydro-5H-benzo[7]annulen-5-ylidene)-2-methylpropane-2-sulfinamide in Example 84, Step 5. The crude product was purified by silica-gel column chromatography (petroleum ether/EtOAc, 5:1) to give (S,E)-N-(1-fluoro-2-hydroxy-6,7,8,9-tetrahydro-5H-benzo[7]annulen-5-ylidene)-2-methylpropane-2-sulfinamide as a yellow solid (6.0 g, yield: 78%). ¹H NMR (400 MHz, DMSO-d$_6$) δ:10.30 (s, 1H), 7.23 (d, J=8.4 Hz, 1H), 6.84 (t, J=8.4 Hz, 1H), 3.13-2.77 (m, 4H), 1.74-1.69 (m, 4H), 1.18 (s, 9H).

6. Synthesis of (S)—N—((R)-1-fluoro-2-hydroxy-6,7,8,9-tetrahydro-5H-benzo[7]annulen-5-yl)-2-methylpropane-2-sulfinamide

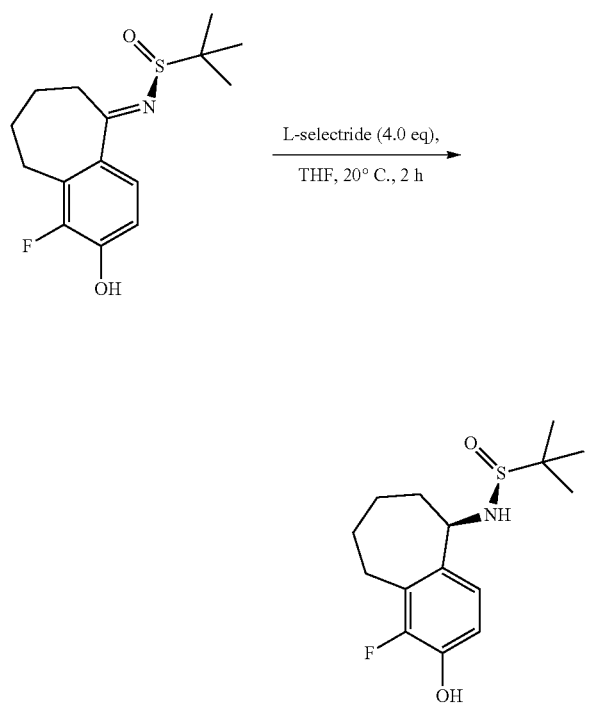 [SMILES: CC(C)(C)[S@](=O)/N=C1\CCCCc2cc(O)c(F)cc21 ; CC(C)(C)[S@](=O)N[C@@H]1CCCCc2cc(O)c(F)cc21]

To a solution of (S,E)-N-(1-fluoro-2-hydroxy-6,7,8,9-tetrahydro-5H-benzo[7]annulen-5-ylidene)-2-methylpropane-2-sulfinamide (2.0 g, 6.72 mmol) in THF (40 mL) at 20° C. was added dropwise L-selectride (26.9 mL, 26.9 mmol). The reaction mixture was stirred at 20° C. for 2 h. Saturated aqueous NH$_4$Cl solution (30 mL) was added and the reaction mixture was poured into H$_2$O (100 mL). The aqueous phase was extracted with EtOAc (100 mL×2) and the combined organic extracts were washed with brine (100 mL), dried (Na$_2$SO$_4$) and filtered. The filtrate was concentrated in vacuo and the crude material was purified by prep-HPLC (CH$_3$CN/H$_2$O with 0.05% NH$_4$OH as mobile phase) to give (S)—N—((R)-1-fluoro-2-hydroxy-6,7,8,9-tetrahydro-5H-benzo[7]annulen-5-yl)-2-methylpropane-2-sulfinamide as a white solid (500 mg, yield: 25%). ¹H NMR (400 MHz, DMSO-d$_6$) δ:9.56 (s, 1H), 6.86 (d, J=8.4 Hz, 1H), 6.65 (t, J=8.4 Hz, 1H), 5.14 (d, J=3.6 Hz, 1H), 4.34 (s, 1H), 2.87-2.65 (m, 2H), 1.92-1.48 (m, 6H), 1.11 (s, 9H).

7. Synthesis of (R)-5-amino-1-fluoro-6,7,8,9-tetrahydro-5H-benzo[7]annulen-2-ol

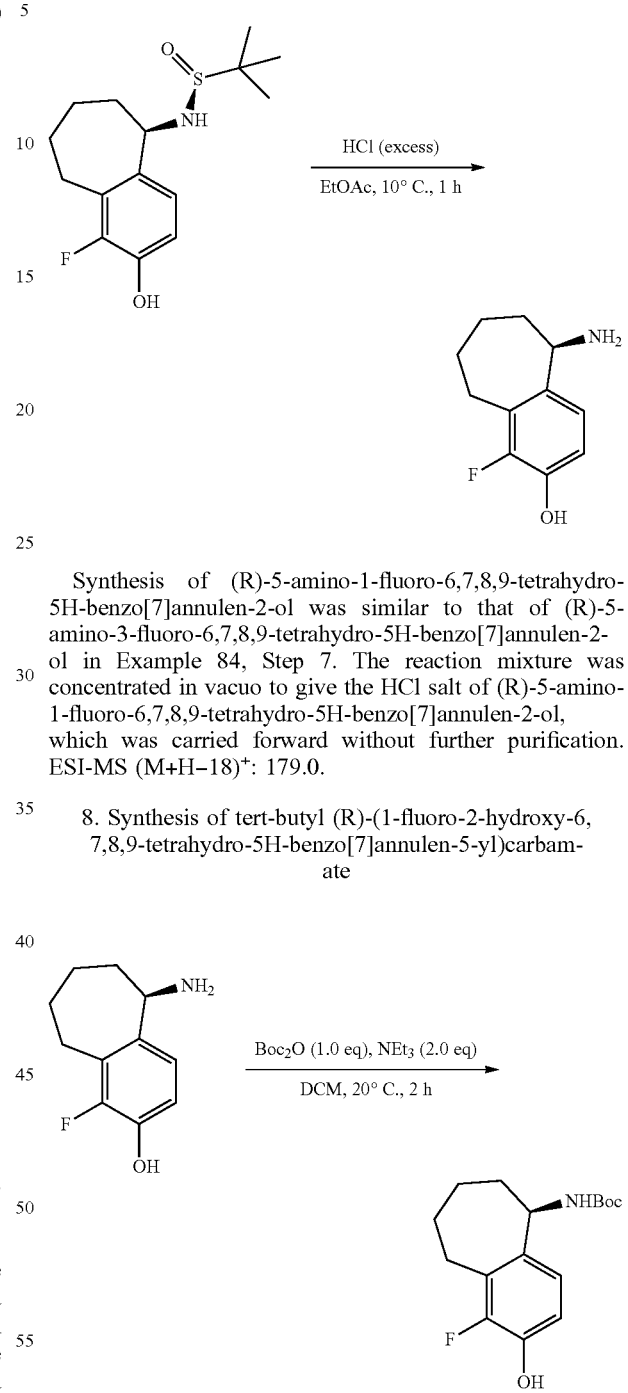

Synthesis of (R)-5-amino-1-fluoro-6,7,8,9-tetrahydro-5H-benzo[7]annulen-2-ol was similar to that of (R)-5-amino-3-fluoro-6,7,8,9-tetrahydro-5H-benzo[7]annulen-2-ol in Example 84, Step 7. The reaction mixture was concentrated in vacuo to give the HCl salt of (R)-5-amino-1-fluoro-6,7,8,9-tetrahydro-5H-benzo[7]annulen-2-ol, which was carried forward without further purification. ESI-MS (M+H−18)⁺: 179.0.

8. Synthesis of tert-butyl (R)-(1-fluoro-2-hydroxy-6,7,8,9-tetrahydro-5H-benzo[7]annulen-5-yl)carbamate To a solution of (R)-5-amino-1-fluoro-6,7,8,9-tetrahydro-5H-benzo[7]annulen-2-ol (360 mg, 1.84 mmol) in DCM (5 mL) was added Et$_3$N (373 mg, 3.69 mmol) and Boc$_2$O (402 mg, 1.84 mmol). The reaction mixture was stirred at 20° C. for 2 h. The reaction mixture was concentrated in vacuo to give crude material, which was purified by silica-gel column chromatography (petroleum ether/EtOAc, 20:1) to give tert-butyl (R)-(1-fluoro-2-hydroxy-6,7,8,9-tetrahydro-5H-benzo[7]annulen-5-yl)carbamate as a white solid (250 mg, yield:

46% over 2 steps). ESI-MS (M+H−18)$^+$: 281.0. $^1$H NMR (400 MHz, DMSO-d$_6$) δ:9.46 (s, 1H), 7.37 (d, J=7.6 Hz, 1H), 6.75 (d, J=8.4 Hz, 1H), 6.66 (t, J=8.0 Hz, 1H), 4.59 (t, J=8.8 Hz, 1H), 3.07-3.03 (m, 1H), 2.45-2.42 (m, 1H), 1.77-1.64 (m, 4H), 1.47-1.45 (m, 1H), 1.37 (s, 9H), 1.28-1.16 (m, 1H).

9. Synthesis of (R)-5-((tert-butoxycarbonyl)amino)-1-fluoro-6,7,8,9-tetrahydro-5H-benzo[7]annulen-2-yl trifluoromethanesulfonate

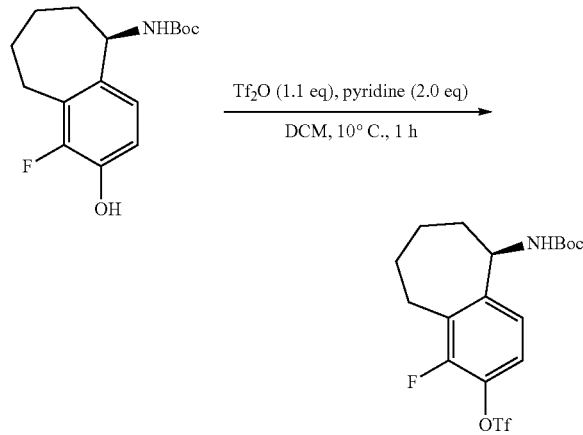

Synthesis of (R)-5-((tert-butoxycarbonyl)amino)-1-fluoro-6,7,8,9-tetrahydro-5H-benzo[7]annulen-2-yl trifluoromethanesulfonate was similar to that of (R)-5-((tert-butoxycarbonyl)amino)-3-fluoro-6,7,8,9-tetrahydro-5H-benzo[7]annulen-2-yl trifluoromethanesulfonate in Example 84, Step 9. The crude product was purified by silica-gel column chromatography (petroleum ether/EtOAc, 10:1) to give (R)-5-((tert-butoxycarbonyl)amino)-1-fluoro-6,7,8,9-tetrahydro-5H-benzo[7]annulen-2-yl trifluoromethanesulfonate as a yellow solid (380 mg, impure), which was carried forward without further purification. $^1$H NMR (400 MHz, DMSO-d$_6$) δ: 7.64 (d, J=7.2 Hz, 1H), 7.47 (t, J=8.4 Hz, 1H), 7.12 (d, J=8.4 Hz, 1H), 4.73 (t, J=9.2 Hz, 1H), 3.16-3.11 (m, 1H), 2.65-2.58 (m, 1H), 1.81-1.74 (m, 4H), 1.54-1.45 (m, 1H), 1.38 (s, 9H), 1.22-1.20 (m, 1H).

10. Synthesis of tert-butyl (R)-(1-fluoro-2-(4,4,5,5-tetramethyl-1,3,2-dioxaborolan-2-yl)-6,7,8,9-tetrahydro-5H-benzo[7]annulen-5-yl)carbamate

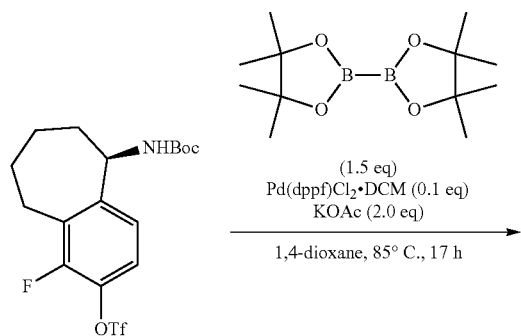

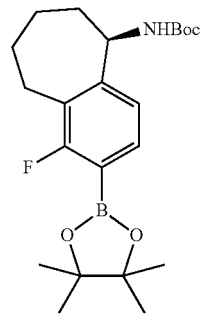

Synthesis of tert-butyl (R)-(1-fluoro-2-(4,4,5,5-tetramethyl-1,3,2-dioxaborolan-2-yl)-6,7,8,9-tetrahydro-5H-benzo[7]annulen-5-yl)carbamate was similar to that of tert-butyl (R)-(3-fluoro-2-(4,4,5,5-tetramethyl-1,3,2-dioxaborolan-2-yl)-6,7,8,9-tetrahydro-5H-benzo[7] annulen-5-yl)carbamate in Example 84, Step 10. The crude product was purified by silica-gel column chromatography (petroleum ether/EtOAc, 10:1) to give tert-butyl (R)-(1-fluoro-2-(4,4,5,5-tetramethyl-1,3,2-dioxaborolan-2-yl)-6,7,8,9-tetrahydro-5H-benzo[7]annulen-5-yl)carbamate as a yellow solid (350 mg, impure), which was carried forward without further purification. Observed boronic acid: ESI-MS (M+H−56)$^+$: 268.0.

11. Synthesis of tert-butyl (R)-(1-fluoro-2-(4-((1-methyl-1H-pyrazol-4-yl)amino)-1,3,5-triazin-2-yl)-6,7,8,9-tetrahydro-5H-benzo[7]annulen-5-yl)carbamate

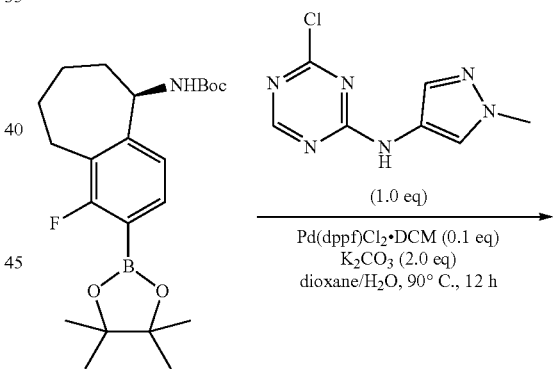

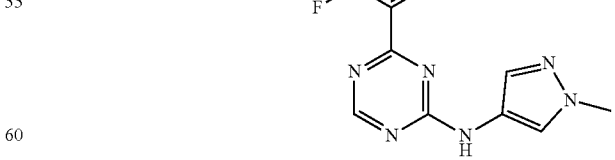

Synthesis of tert-butyl (R)-(1-fluoro-2-(4-((1-methyl-1H-pyrazol-4-yl)amino)-1,3,5-triazin-2-yl)-6,7,8,9-tetrahydro-5H-benzo[7]annulen-5-yl)carbamate was similar to that of tert-butyl (R)-(3-fluoro-2-(4-((1-methyl-1H-pyrazol-3-yl)amino)-1,3,5-triazin-2-yl)-6,7,8,9-tetrahydro-5H-benzo[7]

annulen-5-yl)carbamate in Example 84, Step 11. The crude material was purified by silica-gel column chromatography (petroleum ether/EtOAc, grading from 10:1 to 0:1) to give tert-butyl (R)-(1-fluoro-2-(4-((1-methyl-1H-pyrazol-4-yl)amino)-1,3,5-triazin-2-yl)-6,7,8,9-tetrahydro-5H-benzo[7]annulen-5-yl)carbamate as a yellow solid (300 mg, yield: 89%). ESI-MS (M+H)⁺: 454.3.

12. Synthesis of (R)-4-(5-amino-1-fluoro-6,7,8,9-tetrahydro-5H-benzo[7]annulen-2-yl)-N-(1-methyl-1H-pyrazol-4-yl)-1,3,5-triazin-2-amine

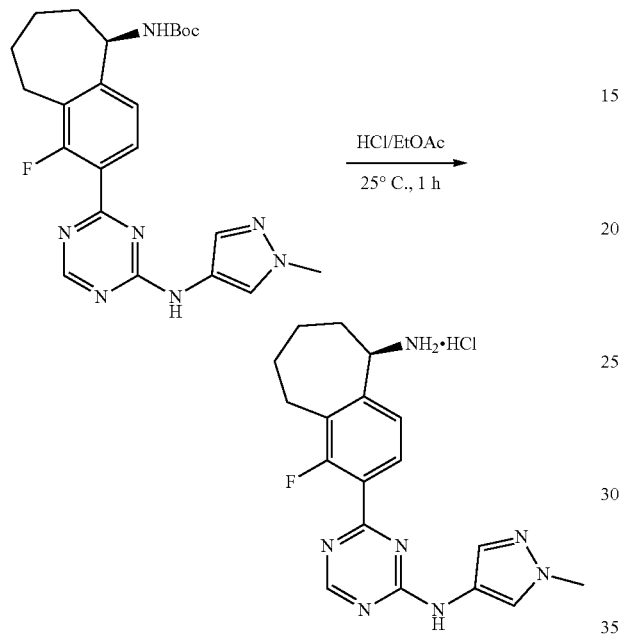

A solution of tert-butyl (R)-(1-fluoro-2-(4-((1-methyl-1H-pyrazol-4-yl)amino)-1,3,5-triazin-2-yl)-6,7,8,9-tetrahydro-5H-benzo[7]annulen-5-yl)carbamate (300 mg, 0.66 mmol) and HCl (10 mL, 4 M solution) in EtOAc (5 mL) was stirred at 25° C. for 1 h. The reaction mixture was concentrated in vacuo to give the HCl salt of (R)-4-(5-amino-1-fluoro-6,7,8,9-tetrahydro-5H-benzo[7]annulen-2-yl)-N-(1-methyl-1H-pyrazol-4-yl)-1,3,5-triazin-2-amine as a yellow solid (200 mg, crude), which was carried forward without further purification. ESI-MS (M+H)⁺: 354.2.

13. Synthesis of (R)-5-(tert-butyl)-N-(1-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide (Compound 88)

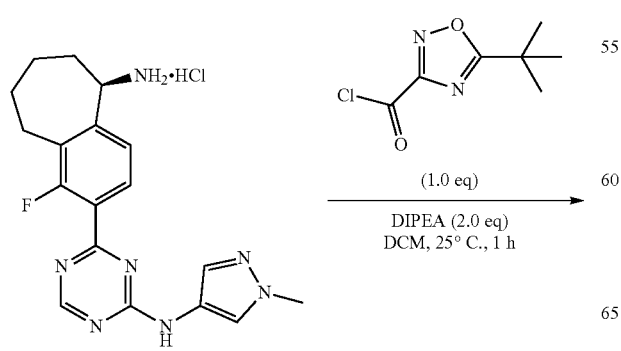

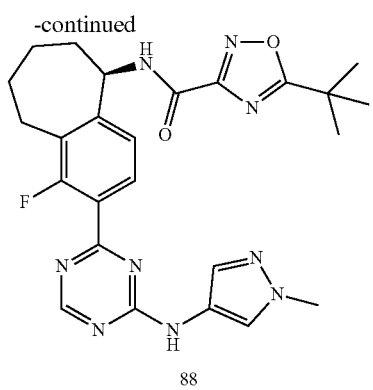

88

To a solution of the HCl salt of (R)-4-(5-amino-1-fluoro-6,7,8,9-tetrahydro-5H-benzo[7]annulen-2-yl)-N-(1-methyl-1H-pyrazol-4-yl)-1,3,5-triazin-2-amine (100 mg, 0.26 mmol) and DIPEA (66 mg, 0.51 mmol) in DCM (10 mL) at 0° C. was added 5-(tert-butyl)-1,2,4-oxadiazole-3-carbonyl chloride (48 mg, 0.26 mmol). The reaction mixture was stirred at 25° C. for 1 h. Additional DCM (30 mL) was added and the organic phase was washed with H₂O (10 mL×3). The organic phase was dried (Na₂SO₄), filtered, and concentrated in vacuo. The crude material was purified by prep-HPLC (CH₃CN/H₂O with 0.05% HCl/H₂O as mobile phase) to give the HCl salt of (R)-5-(tert-butyl)-N-(1-fluoro-2-(4-((1-methyl-1H-pyrazol-4-yl)amino)-1,3,5-triazin-2-yl)-6,7,8,9-tetrahydro-5H-benzo[7]annulen-5-yl)-1,2,4-oxadiazole-3-carboxamide as a yellow solid (65 mg, yield: 47%). ESI-MS (M+Na)⁺: 528.2. ¹H NMR (500 MHz, DMSO-d₆) δ:9.99 (s, 1H), 9.16-9.14 (m, 1H), 8.74 (s, 1H), 7.92-7.80 (m, 2H), 7.63 (s, 1H), 7.25-7.23 (m, 1H), 5.36-5.32 (m, 1H), 3.84 (s, 3H), 3.30-3.25 (m, 1H), 2.75-2.71 (m, 1H), 2.08-2.01 (s, 1H), 1.99-1.86 (m, 4H), 1.49 (s, 9H), 1.45-1.42 (m, 1H).

Example 89: (R)-3-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide (Compound 89)

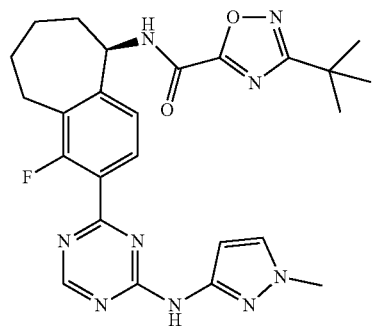

89

1. Synthesis of tert-butyl (R)-(1-fluoro-2-(4-((1-methyl-1H-pyrazol-3-yl)amino)-1,3,5-triazin-2-yl)-6,7,8,9-tetrahydro-5H-benzo[7]annulen-5-yl)carbamate

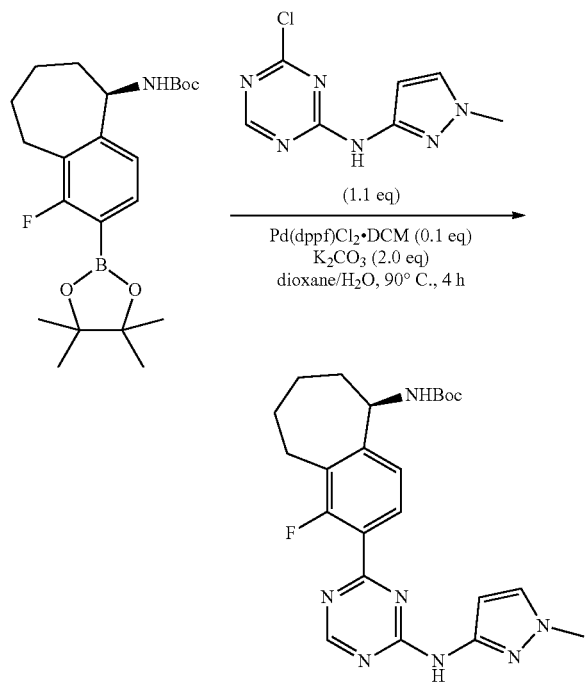

Synthesis of tert-butyl (R)-(1-fluoro-2-(4-((1-methyl-1H-pyrazol-3-yl)amino)-1,3,5-triazin-2-yl)-6,7,8,9-tetrahydro-5H-benzo[7]annulen-5-yl)carbamate was similar to that of tert-butyl (R)-(3-fluoro-2-(4-((1-methyl-1H-pyrazol-3-yl)amino)-1,3,5-triazin-2-yl)-6,7,8,9-tetrahydro-5H-benzo[7]annulen-5-yl)carbamate in Example 84, Step 11. The crude material was purified by silica-gel column chromatography (petroleum ether/EtOAc, grading from 1:0 to 1:2) to give tert-butyl (R)-(1-fluoro-2-(4-((1-methyl-1H-pyrazol-3-yl)amino)-1,3,5-triazin-2-yl)-6,7,8,9-tetrahydro-5H-benzo[7]annulen-5-yl)carbamate as a brown solid (110 mg, yield: 49%). ESI-MS (M+H)+: 454.3.

2. Synthesis of (R)-4-(5-amino-1-fluoro-6,7,8,9-tetrahydro-5H-benzo[7]annulen-2-yl)-N-(1-methyl-1H-pyrazol-3-yl)-1,3,5-triazin-2-amine

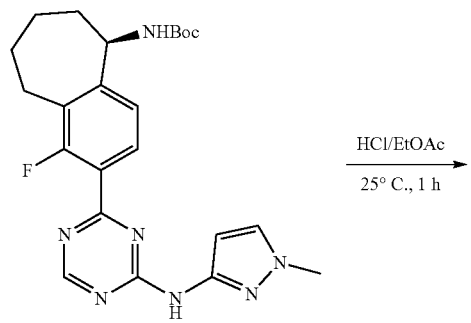

Synthesis of (R)-4-(5-amino-1-fluoro-6,7,8,9-tetrahydro-5H-benzo[7]annulen-2-yl)-N-(1-methyl-1H-pyrazol-3-yl)-1,3,5-triazin-2-amine was similar to that of (R)-4-(5-amino-1-fluoro-6,7,8,9-tetrahydro-5H-benzo[7]annulen-2-yl)-N-(1-methyl-1H-pyrazol-4-yl)-1,3,5-triazin-2-amine in Example 88, Step 12. The reaction mixture was concentrated in vacuo to give the HCl salt of (R)-4-(5-amino-1-fluoro-6,7,8,9-tetrahydro-5H-benzo[7]annulen-2-yl)-N-(1-methyl-1H-pyrazol-3-yl)-1,3,5-triazin-2-amine as a yellow solid (80 mg, crude), which was carried forward without further purification.

3. Synthesis of (R)-3-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide (Compound 89)

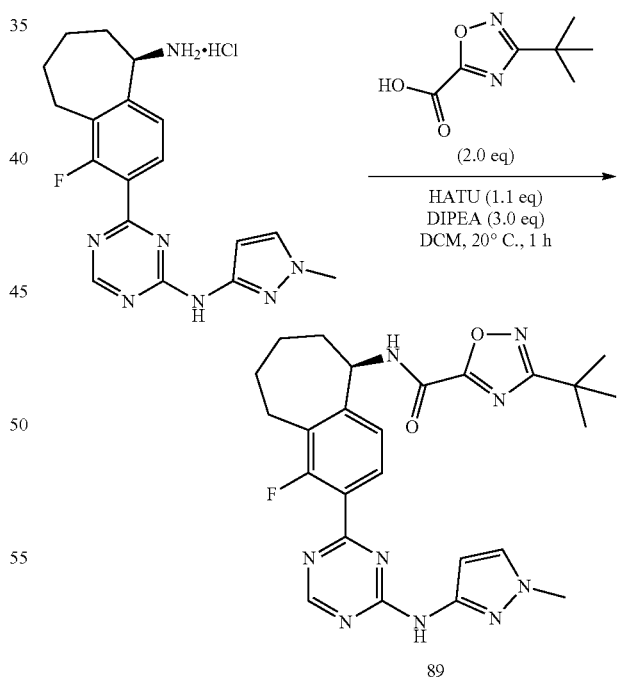

Synthesis of (R)-3-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide was similar to that of (R)-5-(tert-butyl)-N-(3-fluoro-2-(4-((1-methyl-1H-pyrazol-4-yl)amino)-1,3,5-triazin-2-yl)-6,7,8,9-tetrahydro-5H-benzo[7]annulen-5-yl)-

1,2,4-oxadiazole-3-carboxamide in Example 84, Step 13. The crude material was purified by prep-HPLC (CH₃CN/H₂O with 0.05% HCl/H₂O as mobile phase) to give the HCl salt of (R)-3-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-5-carboxamide as a yellow solid (21 mg, yield: 33% over 2 steps). ESI-MS (M+H)⁺: 506.3. ¹H NMR (500 MHz, DMSO-d₆, t=80° C.) δ: 10.09 (s, 1H), 9.54 (d, J=7.5 Hz, 1H), 8.76 (s, 1H), 7.86 (t, J=7.5 Hz, 1H), 7.57 (d, J=2.5 Hz, 1H), 7.24 (d, J=8.0 Hz, 1H), 6.66 (d, J=2.5 Hz, 1H), 5.36-5.33 (m, 1H), 3.79 (s, 3H), 3.33-3.29 (m, 1H), 2.76-2.70 (m, 1H), 2.05-1.89 (m, 5H), 1.43 (s, 9H), 1.41 (s, 1H).

Example 90: (R)-5-(tert-butyl)-N-(8-(4-((1-methyl-1H-pyrazol-4-yl)amino)-1,3,5-triazin-2-yl)-2-(2,2,2-trifluoroethyl)-2,3,4,5-tetrahydro-1H-benzo[c]azepin-5-yl)-1,2,4-oxadiazole-3-carboxamide (Compound 90)

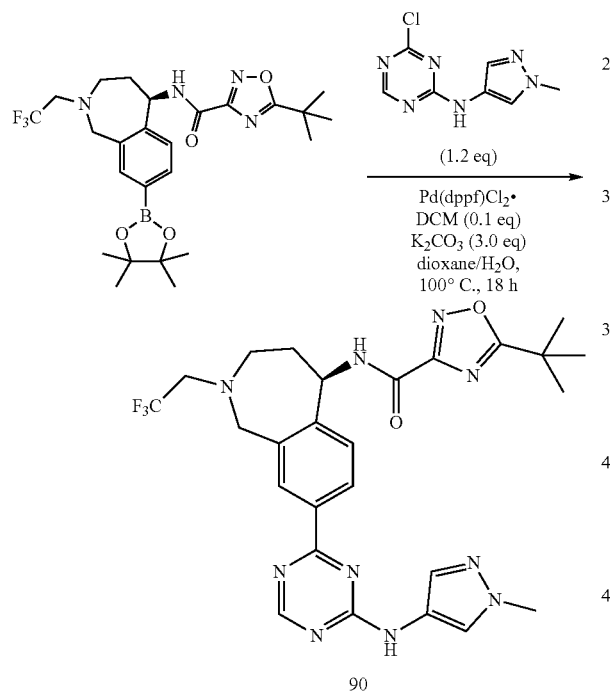

A solution of 5-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-3-carboxamide (75 mg, 0.14 mmol), 4-chloro-N-(1-methylpyrazol-4-yl)-1,3,5-triazin-2-amine (36 mg, 0.17 mmol), K₂CO₃ (60 mg, 0.43 mmol) and Pd(dppf)Cl₂·DCM (12 mg, 0.01 mmol) in 1,4-dioxane (1.15 mL) and H₂O (288 L) was degassed with N₂ for 5 min. The reaction mixture was heated to 100° C. and stirred at that temperature for 18 h. The reaction mixture was concentrated in vacuo and purified by silica-gel column chromatography ([3:1 EtOAc:EtOH]/heptanes, grading from 0% to 50%) to give 5-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide as a light yellow solid (26 mg, yield: 31%). ESI-MS (M+H)⁺: 571.2. ¹H NMR (500 MHz, DMSO-d₆) δ: 10.27 (d, J=12.8 Hz, 1H), 9.56 (br dd, J=15.6 Hz, 8.2 Hz, 1H), 8.86-8.67 (m, 1H), 8.32-8.22 (m, 1H), 8.18 (dd, J=9.8 Hz, 1.8 Hz, 1H), 8.05-7.93 (m, 1H), 7.66-7.54 (m, 1H), 7.42 (dd, J=11.3 Hz, 8.2 Hz, 1H), 5.52-5.41 (m, 1H), 4.31 (br dd, J=15.6 Hz, 5.2 Hz, 1H), 4.08-3.94 (m, 1H), 3.84 (d, J=15.3 Hz, 3H), 3.39-3.32 (m, 1H), 3.24-3.15 (m, 2H), 3.12-2.98 (m, 1H), 2.14-2.03 (m, 1H), 1.82 (br d, J=14.0 Hz, 1H), 1.45 (d, J=1.8 Hz, 9H).

Example 91: 3-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide (Compound 91)

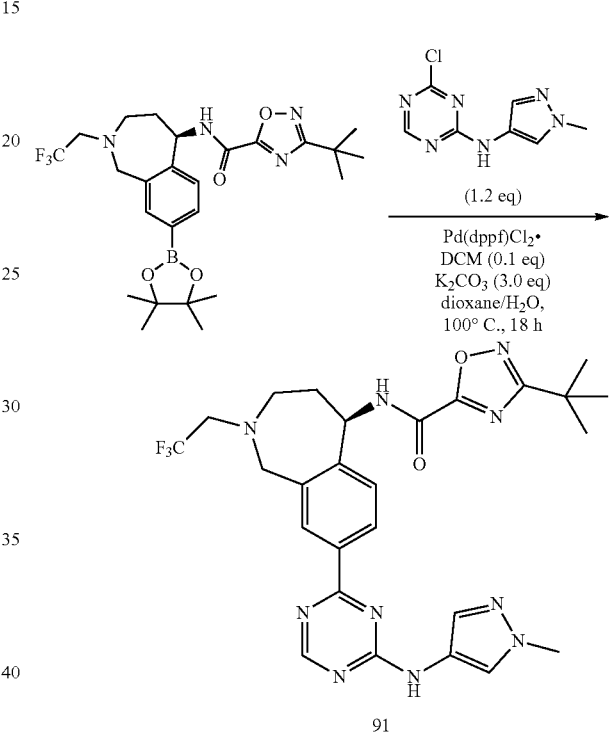

Synthesis of 3-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide was similar to that of 5-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide in Example 25, Step 5. The crude material was purified by silica-gel column chromatography ([3:1 EtOAc:EtOH]/heptanes, grading from 0% to 50%) to give 3-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-5-carboxamide as a light yellow solid (40 mg, yield: 48%). ESI-MS (M+H)⁺: 571.2. ¹H NMR (500 MHz, DMSO-d₆) δ: 10.27 (d, J=13.4 Hz, 1H), 9.95 (br dd, J=16.5 Hz, 7.9 Hz, 1H), 8.83-8.69 (m, 1H), 8.32-8.23 (m, 1H), 8.18 (dd, J=10.1 Hz, 1.5 Hz, 1H), 8.02-7.94 (m, 1H), 7.65-7.54 (m, 1H), 7.45 (dd, J=10.1 Hz, 8.2 Hz, 1H), 5.52-5.38 (m, 1H), 4.31 (br dd, J=15.6 Hz, 4.6 Hz, 1H), 4.07-3.94 (m, 1H), 3.84 (d, J=14.0 Hz, 3H), 3.25-3.15 (m, 2H), 3.13-2.98 (m, 1H), 2.49-2.38 (m, 1H), 2.16-2.04 (m, 1H), 1.84 (br d, J=13.4 Hz, 1H), 1.40 (d, J=1.8 Hz, 9H).

Example 92: 2-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-4-carboxamide (Compound 92)

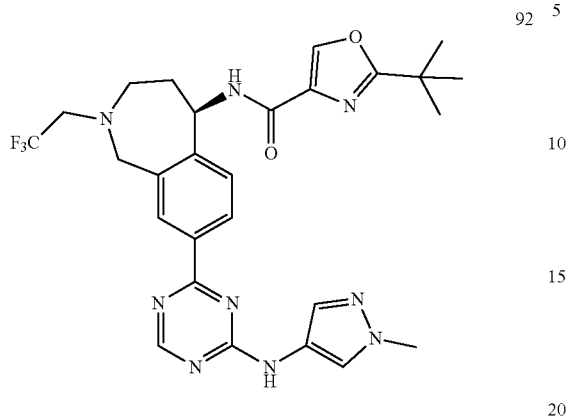

1. Synthesis of tert-butyl (5R)-8-bromo-5-[(2-tert-butyloxazole-4-carbonyl)amino]-1,3,4,5-tetrahydro-2-benzazepine-2-carboxylate

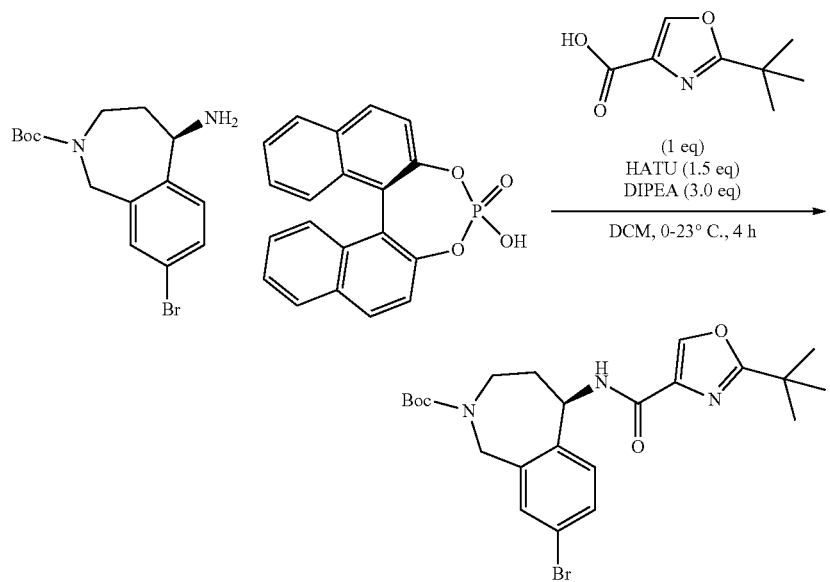

2. Synthesis of tert-butyl (5R)-5-[(2-tert-butyloxazole-4-carbonyl)amino]-8-(4,4,5,5-tetramethyl-1,3,2-dioxaborolan-2-yl)-1,3,4,5-tetrahydro-2-benzazepine-2-carboxylate

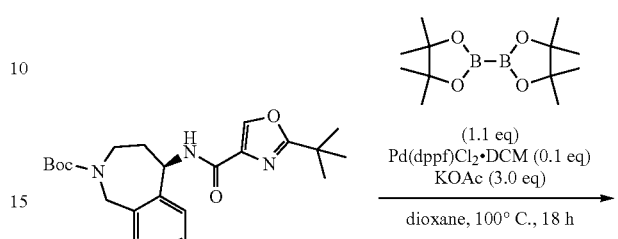

A round bottom flask was charged with 2-tert-butyloxazole-4-carboxylic acid (1.5 g, 8.8 mmol) and DCM (88 mL) and cooled to 0° C. in an ice-water bath. HATU (5.0 g, 13.2 mmol) was added followed by DIPEA (3.4 g, 26.4 mmol, 4.6 mL). tert-Butyl (R)-5-amino-8-bromo-1,3,4,5-tetrahydro-2H-benzo[c]azepine-2-carboxylate compound with (11bR)-4-hydroxydinaphtho[2,1-d:1',2'-f][1,3,2]dioxaphosphepine 4-oxide (1:1) (6 g, 8.8 mmol) was added. The mixture was stirred at 0° C. for one hour, then warmed to room temperature and stirred for three hours. The reaction was concentrated and purified via silica-gel column chromatography ([3:1 EtOAc:EtOH]/heptanes, grading from 0% to 50%) to afford tert-butyl (5R)-8-bromo-5-[(2-tert-butyloxazole-4-carbonyl)amino]-1,3,4,5-tetrahydro-2-benzazepine-2-carboxylate as a white solid (4.3 g, yield: 100%). ESI-MS (M+H)+: 492.1.

-continued

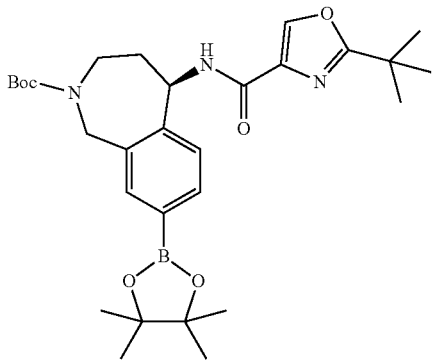

A solution of tert-butyl (5R)-8-bromo-5-[(2-tert-butyloxazole-4-carbonyl)amino]-1,3,4,5-tetrahydro-2-benzazepine-2-carboxylate (4.3 g, 8.8 mmol), bis(pinacolato)diboron (2.5 g, 9.7 mmol), KOAc (2.6 g, 26.4 mmol), and Pd(dppf)Cl$_2$.DCM (718 mg, 0.88 mmol) in 1,4-dioxane (20 mL) was degassed with N$_2$ for 5 min. The reaction mixture was heated to 100° C. and stirred at that temperature for 18 h. The reaction mixture was cooled to rt, diluted with EtOAc, and filtered through a pad of Celite®. The solids were washed with EtOAc, and the combined filtrates were concentrated in vacuo. The crude material was purified by silica-gel column chromatography (EtOAc/heptanes, grading from 0% to 50%) to give tert-butyl (5R)-5-[(2-tert-butyloxazole-4-carbonyl)amino]-8-(4,4,5,5-tetramethyl-1,3,2-dioxaborolan-2-yl)-1,3,4,5-tetrahydro-2-benzazepine-2-carboxylate as an off-white solid (4.4 g, yield: 93%). ESI-MS (M+H)$^+$: 540.3.

3. Synthesis of tert-butyl (5R)-5-[(2-tert-butyloxazole-4-carbonyl)amino]-8-[4-[(1-methylpyrazol-4-yl)amino]-1,3,5-triazin-2-yl]-1,3,4,5-tetrahydro-2-benzazepine-2-carboxylate

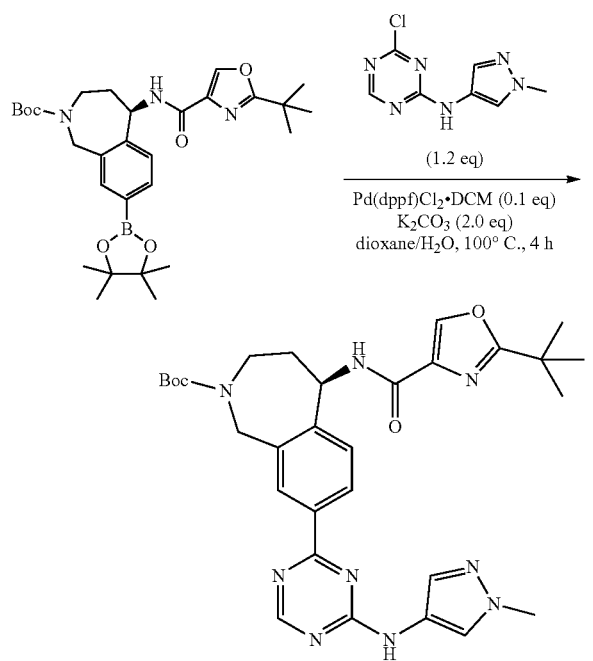

A mixture of tert-butyl (5R)-5-[(2-tert-butyloxazole-4-carbonyl)amino]-8-(4,4,5,5-tetramethyl-1,3,2-dioxaborolan-2-yl)-1,3,4,5-tetrahydro-2-benzazepine-2-carboxylate (750 mg, 1.4 mmol), 4-chloro-N-(1-methylpyrazol-4-yl)-1,3,5-triazin-2-amine (351 mg, 1.7 mmol), K$_2$CO$_3$ (384 mg, 2.8 mmol) and Pd(dppf)Cl$_2$.DCM (114 mg, 0.14 mmol) were dissolved in 1,4-dioxane (11 mL) and H$_2$O (2.8 mL). The reaction mixture was degassed with N$_2$ for 5 minutes, then heated to 100° C. and stirred for 4 h. The reaction was diluted with H$_2$O and extracted with EtOAc (×2). The combined organic layers were washed with brine, dried over sodium sulfate, filtered, and concentrated. The crude material was purified via silica-gel column chromatography ([3:1 EtOAc:EtOH]/heptanes, grading from 0% to 75%) to afford tert-butyl (5R)-5-[(2-tert-butyloxazole-4-carbonyl)amino]-8-[4-[(1-methylpyrazol-4-yl)amino]-1,3,5-triazin-2-yl]-1,3,4,5-tetrahydro-2-benzazepine-2-carboxylate as an orange solid (336.00 mg, yield: 41%). ESI-MS (M+H)$^+$: 587.4.

4. Synthesis of 2-tert-butyl-N-[(5R)-8-[4-[(1-methylpyrazol-4-yl)amino]-1,3,5-triazin-2-yl]-2,3,4,5-tetrahydro-1H-2-benzazepin-5-yl]oxazole-4-carboxamide hydrochloride

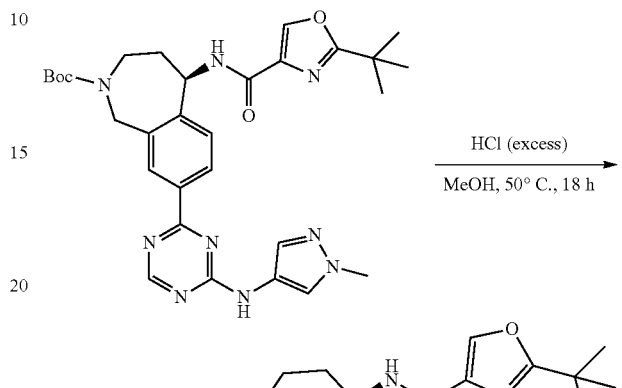

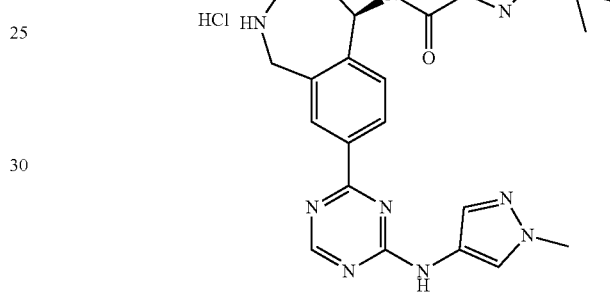

tert-Butyl (5R)-5-[(2-tert-butyloxazole-4-carbonyl)amino]-8-[4-[(1-methylpyrazol-4-yl)amino]-1,3,5-triazin-2-yl]-1,3,4,5-tetrahydro-2-benzazepine-2-carboxylate (336 mg, 0.6 mmol) was dissolved in MeOH (6 mL) and an HCl solution (1.25 M in MeOH, 4.6 mL) was added. The reaction was heated to 50° C. and stirred at that temperature for 18 hours. The reaction was concentrated in vacuo to afford 2-tert-butyl-N-[(5R)-8-[4-[(1-methylpyrazol-4-yl)amino]-1,3,5-triazin-2-yl]-2,3,4,5-tetrahydro-1H-2-benzazepin-5-yl]oxazole-4-carboxamide hydrochloride as a yellow solid (320 mg, yield: 100%). ESI-MS (M+H)$^+$: 488.2.

5. Synthesis of 2-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-4-carboxamide (Compound 92)

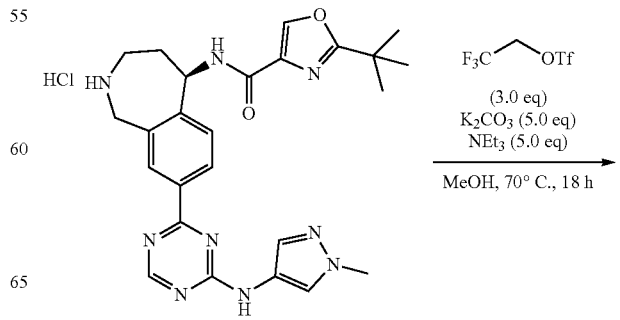

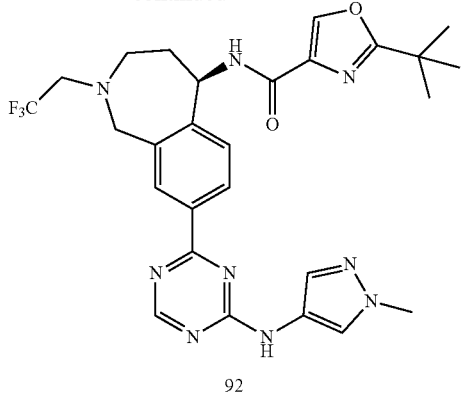

92

To a mixture of 2-tert-butyl-N-[(5R)-8-[4-[(1-methylpyrazol-4-yl)amino]-1,3,5-triazin-2-yl]-2,3,4,5-tetrahydro-1H-2-benzazepin-5-yl]oxazole-4-carboxamide hydrochloride (75 mg, 0.14 mmol) in MeCN (1.2 mL) was added K$_2$CO$_3$ (98 mg, 0.71 mmol), followed by 2,2,2-trifluoroethyl trifluoromethanesulfonate (99 mg, 0.42 mmol, 61 µL) and Et$_3$N (72 mg, 0.71 mmol, 98 µL). The reaction mixture was heated at 70° C. and stirred at that temperature for 18 h. The reaction mixture was diluted with DCM and filtered. The filter cake was washed with DCM and the combined filtrates were concentrated in vacuo. The crude material was purified by silica-gel column chromatography (EtOAc/heptanes, grading from 0% to 100%) to give 2-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-4-carboxamide as an off-white solid (43 mg, yield: 53%). ESI-MS (M+H)$^+$: 570.3. $^1$H NMR (500 MHz, DMSO-d$_6$) δ: 10.26 (d, J=9.8 Hz, 1H), 8.83-8.68 (m, 1H), 8.61-8.57 (m, 1H), 8.53 (br dd, J=16.5 Hz, 8.5 Hz, 1H), 8.31-8.20 (m, 1H), 8.19-8.14 (m, 1H), 8.02-7.93 (m, 1H), 7.63-7.54 (m, 1H), 7.40 (dd, J=12.8 Hz, 7.9 Hz, 1H), 5.45 (br t, J=9.2 Hz, 1H), 4.29 (br dd, J=15.3 Hz, 4.3 Hz, 1H), 4.07-3.93 (m, 1H), 3.84 (d, J=15.3 Hz, 3H), 3.29-3.21 (m, 2H), 3.20-3.05 (m, 2H), 2.20-2.04 (m, 1H), 1.82 (br d, J=14.7 Hz, 1H), 1.38 (d, J=2.4 Hz, 9H).

Example 93: 4-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-2-carboxamide (Compound 93)

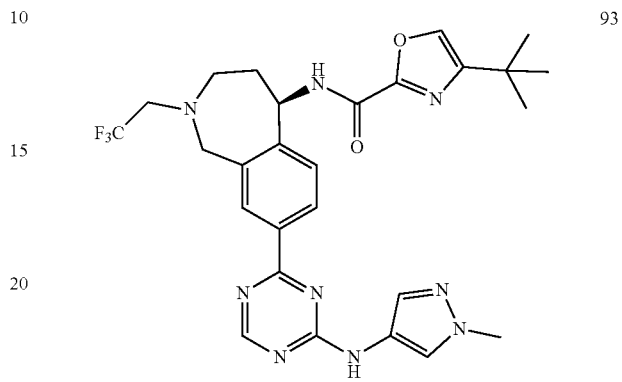

93

1. Synthesis of tert-butyl (5R)-8-bromo-5-[(2-tert-butyloxazole-4-carbonyl)amino]-1,3,4,5-tetrahydro-2-benzazepine-2-carboxylate

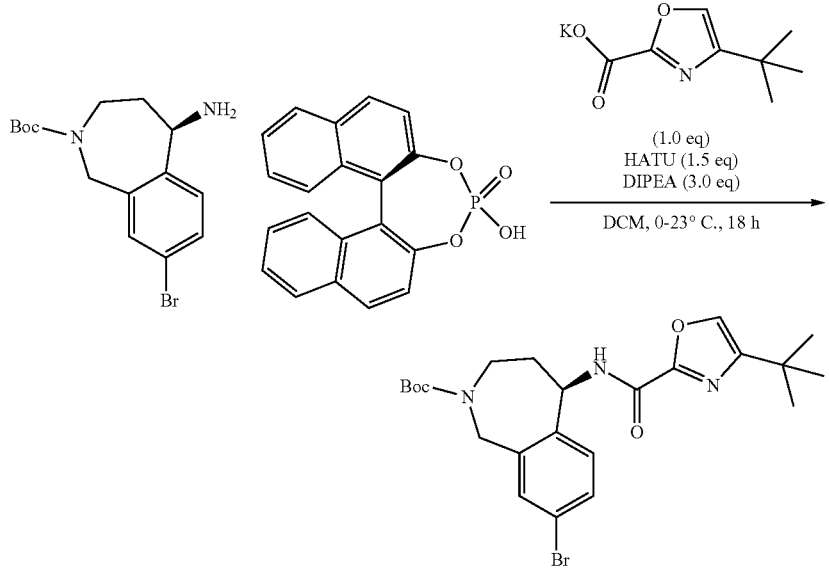

A round bottom flask was charged with potassium 4-tert-butyloxazole-2-carboxylate (916 mg, 4.4 mmol) and DCM (44 mL) and cooled to 0° C. in an ice-water bath. HATU (2.5 g, 6.6 mmol) was added followed by DIPEA (1.7 g, 13 mmol, 2.3 mL). tert-Butyl (R)-5-amino-8-bromo-1,3,4,5-tetrahydro-2H-benzo[c]azepine-2-carboxylate compound with (11bR)-4-hydroxydinaphtho[2,1-d:1',2'-f][1,3,2]dioxaphosphepine 4-oxide (1:1) (3 g, 4.4 mmol) was added. The mixture was stirred at 0° C. for one hour, then warmed to room temperature and stirred overnight. The reaction was concentrated in vacuo and purified via silica-gel column chromatography ([3:1 EtOAc:EtOH]/heptanes, grading from 0% to 50%) to afford tert-butyl (5R)-8-bromo-5-[(4-tert-butyloxazole-2-carbonyl)amino]-1,3,4,5-tetrahydro-2-benzazepine-2-carboxylate as a white solid (2.0 g, yield: 94%). ESI-MS (M+Na)+: 516.1.

2. Synthesis of tert-butyl (5R)-5-[(4-tert-butyloxazole-2-carbonyl)amino]-8-(4,4,5,5-tetramethyl-1,3,2-dioxaborolan-2-yl)-1,3,4,5-tetrahydro-2-benzazepine-2-carboxylate

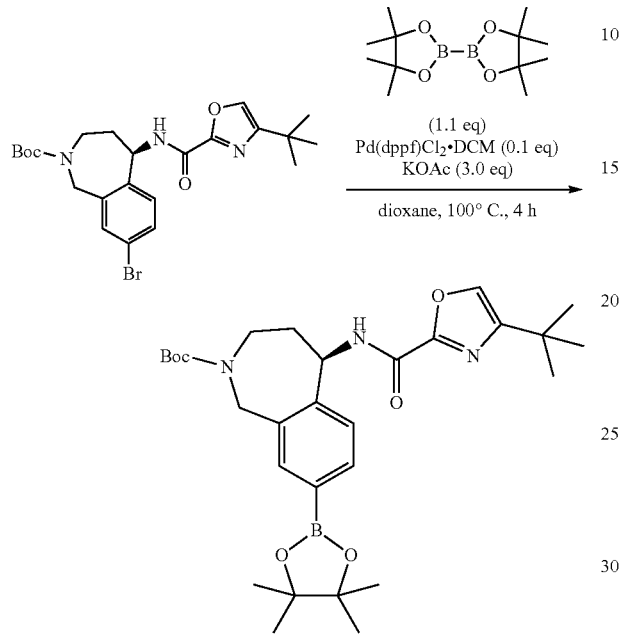

tert-Butyl (5R)-8-bromo-5-[(4-tert-butyloxazole-2-carbonyl)amino]-1,3,4,5-tetrahydro-2-benzazepine-2-carboxylate (2.0 g, 4.1 mmol), bis(pinacolato)diboron (1.2 g, 4.5 mmol), KOAc (1.2 g, 12.4 mmol), and Pd(dppf)Cl$_2$.DCM (337 mg, 0.41 mmol) were dissolved in 1,4-dioxane (10 mL). The reaction mixture was degassed with N$_2$ for five minutes, then heated to 100° C., and stirred at that temperature for 4 hours. The reaction mixture was cooled to room temperature, diluted with EtOAc, and filtered through a pad of Celite®. The solids were washed with EtOAc, and the filtrate was concentrated in vacuo. The residue was purified by silica-gel column chromatography (EtOAc/heptanes, grading from 0% to 50%) to give tert-butyl (5R)-5-[(4-tert-butyloxazole-2-carbonyl)amino]-8-(4,4,5,5-tetramethyl-1,3,2-dioxaborolan-2-yl)-1,3,4,5-tetrahydro-2-benzazepine-2-carboxylate as an off-white solid (2.0 g, yield: 91%). ESI-MS (M+H–56)+: 484.2.

3. Synthesis of tert-butyl (5R)-5-[(4-tert-butyloxazole-2-carbonyl)amino]-8-[4-[(1-methylpyrazol-4-yl)amino]-1,3,5-triazin-2-yl]-1,3,4,5-tetrahydro-2-benzazepine-2-carboxylate

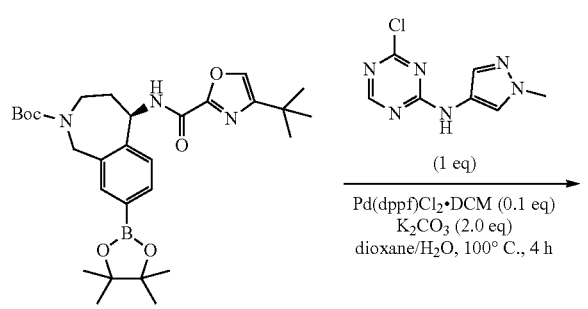

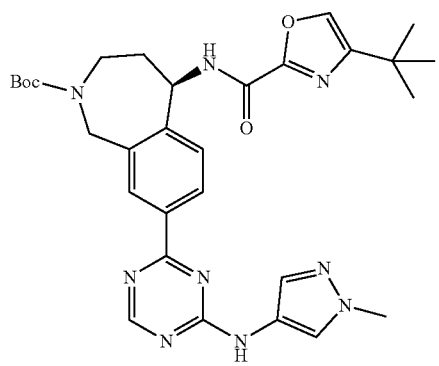

A mixture of tert-butyl (5R)-5-[(4-tert-butyloxazole-2-carbonyl)amino]-8-(4,4,5,5-tetramethyl-1,3,2-dioxaborolan-2-yl)-1,3,4,5-tetrahydro-2-benzazepine-2-carboxylate (750 mg, 1.4 mmol), 4-chloro-N-(1-methylpyrazol-4-yl)-1,3,5-triazin-2-amine (293 mg, 1.4 mmol), K$_2$CO$_3$ (384 mg, 2.8 mmol) and Pd(dppf)Cl$_2$.DCM (114 mg, 0.14 mmol) were dissolved in 1,4-dioxane (5.6 mL) and H$_2$O (1.4 mL). The reaction mixture was degassed with N$_2$ for 5 minutes, then heated to 100° C., and stirred at that temperature for four hours. The reaction was diluted with H$_2$O and extracted with EtOAc (×2). The combined organic layers were washed with brine, dried over sodium sulfate, filtered, and concentrated. The material was purified via silica-gel column chromatography ([3:1 EtOAc:EtOH]/heptanes, grading from 0% to 75%) to afford tert-butyl (5R)-5-[(4-tert-butyloxazole-2-carbonyl)amino]-8-[4-[(1-methylpyrazol-4-yl)amino]-1,3,5-triazin-2-yl]-1,3,4,5-tetrahydro-2-benzazepine-2-carboxylate as an off-white solid (314 mg, yield: 38%).

4. Synthesis of 4-tert-butyl-N-[(5R)-8-[4-[(1-methylpyrazol-4-yl)amino]-1,3,5-triazin-2-yl]-2,3,4,5-tetrahydro-1H-2-benzazepin-5-yl]oxazole-2-carboxamide hydrochloride

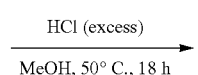

-continued

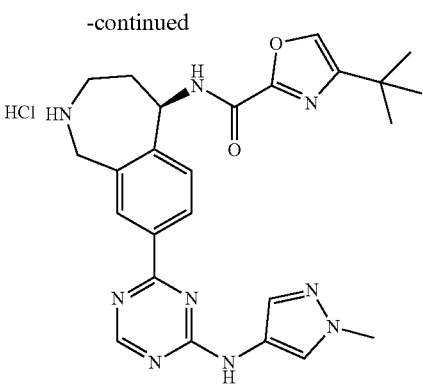

tert-Butyl (5R)-5-[(4-tert-butyloxazole-2-carbonyl)amino]-8-[4-[(1-methylpyrazol-4-yl)amino]-1,3,5-triazin-2-yl]-1,3,4,5-tetrahydro-2-benzazepine-2-carboxylate (314 mg, 0.53 mmol) was dissolved in MeOH (5.3 mL) and an HCl solution (1.25 M in MeOH, 4.3 mL) was added. The reaction was heated to 50° C. and stirred at that temperature for 18 hours. The reaction was concentrated in vacuo to afford 4-tert-butyl-N-[(5R)-8-[4-[(1-methylpyrazol-4-yl)amino]-1,3,5-triazin-2-yl]-2,3,4,5-tetrahydro-1H-2-benzazepin-5-yl]oxazole-2-carboxamide hydrochloride as a yellow solid (300 mg, yield: 100%). ESI-MS (M+H)$^+$: 488.2.

5. Synthesis of 4-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-2-carboxamide (Compound 93)

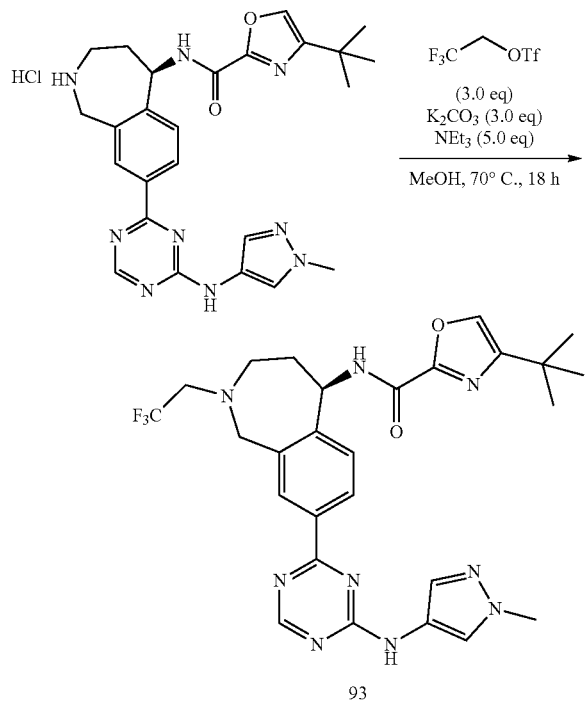

To a mixture of 4-tert-butyl-N-[(5R)-8-[4-[(1-methylpyrazol-4-yl)amino]-1,3,5-triazin-2-yl]-2,3,4,5-tetrahydro-1H-2-benzazepin-5-yl]oxazole-2-carboxamide hydrochloride (100 mg, 0.16 mmol) in CH$_3$CN (1.6 mL) was added K$_2$CO$_3$ (67 mg, 0.48 mmol) followed by 2,2,2-trifluoroethyl trifluoromethanesulfonate (75 mg, 0.32 mmol, 46 µL) and Et$_3$N (81 mg, 0.80 mmol, 111 µL). The mixture was heated at 70° C. for 18 hours. The mixture was cooled to ambient temperature, diluted with DCM, and filtered. The filter residue was washed with DCM and the combined filtrates were concentrated in vacuo. The crude material was purified by prep-HPLC (CH$_3$CN/H$_2$O with 0.05% TFA/H$_2$O as mobile phase) to give the TFA salt of 4-tert-butyl-N-[(5R)-8-[4-[(1-methylpyrazol-4-yl)amino]-1,3,5-triazin-2-yl]-2-(2,2,2-trifluoroethyl)-1,3,4,5-tetrahydro-2-benzazepin-5-yl]oxazole-2-carboxamide as a light yellow solid (77 mg, yield: 70%). ESI-MS (M+H)$^+$: 570.3. $^1$H NMR (500 MHz, DMSO-d$_6$) δ: 10.27 (d, J=11.0 Hz, 1H), 9.36 (br dd, J=19.2 Hz, 8.2 Hz, 1H), 8.84-8.68 (m, 1H), 8.33-8.21 (m, 1H), 8.17 (dd, J=9.8 Hz, 1.8 Hz, 1H), 8.06 (d, J=1.8 Hz, 1H), 8.02-7.94 (m, 1H), 7.63-7.54 (m, 1H), 7.41 (dd, J=12.5 Hz, 8.2 Hz, 1H), 5.49-5.36 (m, 1H), 4.31 (br dd, J=15.0 Hz, 4.0 Hz, 1H), 4.07-3.91 (m, 1H), 3.90-3.79 (m, 3H), 3.37-3.20 (m, 2H), 3.13-2.99 (m, 2H), 2.24-2.05 (m, 1H), 1.83 (br d, J=14.0 Hz, 1H), 1.29 (d, J=2.4 Hz, 9H).

Example 94: (R)-2-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)oxazole-4-carboxamide (Compound 94)

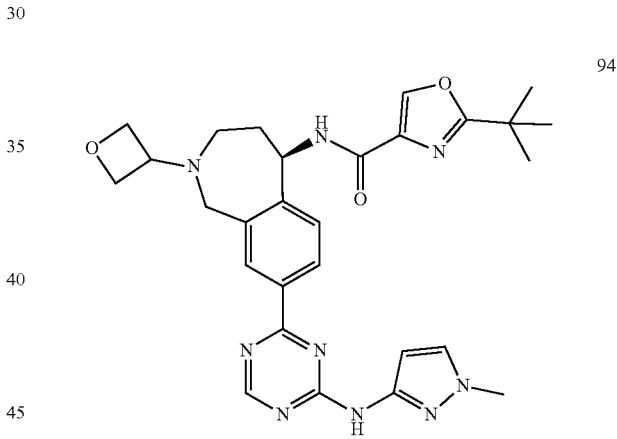

The synthetic strategy for (R)-2-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)oxazole-4-carboxamide was similar to that of 1-tert-butyl-N-[(5R)-8-[4-[(1-methylpyrazol-4-yl)amino]-1,3,5-triazin-2-yl]-2-(oxetan-3-yl)-1,3,4,5-tetrahydro-2-benzazepin-5-yl]triazole-4-carboxamide in Example 24 with the following modifications:
1. 2-(tert-butyl)oxazole-4-carboxylic acid was used in place of 1-(tert-butyl)-1H-1,2,3-triazole-4-carboxylic acid
2. 4-chloro-N-(1-methyl-1H-pyrazol-3-yl)-1,3,5-triazin-2-amine was used in place of 4-chloro-N-(1-methyl-1H-pyrazol-4-yl)-1,3,5-triazin-2-amine ESI-MS (M+H)$^+$: 544.3. $^1$H NMR (500 MHz, DMSO-d$_6$) δ: 10.60 (br s, 1H), 8.76 (br s, 1H), 8.61-8.52 (m, 2H), 8.19 (dd, J=7.9 Hz, 1.2 Hz, 1H), 8.12 (br s, 1H), 7.64 (br s, 1H), 7.39 (d, J=7.9 Hz, 1H), 6.80-6.52 (m, 1H), 5.44 (br t, J=9.2 Hz, 1H), 4.61 (t, J=6.4 Hz, 1H), 4.58-4.48 (m, 2H), 4.44 (t, J=6.1 Hz, 1H), 3.89-3.80 (m, 1H), 3.78 (s, 3H), 3.76-3.67

(m, 2H), 2.95-2.83 (m, 1H), 2.75-2.63 (m, 1H), 2.13 (br d, J=7.9 Hz, 1H), 1.91 (s, 1H), 1.36 (s, 9H).

Example 95: (R)-2-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-4-carboxamide (Compound 95)

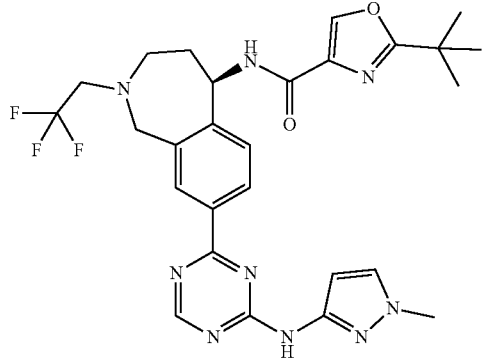

The synthetic strategy for (R)-2-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-4-carboxamide was similar to that of 5-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide in Example 25, with the following modifications:
1. 2-(tert-butyl)oxazole-4-carboxylic acid was used in place of potassium 5-(tert-butyl)-1,2,4-oxadiazole-3-carboxylate
2. 4-chloro-N-(1-methyl-1H-pyrazol-3-yl)-1,3,5-triazin-2-amine was used in place of 4-chloro-N-(1-methyl-1H-pyrazol-4-yl)-1,3,5-triazin-2-amine ESI-MS (M+H)$^+$: 570.3. $^1$H NMR (500 MHz, DMSO-d$_6$) δ: 10.67-10.44 (m, 1H), 8.76 (br s, 1H), 8.59 (s, 1H), 8.52 (br s, 1H), 8.23 (dd, J=7.9 Hz, 1.8 Hz, 1H), 8.16 (br s, 1H), 7.63 (s, 1H), 7.39 (d, J=7.9 Hz, 1H), 6.81-6.53 (m, 1H), 5.44 (br t, J=9.5 Hz, 1H), 4.29 (br d, J=15.3 Hz, 1H), 3.98 (br d, J=15.3 Hz, 1H), 3.78 (s, 3H), 3.29-3.03 (m, 4H), 2.18-2.03 (m, 1H), 1.82 (br d, J=14.0 Hz, 1H), 1.42-1.30 (m, 9H).

Example 96: (R)-4-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-2-carboxamide (Compound 96)

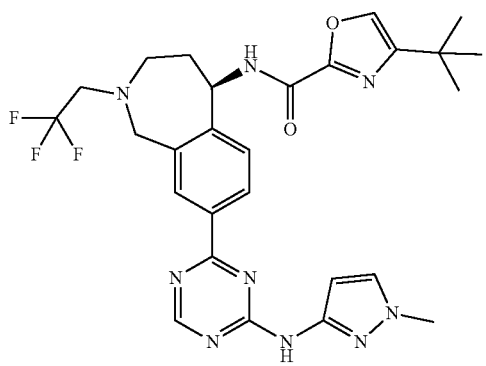

The synthetic strategy for (R)-4-(tert-butyl)-N-(8-(4-((1-methyl-1H-pyrazol-3-yl)amino)-1,3,5-triazin-2-yl)-2-(2,2,2-trifluoroethyl)-2,3,4,5-tetrahydro-1H-benzo[c]azepin-5-yl)oxazole-2-carboxamide was similar to that of 5-tert-butyl-N-[(5R)-8-[4-[(1-methylpyrazol-3-yl)amino]-1,3,5-triazin-2-yl]-2-(2,2,2-trifluoroethyl)-1,3,4,5-tetrahydro-2-benzazepin-5-yl]-1,2,4-oxadiazole-3-carboxamide in Example 25, with the following modifications:
1. 4-(tert-butyl)oxazole-2-carboxylic acid was used in place of potassium 5-(tert-butyl)-1,2,4-oxadiazole-3-carboxylate
2. 4-chloro-N-(1-methyl-1H-pyrazol-3-yl)-1,3,5-triazin-2-amine was used in place of 4-chloro-N-(1-methyl-1H-pyrazol-4-yl)-1,3,5-triazin-2-amine ESI-MS (M+H)$^+$: 570.3. $^1$H NMR (500 MHz, DMSO-d$_6$) δ: 10.61 (br s, 1H), 9.35 (br d, J=7.3 Hz, 1H), 8.76 (br s, 1H), 8.24 (dd, J=7.9 Hz, 1.8 Hz, 1H), 8.16 (s, 1H), 8.06 (s, 1H), 7.62 (d, J=1.8 Hz, 1H), 7.40 (d, J=7.9 Hz, 1H), 6.80-6.48 (m, 1H), 5.43 (br t, J=9.2 Hz, 1H), 4.30 (br d, J=15.3 Hz, 1H), 4.03-3.93 (m, 1H), 3.78 (s, 3H), 3.38-3.27 (m, 2H), 3.26-3.18 (m, 1H), 3.12-3.00 (m, 1H), 2.11 (q, J=11.0 Hz, 1H), 1.82 (br d, J=14.7 Hz, 1H), 1.29 (s, 9H).

Example 97: (R)-2-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)oxazole-4-carboxamide (Compound 97)

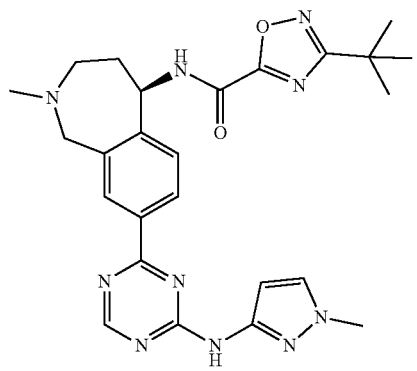

The synthetic strategy for (R)-2-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)oxazole-4-carboxamide was similar to that of 1-tert-butyl-N-[(5R)-8-[4-[(1-methylpyrazol-4-yl)amino]-1,3,5-triazin-2-yl]-2-(oxetan-3-yl)-1,3,4,5-tetrahydro-2-benzazepin-5-yl]triazole-4-carboxamide in Example 24 with the following modifications:
1. potassium 3-(tert-butyl)-1,2,4-oxadiazole-5-carboxylate was used in place of 1-(tert-butyl)-1H-1,2,3-triazole-4-carboxylic acid
2. 4-chloro-N-(1-methyl-1H-pyrazol-3-yl)-1,3,5-triazin-2-amine was used in place of 4-chloro-N-(1-methyl-1H-pyrazol-4-yl)-1,3,5-triazin-2-amine
3. paraformaldehyde was used in place of oxetan-3-one ESI-MS (M+H)$^+$: 503.3. $^1$H NMR (500 MHz, CD$_3$OD) δ: 8.75 (br s, 1H), 8.58-8.48 (m, 2H), 7.61 (br d, J=7.9 Hz, 1H), 7.53 (d, J=1.8 Hz, 1H), 6.73 (br s, 1H), 5.72 (br s, 1H), 4.90-4.86 (m, 1H), 4.65 (d, J=14.0 Hz, 1H), 3.84 (s, 3H), 3.79-3.62 (m, 2H), 3.10 (br s, 3H), 2.41 (br s, 2H), 1.46 (s, 9H).

Example 98: (R)-3-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)-1,2,4-oxadiazole-5-carboxamide (Compound 98)

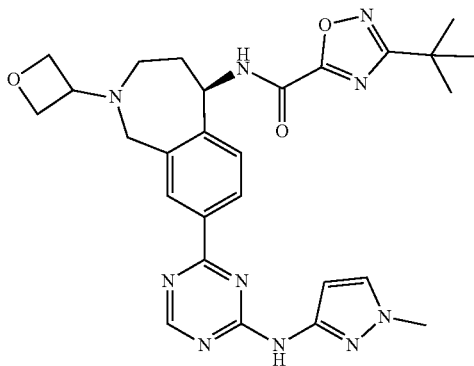

The synthetic strategy for (R)-3-(tert-butyl)-N-(8-(4-((1-methyl-1H-pyrazol-3-yl)amino)-1,3,5-triazin-2-yl)-2-(oxetan-3-yl)-2,3,4,5-tetrahydro-1H-benzo[c]azepin-5-yl)-1,2,4-oxadiazole-5-carboxamide was similar to that of 1-tert-butyl-N-[(5R)-8-[4-[(1-methylpyrazol-4-yl)amino]-1,3,5-triazin-2-yl]-2-(oxetan-3-yl)-1,3,4,5-tetrahydro-2-benzazepin-5-yl]triazole-4-carboxamide in Example 24 with the following modifications:
1. potassium 3-(tert-butyl)-1,2,4-oxadiazole-5-carboxylate was used in place of 1-(tert-butyl)-1H-1,2,3-triazole-4-carboxylic acid
2. 4-chloro-N-(1-methyl-1H-pyrazol-3-yl)-1,3,5-triazin-2-amine was used in place of 4-chloro-N-(1-methyl-1H-pyrazol-4-yl)-1,3,5-triazin-2-amine ESI-MS (M+H)+: 545.4. $^1$H NMR (500 MHz, CD$_3$OD) δ: 8.75 (br s, 1H), 8.52 (br d, J=7.9 Hz, 1H), 8.46 (br s, 1H), 7.61 (d, J=7.9 Hz, 1H), 7.54 (br s, 1H), 6.83-6.62 (m, 1H), 5.77-5.68 (m, 1H), 4.99-4.87 (m, 2H), 4.83-4.63 (m, 3H), 4.56-4.37 (m, 2H), 3.84 (s, 3H), 3.60-3.47 (m, 2H), 2.49-2.32 (m, 2H), 1.45 (s, 9H).

Example 99: 2-(tert-butyl)-N-(2-methyl-4-(4-((1-methyl-1H-pyrazol-4-yl)amino)-1,3,5-triazin-2-yl)benzyl)oxazole-5-carboxamide (Compound 99)

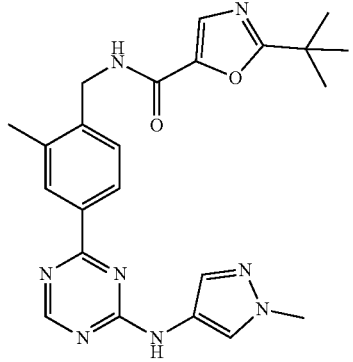

2-(tert-butyl)-N-(2-methyl-4-(4-((1-methyl-1H-pyrazol-4-yl)amino)-1,3,5-triazin-2-yl)benzyl)oxazole-5-carboxamide was synthesized using a method similar to the synthesis of one of the above mentioned examples.

ESI-MS (M+H)+: 447.3. $^1$H NMR (400 MHz, DMSO-d$_6$) δ:10.26 (s, 1H), 8.79-8.70 (m, 1H), 8.63 (m, 1H), 8.54 (d, J=1.0 Hz, 1H), 8.28-8.09 (m, 2H), 8.00-7.95 (m, 1H), 7.63-7.55 (m, 1H), 7.41-7.36 (dd, J=11.9 Hz, 7.9 Hz, 1H), 4.55-4.42 (m, 2H), 3.87-3.83 (m, 3H), 2.43-2.40 (m, 3H), 1.37 (s, 9H).

Example 100: 2-(tert-butyl)-N-(3-fluoro-2-methyl-4-(4-((1-methyl-1H-pyrazol-3-yl)amino)-1,3,5-triazin-2-yl)benzyl)oxazole-4-carboxamide (Compound 100)

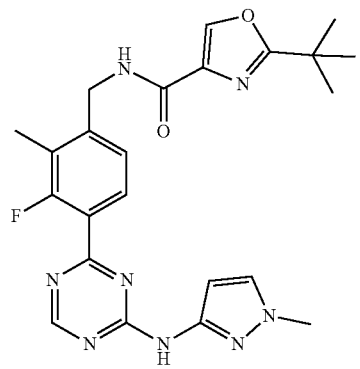

2-(tert-butyl)-N-(3-fluoro-2-methyl-4-(4-((1-methyl-1H-pyrazol-3-yl)amino)-1,3,5-triazin-2-yl)benzyl)oxazole-4-carboxamide was synthesized using a method similar to the synthesis of one of the above mentioned examples.

ESI-MS (M+H)+: 465.4. $^1$H NMR (400 MHz, DMSO-d$_6$) δ: 10.67 (br s, 1H), 8.76 (br s, 1H), 8.68-8.64 (m, 1H), 8.54 (s, 1H), 7.89 (br s, 1H), 7.61 (d, J=2.3 Hz, 1H), 7.20 (d, J=8.0 Hz, 1H), 6.76 (br s, 1H), 4.49 (d, J=6.3 Hz, 2H), 3.76 (s, 3H), 2.30 (s, 3H), 1.36 (m, 9H).

Example 101: (R)-5-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-3-carboxamide (Compound 101)

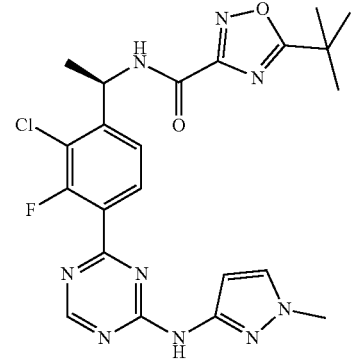

(R)-5-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-3-carboxamide was synthesized using a method similar to the synthesis of one of the above mentioned examples. ESI-MS (M+H)$^+$: 500.2. $^1$H NMR (500 MHz, DMSO-d$_6$, t=80° C.) δ: 10.20 (s, 1H), 9.19 (d, J=7.5 Hz, 1H), 8.79 (s, 1H), 8.07-8.03 (m, 1H), 7.59-7.55 (m, 2H), 6.65 (d, J=1.5 Hz, 1H), 5.53 (t, J=7.0 Hz, 1H), 3.80 (s, 3H), 1.58 (d, J=7.5 Hz, 3H), 1.47 (s, 9H).

Example 102: (R)-3-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-5-carboxamide (Compound 102)

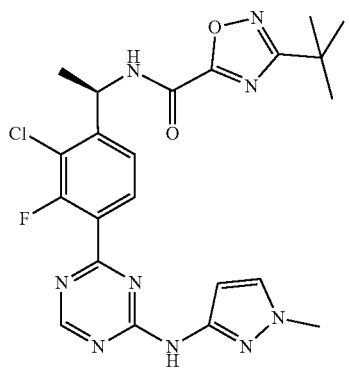

(R)-3-(tert-butyl)-N-(1-(2-chloro-3-fluoro-4-(4-((1-methyl-1H-pyrazol-3-yl)amino)-1,3,5-triazin-2-yl)phenyl)ethyl)-1,2,4-oxadiazole-5-carboxamide was synthesized using a method similar to the synthesis of one of the above mentioned examples.

ESI-MS (M+H)$^+$: 500.2. $^1$H NMR (500 MHz, DMSO-d$_6$, t=80° C.) δ: 10.33 (s, 1H), 9.73-9.70 (m, 1H), 8.79 (s, 1H), 8.06 (t, J=8.0 Hz, 1H), 7.60-7.55 (m, 2H), 6.65 (s, 1H), 5.50 (t, J=6.8 Hz, 1H), 3.79 (s, 3H), 1.58 (d, J=6.8 Hz, 3H), 1.40 (s, 9H).

Example 103: 2-(tert-butyl)-N-(2-chloro-3-fluoro-4-(4-((1-methyl-1H-pyrazol-4-yl)amino)-1,3,5-triazin-2-yl)benzyl)oxazole-4-carboxamide (Compound 103)

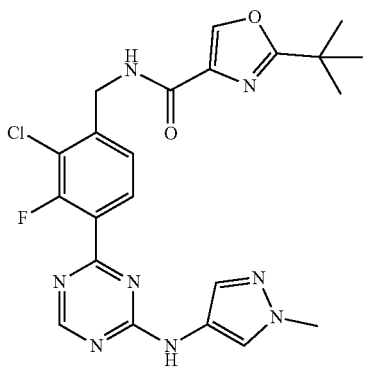

2-(tert-butyl)-N-(2-chloro-3-fluoro-4-(4-((1-methyl-1H-pyrazol-4-yl)amino)-1,3,5-triazin-2-yl)benzyl)oxazole-4-carboxamide was synthesized using a method similar to the synthesis of one of the above mentioned examples.

ESI-MS (M+H)$^+$: 485.5. $^1$H NMR (400 MHz, CDCl$_3$) δ: 8.89-8.74 (br s, 1H), 8.21 (s, 1H), 8.12 (t, J=7.7 Hz, 1H), 8.05-7.97 (m, 1H), 7.84-7.73 (m, 1H), 7.68-7.61 (m, 1H), 7.41-7.30 (m, 1H), 7.27 (s, 1H), 4.83-4.76 (m, 2H), 4.00 (s, 3H), 1.40 (s, 9H).

Example 104: N-(2-chloro-3-fluoro-4-(4-((1-methyl-1H-pyrazol-3-yl)amino)-1,3,5-triazin-2-yl)benzyl)-5-(1-methylcyclopropyl)-1,2,4-oxadiazole-3-carboxamide (Compound 104)

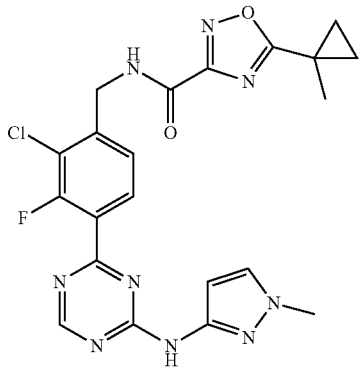

N-(2-chloro-3-fluoro-4-(4-((1-methyl-1H-pyrazol-3-yl)amino)-1,3,5-triazin-2-yl)benzyl)-5-(1-methylcyclopropyl)-1,2,4-oxadiazole-3-carboxamide was synthesized using a method similar to the synthesis of one of the above mentioned examples.

ESI-MS (M+H)$^+$: 484.5. $^1$H NMR (500 MHz, CDCl$_3$) δ: 8.94-8.76 (m, 1H), 8.32-8.09 (m, 1H), 8.09-7.89 (m, 1H), 7.45-7.36 (m, 2H), 7.33 (d, J=2.4 Hz, 1H), 6.96-6.73 (m, 1H), 4.83 (d, J=6.7 Hz, 2H), 3.95-3.79 (m, 3H), 1.60 (s, 3H), 1.53-1.48 (m, 2H), 1.13-1.08 (m, 2H).

Example 105: 1-(tert-butyl)-N-(3-fluoro-2-methyl-4-(4-((1-methyl-1H-pyrazol-4-yl)amino)-1,3,5-triazin-2-yl)benzyl)-1H-1,2,3-triazole-4-carboxamide (Compound 105)

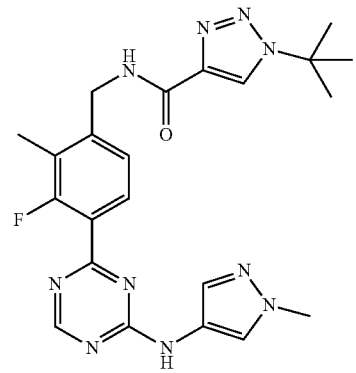

1-(tert-butyl)-N-(3-fluoro-2-methyl-4-(4-((1-methyl-1H-pyrazol-4-yl)amino)-1,3,5-triazin-2-yl)benzyl)-1H-1,2,3-triazole-4-carboxamide was synthesized using a method similar to the synthesis of one of the above mentioned examples.

ESI-MS (M+H)$^+$: 465.6. $^1$H NMR (400 MHz, CDCl$_3$) δ: 10.57 (br s, 1H), 8.74 (br s, 1H), 8.36-8.27 (m, 1H), 8.08-7.97 (m, 2H), 7.91-7.81 (m, 2H), 7.34-7.28 (m, 1H), 4.80-4.65 (m, 2H), 3.99 (s, 3H), 2.43-2.26 (m, 3H), 1.73 (s, 9H).

Example 106: 1-(tert-butyl)-N-(3-fluoro-2-methyl-4-(4-((1-methyl-1H-pyrazol-4-yl)amino)-1,3,5-triazin-2-yl)benzyl)-1H-pyrazole-3-carboxamide (Compound 106)

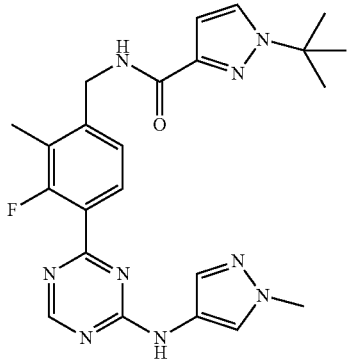

1-(tert-butyl)-N-(3-fluoro-2-methyl-4-(4-((1-methyl-1H-pyrazol-4-yl)amino)-1,3,5-triazin-2-yl)benzyl)-1H-pyrazole-3-carboxamide was synthesized using a method similar to the synthesis of one of the above mentioned examples.

ESI-MS (M+H)$^+$: 464.6. $^1$H NMR (500 MHz, CDCl$_3$) δ: 10.03 (br s, 1H), 8.72 (s, 1H), 8.08-8.02 (m, 1H), 8.01 (s, 1H), 7.84 (s, 1H), 7.57 (d, J=2.5 Hz, 1H), 7.38-7.29 (m, 2H), 6.84 (d, J=2.5 Hz, 1H), 4.82-4.66 (m, 2H), 3.98 (s, 3H), 2.46-2.25 (m, 3H), 1.61 (s, 9H).

Example 107: 2-(tert-butyl)-N-(2-methyl-4-(4-((1-methyl-1H-pyrazol-4-yl)amino)-1,3,5-triazin-2-yl)benzyl)oxazole-4-carboxamide (Compound 107)

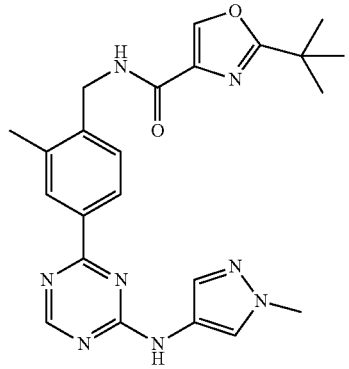

2-(tert-butyl)-N-(2-methyl-4-(4-((1-methyl-1H-pyrazol-4-yl)amino)-1,3,5-triazin-2-yl)benzyl)oxazole-4-carboxamide was synthesized using a method similar to the synthesis of one of the above mentioned examples.

ESI-MS (M+H)$^+$: 447.3. $^1$H NMR (500 MHz, DMSO-d$_6$) δ: 10.27 (s, 1H), 8.79-8.70 (m, 1H), 8.64-8.59 (m, 1H), 8.54 (s, 1H), 8.22-8.13 (m, 2H), 8.00-7.95 (m, 1H), 7.63-7.55 (m, 1H), 7.38 (dd, J=12.0 Hz, 8.0 Hz, 1H), 4.50-4.48 (m, 2H), 3.87-3.83 (m, 3H), 2.43-2.40 (m, 3H), 1.37 (s, 9H).

Example 108: 3-(tert-butyl)-N-(2-methyl-4-(4-((1-methyl-1H-pyrazol-4-yl)amino)-1,3,5-triazin-2-yl)benzyl)isoxazole-5-carboxamide (Compound 108)

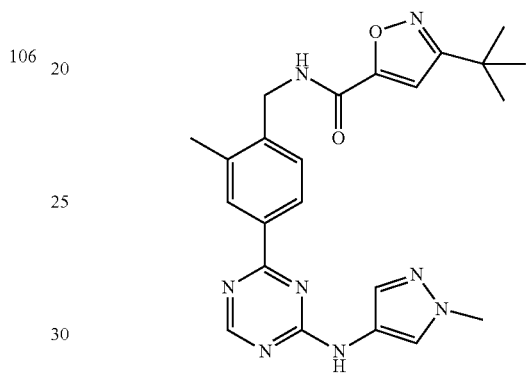

3-(tert-butyl)-N-(2-methyl-4-(4-((1-methyl-1H-pyrazol-4-yl)amino)-1,3,5-triazin-2-yl)benzyl)isoxazole-5-carboxamide was synthesized using a method similar to the synthesis of one of the above mentioned examples.

ESI-MS (M+H)$^+$: 447.3. $^1$H NMR (500 MHz, DMSO-d$_6$) δ: 10.26 (br d, J=4.9 Hz, 1H), 9.44-9.39 (m, 1H), 8.79-8.70 (m, 1H), 8.24-8.14 (m, 2H), 8.00-7.95 (m, 1H), 7.63-7.55 (m, 1H), 7.42 (dd, J=13.4 Hz, 7.9 Hz, 1H), 7.18 (d, J=2.4 Hz, 1H), 4.53-4.50 (m, 2H), 3.87-3.83 (m, 3H), 2.44-2.41 (m, 3H), 1.31 (s, 9H).

Example 109: 1-(tert-butyl)-N-(2-methyl-4-(4-((1-methyl-1H-pyrazol-4-yl)amino)-1,3,5-triazin-2-yl)benzyl)-1H-1,2,3-triazole-4-carboxamide (Compound 109)

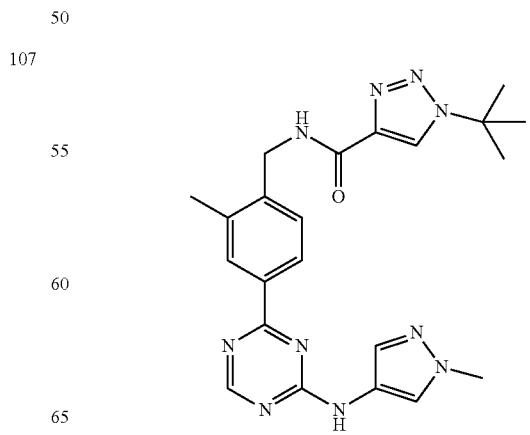

1-(tert-butyl)-N-(2-methyl-4-(4-((1-methyl-1H-pyrazol-4-yl)amino)-1,3,5-triazin-2-yl)benzyl)-1H-1,2,3-triazole-4-carboxamide was synthesized using a method similar to the synthesis of one of the above mentioned examples.

ESI-MS (M+H)$^+$: 447.3. $^1$H NMR (500 MHz, DMSO-d$_6$) δ:10.26 (br d, J=3.7 Hz, 1H), 9.06-9.02 (m, 1H), 8.78-8.69 (m, 2H), 8.21-8.13 (m, 2H), 8.00-7.95 (m, 1H), 7.63-7.55 (m, 1H), 7.39 (dd, J=15.3 Hz, 8.5 Hz, 1H), 4.53-4.51 (m, 2H), 3.87-3.83 (m, 3H), 2.44-2.41 (m, 3H), 1.64 (s, 9H).

Example 110: 5-(tert-butyl)-N-(2-methyl-4-(4-((1-methyl-1H-pyrazol-4-yl)amino)-1,3,5-triazin-2-yl)benzyl)-1,3,4-oxadiazole-2-carboxamide (Compound 110)

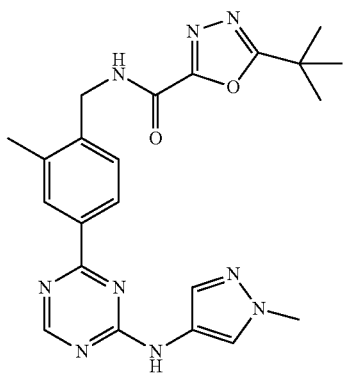

5-(tert-butyl)-N-(2-methyl-4-(4-((1-methyl-1H-pyrazol-4-yl)amino)-1,3,5-triazin-2-yl)benzyl)-1,3,4-oxadiazole-2-carboxamide was synthesized using a method similar to the synthesis of one of the above mentioned examples.

ESI-MS (M+H)$^+$: 448.3. $^1$H NMR (500 MHz, DMSO-d$_6$) δ:10.27 (s, 1H), 9.83-9.78 (m, 1H), 8.79-8.70 (m, 1H), 8.23-8.13 (m, 2H), 7.99-7.95 (m, 1H), 7.64-7.55 (m, 1H), 7.44 (br dd, J=13.1 Hz, 8.2 Hz, 1H), 4.54-4.52 (m, 2H), 3.87-3.83 (m, 3H), 2.44-2.42 (m, 3H), 1.40 (s, 9H).

Example 111: (R)-5-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide (Compound 111)

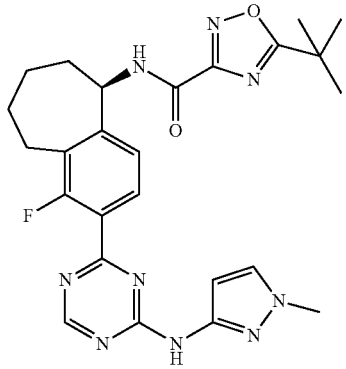

(R)-5-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)-1,2,4-oxadiazole-3-carboxamide was synthesized using a method similar to the synthesis of one of the above mentioned examples.

ESI-MS (M+H)$^+$: 506.3. $^1$H NMR (500 MHz, DMSO-d$_6$, t=80° C.) δ: 10.08 (s, 1H), 9.09 (d, J=8.0 Hz, 1H), 8.74 (s, 1H), 7.88-7.82 (m, 1H), 7.56 (d, J=2.5 Hz, 1H), 7.22 (d, J=8.0 Hz, 1H), 6.65 (d, J=2.5 Hz, 1H), 5.36-5.32 (m, 1H), 3.78 (s, 3H), 3.31-3.25 (m, 1H), 2.76-2.70 (m, 1H), 2.02-1.85 (m, 5H), 1.48 (s, 9H), 1.35-1.30 (m, 1H).

Example 112: (R)-2-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)oxazole-4-carboxamide (Compound 112)

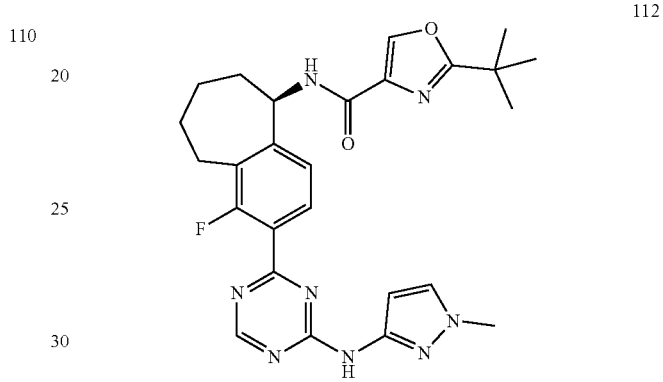

(R)-2-(tert-butyl)-N-(1-fluoro-2-(4-((1-methyl-1H-pyrazol-3-yl)amino)-1,3,5-triazin-2-yl)-6,7,8,9-tetrahydro-5H-benzo[7]annulen-5-yl)oxazole-4-carboxamide was synthesized using a method similar to the synthesis of one of the above mentioned examples.

ESI-MS (M+Na)$^+$: 487.2. $^1$H NMR (500 MHz, DMSO-d$_6$, t=80° C.) δ: 10.03 (s, 1H), 8.75 (s, 1H), 8.45 (s, 1H), 8.13 (d, J=7.5 Hz, 1H), 7.86-7.82 (m, 1H), 7.56 (s, 1H), 7.20 (d, J=8.5 Hz, 1H), 6.66 (d, J=2.0 Hz, 1H), 5.35-5.32 (m, 1H), 3.79 (s, 3H), 3.28-3.23 (m, 1H), 2.79-2.73 (m, 1H), 2.02-1.87 (m, 5H), 1.47-1.40 (m, 10H).

Example 113: N-(3-fluoro-2-methyl-4-(4-((1-methyl-1H-pyrazol-3-yl)amino)-1,3,5-triazin-2-yl)benzyl)-5-(1-methylcyclopropyl)-1,2,4-oxadiazole-3-carboxamide (Compound 113)

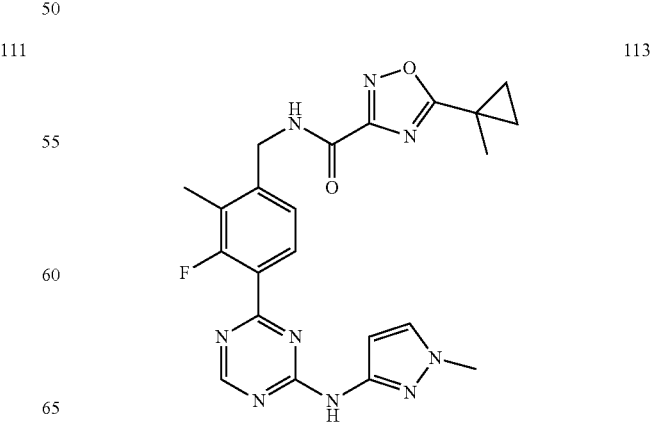

N-(3-fluoro-2-methyl-4-(4-((1-methyl-1H-pyrazol-3-yl)amino)-1,3,5-triazin-2-yl)benzyl)-5-(1-methylcyclopropyl)-1,2,4-oxadiazole-3-carboxamide was synthesized using a method similar to the synthesis of one of the above mentioned examples.

ESI-MS (M+H)$^+$: 464.1. $^1$H NMR (500 MHz, DMSO-d$_6$) δ: 10.15 (s, 1H), 9.08 (s, 1H), 8.76 (s, 1H), 7.89-7.86 (m, 1H), 7.58 (s, 1H), 7.28-7.26 (m, 1H), 6.67 (s, 1H), 4.58-4.56 (m, 2H), 3.80 (s, 3H), 2.34 (s, 3H), 1.57 (s, 3H), 1.40-1.32 (m, 2H), 1.18-1.16 (m, 2H).

Example 114: 4-(tert-butyl)-N-(2-methyl-4-(4-((1-methyl-1H-pyrazol-4-yl)amino)-1,3,5-triazin-2-yl)benzyl)oxazole-2-carboxamide (Compound 114)

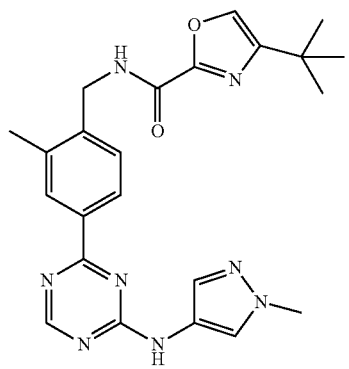

114

4-(tert-butyl)-N-(2-methyl-4-(4-((1-methyl-1H-pyrazol-4-yl)amino)-1,3,5-triazin-2-yl)benzyl)oxazole-2-carboxamide was synthesized using a method similar to the synthesis of one of the above mentioned examples.

ESI-MS (M+H)$^+$: 447.3. $^1$H NMR (500 MHz, DMSO-d$_6$) δ: 10.26 (d, J=5.5 Hz, 1H), 9.34 (td, J=9.2 Hz, 6.1 Hz, 1H), 8.86-8.68 (m, 1H), 8.25-8.13 (m, 2H), 8.04 (d, J=1.2 Hz, 1H), 8.01-7.94 (m, 1H), 7.66-7.50 (m, 1H), 7.40 (dd, J=14.0 Hz, 7.9 Hz, 1H), 4.50 (br t, J=4.9 Hz, 2H), 3.91-3.81 (m, 3H), 2.46-2.39 (m, 3H), 1.27 (s, 9H).

Example 115. In Vitro BTK Kinase Assay: BTK-POLYGAT-LS ASSAY

The purpose of the BTK in vitro assay is to determine compound potency against BTK through the measurement of IC$_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 pL aliquot of a ATP/peptide master mix (final concentration; ATP 10 kM, polyGAT 100 nM) in kinase buffer (10 mM Tris-HCl pH 7.5, 10 mM MgCl$_2$, 200 μM Na$_3$PO$_4$, 5 mM DTT, 0.01% Triton X-100, and 0.2 mg/ml casein) is added to each well. Next, I pL of a 4-fold, 40× compound titration in 100% DMSO solvent is added, followed by adding 15 μL of BTK enzyme mix in 1× kinase buffer (with a final concentration of 0.25 nM). The assay is incubated for 30 minutes before being stopped with 28 μL of a 50 mM EDTA solution. Aliquots (5 μL) of the kinase reaction are transferred to a low volume white 384 well plate (Corning 3674), and 5 μL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. IC$_{50}$ values are calculated using a four parameter fit with 100% enzyme activity determined from the DMSO control and 0% activity from the EDTA control.

Table 1 shows the activity of selected compounds of this invention in the in vitro Btk kinase assay, wherein each compound number corresponds to the compound numbering set forth in Examples 1-114 herein. "††" represents an IC$_{50}$ of equal to or less than 10 nM and greater than 1 nM; and "†††" represents an IC$_{50}$ of equal to or less than 1 nM. N/D represents IC$_{50}$ value not yet determined.

TABLE 1

| IC$_{50}$ (nM) | Compound No. |
| --- | --- |
| ††† | 2, 6, 9, 10, 11, 12, 13, 14, 15, 16, 17, 18, 20, 21, 22, 23, 27, 28, 29, 30, 31, 32, 33, 34, 35, 36, 37, 38, 39, 40, 41, 45, 47, 48, 49, 50, 51, 53, 54, 55, 56, 57, 58, 59, 60, 61, 63, 64, 65, 69, 71, 72, 73, 74, 75, 76, 77, 80, 81, 84, 85, 86, 87, 88, 89, 90, 91, 92, 93, 95, 98, 99, 100, 101, 102, 103, 104, 105, 106, 107, 108, 111, 112, 113, 114 |
| †† | 1, 3, 4, 5, 7, 8, 19, 42, 43, 44, 46, 52, 62, 66, 67, 68, 78, 79, 82, 83, 94, 96, 97, 109, 110 |
| N/D | 70 |

Example 116. In Vitro PD Assay in Human Whole Blood

Human heparinized venous blood was purchased from Bioreclamation, Inc. or SeraCare Life Sciences and shipped overnight. Whole blood was aliquoted into 96-well plate and "spiked" with serial dilutions of test compound in DMSO or with DMSO without drug. The final concentration of DMSO in all wells was 0.1%. The plate was incubated at 37° C. for 30 min. Lysis buffer containing protease and phosphatase inhibitors was added to the drug-containing samples and one of the DMSO-only samples (+PPi, high control), while lysis buffer containing protease inhibitors was added to the other DMSO-only samples (−PPi, low control). All of the lysed whole blood samples were subjected to the total BTK capture and phosphotyrosine detection method described in US20160311802, incorporated herein by reference. ECL values were graphed in Prism and a best-fit curve with restrictions on the maximum and minimum defined by the +PPi high and −PPi low controls was used to estimate the test compound concentration that results in 50% inhibition of ECL signal by interpolation.

Table 2 shows the activity of selected compounds of this invention in the pBTK assay, wherein each compound number corresponds to the compound numbering set forth in Examples 1-114 described herein. "†" represents an IC$_{50}$ of equal to or less than 10,000 nM but greater than 500 nM, "††" represents an IC$_{50}$ of equal to or less than 500 nM but greater than 100 nM; and "†††" represents an IC$_{50}$ of equal to or less than 100 nM. * represents an IC$_{50}$ value of greater than 10,000 nM.

TABLE 2

| IC$_{50}$ (nM) | Compound No. |
| --- | --- |
| ††† | 13, 14, 24, 25, 28, 29, 30, 32, 33, 34, 39, 47, 50, 69, 70, 73, 74, 81, 85, 86, 87, 88, 89, 90, 91, 92, 93 |

TABLE 2-continued

| IC$_{50}$ (nM) | Compound No. |
|---|---|
| †† | 1, 9, 11, 12, 15, 16, 17, 21, 23, 27, 35, 36, 37, 38, 40, 44, 45, 48, 49, 51, 53, 54, 56, 57, 58, 59, 60, 61, 71, 72, 75, 76, 77, 78, 80, 84, 94, 98, 103, 105, 108, 109, 111, 113 |
| † | 2, 3, 5, 6, 20, 22, 31, 41, 42, 43, 46, 52, 55, 62, 63, 64, 65, 66, 68, 79, 82, 95, 96, 97, 99, 100, 101, 102, 104, 106, 107, 112, 114 |
| * | 4 |

What is claimed is:

1. A compound of Formula (I):

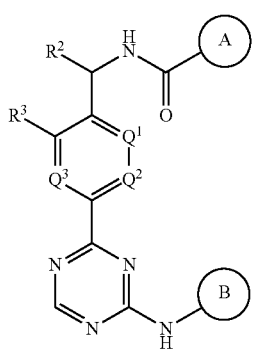

Formula (I)

or a pharmaceutically acceptable salt, wherein:

Ring A is selected from aryl and 5- to 6-membered heteroaryl, wherein said aryl and 5- to 6-membered heteroaryl is optionally substituted with one or more $R^1$;

Ring B is pyrazolyl, wherein said pyrazolyl is optionally substituted with one or more $R^5$;

$Q^1$, $Q^2$, and $Q^3$ are each selected from C—$R^4$ and N, wherein at most one of $Q^1$, $Q^2$, and $Q^3$ is N;

$R^1$ in each occurrence is independently selected from $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)$R^{1a}$, —C(O)$_2R^{1a}$, —C(O)N($R^{1a}$)$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N(Ra)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{10}$;

$R^{1a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{10}$;

$R^2$ is selected from H and $C_{1-6}$alkyl;

$R^3$ is selected from $C_{1-6}$alkyl, $C_{2-6}$alkenyl, $C_{2-6}$alkynyl, 3- to 6-membered monocyclic carbocyclyl, and 4- to 6-membered monocyclic heterocyclyl, halo, —CN, —C(O)$R^{3a}$, —C(O)$_2R^{3a}$, —C(O)N($R^{3a}$)$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —N($R^{3a}$)S(O)$_2R^{3a}$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$ wherein said $C_{1-6}$alkyl, $C_{2-6}$alkenyl, $_{2-6}$alkynyl, 3- to 6-membered monocyclic carbocyclyl, and 4- to 6-membered monocyclic heterocyclyl are optionally substituted with one or more $R^{30}$;

$R^{3a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{30}$;

or $R^2$ and $R^3$, together with their intervening atoms, form a seven-membered carbocyclic or heterocyclic ring, wherein said seven-membered carbocyclic or heterocyclic ring is optionally substituted with one or more $R^{20}$;

$R^4$ in each occurrence is independently selected from H, $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)$R^{4a}$, —C(O)$_2R^{4a}$, —C(O)N($R^{4a}$)$_2$, —N($R^{4a}$)$_2$, —N($R^{4a}$)C(O)$R^{4a}$, —N($R^{4a}$)C(O)$_2R^{4a}$, —N($R^{4a}$)C(O)N($R^{4a}$)$_2$, —N($R^{4a}$)S(O)$_2R^{4a}$, —O$R^{4a}$, —OC(O)$R^{4a}$, —OC(O)N($R^{4a}$)$_2$, —S$R^{4a}$, —S(O)$R^{4a}$, —S(O)$_2R^{4a}$, —S(O)N($R^{4a}$)$_2$, and —S(O)$_2$N($R^{4a}$)$_2$, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{40}$;

$R^{4a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{40}$;

$R^5$ in each occurrence is independently selected from $C_6$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)$R^{5a}$, —C(O)$_2R^{5a}$, —C(O)N($R^{5a}$)$_2$, —N($R^{5a}$)$_2$, —N($R^{5a}$)C(O)$R^{5a}$, —N($R^{5a}$)C(O)$_2R^{5a}$, —N($R^{5a}$)C(O)N($R^{5a}$)$_2$, —N($R^{5a}$)S(O)$_2R^{5a}$, —O$R^{5a}$, —OC(O)$R^{5a}$, —OC(O)N($R^{5a}$)$_2$, —S$R^{5a}$, —S(O)$R^{5a}$, —S(O)$_2R^{5a}$, —S(O)N($R^{5a}$)$_2$, and —S(O)$_2$N($R^{5a}$)$_2$, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{50}$;

$R^{5a}$ in each occurrence is independently selected from H, $C_{1-6}$alkyl, $C_{2-6}$alkenyl, $C_{2-6}$alkynyl, 3- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 3- to 6-membered monocyclic carbocyclyl, and 4- to 6-membered monocyclic heterocyclyl in each occurrence are optionally and independently substituted with one or more $R^{50}$;

$R^{10}$ in each occurrence is independently selected from $C_{1-6}$alkyl, $C_{2-6}$alkenyl, $C_{2-6}$alkynyl, 3- to 6-membered monocyclic carbocyclyl, 4- to 6-membered monocyclic heterocyclyl, halo, —CN, —C(O)$R^{10a}$, —C(O)$_2R^{10a}$, —C(O)N($R^{10a}$)$_2$, —N($R^{10a}$)$_2$, —N($R^{10a}$)C(O)$R^{10a}$, —N(R$^{10a}$)C(O)$_2$R$^{10a}$, —N(R$^{10a}$)C(O)N(R$^{10a}$)$_2$, —N(R$^{10a}$)S(O)$_2$R$^{10a}$, —OR$^{10a}$, —OC(O)R$^{10a}$, —OC(O)N(R$^{10a}$)$_2$, —SR$^{10a}$, —S(O)R$^{10a}$, —S(O)$_2$R$^{10a}$, —S(O)N(R$^{10a}$)$_2$, and —S(O)$_2$N(R$^{10a}$)$_2$;

R$^{10a}$ in each occurrence is independently selected from H, C$_{1-6}$alkyl, C$_{2-6}$alkenyl, C$_{2-6}$alkynyl, 3- to 6-membered monocyclic carbocyclyl, and 4- to 6-membered monocyclic heterocyclyl;

R$^{20}$ in each occurrence is independently selected from C$_{1-6}$alkyl, C$_{2-6}$alkenyl, C$_{2-6}$alkynyl, 3- to 6-membered monocyclic carbocyclyl, 4- to 6-membered monocyclic heterocyclyl, halo, —CN, —C(O)R$^{20a}$, —C(O)$_2$R$^{20a}$, —C(O)N(R$^{20a}$)$_2$, —N(R$^{20a}$)$_2$, —N(R$^{20a}$)C(O)R$^{20a}$, —N(R$^{20a}$)C(O)$_2$R$^{20a}$, —N(R$^{20a}$)C(O)N(R$^{20a}$)$_2$, —N(R$^{20a}$)S(O)$_2$R$^{20a}$, —OR$^{20a}$, —OC(O)R$^{20a}$, —OC(O)N(R$^{20a}$)$_2$, —SR$^{20a}$, —S(O)R$^{20a}$, —S(O)$_2$R$^{20a}$, —S(O)N(R$^{20a}$)$_2$, and —S(O)$_2$N(R$^{20a}$)$_2$, wherein said C$_{1-6}$alkyl, C$_{2-6}$alkenyl, C$_{2-6}$alkynyl, 3- to 6-membered monocyclic carbocyclyl, and 4- to 6-membered monocyclic heterocyclyl in each occurrence are optionally substituted with one or more R$^{25}$;

R$^{20a}$ in each occurrence is independently selected from H, C$_{1-6}$alkyl, C$_{2-6}$alkenyl, C$_{2-6}$alkynyl, 3- to 6-membered monocyclic carbocyclyl, and 4- to 6-membered monocyclic heterocyclyl, wherein said C$_{1-6}$alkyl, C$_{2-6}$alkenyl, C$_{2-6}$alkynyl, 3- to 6-membered monocyclic carbocyclyl, and 4- to 6-membered monocyclic heterocyclyl in each occurrence are optionally and independently substituted with one or more R$^{25}$;

R$^{25}$ in each occurrence is independently selected from C$_{1-6}$alkyl, C$_{2-6}$alkenyl, C$_{2-6}$alkynyl, 3- to 6-membered monocyclic carbocyclyl, 4- to 6-membered monocyclic heterocyclyl, halo, —CN, —C(O)R$^{25a}$, —C(O)$_2$R$^{25a}$, —C(O)N(R$^{25a}$)$_2$, —N(R$^{25a}$)$_2$, —N(R$^{25a}$)C(O)R$^{25a}$, —N(R$^{25a}$)C(O)$_2$R$^{25a}$, —N(R$^{25a}$)C(O)N(R$^{25a}$)$_2$, —N(R$^{25a}$)S(O)$_2$R$^{25a}$, —OR$^{25a}$, —OC(O)R$^{25a}$, —OC(O)N(R$^{25a}$)$_2$, —SR$^{25a}$, —S(O)R$^{25a}$, —S(O)$_2$R$^{25a}$, —S(O)N(R$^{25a}$)$_2$, and —S(O)$_2$N(R$^{25a}$)$_2$;

R$^{25a}$ in each occurrence is independently selected from H, C$_{1-6}$alkyl, C$_{2-6}$alkenyl, C$_{2-6}$alkynyl, 3- to 6-membered monocyclic carbocyclyl, and 4- to 6-membered monocyclic heterocyclyl;

R$^{30}$ in each occurrence is independently selected from C$_{1-6}$alkyl, C$_{2-6}$alkenyl, C$_{2-6}$alkynyl, 3- to 6-membered monocyclic carbocyclyl, 4- to 6-membered monocyclic heterocyclyl, halo, —CN, —C(O)R$^{30a}$, —C(O)$_2$R$^{30a}$, —C(O)N(R$^{3a}$)$_2$, —N(R$^{3a}$)$_2$, —N(R$^{30a}$)C(O)R$^{30a}$, —N(R$^{30a}$)C(O)$_2$R$^{30a}$, —N(R$^{30a}$)C(O)N(R$^{30a}$)$_2$, —N(R$^{30a}$)S(O)$_2$R$^{30a}$, —OR$^{30a}$, —OC(O)R$^{30a}$, —OC(O)N(R$^{30a}$)$_2$, —SR$^{30a}$, —S(O)R$^{30a}$, —S(O)$_2$R$^{30a}$, —S(O)N(R$^{30a}$)$_2$, and —S(O)$_2$N(R$^{30a}$)$_2$;

R$^{30a}$ in each occurrence is independently selected from H, C$_{1-6}$alkyl, C$_{2-6}$alkenyl, C$_{2-6}$alkynyl, 3- to 6-membered monocyclic carbocyclyl, and 4- to 6-membered monocyclic heterocyclyl;

R$^{40}$ in each occurrence is independently selected from C$_{1-6}$alkyl, C$_{2-6}$alkenyl, C$_{2-6}$alkynyl, 3- to 6-membered monocyclic carbocyclyl, 4- to 6-membered monocyclic heterocyclyl, halo, —CN, —C(O)R$^{40a}$, —C(O)$_2$R$^{40a}$, —C(O)N(R$^{40a}$)$_2$, —N(R$^{40a}$)$_2$, —N(R$^{40a}$)C(O)R$^{40a}$, —N(R$^{40a}$)C(O)$_2$R$^{40a}$, —N(R$^{40a}$)C(O)N(R$^{40a}$)$_2$, —N(R$^{40a}$)S(O)$_2$R$^{40a}$, —OR$^{40a}$, —OC(O)R$^{40a}$, —OC(O)N(R$^{40a}$)$_2$, —SR$^{40a}$, —S(O)R$^{40a}$, —S(O)$_2$R$^{40a}$, —S(O)N(R$^{40a}$)$_2$, and —S(O)$_2$N(R$^{40a}$)$_2$;

R$^{40a}$ in each occurrence is independently selected from H, C$_{1-6}$alkyl, C$_{2-6}$alkenyl, C$_{2-6}$alkynyl, 3- to 6-membered monocyclic carbocyclyl, and 4- to 6-membered monocyclic heterocyclyl;

R$^{50}$ in each occurrence is independently selected from C$_{1-6}$alkyl, C$_{2-6}$alkenyl, C$_{2-6}$alkynyl, 3- to 6-membered monocyclic carbocyclyl, 4- to 6-membered monocyclic heterocyclyl, halo, —CN, —C(O)R$^{50a}$, —C(O)$_2$R$^{50a}$, —C(O)N(R$^{50a}$)$_2$, —N(R$^{50a}$)$_2$, —N(R$^{50a}$)C(O)R$^{50a}$, —N(R$^{50a}$)C(O)$_2$R$^{50a}$, —N(R$^{50a}$)C(O)N(R$^{50a}$)$_2$, —N(R$^{50a}$)S(O)$_2$R$^{50a}$, —OR$^{50a}$, —OC(O)R$^{50a}$, —OC(O)N(R$^{50a}$)$_2$, —SR$^{50a}$, —S(O)R$^{50a}$, —S(O)$_2$R$^{50a}$, —S(O)N(R$^{50a}$)$_2$, and —S(O)$_2$N(R$^{50a}$)$_2$; and R$^{50a}$ in each occurrence is independently selected from H, C$_{1-6}$alkyl, C$_{2-6}$alkenyl, C$_{2-6}$alkynyl, 3- to 6-membered monocyclic carbocyclyl, and 4- to 6-membered monocyclic heterocyclyl.

2. The compound of claim 1, wherein Q$^1$, Q$^2$, and Q$^3$ are each independently C—R$^4$.

3. The compound of claim 1, wherein the compound is represented by Formula (II) or formula (II'):

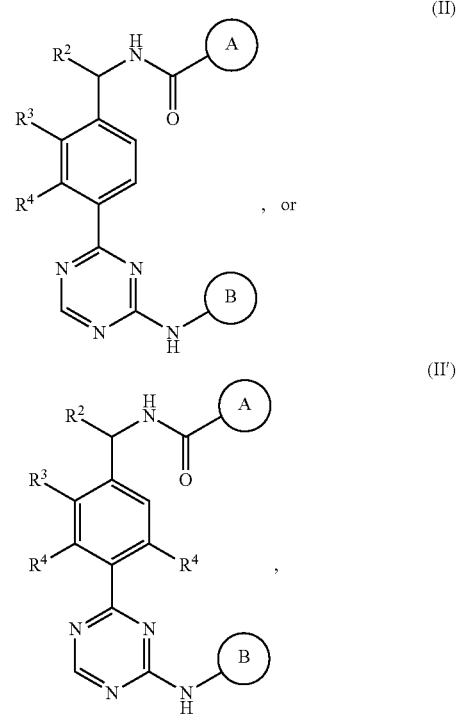

or a pharmaceutically acceptable salt thereof.

4. The compound of claim 3, wherein Ring A is selected from the group consisting of pyrazole, imidazole, oxazole, isoxazole, thiazole, isothiazole, 1,2,3-oxadiazole, 1,3,4-oxadiazole, 1,2,4-oxadizole, 1,2,3-thiadiazole, 1,3,4-thiadiazole, 1,2,4-thiadiazole, 1,2,3-triazole, 1,2,4-triazole, and tetrazole, each of which is optionally substituted with 1 or 2 independently selected R$^1$.

5. The compound of claim 4, wherein R$^1$ in each occurrence is independently halo, C$_{1-6}$alkyl or C$_{3-5}$cycloalkyl; wherein said C$_{1-6}$alkyl and C$_{3-5}$cycloalkyl are optionally substituted with one to three R$^{10}$; and R$^{10}$ in each occurrence is independently selected from halo, —CN and C$_{1-6}$alkyl, wherein said C$_{1-6}$alkyl in each occurrence is independently and optionally substituted with one to three halo.

6. The compound of claim 3, wherein Ring A is represented by the following formula:

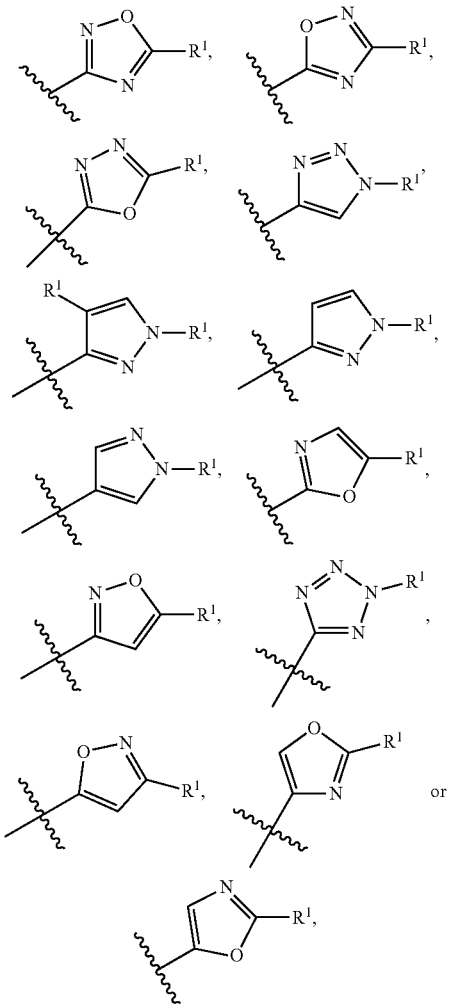

wherein R¹ in each occurrence is independently selected from halo, $C_{3-5}$cycloalkyl and $C_{1-6}$alkyl, wherein said $C_{3-5}$cycloalkyl and $C_{1-6}$alkyl are optionally substituted with one to three R¹⁰;

R¹⁰ in each occurrence is independently selected from halo and $C_{1-6}$alkyl, wherein $C_{1-6}$alkyl is optionally substituted with one to three halo.

7. The compound of claim 3, wherein Ring B is represented by the following formula:

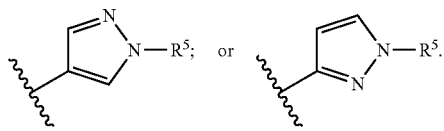

8. The compound of claim 7, wherein R⁵ is $C_{1-4}$alkyl optionally substituted with one to three fluoro.

9. The compound of claim 3, wherein
R² is H or $C_{1-3}$alkyl;
R³ is halo, $C_{3-5}$cycloalkyl or $C_{1-4}$alkyl, wherein said $C_{1-4}$alkyl and $C_{3-5}$alkyl are each optionally substituted with one to three fluoro; and
R⁴ is H, halo or $C_{1-3}$alkyl.

10. The compound of claim 1, wherein the compound is represented by formula (IIIA), (IIIB), (IIIA') or (IIIB'):

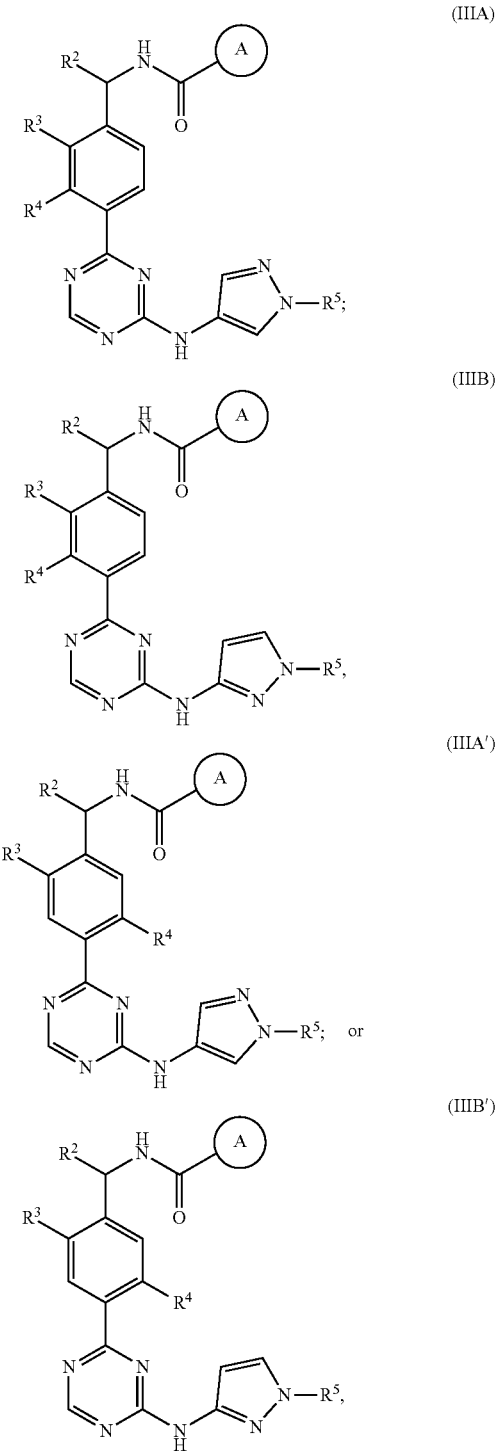

or a pharmaceutically acceptable salt thereof, wherein:

ring A is represented by the following formula:

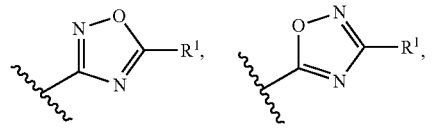

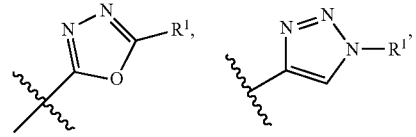

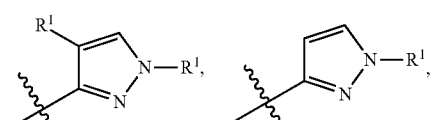

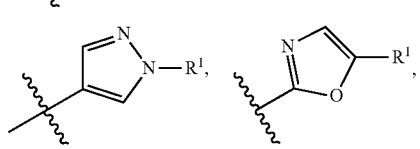

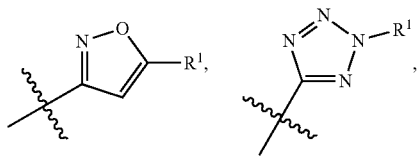

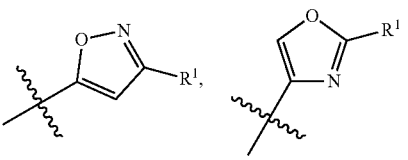

or

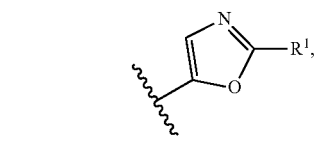

$R^1$ in each occurrence is independently selected from halo, $C_{3-5}$cycloalkyl and $C_{1-6}$alkyl, wherein said $C_{3-5}$cycloalkyl and $C_{1-6}$alkyl are optionally substituted with one to three $R^{10}$; $R^{10}$ in each occurrence is independently selected from halo or $C_{1-6}$alkyl, wherein said $C_{1-6}$alkyl is optionally substituted with one to three halo;

$R^3$ is halo, $C_{3-5}$cycloalkyl or $C_{1-4}$alkyl, wherein said $C_{1-4}$alkyl and $C_{3-5}$cycloalkyl are optionally substituted with one to three fluoro;

$R^4$ is H, $C_{1-4}$alkyl or halo; and $R^5$ is $C_{1-4}$alkyl.

11. The compound of claim 1, wherein the compound is represented by the following formula:

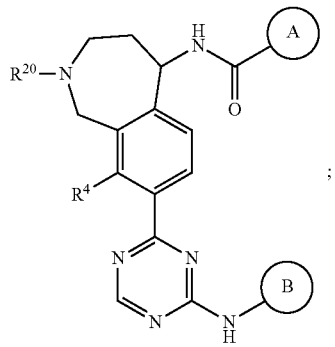

(IV)

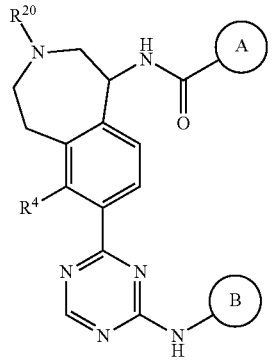

(V)

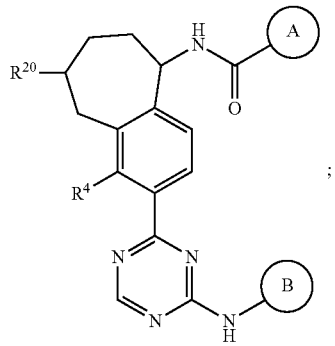

(VI)

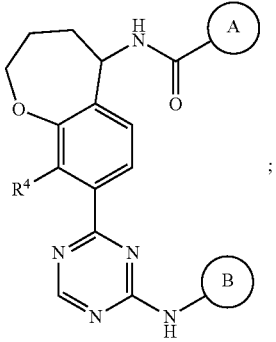

(VII)

(VIII)
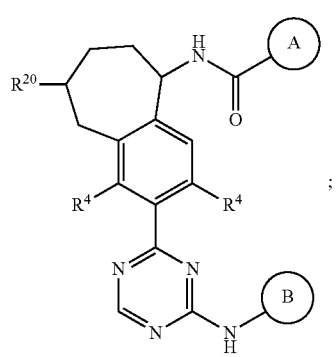
(IVA)
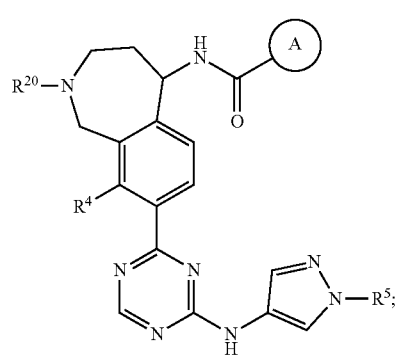
(IVB)
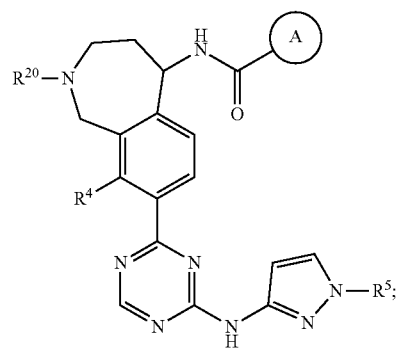
(VA)
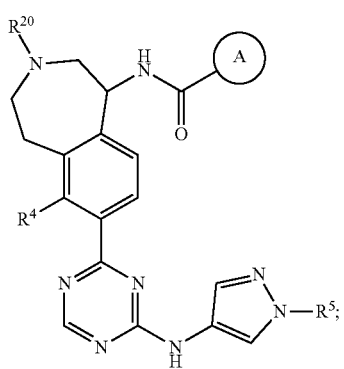
(VB)
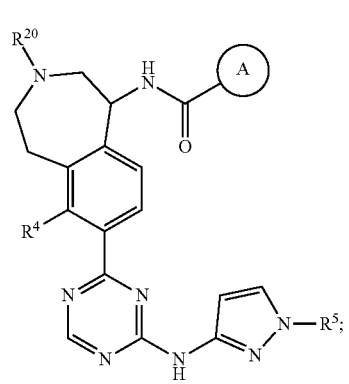
(VIA)
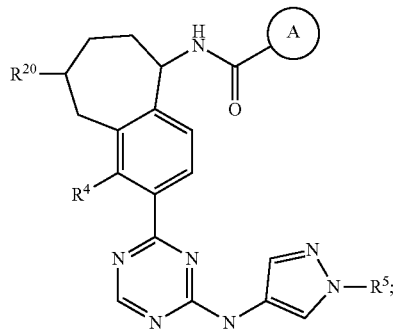
(VIB)
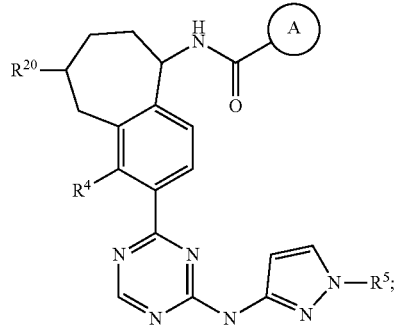
(VIIA)
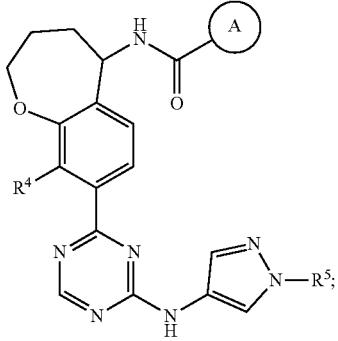

-continued
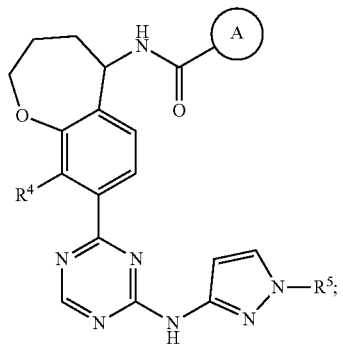
(VIIB)
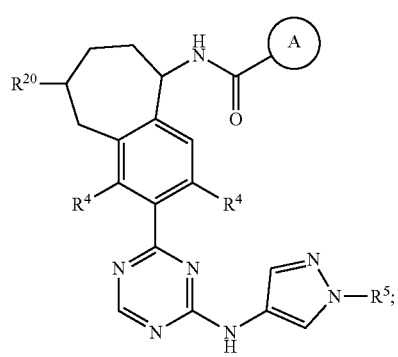
(VIIIA)
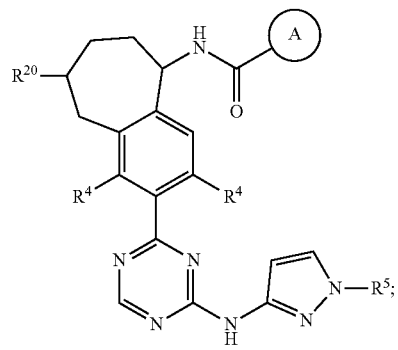
(VIIIB)
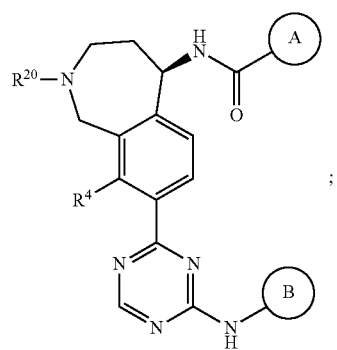
(IV')
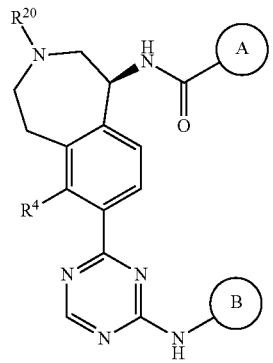
(V')
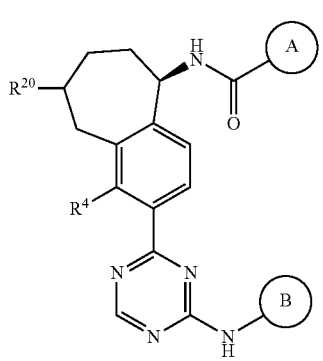
(VI')
; or
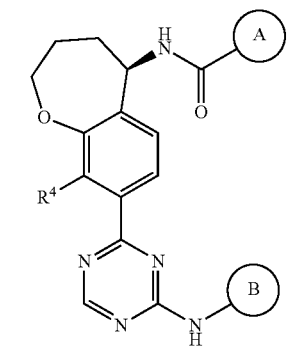
(VII')
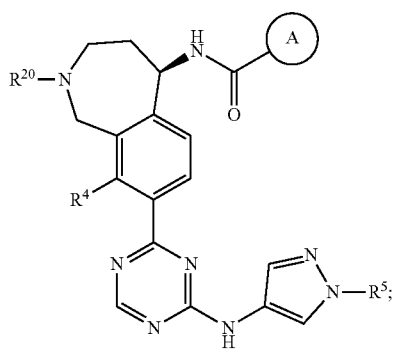
(IVA')

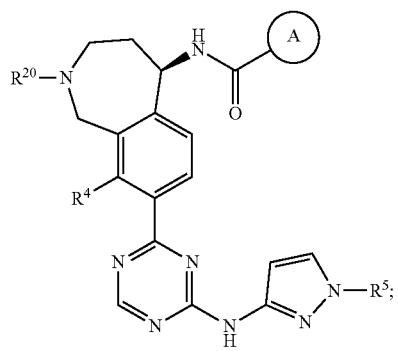 (IVB′)
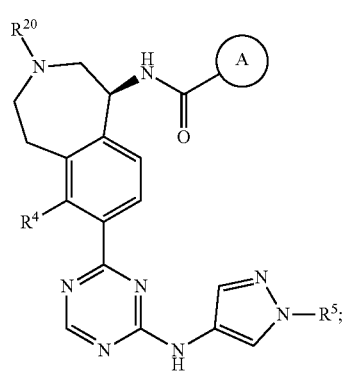 (VA′)
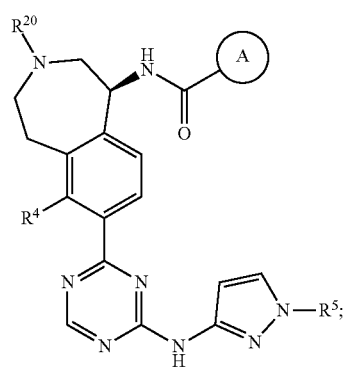 (VB′)
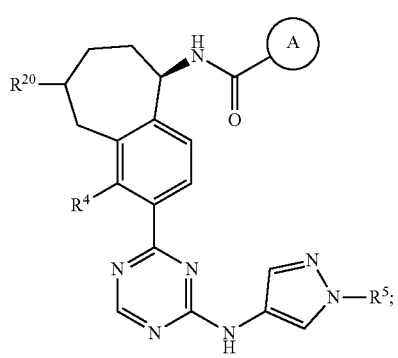 (VIA′)
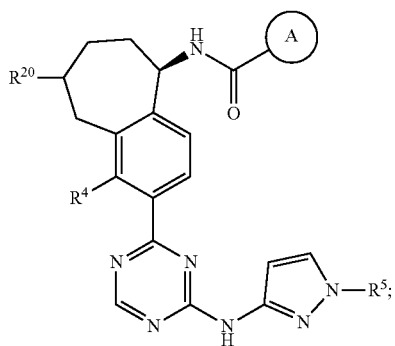 (VIB′)
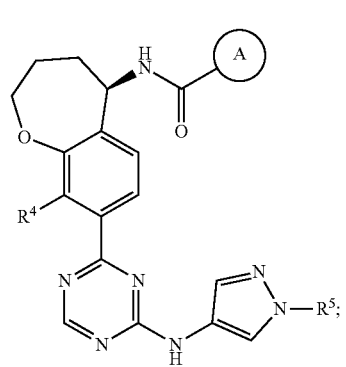 (VIIA′)
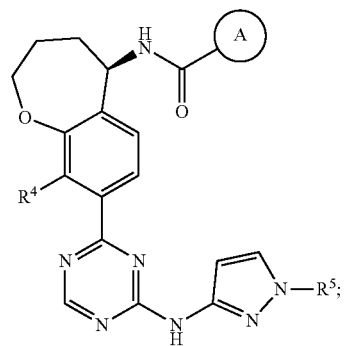 (VIIB′)
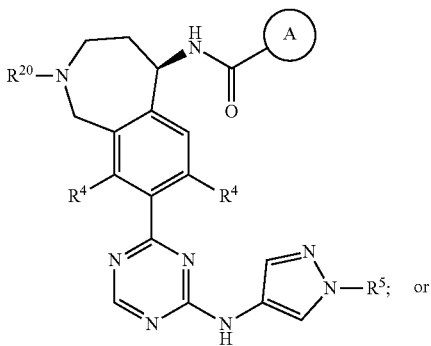 (VIIIA′) or

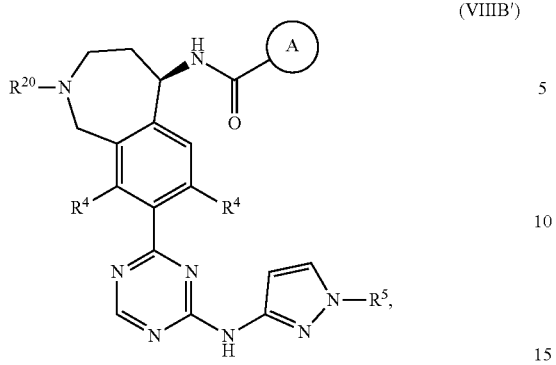

(VIIIB')

or a pharmaceutically acceptable salt thereof.

12. The compound of claim 11, wherein:

$R^{20}$ is selected from H, $C_{1-6}$alkyl, $C_{4-6}$cycloalkyl, saturated 4- to 6-membered monocyclic heterocyclyl, —C(O)$R^{20a}$, —C(O)$_2R^{20a}$, and —S(O)$_2R^{20a}$, wherein said $C_{1-6}$alkyl, $C_{4-6}$cycloalkyl, and saturated 4- to 6-membered monocyclic heterocyclyl are optionally substituted with one to three $R^{25}$;

$R^{20a}$ in each occurrence is independently selected from H, $C_{1-6}$alkyl, $C_{3-6}$cycloalkyl, and saturated 4- to 6-membered monocyclic heterocyclyl, wherein said $C_{1-6}$alkyl, $C_{3-6}$cycloalkyl, and saturated 4- to 6-membered monocyclic heterocyclyl in each occurrence are optionally and independently substituted with one or more $R^{25}$;

$R^{25}$ in each occurrence is independently selected from $C_{1-6}$alkyl, $C_{3-6}$cycloalkyl, saturated 4- to 6-membered monocyclic heterocyclyl, halo, —CN, —N($R^{25a}$)$_2$, and —O$R^{25a}$; and $R^{25a}$ in each occurrence is independently H or $C_{1-6}$alkyl.

13. The compound of claim 12, wherein $R^{20}$ is $C_{1-6}$alkyl or saturated 4- to 6-membered monocyclic heterocyclyl, wherein said $C_{1-6}$alkyl and saturated 4- to 6-membered monocyclic heterocyclyl are optionally substituted with one to three $R^{25}$; and $R^{25}$ in each occurrence is independently halo.

14. The compound of claim 12, wherein $R^{20}$ is $C_{1-6}$alkyl or saturated 4- to 6-membered monocyclic heterocyclyl selected from azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, and dioxinyl, wherein aid $C_{1-6}$alkyl is optionally substituted with one to three halo.

15. The compound of claim 11, wherein the compound is represented by formula (VI), (VIII), (VIA), (VIB), (VIIIA), (VIIIB), (VIII'), (VIA'), (VIB'), (VIIIA') or (VIIIB'):

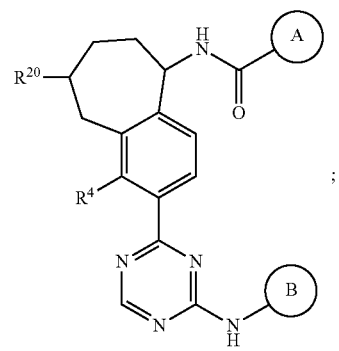

(VI)

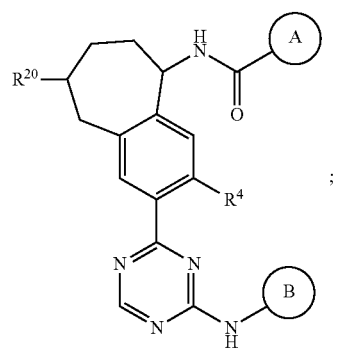

(VIII)

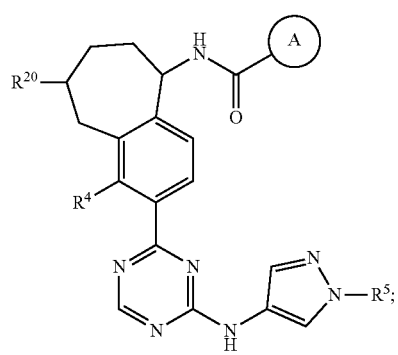

(VIA)

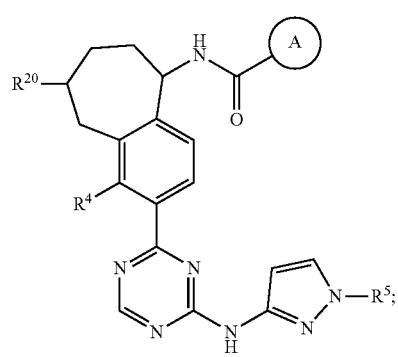

(VIB)

-continued (VIIIA)
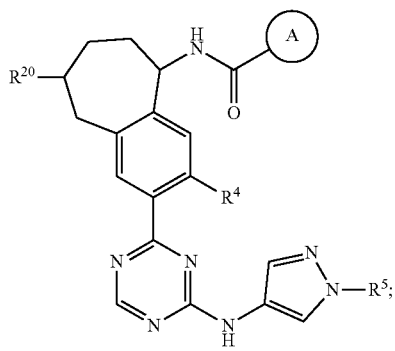

(VIIIB)
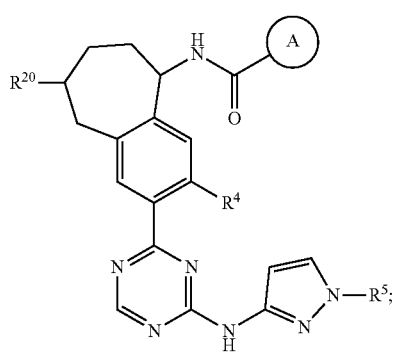

(VI′)
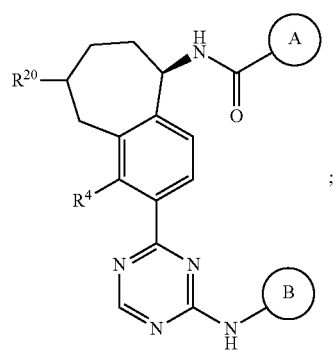

(VIII′)
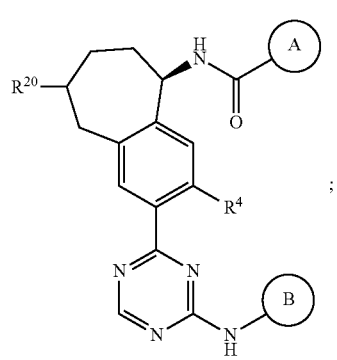

-continued (VIA′)
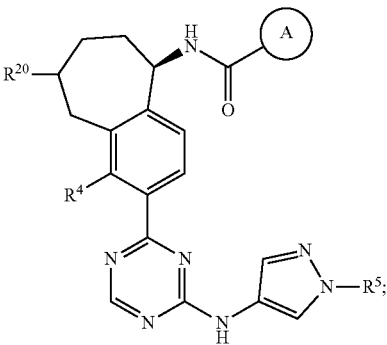

(VIB′)
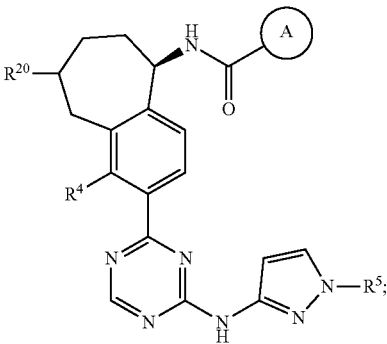

(VIIIA′)
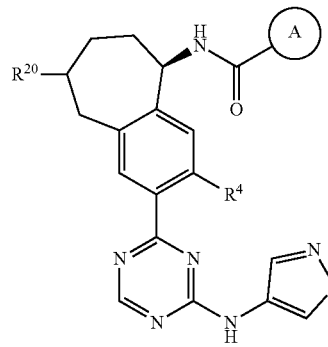

or (VIIIB′)
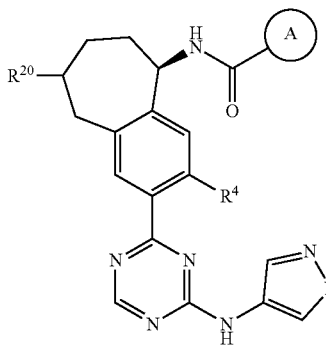

or a pharmaceutically acceptable salt thereof, wherein:
R$^{20}$ is selected from H, C$_{1-6}$alkyl, C$_{3-6}$cycloalkyl, saturated 4- to 6-membered monocyclic heterocyclyl, halo, —OR$^{20a}$, —OC(O)R$^{20a}$, —OC(O)N(R$^{20a}$)$_2$, and —SR$^{20a}$, wherein said C$_{1-6}$alkyl, C$_{3-6}$ cycloalkyl, and saturated 4- to 6-membered monocyclic heterocyclyl are optionally substituted with one to three R$^{25}$;

$R^{20a}$ in each occurrence is independently H or $C_{1-6}$alkyl, wherein said $C_{1-6}$alkyl in each occurrence is optionally and independently substituted with one $R^{25}$; and $R^{25}$ in each occurrence is independently selected from $C_{1-6}$alkyl.

16. The compound of claim 15, wherein $R^{20}$ is H.

17. The compound of claim 1, wherein the compound is represented by the following formula:

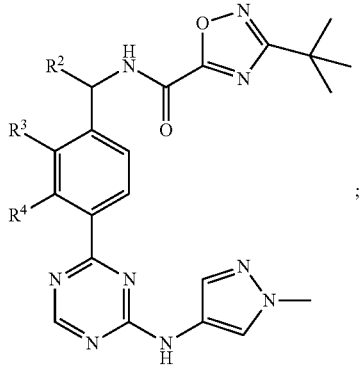

(IXA)

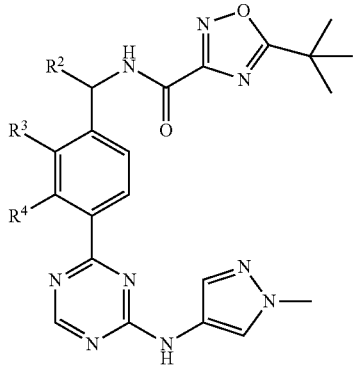

(IXB)

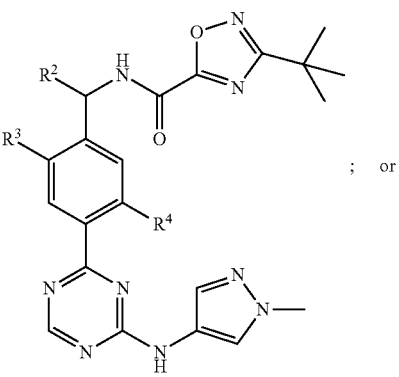

(IXC)

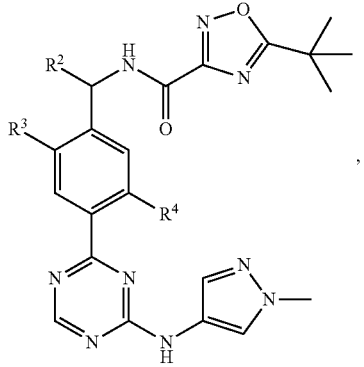

(IXD)

or a pharmaceutically acceptable salt thereof, wherein:

$R^2$ is H or $C_{1-4}$alkyl;

$R^3$ is halo or $C_{1-4}$alkyl, wherein said $C_{1-4}$alkyl is optionally substituted with one to three fluoro;

or $R^2$ and $R^3$, together with their intervening atoms, form a seven-membered carbocyclic or heterocyclic ring, wherein said seven-membered carbocyclic or heterocyclic ring is optionally substituted with one or more $R^{20}$, wherein $R^{20}$ is H or $C_{1-6}$alkyl optionally substituted with one to three $R^{25}$, $R^{25}$ is halo; and $R^4$ is H or halo.

18. The compound of claim 17, wherein the compound is represented by formula (IXA') or (IXB'):

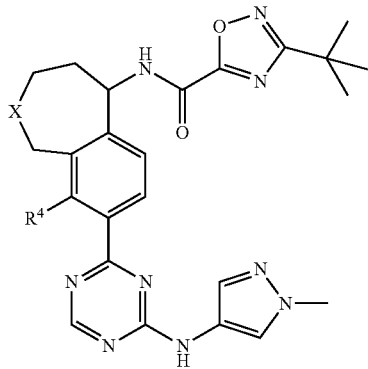

(IXA')

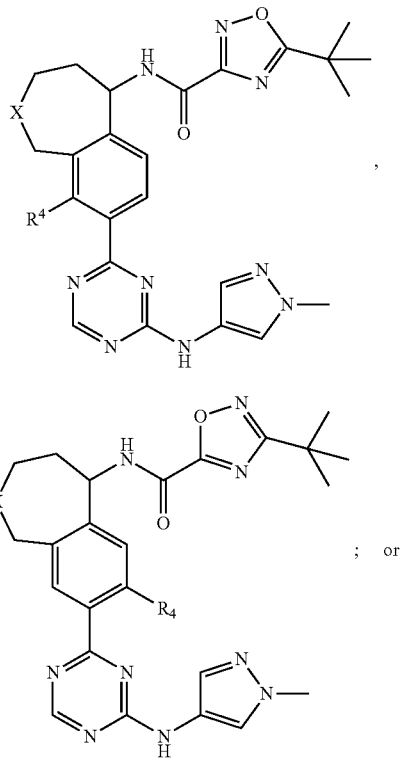

(IXB')

(IXC')

; or

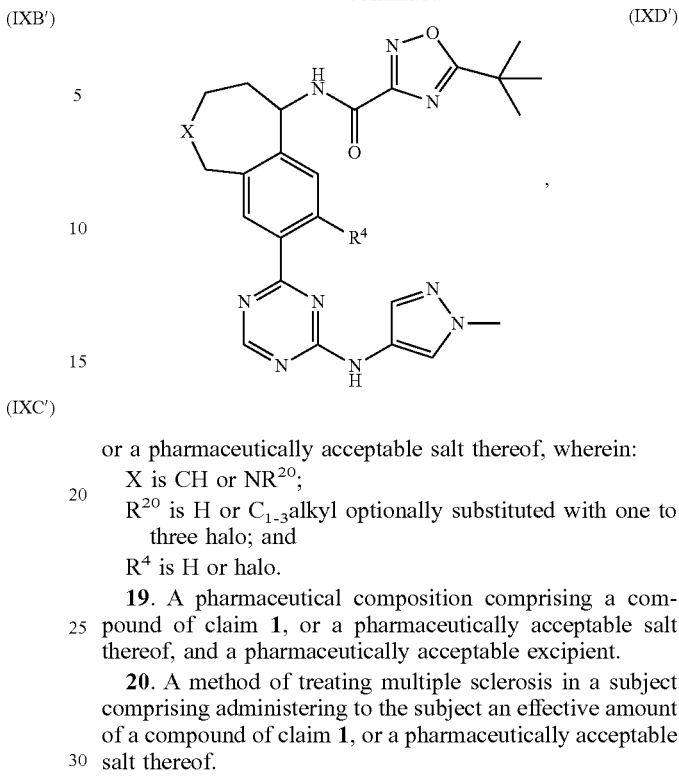

(IXD')

or a pharmaceutically acceptable salt thereof, wherein:
X is CH or $NR^{20}$;
$R^{20}$ is H or $C_{1-3}$alkyl optionally substituted with one to three halo; and
$R^4$ is H or halo.

19. A pharmaceutical composition comprising a compound of claim 1, or a pharmaceutically acceptable salt thereof, and a pharmaceutically acceptable excipient.

20. A method of treating multiple sclerosis in a subject comprising administering to the subject an effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 10,899,753 B2
APPLICATION NO. : 16/410725
DATED : January 26, 2021
INVENTOR(S) : Brian T. Hopkins et al.

It is certified that error appears in the above-identified patent and that said Letters Patent is hereby corrected as shown below:

In the Claims

Column 295, Line 47, Claim 1, replace $-OC(O)NRa)_2$ with ---$OC(O)N(R^{1a})_2$---.

Column 297, Line 49, Claim 1, replace $-C(O)N(R^{3a})_2, -N(R^{3a})_2$ with ---$C(O)N(R^{30a})_2, -N(R^{30a})_2$---.

Signed and Sealed this
Eleventh Day of October, 2022

Katherine Kelly Vidal
*Director of the United States Patent and Trademark Office*